United States Patent
Hosoda et al.

(10) Patent No.: US 10,689,354 B2
(45) Date of Patent: Jun. 23, 2020

(54) AMINOAZOLE DERIVATIVE

(71) Applicant: Teijin Pharma Limited, Tokyo (JP)

(72) Inventors: Shinnosuke Hosoda, Tokyo (JP); Gen Unoki, Tokyo (JP); Hidekazu Watanabe, Tokyo (JP); Kosuke Sasaki, Tokyo (JP); Jun Shibata, Tokyo (JP); Emi Yokoyama, Tokyo (JP); Kyohei Horie, Tokyo (JP); Kenichiro Takagi, Tokyo (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 16/060,701

(22) PCT Filed: Dec. 9, 2016

(86) PCT No.: PCT/JP2016/086784
§ 371 (c)(1),
(2) Date: Jun. 8, 2018

(87) PCT Pub. No.: WO2017/099237
PCT Pub. Date: Jun. 15, 2017

(65) Prior Publication Data
US 2019/0031628 A1 Jan. 31, 2019

(30) Foreign Application Priority Data
Dec. 11, 2015 (JP) .................................. 2015-242065

(51) Int. Cl.
*C07D 263/48* (2006.01)
*C07C 335/12* (2006.01)
(Continued)

(52) U.S. Cl.
CPC .......... *C07D 277/56* (2013.01); *A61K 31/421* (2013.01); *A61K 31/422* (2013.01); *A61K 31/426* (2013.01); *A61K 31/427* (2013.01); *A61K 31/428* (2013.01); *A61K 31/4245* (2013.01); *A61K 31/433* (2013.01); *A61K 31/4439* (2013.01); *A61K 31/454* (2013.01); *A61K 31/4709* (2013.01); *A61K 31/4725* (2013.01); *A61K 31/497* (2013.01); *A61K 31/498* (2013.01); *A61K 31/501* (2013.01); *A61K 31/5377* (2013.01); *A61P 5/26* (2018.01); *C07C 335/12* (2013.01); *C07C 335/18* (2013.01); *C07D 249/08* (2013.01); *C07D 263/48* (2013.01); *C07D 277/82* (2013.01);
(Continued)

(58) Field of Classification Search
CPC .. C07D 277/56; C07D 249/08; A61K 31/421; C07C 335/18
See application file for complete search history.

(56) References Cited

U.S. PATENT DOCUMENTS 5,256,632 A 10/1993 Wolf et al.
5,834,468 A 11/1998 Breault et al.
(Continued)

FOREIGN PATENT DOCUMENTS

| JP | 6-80653 A | 3/1994 |
| JP | 09-040607 A | 2/1997 |
| JP | 2005-537333 A | 12/2005 |
| JP | 2007-302617 A | 11/2007 |

(Continued)

OTHER PUBLICATIONS

Juan J. Marugan; "Evaluation of 2-Thioxo-2,3,5,6,7,8-hexahydropyrimido [4,5-d] pyrimidin-4 (1H)-one analogues as GAA activators," European Journal of Medicinal Chemistry; Feb. 1, 2010 ; 18 pages vol. 45.
International Search Report of PCT/JP2016/086784 filed Jan. 17, 2017.

*Primary Examiner* — Emily A Bernhardt
*Assistant Examiner* — Laura M Daniel
(74) *Attorney, Agent, or Firm* — Sughrue Mion, PLLC

(57) ABSTRACT

A compound, represented by the following formula or a medically acceptable salt thereof, having an effect of regulating the activity of an androgen receptor. In the formula, X represents S, O; Z represents $(R^a)_n$-A-$(CR^{13}R^{14})_{0-1}$—$(CR^{11}R^{12})_{0-1}$; A represents aryl, heteroaryl; $R^1$ represents alkyl, cycloalkyl, alkenyl, alkynyl, alkoxyalkyl, aryl, arylalkyl, heterocycle, heterocyclic alkyl; $R^2$ represents hydrogen, halogen, alkyl, cycloalkyl, phenyl; R3 represents hydrogen, halogen, alkyl, cycloalkyl, alkoxyalkyl, alkenyl, alkynyl, cycloalkenyl, aryl, arylalkyl, heterocycle, heterocyclic alkyl, acyl, cycloalkylcarbonyl, benzoyl, spiroalkyl, adamantyl, silyl, $R^{31}R^{32}NCO$—; $R^4$ and $R^5$ represent hydrogen, halogen, alkyl, phenyl, and cycloalkyl.

[Chem. 1]

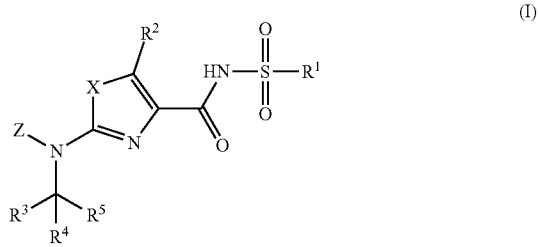

14 Claims, No Drawings

(51) Int. Cl.
*A61K 31/421* (2006.01)
*A61P 5/26* (2006.01)
*C07D 277/56* (2006.01)
*C07C 335/18* (2006.01)
*C07D 249/08* (2006.01)
*C07D 417/12* (2006.01)
*A61K 31/4725* (2006.01)
*A61K 31/498* (2006.01)
*A61K 31/428* (2006.01)
*A61K 31/426* (2006.01)
*A61K 31/497* (2006.01)
*A61K 31/427* (2006.01)
*A61K 31/4439* (2006.01)
*A61K 31/454* (2006.01)
*A61K 31/4709* (2006.01)
*A61K 31/4245* (2006.01)
*C07D 413/12* (2006.01)
*A61K 31/422* (2006.01)
*C07D 277/82* (2006.01)
*A61K 31/501* (2006.01)
*A61K 31/433* (2006.01)
*A61K 31/5377* (2006.01)

(52) U.S. Cl.
CPC ......... *C07D 413/12* (2013.01); *C07D 417/12* (2013.01)

(56) References Cited

U.S. PATENT DOCUMENTS

| | | | |
|---|---|---|---|
| 6,242,474 | B1 | 6/2001 | Yamasaki et al. |
| 6,352,985 | B1 | 3/2002 | Yamasaki et al. |
| 6,420,409 | B1 | 7/2002 | Yamasaki et al. |
| 2003/0138416 | A1 | 7/2003 | Lau |
| 2005/0032849 | A1* | 2/2005 | Phadke ............... C07C 335/12 514/357 |
| 2008/0207708 | A1 | 8/2008 | Bit et al. |
| 2009/0036419 | A1 | 2/2009 | Chen et al. |
| 2010/0152187 | A1 | 7/2010 | Fu et al. |
| 2013/0231392 | A1 | 9/2013 | Kobayashi et al. |
| 2014/0336167 | A1 | 11/2014 | Sweis et al. |

FOREIGN PATENT DOCUMENTS

| | | |
|---|---|---|
| JP | 2009-513563 A | 4/2009 |
| JP | 2015-516437 A | 6/2015 |
| WO | 98/15530 A1 | 4/1998 |
| WO | 99/00359 A1 | 1/1999 |
| WO | 99/00373 A1 | 1/1999 |
| WO | 2004/041277 A1 | 5/2004 |
| WO | 2006/114274 A1 | 11/2006 |
| WO | 2010/012793 A1 | 2/2010 |
| WO | 2010/018714 A1 | 2/2010 |
| WO | 2014/017093 A1 | 1/2014 |

* cited by examiner

AMINOAZOLE DERIVATIVE

CROSS REFERENCE TO RELATED APPLICATIONS

This application is a National Stage entry of International Application No. PCT/JP2016/086784, filed Dec. 9, 2016, claiming priority based on Japanese Patent Application No. 2015-242065, filed Dec. 11, 2015.

TECHNICAL FIELD

The present invention relates to a useful amino azole derivative as a pharmaceutical compound. More particularly, it relates to an amino azole derivative and a medically acceptable salt thereof which are useful for treatment or prevention of androgen receptor-related diseases such as sarcopenia and disuse muscle atrophy, cachexia or muscular dystrophy.

BACKGROUND ART

Endogenous steroidal androgen such as testosterone or 5α-dihydrotestosterone (DHT) exerts physiological and pathophysiological actions by binding to an androgen receptor (referred to as "AR"), a nuclear receptor. AR induces cell strain-specific gene expression in a target tissue. AR consists of three main functional domains including a ligand binding domain (LBD), a DNA binding domain and an amino terminal domain. A substance which binds to AR and shows an endogenous steroidal androgenic action is called AR agonist, while the one which inhibits the action of AR ligand is called AR antagonist. After AR binds to a ligand and the product is delivered into a nucleus, the product forms a complex with plural proteins such as a transcription coupling factor and a cell strain-specific coupling factor and binds to a target gene or an androgen responsive element (ARE), which is a DNA sequence (binding motif) in the region of a promoter or enhancer of genes that AR easily binds to, and thereby controls the production of protein encoded by a specific gene.

Androgen has actions such as a protein anabolic action, a gonadotropin secretion inhibitory action, and the promoting action of erythropoiesis as well as that in the reproductive system, and target cells for androgen are variously distributed into organs including external sex organs, accessory sex organs as well as brain, pituitary gland, muscle tissues, bones, and kidneys (NPL 1). The androgenic protein anabolic action includes the increase of a skeletal muscle mass and skeletal muscular strength, and the increase of bone quantity and bone density (NPL 2). Therefore, androgen is expected to be useful for prevention and/or treatment for disuse muscle atrophy occurring as a result of inactivity by sarcopenia and bedridden or immobilization resulting from plaster cast fixation, cachexia (such as cancers, heart failure, chronic obstructive pulmonary disease and end-stage renal disease and the like), furthermore, muscular dystrophy (such as Duchenne dystrophy, myotonic dystrophy and the like).

However, steroidal androgen has a poor first-pass effect in the liver, and hepatotoxicity and cross reactivity with other steroid hormone receptors such as glucocorticoid receptor (GR) have become problem (NPL 1). Therefore, a selective androgen receptor modifier (SARM) as nonsteroidal androgen, which increases a skeletal muscle mass, muscular strength, bone quantity and bone density by binding to AR, is highly promising by selective binding to AR compared to other steroid hormone receptors without danger of hepatotoxicity. Therefore, many SARMs are under development in an early development stage (NPL 3). Ostelin (brand name) has the most developed and its phase I and phase II clinical trials have been completed (NPL 4). In addition, SARM is expected to be effective for the use in the promotion of regeneration and restoration of muscles (NPL 5), in the area of hormonal male contraception and benign prostatic hypertrophy (BPH) and wound healing (NPL 6).

In PTL's 1-5, a compound is disclosed whose partial structure is coincident with the amino azole derivative of the present invention. However, the same compound is not described and there is no description about their relations to AR. A compound with the activity of AR antagonist is described in NPL 7, but its chemical structure is different from the amino azole derivative of the present invention. Further, NPL 7 does not suggest that the amino azole derivative of the present invention has an AR agonist activity.

CITATION LIST

Patent Literature

[PTL 1]
WO 2010/012793A1
[PTL 2]
EP752421A1
[PTL 3]
Japanese Patent Laid-Open No. 2007-302617
[PTL 4]
WO 2006/114274A1
[PTL 5]
WO 2014/017093A1

Non Patent Literature

[NPL 1]
N. Engl. J. Med. 334, 707-714, 1996
[NPL 2]
J. Ger., Series A: Biol. Sci. Med. Sci. 59: 461-465, 2004
[NPL 3]
J. Med. Chem. 52(12):3597-617, 2009
[NPL 4]
Future Oncology 5(8):1211-20, 2009
[NPL 5]
J. Ger., Series A: Biol. Sci. Med. Sci. 68 (1): 17-26, 2013
[NPL 6]
Eplasty 9:e9, 2009
[NPL 7]
Bioorganic & Medicinal Chemistry 16, 6799-6812, 2008

SUMMARY OF INVENTION

Technical Problem

The purpose of the present invention is to provide a novel compound having the active regulating action of AR. In addition, it is to provide a therapeutic or prophylactic agent containing a novel compound having the active regulating action of AR as an active ingredient for AR-related diseases such as sarcopenia and disuse muscle atrophy, cachexia, muscular dystrophy or the like.

Solution to Problem

As a result of diligent studies for the above-mentioned purpose, the present inventors arrived at the following invention.

That is, the present invention is a compound (hereinafter referred to as the compound of the present invention) represented by the following formula (I) or a medically acceptable salt thereof,

[Chem. 1]

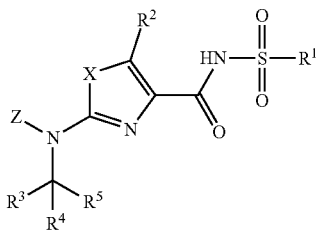
(I)

wherein,

X represents a sulfur atom or an oxygen atom,

Z represents a group selected among the following $Z^1$ to $Z^3$,

[Chem. 2]

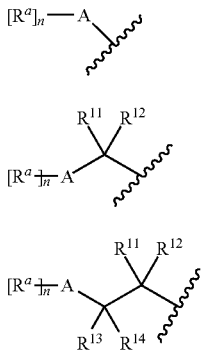

A represents a C6-C12 aryl or a 5-12 membered heteroaryl group, $R^{11}$ to $R^{14}$ represent each independently a hydrogen atom, a halogen, a hydroxyl group, a C1-C3 alkyl group optionally substituted with a halogen or a hydroxyl group, a C1-C3 alkoxy group optionally substituted with a halogen or a hydroxyl group, and two selected from $R^{11}$ to $R^{14}$ may form a ring, n is an integer of 0 or more and 3 or less, $R^a$'s are the same or different, and represent a halogen, a hydroxyl group, a C1-C6 alkyl group (optionally substituted with a halogen, a hydroxyl group, a phenoxy group or a benzyloxy group), a C3-C8 cycloalkyl group optionally substituted with a halogen, C1-C6 alkoxy group (optionally substituted with a halogen, a hydroxyl group, a carboxyl group, a carbamoyl group optionally substituted with a C1-C4 alkyl group, a C1-C4 alkoxy group or a benzyloxy group), a C3-C8 cycloalkoxy group optionally substituted with a halogen, a C1-C4 alkoxy C1-C4 alkyl group (optionally substituted with a halogen, a hydroxyl group, a cyano group, a C1-C4 alkoxy group or a benzyloxy group), a phenoxy group, a benzyloxy group, a cyano group, a nitro group, a carboxyl group, a C1-C6 acyl group, a C1-C4 alkoxycarbonyl group, an amino group, a C1-C6 monoalkylamino group, a C1-C6 dialkylamino group, a carbamoyl group optionally substituted with a C1-C4 alkyl group, a C6-C12 aryl group (optionally substituted with a halogen, a cyano group, a C1-C4 alkyl group optionally substituted with a halogen, or a hydroxyl group), a 3-12 membered heterocyclic group optionally substituted with a halogen, a sulfanyl group optionally substituted with a C1-C6 alkyl group optionally substituted with a halogen, a C1-C6 alkylsulfinyl group optionally substituted with a halogen, a C1-C6 alkylsulfonyl group optionally substituted with a halogen, or a pentafluorosulfanyl group, $R^1$ represents a C1-C9 alkyl group (optionally substituted with a halogen, a hydroxyl group, a cyano group, a carboxyl group, a C1-C4 alkoxycarbonyl group, an amino group, a C1-C6 monoalkylamino group, a C1-C6 dialkylamino group or a C1-C6 alkylsulfonyl group), a C3-C8 cycloalkyl group (optionally substituted with a halogen, a hydroxyl group or a cyano group), C2-C6 alkenyl group optionally substituted with a halogen or a phenyl group, a C2-C6 alkynyl group optionally substituted with a halogen or a phenyl group, C1-C6 alkoxy C1-C6 alkyl group (optionally substituted with a halogen, a hydroxyl group, a cyano group or a C1-C4 alkoxy group), a C6-C12 aryl group optionally substituted with 1 to 3 moieties of $R^c$, a C6-C12 aryl C1-C6 alkyl group optionally substituted with 1 to 3 moieties of $R^d$, a 3-12 membered heterocyclic group optionally substituted with 1 to 3 moieties of $R^e$, or a 3-12 membered heterocyclic C1-C6 alkyl group optionally substituted with 1 to 3 moieties of $R^f$, $R^2$ represents a hydrogen atom, a halogen, a C1-C6 alkyl group (optionally substituted with a halogen, a hydroxyl group or a cyano group), a C3-C8 cycloalkyl group (optionally substituted with a halogen, a hydroxyl group or a cyano group) or a phenyl group (optionally substituted with a halogen, a hydroxyl group or a cyano group), $R^3$ represents a hydrogen atom, a halogen, a C1-C12 alkyl group (optionally substituted with a halogen, a hydroxyl group, a cyano group, a carboxyl group, a C3-C8 cycloalkyl group optionally substituted with a halogen or a hydroxyl group, a C3-C8 cycloalkoxy group optionally substituted with a halogen or a hydroxyl group, a C1-C4 alkoxy group optionally substituted with a phenyl group, a C1-C4 alkoxycarbonyl group, an amino group, a C1-C6 monoalkylamino group, a C1-C6 dialkylamino group, a C1-C6 alkylsulfonyl group, a phenoxy group or a silyl group substituted with a C1-C4 alkyl group or a phenyl group), a C3-C8 cycloalkyl group (optionally substituted with a halogen, a hydroxyl group, a cyano group, a carboxyl group, a C1-C4 alkyl group optionally substituted with a halogen or a hydroxyl group, a C1-C4 alkoxy group optionally substituted with a halogen or a hydroxyl group, a C1-C4 alkoxycarbonyl group, an amino group, a C1-C6 monoalkylamino group, a C1-C6 dialkylamino group or a C1-C6 alkylsulfonyl group), a C1-C6 alkoxy C1-C6 alkyl group (optionally substituted with a halogen, a hydroxyl group, a cyano group or a C1-C4 alkoxy group), a C2-C9 alkenyl group (optionally substituted with a halogen, a hydroxyl group or a cyano group), a C2-C9 alkynyl group optionally substituted with a halogen or a cyano group, a C3-C8 cycloalkenyl group (optionally substituted with halogen, a hydroxyl group or a cyano group), a C6-C12 aryl group optionally substituted with 1 to 5 moieties of $R^g$, a C6-C12 aryl C1-C6 alkyl group optionally substituted with 1 to 5 moieties of $R^h$, a 3-12 membered heterocyclic group optionally substituted with 1 to 5 moieties of $R^i$, a 3-12 membered heterocyclic C1-C6 alkyl group optionally substituted with 1 to 5 moieties of $R^j$, a C1-C9 acyl group (optionally substituted with a halogen, a hydroxyl group or a cyano group), a C3-C8 cycloalkylcarbonyl group, a benzoyl group, a C5-C12 spiroalkyl group, an adamantyl group, a silyl group substituted with 1 to 3 moieties of C1-C4 alkyl group or a phenyl group, or R³⁰,

[Chem. 3]

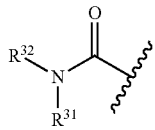

wherein,

R³⁰ is a substituent represented by the above-mentioned formula,

R³¹ and R³² represent each independently a hydrogen atom, a C1-C6 alkyl group optionally substituted with a halogen, a C3-C8 cycloalkyl group optionally substituted with a halogen, or a phenyl group optionally substituted with a halogen, and R³¹ and R³² may form a ring by connecting directly with each other or via an oxygen atom, a nitrogen atom or a sulfur atom, R⁴ and R⁵ represent each independently a hydrogen atom, a halogen, a C1-C6 alkyl group (optionally substituted with a halogen, a hydroxyl group or a cyano group), a phenyl group or a C3-C8 cycloalkyl group (optionally substituted with a halogen, a hydroxyl group or a cyano group), and R³ and R⁴ may form a ring, R^c, R^d, R^e and R^f represent a halogen, a hydroxyl group, a C1-C6 alkyl group optionally substituted with a halogen, a C3-C8 cycloalkyl group optionally substituted with a halogen, a C1-C6 alkoxy group optionally substituted with a halogen, a C3-C8 cycloalkoxy group optionally substituted with a halogen, a C1-C4 alkoxy C1-C4 alkyl group (optionally substituted with a halogen, a hydroxyl group, a phenyl group or a C1-C4 alkoxy group), a cyano group, a nitro group, an oxo group, a carboxyl group, a C1-C6 acyl group, a C1-C4 alkoxycarbonyl group, an amino group, a C1-C6 monoalkylamino group, a C1-C6 dialkylamino group, a sulfanyl group, a C1-C6 alkylsulfanyl group optionally substituted with a halogen, a C1-C6 alkylsulfinyl group optionally substituted with a halogen, or a C1-C6 alkylsulfonyl group optionally substituted with a halogen, R^g, R^h, R^i and R^j represent a halogen, a hydroxyl group, an amino group, a C1-C6 monoalkylamino group, a C1-C6 dialkylamino group, an acetamido group, a C1-C6 alkyl group (optionally substituted with a halogen, a hydroxyl group, a phenoxy group or a benzyloxy group), a C3-C8 cycloalkyl group, a C2-C6 alkenyl group (optionally substituted with a halogen, a hydroxyl group or a cyano group), a C2-C6 alkynyl group optionally substituted with a halogen or a cyano group, a C1-C6 alkoxy group (optionally substituted with a halogen, a hydroxyl group, a C1-C4 alkoxy group, an amino group, a C1-C6 monoalkylamino group, a C1-C6 dialkylamino group, a C6-C10 aryl group or a 3-10 membered heterocyclic group optionally substituted with an oxo group), a C1-C6 alkoxy C1-C6 alkyl group (optionally substituted with a halogen, a phenyl group, a phenoxy group or a benzyloxy group), a C3-C8 cycloalkoxy group, a cyano group, a nitro group, an oxo group, a carboxyl group, a sulfanyl group, a C1-C6 alkylsulfanyl group optionally substituted with a halogen, a C1-C6 alkylsulfinyl group optionally substituted with a halogen, a phenylsulfonyl group optionally substituted with a C1-C4 alkyl group, a C1-C6 alkylsulfonyl group optionally substituted with a halogen, a C1-C6 acyl group, a C1-C4 alkoxycarbonyl group, a phenyl group (optionally substituted with a halogen, a cyano group, a trifluoromethyl group or a hydroxyl group), a 3-12 membered heterocyclic group optionally substituted with a halogen or an oxo group, a phenoxy group, a C6-C12 aryl C1-C6 alkoxy group, a 3-12 membered heterocyclic C1-C6 alkoxy group or a group represented by the formula R³⁰—CH₂—O— (R³⁰ is as defiined above.).

For the compound of the present invention, a part that is capable of having multiple substituents based on the chemical structure may possess one or more substituents optionally selected from a group of selectable substituents when the number of substituents is not specified.

In addition, "optionally substituted" in the description of the present invention means that substitution may be performed as many times as possible based on the chemical structures of the substituents and the group to be substituted. When several substituents are present, their substituents may be the same or different. For example, multiple R^c may be identical or different when R^c is substituted at multiple sites.

Further, the present invention also includes a solvate of the compound of the present invention and a solvate of a medically acceptable salt of the compound of the present invention.

In addition, the present invention is a pharmaceutical composition containing a compound of the present invention or a medically acceptable salt thereof and a pharmaceutically acceptable carrier thereof.

In addition, the present invention is an AR activity regulator containing a compound of the present invention or a medically acceptable salt thereof as an active ingredient.

Furthermore, the present invention is a therapeutic or a prophylactic agent containing a compound of the present invention or a medically acceptable salt thereof as an active ingredient for AR-related diseases such as sarcopenia, disuse muscle atrophy, cachexia and/or muscular dystrophy.

Advantageous Effects of Invention

The compound of the present invention is nonsteroidal androgen and SARM as well. SARM can be widely applied for clinical conditions such as disuse muscle atrophy resulting from inactivity caused by sarcopenia and bedridden or immobilization by plaster cast fixation, cachexia (e.g. cancers, heart failure, chronic obstructive pulmonary disease, end-stage renal disease and the like), or muscular dystrophy (e.g., Duchenne dystrophy, myotonic dystrophy and the like).

The compound of the present invention has advantages such as tissue selective activity, feasibility of oral administration, AR selectivity and the lack of androgenic effect compared to steroidal androgen.

DESCRIPTION OF EMBODIMENTS

Terms used alone or in combination in the present description will be explained below. The explanation of each substituent shall be common in each site, unless otherwise particularly specified.

The term "C1-C6" means that the number of carbon atoms is 1 to 6.

In addition, "5-7 membered" means a structure composed of 5-7 non-hydrogen atoms.

The term "halogen" in the present invention means a fluorine atom, a chlorine atom, a bromine atom or an iodine atom.

The meaning of each group in the present description will be explained as follows, but the scope of the group is not limited to groups that are illustrated for each exemplification.

The alkyl group in the present invention is a linear- or branched-chain aliphatic hydrocarbon group. Examples of C1-C6 alkyl group are methyl group, ethyl group, propyl group, isopropyl group, butyl group, isobutyl group, tert-butyl group, pentyl group, isopentyl group, hexyl group and the like.

The cycloalkyl group in the present invention is a monocyclic aliphatic hydrocarbon group. Examples of C3-C8 cycloalkyl group are cyclopropyl group, cyclopentyl group, cyclohexyl group and the like.

The alkoxy group in the present invention is a group formed by bonding the above-mentioned alkyl group to an oxygen atom and capable of bonding via the oxygen atom. Examples of C1-C6 alkoxy group are methoxy group, ethoxy group, propoxy group, isopropoxy group, butoxy group, isobutoxy group, tert-butoxy group, pentyloxy group, isopentyloxy group, hexyloxy group and the like.

The cycloalkoxy group in the present invention is a group formed by bonding the above-mentioned cycloalkyl group to an oxygen atom and capable of bonding via the oxygen atom. Examples of the C3-C8 cycloalkoxy group are cyclopropyloxy group, cyclohexyloxy group, cyclooctyloxy group and the like.

The alkoxyalkyl group in the present invention is a group formed by bonding the above-mentioned alkoxy group to an alkyl group and capable of bonding via the alkyl group. Examples of the C1-C6 alkoxy C1-C6 alkyl group are methoxymethyl group, methoxyethyl group, methoxybutyl group, ethoxymethyl group, butoxymethyl group and the like.

The alkylsulfanyl group in the present invention is a group formed by bonding the above-mentioned alkyl group to a sulfur atom and capable of bonding via the sulfur atom. Examples of the C1-C6 alkylsulfanyl group are methylsulfanyl group, ethylsulfanyl group, propylsulfanyl group, isopropylsulfanyl group, butylsulfanyl group, isobutylsulfanyl group, pentylsulfanyl group, isopentylsulfanyl group, hexylsulfanyl group and the like.

The alkenyl group in the present invention is a group formed by replacing one of carbon-carbon single bonds of the above-mentioned alkyl group with a double bond. Examples of the C2-C6 alkenyl group are vinyl group, 2-propenyl group, 2-methyl-2-butenyl group and the like.

The cycloalkenyl group in the present invention is a group formed by replacing one of carbon-carbon single bonds of the above-mentioned cycloalkyl group with a double bond. Examples of the C3-C8 cycloalkenyl group are 2-cyclopenten-1-yl group, 2-cyclohexen-1-yl group and the like.

The alkynyl group in the present invention is a group formed by replacing one of carbon-carbon single bonds of the above-mentioned alkyl group with a triple bond. Examples of the C2-C6 alkynyl group are ethynyl group, prop-1-yn-1-yl group, propargyl group and the like.

The alkylsulfonyl group in the present invention is a group formed by bonding the above-mentioned alkyl group to a sulfonyl group and capable of bonding via the sulfonyl group. Examples of the C1-C6 alkylsulfonyl group are methylsulfonyl group, ethylsulfonyl group, isopropylsulfonyl group and the like.

The monoalkylamino group in the present invention is a group consisting of an alkyl group and an amino group. Examples of the C1-C6 monoalkylamino group are methylamino group, ethylamino group, propylamino group, isopropylamino group, butylamino group, isobutylamino group, sec-butylamino group, tert-butylamino group, pentylamino group, hexylamino group and the like.

The C1-C6 dialkylamino group in the present invention is an amino group in which substitution reaction by two, same or different, C1-C6 alkyl groups is performed to the nitrogen atom. Examples of the C1-C6 dialkylamino group are dimethylamino group, diethylamino group, dipropylamino group, diisopropylamino group, dibutylamino group, diisobutylamino group, di(sec-butyl)amino group, di(tert-butyl)amino group, dipentylamino group, dihexylamino group and the like.

The aryl group in the present invention is a group formed by removing, from an aromatic hydrocarbon having one or two rings, one hydrogen atom binding to one of the ring(s). In the case of the aryl having two rings, if one ring is an aromatic hydrocarbon, the other ring may not be aromatic. Examples of C6-C12 aryl group are phenyl group, naphthyl group, indenyl group, tetrahydronaphthyl group, indanyl group and the like.

The C6-C12 aryl C1-C6 alkyl group in the present invention is a group formed by substituting one of hydrogen atoms of the C1-C6 alkyl group with the C6-C12 aryl group. Examples of C6-C12 aryl C1-C6 alkyl group are benzyl group, phenethyl group, (2-naphthyl)methyl group, 3-phenylpropyl group, 4-phenylbutyl group and the like.

The heterocyclic group in the present invention means heteroaryl group and heterocycloalkyl group.

The heteroaryl group in the present invention is a group formed by removing, from an aromatic heteroring containing 1-5 hetero atoms selected among a sulfur atom, a nitrogen atom and an oxygen atom and having one or two rings, one hydrogen atom binding to one of the ring(s). Also, in the case of a heteroaryl group having two rings, if one ring is an aromatic ring, the other ring may not be aromatic. Examples of 3-12 membered heteroaryl group are, furanyl group, thienyl group, pyrrolyl group, imidazolyl group, pyrazolyl group, triazolyl group, tetrazolyl group, thiazolyl group, oxazolyl group, isoxazolyl group, oxadiazolyl group, thiadiazolyl group, isothiazolyl group, pyridinyl group, pyridazinyl group, pyrazinyl group, pyrimidinyl group, quinolinyl group, isoquinolinyl group, benzofuranyl group, benzothienyl group, indolyl group, indazolyl group, chromanyl group, benzothiazolyl group, benzimidazolyl group, benzoxazolyl group, dihydrobenzofuranyl group, dihydrobenzodioxynyl group and the like.

The heterocycloalkyl group in the present invention is a groups formed by removing, from an aliphatic heteroring containing 1-4 hetero atoms selected among a sulfur atom, a nitrogen atom and an oxygen atom, optionally partially unsaturated or saturated and having one or two rings, one hydrogen atom binding to one of the ring(s). Examples of 3-10 membered heterocycloalkyl group are morpholino group, piperidyl group, dioxolyl group, tetrahydrofuranyl group, tetrahydropyranyl group, a tetrahydrothienyl group and the like.

The 3-12 membered heterocyclic C1-C6 alkyl group in the present invention is a group formed by substituting one of hydrogen atoms of the C1-C6 alkyl group with the 3-12 membered heterocyclic group. Examples of 3-12 membered heterocyclic C1-C6 alkyl group are pyridylmethyl group, tetrahydropyranylmethyl group and the like.

The C6-C12 aryl C1-C6 alkoxy group in the present invention is a group formed by substituting one of hydrogen atoms of the C1-C6 alkoxy group with the C6-C12 aryl. Examples of C6-C12 aryl C1-C6 alkoxy group are benzyloxy group, phenethyloxy group and the like.

The 3-12 membered heterocyclic C1-C6 alkoxy group in the present invention is a group formed by substituting one of hydrogen atoms of the C1-C6 alkoxy group with the 3-12 membered heterocyclic group. Examples of the 3-12 membered heterocyclic C1-C6 alkoxy group are pyridylmethoxy group, tetrahydropyranylmethoxy group and the like.

The C1-C6 acyl group in the present invention is a group formed by bonding a C1-C5 alkyl group or a hydrogen atom to a carbonyl group and capable of bonding via the carbonyl group. Examples of C1-C6 acyl group are formyl group, acetyl group, propionyl group, butyryl group, isobutyryl group, valeryl group, isovaleryl group, pivaloyl group and the like.

The C2-C4 alkoxycarbonyl group in the present invention is a group formed by bonding a C1-C3 alkoxy group to a carbonyl group and capable of bonding via the carbonyl group. Examples of C2-C4 alkoxycarbonyl group are methoxycarbonyl group, ethoxycarbonyl group, isopropoxycarbonyl group and the like.

The spiroalkyl group in the present invention is an aliphatic hydrocarbon group having a spiro ring structure. Examples of C5-C12 spiroalkyl group are spiro[2.5]octyl group and the like.

The compound of the present invention is a compound represented by the above formula (I).

The following compounds are shown as preferable in the compounds of present invention.

In the above-mentioned formula (I),

X is a sulfur atom or an oxygen atom, and preferably a sulfur atom.

Z has a structure of the one selected from Z1 to Z3, preferably Z1 or Z3, and more preferably Z1.

A in Z is a C6-C12 aryl or a 5-12 membered heteroaryl group, the C6-C12 aryl is preferably phenyl group or naphthyl group, and the 5-12 membered heteroaryl group is preferably pyridyl group, pyridazyl group, pyrazinyl group, pyronyl group, thiophenyl group, oxazolyl group, thiazolyl group, pyrazolyl group, oxadiazolyl group, benzofuranyl group, benzothiophenyl group, indolyl group or benzopyrazinyl group.

$R^a$ is preferably halogen, hydroxyl group, C1-C6 alkyl group optionally substituted with halogen, C1-C6 alkoxy group optionally substituted with halogen, cyano group or pentafluoro sulfanylgroup.

$[R^a]_n$-A is preferably phenyl group, 4-fluorophenyl group, 3,4-difluorophenyl group, 4-chlorophenyl group, 2,4-dichlorophenyl group, 4-(trifluoromethyl)phenyl group, 4-(trifluoromethoxy)phenyl group, 4-cyanophenyl group, 4-cyano-3-fluorophenyl group, 4-cyano-3-(trifluoromethyl)phenyl group or 6-(trifluoromethyl)pyridin-3-yl group.

Z as a whole is preferably 4-(trifluoromethyl)phenyl group, 4-cyanophenyl group, 4-cyano-2-fluorophenyl group, 4-cyano-3-fluorophenyl group, 4-cyano-3-(trifluoromethyl)phenyl group, 6-(trifluoromethyl)pyridin-3-yl group, phenethyl group, 3-fluorophenethyl group, 4-fluorophenethyl group, 3,4-difluorophenethyl group, 4-chlorophenethyl group, 2,4-dichlorophenethyl group, 3,4-dichlorophenethyl group, 4-(trifluoromethyl)phenethyl group, 4-(difluoromethoxy)phenethyl group, 4-(trifluoromethoxy)phenethyl group, 4-cyanophenethyl group, 2-(1,3-benzodioxol-5-yl) ethyl group, 2-(4-cyanopyrazol-1-yl)ethyl group, trans-2-phenylcyclopropyl group or 2-cyclohexylethyl group.

$R^{11}$, $R^{12}$, $R^{13}$ and $R^{14}$ are preferably hydrogen atom, halogen, methyl group or cyclopropane ring containing $R^{11}$ and $R^{13}$.

$R^1$ is preferably C1-C6 alkyl group (optionally substituted with halogen, hydroxyl group, cyano group, carboxyl group, C1-C4 alkoxycarbonyl group, amino group, C1-C6 monoalkylamino group, C1-C6 dialkylamino group or C1-C6 alkylsulfonyl group), C3-C8 cycloalkyl group optionally substituted with halogen or hydroxyl group, C1-C6 alkoxy C1-C6 alkyl group (optionally substituted with halogen, cyano group, hydroxyl group or C1-C4 alkoxy group), C6-C10 aryl group optionally substituted with 1 to 3 moieties of $R^c$, C6-C10 aryl C1-C6 alkyl group optionally substituted with 1 to 3 moieties of $R^d$, 3-10 membered heterocyclic group optionally substituted with 1 to 3 moieties of $R^e$ or 3-10 membered heterocyclic C1-C6 alkyl group optionally substituted with 1 to 3 moieties of $R^f$, and more preferably C1-C6 alkyl group (optionally substituted with halogen, hydroxyl group, cyano group, carboxyl group, C1-C4 alkoxycarbonyl group, amino group, C1-C6 monoalkylamino group, C1-C6 dialkylamino group or C1-C6 alkylsulfonyl group) or C1-C6 alkoxy C1-C6 alkyl group (optionally substituted with halogen, hydroxyl group, cyano group or C1-C4 alkoxy group). $R^1$ is particularly preferably methyl group, ethyl group, cyclopropyl group, 4-hydroxybutyl group, 3-methoxypropyl group, 4-methoxybutyl group, trifluoromethyl group, (tetrahydrofuran-3-yl)methyl group, 3-pyridylmethyl group or 4-pyridylmethyl group.

$R^2$ is preferably hydrogen atom, halogen, C1-C6 alkyl group (optionally substituted with halogen, hydroxyl group or cyano group) or C3-C8 cycloalkyl group optionally substituted with halogen, more preferably hydrogen atom, halogen or C1-C4 alkyl group optionally substituted with halogen, and further preferably chlorine atom, bromine atom, methyl group, ethyl group, isopropyl group, cyclopropyl group, difluoromethyl group or trifluoromethyl group.

$R^3$ is preferably hydrogen atom, C1-C9 alkyl group (optionally substituted with halogen, hydroxyl group or C1-C4 alkoxy group), C3-C8 cycloalkyl group optionally substituted with halogen or hydroxyl group, C2-C9 alkenyl group optionally substituted with halogen or hydroxyl group, C1-C4 alkoxy C1-C4 alkyl group (optionally substituted with halogen, hydroxyl group, cyano group or C1-C3 alkoxy group), C6-C10 aryl group optionally substituted with 1 to 3 moieties of $R^g$, C6-C10 aryl C1-C3 alkyl group optionally substituted with 1 to 3 moieties of $R^h$, 5-10 membered heterocyclic group optionally substituted with 1 to 3 moieties of $R^i$, 5-10 membered heterocyclic C1-C3 alkyl group optionally substituted with 1 to 3 moieties of $R^j$, or C1-C9 acyl group.

Among these, the C6-C10 aryl is preferably phenyl group or naphthyl group. The 5-10 membered heterocyclic group is preferably pyridyl group, pyridazyl group, pyrazinyl group, furyl group, thiophenyl group, oxazolyl group, thiazolyl group, pyrazolyl group, oxadiazolyl group, benzofuranyl group, benzothiophenyl group, benzothiazolyl group, indolyl group, benzopyrazinyl group, benzoxadiazolyl group, benzothiadiazolyl group, quinolyl group, isoquinolyl group, dihydrobenzofuranyl group, benzodioxolyl group, dihydrobenzodioxynyl group, chromanyl group, indanyl group or tetrahydronaphthylgroup. The arylalkyl group is preferably benzyl group or naphthylmethyl group. The heterocyclic alkyl group is preferably pyridylmethyl group, thiophenylmethyl group, oxazolylmethyl group or thiazolylmethyl group.

$R^g$ and $R^i$ are preferably halogen, hydroxyl group, C1-C3 dialkylamino group, C1-C6 alkyl group (optionally substituted with halogen, hydroxyl group or phenoxy group), C1-C6 alkoxy group optionally substituted with halogen, C1-C4 alkoxy C1-C4 alkyl group optionally substituted with halogen, cyano group, C1-C4 alkylsulfinyl group optionally substituted with halogen, C1-C4 alkylsulfonyl group optionally substituted with halogen, phenoxy group, benzyloxy group, or pyridylmethoxy group.

$R^h$ and $R^j$ are preferably halogen, hydroxyl group, C1-C6 alkyl group optionally substituted with halogen or hydroxyl group, C1-C6 alkoxy group optionally substituted with halogen, C1-C4 alkoxy C1-C4 alkyl group optionally substituted with halogen, or cyano group.

$R^4$ is preferably hydrogen atom, halogen or C1-C4 alkyl group, and more preferably hydrogen atom.

$R^5$ is preferably hydrogen atom.

In the compounds of the present invention, the following group of compounds is preferable.

That is, it is a group of compounds,
wherein,
X is sulfur atom or oxygen atom,
Z is Z1,
A is C6-C12 aryl group,
n is 1,
$R^a$ is halogen, hydroxyl group, C1-C6 alkyl group (optionally substituted with halogen, hydroxyl group, phenoxy group or benzyloxy group), C3-C8 cycloalkyl group optionally substituted with halogen, C1-C6 alkoxy group (optionally substituted with halogen, hydroxyl group, carboxyl group, carbamoyl group optionally substituted with C1-C4 alkyl group, C1-C4 alkoxy group or benzyloxy group), C3-C8 cycloalkoxy group optionally substituted with halogen, C1-C4 alkoxy C1-C4 alkyl group (optionally substituted with halogen, hydroxyl group, cyano group, C1-C4 alkoxy group or benzyloxy group), phenoxy group, benzyloxy group, cyano group, nitro group, carboxyl group, C1-C6 acyl group, C1-C4 alkoxycarbonyl group, amino group, C1-C6 monoalkylamino group, C1-C6 dialkylamino group, carbamoyl group optionally substituted with C1-C4 alkyl group, C6-C12 aryl group (optionally substituted with halogen, cyano group, C1-C4 alkyl group optionally substituted with halogen, or hydroxyl group), 3-12 membered heterocyclic group optionally substituted with halogen, sulfanyl group optionally substituted with C1-C6 alkyl group optionally substituted with halogen, C1-C6 alkylsulfinyl group optionally substituted with halogen, C1-C6 alkylsulfonyl group optionally substituted with halogen, or pentafluorosulfanyl group, $R^1$ is C1-C9 alkyl group (optionally substituted with halogen, hydroxyl group, cyano group, carboxyl group, C1-C4 alkoxycarbonyl group, amino group, C1-C6 monoalkylamino group, C1-C6 dialkylamino group or C1-C6 alkylsulfonyl group), or C1-C6 alkoxy C1-C6 alkyl group (optionally substituted with halogen, hydroxyl group, cyano group or C1-C4 alkoxy group), $R^2$ is hydrogen atom, halogen, C1-C6 alkyl group (optionally substituted with halogen, hydroxyl group or cyano group), or C3-C8 cycloalkyl group optionally substituted with halogen, $R^3$ is hydrogen atom, halogen, C1-C12 alkyl group (optionally substituted with halogen, hydroxyl group, cyano group, carboxyl group, C3-C8 cycloalkyl group optionally substituted with halogen or hydroxyl group, C3-C8 cycloalkoxy group optionally substituted with halogen or hydroxyl group, C1-C4 alkoxy group optionally substituted with phenyl group, C1-C4 alkoxycarbonyl group, amino group, C1-C6 monoalkylamino group, C1-C6 dialkylamino group, C1-C6 alkylsulfonyl group, phenoxy group or silyl group substituted with C1-C4 alkyl group or phenyl group), C3-C8 cycloalkyl group (optionally substituted with halogen, hydroxyl group, cyano group, carboxyl group, C1-C4 alkyl group optionally substituted with halogen or hydroxyl group, C1-C4 alkoxy group optionally substituted with halogen or hydroxyl group, C1-C4 alkoxycarbonyl group, amino group, C1-C6 monoalkylamino group, C1-C6 dialkylamino group or C1-C6 alkylsulfonyl group), C1-C6 alkoxy C1-C6 alkyl group (optionally substituted with halogen, hydroxyl group, cyano group or C1-C4 alkoxy group), C2-C9 alkenyl group (optionally substituted with halogen, hydroxyl group or cyano group), C2-C9 alkynyl group optionally substituted with halogen or cyano group, C3-C8 cycloalkenyl group (optionally substituted with halogen, hydroxyl group or cyano group), C6-C12 aryl group optionally substituted with 1 to 5 moieties of $R^g$, C6-C12 aryl C1-C6 alkyl group optionally substituted with 1 to 5 moieties of $R^h$, 3-12 membered heterocyclic group optionally substituted with 1 to 5 moieties of $R^i$, 3-12 membered heterocyclic C1-C6 alkyl group optionally substituted with 1 to 5 moieties of $R^j$, C1-C9 acyl group (optionally substituted with halogen, hydroxyl group or cyano group), C3-C8 cycloalkylcarbonyl group, benzoyl group, C5-C12 spiroalkyl group, adamantyl group, silyl group substituted with 1 to 3 moieties of C1-C4 alkyl group or phenyl group, or $R^{30}$, $R^4$ and $R^5$ are hydrogen atoms, $R^g$, $R^h$, $R^i$ and $R^j$ are halogen, hydroxyl group, amino group, C1-C6 monoalkylamino group, C1-C6 dialkylamino group, acetamido group, C1-C6 alkyl group (optionally substituted with halogen, hydroxyl group, phenoxy group or benzyloxy group), C3-C8 cycloalkyl group, C2-C6 alkenyl group (optionally substituted with halogen, hydroxyl group or cyano group), C2-C6 alkynyl group optionally substituted with halogen or cyano group, C1-C6 alkoxy group (optionally substituted with halogen, hydroxyl group, C1-C4 alkoxy group, amino group, C1-C6 monoalkylamino group, C1-C6 dialkylamino group, C6-C10 aryl group, or 3-10 membered heterocyclic group optionally substituted with oxo group), C1-C6 alkoxy C1-C6 alkyl group (optionally substituted with halogen, phenyl group, phenoxy group or benzyloxy group), C3-C8 cycloalkoxy group, cyano group, nitro group, oxo group, carboxyl group, sulfanyl group, C1-C6 alkylsulfanyl group optionally substituted with halogen, C1-C6 alkylsulfinyl group optionally substituted with halogen, phenylsulfonyl group optionally substituted with C1-C4 alkyl group, C1-C6 alkylsulfonyl group optionally substituted with halogen, C1-C6 acyl group, C1-C4 alkoxycarbonyl group, phenyl group (optionally substituted with halogen, cyano group, trifluoromethyl group or hydroxyl group), 3-12 membered heterocyclic group optionally substituted with halogen or oxo group, phenoxy group, C6-C12 aryl C1-C6 alkoxy group, 3-12 membered heterocyclic C1-C6 alkoxy group, or group represented by the formula $R^{30}$—CH$_2$—O—.

The compound of the present invention has an excellent activity regulating effect on an androgen receptor. The specific examples of the compounds of the present invention are shown as follows.

TABLE 1
| Compound number | Structure |
|---|---|
| 1-5 | 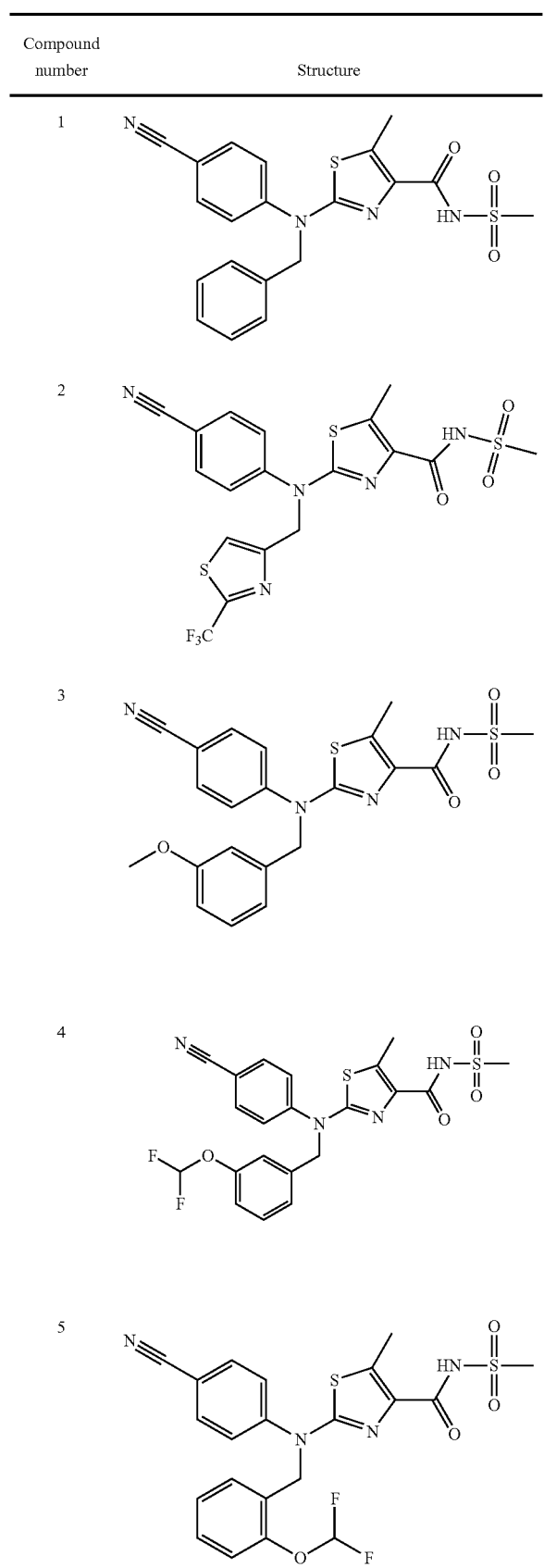 |
| 6-10 | 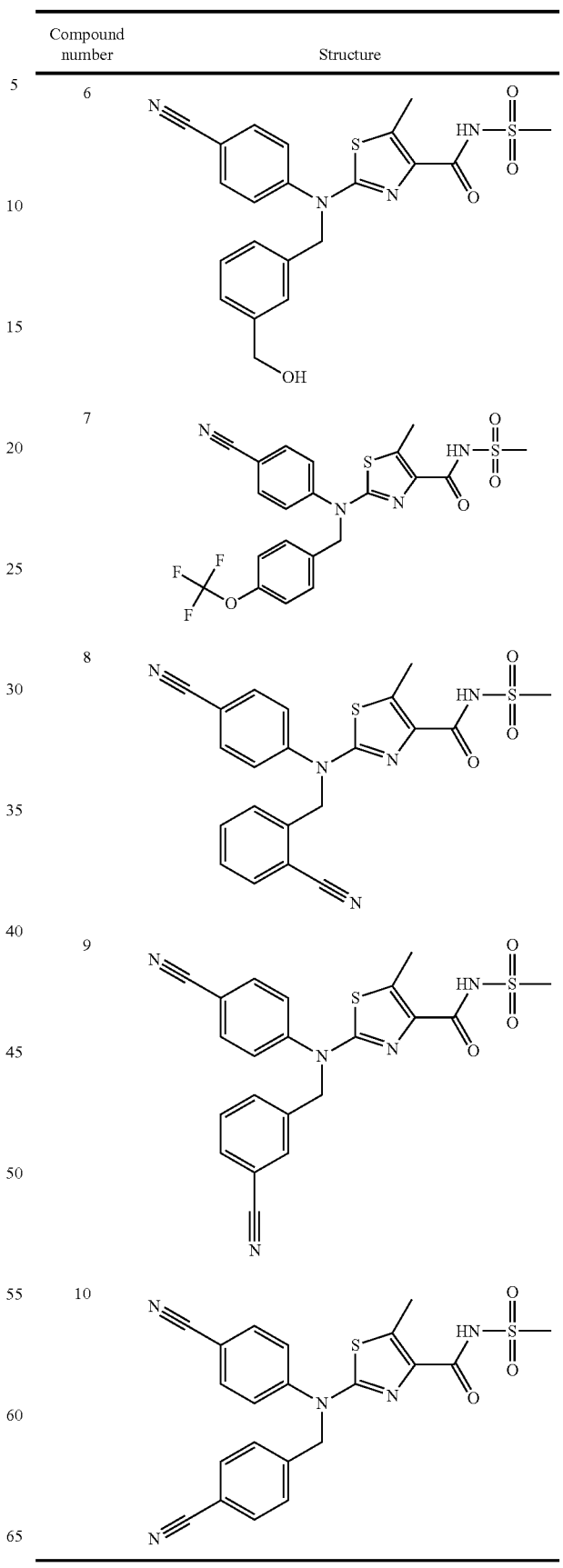 |
TABLE 1-continued

TABLE 2

| Compound number | Structure |
|---|---|
| 11 | 4-cyanophenyl-N-(4-(methylthio)benzyl)-2-amino-5-methylthiazole-4-carboxylic acid methanesulfonamide |
| 12 | 4-cyanophenyl-N-(4-(methylsulfonyl)benzyl)-2-amino-5-methylthiazole-4-carboxylic acid methanesulfonamide |
| 13 | 4-cyanophenyl-N-(2-fluorobenzyl)-2-amino-5-methylthiazole-4-carboxylic acid methanesulfonamide |
| 14 | 4-cyanophenyl-N-(3-fluorobenzyl)-2-amino-5-methylthiazole-4-carboxylic acid methanesulfonamide |
| 15 | 4-cyanophenyl-N-(4-fluorobenzyl)-2-amino-5-methylthiazole-4-carboxylic acid methanesulfonamide |
| 16 | 4-cyanophenyl-N-(3-methylbenzyl)-2-amino-5-methylthiazole-4-carboxylic acid methanesulfonamide |
| 17 | 4-cyanophenyl-N-(4-methylbenzyl)-2-amino-5-methylthiazole-4-carboxylic acid methanesulfonamide |
| 18 | 4-cyanophenyl-N-(3-chlorobenzyl)-2-amino-5-methylthiazole-4-carboxylic acid methanesulfonamide |
| 19 | 4-cyanophenyl-N-(cyclopentylmethyl)-2-amino-5-methylthiazole-4-carboxylic acid methanesulfonamide |
| 20 | 4-cyanophenyl-N-(2-phenoxyethyl)-2-amino-5-methylthiazole-4-carboxylic acid methanesulfonamide |

TABLE 3

| Compound number | Structure |
|---|---|
| 21 | (4-methoxyphenyl)(benzyl)amino-5-methylthiazole-4-carboxylic acid methanesulfonamide |
| 22 | (4-(2-methoxyethoxy)phenyl)(benzyl)amino-5-methylthiazole-4-carboxylic acid methanesulfonamide |
| 23 | (4-cyanophenyl)(4-chlorobenzyl)amino-5-methylthiazole-4-carboxylic acid methanesulfonamide |
| 24 | (4-cyanophenyl)(3-trifluoromethylbenzyl)amino-5-methylthiazole-4-carboxylic acid methanesulfonamide |
| 25 | (4-cyanophenyl)(naphthalen-2-ylmethyl)amino-5-methylthiazole-4-carboxylic acid methanesulfonamide |
| 26 | (4-cyanophenyl)(benzofuran-5-ylmethyl)amino-5-methylthiazole-4-carboxylic acid methanesulfonamide |

TABLE 3-continued

| Compound number | Structure |
|---|---|
| 27 | (2-(trifluoromethoxy)phenyl)(benzyl)amino-5-methylthiazole-4-carboxylic acid methanesulfonamide |
| 28 | (4-fluorophenyl)(benzyl)amino-5-methylthiazole-4-carboxylic acid methanesulfonamide |
| 29 | (3-fluorophenyl)(benzyl)amino-5-methylthiazole-4-carboxylic acid methanesulfonamide |
| 30 | (2-fluorophenyl)(benzyl)amino-5-methylthiazole-4-carboxylic acid methanesulfonamide |
| 31 | (4-chlorophenyl)(benzyl)amino-5-methylthiazole-4-carboxylic acid methanesulfonamide |

TABLE 3-continued

| Compound number | Structure |
|---|---|
| 32 | *N-benzyl-N-(3-chlorophenyl) substituted 5-methylthiazole-4-carboxamide methanesulfonamide* |

TABLE 4

| Compound number | Structure |
|---|---|
| 33 | *N-benzyl-N-(2-chlorophenyl) substituted 5-methylthiazole-4-carboxamide methanesulfonamide* |
| 34 | *N-benzyl-N-(4-(trifluoromethoxy)phenyl) substituted 5-methylthiazole-4-carboxamide methanesulfonamide* |
| 35 | *N-benzyl-N-(3-(trifluoromethoxy)phenyl) substituted 5-methylthiazole-4-carboxamide methanesulfonamide* |
| 36 | *N-benzyl-N-(2,4-difluorophenyl) substituted 5-methylthiazole-4-carboxamide methanesulfonamide* |
| 37 | *N-benzyl-N-(3,4-dichlorophenyl) substituted 5-methylthiazole-4-carboxamide methanesulfonamide* |
| 38 | *N-benzyl-N-(4-(benzyloxy)phenyl) substituted 5-methylthiazole-4-carboxamide methanesulfonamide* |
| 39 | *N-((4,4-difluorocyclohexyl)methyl)-N-(4-cyanophenyl) substituted 5-methylthiazole-4-carboxamide methanesulfonamide* |
| 40 | *N-(4-cyanophenyl)-N-((2-methylthiazol-4-yl)methyl) substituted 5-methylthiazole-4-carboxamide methanesulfonamide* |
| 41 | *N-(4-cyanophenyl)-N-(4-(difluoromethoxy)benzyl) substituted 5-methylthiazole-4-carboxamide methanesulfonamide* |

TABLE 4-continued

| Compound number | Structure |
| --- | --- |
| 42 | (4-cyanophenyl)(pyridin-2-ylmethyl)amino-5-methylthiazole-4-carboxylic acid methanesulfonamide |
| 43 | (4-cyanophenyl)(pyridin-3-ylmethyl)amino-5-methylthiazole-4-carboxylic acid methanesulfonamide |
| 44 | (4-cyanophenyl)(pyridin-4-ylmethyl)amino-5-methylthiazole-4-carboxylic acid methanesulfonamide |

TABLE 5

| Compound number | Structure |
| --- | --- |
| 45 | (4-cyanophenyl)(2-methylbenzyl)amino-5-methylthiazole-4-carboxylic acid methanesulfonamide |
| 46 | (4-cyanophenyl)(4-(trifluoromethyl)benzyl)amino-5-methylthiazole-4-carboxylic acid methanesulfonamide |

TABLE 5-continued

| Compound number | Structure |
| --- | --- |
| 47 | benzyl(2-methoxyphenyl)amino-5-methylthiazole-4-carboxylic acid methanesulfonamide |
| 48 | benzyl(3,4-difluorophenyl)amino-5-methylthiazole-4-carboxylic acid methanesulfonamide |
| 49 | benzyl(pyridin-3-yl)amino-5-methylthiazole-4-carboxylic acid methanesulfonamide |
| 50 | (benzo[d]thiazol-6-ylmethyl)(4-cyanophenyl)amino-5-methylthiazole-4-carboxylic acid methanesulfonamide |
| 51 | (benzo[b]thiophen-2-ylmethyl)(4-cyanophenyl)amino-5-methylthiazole-4-carboxylic acid methanesulfonamide |

TABLE 5-continued

| Compound number | Structure |
|---|---|
| 52 | (structure) |
| 53 | (structure) |
| 54 | (structure) |

TABLE 6

| Compound number | Structure |
|---|---|
| 55 | (structure) |
| 56 | (structure) |
| 57 | (structure) |
| 58 | (structure) |
| 59 | (structure) |
| 60 | (structure) |
| 61 | (structure) |

TABLE 6-continued
| Compound number | Structure |
|---|---|
| 62 | 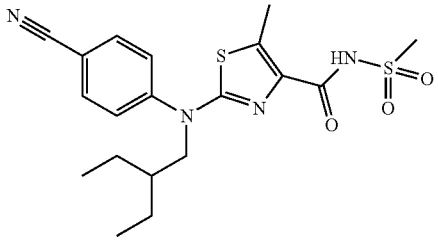 |
| 63 | 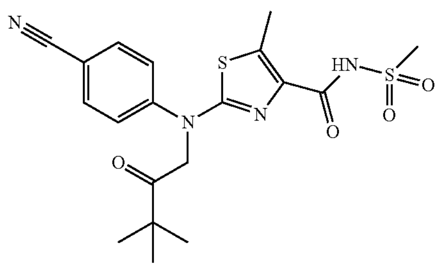 [SMILES: Cc1sc(N(CC(=O)C(C)(C)C)c2ccc(C#N)cc2)nc1C(=O)NS(C)(=O)=O] |
| 64 | 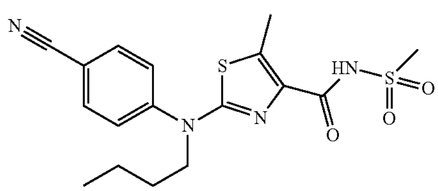 [SMILES: CCCCN(c1ccc(C#N)cc1)c1nc(C(=O)NS(C)(=O)=O)c(C)s1] |
TABLE 7
| Compound number | Structure |
|---|---|
| 65 | 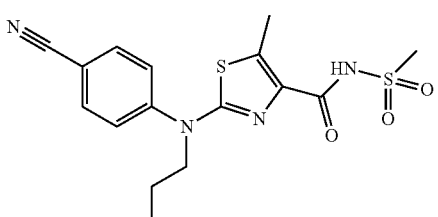 |
| 66 | 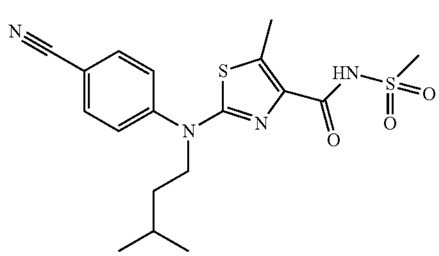 [SMILES: Cc1sc(N(CCC(C)C)c2ccc(C#N)cc2)nc1C(=O)NS(C)(=O)=O] |
TABLE 7-continued
| Compound number | Structure |
|---|---|
| 67 | 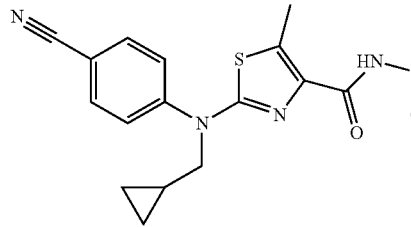 |
| 68 | 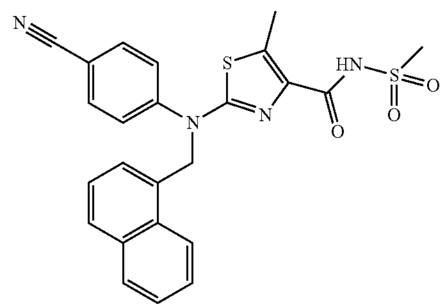 [SMILES: Cc1sc(N(Cc2cccc3ccccc23)c2ccc(C#N)cc2)nc1C(=O)NS(C)(=O)=O] |
| 69 | 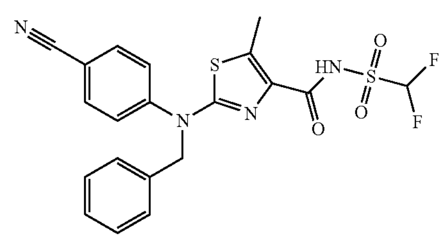 [SMILES: Cc1sc(N(Cc2ccccc2)c2ccc(C#N)cc2)nc1C(=O)NS(=O)(=O)C(F)F] |
| 70 | 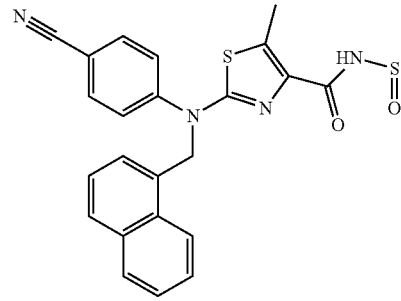 |
| 71 | 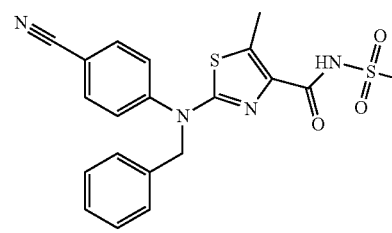 |

TABLE 7-continued
| Compound number | Structure |
|---|---|
| 72 | 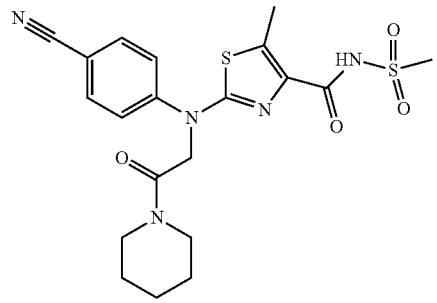 [SMILES: Cc1sc(N(CC(=O)N2CCCCC2)c2ccc(C#N)cc2)nc1C(=O)NS(C)(=O)=O] |
| 73 | 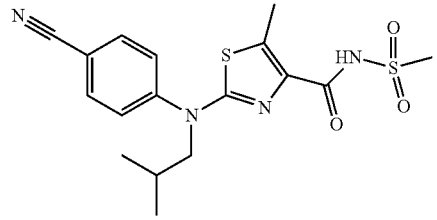 [SMILES: Cc1sc(N(CC(C)C)c2ccc(C#N)cc2)nc1C(=O)NS(C)(=O)=O] |
| 74 | 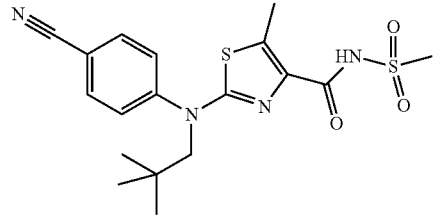 [SMILES: Cc1sc(N(CC(C)(C)C)c2ccc(C#N)cc2)nc1C(=O)NS(C)(=O)=O] |
| 75 | 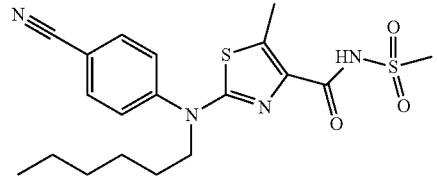 [SMILES: CCCCCCN(c1ccc(C#N)cc1)c1nc(C(=O)NS(C)(=O)=O)c(C)s1] |
| 76 | 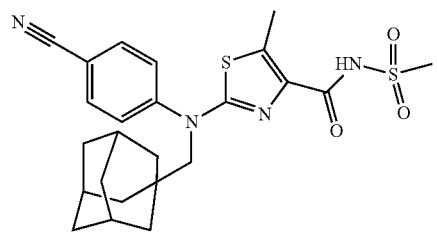 [SMILES: Cc1sc(N(CC23CC4CC(CC(C4)C2)C3)c2ccc(C#N)cc2)nc1C(=O)NS(C)(=O)=O] |
TABLE 8
| Compound number | Structure |
|---|---|
| 77 | 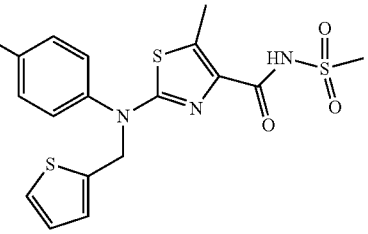 |
| 78 | 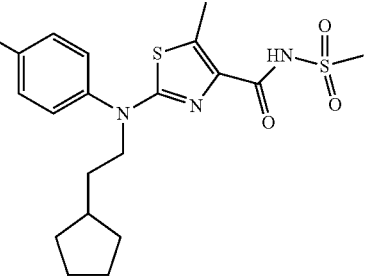 |
| 79 | 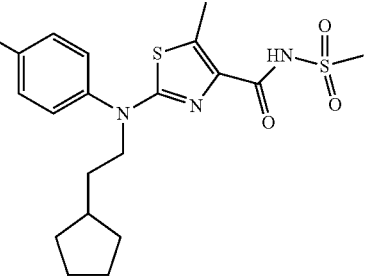 |
| 80 | 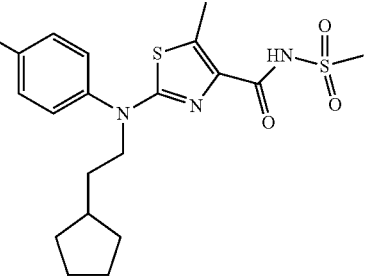 |
| 81 | 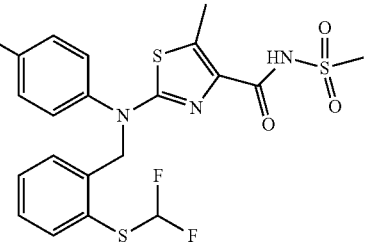 |

TABLE 8-continued

| Compound number | Structure |
|---|---|
| 82 | 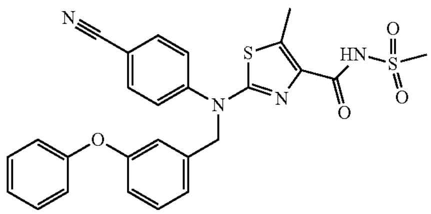 [SMILES: Cc1sc(N(Cc2cccc(Oc3ccccc3)c2)c2ccc(C#N)cc2)nc1C(=O)NS(C)(=O)=O] |
| 83 | 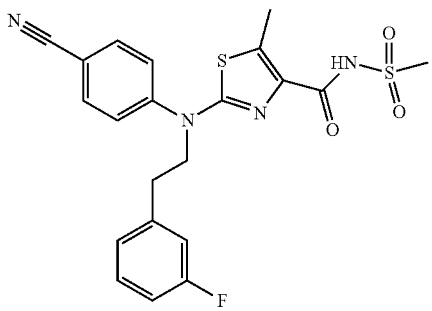 [SMILES: Cc1sc(N(CCc2cccc(F)c2)c2ccc(C#N)cc2)nc1C(=O)NS(C)(=O)=O] |
| 84 | 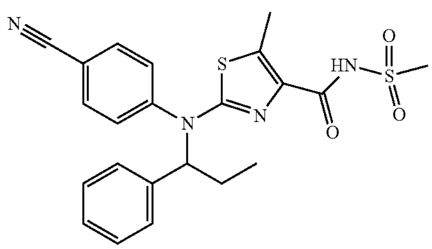 [SMILES: CCC(c1ccccc1)N(c1ccc(C#N)cc1)c1nc(C(=O)NS(C)(=O)=O)c(C)s1] |
| 85 | 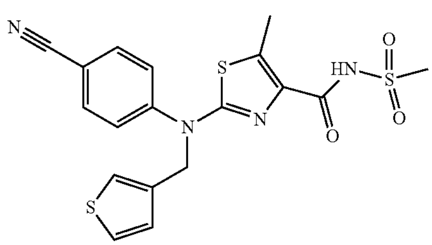 [SMILES: Cc1sc(N(Cc2ccsc2)c2ccc(C#N)cc2)nc1C(=O)NS(C)(=O)=O] |
| 86 | 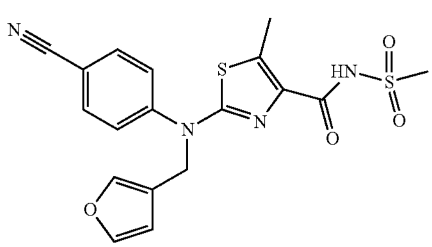 [SMILES: Cc1sc(N(Cc2ccoc2)c2ccc(C#N)cc2)nc1C(=O)NS(C)(=O)=O] |

TABLE 9

| Compound number | Structure |
|---|---|
| 87 | 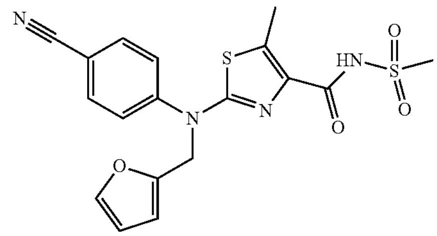 [SMILES: Cc1sc(N(Cc2ccco2)c2ccc(C#N)cc2)nc1C(=O)NS(C)(=O)=O] |
| 88 | 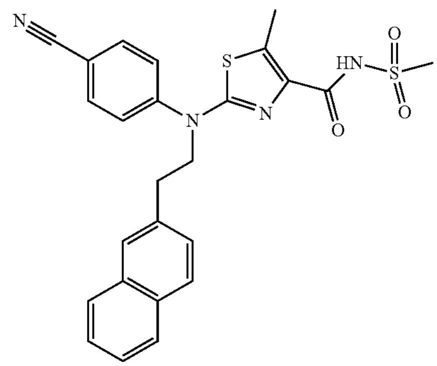 [SMILES: Cc1sc(N(CCc2ccc3ccccc3c2)c2ccc(C#N)cc2)nc1C(=O)NS(C)(=O)=O] |
| 89 | 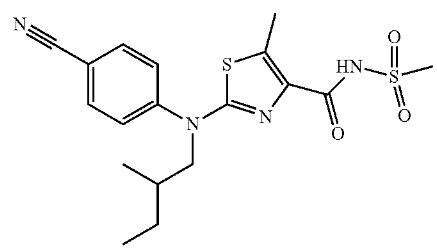 [SMILES: CCC(C)CN(c1ccc(C#N)cc1)c1nc(C(=O)NS(C)(=O)=O)c(C)s1] |
| 90 | 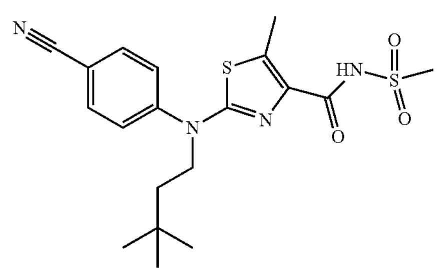 [SMILES: Cc1sc(N(CCC(C)(C)C)c2ccc(C#N)cc2)nc1C(=O)NS(C)(=O)=O] |
| 91 | 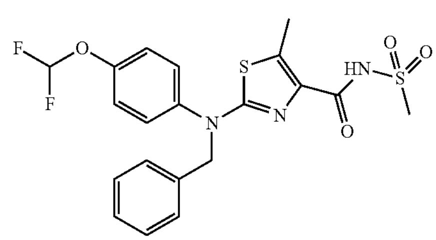 [SMILES: Cc1sc(N(Cc2ccccc2)c2ccc(OC(F)F)cc2)nc1C(=O)NS(C)(=O)=O] |

TABLE 9-continued

| Compound number | Structure |
|---|---|
| 92 | 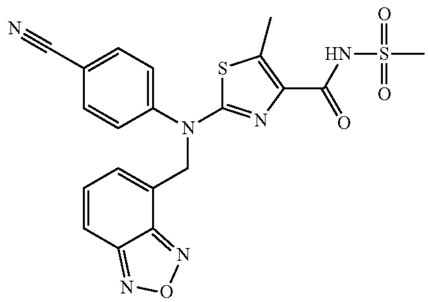 [SMILES: Cc1sc(N(Cc2cccc3nonc23)c2ccc(C#N)cc2)nc1C(=O)NS(C)(=O)=O] |
| 93 | 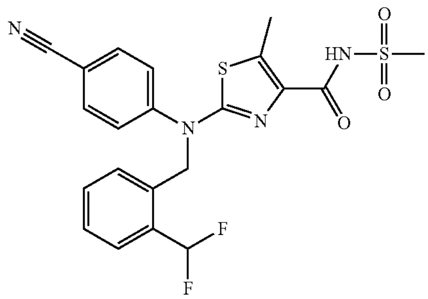 [SMILES: Cc1sc(N(Cc2ccccc2C(F)F)c2ccc(C#N)cc2)nc1C(=O)NS(C)(=O)=O] |
| 94 | 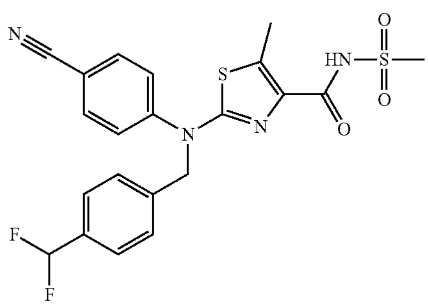 [SMILES: Cc1sc(N(Cc2ccc(C(F)F)cc2)c2ccc(C#N)cc2)nc1C(=O)NS(C)(=O)=O] |
| 95 | 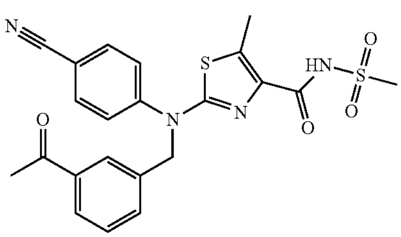 [SMILES: CC(=O)c1cccc(CN(c2ccc(C#N)cc2)c2nc(C(=O)NS(C)(=O)=O)c(C)s2)c1] |
| 96 | 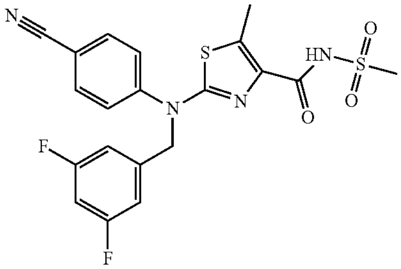 [SMILES: Cc1sc(N(Cc2cc(F)cc(F)c2)c2ccc(C#N)cc2)nc1C(=O)NS(C)(=O)=O] |

TABLE 10

| Compound number | Structure |
|---|---|
| 97 | 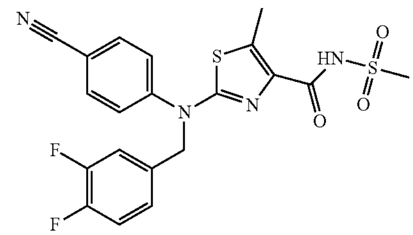 |
| 98 | 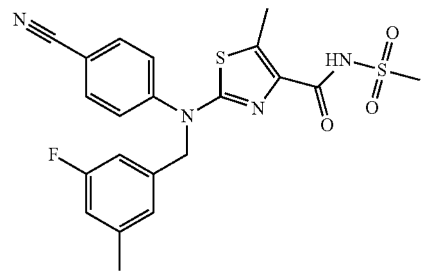 [SMILES: Cc1cc(F)cc(CN(c2ccc(C#N)cc2)c2nc(C(=O)NS(C)(=O)=O)c(C)s2)c1] |
| 99 | 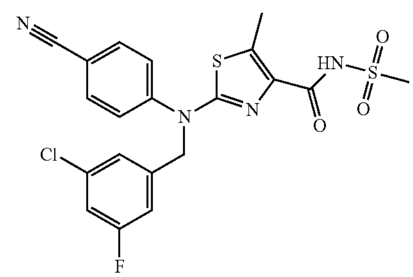 [SMILES: Cc1sc(N(Cc2cc(F)cc(Cl)c2)c2ccc(C#N)cc2)nc1C(=O)NS(C)(=O)=O] |
| 100 | 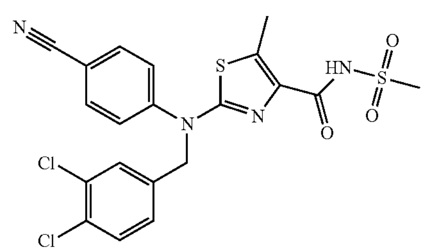 [SMILES: Cc1sc(N(Cc2ccc(Cl)c(Cl)c2)c2ccc(C#N)cc2)nc1C(=O)NS(C)(=O)=O] |
| 101 | 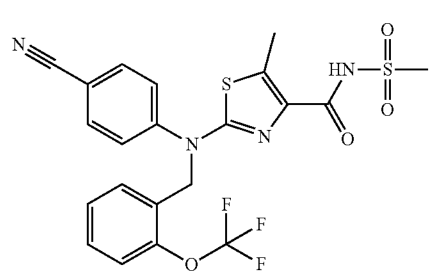 [SMILES: Cc1sc(N(Cc2ccccc2OC(F)(F)F)c2ccc(C#N)cc2)nc1C(=O)NS(C)(=O)=O] |

TABLE 10-continued

| Compound number | Structure |
|---|---|
| 102 | 4-cyanophenyl-N-(2,3-difluorobenzyl)-2-amino-5-methylthiazole-4-carboxylic acid methanesulfonamide |
| 103 | 4-cyanophenyl-N-(2,5-difluorobenzyl)-2-amino-5-methylthiazole-4-carboxylic acid methanesulfonamide |
| 104 | 4-cyanophenyl-N-(2,4-difluorobenzyl)-2-amino-5-methylthiazole-4-carboxylic acid methanesulfonamide |
| 105 | 4-cyanophenyl-N-(5-fluoro-2-methoxybenzyl)-2-amino-5-methylthiazole-4-carboxylic acid methanesulfonamide |
| 106 | 4-cyanophenyl-N-(2-chloro-4-fluorobenzyl)-2-amino-5-methylthiazole-4-carboxylic acid methanesulfonamide |

TABLE 11

| Compound number | Structure |
|---|---|
| 107 | 4-cyanophenyl-N-(3-chloro-2-fluorobenzyl)-2-amino-5-methylthiazole-4-carboxylic acid methanesulfonamide |
| 108 | 4-cyanophenyl-N-(2-chloro-5-fluorobenzyl)-2-amino-5-methylthiazole-4-carboxylic acid methanesulfonamide |
| 109 | 4-cyanophenyl-N-(2,3,5-trifluorobenzyl)-2-amino-5-methylthiazole-4-carboxylic acid methanesulfonamide |
| 110 | 4-cyanophenyl-N-(2,4,5-trifluorobenzyl)-2-amino-5-methylthiazole-4-carboxylic acid methanesulfonamide |
| 111 | 4-cyanophenyl-N-(2,4-difluoro-3-methoxybenzyl)-2-amino-5-methylthiazole-4-carboxylic acid methanesulfonamide |

TABLE 11-continued
| Compound number | Structure |
|---|---|
| 112 | 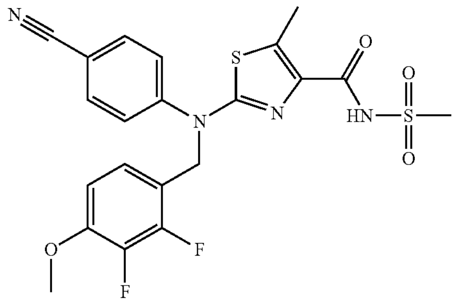 [SMILES: COc1ccc(CN(c2ccc(C#N)cc2)c2nc(C(=O)NS(C)(=O)=O)c(C)s2)c(F)c1F] |
| 113 | 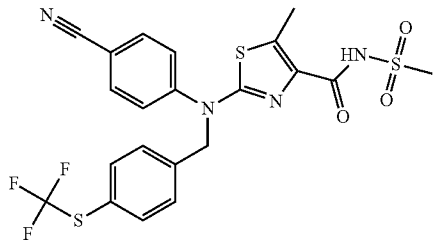 [SMILES: Cc1sc(N(Cc2ccc(SC(F)(F)F)cc2)c2ccc(C#N)cc2)nc1C(=O)NS(C)(=O)=O] |
| 114 | 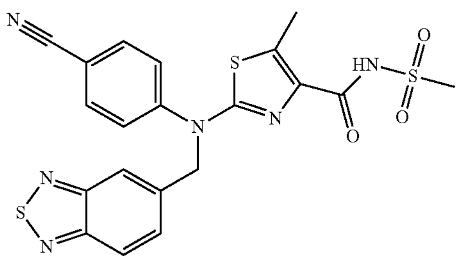 [SMILES: Cc1sc(N(Cc2ccc3nsnc3c2)c2ccc(C#N)cc2)nc1C(=O)NS(C)(=O)=O] |
| 115 | 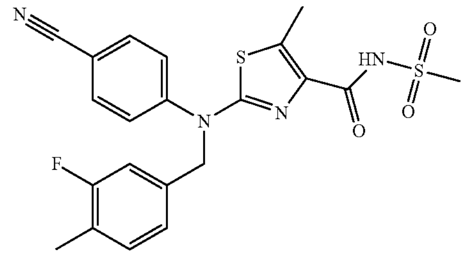 [SMILES: Cc1ccc(CN(c2ccc(C#N)cc2)c2nc(C(=O)NS(C)(=O)=O)c(C)s2)cc1F] |
| 116 | 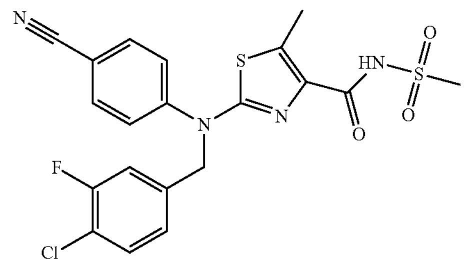 [SMILES: Cc1sc(N(Cc2ccc(Cl)c(F)c2)c2ccc(C#N)cc2)nc1C(=O)NS(C)(=O)=O] |
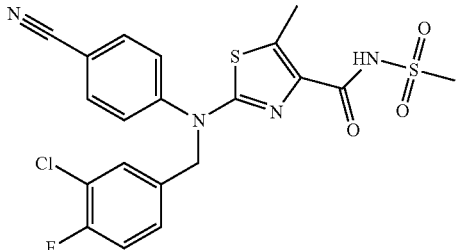
TABLE 12
| Compound number | Structure |
|---|---|
| 117 | 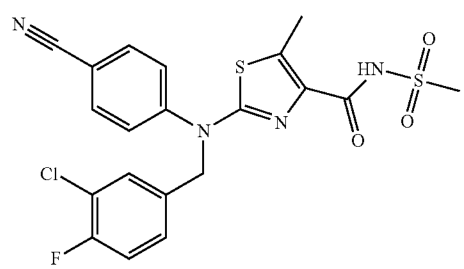 [SMILES: Cc1sc(N(Cc2ccc(F)c(Cl)c2)c2ccc(C#N)cc2)nc1C(=O)NS(C)(=O)=O] |
| 118 | 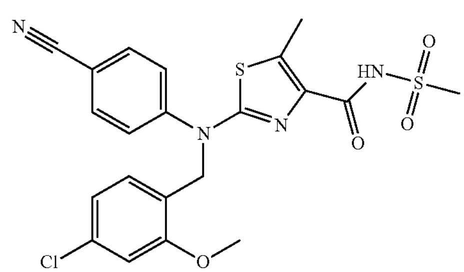 [SMILES: COc1cc(Cl)ccc1CN(c1ccc(C#N)cc1)c1nc(C(=O)NS(C)(=O)=O)c(C)s1] |
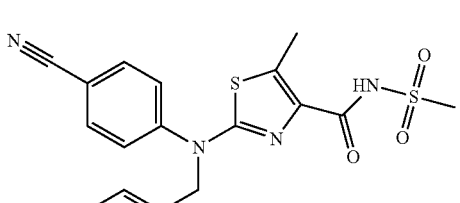

TABLE 12-continued

| Compound number | Structure |
|---|---|
| 119 | 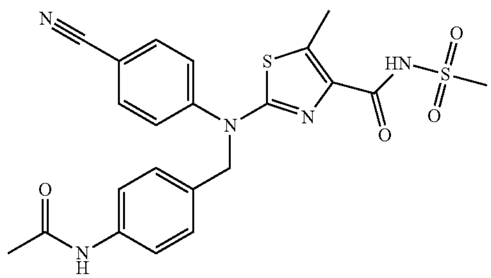 [SMILES: CC(=O)Nc1ccc(CN(c2ccc(C#N)cc2)c2nc(C(=O)NS(C)(=O)=O)c(C)s2)cc1] |
| 120 | 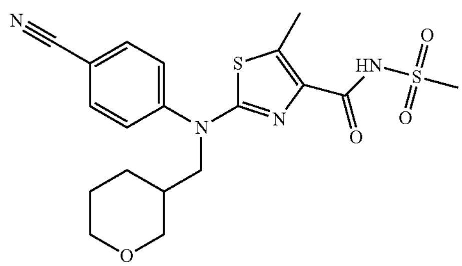 [SMILES: Cc1sc(N(CC2CCCOC2)c2ccc(C#N)cc2)nc1C(=O)NS(C)(=O)=O] |
| 121 | 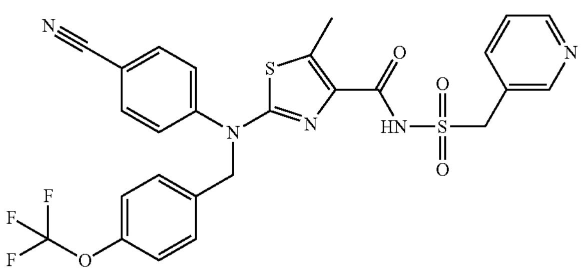 [SMILES: Cc1sc(N(Cc2ccc(OC(F)(F)F)cc2)c2ccc(C#N)cc2)nc1C(=O)NS(=O)(=O)Cc1cccnc1] |
| 122 | 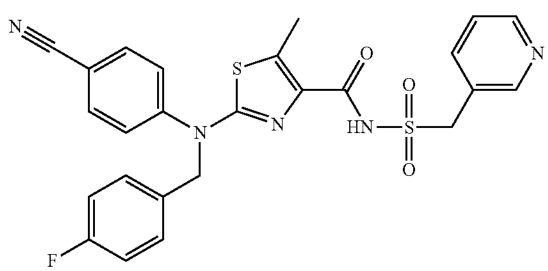 [SMILES: Cc1sc(N(Cc2ccc(F)cc2)c2ccc(C#N)cc2)nc1C(=O)NS(=O)(=O)Cc1cccnc1] |
| 123 | 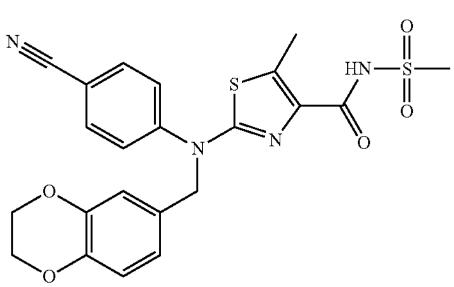 [SMILES: Cc1sc(N(Cc2ccc3c(c2)OCCO3)c2ccc(C#N)cc2)nc1C(=O)NS(C)(=O)=O] |

TABLE 12-continued

| Compound number | Structure |
|---|---|
| 124 | (chemical structure) |
| 125 | (chemical structure) |
| 126 | (chemical structure) |

TABLE 13

| Compound number | Structure |
|---|---|
| 127 | (chemical structure) |
| 128 | (chemical structure) |
| 129 | (chemical structure) |
| 130 | (chemical structure) |

TABLE 13-continued
| Compound number | Structure |
|---|---|
| 131 | 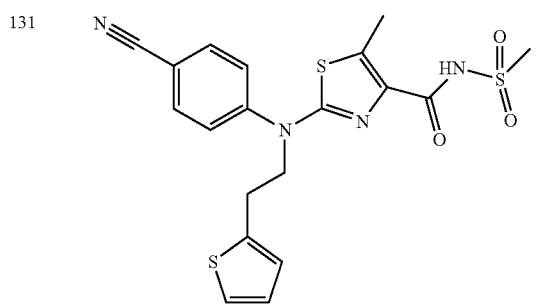 |
| 132 | 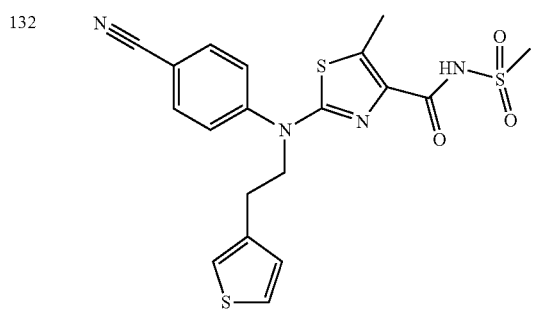 |
| 133 | 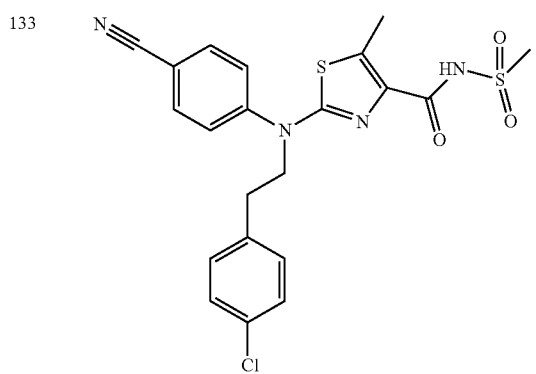 |
| 134 | 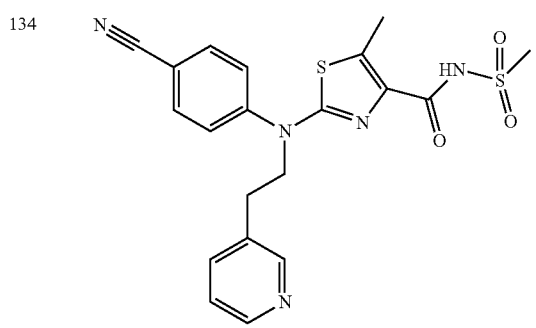 |
TABLE 13-continued
| Compound number | Structure |
|---|---|
| 135 | 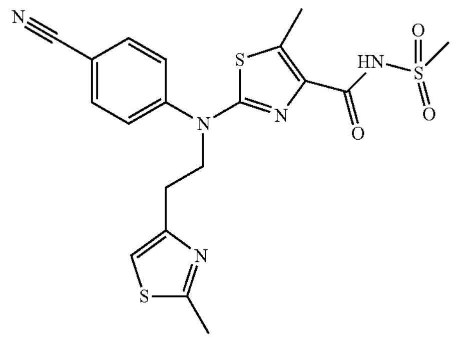 [SMILES: Cc1nc(CCN(c2ccc(C#N)cc2)c2nc(C(=O)NS(C)(=O)=O)c(C)s2)cs1] |
| 136 | 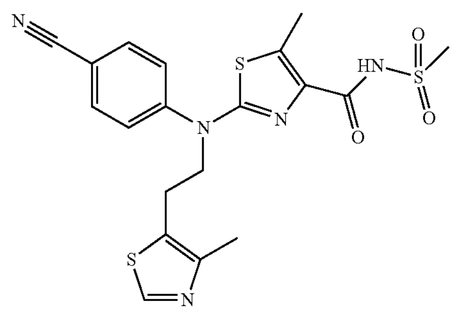 [SMILES: Cc1ncsc1CCN(c1ccc(C#N)cc1)c1nc(C(=O)NS(C)(=O)=O)c(C)s1] |
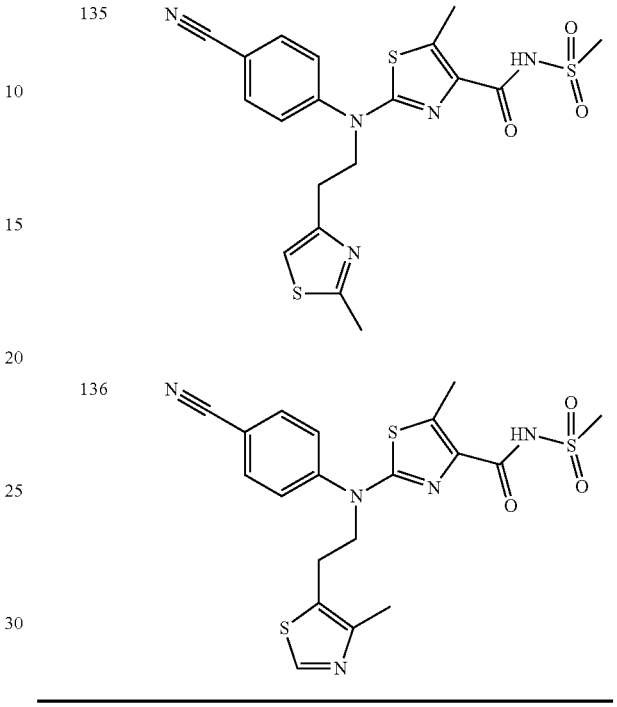
TABLE 14
| Compound number | Structure |
|---|---|
| 137 | 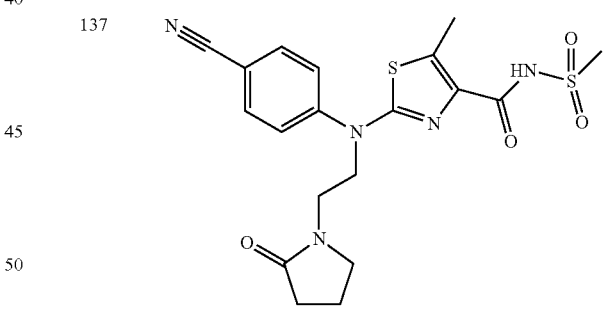 |
| 138 | 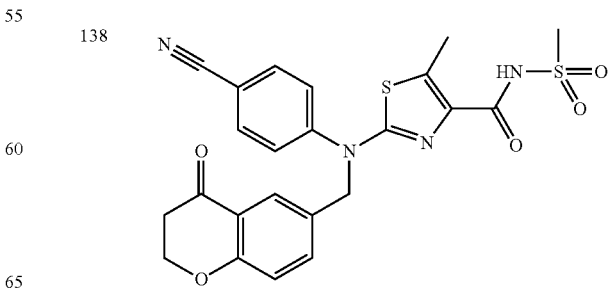 |

TABLE 14-continued

| Compound number | Structure |
|---|---|
| 139 | 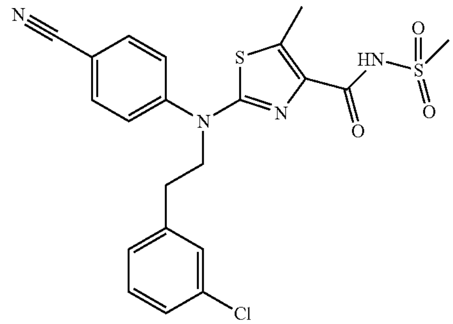 [SMILES: Cc1sc(N(CCc2cccc(Cl)c2)c2ccc(C#N)cc2)nc1C(=O)NS(C)(=O)=O] |
| 140 | 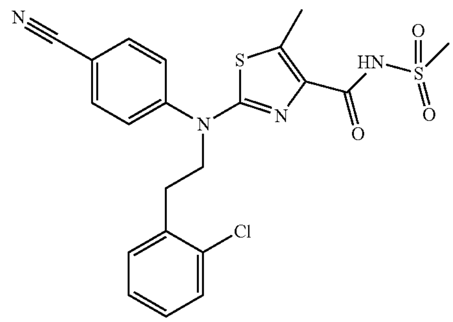 [SMILES: Cc1sc(N(CCc2ccccc2Cl)c2ccc(C#N)cc2)nc1C(=O)NS(C)(=O)=O] |
| 141 | 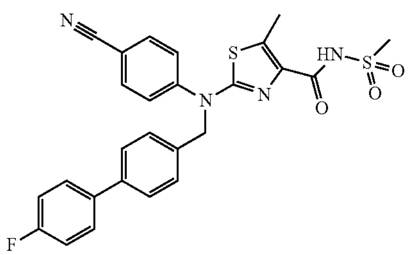 [SMILES: Cc1sc(N(Cc2ccc(-c3ccc(F)cc3)cc2)c2ccc(C#N)cc2)nc1C(=O)NS(C)(=O)=O] |
| 142 | 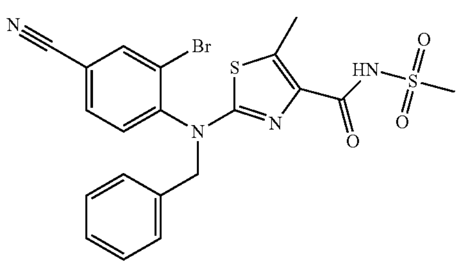 [SMILES: Cc1sc(N(Cc2ccccc2)c2ccc(C#N)cc2Br)nc1C(=O)NS(C)(=O)=O] |
| 143 | 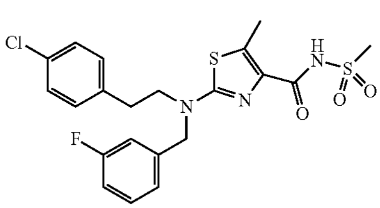 [SMILES: Cc1sc(N(CCc2ccc(Cl)cc2)Cc2cccc(F)c2)nc1C(=O)NS(C)(=O)=O] |
| 144 | 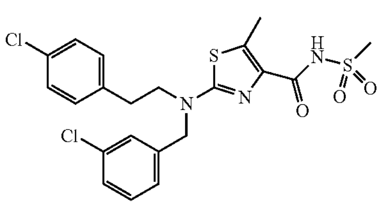 [SMILES: Cc1sc(N(CCc2ccc(Cl)cc2)Cc2cccc(Cl)c2)nc1C(=O)NS(C)(=O)=O] |
| 145 | |
| 146 | Racemate |

TABLE 15

| Compound number | Structure |
|---|---|
| 147 | 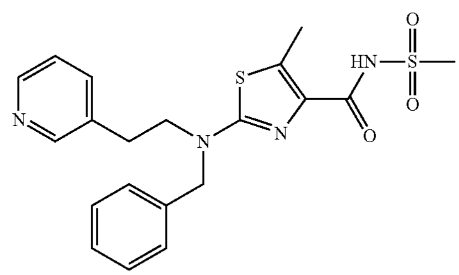 [SMILES: Cc1sc(N(CCc2cccnc2)Cc2ccccc2)nc1C(=O)NS(C)(=O)=O] |
| 148 | 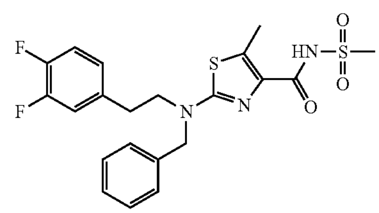 [SMILES: Cc1sc(N(CCc2ccc(F)c(F)c2)Cc2ccccc2)nc1C(=O)NS(C)(=O)=O] |
| 149 | Racemate |

TABLE 15-continued
| Compound number | Structure |
|---|---|
| 150 | 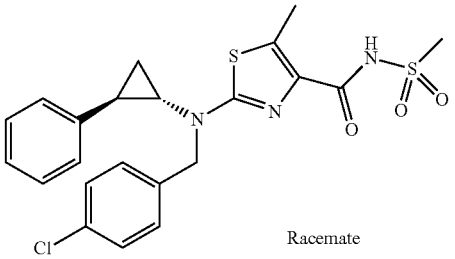 [SMILES: Cc1sc(N(Cc2ccc(Cl)cc2)[C@H]2C[C@@H]2c2ccccc2)nc1C(=O)NS(C)(=O)=O] Racemate |
| 151 | 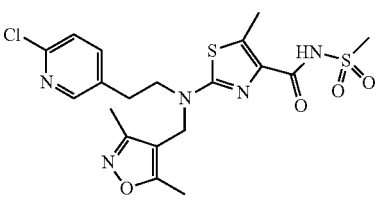 [SMILES: Cc1noc(C)c1CN(CCc1ccc(Cl)nc1)c1nc(C(=O)NS(C)(=O)=O)c(C)s1] |
| 152 | 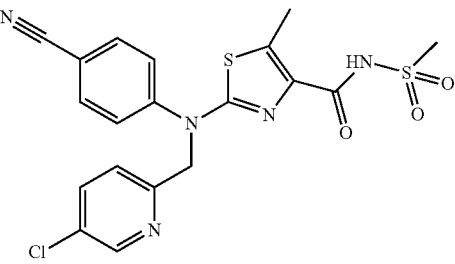 [SMILES: Cc1sc(N(Cc2ccc(Cl)cn2)c2ccc(C#N)cc2)nc1C(=O)NS(C)(=O)=O] |
| 153 | 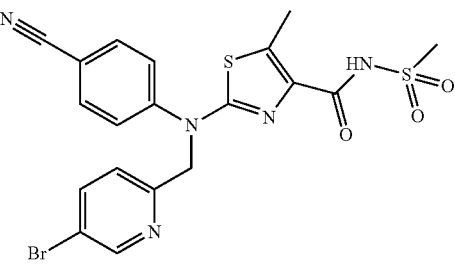 |
| 154 | 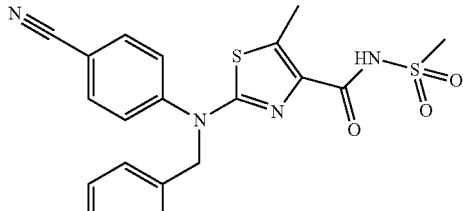 |
| 155 | 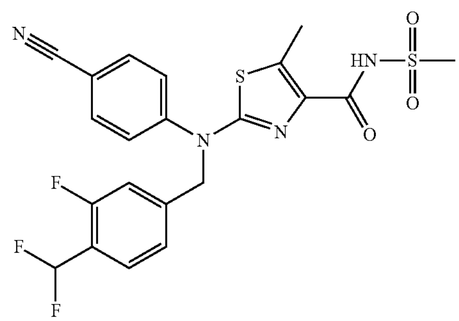 [SMILES: Cc1sc(N(Cc2ccc(C(F)F)c(F)c2)c2ccc(C#N)cc2)nc1C(=O)NS(C)(=O)=O] |
| 156 | 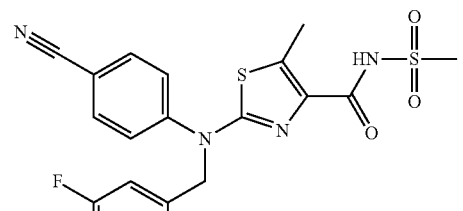 |
TABLE 16
| Compound number | Structure |
|---|---|
| 157 | 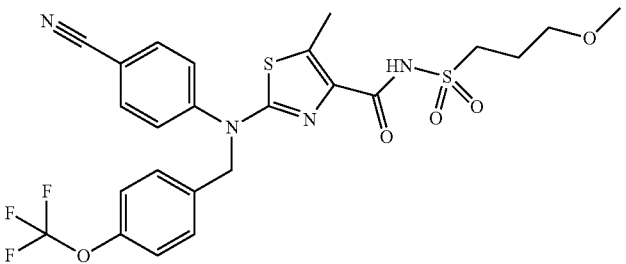 [SMILES: COCCCS(=O)(=O)NC(=O)c1nc(N(Cc2ccc(OC(F)(F)F)cc2)c2ccc(C#N)cc2)sc1C] |

TABLE 16-continued
| Compound number | Structure |
|---|---|
| 158 | 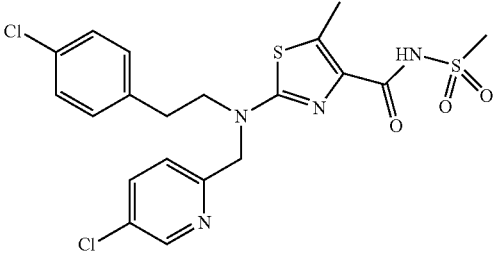 [SMILES: Cc1sc(N(CCc2ccc(Cl)cc2)Cc2ccc(Cl)cn2)nc1C(=O)NS(C)(=O)=O] |
| 159 | 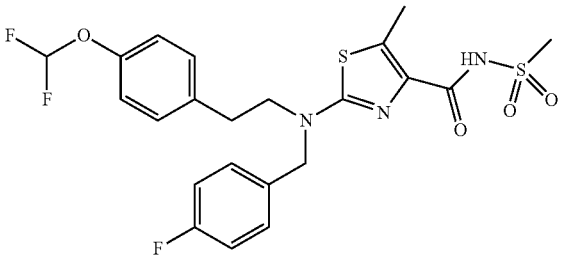 [SMILES: Cc1sc(N(CCc2ccc(OC(F)F)cc2)Cc2ccc(F)cc2)nc1C(=O)NS(C)(=O)=O] |
| 160 | 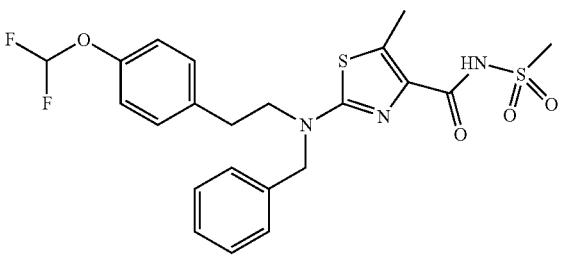 [SMILES: Cc1sc(N(CCc2ccc(OC(F)F)cc2)Cc2ccccc2)nc1C(=O)NS(C)(=O)=O] |
| 161 | 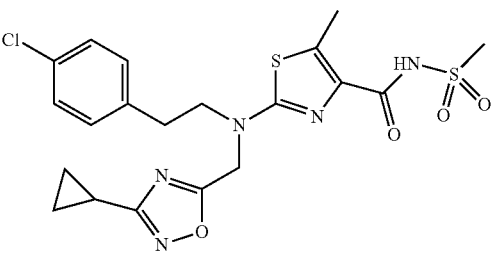 [SMILES: Cc1sc(N(CCc2ccc(Cl)cc2)Cc2nc(C3CC3)no2)nc1C(=O)NS(C)(=O)=O] |
| 162 | 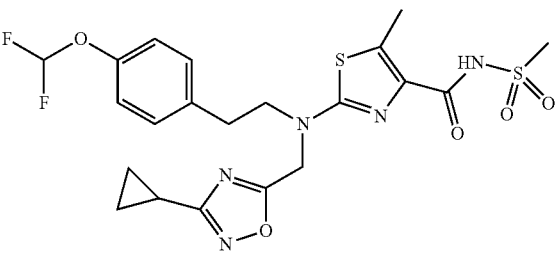 [SMILES: Cc1sc(N(CCc2ccc(OC(F)F)cc2)Cc2nc(C3CC3)no2)nc1C(=O)NS(C)(=O)=O] |
| 163 | 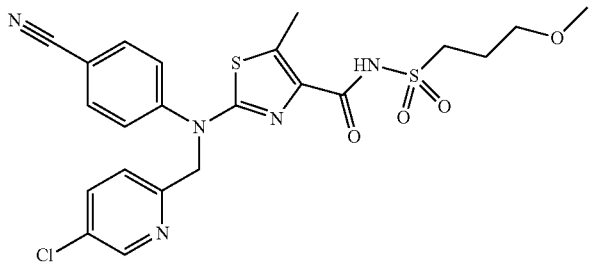 [SMILES: COCCCS(=O)(=O)NC(=O)c1nc(N(Cc2ccc(Cl)cn2)c2ccc(C#N)cc2)sc1C] |

TABLE 16-continued
| Compound number | Structure |
|---|---|
| 164 | 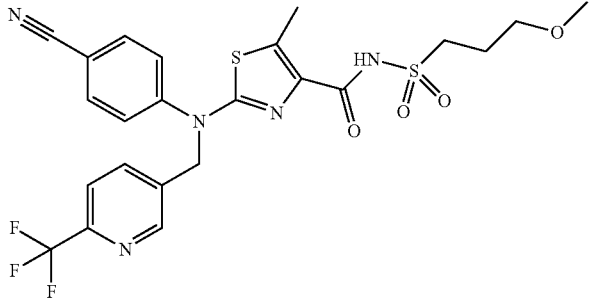 [SMILES: COCCCS(=O)(=O)NC(=O)c1nc(N(Cc2ccc(C(F)(F)F)nc2)c2ccc(C#N)cc2)sc1C] |
| 165 | 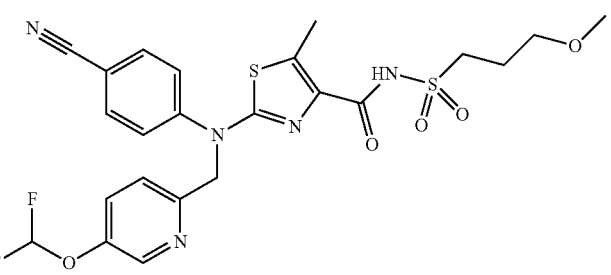 |
| 166 | 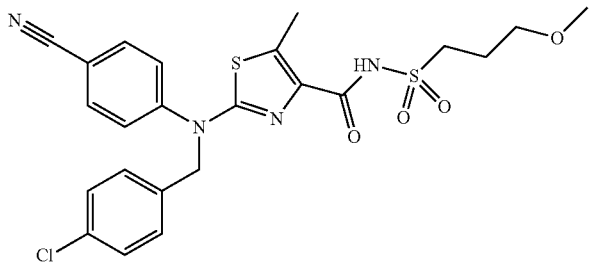 [SMILES: COCCCS(=O)(=O)NC(=O)c1nc(N(Cc2ccc(Cl)cc2)c2ccc(C#N)cc2)sc1C] |
| 167 | 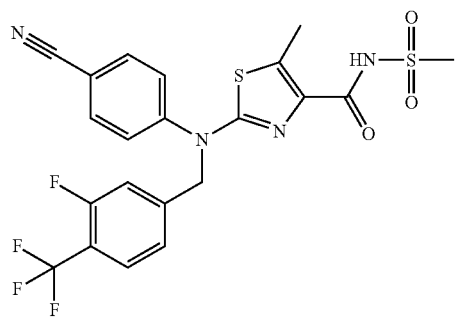 [SMILES: Cc1sc(N(Cc2ccc(C(F)(F)F)c(F)c2)c2ccc(C#N)cc2)nc1C(=O)NS(C)(=O)=O] |
| 168 | 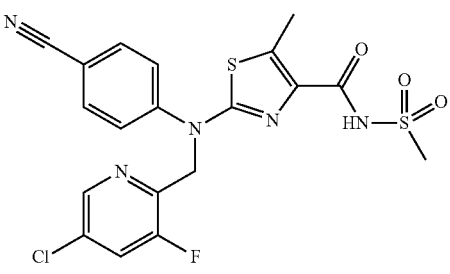 [SMILES: Cc1sc(N(Cc2ncc(Cl)cc2F)c2ccc(C#N)cc2)nc1C(=O)NS(C)(=O)=O] |

TABLE 17
| Compound number | Structure |
|---|---|
| 169 | 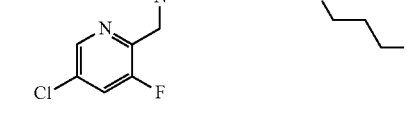 |
| 170 | 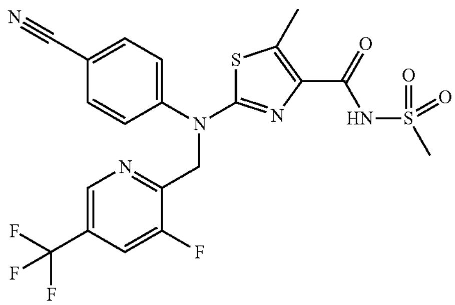 [SMILES: Cc1sc(N(Cc2ncc(C(F)(F)F)cc2F)c2ccc(C#N)cc2)nc1C(=O)NS(C)(=O)=O] |
| 171 | 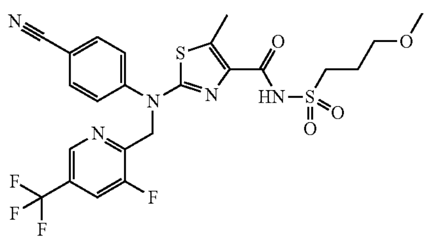 [SMILES: COCCCS(=O)(=O)NC(=O)c1nc(N(Cc2ncc(C(F)(F)F)cc2F)c2ccc(C#N)cc2)sc1C] |
| 172 | 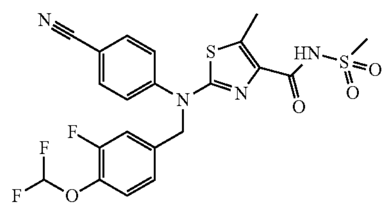 [SMILES: Cc1sc(N(Cc2ccc(OC(F)F)c(F)c2)c2ccc(C#N)cc2)nc1C(=O)NS(C)(=O)=O] |
| 173 | 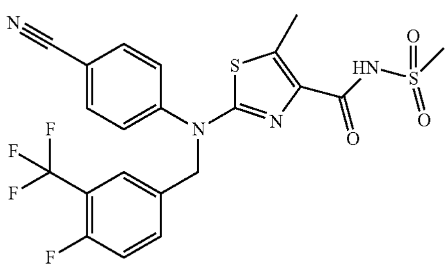 [SMILES: Cc1sc(N(Cc2ccc(F)c(C(F)(F)F)c2)c2ccc(C#N)cc2)nc1C(=O)NS(C)(=O)=O] |
| 174 | 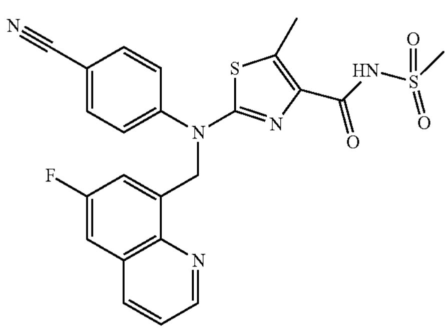 [SMILES: Cc1sc(N(Cc2cc(F)cc3cccnc23)c2ccc(C#N)cc2)nc1C(=O)NS(C)(=O)=O] |
TABLE 17-continued
| Compound number | Structure |
|---|---|
| 175 | 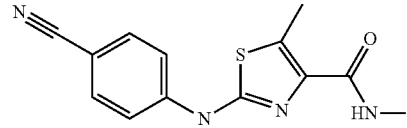 |
| 176 | 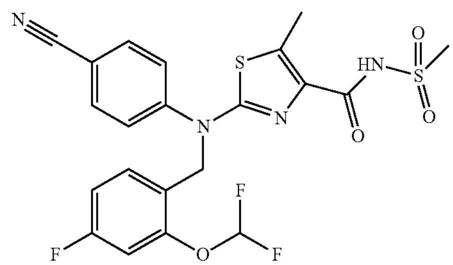 [SMILES: Cc1sc(N(Cc2ccc(F)cc2OC(F)F)c2ccc(C#N)cc2)nc1C(=O)NS(C)(=O)=O] |
| 177 | 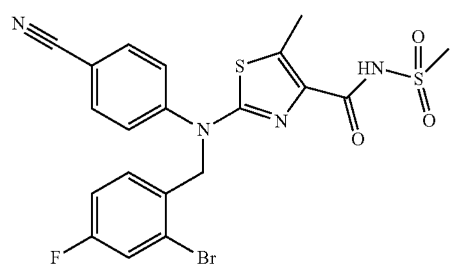 [SMILES: Cc1sc(N(Cc2ccc(F)cc2Br)c2ccc(C#N)cc2)nc1C(=O)NS(C)(=O)=O] |
| 178 | 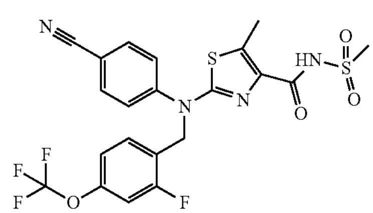 [SMILES: Cc1sc(N(Cc2ccc(OC(F)(F)F)cc2F)c2ccc(C#N)cc2)nc1C(=O)NS(C)(=O)=O] |

TABLE 18

| Compound number | Structure |
|---|---|
| 179 | *structure: 4-cyanophenyl-N-[(5-fluoro-3-chloropyridin-2-yl)methyl]-amino linked to 5-methyl-thiazole-4-carboxylic acid methanesulfonamide* |
| 180 | *structure: 4-cyanophenyl-N-[(3,5-dichloropyridin-2-yl)methyl]-amino linked to 5-methyl-thiazole-4-carboxylic acid methanesulfonamide* |
| 181 | *structure: 4-cyanophenyl-N-[(4-bromo-3-fluorobenzyl)]-amino linked to 5-methyl-thiazole-4-carboxylic acid methanesulfonamide* |
| 182 | *structure: 4-cyanophenyl-N-[(4-bromo-2-cyanobenzyl)]-amino linked to 5-methyl-thiazole-4-carboxylic acid methanesulfonamide* |
| 183 | *structure: 4-cyanophenyl-N-[(4-bromo-2-chlorobenzyl)]-amino linked to 5-methyl-thiazole-4-carboxylic acid methanesulfonamide* |

TABLE 18-continued

| Compound number | Structure |
|---|---|
| 184 | 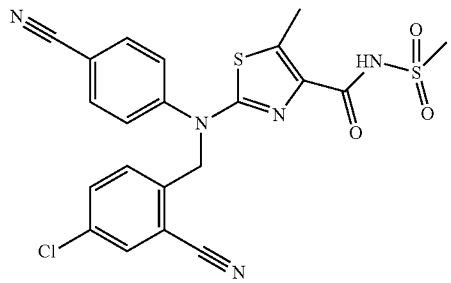 [SMILES: Cc1sc(N(Cc2ccc(Cl)cc2C#N)c2ccc(C#N)cc2)nc1C(=O)NS(C)(=O)=O] |
| 185 | 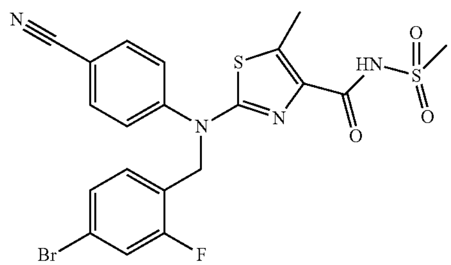 [SMILES: Cc1sc(N(Cc2ccc(Br)cc2F)c2ccc(C#N)cc2)nc1C(=O)NS(C)(=O)=O] |
| 186 | 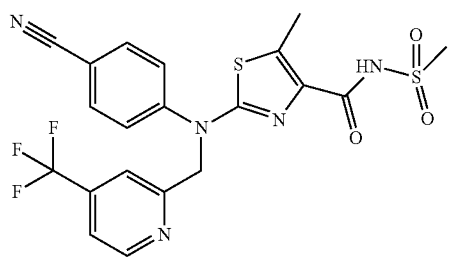 [SMILES: Cc1sc(N(Cc2cc(C(F)(F)F)ccn2)c2ccc(C#N)cc2)nc1C(=O)NS(C)(=O)=O] |
| 187 | 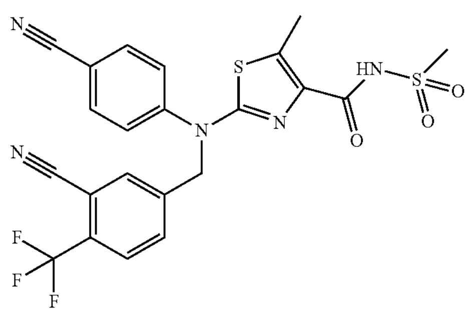 [SMILES: Cc1sc(N(Cc2ccc(C(F)(F)F)c(C#N)c2)c2ccc(C#N)cc2)nc1C(=O)NS(C)(=O)=O] |
| 188 | 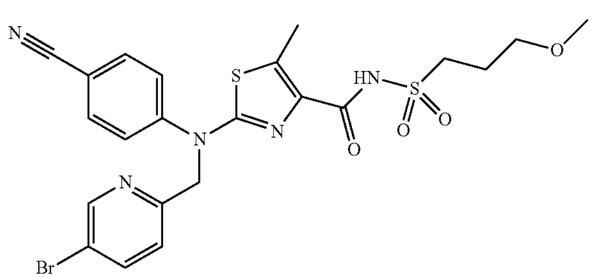 [SMILES: COCCCS(=O)(=O)NC(=O)c1nc(N(Cc2ccc(Br)cn2)c2ccc(C#N)cc2)sc1C] |

TABLE 19
| Compound number | Structure |
|---|---|
| 189 | 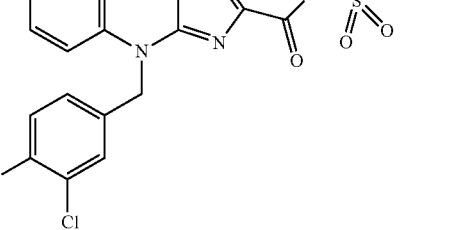 |
| 190 | 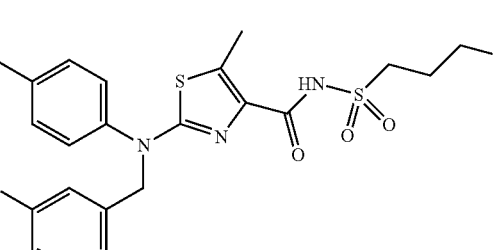 |
| 191 | 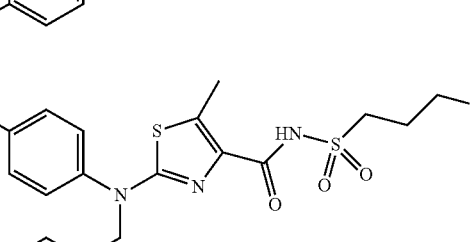 |
| 192 | 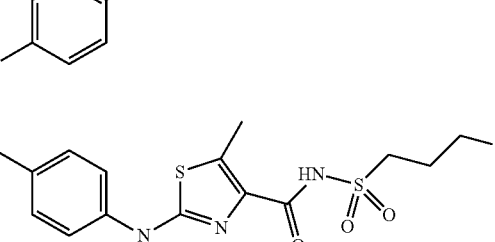 |
| 193 | 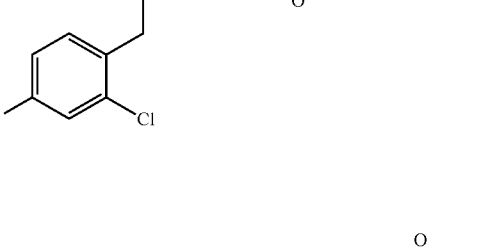 |

TABLE 19-continued

| Compound number | Structure |
|---|---|
| 194 | 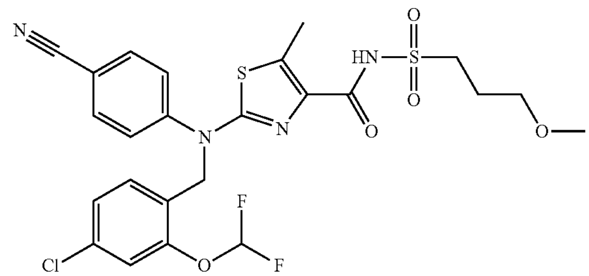 [SMILES: COCCCS(=O)(=O)NC(=O)c1nc(N(Cc2ccc(Cl)cc2OC(F)F)c2ccc(C#N)cc2)sc1C] |
| 195 | 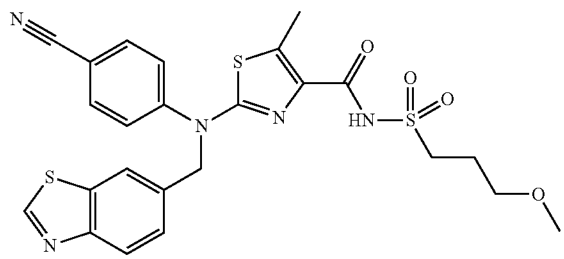 [SMILES: COCCCS(=O)(=O)NC(=O)c1nc(N(Cc2ccc3ncsc3c2)c2ccc(C#N)cc2)sc1C] |
| 196 | 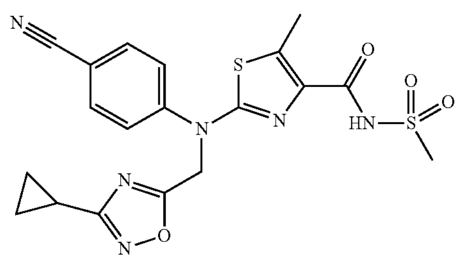 [SMILES: Cc1sc(N(Cc2nc(C3CC3)no2)c2ccc(C#N)cc2)nc1C(=O)NS(C)(=O)=O] |
| 197 | 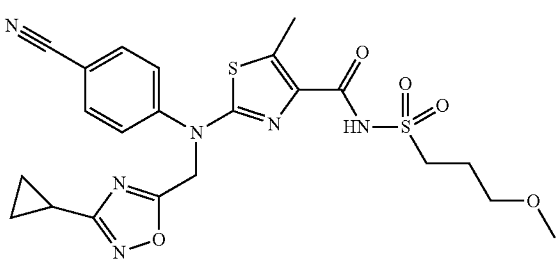 [SMILES: COCCCS(=O)(=O)NC(=O)c1nc(N(Cc2nc(C3CC3)no2)c2ccc(C#N)cc2)sc1C] |
| 198 | 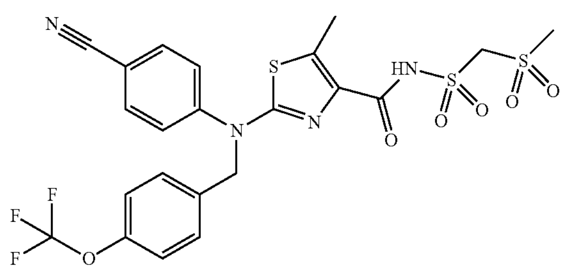 [SMILES: Cc1sc(N(Cc2ccc(OC(F)(F)F)cc2)c2ccc(C#N)cc2)nc1C(=O)NS(=O)(=O)CS(C)(=O)=O] |
| 199 | 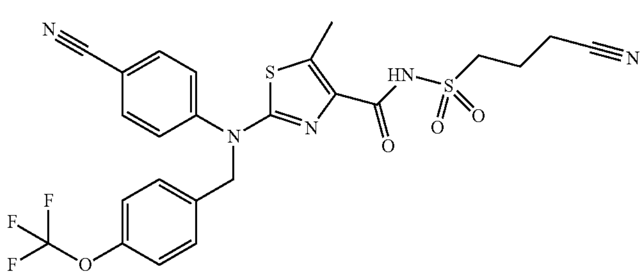 [SMILES: Cc1sc(N(Cc2ccc(OC(F)(F)F)cc2)c2ccc(C#N)cc2)nc1C(=O)NS(=O)(=O)CCCC#N] |

TABLE 19-continued

| Compound number | Structure |
|---|---|
| 200 | (structure) |

TABLE 20

| Compound number | Structure |
|---|---|
| 201 | (structure) |
| 202 | (structure) |
| 203 | (structure) |
| 204 | (structure) |

TABLE 20-continued
| Compound number | Structure |
|---|---|
| 205 | 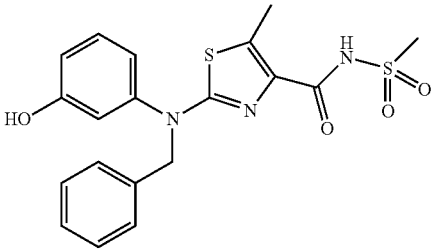 [SMILES: Cc1sc(N(Cc2ccccc2)c2cccc(O)c2)nc1C(=O)NS(C)(=O)=O] |
| 206 | 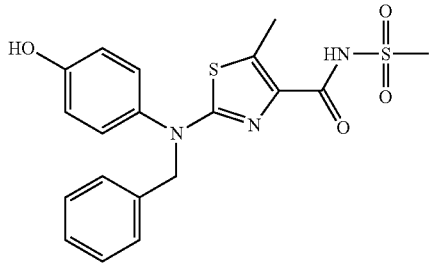 [SMILES: Cc1sc(N(Cc2ccccc2)c2ccc(O)cc2)nc1C(=O)NS(C)(=O)=O] |
| 207 | 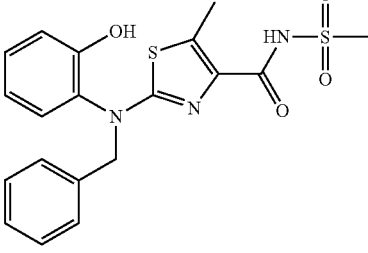 |
| 208 | 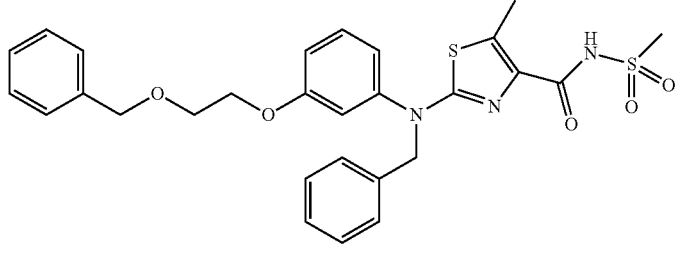 [SMILES: Cc1sc(N(Cc2ccccc2)c2cccc(OCCOCc3ccccc3)c2)nc1C(=O)NS(C)(=O)=O] |
| 209 | 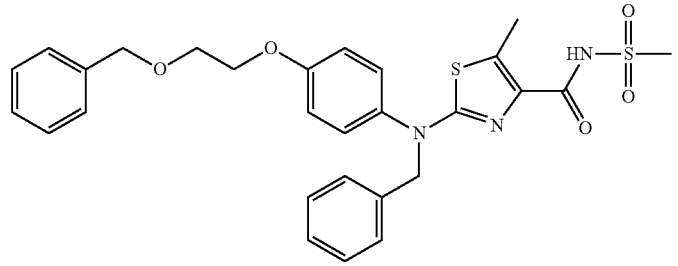 [SMILES: Cc1sc(N(Cc2ccccc2)c2ccc(OCCOCc3ccccc3)cc2)nc1C(=O)NS(C)(=O)=O] |

TABLE 20-continued

| Compound number | Structure |
|---|---|
| 210 | (structure) |
| 211 | (structure) |
| 212 | (structure) |

TABLE 21

| Compound number | Structure |
|---|---|
| 213 | (structure) |
| 214 | (structure) |

TABLE 21-continued

| Compound number | Structure |
|---|---|
| 215 | (structure) |
| 216 | (structure) |
| 217 | (structure) |

TABLE 21-continued

| Compound number | Structure |
|---|---|
| 218 | 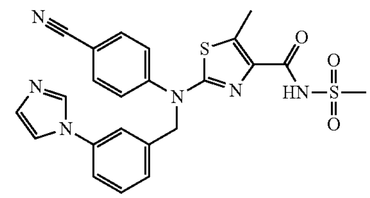 [SMILES: Cc1sc(N(Cc2cccc(-n3ccnc3)c2)c2ccc(C#N)cc2)nc1C(=O)NS(C)(=O)=O] |
| 219 | 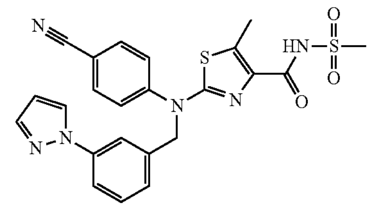 [SMILES: Cc1sc(N(Cc2cccc(-n3cccn3)c2)c2ccc(C#N)cc2)nc1C(=O)NS(C)(=O)=O] |
| 220 | 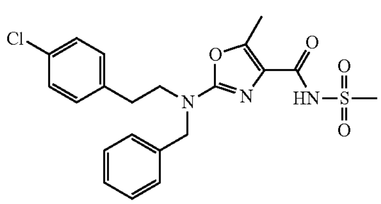 [SMILES: Cc1oc(N(CCc2ccc(Cl)cc2)Cc2ccccc2)nc1C(=O)NS(C)(=O)=O] |
| 221 | 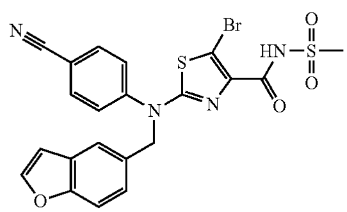 [SMILES: CS(=O)(=O)NC(=O)c1nc(N(Cc2ccc3occc3c2)c2ccc(C#N)cc2)sc1Br] |

TABLE 21-continued

| Compound number | Structure |
|---|---|
| 222 | 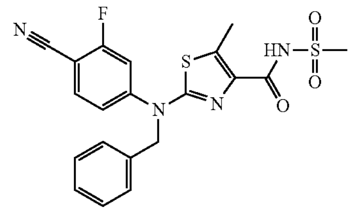 [SMILES: Cc1sc(N(Cc2ccccc2)c2ccc(C#N)c(F)c2)nc1C(=O)NS(C)(=O)=O] |
| 223 | 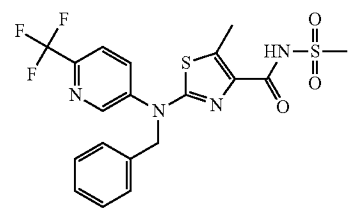 [SMILES: Cc1sc(N(Cc2ccccc2)c2ccc(C(F)(F)F)nc2)nc1C(=O)NS(C)(=O)=O] |
| 224 | 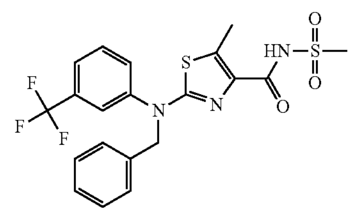 [SMILES: Cc1sc(N(Cc2ccccc2)c2cccc(C(F)(F)F)c2)nc1C(=O)NS(C)(=O)=O] |

TABLE 22

| Compound number | Structure |
|---|---|
| 225 | 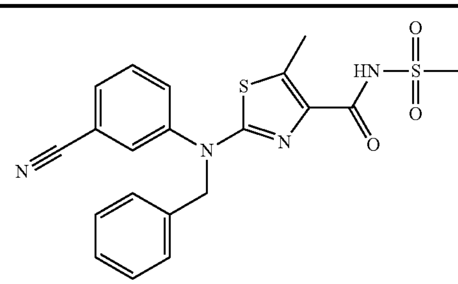 |
| 226 | 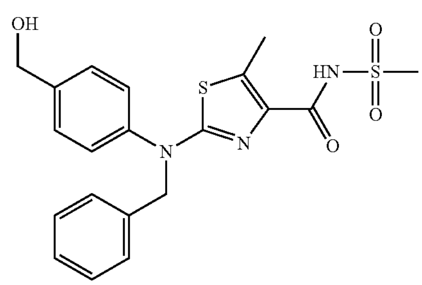 [SMILES: Cc1sc(N(Cc2ccccc2)c2ccc(CO)cc2)nc1C(=O)NS(C)(=O)=O] |

TABLE 22-continued

| Compound number | Structure |
|---|---|
| 227 | 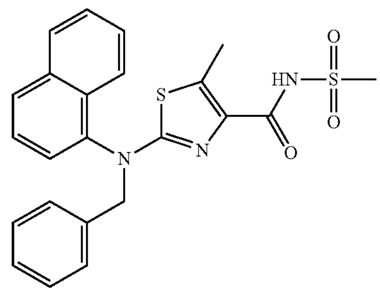 [SMILES: Cc1sc(N(Cc2ccccc2)c2cccc3ccccc23)nc1C(=O)NS(C)(=O)=O] |
| 228 | 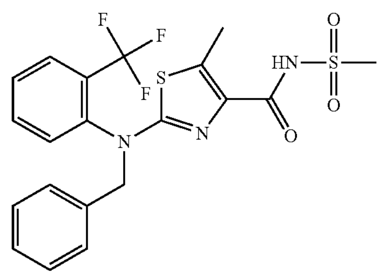 [SMILES: Cc1sc(N(Cc2ccccc2)c2ccccc2C(F)(F)F)nc1C(=O)NS(C)(=O)=O] |
| 229 | 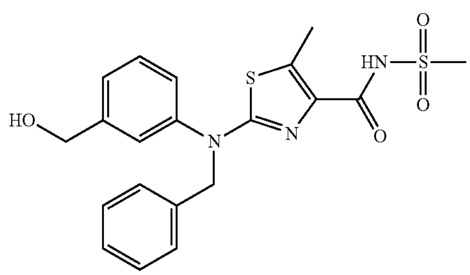 [SMILES: Cc1sc(N(Cc2ccccc2)c2cccc(CO)c2)nc1C(=O)NS(C)(=O)=O] |
| 230 | 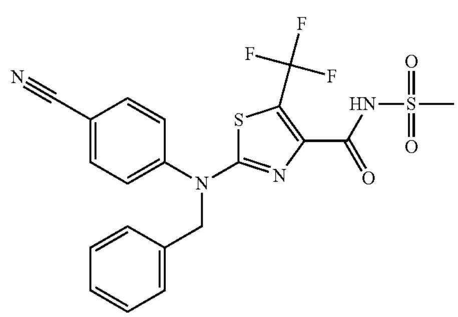 [SMILES: CS(=O)(=O)NC(=O)c1nc(N(Cc2ccccc2)c2ccc(C#N)cc2)sc1C(F)(F)F] |
| 231 | 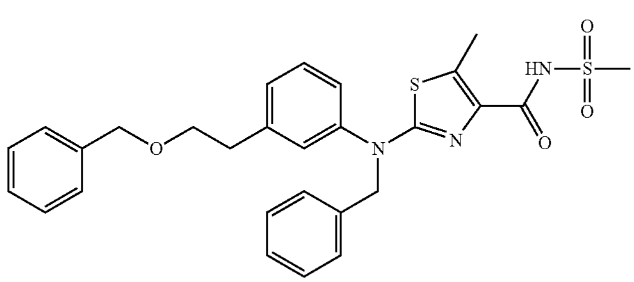 [SMILES: Cc1sc(N(Cc2ccccc2)c2cccc(CCOCc3ccccc3)c2)nc1C(=O)NS(C)(=O)=O] |

TABLE 22-continued

| Compound number | Structure |
|---|---|
| 232 | 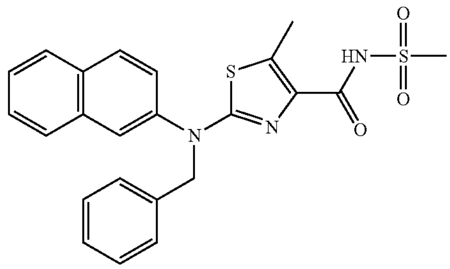 [SMILES: Cc1sc(N(Cc2ccccc2)c2ccc3ccccc3c2)nc1C(=O)NS(C)(=O)=O] |
| 233 | 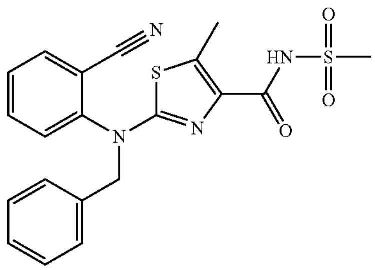 [SMILES: Cc1sc(N(Cc2ccccc2)c2ccccc2C#N)nc1C(=O)NS(C)(=O)=O] |
| 234 | 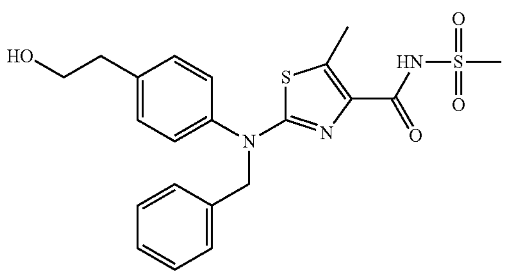 [SMILES: Cc1sc(N(Cc2ccccc2)c2ccc(CCO)cc2)nc1C(=O)NS(C)(=O)=O] |

TABLE 23

| Compound number | Structure |
|---|---|
| 235 | 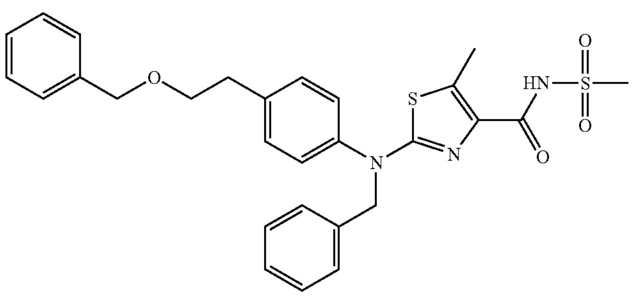 [SMILES: Cc1sc(N(Cc2ccccc2)c2ccc(CCOCc3ccccc3)cc2)nc1C(=O)NS(C)(=O)=O] |
| 236 | 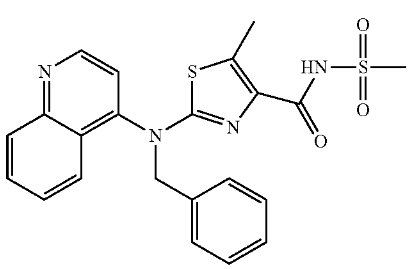 [SMILES: Cc1sc(N(Cc2ccccc2)c2ccnc3ccccc23)nc1C(=O)NS(C)(=O)=O] |

TABLE 23-continued

| Compound number | Structure |
|---|---|
| 237 | 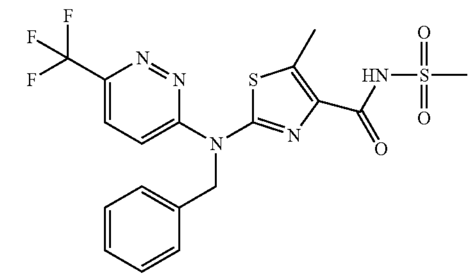 [SMILES: Cc1sc(N(Cc2ccccc2)c2ccc(C(F)(F)F)nn2)nc1C(=O)NS(C)(=O)=O] |
| 238 | 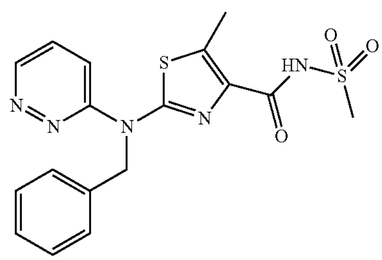 [SMILES: Cc1sc(N(Cc2ccccc2)c2cccnn2)nc1C(=O)NS(C)(=O)=O] |
| 239 | 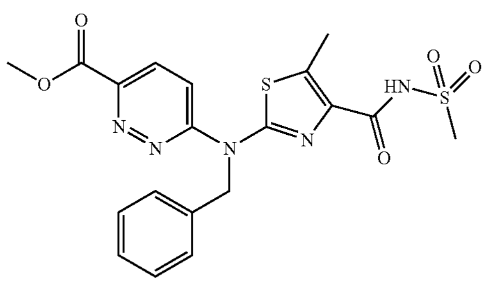 [SMILES: COC(=O)c1ccc(N(Cc2ccccc2)c2nc(C(=O)NS(C)(=O)=O)c(C)s2)nn1] |
| 240 | 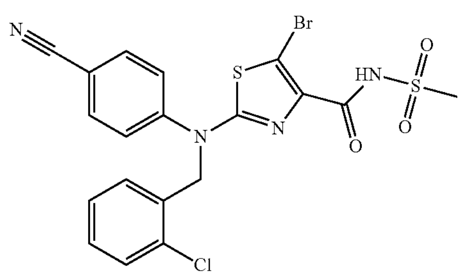 |
| 241 | 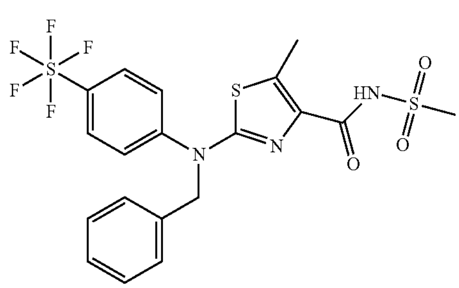 [SMILES: Cc1sc(N(Cc2ccccc2)c2ccc(S(F)(F)(F)(F)F)cc2)nc1C(=O)NS(C)(=O)=O] |

TABLE 23-continued

| Compound number | Structure |
|---|---|
| 242 | 5-bromo-2-[(4-cyanophenyl)(2-fluorobenzyl)amino]-N-(methylsulfonyl)thiazole-4-carboxamide |
| 243 | 5-bromo-2-[(4-cyanophenyl)(3-fluorobenzyl)amino]-N-(methylsulfonyl)thiazole-4-carboxamide |
| 244 | 5-bromo-2-[(4-cyanophenyl)(4-fluorobenzyl)amino]-N-(methylsulfonyl)thiazole-4-carboxamide |
| 245 | 5-bromo-2-[(4-cyanophenyl)(3-methylbenzyl)amino]-N-(methylsulfonyl)thiazole-4-carboxamide |
| 246 | 5-bromo-2-[(4-cyanophenyl)(4-methylbenzyl)amino]-N-(methylsulfonyl)thiazole-4-carboxamide |

TABLE 24

| Compound number | Structure |
|---|---|
| 247 | *(4-cyanophenyl)(3-chlorobenzyl)amino-5-bromothiazole-4-carboxylic acid methanesulfonamide)* |
| 248 | *(4-cyanophenyl)(4-chlorobenzyl)amino-5-bromothiazole-4-carboxylic acid methanesulfonamide* |
| 249 | *(4-cyanophenyl)(2-methoxybenzyl)amino-5-bromothiazole-4-carboxylic acid methanesulfonamide* |
| 250 | *(4-cyanophenyl)(4-methoxybenzyl)amino-5-bromothiazole-4-carboxylic acid methanesulfonamide* |
| 251 | *(4-cyanophenyl)(4-trifluoromethylbenzyl)amino-5-bromothiazole-4-carboxylic acid methanesulfonamide* |

TABLE 24-continued

| Compound number | Structure |
|---|---|
| 252 | *(4-cyanophenyl)(3-trifluoromethoxybenzyl)amino-5-bromothiazole-4-carboxylic acid methanesulfonamide* |
| 253 | *(4-cyanophenyl)(4-trifluoromethoxybenzyl)amino-5-bromothiazole-4-carboxylic acid methanesulfonamide* |
| 254 | *(4-cyanophenyl)(2-difluoromethoxybenzyl)amino-5-bromothiazole-4-carboxylic acid methanesulfonamide* |
| 255 | *(4-cyanophenyl)(3-difluoromethoxybenzyl)amino-5-bromothiazole-4-carboxylic acid methanesulfonamide* |
| 256 | *(4-cyanophenyl)(4-difluoromethoxybenzyl)amino-5-bromothiazole-4-carboxylic acid methanesulfonamide* |

TABLE 25

| Compound number | Structure |
|---|---|
| 257 | *(4-cyanophenyl)(2-fluorobenzyl)amino-5-chlorothiazole-4-carboxylic acid methanesulfonamide* |

TABLE 25-continued
| Compound number | Structure |
|---|---|
| 258 | 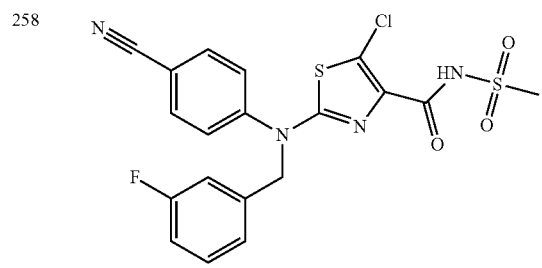 |
| 259 | 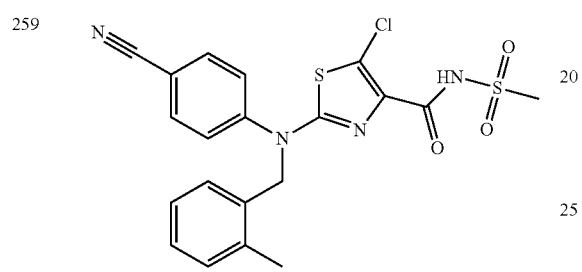 |
| 260 | 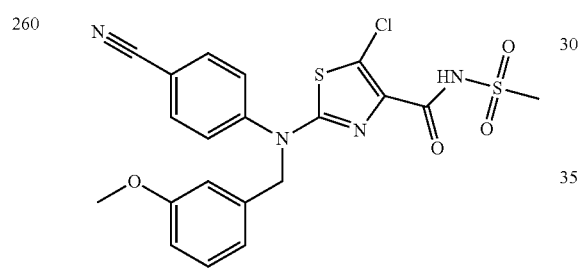 |
| 261 | 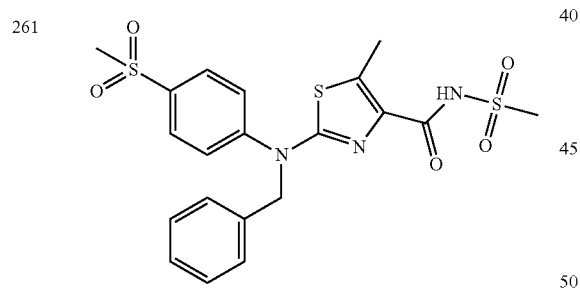 |
| 262 | 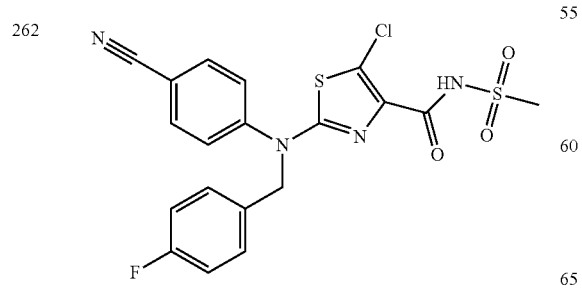 |
TABLE 25-continued
| Compound number | Structure |
|---|---|
| 263 | 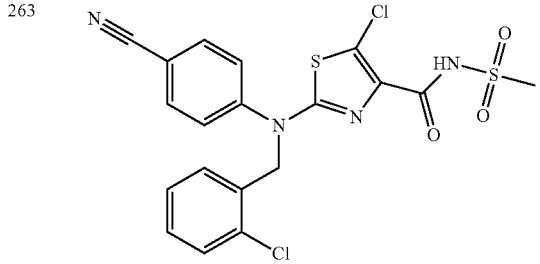 |
| 264 | 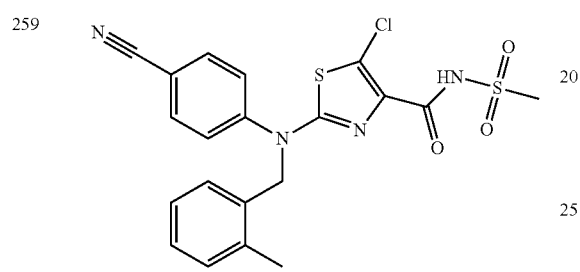 |
| 265 | 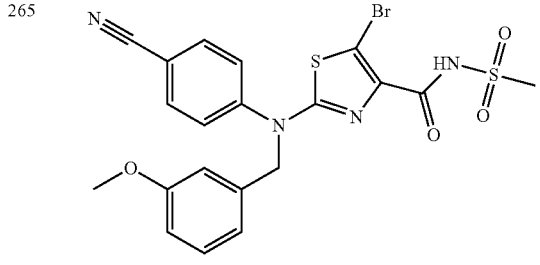 |
| 266 | 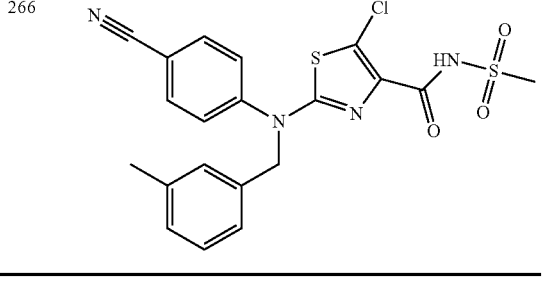 |
TABLE 26
| Compound number | Structure |
|---|---|
| 267 | 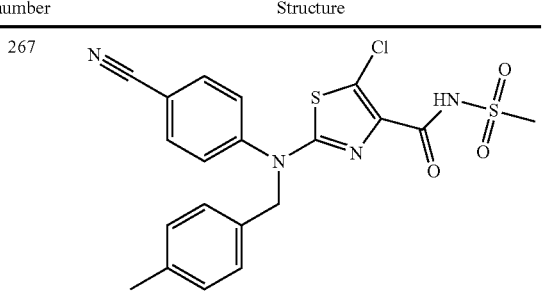 |

TABLE 26-continued
| Compound number | Structure |
|---|---|
| 268 | 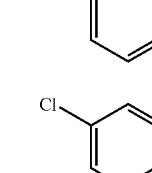 |
| 269 | 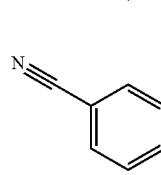 |
| 270 | 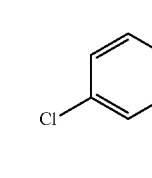 |
| 271 | 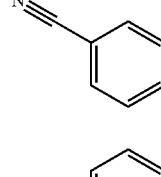 |
| 272 | 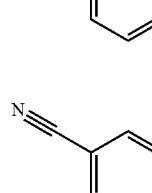 |
| 273 | 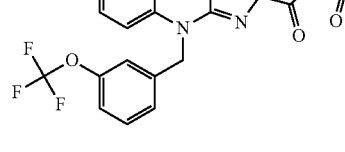 |
| 274 |  |
| 275 | 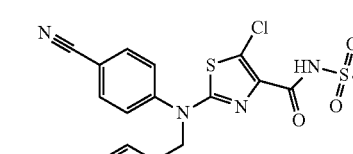 |
| 276 | 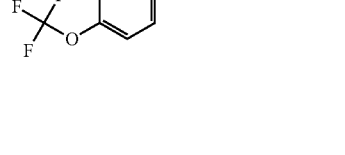 |

TABLE 27
| Compound number | Structure |
|---|---|
| 277 | 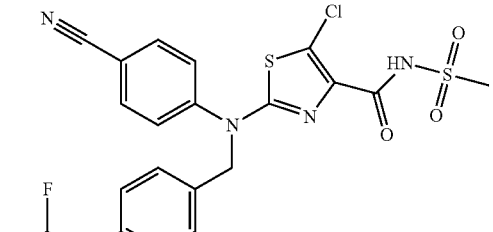 |
| 278 | 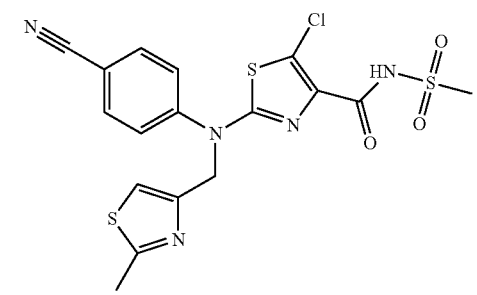 |
| 279 | 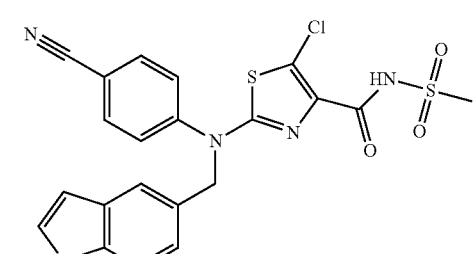 |
| 280 | 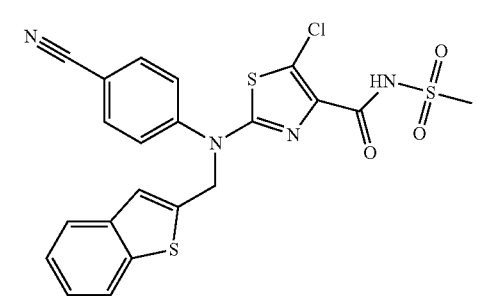 |
| 281 | 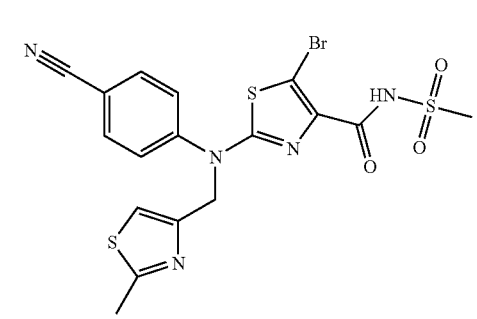 [SMILES: Cc1nc(CN(c2ccc(C#N)cc2)c2nc(C(=O)NS(C)(=O)=O)c(Cl)s2)cs1] |

TABLE 27-continued

| Compound number | Structure |
|---|---|
| 282 | 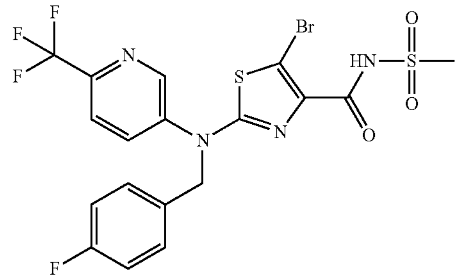 [SMILES: CS(=O)(=O)NC(=O)c1nc(N(Cc2ccc(F)cc2)c2ccc(C(F)(F)F)nc2)sc1Br] |
| 283 | 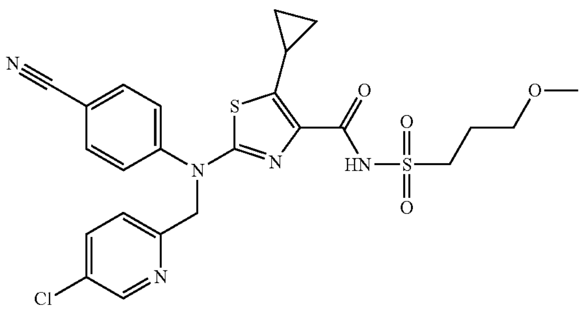 [SMILES: COCCCS(=O)(=O)NC(=O)c1nc(N(Cc2ccc(Cl)cn2)c2ccc(C#N)cc2)sc1C1CC1] |
| 284 | 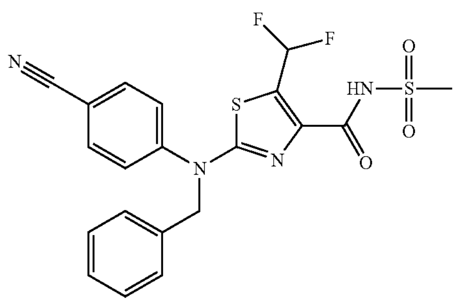 [SMILES: CS(=O)(=O)NC(=O)c1nc(N(Cc2ccccc2)c2ccc(C#N)cc2)sc1C(F)F] |
| 285 | 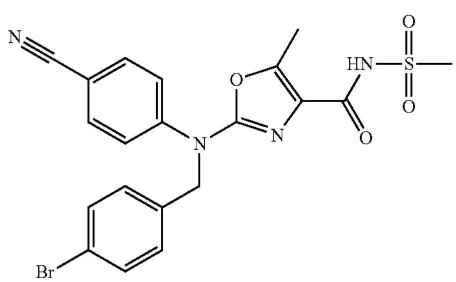 |
| 286 | 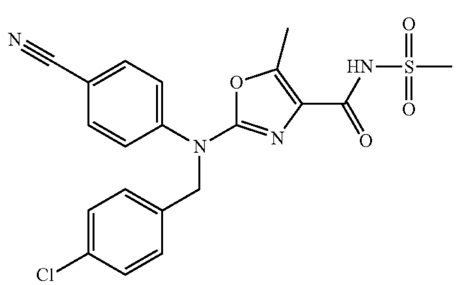 [SMILES: Cc1oc(N(Cc2ccc(Cl)cc2)c2ccc(C#N)cc2)nc1C(=O)NS(C)(=O)=O] |

TABLE 28
| Compound number | Structure |
|---|---|
| 287 | 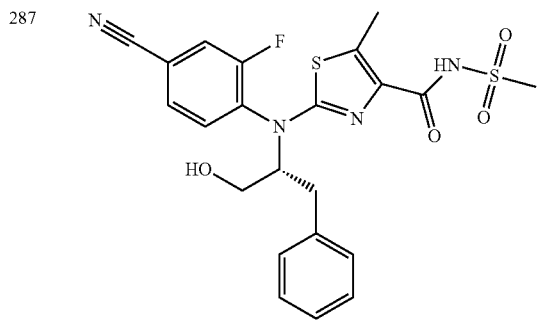 |
| 288 | 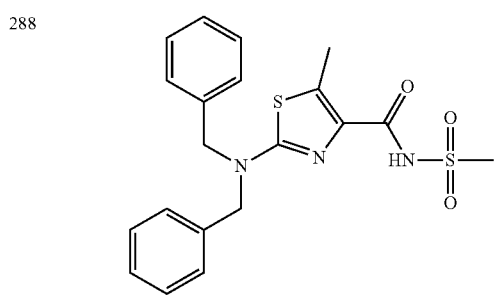 |
| 289 | 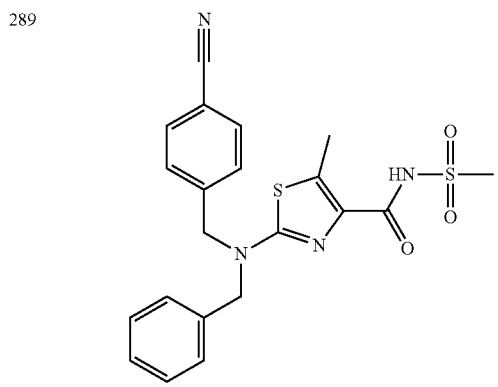 |
| 290 | 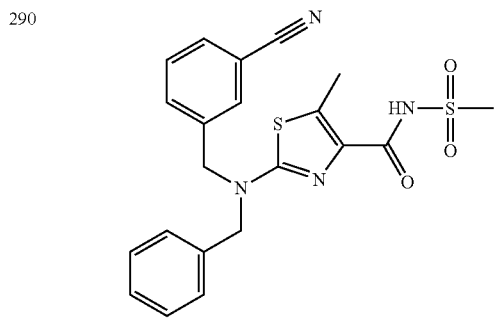 |
TABLE 28-continued
| Compound number | Structure |
|---|---|
| 291 | 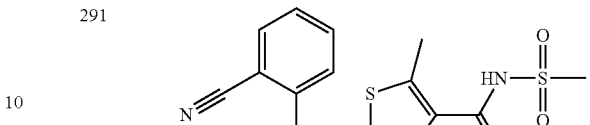 |
| 292 | 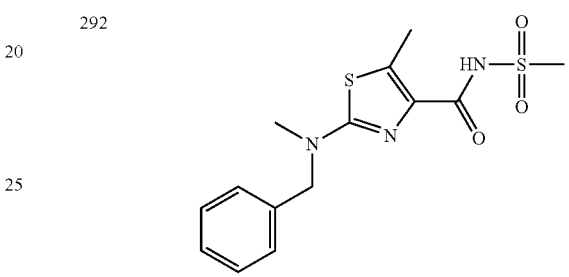 |
| 293 | 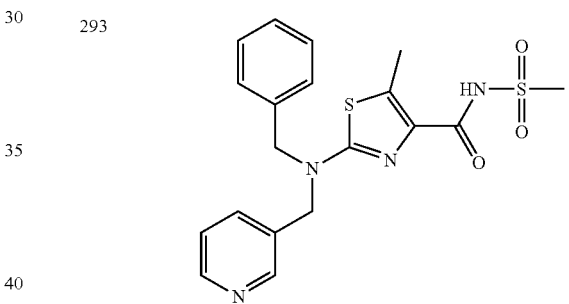 |
| 294 | 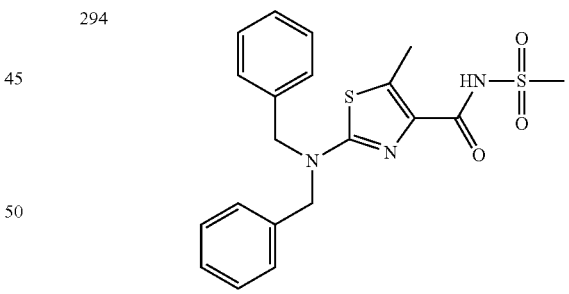 |
| 295 | 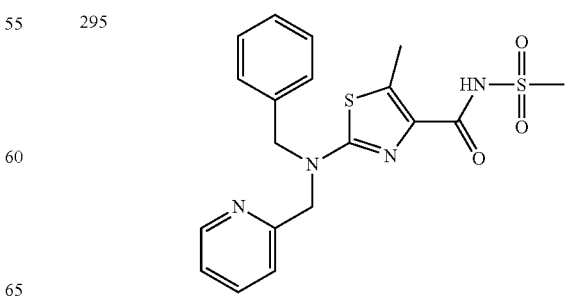 |

TABLE 28-continued

| Compound number | Structure |
|---|---|
| 296 | (structure) |

TABLE 29

| Compound number | Structure |
|---|---|
| 297 | (structure) |
| 298 | (structure) |
| 299 | (structure) |
| 300 | (structure) |
| 301 | (structure) |

TABLE 29-continued

| Compound number | Structure |
|---|---|
| 302 | (structure) |
| 303 | (structure) |
| 304 | (structure) |
| 305 | (structure) |
| 306 | (structure) |

TABLE 30
| Compound number | Structure |
|---|---|
| 307 | 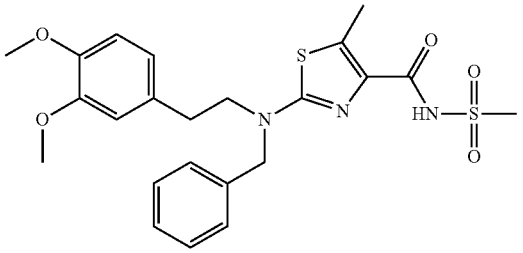 |
| 308 | 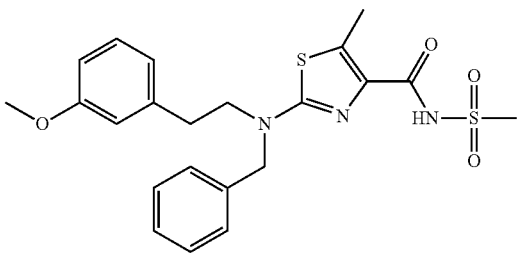 |
| 309 | 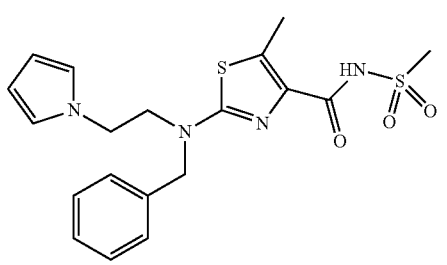 [SMILES: Cc1sc(N(CCn2cccc2)Cc2ccccc2)nc1C(=O)NS(C)(=O)=O] |
| 310 | 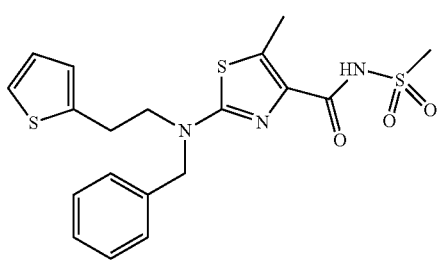 [SMILES: Cc1sc(N(CCc2cccs2)Cc2ccccc2)nc1C(=O)NS(C)(=O)=O] |
| 311 | 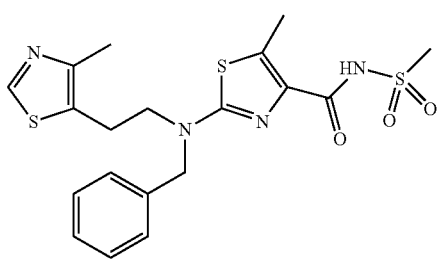 [SMILES: Cc1ncsc1CCN(Cc1ccccc1)c1nc(C(=O)NS(C)(=O)=O)c(C)s1] |
| 312 | 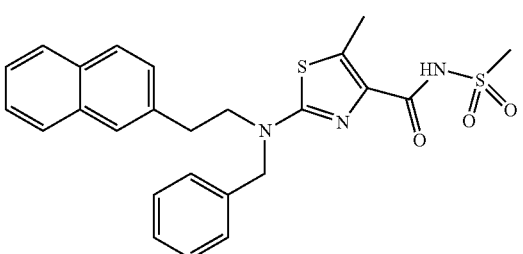 |

TABLE 30-continued

| Compound number | Structure |
|---|---|
| 313 | 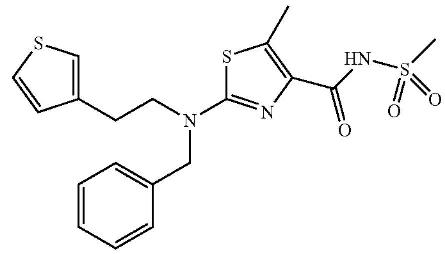 [SMILES: Cc1sc(N(CCc2ccsc2)Cc2ccccc2)nc1C(=O)NS(C)(=O)=O] |
| 314 | 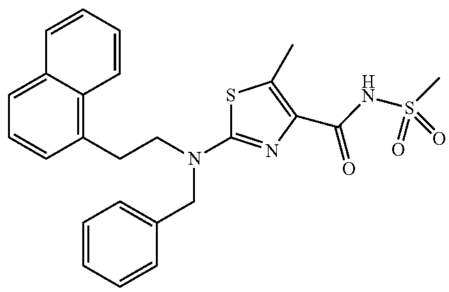 [SMILES: Cc1sc(N(CCc2cccc3ccccc23)Cc2ccccc2)nc1C(=O)NS(C)(=O)=O] |
| 315 | 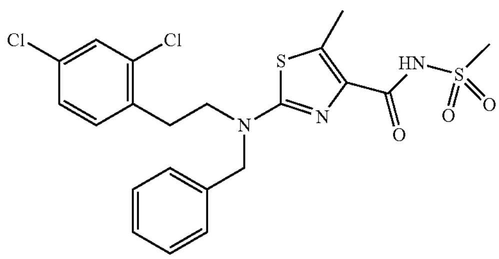 [SMILES: Cc1sc(N(CCc2ccc(Cl)cc2Cl)Cc2ccccc2)nc1C(=O)NS(C)(=O)=O] |
| 316 | 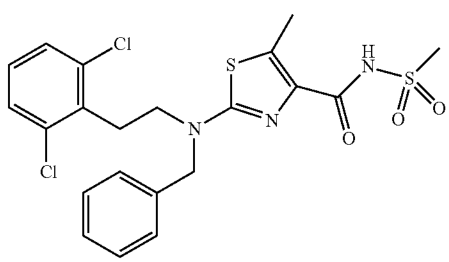 [SMILES: Cc1sc(N(CCc2c(Cl)cccc2Cl)Cc2ccccc2)nc1C(=O)NS(C)(=O)=O] |
| 317 | 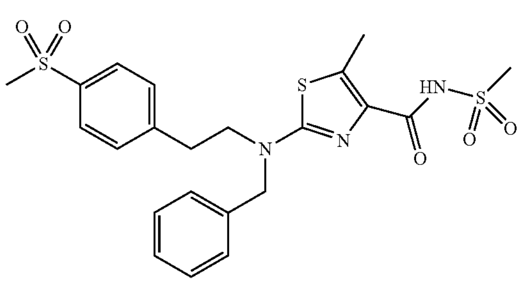 [SMILES: Cc1sc(N(CCc2ccc(S(C)(=O)=O)cc2)Cc2ccccc2)nc1C(=O)NS(C)(=O)=O] |

TABLE 30-continued
| Compound number | Structure |
|---|---|
| 318 | 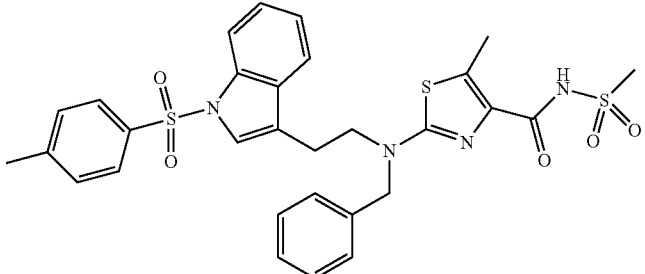 |
TABLE 31
| Compound number | Structure |
|---|---|
| 319 | 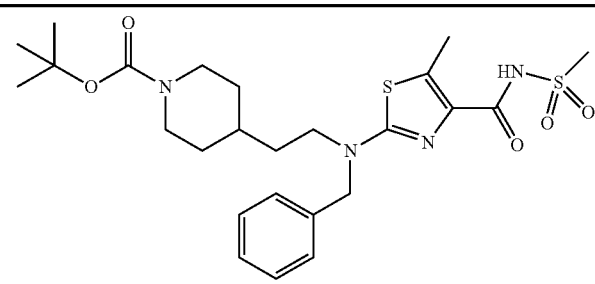 |
| 320 | 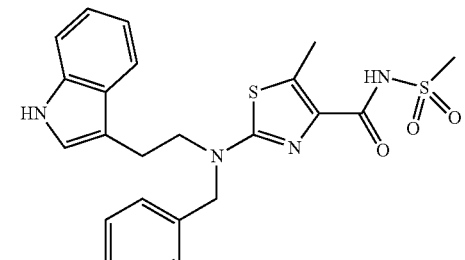 |
| 321 | 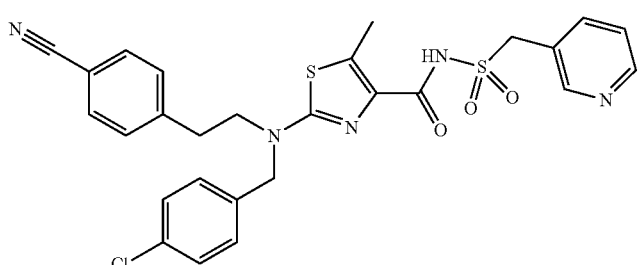 |
| 322 | 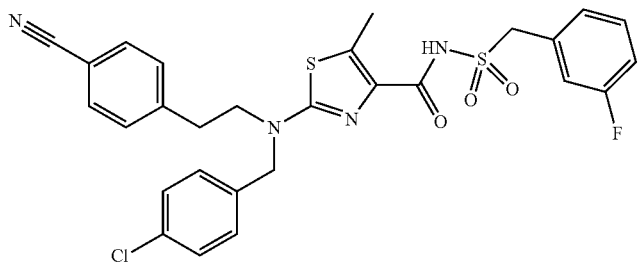 [SMILES: Cc1sc(N(CCc2ccc(C#N)cc2)Cc2ccc(Cl)cc2)nc1C(=O)NS(=O)(=O)Cc1cccc(F)c1] |

TABLE 31-continued
| Compound number | Structure |
|---|---|
| 323 | 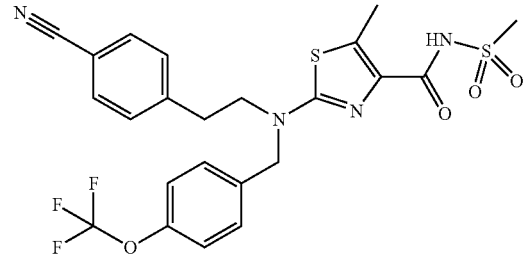 [SMILES: Cc1sc(N(CCc2ccc(C#N)cc2)Cc2ccc(OC(F)(F)F)cc2)nc1C(=O)NS(C)(=O)=O] |
| 324 | 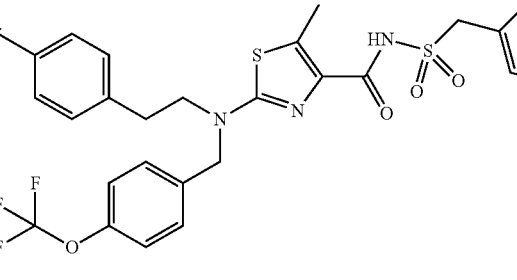 |
| 325 | 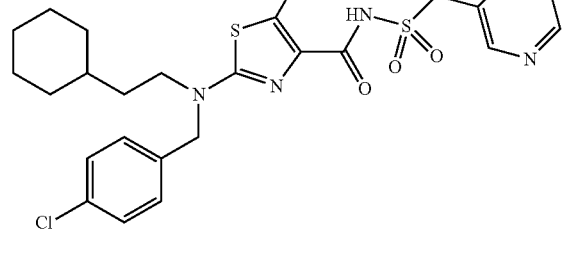 |
| 326 | 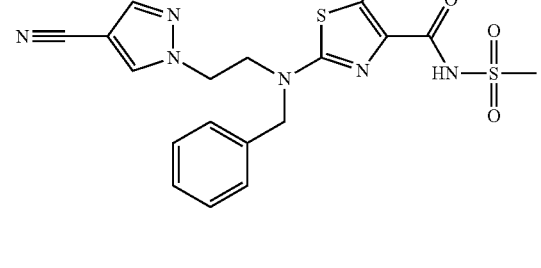 |
| 327 | 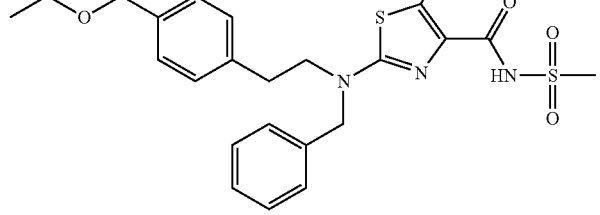 |

TABLE 31-continued
| Compound number | Structure |
|---|---|
| 328 | 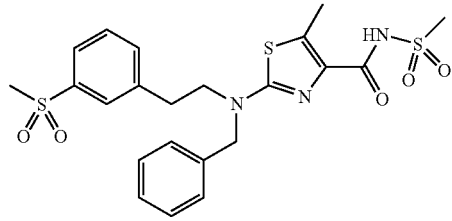 [SMILES: Cc1sc(N(CCc2cccc(S(C)(=O)=O)c2)Cc2ccccc2)nc1C(=O)NS(C)(=O)=O] |
| 329 | |
| 330 | |
| TABLE 32 | | TABLE 32-continued | |
|---|---|---|---|
| Compound number | Structure | Compound number | Structure |
| 331 | | 333 | 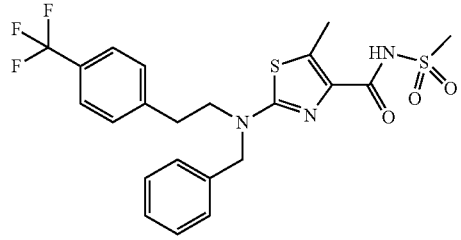 |
| 332 | 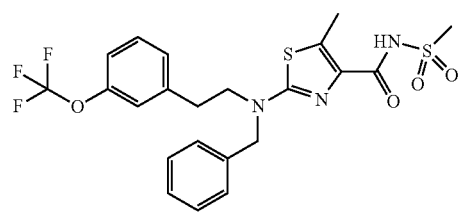 [SMILES: Cc1sc(N(CCc2cccc(OC(F)(F)F)c2)Cc2ccccc2)nc1C(=O)NS(C)(=O)=O] | 334 | 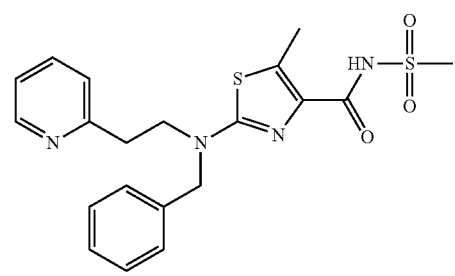 [SMILES: Cc1sc(N(CCc2ccccn2)Cc2ccccc2)nc1C(=O)NS(C)(=O)=O] |

TABLE 32-continued
| Compound number | Structure |
|---|---|
| 335 | 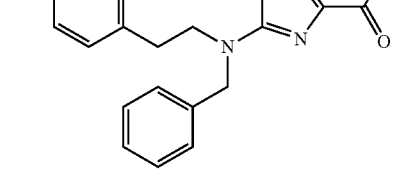 |
| 336 | 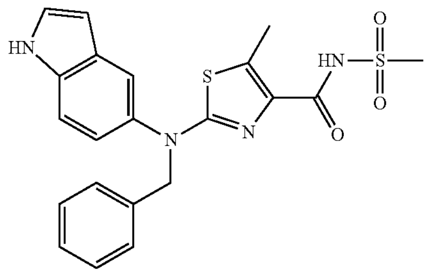 [SMILES: Cc1sc(N(Cc2ccccc2)c2ccc3[nH]ccc3c2)nc1C(=O)NS(C)(=O)=O] |
| 337 | 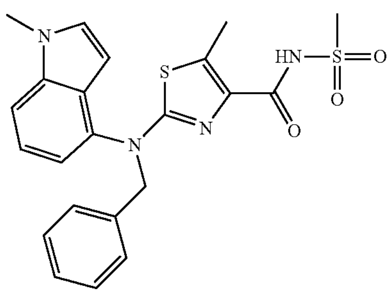 [SMILES: Cc1sc(N(Cc2ccccc2)c2cccc3c2ccn3C)nc1C(=O)NS(C)(=O)=O] |
| 338 | 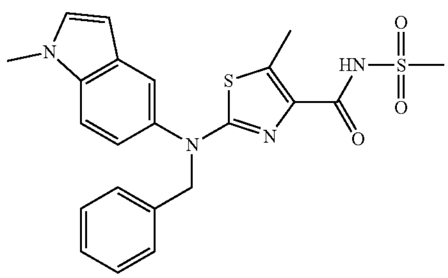 |
| 339 | 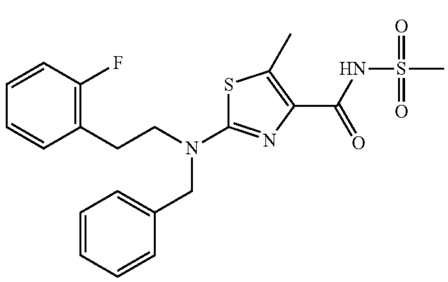 [SMILES: Cc1sc(N(CCc2ccccc2F)Cc2ccccc2)nc1C(=O)NS(C)(=O)=O] |
TABLE 32-continued
| Compound number | Structure |
|---|---|
| 340 | 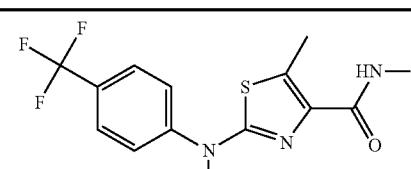 |
TABLE 33
| Compound number | Structure |
|---|---|
| 341 | 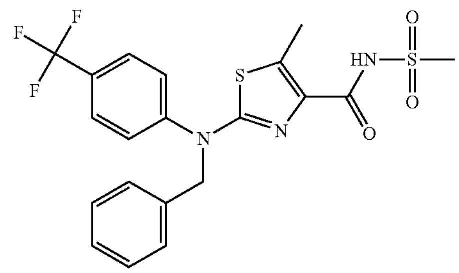 [SMILES: Cc1sc(N(Cc2ccccc2)c2ccc(C(F)(F)F)cc2)nc1C(=O)NS(C)(=O)=O] |
| 342 | 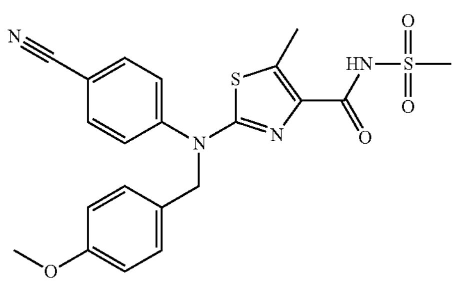 [SMILES: COc1ccc(CN(c2ccc(C#N)cc2)c2nc(C(=O)NS(C)(=O)=O)c(C)s2)cc1] |
| 343 | 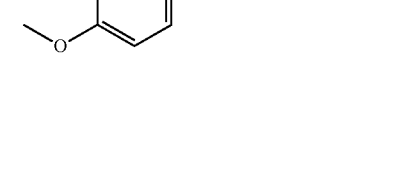 |

TABLE 33-continued

| Compound number | Structure |
|---|---|
| 344 | (structure) |
| 345 | (structure) |
| 346 | (structure) |
| 347 | (structure) Racemate |
| 348 | (structure) Racemate |
| 349 | (structure) Racemate |
| 350 | (structure) |
| 351 | (structure) |
| 352 | (structure) cis/trans mixture |

TABLE 34

| Compound number | Structure |
|---|---|
| 353 | (structure shown) Racemate |
| 354 | (structure shown) Racemate |
| 355 | (structure shown) |
| 356 | (structure shown) |
| 357 | (structure shown) |“

TABLE 34-continued

| Compound number | Structure |
|---|---|
| 358 | (structure shown) |
| 359 | (structure shown) |
| 360 | (structure shown) |
| 361 | (structure shown) |
| 362 | (structure shown) |

TABLE 34-continued
| Compound number | Structure |
|---|---|
| 363 | 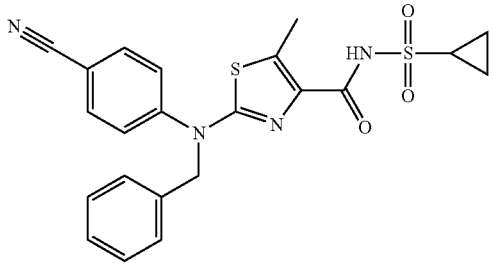 [SMILES: Cc1sc(N(Cc2ccccc2)c2ccc(C#N)cc2)nc1C(=O)NS(=O)(=O)C1CC1] |
| 364 | 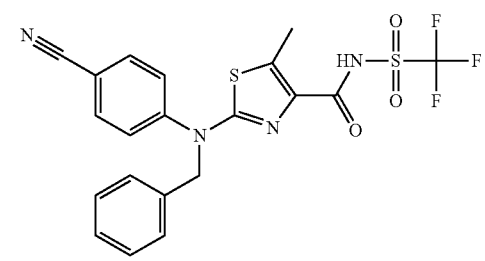 [SMILES: Cc1sc(N(Cc2ccccc2)c2ccc(C#N)cc2)nc1C(=O)NS(=O)(=O)C(F)(F)F] |
TABLE 35
| Compound number | Structure |
|---|---|
| 365 | 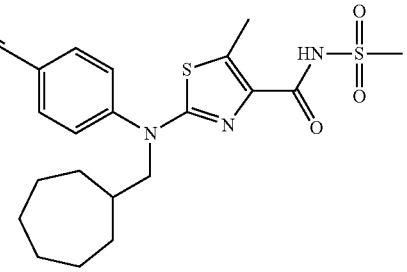 |
| 366 | 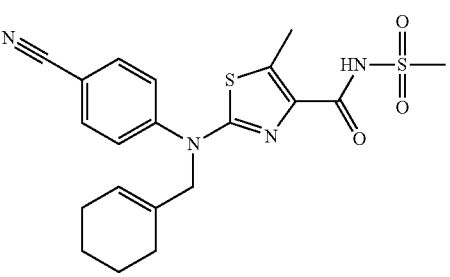 [SMILES: Cc1sc(N(CC2=CCCCC2)c2ccc(C#N)cc2)nc1C(=O)NS(C)(=O)=O] |
| 367 | 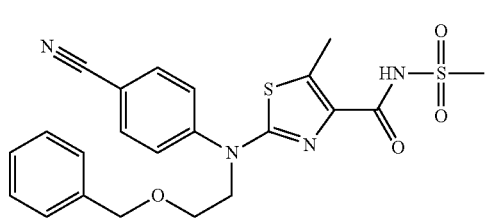 [SMILES: Cc1sc(N(CCOCc2ccccc2)c2ccc(C#N)cc2)nc1C(=O)NS(C)(=O)=O] |
| 368 | 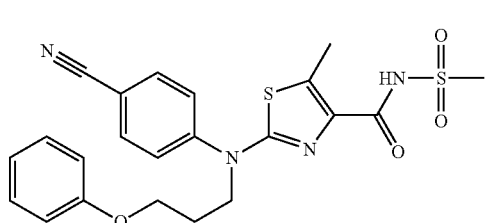 |

TABLE 35-continued
| Compound number | Structure |
|---|---|
| 369 | 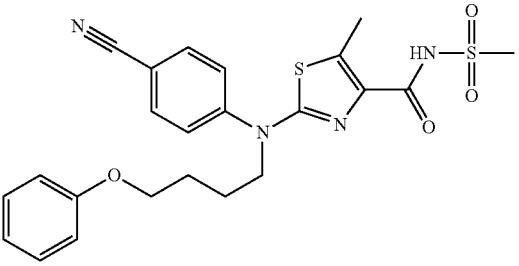 [SMILES: Cc1sc(N(CCCCOc2ccccc2)c2ccc(C#N)cc2)nc1C(=O)NS(C)(=O)=O] |
| 370 | 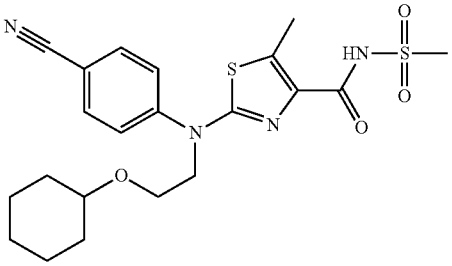 [SMILES: Cc1sc(N(CCOC2CCCCC2)c2ccc(C#N)cc2)nc1C(=O)NS(C)(=O)=O] |
| 371 | 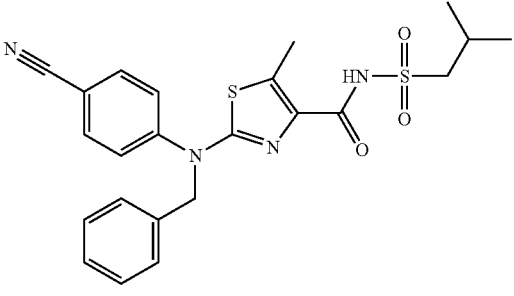 [SMILES: Cc1sc(N(Cc2ccccc2)c2ccc(C#N)cc2)nc1C(=O)NS(=O)(=O)CC(C)C] |
| 372 | 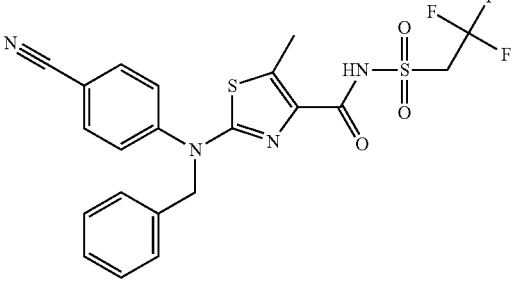 |
| 373 | 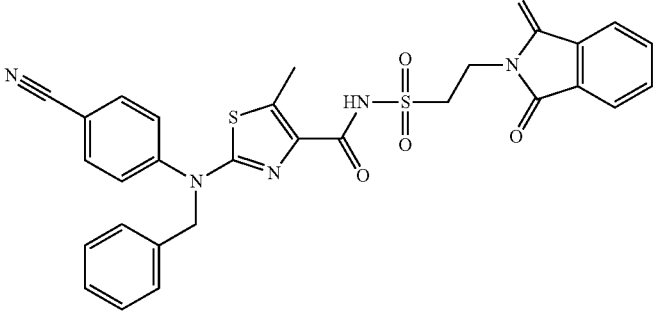 |

TABLE 35-continued

| Compound number | Structure |
|---|---|
| 374 | 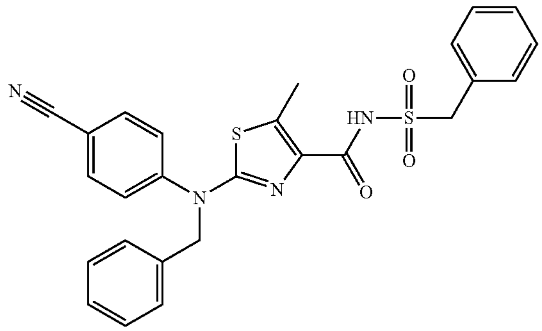 [SMILES: Cc1sc(N(Cc2ccccc2)c2ccc(C#N)cc2)nc1C(=O)NS(=O)(=O)Cc1ccccc1] |
| 375 | 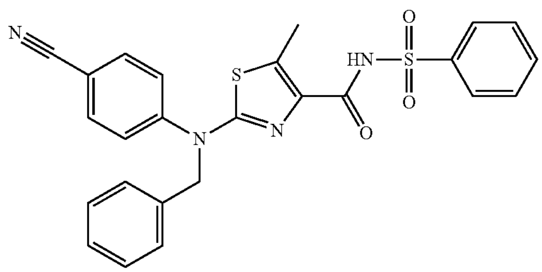 [SMILES: Cc1sc(N(Cc2ccccc2)c2ccc(C#N)cc2)nc1C(=O)NS(=O)(=O)c1ccccc1] |
| 376 | 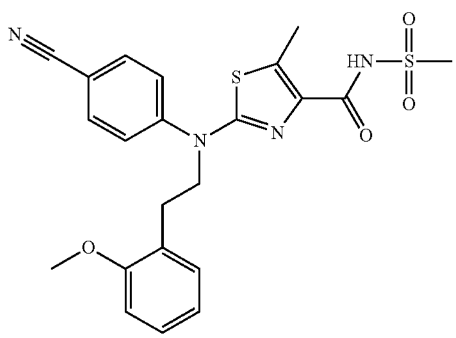 [SMILES: COc1ccccc1CCN(c1ccc(C#N)cc1)c1nc(C(=O)NS(C)(=O)=O)c(C)s1] |

TABLE 36

| Compound number | Structure |
|---|---|
| 377 | 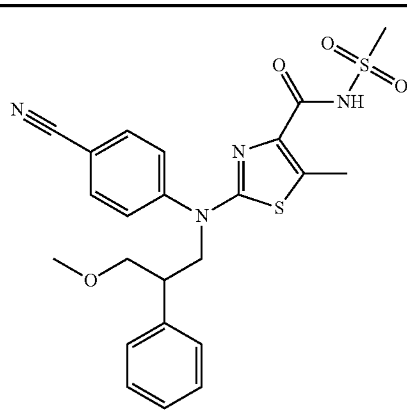 |

TABLE 36-continued

| Compound number | Structure |
| --- | --- |
| 378 | 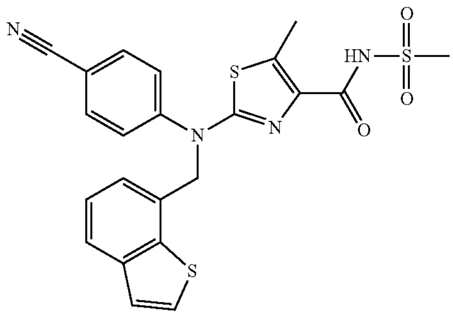 [SMILES: Cc1sc(N(Cc2cccc3ccsc23)c2ccc(C#N)cc2)nc1C(=O)NS(C)(=O)=O] |
| 379 | 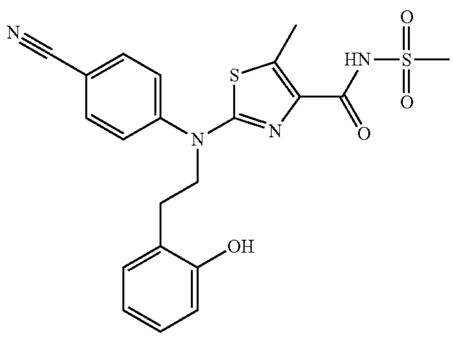 [SMILES: Cc1sc(N(CCc2ccccc2O)c2ccc(C#N)cc2)nc1C(=O)NS(C)(=O)=O] |
| 380 | 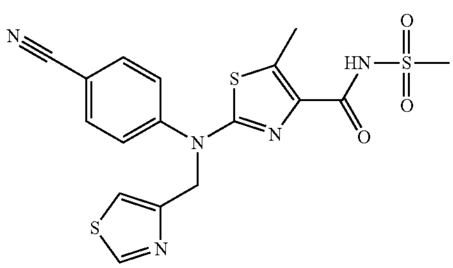 [SMILES: Cc1sc(N(Cc2cscn2)c2ccc(C#N)cc2)nc1C(=O)NS(C)(=O)=O] |
| 381 | 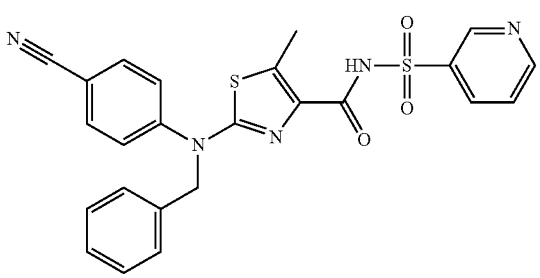 [SMILES: Cc1sc(N(Cc2ccccc2)c2ccc(C#N)cc2)nc1C(=O)NS(=O)(=O)c1cccnc1] |
| 382 | 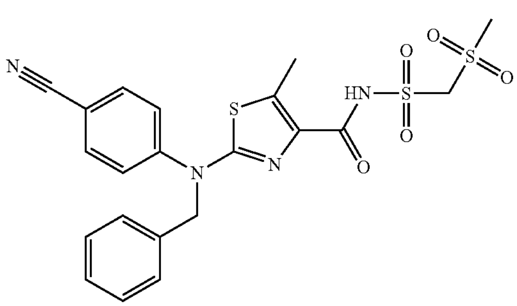 [SMILES: Cc1sc(N(Cc2ccccc2)c2ccc(C#N)cc2)nc1C(=O)NS(=O)(=O)CS(C)(=O)=O] |

TABLE 36-continued

| Compound number | Structure |
|---|---|
| 383 | 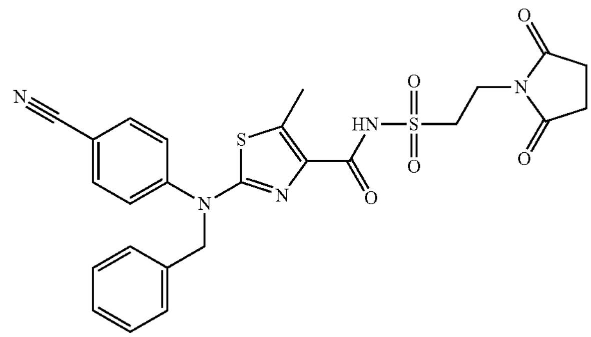 [SMILES: Cc1sc(N(Cc2ccccc2)c2ccc(C#N)cc2)nc1C(=O)NS(=O)(=O)CCN1C(=O)CCC1=O] |
| 384 | 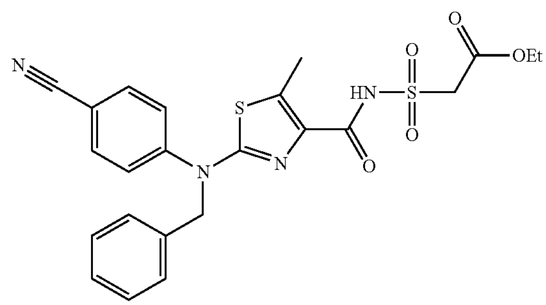 [SMILES: CCOC(=O)CS(=O)(=O)NC(=O)c1nc(N(Cc2ccccc2)c2ccc(C#N)cc2)sc1C] |
| 385 | 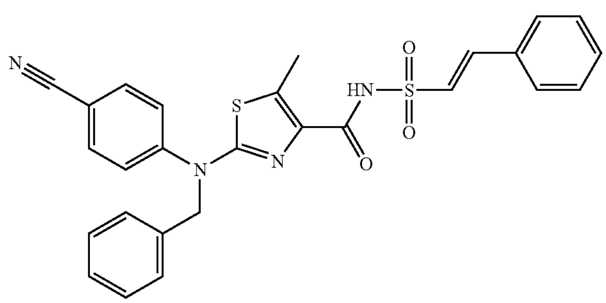 [SMILES: Cc1sc(N(Cc2ccccc2)c2ccc(C#N)cc2)nc1C(=O)NS(=O)(=O)/C=C/c1ccccc1] |
| 386 | 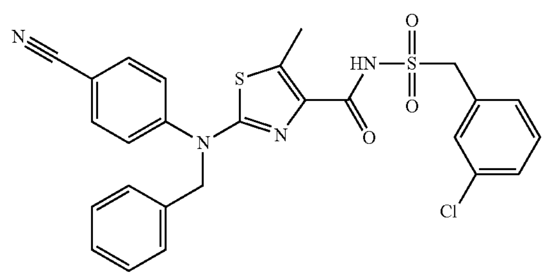 [SMILES: Cc1sc(N(Cc2ccccc2)c2ccc(C#N)cc2)nc1C(=O)NS(=O)(=O)Cc1cccc(Cl)c1] |

TABLE 37

| Compound number | Structure |
|---|---|
| 387 | 4-cyanophenyl-benzyl-amino thiazole (5-methyl) carboxamide N-sulfonyl-CH2CH2CF3 |
| 388 | 4-cyanophenyl-(d7-benzyl)-amino thiazole (5-methyl) carboxamide N-sulfonyl-methyl |
| 389 | 4-cyanophenyl-((1H-benzimidazol-6-yl)methyl)-amino thiazole (5-methyl) carboxamide N-sulfonyl-methyl |
| 390 | 4-cyanophenyl-(quinolin-8-ylmethyl)-amino thiazole (5-methyl) carboxamide N-sulfonyl-methyl |
| 391 | 4-cyanophenyl-benzyl-amino thiazole (5-methyl) carboxamide N-sulfonyl-CH2CH2-phenyl |

TABLE 37-continued
| Compound number | Structure |
|---|---|
| 392 | 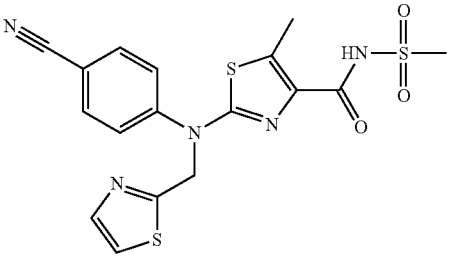 [SMILES: Cc1sc(N(Cc2nccs2)c2ccc(C#N)cc2)nc1C(=O)NS(C)(=O)=O] |
| 393 | 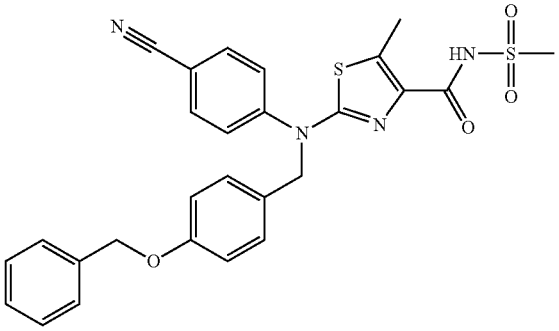 [SMILES: Cc1sc(N(Cc2ccc(OCc3ccccc3)cc2)c2ccc(C#N)cc2)nc1C(=O)NS(C)(=O)=O] |
| 394 | 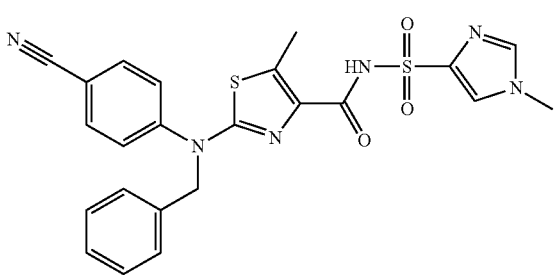 [SMILES: Cc1sc(N(Cc2ccccc2)c2ccc(C#N)cc2)nc1C(=O)NS(=O)(=O)c1cn(C)cn1] |
| 395 | 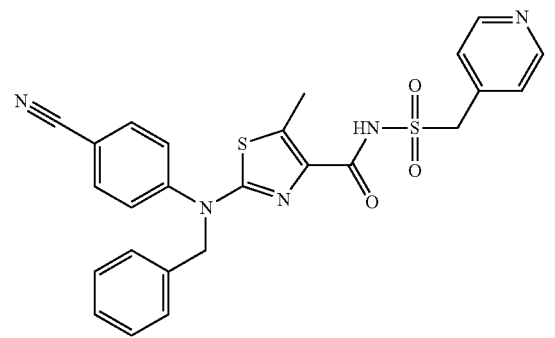 [SMILES: Cc1sc(N(Cc2ccccc2)c2ccc(C#N)cc2)nc1C(=O)NS(=O)(=O)Cc1ccncc1] |
| 396 | 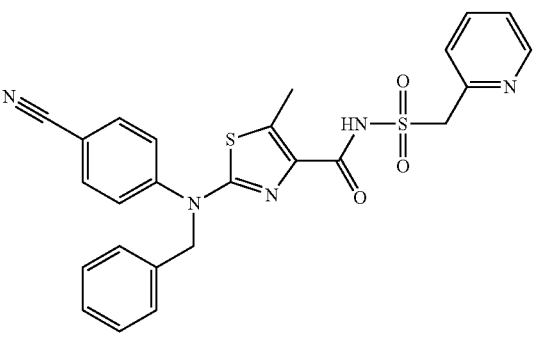 [SMILES: Cc1sc(N(Cc2ccccc2)c2ccc(C#N)cc2)nc1C(=O)NS(=O)(=O)Cc1ccccn1] |

TABLE 37-continued

| Compound number | Structure |
|---|---|
| 397 | (structure) |
| 398 | (structure) |

TABLE 38

| Compound number | Structure |
|---|---|
| 399 | (structure) |
| 400 | (structure) |
| 401 | (structure) |
| 402 | (structure) |

TABLE 38-continued
| Compound number | Structure |
|---|---|
| 403 | 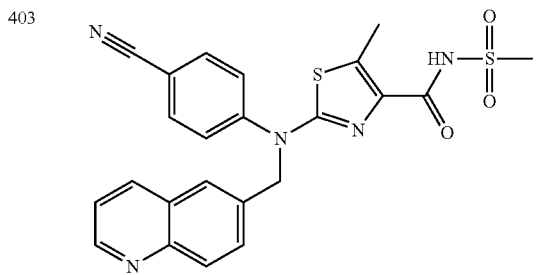 |
| 404 | 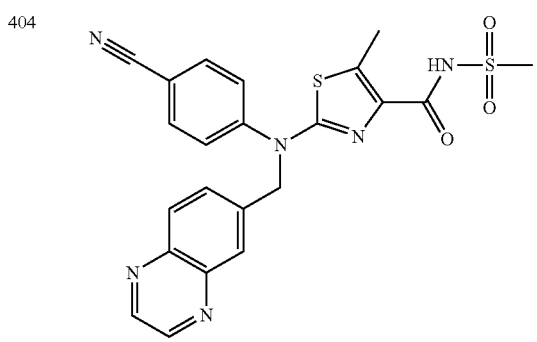 |
| 405 | 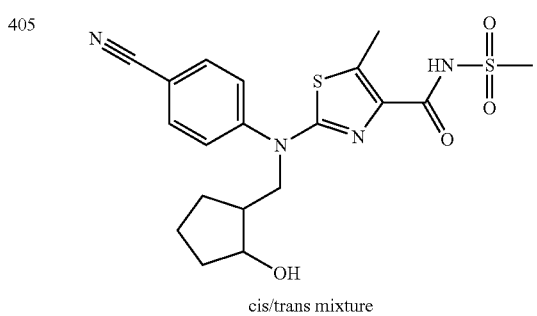<br>cis/trans mixture |
| 406 | 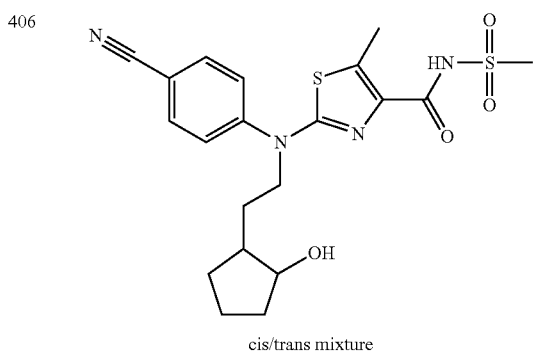<br>cis/trans mixture |
TABLE 38-continued
| Compound number | Structure |
|---|---|
| 407 | 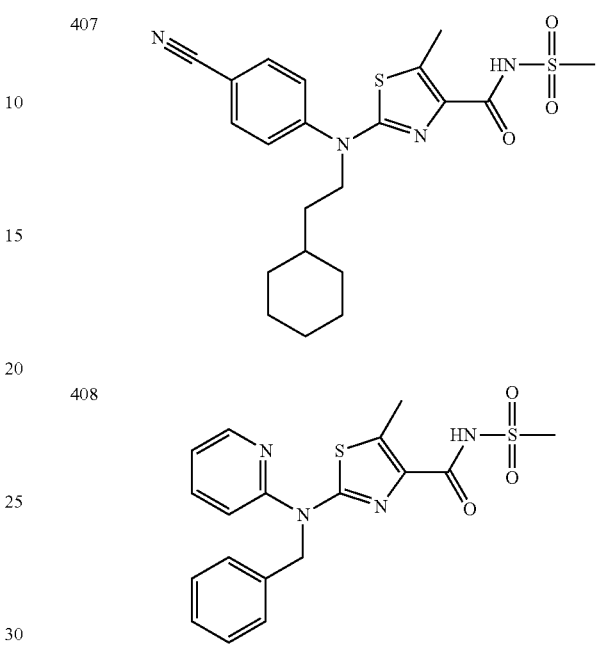 |
| 408 | |
TABLE 39
| Compound number | Structure |
|---|---|
| 409 | 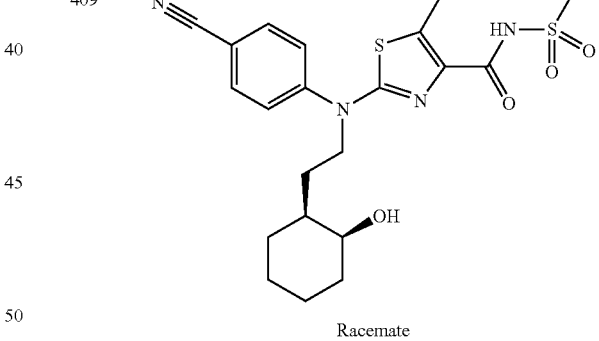<br>Racemate |
| 410 | Racemate |

TABLE 39-continued
| Compound number | Structure |
|---|---|
| 411 | 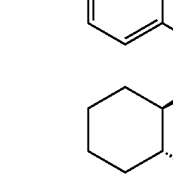 Racemate |
| 412 | 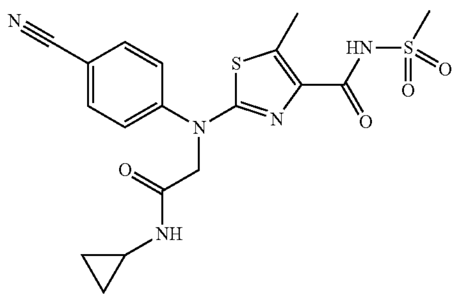 [SMILES: Cc1sc(N(CC(=O)NC2CC2)c2ccc(C#N)cc2)nc1C(=O)NS(C)(=O)=O] |
| 413 | 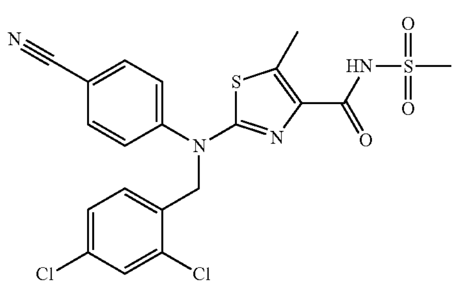 [SMILES: Cc1sc(N(Cc2ccc(Cl)cc2Cl)c2ccc(C#N)cc2)nc1C(=O)NS(C)(=O)=O] |
| 414 | 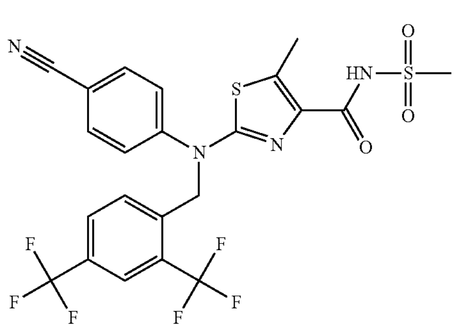 [SMILES: Cc1sc(N(Cc2ccc(C(F)(F)F)cc2C(F)(F)F)c2ccc(C#N)cc2)nc1C(=O)NS(C)(=O)=O] |
| 415 | 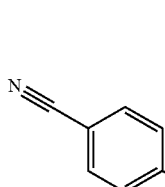 |
| 416 | |
| 417 | |
| 418 | |

TABLE 40
| Compound number | Structure |
|---|---|
| 419 | 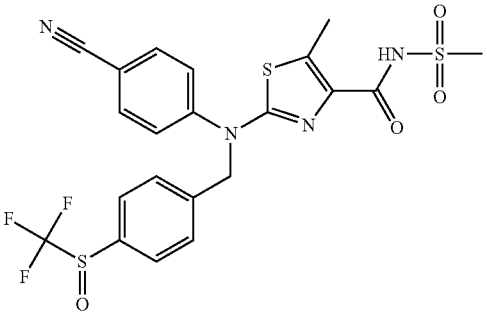 [SMILES: Cc1sc(N(Cc2ccc(S(=O)C(F)(F)F)cc2)c2ccc(C#N)cc2)nc1C(=O)NS(C)(=O)=O] |
| 420 | 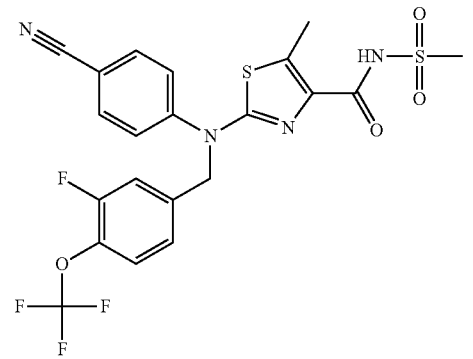 [SMILES: Cc1sc(N(Cc2ccc(OC(F)(F)F)c(F)c2)c2ccc(C#N)cc2)nc1C(=O)NS(C)(=O)=O] |
| 421 | 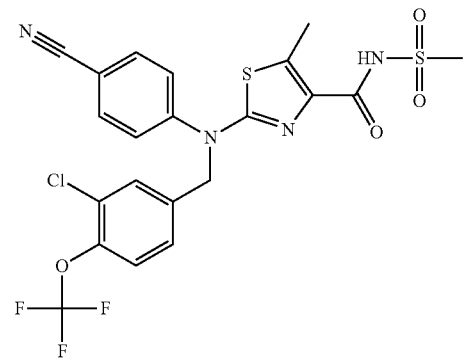 [SMILES: Cc1sc(N(Cc2ccc(OC(F)(F)F)c(Cl)c2)c2ccc(C#N)cc2)nc1C(=O)NS(C)(=O)=O] |
| 422 | 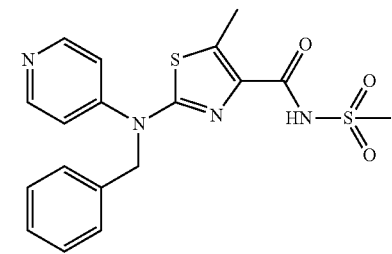 [SMILES: Cc1sc(N(Cc2ccccc2)c2ccncc2)nc1C(=O)NS(C)(=O)=O] |

TABLE 40-continued

| Compound number | Structure |
|---|---|
| 423 | 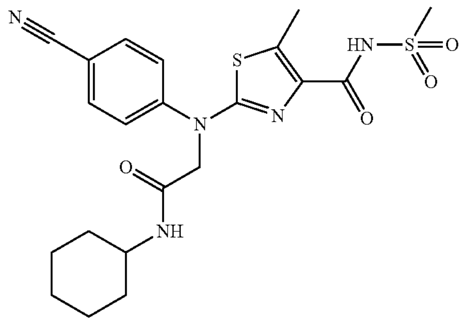 [SMILES: Cc1sc(N(CC(=O)NC2CCCCC2)c2ccc(C#N)cc2)nc1C(=O)NS(C)(=O)=O] |
| 424 | 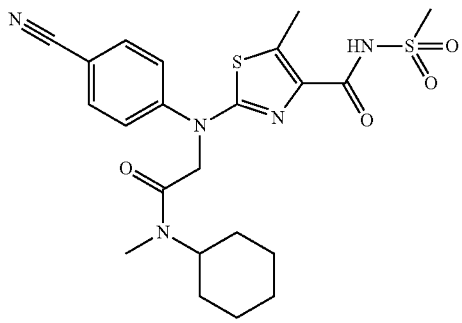 [SMILES: Cc1sc(N(CC(=O)N(C)C2CCCCC2)c2ccc(C#N)cc2)nc1C(=O)NS(C)(=O)=O] |
| 425 | 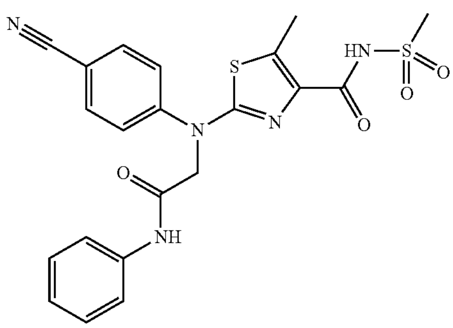 [SMILES: Cc1sc(N(CC(=O)Nc2ccccc2)c2ccc(C#N)cc2)nc1C(=O)NS(C)(=O)=O] |
| 426 | 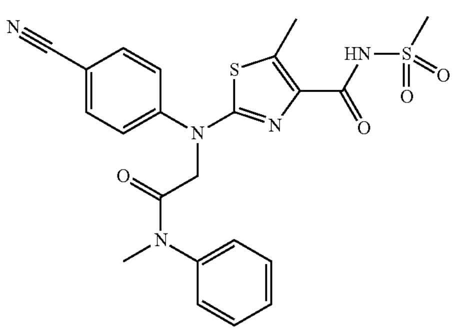 [SMILES: Cc1sc(N(CC(=O)N(C)c2ccccc2)c2ccc(C#N)cc2)nc1C(=O)NS(C)(=O)=O] |

TABLE 40-continued
| Compound number | Structure |
|---|---|
| 427 | 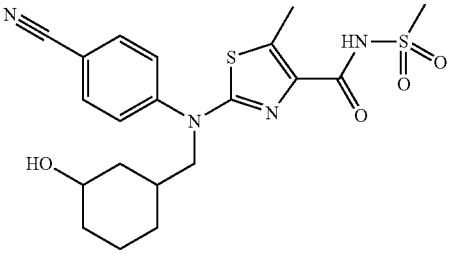<br>cis/trans mixture |
| 428 | 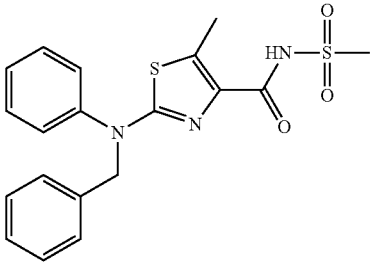 [SMILES: Cc1sc(N(Cc2ccccc2)c2ccccc2)nc1C(=O)NS(C)(=O)=O] |
| 429 | 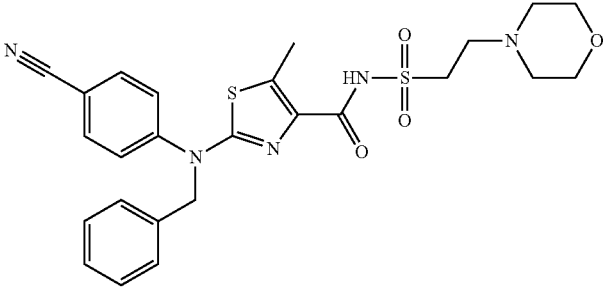 [SMILES: Cc1sc(N(Cc2ccccc2)c2ccc(C#N)cc2)nc1C(=O)NS(=O)(=O)CCN1CCOCC1] |
| 430 | 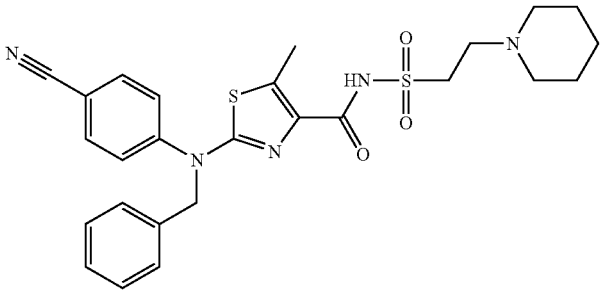 [SMILES: Cc1sc(N(Cc2ccccc2)c2ccc(C#N)cc2)nc1C(=O)NS(=O)(=O)CCN1CCCCC1] |

TABLE 41

| Compound number | Structure |
|---|---|
| 431 | 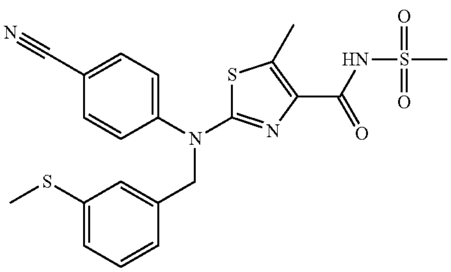 |
| 432 | 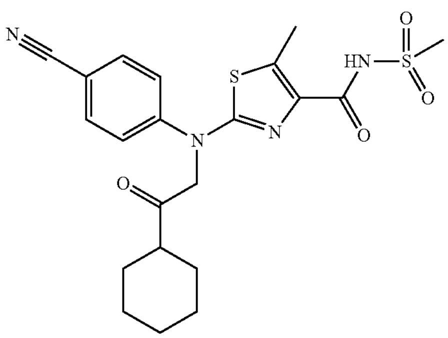 [SMILES: Cc1sc(N(CC(=O)C2CCCCC2)c2ccc(C#N)cc2)nc1C(=O)NS(C)(=O)=O] |
| 433 | 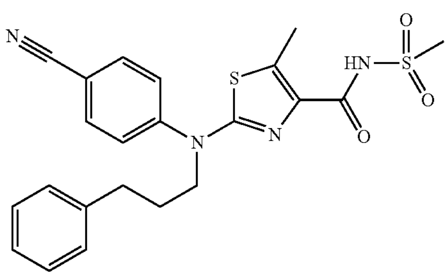 [SMILES: Cc1sc(N(CCCc2ccccc2)c2ccc(C#N)cc2)nc1C(=O)NS(C)(=O)=O] |
| 434 | 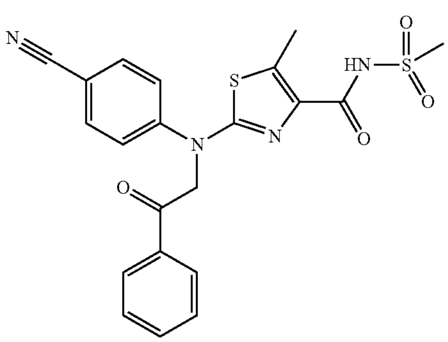 [SMILES: Cc1sc(N(CC(=O)c2ccccc2)c2ccc(C#N)cc2)nc1C(=O)NS(C)(=O)=O] |
| 435 | 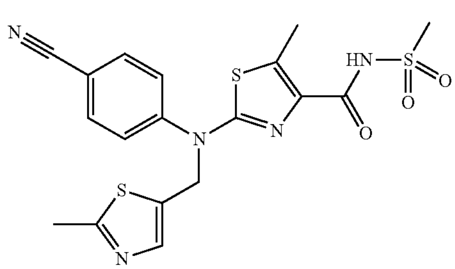 [SMILES: Cc1ncc(CN(c2ccc(C#N)cc2)c2nc(C(=O)NS(C)(=O)=O)c(C)s2)s1] |

TABLE 41-continued

| Compound number | Structure |
|---|---|
| 436 | Racemate |
| 437 | 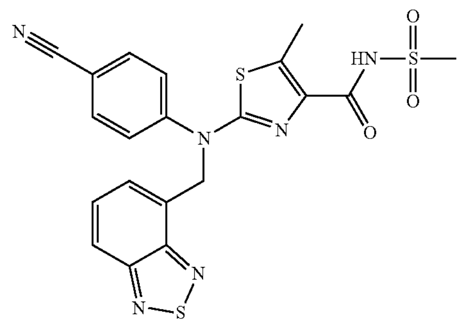 [SMILES: Cc1sc(N(Cc2cccc3nsnc23)c2ccc(C#N)cc2)nc1C(=O)NS(C)(=O)=O] |
| 438 | 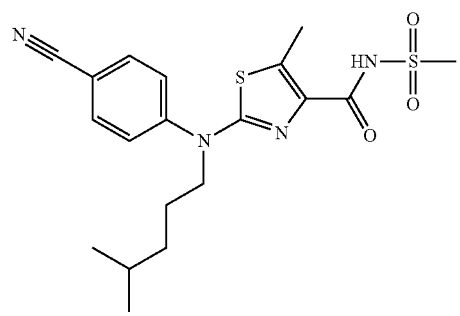 [SMILES: Cc1sc(N(CCCC(C)C)c2ccc(C#N)cc2)nc1C(=O)NS(C)(=O)=O] |
| 439 | 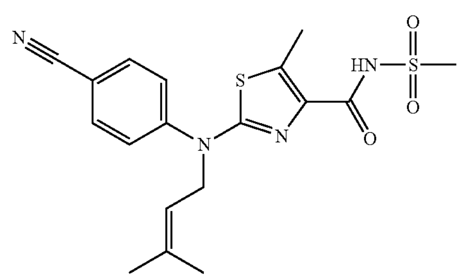 [SMILES: CC(C)=CCN(c1ccc(C#N)cc1)c1nc(C(=O)NS(C)(=O)=O)c(C)s1] |
| 440 | 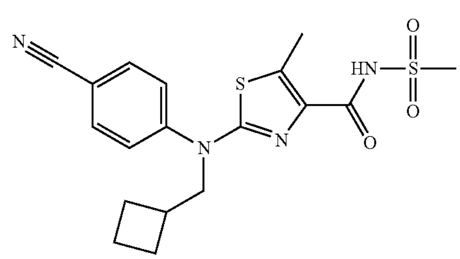 [SMILES: Cc1sc(N(CC2CCC2)c2ccc(C#N)cc2)nc1C(=O)NS(C)(=O)=O] |

TABLE 42
| Compound number | Structure |
|---|---|
| 441 | 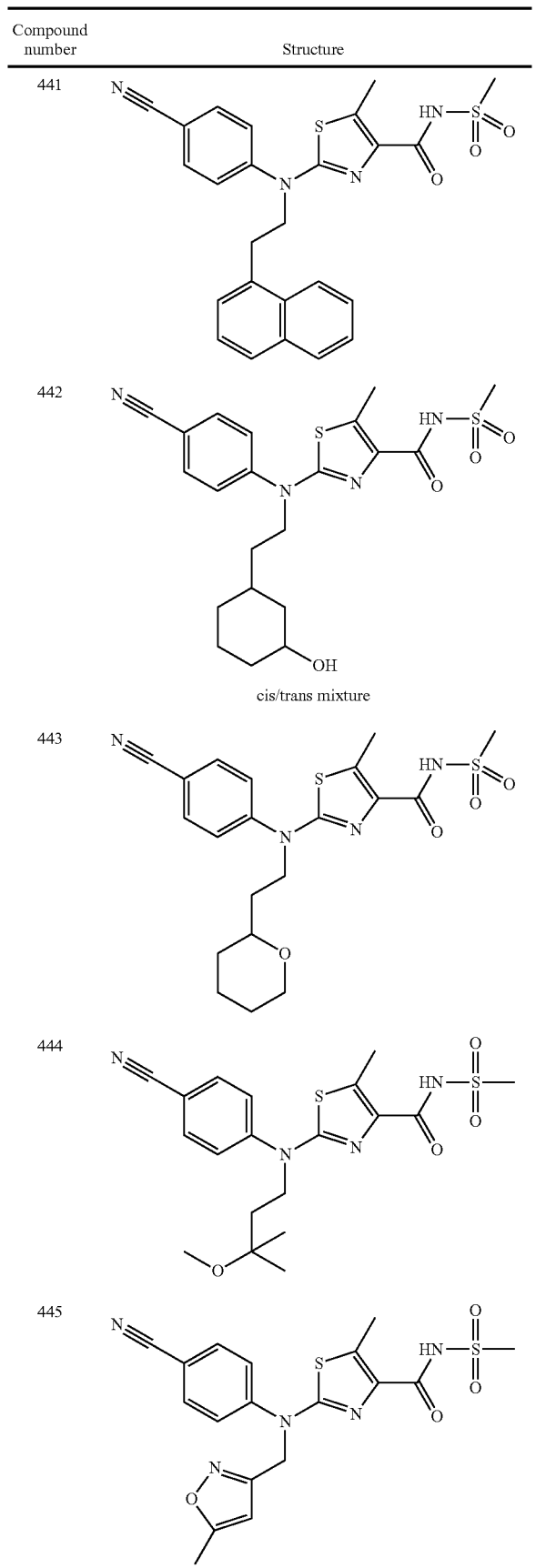 |
| 442 | 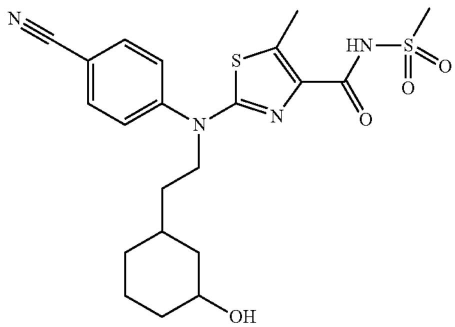 |
| 443 | 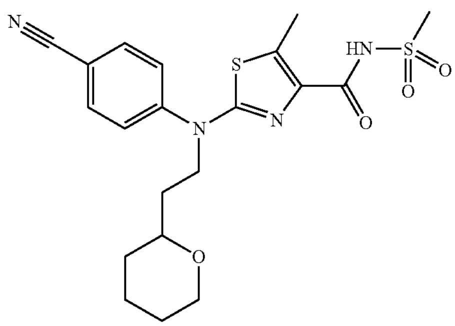 [SMILES: Cc1sc(N(CCC2CCCCO2)c2ccc(C#N)cc2)nc1C(=O)NS(C)(=O)=O] |
| 444 | 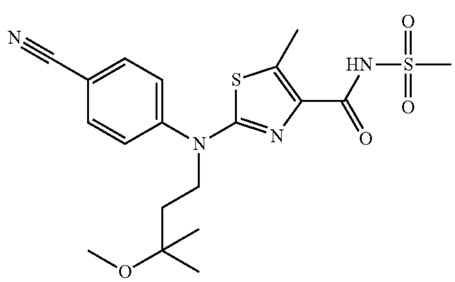 [SMILES: COC(C)(C)CCN(c1ccc(C#N)cc1)c1nc(C(=O)NS(C)(=O)=O)c(C)s1] |
| 445 | 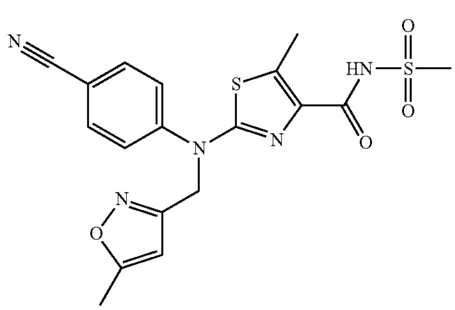 [SMILES: Cc1cc(CN(c2ccc(C#N)cc2)c2nc(C(=O)NS(C)(=O)=O)c(C)s2)no1] |
TABLE 42-continued
| Compound number | Structure |
|---|---|
| 446 | 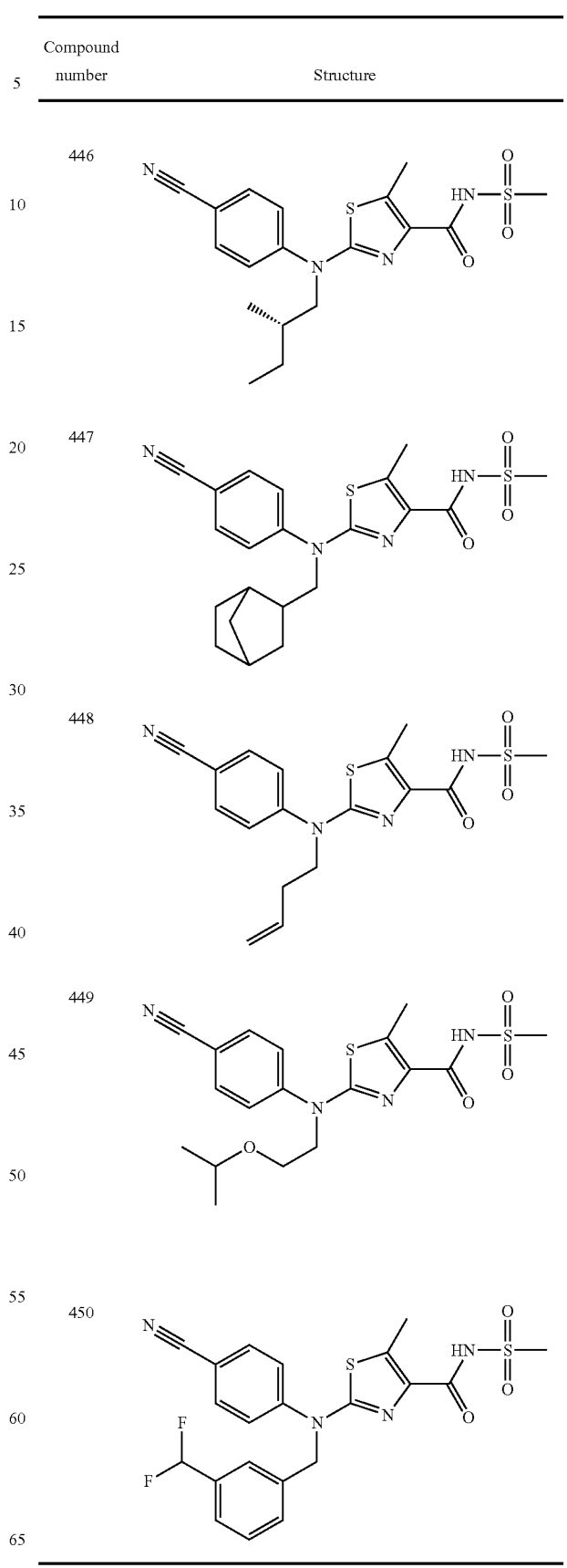 |
| 447 | 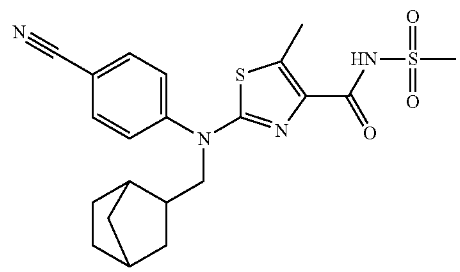 [SMILES: Cc1sc(N(CC2CC3CCC2C3)c2ccc(C#N)cc2)nc1C(=O)NS(C)(=O)=O] |
| 448 | 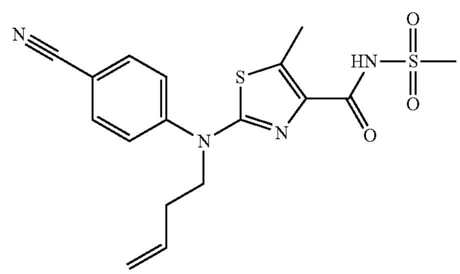 [SMILES: C=CCCN(c1ccc(C#N)cc1)c1nc(C(=O)NS(C)(=O)=O)c(C)s1] |
| 449 | 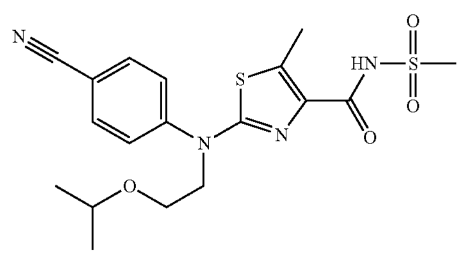 [SMILES: Cc1sc(N(CCOC(C)C)c2ccc(C#N)cc2)nc1C(=O)NS(C)(=O)=O] |
| 450 | 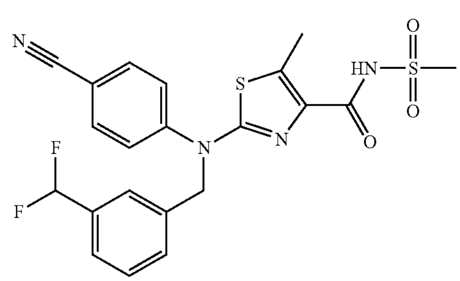 [SMILES: Cc1sc(N(Cc2cccc(C(F)F)c2)c2ccc(C#N)cc2)nc1C(=O)NS(C)(=O)=O] |

TABLE 43
| Compound number | Structure |
|---|---|
| 451 | 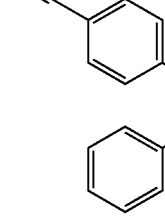 |
| 452 | 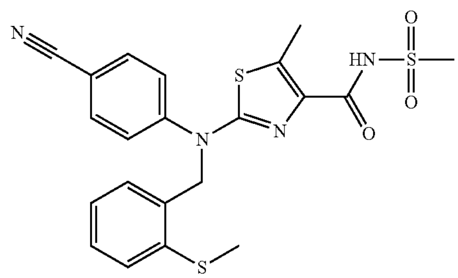 [SMILES: CSc1ccccc1CN(c1ccc(C#N)cc1)c1nc(C(=O)NS(C)(=O)=O)c(C)s1] |
| 453 | Racemate |
| 454 | 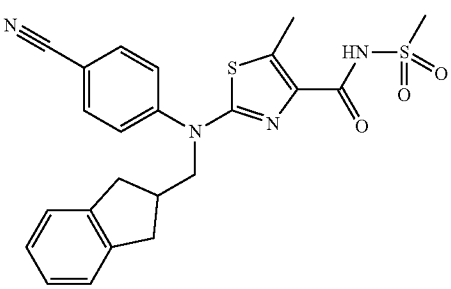 [SMILES: Cc1sc(N(CC2Cc3ccccc3C2)c2ccc(C#N)cc2)nc1C(=O)NS(C)(=O)=O] |
| 455 | 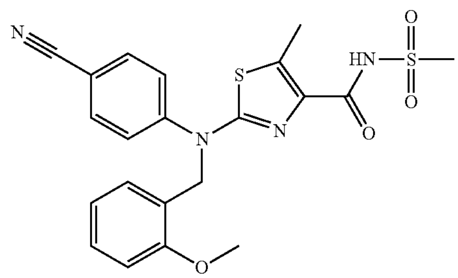 |
TABLE 43-continued
| Compound number | Structure |
|---|---|
| 456 | 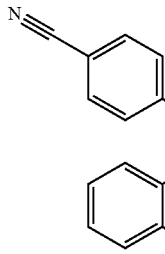 |
| 457 | Racemate |
| 458 | 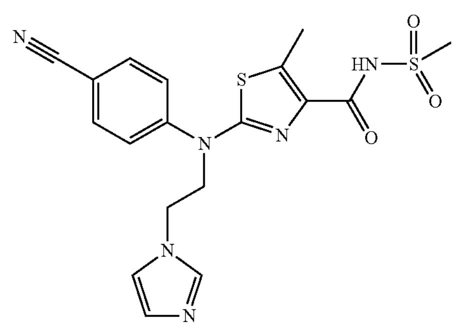 [SMILES: Cc1sc(N(CCn2ccnc2)c2ccc(C#N)cc2)nc1C(=O)NS(C)(=O)=O] |
| 459 | Racemate |

TABLE 43-continued
| Compound number | Structure |
|---|---|
| 460 | 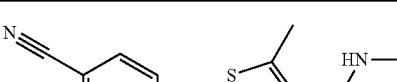 |
TABLE 44
| Compound number | Structure |
|---|---|
| 461 | 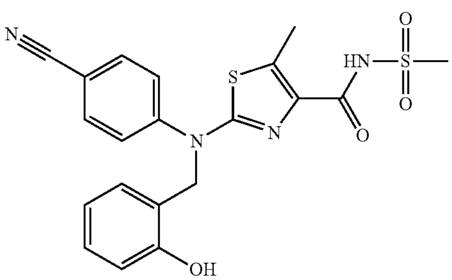 [SMILES: Cc1sc(N(Cc2ccccc2O)c2ccc(C#N)cc2)nc1C(=O)NS(C)(=O)=O] |
| 462 | 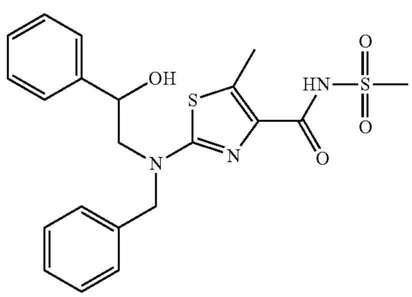 [SMILES: Cc1sc(N(Cc2ccccc2)CC(O)c2ccccc2)nc1C(=O)NS(C)(=O)=O] |
| 463 | 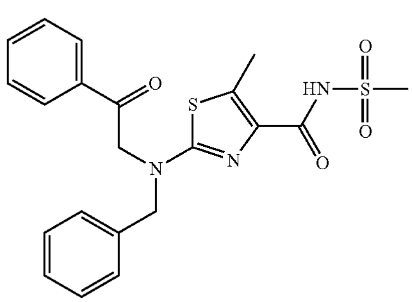 [SMILES: Cc1sc(N(CC(=O)c2ccccc2)Cc2ccccc2)nc1C(=O)NS(C)(=O)=O] |
TABLE 44-continued
| Compound number | Structure |
|---|---|
| 464 | 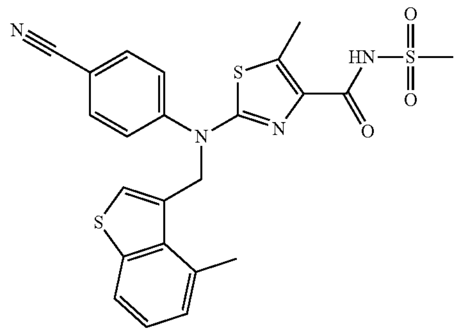 [SMILES: Cc1sc(N(Cc2csc3cccc(C)c23)c2ccc(C#N)cc2)nc1C(=O)NS(C)(=O)=O] |
| 465 | 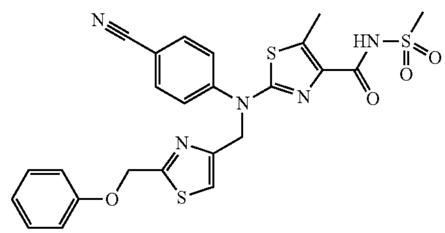 [SMILES: Cc1sc(N(Cc2csc(COc3ccccc3)n2)c2ccc(C#N)cc2)nc1C(=O)NS(C)(=O)=O] |
| 466 | 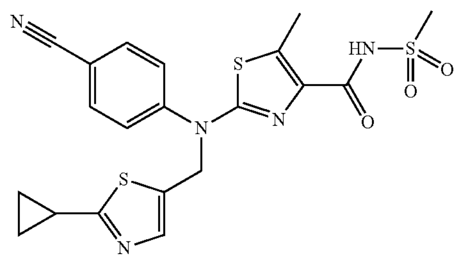 [SMILES: Cc1sc(N(Cc2cnc(C3CC3)s2)c2ccc(C#N)cc2)nc1C(=O)NS(C)(=O)=O] |
| 467 | 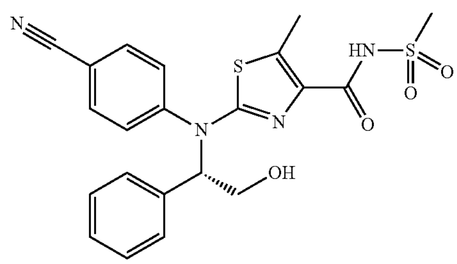 [SMILES: Cc1sc(N(c2ccc(C#N)cc2)[C@H](CO)c2ccccc2)nc1C(=O)NS(C)(=O)=O] |
| 468 | 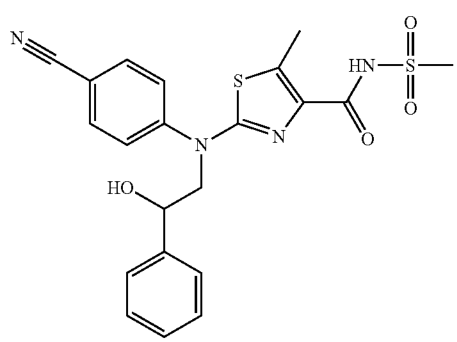 [SMILES: Cc1sc(N(CC(O)c2ccccc2)c2ccc(C#N)cc2)nc1C(=O)NS(C)(=O)=O] |

TABLE 44-continued

| Compound number | Structure |
|---|---|
| 469 | (6-(trifluoromethyl)pyridin-3-yl)-N-(4-fluorobenzyl) thiazole methylsulfonamide |
| 470 | (6-(trifluoromethyl)pyridin-3-yl)-N-(4-chlorobenzyl) thiazole methylsulfonamide |
| 471 | (6-(trifluoromethyl)pyridin-3-yl)-N-(4-(trifluoromethoxy)benzyl) thiazole methylsulfonamide |
| 472 | (6-(trifluoromethyl)pyridin-3-yl)-N-(4-(difluoromethoxy)benzyl) thiazole methylsulfonamide |

TABLE 45

| Compound number | Structure |
|---|---|
| 473 | (4-cyanophenyl)-N-((3-hydroxycycloheptyl)methyl) thiazole methylsulfonamide, Racemate |
| 474 | (4-cyanophenyl)-N-((3-hydroxycycloheptyl)methyl) thiazole methylsulfonamide, Racemate |
| 475 | (4-cyanophenyl)-N-(3-(dimethylamino)phenethyl) thiazole methylsulfonamide |
| 476 | (4-cyanophenyl)-N-(2-(trimethylsilyl)ethyl) thiazole methylsulfonamide |
| 477 | (4-cyanophenyl)-N-((dimethyl(phenyl)silyl)methyl) thiazole methylsulfonamide |

TABLE 45-continued

| Compound number | Structure |
|---|---|
| 478 | (4-cyanophenyl)-N-(2,3-dihydrobenzofuran-5-ylmethyl) substituted thiazole-methylsulfonamide |
| 479 | (4-cyanophenyl)-N-(benzofuran-2-ylmethyl) substituted thiazole-methylsulfonamide |
| 480 | (4-cyanophenyl)-N-[2-(4-dimethylaminophenyl)ethyl] substituted thiazole-methylsulfonamide |
| 481 | (4-cyanophenyl)-N-[2-(1-methylpyrrolidin-2-yl)ethyl] substituted thiazole-methylsulfonamide |

TABLE 45-continued

| Compound number | Structure |
|---|---|
| 482 | (4-cyanophenyl)-N-[2-(bicyclo[2.2.1]heptan-2-yl)ethyl] substituted thiazole-methylsulfonamide |

TABLE 46

| Compound number | Structure |
|---|---|
| 483 | (4-cyanophenyl)-N-[(1S)-2-hydroxy-1-phenylethyl] substituted thiazole-methylsulfonamide |
| 484 | (4-cyanophenyl)-N-[(1-hydroxy-2,3-dihydro-1H-inden-5-yl)methyl] substituted thiazole-methylsulfonamide |
| 485 | (4-cyanophenyl)-N-(3-cyclopentylpropyl) substituted thiazole-methylsulfonamide |

TABLE 46-continued

| Compound number | Structure |
| --- | --- |
| 486 | (4-cyanophenyl)(4-hydroxychroman-6-ylmethyl)amino thiazole N-methylsulfonyl carboxamide |
| 487 | (4-cyano-2-fluorophenyl)(benzyl)amino thiazole N-methylsulfonyl carboxamide |
| 488 | (2-(pyridin-3-yl)ethyl)(4-chlorobenzyl)amino thiazole N-methylsulfonyl carboxamide |
| 489 | (4-cyanophenyl)(spiro[2.5]octan-6-ylmethyl)amino thiazole N-methylsulfonyl carboxamide |
| 490 | (4-cyanophenyl)((3-(benzyloxy)pyridin-2-yl)methyl)amino thiazole N-methylsulfonyl carboxamide |
| 491 | (4-cyanophenyl)((6-methoxypyridin-2-yl)methyl)amino thiazole N-methylsulfonyl carboxamide |
| 492 | (4-cyanophenyl)((3-hydroxypyridin-2-yl)methyl)amino thiazole N-methylsulfonyl carboxamide |
| 493 | (4-cyanophenyl)((6-oxo-1,6-dihydropyridin-2-yl)methyl)amino thiazole N-methylsulfonyl carboxamide |
| 494 | (4-cyanophenyl)((2-(4-fluorophenyl)thiazol-5-yl)methyl)amino thiazole N-methylsulfonyl carboxamide |

TABLE 47

| Compound number | Structure |
|---|---|
| 495 | 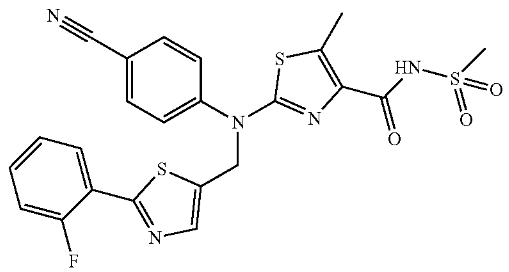 [SMILES: Cc1sc(N(Cc2cnc(-c3ccccc3F)s2)c2ccc(C#N)cc2)nc1C(=O)NS(C)(=O)=O] |
| 496 | 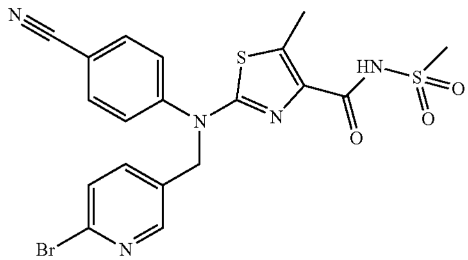 [SMILES: Cc1sc(N(Cc2ccc(Br)nc2)c2ccc(C#N)cc2)nc1C(=O)NS(C)(=O)=O] |
| 497 | 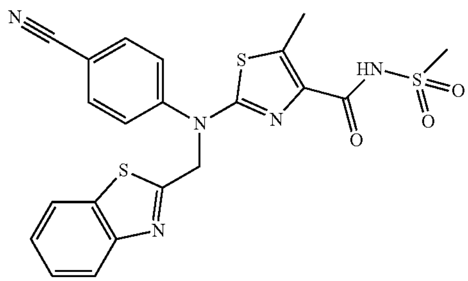 [SMILES: Cc1sc(N(Cc2nc3ccccc3s2)c2ccc(C#N)cc2)nc1C(=O)NS(C)(=O)=O] |
| 498 | 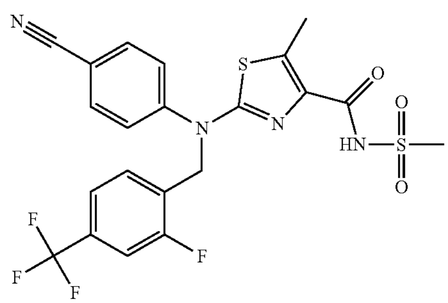 [SMILES: Cc1sc(N(Cc2ccc(C(F)(F)F)cc2F)c2ccc(C#N)cc2)nc1C(=O)NS(C)(=O)=O] |
| 499 | 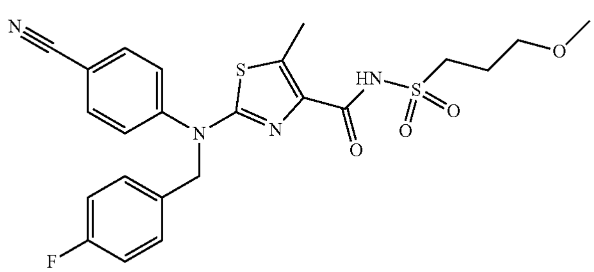 [SMILES: COCCCS(=O)(=O)NC(=O)c1nc(N(Cc2ccc(F)cc2)c2ccc(C#N)cc2)sc1C] |

TABLE 47-continued

| Compound number | Structure |
|---|---|
| 500 | (4-cyanophenyl)(4-(trifluoromethoxy)benzyl)amino-5-methylthiazole-4-carboxamide N-(pyridin-4-ylmethylsulfonyl) |
| 501 | (4-cyanophenyl)(4-fluorobenzyl)amino-5-methylthiazole-4-carboxamide N-(pyridin-4-ylmethylsulfonyl) |
| 502 | (4-chlorophenethyl)((6-methoxypyridin-2-yl)methyl)amino-5-methylthiazole-4-carboxamide N-methylsulfonyl |
| 503 | (4-chlorophenethyl)(4-cyanobenzyl)amino-5-methylthiazole-4-carboxamide N-methylsulfonyl |
| 504 | (4-chlorophenethyl)((2-methylthiazol-4-yl)methyl)amino-5-methylthiazole-4-carboxamide N-methylsulfonyl |

TABLE 47-continued

| Compound number | Structure |
|---|---|
| 505 | *(structure)* |
| 506 | *(structure)* |

TABLE 48

| Compound number | Structure |
|---|---|
| 507 | *(structure)* |
| 508 | *(structure)* |
| 509 | *(structure)* |

TABLE 48-continued
| Compound number | Structure |
|---|---|
| 510 | 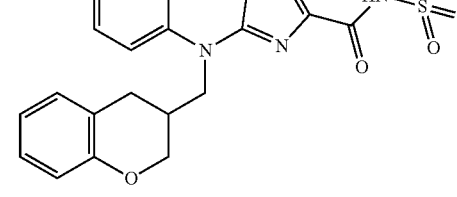 |
| 511 | 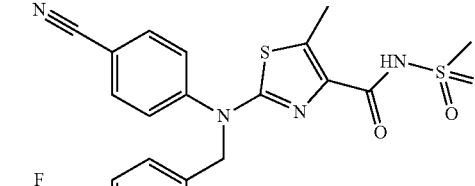 |
| 512 | 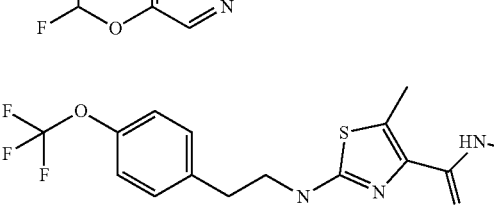 |
| 513 | 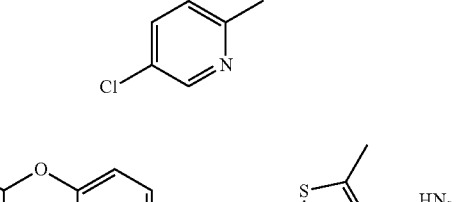 |
| 514 | 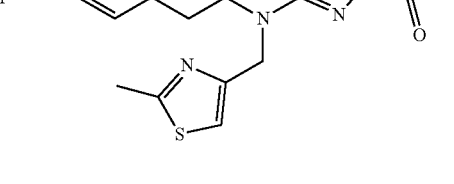 |

TABLE 48-continued

| Compound number | Structure |
|---|---|
| 515 | 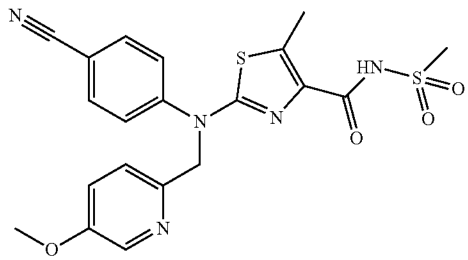 [SMILES: COc1ccc(CN(c2ccc(C#N)cc2)c2nc(C(=O)NS(C)(=O)=O)c(C)s2)nc1] |
| 516 | 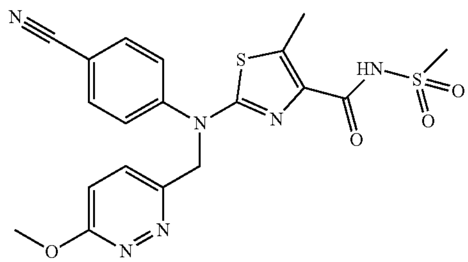 [SMILES: COc1ccc(CN(c2ccc(C#N)cc2)c2nc(C(=O)NS(C)(=O)=O)c(C)s2)nn1] |
| 517 | 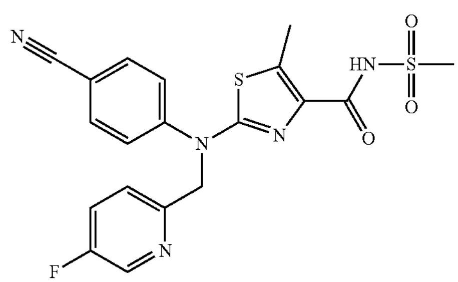 [SMILES: Cc1sc(N(Cc2ccc(F)cn2)c2ccc(C#N)cc2)nc1C(=O)NS(C)(=O)=O] |
| 518 | 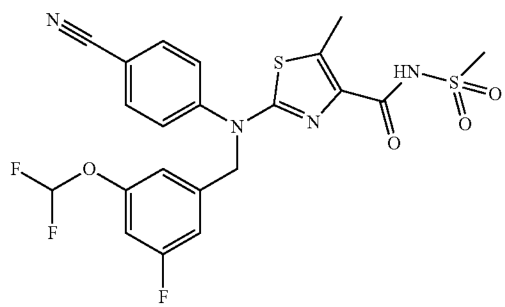 [SMILES: Cc1sc(N(Cc2cc(F)cc(OC(F)F)c2)c2ccc(C#N)cc2)nc1C(=O)NS(C)(=O)=O] |

TABLE 49

| Compound number | Structure |
|---|---|
| 519 | 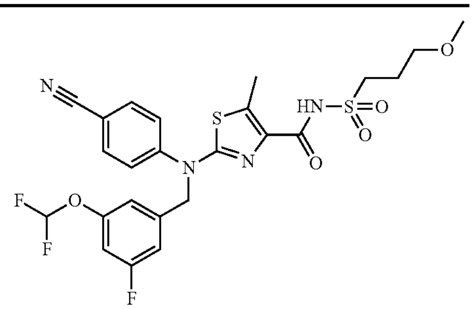 |

TABLE 49-continued

| Compound number | Structure |
|---|---|
| 520 | 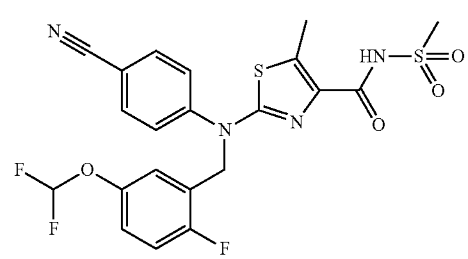 [SMILES: Cc1sc(N(Cc2cc(OC(F)F)ccc2F)c2ccc(C#N)cc2)nc1C(=O)NS(C)(=O)=O] |

TABLE 49-continued

| Compound number | Structure |
| --- | --- |
| 521 | (structure) |
| 522 | (structure) |
| 523 | (structure) |
| 524 | (structure) |
| 525 | (structure) |
| 526 | (structure) |
| 527 | (structure) |
| 528 | (structure) |
| 529 | (structure) |
| 530 | (structure) |

TABLE 50
| Compound number | Structure |
|---|---|
| 531 | 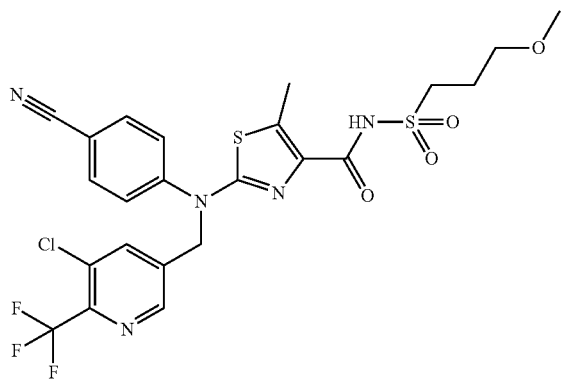 |
| 532 | 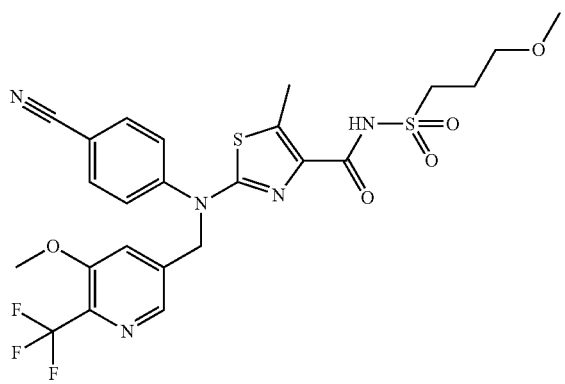 [SMILES: COCCCS(=O)(=O)NC(=O)c1nc(N(Cc2cnc(C(F)(F)F)c(OC)c2)c2ccc(C#N)cc2)sc1C] |
| 533 | 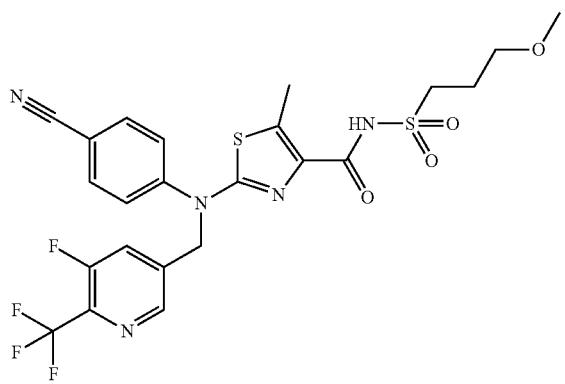 [SMILES: COCCCS(=O)(=O)NC(=O)c1nc(N(Cc2cnc(C(F)(F)F)c(F)c2)c2ccc(C#N)cc2)sc1C] |
| 534 | 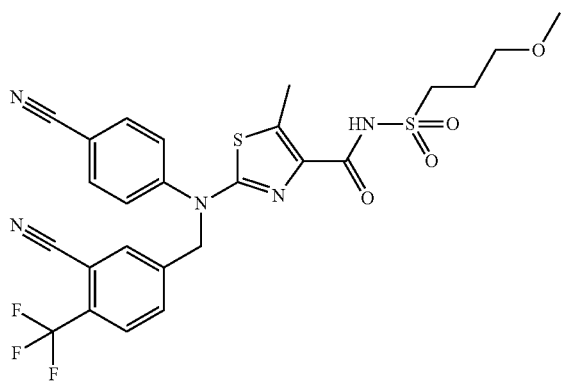 [SMILES: COCCCS(=O)(=O)NC(=O)c1nc(N(Cc2ccc(C(F)(F)F)c(C#N)c2)c2ccc(C#N)cc2)sc1C] |

TABLE 50-continued
| Compound number | Structure |
| --- | --- |
| 535 | 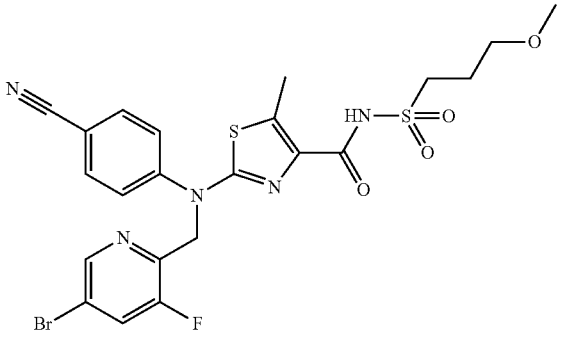 [SMILES: COCCCS(=O)(=O)NC(=O)c1nc(N(Cc2ncc(Br)cc2F)c2ccc(C#N)cc2)sc1C] |
| 536 | 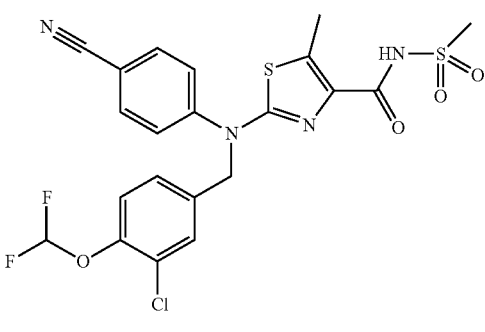 [SMILES: Cc1sc(N(Cc2ccc(OC(F)F)c(Cl)c2)c2ccc(C#N)cc2)nc1C(=O)NS(C)(=O)=O] |
| 537 | 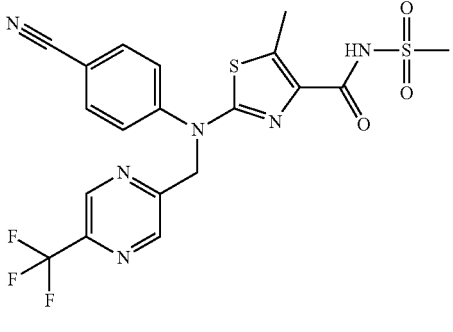 [SMILES: Cc1sc(N(Cc2cnc(C(F)(F)F)cn2)c2ccc(C#N)cc2)nc1C(=O)NS(C)(=O)=O] |
| 538 | 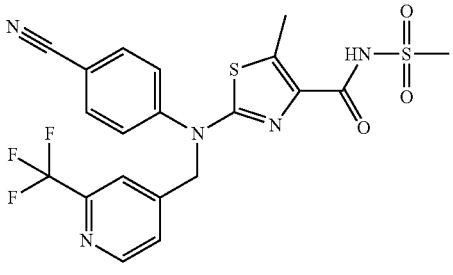 [SMILES: Cc1sc(N(Cc2ccnc(C(F)(F)F)c2)c2ccc(C#N)cc2)nc1C(=O)NS(C)(=O)=O] |
| 539 | 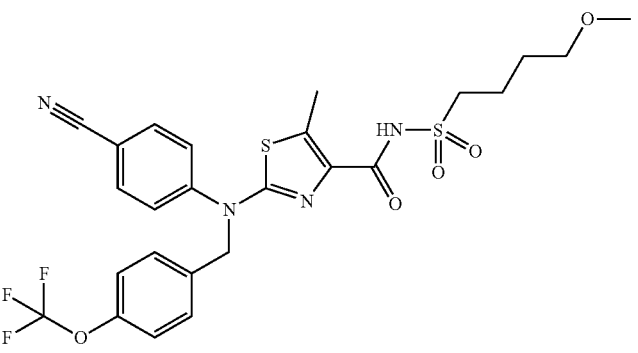 [SMILES: COCCCCS(=O)(=O)NC(=O)c1nc(N(Cc2ccc(OC(F)(F)F)cc2)c2ccc(C#N)cc2)sc1C] |

TABLE 50-continued
| Compound number | Structure |
|---|---|
| 540 | 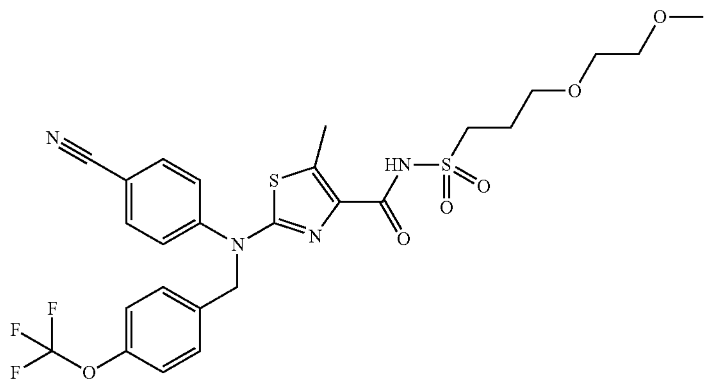 [SMILES: COCCOCCCS(=O)(=O)NC(=O)c1nc(N(Cc2ccc(OC(F)(F)F)cc2)c2ccc(C#N)cc2)sc1C] |
| 541 | 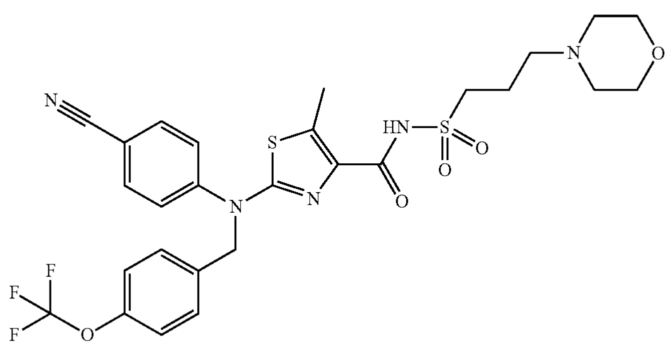 [SMILES: Cc1sc(N(Cc2ccc(OC(F)(F)F)cc2)c2ccc(C#N)cc2)nc1C(=O)NS(=O)(=O)CCCN1CCOCC1] |
| 542 | 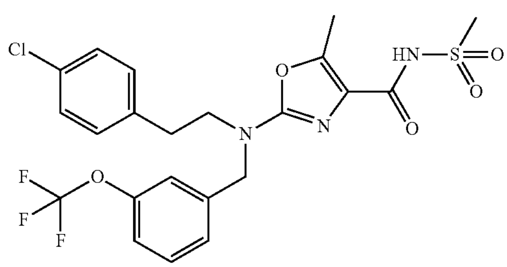 [SMILES: Cc1oc(N(CCc2ccc(Cl)cc2)Cc2cccc(OC(F)(F)F)c2)nc1C(=O)NS(C)(=O)=O] |
TABLE 51
| Compound number | Structure |
|---|---|
| 543 | |СК
TABLE 51-continued
| Compound number | Structure |
|---|---|
| 544 | 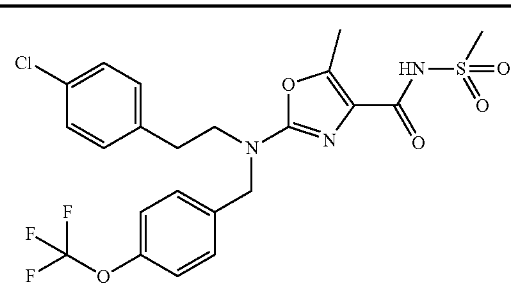 |

TABLE 51-continued

| Compound number | Structure |
|---|---|
| 545 | (4-chlorophenethyl)(benzothiazol-6-ylmethyl)amino-5-methyloxazole-4-carboxylic acid methanesulfonamide |
| 546 | (4-chlorophenethyl)((2-methylthiazol-4-yl)methyl)amino-5-methyloxazole-4-carboxylic acid methanesulfonamide |
| 547 | (4-chlorophenethyl)(2-(2-hydroxycyclohexyl)ethyl)amino-5-methyloxazole-4-carboxylic acid methanesulfonamide — Racemate |
| 548 | (4-cyanophenethyl)(4-chlorobenzyl)amino-5-methyloxazole-4-carboxylic acid methanesulfonamide |
| 549 | (4-chlorophenethyl)((5-chloropyridin-2-yl)methyl)amino-5-methyloxazole-4-carboxylic acid methanesulfonamide |
| 550 | (4-chlorophenethyl)(4-fluorobenzyl)amino-5-methyloxazole-4-carboxylic acid methanesulfonamide |
| 551 | (4-chlorophenethyl)((6-(trifluoromethyl)pyridin-3-yl)methyl)amino-5-methyloxazole-4-carboxylic acid methanesulfonamide |
| 552 | (4-cyanophenethyl)(4-fluorobenzyl)amino-5-methyloxazole-4-carboxylic acid methanesulfonamide |
| 553 | (4-cyanophenethyl)((4-(difluoromethoxy)benzyl))amino-5-methyloxazole-4-carboxylic acid methanesulfonamide |
| 554 | (4-cyanophenethyl)(2-chloro-4-fluorobenzyl)amino-5-methyloxazole-4-carboxylic acid methanesulfonamide |

TABLE 52
| Compound number | Structure |
|---|---|
| 555 | 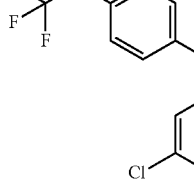 |
| 556 | 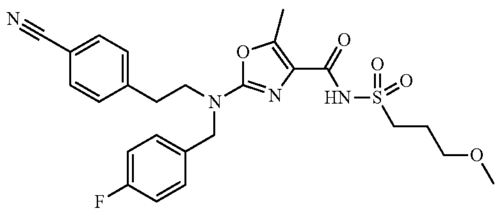 [SMILES: COCCCS(=O)(=O)NC(=O)c1nc(N(CCc2ccc(C#N)cc2)Cc2ccc(F)cc2)oc1C] |
| 557 | 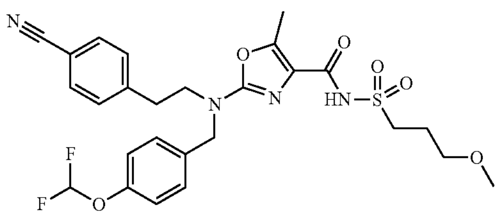 [SMILES: COCCCS(=O)(=O)NC(=O)c1nc(N(CCc2ccc(C#N)cc2)Cc2ccc(OC(F)F)cc2)oc1C] |
| 558 | 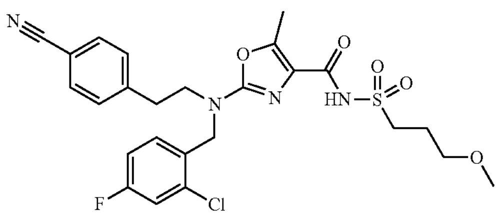 [SMILES: COCCCS(=O)(=O)NC(=O)c1nc(N(CCc2ccc(C#N)cc2)Cc2ccc(F)cc2Cl)oc1C] |
| 559 | 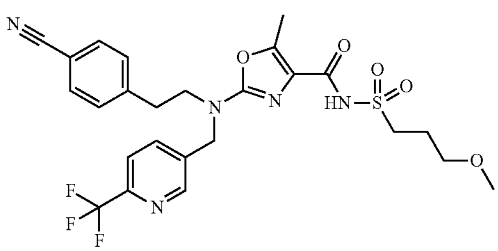 [SMILES: COCCCS(=O)(=O)NC(=O)c1nc(N(CCc2ccc(C#N)cc2)Cc2ccc(C(F)(F)F)nc2)oc1C] |
| 560 | 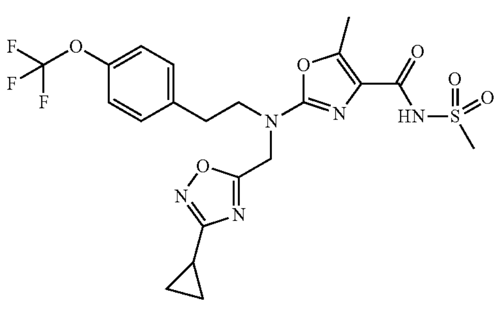 [SMILES: Cc1oc(N(CCc2ccc(OC(F)(F)F)cc2)Cc2nc(C3CC3)no2)nc1C(=O)NS(C)(=O)=O] |
TABLE 52-continued
| Compound number | Structure |
|---|---|
| 561 | 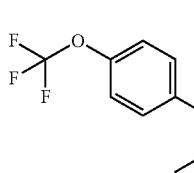 |
| 562 | 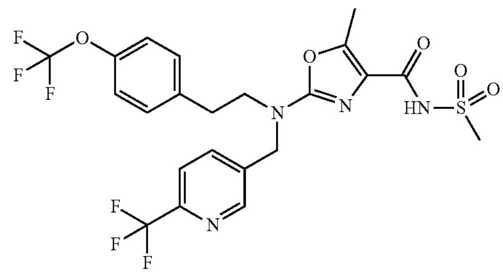 [SMILES: Cc1oc(N(CCc2ccc(OC(F)(F)F)cc2)Cc2ccc(C(F)(F)F)nc2)nc1C(=O)NS(C)(=O)=O] |
| 563 | 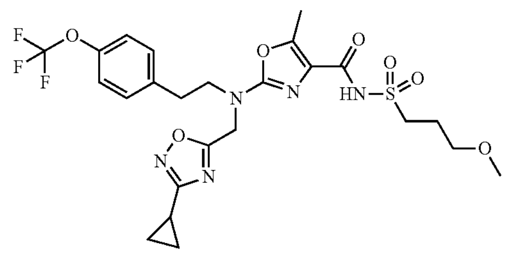 [SMILES: COCCCS(=O)(=O)NC(=O)c1nc(N(CCc2ccc(OC(F)(F)F)cc2)Cc2nc(C3CC3)no2)oc1C] |
| 564 | 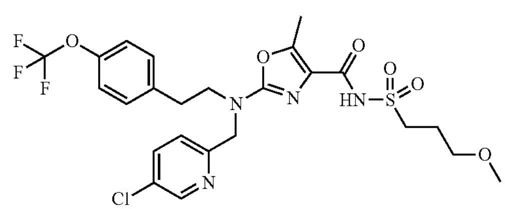 [SMILES: COCCCS(=O)(=O)NC(=O)c1nc(N(CCc2ccc(OC(F)(F)F)cc2)Cc2ccc(Cl)cn2)oc1C] |
| 565 | 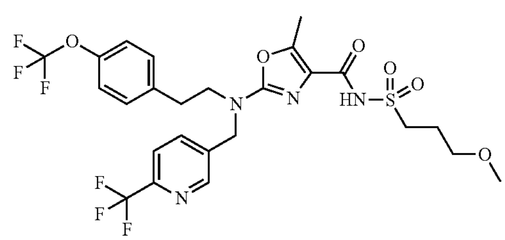 [SMILES: COCCCS(=O)(=O)NC(=O)c1nc(N(CCc2ccc(OC(F)(F)F)cc2)Cc2ccc(C(F)(F)F)nc2)oc1C] |
| 566 | 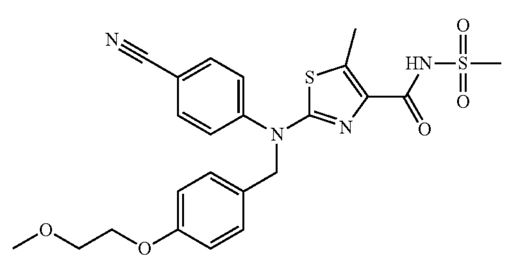 |

TABLE 53

| Compound number | Structure |
|---|---|
| 567 | (structure) |
| 568 | (structure) |
| 569 | (structure) |
| 570 | (structure) |
| 571 | (structure) |

TABLE 53-continued

| Compound number | Structure |
|---|---|
| 572 | (structure) |
| 573 | (structure) |
| 574 | (structure) |
| 575 | (structure) |
| 576 | (structure) |

TABLE 53-continued

| Compound number | Structure |
|---|---|
| 577 | (structure) |
| 578 | (structure) |

TABLE 54

| Compound number | Structure |
|---|---|
| 579 | (structure) |
| 580 | (structure) |
| 581 | (structure) |

TABLE 54-continued

| Compound number | Structure |
|---|---|
| 582 | (structure) |
| 583 | (structure) |
| 584 | (structure) |
| 585 | (structure) |
| 586 | (structure) |
| 587 | (structure) |

TABLE 54-continued
| Compound number | Structure |
|---|---|
| 588 | 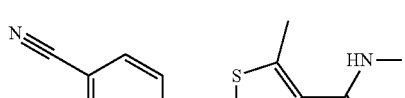 |
TABLE 55
| Compound number | Structure |
|---|---|
| 589 | 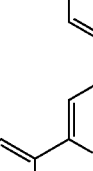 |
| 590 | 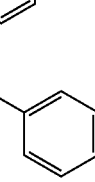 |
| 591 | 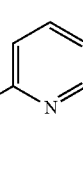 |
TABLE 55-continued
| Compound number | Structure |
|---|---|
| 592 | 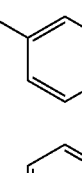 |
| 593 | 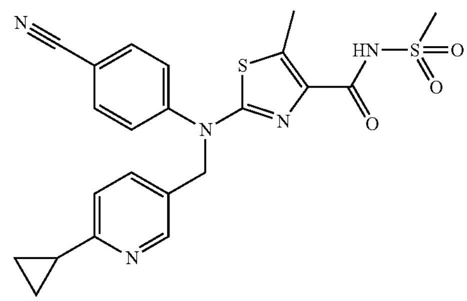 [SMILES: Cc1sc(N(Cc2ccc(C3CC3)nc2)c2ccc(C#N)cc2)nc1C(=O)NS(C)(=O)=O] |
| 594 | 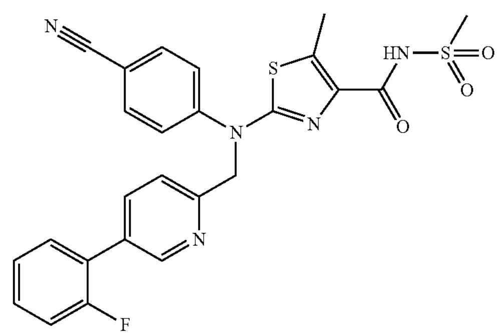 [SMILES: Cc1sc(N(Cc2ccc(-c3ccccc3F)cn2)c2ccc(C#N)cc2)nc1C(=O)NS(C)(=O)=O] |
| 595 | 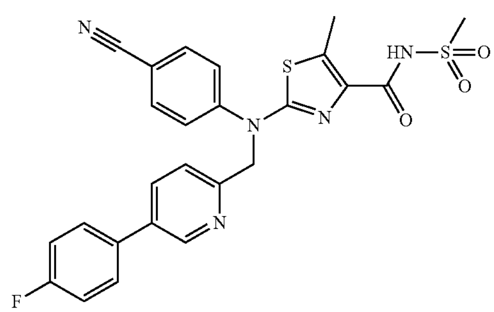 [SMILES: Cc1sc(N(Cc2ccc(-c3ccc(F)cc3)cn2)c2ccc(C#N)cc2)nc1C(=O)NS(C)(=O)=O] |
| 596 | 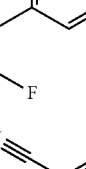 |

TABLE 55-continued

| Compound number | Structure |
|---|---|
| 597 | (4-cyanophenyl)(benzyl)amino-thiazole-4-carboxylic acid methylsulfonamide |
| 598 | (4-cyanophenyl)(benzyl)amino-5-methyl-oxazole-4-carboxylic acid methylsulfonamide |

TABLE 56

| Compound number | Structure |
|---|---|
| 599 | (4-cyanophenyl)(benzyl)amino-5-ethyl-thiazole-4-carboxylic acid methylsulfonamide |
| 600 | (4-cyanophenyl)(benzyl)amino-5-isopropyl-thiazole-4-carboxylic acid methylsulfonamide |
| 601 | (4-cyanophenyl)(benzyl)amino-5-phenyl-thiazole-4-carboxylic acid methylsulfonamide |
| 602 | (5-cyanopyridin-2-yl)(benzyl)amino-5-methyl-thiazole-4-carboxylic acid methylsulfonamide |
| 603 | (4-cyanophenyl)(benzyl)amino-5-bromo-thiazole-4-carboxylic acid methylsulfonamide |
| 604 | (6-cyanopyridin-3-yl)(benzyl)amino-5-methyl-thiazole-4-carboxylic acid methylsulfonamide |
| 605 | (3-(2-hydroxyethyl)phenyl)(benzyl)amino-5-methyl-thiazole-4-carboxylic acid methylsulfonamide |

TABLE 56-continued

| Compound number | Structure |
|---|---|
| 606 | 2-[N-benzyl-N-(2-(hydroxymethyl)phenyl)amino]-5-methyl-N-(methylsulfonyl)thiazole-4-carboxamide |
| 607 | 2-[N-(4-cyanophenyl)-N-(4-(trifluoromethoxy)benzyl)amino]-5-methyl-N-(methylsulfonyl)oxazole-4-carboxamide |
| 608 | 2-[N-(4-cyanophenyl)-N-(3,4-dichlorobenzyl)amino]-5-methyl-N-(methylsulfonyl)oxazole-4-carboxamide |
| 609 | 2-[N-(benzo[b]thiophen-2-ylmethyl)-N-(4-cyanophenyl)amino]-5-bromo-N-(methylsulfonyl)thiazole-4-carboxamide |
| 610 | 2-[N-(4-cyanophenyl)-N-(4-fluorobenzyl)amino]-5-methyl-N-(methylsulfonyl)oxazole-4-carboxamide |

TABLE 57

| Compound number | Structure |
|---|---|
| 611 | 2-[N-(3-chlorobenzyl)-N-(4-cyanophenyl)amino]-5-methyl-N-(methylsulfonyl)oxazole-4-carboxamide |
| 612 | 2-[N-(4-cyanophenyl)-N-(3-fluorobenzyl)amino]-5-methyl-N-(methylsulfonyl)oxazole-4-carboxamide |
| 613 | 2-[N-(4-cyanophenyl)-N-(3-(trifluoromethoxy)benzyl)amino]-5-methyl-N-(methylsulfonyl)oxazole-4-carboxamide |
| 614 | 2-[N-(4-cyanophenyl)-N-(2-(difluoromethoxy)benzyl)amino]-5-methyl-N-(methylsulfonyl)oxazole-4-carboxamide |
| 615 | 2-[N-(4-cyanophenyl)-N-(4-cyanobenzyl)amino]-5-methyl-N-(methylsulfonyl)oxazole-4-carboxamide |

TABLE 57-continued
| Compound number | Structure |
|---|---|
| 616 | 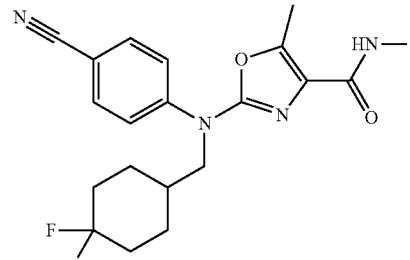 |
| 617 | 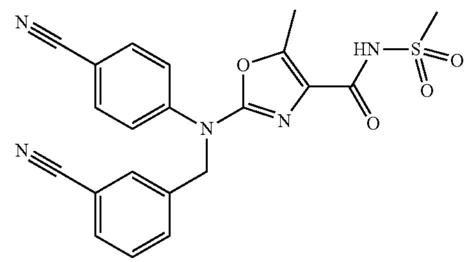 [SMILES: Cc1oc(N(Cc2cccc(C#N)c2)c2ccc(C#N)cc2)nc1C(=O)NS(C)(=O)=O] |
| 618 | 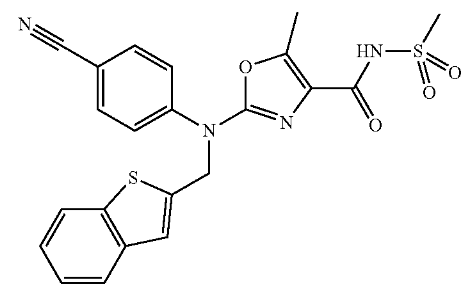 [SMILES: Cc1oc(N(Cc2cc3ccccc3s2)c2ccc(C#N)cc2)nc1C(=O)NS(C)(=O)=O] |
| 619 | 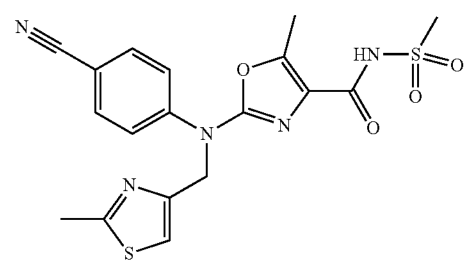 [SMILES: Cc1nc(CN(c2ccc(C#N)cc2)c2nc(C(=O)NS(C)(=O)=O)c(C)o2)cs1] |
| 620 | 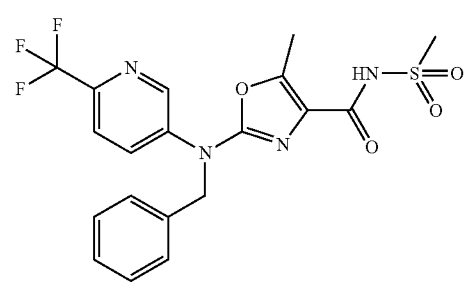 [SMILES: Cc1oc(N(Cc2ccccc2)c2ccc(C(F)(F)F)nc2)nc1C(=O)NS(C)(=O)=O] |
TABLE 57-continued
| Compound number | Structure |
|---|---|
| 621 | 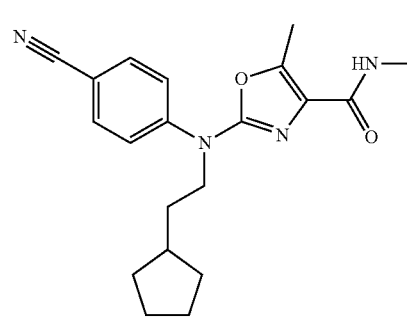 |
| 622 | |
TABLE 58
| Compound number | Structure |
|---|---|
| 623 | 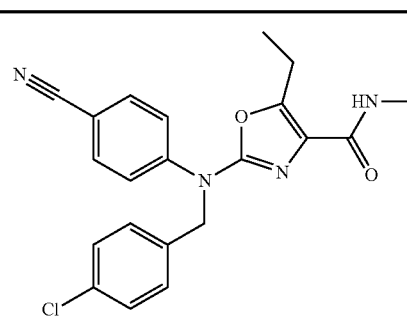 |
| 624 | 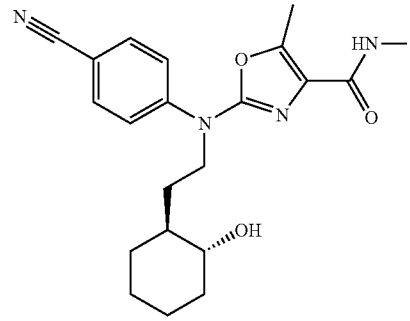 |
| | Racemate |

TABLE 58-continued

| Compound number | Structure |
|---|---|
| 625 | |
| 626 | |
| 627 | |
| 628 | |
| 629 | Racemate |
| 630 | 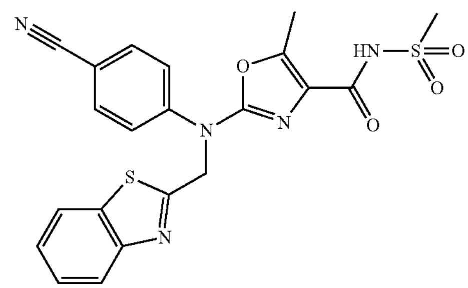 [SMILES: Cc1oc(N(Cc2nc3ccccc3s2)c2ccc(C#N)cc2)nc1C(=O)NS(C)(=O)=O] |
| 631 | 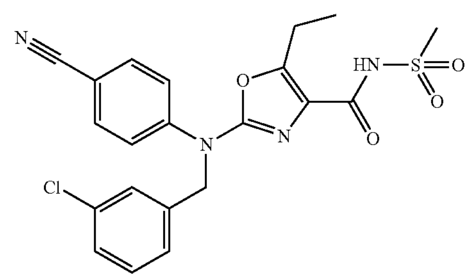 [SMILES: CCc1oc(N(Cc2cccc(Cl)c2)c2ccc(C#N)cc2)nc1C(=O)NS(C)(=O)=O] |
| 632 | 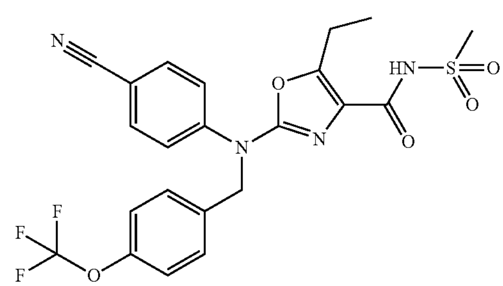 [SMILES: CCc1oc(N(Cc2ccc(OC(F)(F)F)cc2)c2ccc(C#N)cc2)nc1C(=O)NS(C)(=O)=O] |
| 633 | 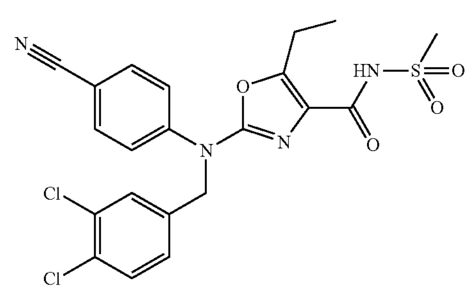 [SMILES: CCc1oc(N(Cc2ccc(Cl)c(Cl)c2)c2ccc(C#N)cc2)nc1C(=O)NS(C)(=O)=O] |

TABLE 58-continued
| Compound number | Structure |
|---|---|
| 634 | 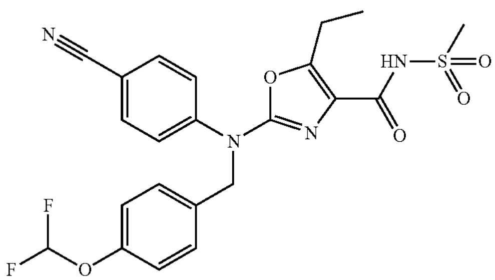 [SMILES: CCc1oc(N(Cc2ccc(OC(F)F)cc2)c2ccc(C#N)cc2)nc1C(=O)NS(C)(=O)=O] |
TABLE 59
| Compound number | Structure |
|---|---|
| 635 | |
| 636 | |
| 637 | |
| 638 | 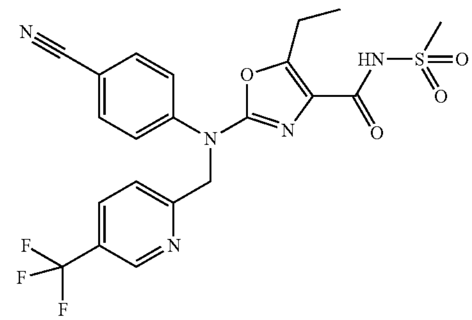 [SMILES: CCc1oc(N(Cc2ccc(C(F)(F)F)cn2)c2ccc(C#N)cc2)nc1C(=O)NS(C)(=O)=O] |
| 639 | 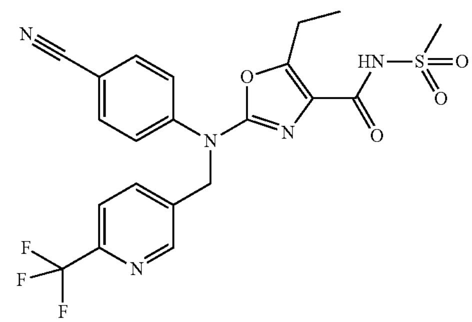 [SMILES: CCc1oc(N(Cc2ccc(C(F)(F)F)nc2)c2ccc(C#N)cc2)nc1C(=O)NS(C)(=O)=O] |
| 640 | 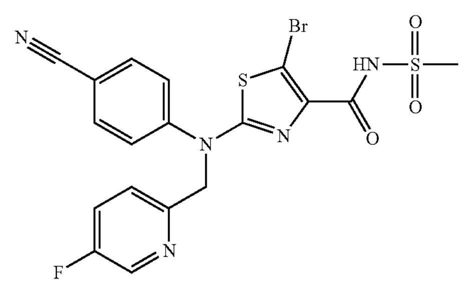 [SMILES: CS(=O)(=O)NC(=O)c1nc(N(Cc2ccc(F)cn2)c2ccc(C#N)cc2)sc1Br] |
| 641 | 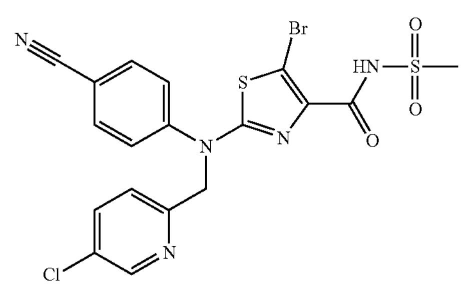 [SMILES: CS(=O)(=O)NC(=O)c1nc(N(Cc2ccc(Cl)cn2)c2ccc(C#N)cc2)sc1Br] |
| 642 | 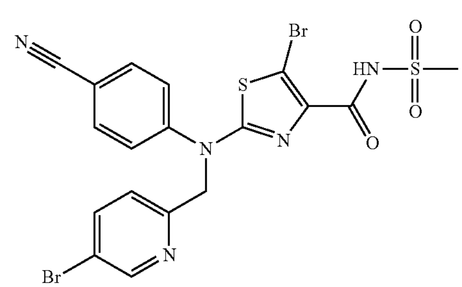 |

TABLE 59-continued
| Compound number | Structure |
|---|---|
| 643 | 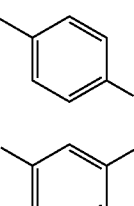 |
| 644 | 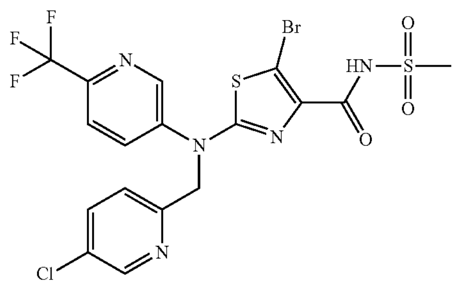 [SMILES: CS(=O)(=O)NC(=O)c1nc(N(Cc2ccc(Cl)cn2)c2ccc(C(F)(F)F)nc2)sc1Br] |
| 645 | 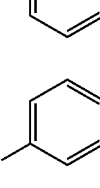 |
| 646 | 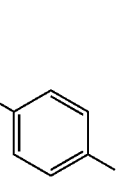 |
TABLE 60
| Compound number | Structure |
|---|---|
| 647 | 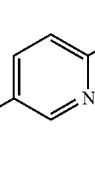 |
| 648 | 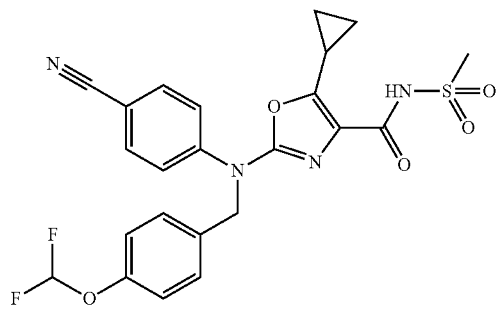 [SMILES: CS(=O)(=O)NC(=O)c1nc(N(Cc2ccc(OC(F)F)cc2)c2ccc(C#N)cc2)oc1C1CC1] |
| 649 | 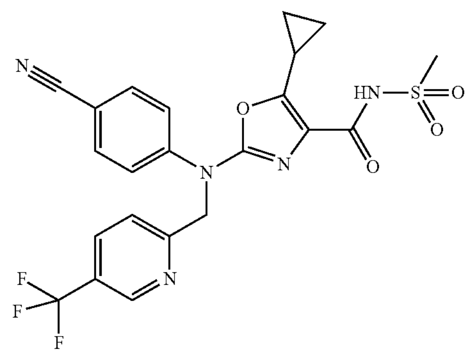 [SMILES: CS(=O)(=O)NC(=O)c1nc(N(Cc2ccc(C(F)(F)F)cn2)c2ccc(C#N)cc2)oc1C1CC1] |
| 650 | 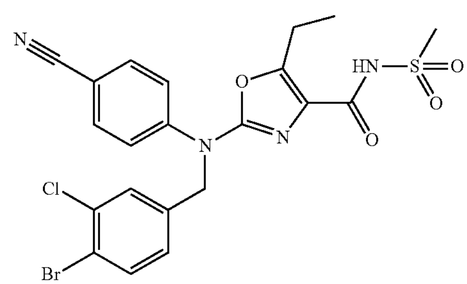 |
| 651 | 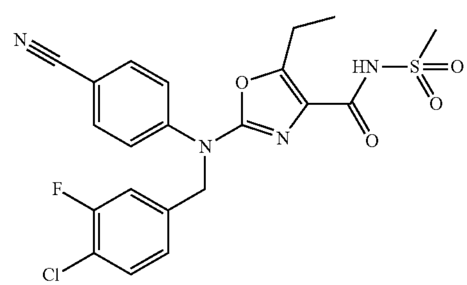 |

TABLE 60-continued

| Compound number | Structure |
|---|---|
| 652 | (structure) |
| 653 | (structure) |
| 654 | (structure) |
| 655 | (structure) |
| 656 | (structure) |//

TABLE 60-continued

| Compound number | Structure |
|---|---|
| 657 | (structure) |
| 658 | (structure) |

TABLE 61

| Compound number | Structure |
|---|---|
| 659 | (structure) |
| 660 | (structure) |

TABLE 61-continued
| Compound number | Structure |
|---|---|
| 661 | 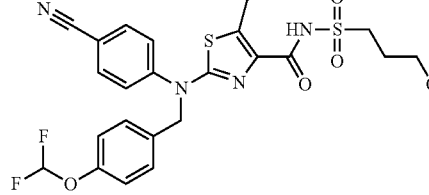 |
| 662 | 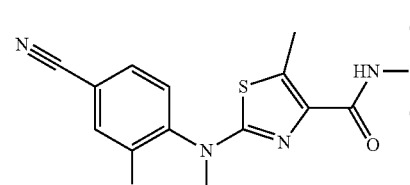 |
| 663 | 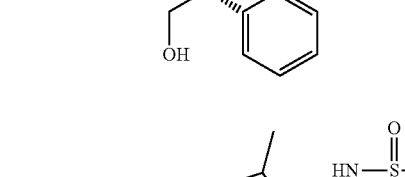 |
| 664 | 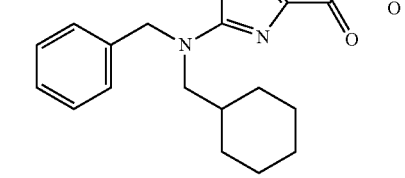 |
| 665 | 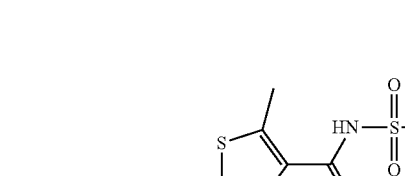 |
| 666 | |
| 667 | |
| 668 | |
| 669 | |
| 670 | |

TABLE 62

| Compound number | Structure |
|---|---|
| 671 | (3-chlorophenethyl)(benzyl)amino-5-methylthiazole-4-carboxylic acid methanesulfonamide |
| 672 | (3-cyanophenethyl)(benzyl)amino-5-methylthiazole-4-carboxylic acid methanesulfonamide |
| 673 | (2-phenylpropyl)(benzyl)amino-5-methylthiazole-4-carboxylic acid methanesulfonamide |
| 674 | (1-methyl-2-phenylethyl)(benzyl)amino-5-methylthiazole-4-carboxylic acid methanesulfonamide |
| 675 | ((6-cyanobenzo[b]thiophen-3-yl)methyl)(benzyl)amino-5-methylthiazole-4-carboxylic acid methanesulfonamide |

TABLE 62-continued

| Compound number | Structure |
|---|---|
| 676 | ((6-(trifluoromethyl)benzo[b]thiophen-3-yl)methyl)(benzyl)amino-5-methylthiazole-4-carboxylic acid methanesulfonamide |
| 677 | ((6-(trifluoromethyl)benzo[b]thiophen-3-yl)methyl)(4-chlorobenzyl)amino-5-methylthiazole-4-carboxylic acid methanesulfonamide |
| 678 | (4-methoxyphenethyl)(benzyl)amino-5-methylthiazole-4-carboxylic acid methanesulfonamide |
| 679 | (2-(2H-1,2,3-triazol-2-yl)ethyl)(benzyl)amino-5-methylthiazole-4-carboxylic acid methanesulfonamide |
| 680 | (2-(1H-1,2,4-triazol-1-yl)ethyl)(benzyl)amino-5-methylthiazole-4-carboxylic acid methanesulfonamide |

TABLE 62-continued

| Compound number | Structure |
|---|---|
| 681 | (structure) |
| 682 | (structure) |

TABLE 63

| Compound number | Structure |
|---|---|
| 683 | (structure) |
| 684 | (structure) |
| 685 | (structure) |

TABLE 63-continued

| Compound number | Structure |
|---|---|
| 686 | (structure) |
| 687 | (structure) |
| 688 | (structure) |
| 689 | (structure) |
| 690 | (structure) |

TABLE 63-continued

| Compound number | Structure |
| --- | --- |
| 691 | 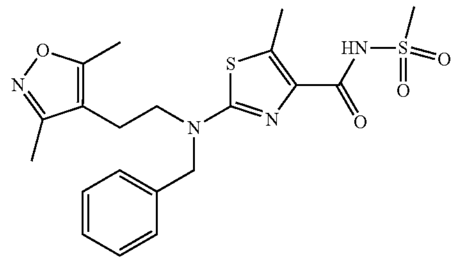 [SMILES: Cc1noc(C)c1CCN(Cc1ccccc1)c1nc(C(=O)NS(C)(=O)=O)c(C)s1] |
| 692 | 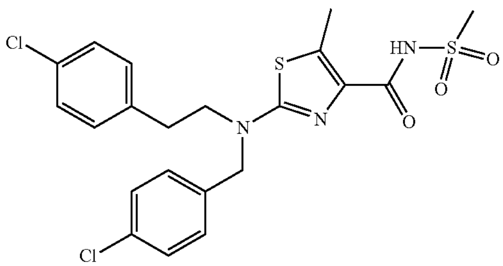 [SMILES: Cc1sc(N(CCc2ccc(Cl)cc2)Cc2ccc(Cl)cc2)nc1C(=O)NS(C)(=O)=O] |
| 693 | 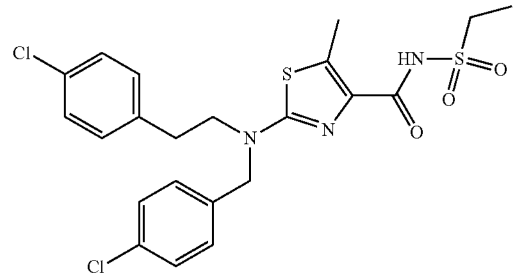 [SMILES: CCS(=O)(=O)NC(=O)c1nc(N(CCc2ccc(Cl)cc2)Cc2ccc(Cl)cc2)sc1C] |
| 694 | 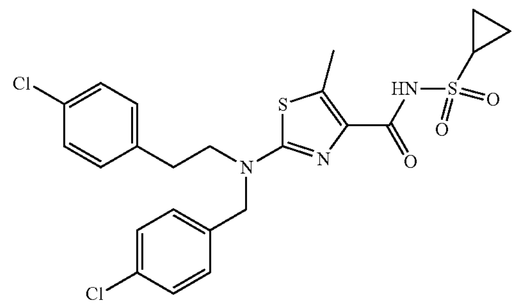 [SMILES: Cc1sc(N(CCc2ccc(Cl)cc2)Cc2ccc(Cl)cc2)nc1C(=O)NS(=O)(=O)C1CC1] |

TABLE 64

| Compound number | Structure |
| --- | --- |
| 695 | 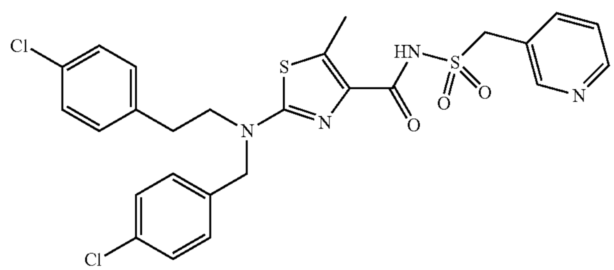 [SMILES: Cc1sc(N(CCc2ccc(Cl)cc2)Cc2ccc(Cl)cc2)nc1C(=O)NS(=O)(=O)Cc1cccnc1] |
| 696 | 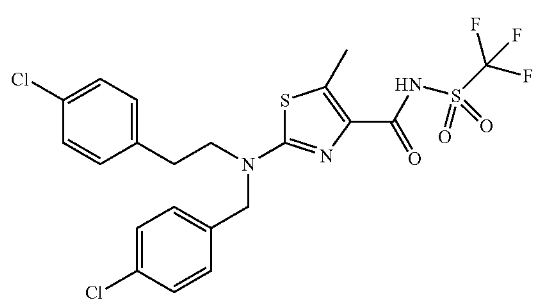 [SMILES: Cc1sc(N(CCc2ccc(Cl)cc2)Cc2ccc(Cl)cc2)nc1C(=O)NS(=O)(=O)C(F)(F)F] |

TABLE 64-continued
| Compound number | Structure |
|---|---|
| 697 | 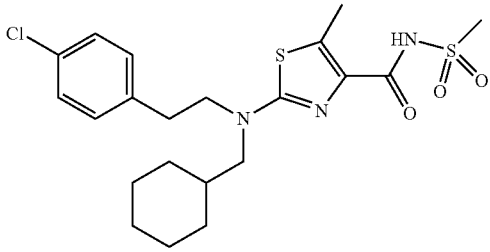 [SMILES: Cc1sc(N(CCc2ccc(Cl)cc2)CC2CCCCC2)nc1C(=O)NS(C)(=O)=O] |
| 698 | 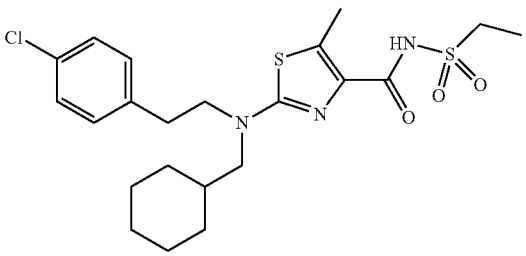 [SMILES: CCS(=O)(=O)NC(=O)c1nc(N(CCc2ccc(Cl)cc2)CC2CCCCC2)sc1C] |
| 699 | 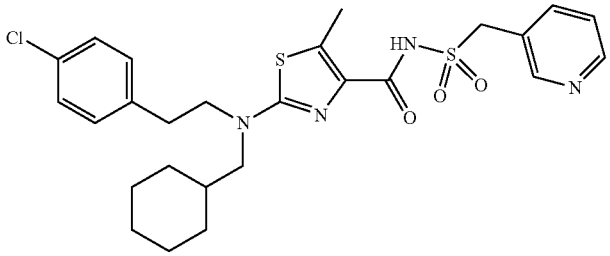 [SMILES: Cc1sc(N(CCc2ccc(Cl)cc2)CC2CCCCC2)nc1C(=O)NS(=O)(=O)Cc1cccnc1] |
| 700 | 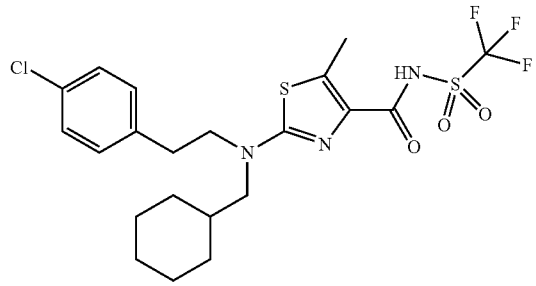 [SMILES: Cc1sc(N(CCc2ccc(Cl)cc2)CC2CCCCC2)nc1C(=O)NS(=O)(=O)C(F)(F)F] |
| 701 | 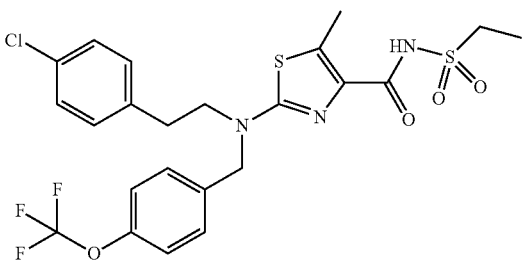 [SMILES: CCS(=O)(=O)NC(=O)c1nc(N(CCc2ccc(Cl)cc2)Cc2ccc(OC(F)(F)F)cc2)sc1C] |

TABLE 64-continued
| Compound number | Structure |
|---|---|
| 702 | 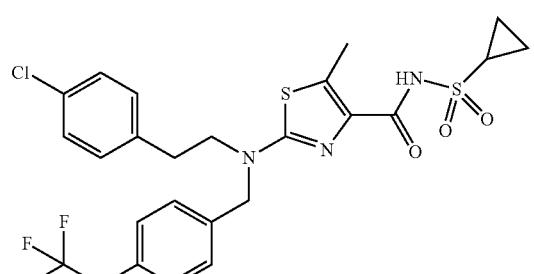 |
| 703 | 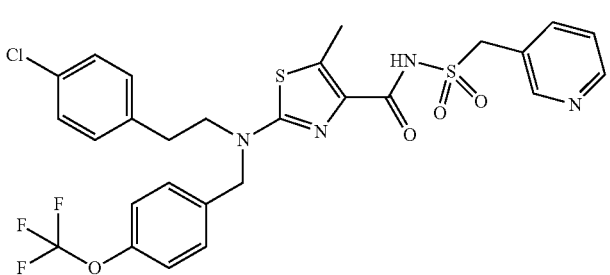 [SMILES: Cc1sc(N(CCc2ccc(Cl)cc2)Cc2ccc(OC(F)(F)F)cc2)nc1C(=O)NS(=O)(=O)Cc1cccnc1] |
| 704 | 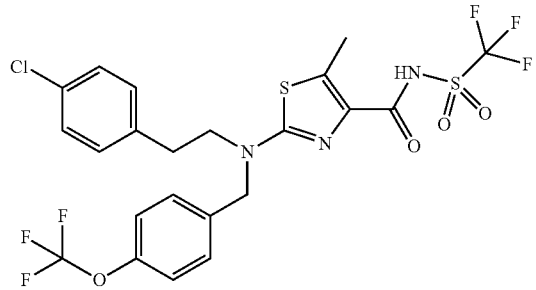 [SMILES: Cc1sc(N(CCc2ccc(Cl)cc2)Cc2ccc(OC(F)(F)F)cc2)nc1C(=O)NS(=O)(=O)C(F)(F)F] |
| 705 | 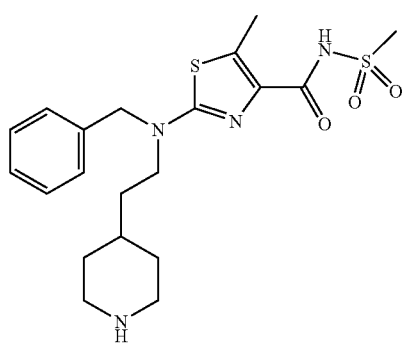 [SMILES: Cc1sc(N(CCC2CCNCC2)Cc2ccccc2)nc1C(=O)NS(C)(=O)=O] |
| 706 | 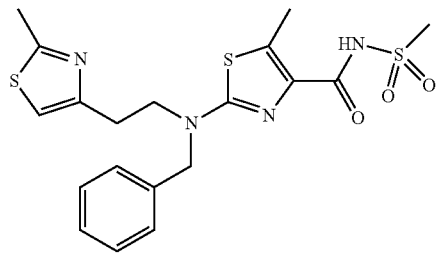 [SMILES: Cc1nc(CCN(Cc2ccccc2)c2nc(C(=O)NS(C)(=O)=O)c(C)s2)cs1] |

TABLE 65

| Compound number | Structure |
|---|---|
| 707 | 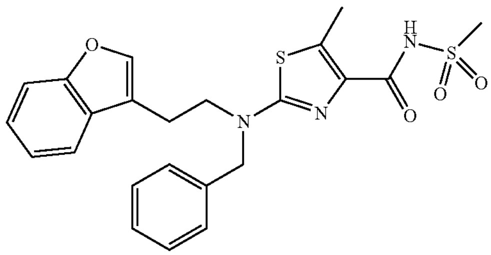 [SMILES: Cc1sc(N(CCc2coc3ccccc23)Cc2ccccc2)nc1C(=O)NS(C)(=O)=O] |
| 708 | 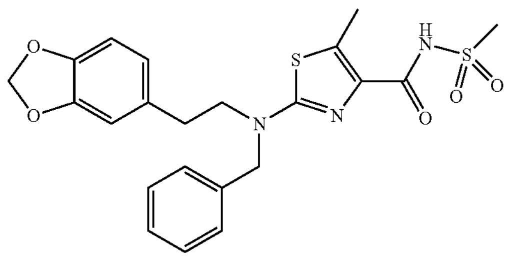 [SMILES: Cc1sc(N(CCc2ccc3c(c2)OCO3)Cc2ccccc2)nc1C(=O)NS(C)(=O)=O] |
| 709 | 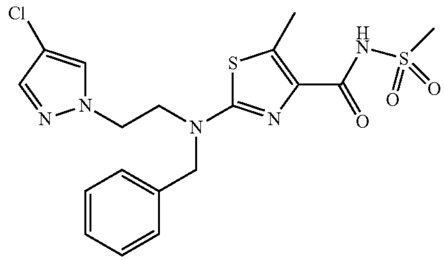 [SMILES: Cc1sc(N(CCn2cc(Cl)cn2)Cc2ccccc2)nc1C(=O)NS(C)(=O)=O] |
| 710 | 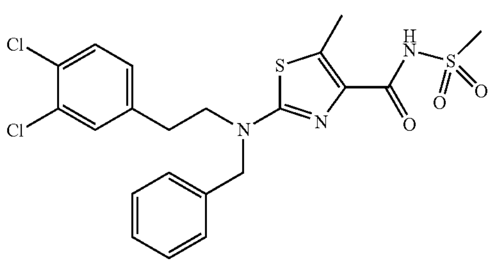 [SMILES: Cc1sc(N(CCc2ccc(Cl)c(Cl)c2)Cc2ccccc2)nc1C(=O)NS(C)(=O)=O] |
| 711 | 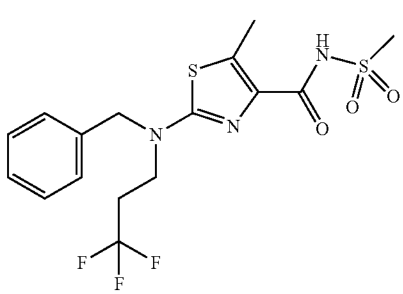 [SMILES: Cc1sc(N(CCC(F)(F)F)Cc2ccccc2)nc1C(=O)NS(C)(=O)=O] |

TABLE 65-continued
| Compound number | Structure |
|---|---|
| 712 | 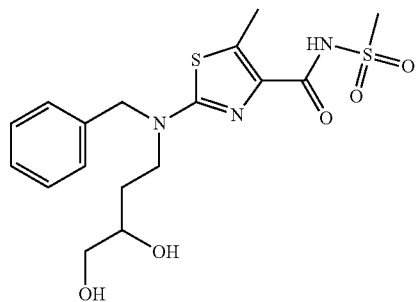 [SMILES: Cc1sc(N(CCC(O)CO)Cc2ccccc2)nc1C(=O)NS(C)(=O)=O] |
| 713 | 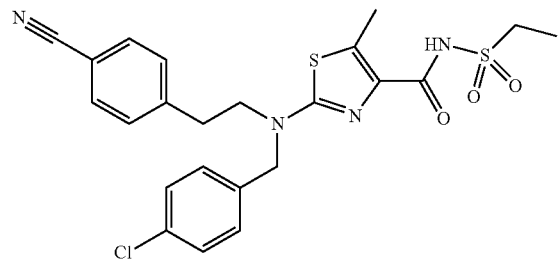 [SMILES: CCS(=O)(=O)NC(=O)c1nc(N(CCc2ccc(C#N)cc2)Cc2ccc(Cl)cc2)sc1C] |
| 714 | 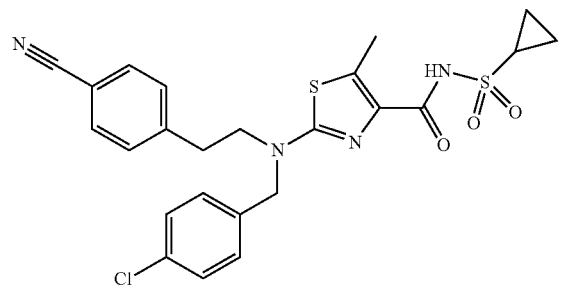 [SMILES: Cc1sc(N(CCc2ccc(C#N)cc2)Cc2ccc(Cl)cc2)nc1C(=O)NS(=O)(=O)C1CC1] |
| 715 | 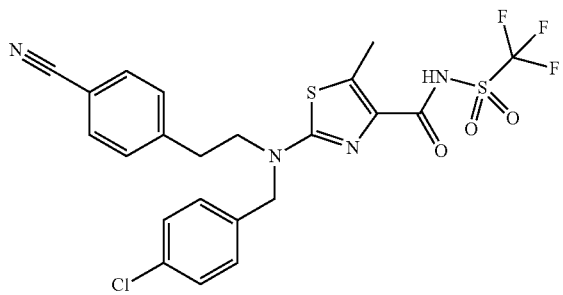 [SMILES: Cc1sc(N(CCc2ccc(C#N)cc2)Cc2ccc(Cl)cc2)nc1C(=O)NS(=O)(=O)C(F)(F)F] |
| 716 | 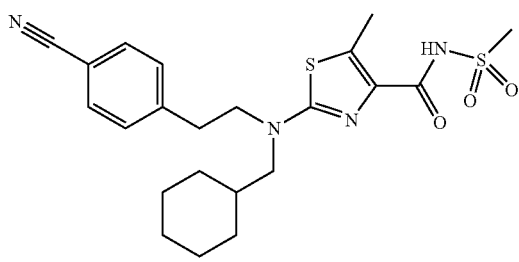 [SMILES: Cc1sc(N(CCc2ccc(C#N)cc2)CC2CCCCC2)nc1C(=O)NS(C)(=O)=O] |

TABLE 65-continued

| Compound number | Structure |
|---|---|
| 717 | 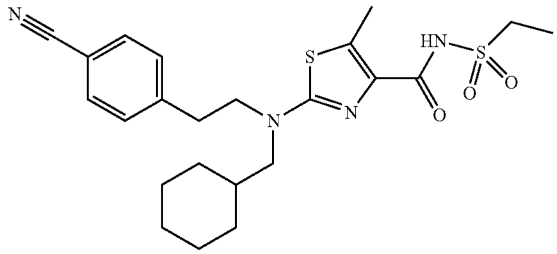 [SMILES: CCS(=O)(=O)NC(=O)c1nc(N(CCc2ccc(C#N)cc2)CC2CCCCC2)sc1C] |
| 718 | 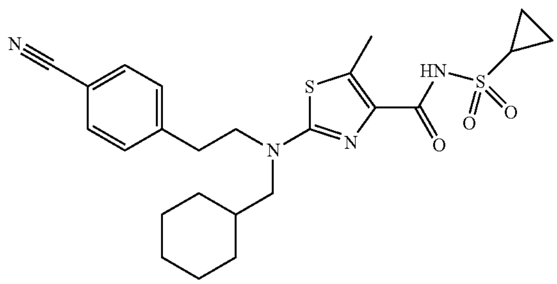 [SMILES: Cc1sc(N(CCc2ccc(C#N)cc2)CC2CCCCC2)nc1C(=O)NS(=O)(=O)C1CC1] |
| 719 | 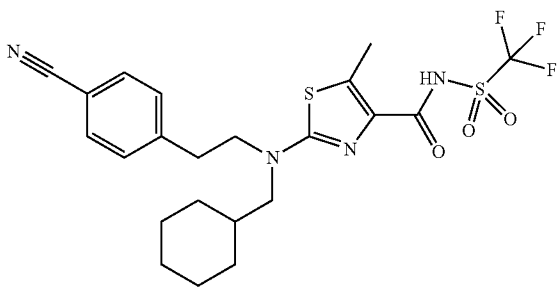 [SMILES: Cc1sc(N(CCc2ccc(C#N)cc2)CC2CCCCC2)nc1C(=O)NS(=O)(=O)C(F)(F)F] |
| 720 | 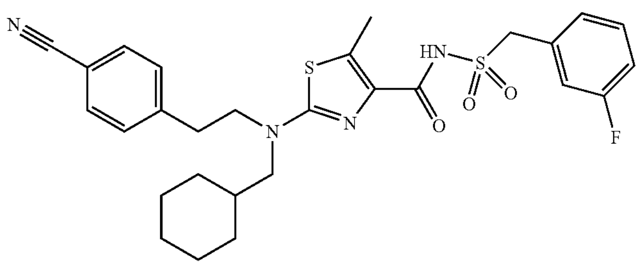 [SMILES: Cc1sc(N(CCc2ccc(C#N)cc2)CC2CCCCC2)nc1C(=O)NS(=O)(=O)Cc1cccc(F)c1] |

TABLE 66

| Compound number | Structure |
|---|---|
| 721 | 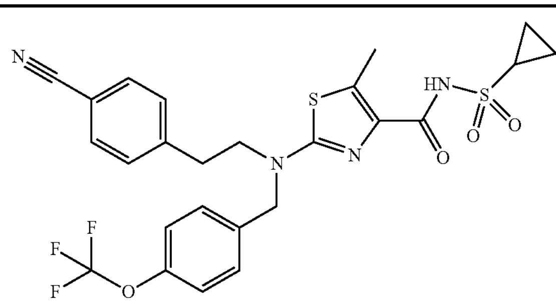 |

TABLE 66-continued

| Compound number | Structure |
|---|---|
| 722 | 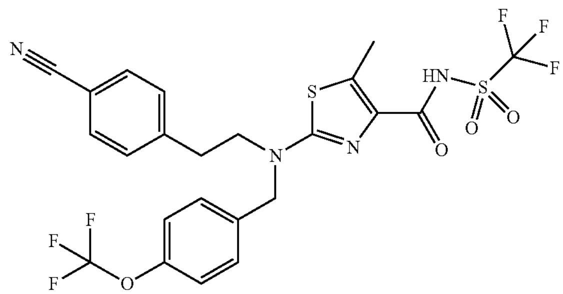 [SMILES: Cc1sc(N(CCc2ccc(C#N)cc2)Cc2ccc(OC(F)(F)F)cc2)nc1C(=O)NS(=O)(=O)C(F)(F)F] |
| 723 | 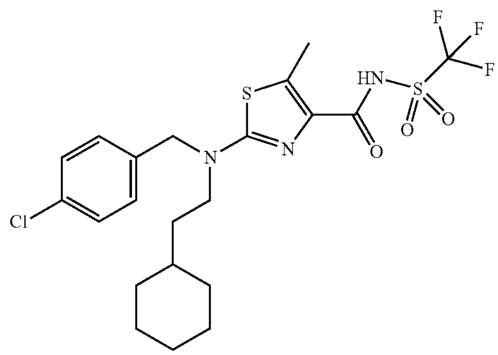 [SMILES: Cc1sc(N(CCC2CCCCC2)Cc2ccc(Cl)cc2)nc1C(=O)NS(=O)(=O)C(F)(F)F] |
| 724 | 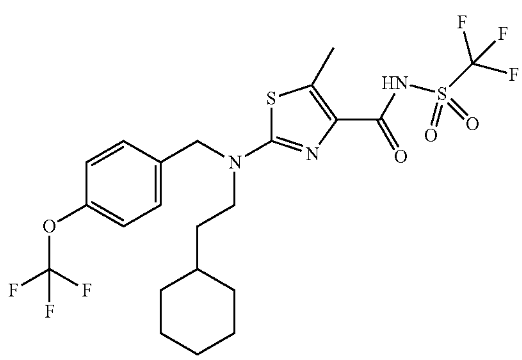 [SMILES: Cc1sc(N(CCC2CCCCC2)Cc2ccc(OC(F)(F)F)cc2)nc1C(=O)NS(=O)(=O)C(F)(F)F] |
| 725 | 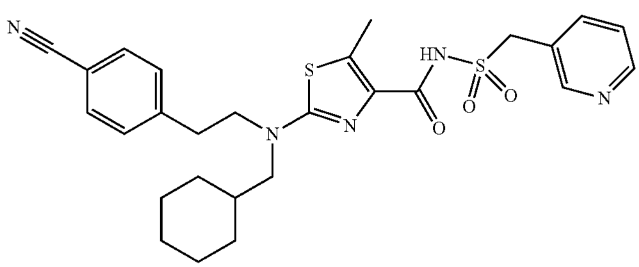 [SMILES: Cc1sc(N(CCc2ccc(C#N)cc2)CC2CCCCC2)nc1C(=O)NS(=O)(=O)Cc1cccnc1] |
| 726 | 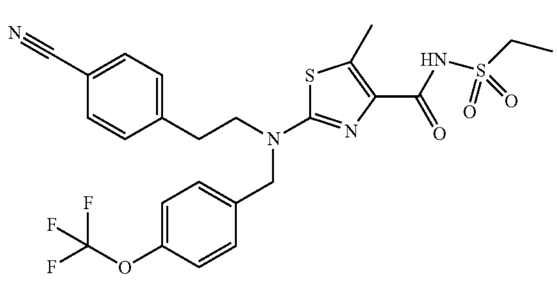 [SMILES: CCS(=O)(=O)NC(=O)c1nc(N(CCc2ccc(C#N)cc2)Cc2ccc(OC(F)(F)F)cc2)sc1C] |

TABLE 66-continued

| Compound number | Structure |
|---|---|
| 727 | 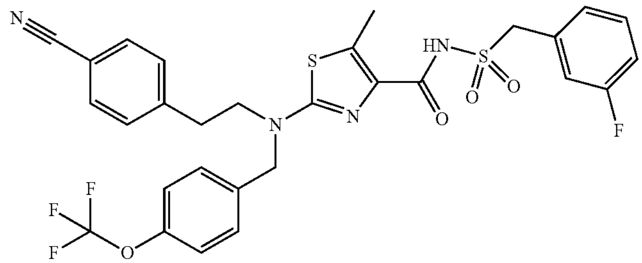 |
| 728 | 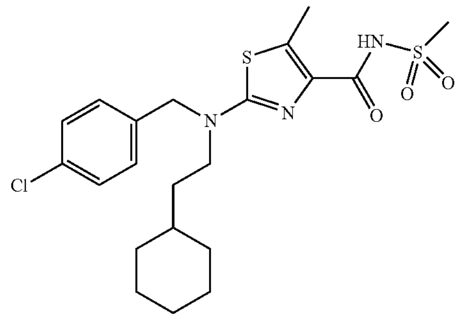 [SMILES: Cc1sc(N(CCC2CCCCC2)Cc2ccc(Cl)cc2)nc1C(=O)NS(C)(=O)=O] |
| 729 | 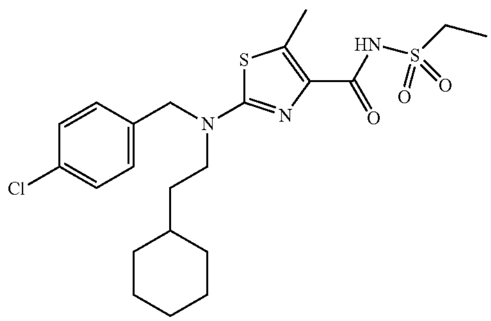 [SMILES: CCS(=O)(=O)NC(=O)c1nc(N(CCC2CCCCC2)Cc2ccc(Cl)cc2)sc1C] |
| 730 | 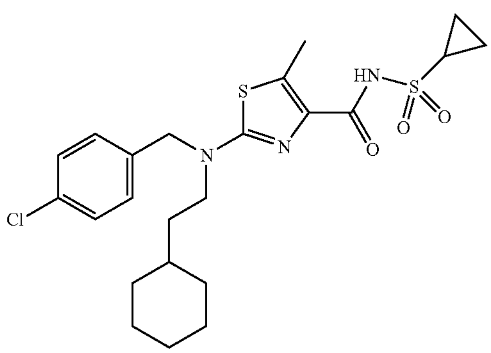 [SMILES: Cc1sc(N(CCC2CCCCC2)Cc2ccc(Cl)cc2)nc1C(=O)NS(=O)(=O)C1CC1] |
| 731 | 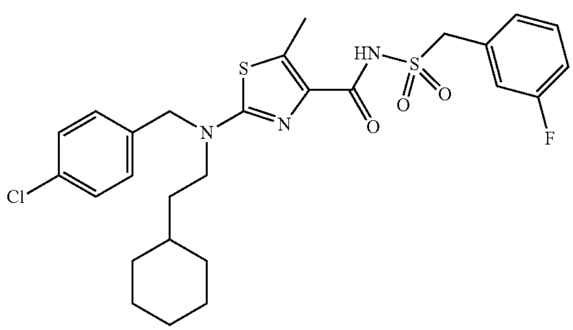 [SMILES: Cc1sc(N(CCC2CCCCC2)Cc2ccc(Cl)cc2)nc1C(=O)NS(=O)(=O)Cc1cccc(F)c1] |

TABLE 66-continued

| Compound number | Structure |
|---|---|
| 732 | 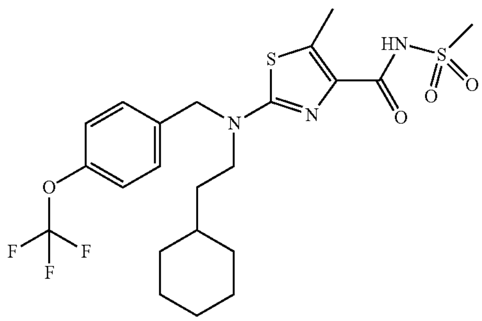 [SMILES: Cc1sc(N(CCC2CCCCC2)Cc2ccc(OC(F)(F)F)cc2)nc1C(=O)NS(C)(=O)=O] |

TABLE 67

| Compound number | Structure |
|---|---|
| 733 | 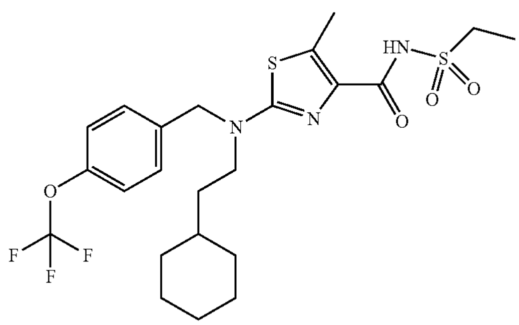 [SMILES: CCS(=O)(=O)NC(=O)c1nc(N(CCC2CCCCC2)Cc2ccc(OC(F)(F)F)cc2)sc1C] |
| 734 | 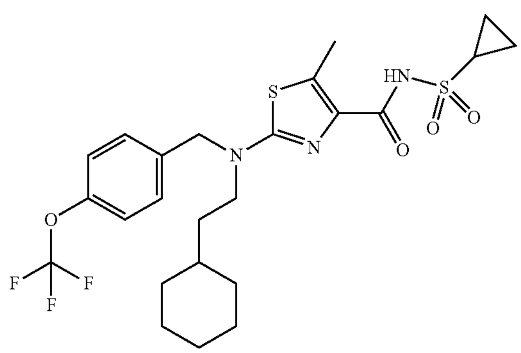 [SMILES: Cc1sc(N(CCC2CCCCC2)Cc2ccc(OC(F)(F)F)cc2)nc1C(=O)NS(=O)(=O)C1CC1] |
| 735 | 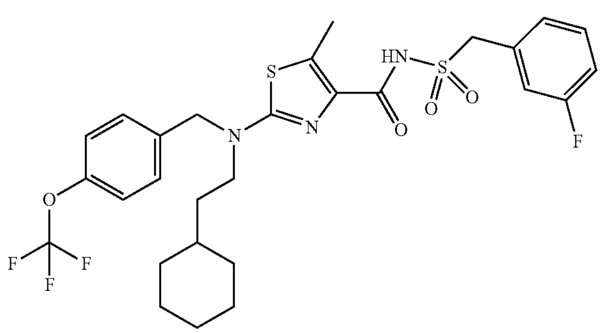 [SMILES: Cc1sc(N(CCC2CCCCC2)Cc2ccc(OC(F)(F)F)cc2)nc1C(=O)NS(=O)(=O)Cc1cccc(F)c1] |

TABLE 67-continued

| Compound number | Structure |
|---|---|
| 736 | 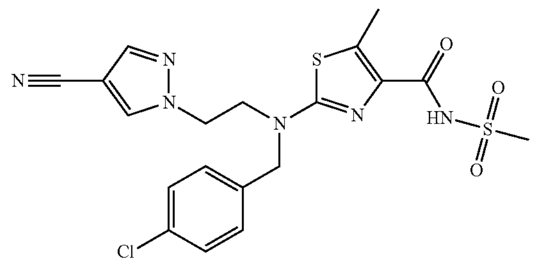 [SMILES: Cc1sc(N(CCn2cc(C#N)cn2)Cc2ccc(Cl)cc2)nc1C(=O)NS(C)(=O)=O] |
| 737 | 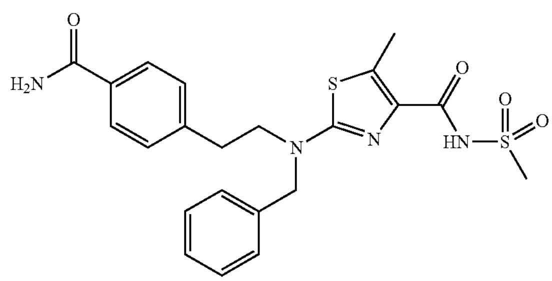 [SMILES: Cc1sc(N(CCc2ccc(C(N)=O)cc2)Cc2ccccc2)nc1C(=O)NS(C)(=O)=O] |
| 738 | 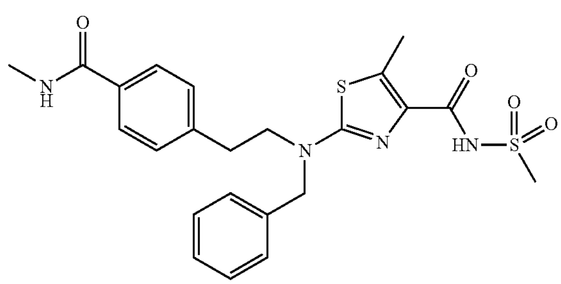 [SMILES: CNC(=O)c1ccc(CCN(Cc2ccccc2)c2nc(C(=O)NS(C)(=O)=O)c(C)s2)cc1] |
| 739 | 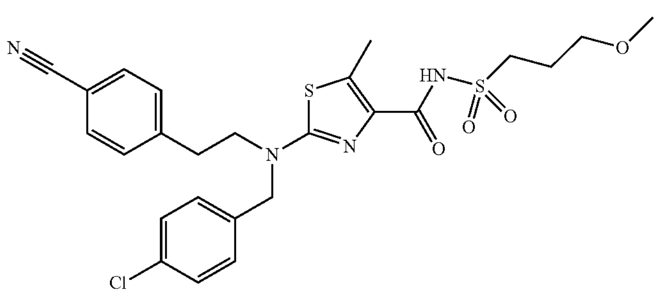 [SMILES: COCCCS(=O)(=O)NC(=O)c1nc(N(CCc2ccc(C#N)cc2)Cc2ccc(Cl)cc2)sc1C] |
| 740 | 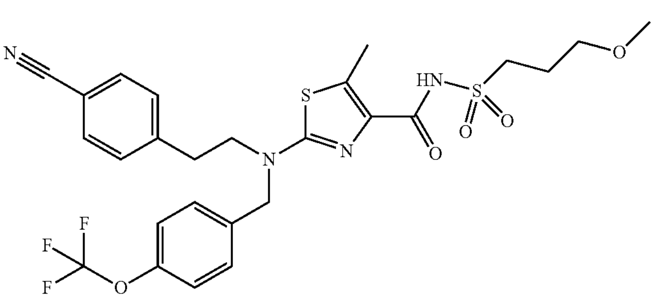 [SMILES: COCCCS(=O)(=O)NC(=O)c1nc(N(CCc2ccc(C#N)cc2)Cc2ccc(OC(F)(F)F)cc2)sc1C] |

TABLE 67-continued

| Compound number | Structure |
|---|---|
| 741 | (structure) |
| 742 | (structure) |
| 743 | (structure) |
| 744 | (structure) |

TABLE 68

| Compound number | Structure |
|---|---|
| 745 | (structure) |
| 746 | (structure) |

Among these, preferable compounds are those of the compound number 1, 2, 4, 5, 7, 14, 15, 23, 26, 39, 40, 41, 50, 51, 70, 94, 97, 106, 129, 141, 152, 153, 154, 157, 165, 167, 172, 187, 252, 285, 286, and more preferable are the compound number 5, 7, 15, 23, 26, 41, 50, 97, 152, 154, 165, 187.

A compound of the present invention can be converted into a medically acceptable salt as needed. Examples of the salt are salts with inorganic acid such as hydrochloric acid, hydrobromic acid, hydroiodic acid, sulfuric acid, nitric acid, phosphoric acid, carbonic acid and the like; salts with organic acid such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, para-toluenesulfonic acid and the like; salt with amino acid such as lysine, arginine, ornithine, glutaminic acid, aspartic acid and the like; salts with alkali metal such as sodium, potassium, lithium and the like; salts with alkaline earth metal such as calcium, magnesium and the like; salts with metal such as aluminum, zinc, iron and the like; salts with organic base such as methylamine, ethylamine, diethylamine, trimethylamine, triethylamine, ethylenediamine, piperidine, piperazine, pyridine, picoline, ethanolamine, diethanolamine, triethanolamine, cyclohexylamine, dicyclohexylamine, N-methylglucamine, N,N'-dibenzylethylenediamine and the like; ammonium salt and the like. Note that which salt among these can be actually formed depends on the chemical structure of the individual compound of the present invention.

The compound of the present invention or medically acceptable salt thereof can be converted into solvate as needed. Examples of the solvents used are water, methanol, ethanol, 1-propanol, 2-propanol, butanol, tert-butanol, acetonitrile, acetone, methyl ethyl ketone, chloroform, ethyl acetate, diethyl ether, tert-butyl methyl ether, benzene, toluene, DMF, DMSO and the like. Specifically, preferable are water, methanol, ethanol, 1-propanol, 2-propanol, acetonitrile, acetone, methyl ethyl ketone and ethyl acetate.

When the compound of the present invention has an isomer, such an isomer also is included as the compound of the present invention. Such isomers include, for example, isomers in a ring or condensed ring (E, Z, cis, trans form), isomers in the presence of asymmetric carbons (R, S isomer, α, β configuration, enantiomer, diastereomer), optically active isomers having optical activity (D, L, d, l form), tautomer, polarity form by chromatography isolation (high polarity form, low polarity form), an equilibrium compound, a rotamer, mixtures thereof at arbitrary ratio and a racemic mixture.

It is preferable to use the above-mentioned preferable compound of the present invention for (a) a pharmaceutical composition containing a compound of the present invention or a medically acceptable salt thereof, a pharmaceutically acceptable carrier thereof, (b) an AR activity regulator containing the compound of the present invention or a medically acceptable salt thereof as an active ingredient, and (c) a therapeutic or prophylactic agent for AR-related diseases containing of the compound of the present invention or a medically acceptable salt thereof as an active ingredient.

The compound of the present invention can be synthesized by utilizing characteristics based on the basic structure or the types of substituents and using various kinds of well-known synthetic methods. In such a case, depending on the type of functional groups, the protection of the functional group with a suitable protecting group at the stage of raw materials or its intermediates, or the substitution of the functional group with a group that can be easily converted to the functional group may be beneficial on the manufacturing technology. Such functional groups, for example, include an amino group, a hydroxyl group, and a carboxyl group. In addition, these functional groups can include, for example, protecting groups mentioned in "Protective Groups in Organic Synthesis" (fourth edition, 2007) by Greene (T. W. Greene) and Wuts (P. G. M. Wuts), and they can be appropriately selected in accordance with reaction conditions. In such a method, after the completion of a reaction by introducing a protecting group, a desired compound can be obtained by eliminating the protecting group or converting to a desired group as needed.

Among the compounds of the present invention, a compound wherein $R^5$ is a hydrogen atom can be synthesized by the method shown in the following scheme A. In other words, for a compound (A-III) obtained by the bromination of commercially available keto ester (A-I) or hydroxy ester (A-II), a cyclization reaction with an urea compound or a thiourea compound is conducted to yield a compound (A-IV). A compound (A-V) is obtained by the alkylation of the compound (A-IV). This compound is hydrolyzed to yield a compound (A-VI). Furthermore, a compound (A-VII) can be obtained by a condensation reaction with a sulfonamide compound.

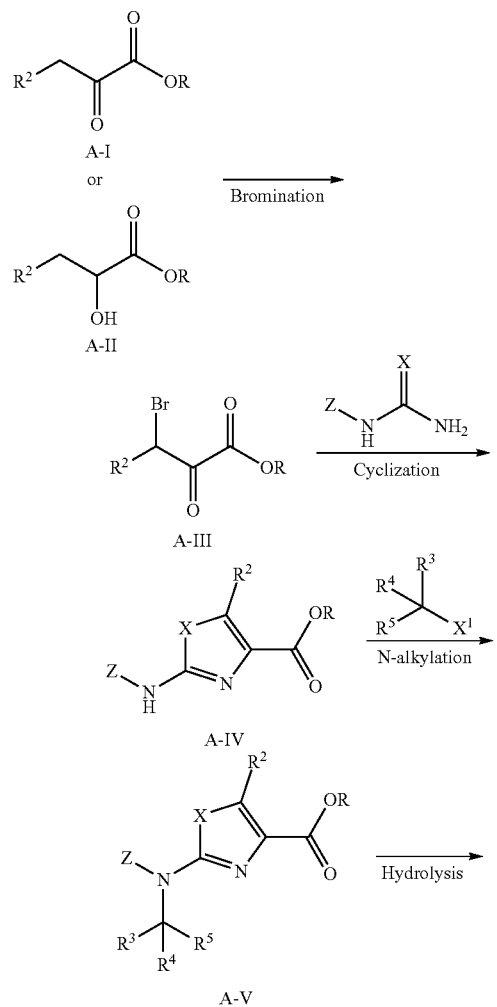

Scheme A

[Chem. 4]

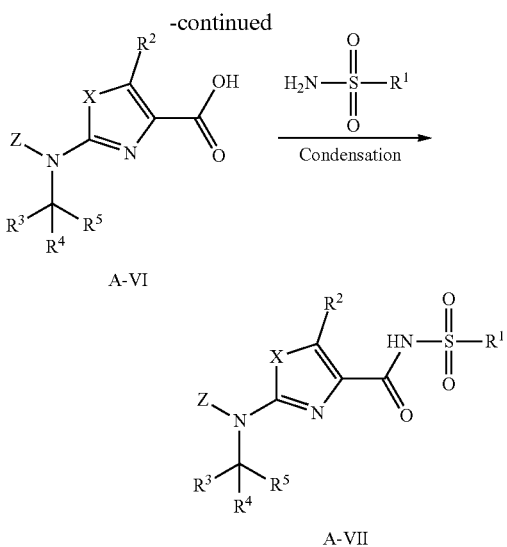

A-VI

A-VII

Preferable agents for the bromination of a compound (A-III) converting from a compound (A-I) or (A-II) in the scheme A include bromine and N-bromosuccinimide (NBS). In addition, solvents in this reaction, though not particularly limited, include, for example, esters such as ethyl acetate and the like; halogen solvents such as acetonitrile, dichloromethane, chloroform, carbon tetrachloride and the like; or mixed solvents thereof.

This reaction is conducted at −20° C. to 100° C., but preferably at 0° C. to 80° C.

The cyclization reaction from a compound (A-III) to a compound (A-IV) proceeds by mixing an urea compound or a thiourea compound with a compound (A-III). This reaction is conducted at 0° C. to 100° C., but preferably at room temperature up to 70° C. For solvents, alcohols such as methanol or ethanol and the like; ketones such as the acetone and the like; ethers such as tetrahydrofuran and the like; water; or mixed solvents thereof may be used or the reaction may be conducted without solvents.

N-alkylation of a compound (A-V) from the compound (A-IV) is a step to yield the compound (A-V) in a reaction using a base and a halide compound, or a reaction using sulfonic acid ester prepared from sulfonyl alcohol and a base. Halide compounds, if used, include chloride, bromide and iodide, but preferably chloride and bromide. The reaction temperature in the presence of a halide compound is preferably −20° C. to 100° C., and more preferably 0° C. to 70° C. On the other hand, when sulfonic acid ester is used with a base at the same time, the sulfonyl alcohol used as a reagent includes methanesulfonyl alcohol, ethanesulfonyl alcohol, trifluoromethanesulfonyl alcohol, benzenesulfonyl alcohol, p-toluenesulfonyl alcohol, but preferably methanesulfonyl alcohol or p-toluenesulfonyl alcohol among all. The reaction temperature in the presence of a sulfonic acid ester compound is preferably room temperature up to 150° C., and more preferably 50° C. to 100° C.

The bases can include sodium hydride, potassium carbonate, cesium carbonate, triethylamine and diisopropylethylamine, but preferably sodium hydride and cesium carbonate. In addition, the solvents in this reaction, though not particularly limited, include, for example, ethers such as tetrahydrofuran, 1,4-dioxane, 1,2-dimethoxyethane, 1,2-diethoxyethane and the like; amides such as dimethylformamide, N-methylpyrrolidone and the like; aromatic hydrocarbons such as toluene, xylene and the like; or mixed solvents thereof.

Furthermore, $R^2$, $R^3$ and/or $R^4$ can be converted to a target structure at this step using a method known to a person skilled in the art in accordance with its structure.

For the hydrolysis reaction from the compound (A-V) to the compound (A-VI), an appropriate method can be chosen depending on the ester species. When methyl ester or ethyl ester is used as ester, the reaction is usually performed for 1-24 hours in a mixed solvent composed of an inert solvent and water by adding an equivalent amount or small excess of a base to the compound (A-V). Favorable bases can include sodium hydroxide, potassium hydroxide and lithium hydroxide. In addition, the reaction is preferably performed in a mixture of an organic solvent such as tetrahydrofuran, or alcohols such as methanol and ethanol and water, although the solvent is not particularly limited. In addition, the present reaction may be performed by just adding a base and water without performing post-processing after the completion of reaction to form the compound (A-V) from the compound (A-IV) which is the pre-stage.

Amide condensation reaction from a compound (A-VI) to a compound (A-VII) can be conducted by using an amide condensation agent. Equivalence of sulfonamide to (A-VI) is in a range of 1-5 equivalence, and preferably 1-1.5 equivalence. In addition, solvents in this reaction, though not particularly limited, include, for example, ethers such as tetrahydrofuran, 1,4-dioxane, 1,2-dimethoxyethane, 1,2-diethoxyethane and the like; halogen solvents such as dichloromethane, chloroform and the like; or mixed solvents thereof. For the condensation agent, commercially available general amide condensation agents, for example, 1-ethyl-3-(3-dimethylaminopropyl) carbodiimide hydrochloride, 1,1-carbonyldiimidazole, O-(7-azabenzotriazol-1-yl)-1,1,3,3-tetramethyluronium hexafluorophosphate, O-(benzotriazol-1-yl)-1,1,3,3-tetramethyluronium hexafluorophosphate and the like can be used. In addition, it is preferable to use them in conjunction with a condensation auxiliary agent together to promote this reaction. Such condensation auxiliary agents include N-hydroxytriazoles such as 1-hydroxybenzotriazole and the like; aromatic amines such as pyridine, 4-dimethylaminopyridine and the like.

In addition, derivatization of the compound (A-VII) from the compound (A-VI) may be conducted by the condensation with a sulfonamide compound after converting (A-VI) into an acid halogen compound (B-I) to yield the compound (A-VII) as shown in the scheme B.

Scheme B

[Chem. 5]

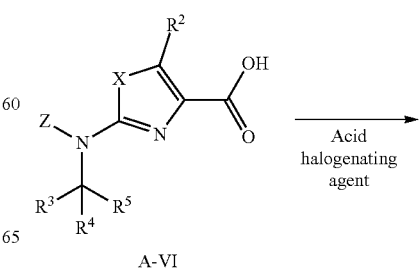

A-VI

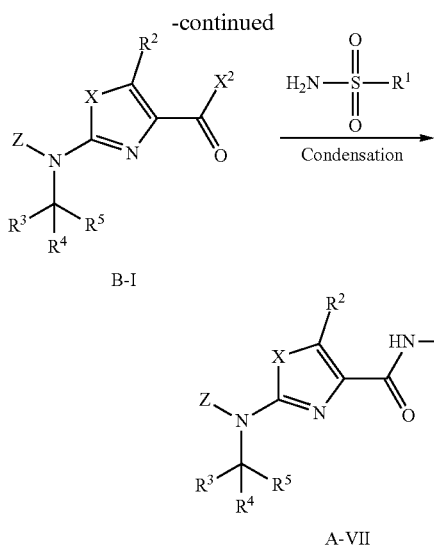

B-I

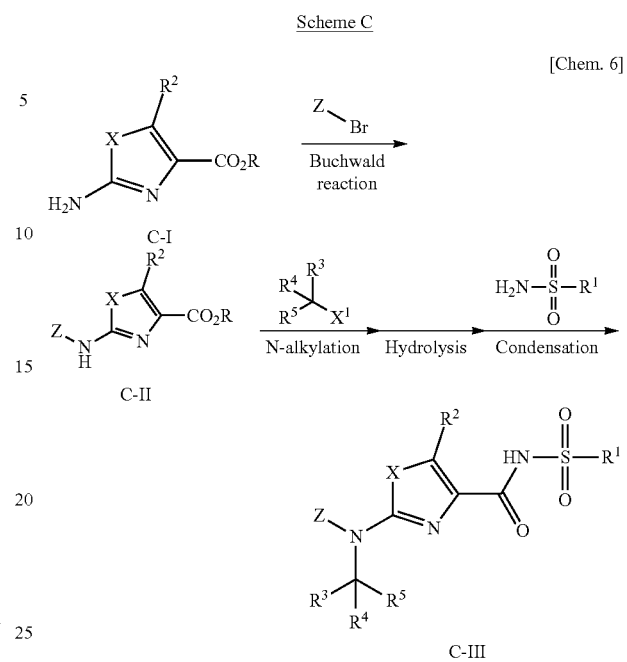

A-VII

Scheme C

[Chem. 6]

C-I

C-II

C-III

Halogen species $X^2$ of the acid halogen compound (B-I) include chlorine and bromine, and preferably chlorine. Acid halogenating agents used in the reaction from (A-VI) to (B-I) include thionyl chloride, oxalyl chloride, phosphoryl chloride, sulfuryl chloride, phosphorus trichloride, phosphorus pentachloride and phosphorus tribromide, but above all, thionyl chloride and oxalyl chloride are preferable. Solvents in this reaction, though not particularly limited, include, for example, aromatic hydrocarbons such as toluene, xylene and the like; saturated hydrocarbons such as n-hexane, n-heptane and the like; esters such as ethyl acetate and the like; ethers such as tetrahydrofuran and the like; halogenated hydrocarbons such as dichloromethane and the like; or mixed solvents thereof. This reaction proceeds at 0° C. to 120° C., but it is preferable to perform the reaction at 50° C. to 100° C.

In the condensation reaction from (B-I) to (A-VII), a 1-5 equivalent sulfonamide compound to (B-I), preferably 1-1.5 equivalent is used. In addition, solvents in this reaction include ethers such as tetrahydrofuran, 1,4-dioxane, 1,2-dimethoxyethane, 1,2-diethoxyethane and the like; halogen solvents such as dichloromethane, chloroform and the like; or mixed solvents thereof, but the reaction can be performed without solvent. This reaction proceeds at 0° C. to 100° C., but it is preferable to perform the reaction at room temperature to 50° C. In addition, for a base in this reaction, it is preferable to use inorganic bases such as sodium bicarbonate, sodium carbonate, potassium carbonate, potassium bicarbonate, sodium hydroxide, potassium hydroxide and the like; tertiary amines such as triethylamine, diisopropylethylamine and the like; or aromatic amines such as pyridine, 4-dimethylaminopyridine and the like.

In addition, among the compounds of the present invention, a compound wherein Z is Z1 and $R^5$ is a hydrogen atom can be also synthesized by the method of the following scheme C. In other words, a compound (C-II) can be obtained by using Buchwald reaction for primary amine (C-I), which is commercially available or can be synthesized by a well-known method, in the presence of an aryl bromide derivative. (C-III) can be obtained by conducting the similar reaction to that of (A-VII) from (A-IV) in the scheme A to (C-II).

The reaction converting from the compound (C-I) to (C-II) proceeds by heating the compound (C-I) with an aryl bromide derivative, a palladium catalyst, a ligand and a base in an inert solvent. In addition, depending on the substrate, an aryl chloride derivative, an aryl iodide derivative or an aryl trifluoromethanesulfonate derivative can be used instead of the aryl bromide derivative. The reaction is preferably conducted under an inert gas atmosphere. For the palladium catalyst, it is preferable to use tris(dibenzylidene acetone)dipalladium(0) and the like. In addition, for ligands, it is preferable to use 2,2'-bis(diphenylphosphino)-1,1'-binaphthyl, 2-(dicyclohexylphosphino)biphenyl, 2-dicyclohexylphosphino-2',4',6'-triisopropyl-1,1'-biphenyl, 4,5-bis(diphenylphosphino)-9,9-dimethyl xanthene and the like. In addition, bases include sodium carbonate, potassium carbonate, cesium carbonate and the like. In addition, although solvents in this reaction are not particularly limited, it is preferable to use, for example, ethers such as tetrahydrofuran, 1,4-dioxane, 1,2-dimethoxyethane, 1,2-diethoxyethane and the like; amides such as dimethylformamide, N-methylpyrrolidone and the like; alcohols such as ethanol, 2-propanol, tert-butanol and the like; aromatic hydrocarbons such as toluene, xylene and the like; water; or mixed solvents thereof. This reaction proceeds at 50° C. to 150° C., but is preferably carried out at 70° C. to 120° C. Furthermore, $R^2$ and/or Z can be converted using a method known to a person skilled in the art depending on desired structures at this stage.

In the reaction converting the compound (C-II) to (C-III), the compound (C-III) can be synthesized in the similar reactions to that from (A-IV) to (A-VII) in the scheme A. In addition, after the completion of N-alkylation $R^2$, $R^3$, $R^4$, $R^5$ and Z can be converted using a method known to a person skilled in the art depending on desired structures.

Moreover, among compounds of the present invention, a compound wherein X is a sulfur atom can be synthesized by a method of the following scheme D. In other words, (D-II) is obtained by performing thioureation of amine (D-I) which is commercially available or can be synthesized by a well-known method using benzoyl isothiocyanate and subsequent hydrolysis. The compound (D-III) is obtained by reacting (A-III) used in the scheme A with the compound (D-II). The compound (D-IV) is obtained by alkylation of the compound (D-III). The compound (D-V) can be obtained by hydrolyzing the compound (D-III) followed by condensation reaction with a sulfonamide compound.

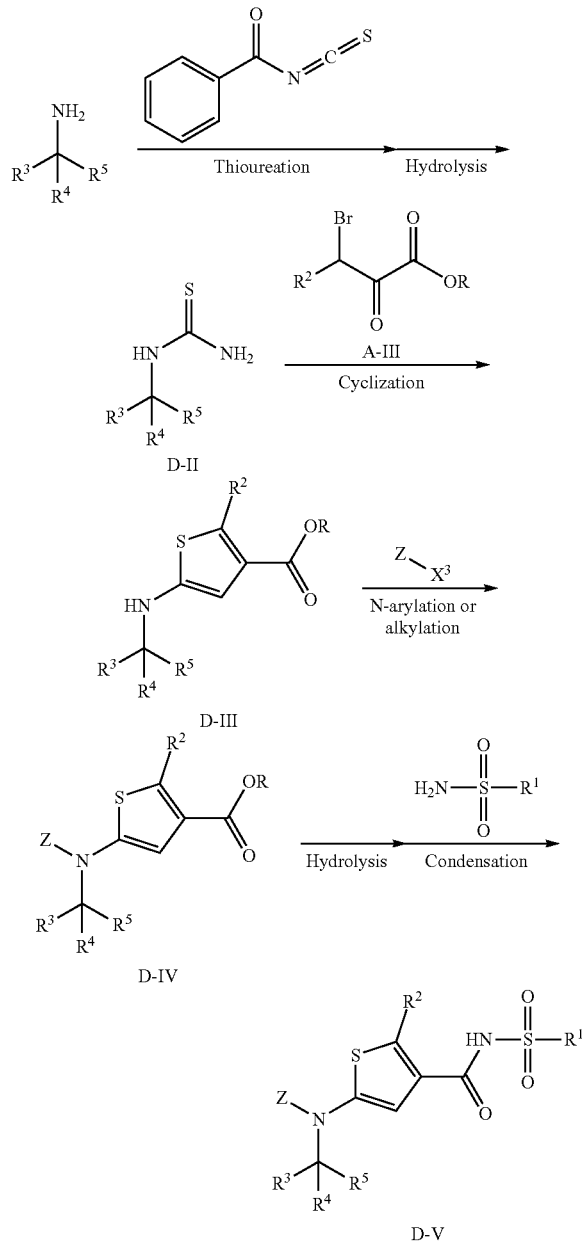

Scheme D

[Chem. 7]

In the reaction of the compound (D-I) to form (D-II), firstly, thioureation is carried out by stirring the compound (D-I) and benzoyl isothiocyanate or an analog thereof in the presence or absence of a solvent. Subsequently, the compound (D-II) is obtained by adding a base and water in a solvent. Solvents of this reaction include, for example, aromatic hydrocarbons such as toluene, xylene and the like; ketones such as acetone and the like; ethers such as tetrahydrofuran, 1,4-dioxane and the like; alcohols such as methanol, ethanol and the like; halogenated hydrocarbons such as dichloromethane and the like; acetonitrile; and mixed solvents thereof. This reaction proceeds at 0° C. to 100° C., and preferably it is conducted at room temperature to 70° C. In addition, for bases in the second stage, though not particularly limited, for example, sodium hydroxide, potassium hydroxide or the like is used.

In the reaction of the compound (D-II) to form (D-III), the similar conditions to those used in the reaction of the compound (A-III) to form (A-IV) as in the scheme A is used in the presence of the compound (A-III).

In the reaction of the compound (D-III) to form (D-IV) wherein Z is Z1, the compound (D-IV) can be obtained by a reaction using a base and aryl halide. As a such halide compound, fluoride is preferred. Bases can include sodium hydride, potassium carbonate, cesium carbonate, triethylamine and diisopropylethylamine, and preferably sodium hydride. In addition, the solvent in this reaction, though not particularly limited, preferably includes, for example, ethers such as tetrahydrofuran, 1,4-dioxane, 1,2-dimethoxyethane, 1,2-diethoxyethane and the like; amides such as dimethylformamide, dimethyl acetamide, N-methylpyrrolidone and the like; and mixed solvents thereof. In addition, in the reaction using a base or an alkyl halide compound wherein Z is Z2 or Z3, the compound (D-IV) can be obtained by the reaction using a base and an alkylhalide. Such alkyl halide compounds include chloride, bromide and iodide, preferably chloride and bromide above all. In addition, sulfonic acid ester prepared from a sulfonyl alcohol compound instead of an alkyl halide compound can be used. When a sulfonic acid ester is used with a base together at the same time, sulfonyl alcohol used as a reagent includes methanesulfonyl alcohol, ethanesulfonyl alcohol, trifluoromethanesulfonyl alcohol, benzenesulfonyl alcohol and p-toluenesulfonyl alcohol, and preferably methanesulfonyl alcohol or p-toluenesulfonyl alcohol among others. The reaction proceeds at −20° C. to 120° C., but preferably it is performed at 0° C. to 100° C. Bases can include sodium hydride, potassium carbonate, cesium carbonate, triethylamine, diisopropylethylamine and the like, and preferably sodium hydride and cesium carbonate. In addition, solvents in this reaction, though not particularly limited, include, for example, ethers such as tetrahydrofuran, 1,4-dioxane, 1,2-dimethoxyethane, 1,2-diethoxyethane and the like; amides such as dimethylformamide, N-methylpyrrolidone and the like; aromatic hydrocarbons such as toluene, xylene; and mixed solvents thereof.

Furthermore, at this step of the reaction, $R^2$, $R^3$, $R^4$, $R^5$ and/or Z can be converted using a method known to a person skilled in the art depending on a target structure.

For the reaction of the compound (D-IV) to form (D-V), the similar conditions to those used in the reaction of the compound (A-V) to form (A-VII) in the scheme A are used.

In addition, among the compounds of the present invention, a compound wherein X is a sulfur atom and $R^5$ is a hydrogen atom can be synthesized by reductive amination as shown in the scheme E(1). Alternatively, among the compounds of the present invention, a compound wherein Z is Z2 or Z3, $R^5$ and $R^{12}$ are both hydrogen atoms can be synthesized by reductive amination as shown in the scheme E(2).

Scheme E

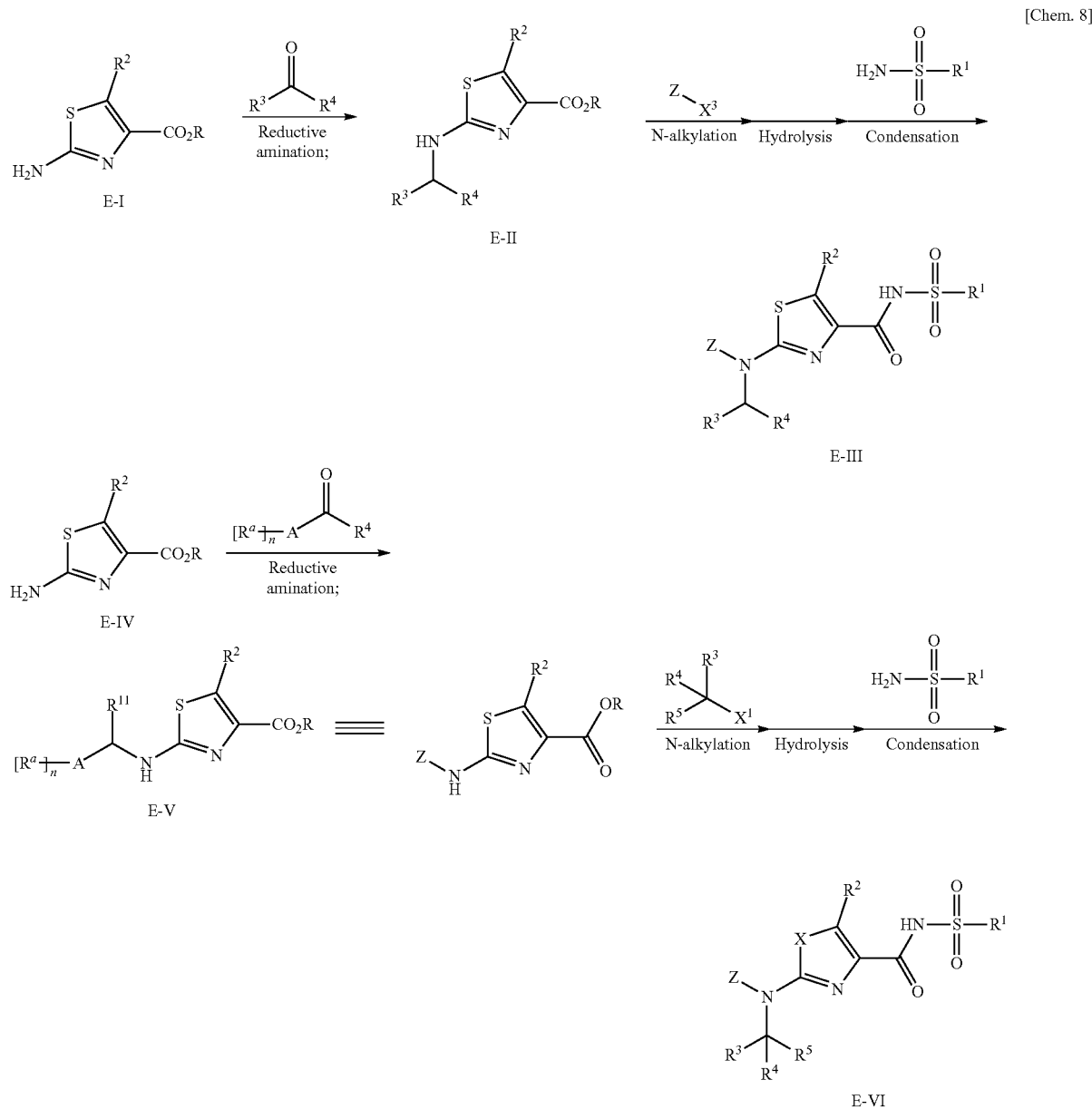

In the reaction of the compound (E-I) to form (E-II), the compound (E-II) is obtained by stirring the compound (E-I) in a solvent in the presence of an acid and a hydride reducing agent. Solvents of this reaction include, for example, alcohols such as methanol and the like; amides such as NMP and the like; halogenated hydrocarbons such as dichloromethane and the like; acetonitrile; water; and mixed solvents thereof. For the acid, for example, acetic acid is preferable. For the hydride reducing agent, sodium cyanoborohydride, sodium triacetoxyborohydride or 2-picoline borane is preferred. In the reaction of the compound of (E-II) to form (E-III), the compound (D-V) is synthesized using the similar conditions to those used in the reaction of the compound (D-III) to form (D-V) in the scheme D.

Regarding the reaction of the compound (E-IV) to form (E-V), the similar conditions to those used in the reaction of (E-I) to form (E-II) can be applied. In the reaction of the compound (E-V) to form (E-VI), the compound (E-VI) can be synthesized using the similar conditions to those used in the reaction of the compound (A-IV) to form (A-VII) in the scheme A.

In addition, among compounds of the present inventions, a compound wherein X is a sulfur atom and Z is Z3 can be synthesized by the method in the following scheme F. In other words, an alcohol compound (F-I) is subjected to trifluoromethane sulfonylation to yield a compound (F-II). This compound is subjected to the reaction with the compound (D-III) in the scheme D to yield a compound (F-III). The compound (F-IV) can be obtained from (F-III) by performing a reaction similar to that of (A-V) to form (A-VII) in the scheme A.

Scheme F

[Chem. 9]

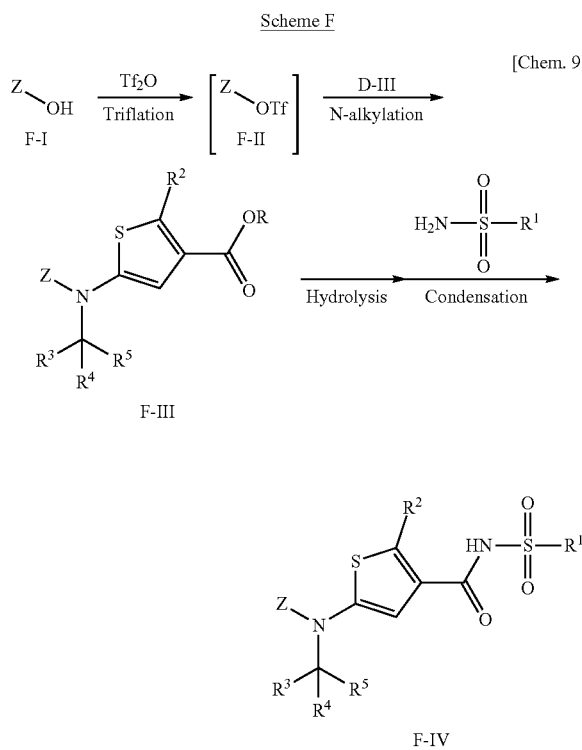

Scheme G

[Chem. 10]

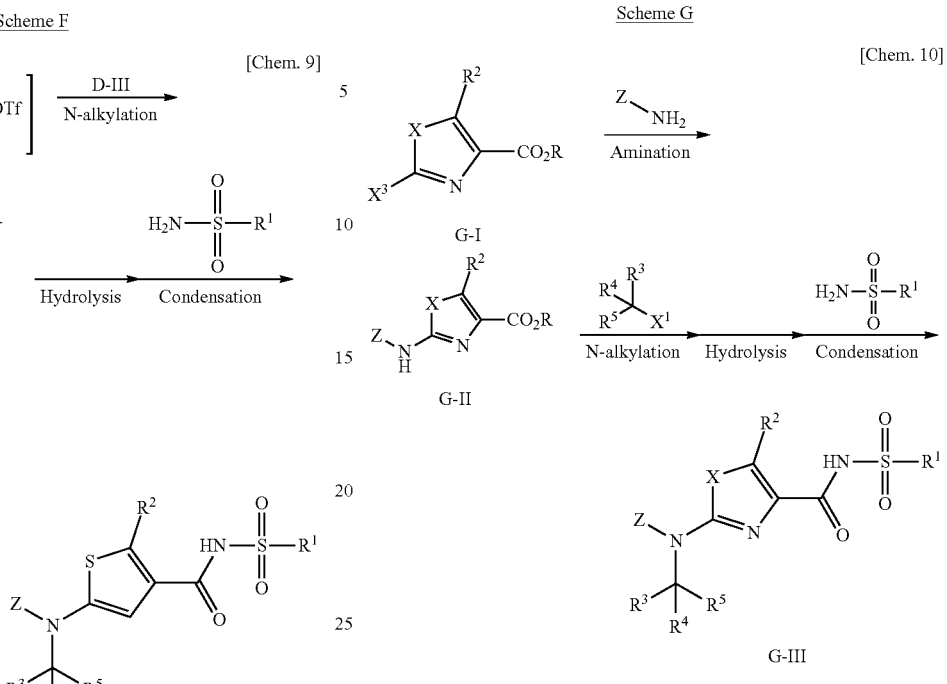

The reaction of the compound (F-I) to form (F-II) proceeds by stirring in a solvent in the presence of trifluoromethanesulfonic acid anhydride and a base. As solvents used in this reaction, ether-based solvents such as tetrahydrofuran and the like or halogenated hydrocarbons such as dichloromethane and the like are preferable. As bases, pyridine, 2,6-lutidine or triethylamine is preferable. This reaction proceeds at room temperature to −78° C., but it is preferable to conduct the reaction at 0° C. to −50° C.

In the reaction of the compound (F-II) to form (F-III), a compound (F-III) can be obtained by using a base and the compound (D-III) shown in the scheme D. The reaction temperature is preferably 0° C. to 80° C., and more preferably room temperature to 50° C. The bases can include sodium hydride, potassium carbonate, cesium carbonate, triethylamine, diisopropylethylamine and the like, but preferably sodium hydride or cesium carbonate among others. The solvents in this reaction, though not particularly limited, include, for example, ethers such as tetrahydrofuran, 1,4-dioxane, 1,2-dimethoxyethane, 1,2-diethoxyethane and the like; amides such as dimethylformamide, N-methylpyrrolidone and the like; aromatic hydrocarbons such as toluene, xylene and the like; or mixed solvents thereof.

Furthermore, at this stage, $R^2$, $R^3$, $R^4$, $R^5$ and/or Z can be converted using a method known to a person skilled in the art depending on target structures.

In the reaction of the compound (F-III) to form (F-IV), the compound (F-IV) can be synthesized using the similar conditions to those used in the reaction of the compound (A-V) to form (A-VII) in the scheme A.

In addition, a compound wherein Z is Z1 or Z3 can be synthesized from halo azole (G-I) as a raw material as shown in the scheme Z.

In the reaction of a compound (G-I) to form (G-II) wherein Z is Z, the compound (G-II) is obtained by heating and stirring the compound (G-I) in the presence of a palladium catalyst, a base and a ligand. Reagents and conditions that can be used for the reaction are similar to those in the reaction of the compound (C-I) to form (C-II) in the scheme C.

In addition, when Z is Z3, the compound (G-II) is obtained by stirring the compound (G-I) while heating in a solvent in the presence of a base. For $X^3$, a chlorine atom or a bromine atom is preferable. It is preferable to conduct this reaction under microwave radiation conditions. In this case, the solvent is not particularly limited as long as it can be used in a microwave reaction, and dimethylsulfoxide or N-methylpyrrolidone is preferable. In addition, in this reaction it is preferable to use an inorganic base such as sodium bicarbonate, sodium carbonate, potassium carbonate, potassium bicarbonate, sodium hydroxide, potassium hydroxide and the like or tertiary amines such as triethylamine, diisopropylethylamine or the like as a base. This reaction proceeds at 100° C. to 200° C., but it is preferable to conduct the reaction at 120° C. to 170° C.

In the reaction of the compound (G-II) to form (G-III), the compound (G-III) can be synthesized using the similar conditions to those used in the reaction of the compound (A-V) to form (A-VII) as shown in the scheme A.

Therapeutic or prophylactic agent containing a compound of the present invention or a medically acceptable salt thereof, or a solvate thereof as an active ingredient can be prepared using a carrier, a diluting agent, and other additives that are usually used for preparation of formulations. Carriers and diluting agents for the preparations may be in the form of either solid or liquid, for example, they include commonly used reagents such as lactose, magnesium stearate, starch, talc, gelatin, agar, pectin, gum Arabic, olive oil, sesame oil, cocoa butter, ethylene glycol and the like. The administration may be in any form of either oral administration such as tablets, pills, capsules, granules, powder drugs, liquid drugs and the like, or parenteral administration such as injections including IV infusions and muscular injections, suppositories, and subcutaneous injections.

The effective dose of an active ingredient in an AR activity regulator, a therapeutic or prophylactic agent of the present invention is different depending on administration routes, symptoms of the patients, age, sex, body weight, and the type of diseases. Generally the dosage is in a range of 0.01-1000 mg/day per adult, dosing frequency is usually 1 to 3 times/day or 1 to 7 times/week. However, because dosage will vary depending on various kinds of conditions, quantity less than the dose mentioned above may be sufficient, or an excess amount of the dose more than ranges mentioned above may be required.

EXAMPLES

Embodiments of the present invention by examples in greater detail will be explained as follows, but the present invention is not limited thereto. Example number and compound number of the compound prepared in the Examples are the same.

In addition, abbreviations in the present invention are as follows.
DMF=N,N-dimethylformamide
DMSO=dimethylsulfoxide
TBME=methyltert-butyl ether
TFA=trifluoroacetic acid
THF=tetrahydrofuran
AIBN=2,2'-azobis(isobutyronitrile)
NBS=N-bromosuccinimide
NCS=N-chlorosuccinimide
DMAP=4-dimethylaminopyridine
WSC=1-(3-dimethylaminopropyl)-3-ethylcarbodiimide hydrochloride
$Pd_2(dba)_3$=tris(dibenzylidene acetone)dipalladium (0)
dppf=1,1'-bis(diphenylphosphino)ferrocene
X-phos=2-dichlorohexylphosphino-2',4',6'-triisopropylbiphenyl
xantphos=4,5-bis(diphenylphosphino)-9,9-dimethylxanthene The structure of an isolated novel compound was confirmed by $^1$H-NMR and/or mass spectrometry using UPLC-MS (super-high-speed liquid chromatography-mass spectrometer).

The results of LCMS are shown as a value of $[M+H]^+$ of each compound observed with the following device under the following analysis conditions (measured value of molecular weight: i.e., measured value of a molecular mass [M] of the compound plus a proton $[H]^+$ added) and the retention time. Regarding [Br] mentioned herein shows that a strong peak derived from M+2, an isotope of the bromine atom, was observed.
Device: WATERSACQUITY UPLC/MS
Column: ACQUITY UPLC_R BEH C18 2.1*50 mm 1.7 μm
UV: PDA detection (254 nm)
Column temperature: 40° C.
Sample concentration: 0.5 mg/mL (DMSO)
[Gradient Condition]
Solvent: Solution A; $H_2O$/acetonitrile=95/5 (0.05% TFA), Solution B; $H_2O$/acetonitrile=5/95 (0.05% TFA)
Flow rate: 0.6 mL/min
Gradient: 0.0 minute for (Solution A/Solution B=98/2), 0.2 minutes for (Solution A/Solution B=98/2), 3.0 minutes for (Solution A/Solution B=0/100), 4.2 minutes for (Solution A/Solution B=0/100), 4.21 minutes for (Solution A/Solution B=98/2), 5.2 minutes (Solution A/Solution B=98/2):

Reference Example 1

1-(bromomethyl)-4-(difluoromethyl)benzene

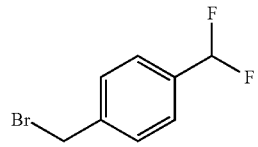

[Chem. 11]

(1) A solution of 1-bromo-4-(difluoromethyl)benzene (5.00 g, 24.1 mmol) in THF (75 mL) was cooled to −78° C. while stirring, and a solution of n-butyllithium in n-hexane (1.57 M, 16.9 mL, 26.6 mmol) was added dropwise and the resultant mixture was stirred for 30 minutes. After adding DMF (4.09 mL, 53.1 mmol) and elevating the temperature to 0° C. over 1 hour, the resultant solution was stirred for 14 hours while gradually returning the temperature to room temperature. The reaction solution was neutralized by adding an ammonium chloride aqueous solution and extraction was performed with diethyl ether twice. Organic fractions were combined and washed with a saturated salt solution and dried over magnesium sulfate. The solvent was removed by distillation under reduced pressure and the resultant residue was purified by column chromatography to obtain 4-(difluoromethyl)benzaldehyde (2.49 g, 66%).

$^1$H-NMR (CDCl$_3$) δ: 10.08 (1H, s), 7.99 (2H, d, J=8.3 Hz), 7.70 (2H, d, J=8.3 Hz), 6.72 (1H, t, J=55.9 Hz).

(2) An ethanol solution (50 mL) of 4-(difluoromethyl) benzaldehyde (2.49 g, 16.0 mmol) was cooled down to 0° C. while stirring, to which was added sodium borohydride (1.21 g, 31.9 mmol), and the resultant mixture was stirred for 4 hours while gradually returning the temperature to room temperature. The solvent was removed by distillation and the resultant was extracted with ethyl acetate twice after adding an ammonium chloride aqueous solution. Organic fractions were combined and washed with a saturated salt solution and dried over magnesium sulfate. The solvent was removed by distillation under reduced pressure to obtain [4-(difluoromethyl)phenyl]methanol (2.30 g, 91%). The obtained compound was used for the next reaction without further purification.

$^1$H-NMR (CDCl$_3$) δ: 7.51 (2H, d, J=7.8 Hz), 7.46 (2H, d, J=8.3 Hz), 6.65 (1H, t, J=56.3 Hz), 4.76 (2H, s), 1.76 (1H, s)

(3) A dichloromethane (40 m L) solution of [4-(difluoromethyl)phenyl] methanol (2.16 g, 13.7 mmol) was cooled to 0° C. while stirring and phosphorus tribromide (1.30 mL, 13.7 mmol) was added, and the mixture was stirred for 4 hours while gradually returning the temperature to room temperature. To the reaction solution was added a sodium bromide aqueous solution, and the mixture was extracted with dichloromethane twice. Organic fractions were combined, washed with a saturated salt solution and dried over magnesium sulfate. The solvent was removed by distillation under reduced pressure to obtain 1-(bromomethyl)-4-(difluoromethyl)benzene (1.67 g, 55%) by purifying the resultant residue by column chromatography.

¹H-NMR (CDCl₃) δ: 9.13 (1H, s), 7.72 (2H, d, J=8.8 Hz), 7.42 (2H, d, J=8.8 Hz), 7.23 (2H, d, J=8.3 Hz), 7.11 (2H, d, J=8.8 Hz), 6.51 (1H, t, J=73.7 Hz), 5.13 (2H, s), 3.38 (3H, s).

Reference Example 2

6-(bromomethyl)chroman-4-one

[Chem. 12]

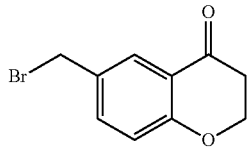

To a chlorobenzene (10 mL) solution of 6-methylchroman-4-one (500 mg, 3.08 mmol) was added AIBN (101 mg, 0.617 mmol) and 1,3-dibromo-5,5-dimethyl hydantoin (538 mg, 1.88 mmol) while stirring, and the resultant mixture was heated and stirred at 80° C. for 2.5 hours. Water was added to the reaction solution and the mixture was extracted with dichloromethane twice. Organic fractions were combined and washed with a saturated salt solution and dried over magnesium sulfate.

The solvent was removed by distillation under reduced pressure to obtain 6-(bromomethyl)chroman-4-one (530 mg, 71%) by purifying the resultant residue by column chromatography.

¹H-NMR (CDCl₃) δ: 7.91 (1H, d, J=2.4 Hz), 7.52 (1H, dd, J=8.8, 2.4 Hz), 6.97 (1H, d, J=8.3 Hz), 4.55 (2H, t, J=6.6 Hz), 4.47 (2H, s), 2.82 (2H, t, J=6.6 Hz).

Reference Example 3

((3-(bromomethyl)benzyl)oxy)(tert-butyl)dimethylsilane

[Chem. 13]

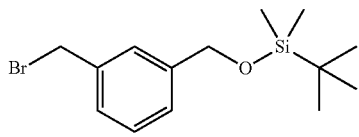

To a dichloromethane (4 mL) solution of (3-(((tert-butyldimethylsilyl)oxy)methyl)phenyl)methanol (205 mg, 0.811 mmol) were added carbon tetrabromide (269 mg, 0.811 mmol) and triphenylphosphine (213 mg, 0.811 mmol) while stirring at room temperature, and the mixture was stirred at room temperature for 2 hours. The solvent was removed by distillation under reduced pressure to obtain ((3-(bromomethyl)benzyl)oxy)(tert-butyl)dimethylsilane (85.6 mg, 33%) by purifying the resultant residue by column chromatography.

¹H-NMR (CDCl₃) δ: 7.35-7.26 (4H, m), 4.73 (2H, s), 4.50 (2H, s), 0.95 (9H, s), 0.10 (6H, s).

The following intermediates were synthesized from corresponding aryl halides, heteroaryl halides, methyl aryl, methyl heteroaryl, or aldehyde or alcohol that were intermediates of Reference Example 1 in accordance with a method of Reference Examples 1 to 3 using protection with an appropriate protecting group and de-protection if needed.

[Chem. 14]

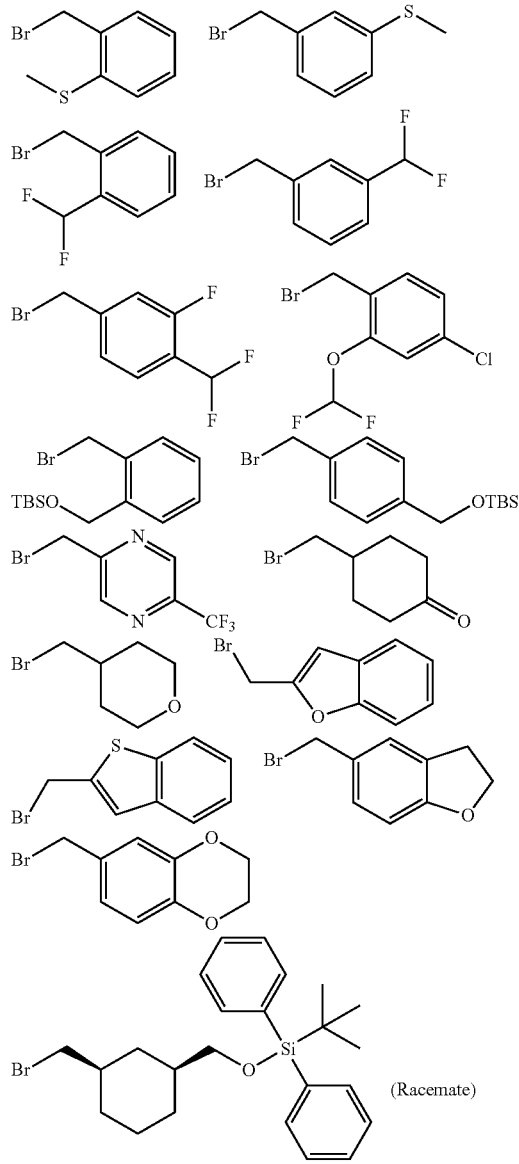

Reference Example 4

(4-(difluoromethyl)-2-fluorophenyl)methanol

[Chem. 15]

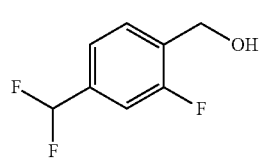

(1) While stirring methyl 2-fluoro-4-formylbenzoate (348 mg, 1.91 mmol), bis(2-methoxyethyl)amino sulfur trifluoride (1.01 mL, 5.73 mmol) in the absence of a solvent, and ethanol (0.022 mL, 0.38 mmol) were added, and the resultant mixture was stirred while heating at 65° C. for 14 hours. A sodium bicarbonate aqueous solution was slowly added, and the mixture was extracted with ethyl acetate and dried over magnesium sulfate. After the removal of the solvent, the target methyl 4-(difluoromethyl)-2-fluorobenzoate (267 mg, 68%) was obtained by purifying by column chromatography.

$^1$H-NMR (CDCl$_3$) δ: 8.04 (1H, t, J=7.6 Hz), 7.36 (1H, d, J=8.3 Hz), 7.32 (1H, d, J=10.7 Hz), 6.66 (1H, t, J=56.1 Hz), 3.96 (3H, s).

(2) A THF (5 mL) solution containing methyl 4-(difluoromethyl)-2-fluorobenzoate (312 mg, 1.53 mmol) was stirred at 0° C. To this solution was added lithium aluminum hydride (75.4 mg, 1.99 mmol), and the mixture was stirred for 3 hours while returning the temperature to room temperature. Water (0.075 mL), 5 M sodium hydroxide aqueous solution (0.056 mL), and water (0.25 mL) were added in this order and a solid material was filtered with a glass filter to quantitatively obtain (4-(difluoromethyl)-2-fluorophenyl) methanol by removing the solvent of the filtrate by distillation.

$^1$H-NMR (CDCl$_3$) δ: 7.50 (1H, t, J=7.6 Hz), 7.28 (1H, d, J=7.8 Hz), 7.24 (1H, d, J=9.8 Hz), 6.62 (1H, t, J=56.1 Hz), 4.52 (2H, s).

Reference Example 5

(5-(difluoromethoxy) pyridin-2-yl)methanol

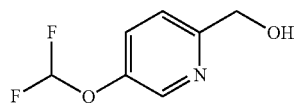

[Chem. 16]

(1) To a DMF (23 mL) solution containing 2-bromo-5-hydroxypyridine (2.00 g, 11.5 mmol) were added sodium chlorodifluoroacetate (2.19 g, 14.4 mmol) and potassium carbonate (4.24 g, 18.4 mmol), and the mixture was stirred for 8 hours while heating at 80° C. After the reaction solution was diluted with diethyl ether, an organic fraction was isolated and washed with water, and then dried over magnesium sulfate. After removing the solvent, the target 2-bromo-5-(difluoromethoxy)pyridine (1.28 g, 50%) was obtained by purifying by column chromatography.

$^1$H-NMR (CDCl$_3$) δ: 8.27 (1H, d, J=2.4 Hz), 7.50 (1H, d, J=8.8 Hz), 7.38 (1H, dd, J=8.8, 2.9 Hz), 6.54 (1H, t, J=72.2 Hz).

(2) To a DMF (15 mL) solution containing 2-bromo-5-(difluoromethoxy)pyridine (1.28 g, 5.71 mmol) dissolved in were added ethanol (15 mL), palladium acetate (128 mg, 0.571 mmol), dppf (634 mg, 1.14 mmol) and triethylamine (1.59 mL, 11.4 mmol), and the mixture was stirred at 50° C. for 14 hours under carbon monoxide atmosphere. The reaction solution was diluted with ethyl acetate and the organic fraction was separated, washed with water, and then dried over magnesium sulfate. After removing the solvent, ethyl 5-(difluoromethoxy)picolinate (1.14 g, 5.20 mmol, 92%) was obtained by purifying by column chromatography. This was dissolved in methanol and the mixture was stirred at 0° C. To this solution was added a diisobutylaluminum hydride-toluene solution (1.01 M, 15.5 mL, 15.6 mmol) at 0° C., and the mixture was stirred for 40 minutes. Furthermore, sodium borohydride (197 mg, 5.20 mmol) and methanol (2 mL) were added, and the mixture was stirred at 0° C. for 30 minutes. After adding sodium sulfate deca hydrate, the mixture was stirred at room temperature for 1 hour, and a solid material was filtered. The solvent of the filtrate was removed, and the residue was purified by column chromatography to obtain the target (5-(difluoromethoxy) pyridin-2-yl)methanol (1.10 g, 97%).

$^1$H-NMR (CDCl$_3$) δ: 8.44 (1H, d, J=2.4 Hz), 7.50 (1H, dd, J=8.3, 2.4 Hz), 7.30 (1H, d, J=8.3 Hz), 6.54 (1H, t, J=72.7 Hz), 4.77 (2H, d, J=3.9 Hz), 3.43 (1H, s).

Reference Example 6

(cis-3-((t-butyldimethylsilyl)oxy)cycloheptyl)methanol and (trans-3-((t-butyldimethylsilyl)oxy)cycloheptyl)methanol

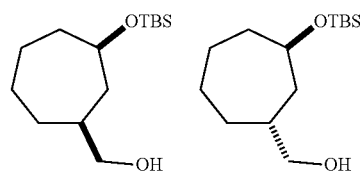

[Chem. 17]

(1) Copper (I) bromide dimethyl sulfide chelate (186.6 mg, 0.91 mmol) was dissolved in THF (45 mL), and the mixture was stirred at −10° C. To this solution was added dropwise 1.0 M THF solution (10.9 mL) of vinyl magnesium bromide, and the mixture was stirred at −10° C. for 1 hour. Then, the mixture was cooled to −78° C. and commercially available 2-cycloheptene-1-on (1.00 g, 9.01 mmol) was slowly added dropwise and the mixture was stirred at −78° C. for 1 hour. After adding a saturated ammonium chloride aqueous solution to the reaction solution, the mixture was extracted with ethyl acetate, and dried over magnesium sulfate. After removing the solvent, the target 3-vinylcycloheptane (0.20 g, 16%) was obtained by purifying by column chromatography.

$^1$H-NMR (CDCl$_3$) δ: 5.83-5.75 (1H, m), 4.99 (2H, dd, J=19.8, 14.4 Hz), 2.56-2.48 (5H, m), 1.99-1.85 (2H, m), 1.75-1.57 (2H, m), 1.51-1.39 (2H, m).

(2) An EtOH/THF=1:1 (6.5 mL) solution containing 3-vinylcycloheptane (0.27 g, 1.95 mmol) was cooled to 0° C. and stirred. To this solution was added sodium borohydride (96.1 mg, 2.54 mmol), and the mixture was returned to room temperature and stirred for 1 hour. To this reaction solution was added water, the mixture was extracted with ethyl acetate, and the organic fraction was dried over magnesium sulfate. After removing the solvent, an alcohol form (0.24 g, 90%) was obtained by purifying by column chromatography. The resultant alcohol form (0.24 g, 1.76 mmol) was dissolved in DMF and the mixture was stirred at 0° C. To this solution was added imidazole (0.44 g, 3.88 mmol) and t-butyldimethylsilyl chloride (0.30 g, 1.97 mmol), and the mixture was stirred at room temperature overnight. To this reaction solution was added a sodium bicarbonate aqueous solution, and the mixture was extracted with n-hexane, and dried over magnesium sulfate. After removing the solvent, the resultant residue was purified by column chromatography to obtain t-butyldimethylsilyl-((3-vinylcycloheptyl) oxy)silane (0.32 g, 73%).

(3) To a THF (4.3 mL) solution containing t-butyldimethylsilyl-((3-vinylcycloheptyl)oxy)silane (0.33 g, 1.28 mmol) were added N-methylmorpholine N-oxide (0.32 g, 2.82 mmol) and a 2.5 wt. % solution of osmium tetraoxide in 2-methyl-2-propanol (0.51 mL), and the mixture was stirred at room temperature overnight. To this reaction solution were added a sodium sulfite aqueous solution and an ammonium chloride aqueous solution in this order, and the mixture was extracted with ethyl acetate. The resultant organic fraction was washed with a saturated salt solution, and dried over magnesium sulfate. After removing the solvent, the resultant residue was dissolved in ethanol:water=1:1 (10 mL), and sodium periodate (0.69 g, 3.2 mmol) was added, then the mixture was stirred at room temperature for 2 hours. To this reaction solution was added water, and the mixture was extracted with diethyl ether. The organic fraction was dried over magnesium sulfate and the solvent was removed by distillation. The resultant residue dissolved in ethanol (4.3 mL) was cooled to 0° C. and sodium borohydride (0.10 g, 2.6 mmol) was added, and the resultant mixture was stirred at room temperature for 1 hour. To this reaction solution was added water, the mixture was extracted with ethyl acetate, and the organic fraction was dried over magnesium sulfate. After the solvent was removed by distillation, (cis-3-((t-butyldimethylsilyl)oxy)cycloheptyl)methanol (0.11 g, 33%) and (trans-3-((t-butyldimethylsilyl)oxy)cycloheptyl)methanol (0.12 g, 36%) were obtained by purifying by column chromatography, respectively.

cis isomer: $^1$H-NMR (CDCl$_3$) δ: 4.06-4.01 (1H, m), 3.42 (2H, d, J=6.8 Hz), 1.99-1.08 (11H, m), 0.89 (9H, s), 0.04 (6H, s).

trans isomer: $^1$H-NMR (CDCl$_3$) δ: 3.83-3.80 (1H, m), 3.44 (2H, d, J=6.3 Hz), 1.89-1.24 (11H, m), 0.89 (9H, s), 0.05 (6H, s).

The following intermediates were synthesized from a corresponding ester, aryl halide, heteroaryl halide, ketone or alkene which is an intermediate in Reference Example 6, in accordance with either method from Reference Examples 4 to 6 with protection using an appropriate protecting groups and de-protection if needed. In addition, each following stereoscopic indication shows a relative configuration and indicates stereoisomer other than stereoisomer explicitly indicated.

[Chem. 18]

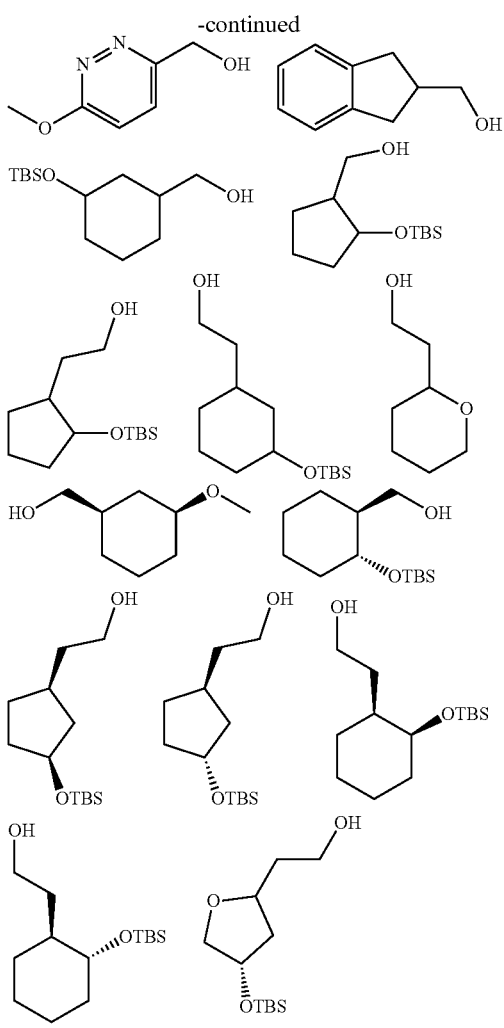

Reference Example 7

1-(4-chlorophenethyl)thiourea

[Chem. 19]

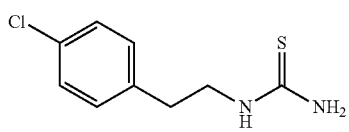

To a THF (100 mL) solution containing 2-(4-chlorophenyl)ethanamine (1.40 mL, 10.0 mmol) was added benzoyl isothiocyanate (1.44 mL, 10.0 mmol), and the mixture was stirred at room temperature overnight. The solvent was removed to obtain a yellow oily substance. Hexane (100 mL) was added and the resultant solid was filtered. To a solution of the solid dissolved in ethanol (100 mL) was added to 1 M sodium hydroxide aqueous solution (10.0 mL), and the mixture was stirred at 60° C. overnight. The reaction solution was cooled to room temperature, a part of the solvent was removed by distillation, and the mixture was concentrated to about 20 mL. Water (100 mL) was added and the mixture was extracted with ethyl acetate (100 mL) three times. And the combined organic fractions were washed with a saturated salt solution and dried over magnesium sulfate. After removing the solvent, the mixture was washed with TBME to obtain 1-(4-chlorophenethyl)thiourea (1.66 g, 77%) as a white solid. The mixture was used for the next reaction without further purification.

The following intermediates were synthesized from a corresponding primary amine compounds in accordance with the method described in Reference Example 7.

[Chem. 20]

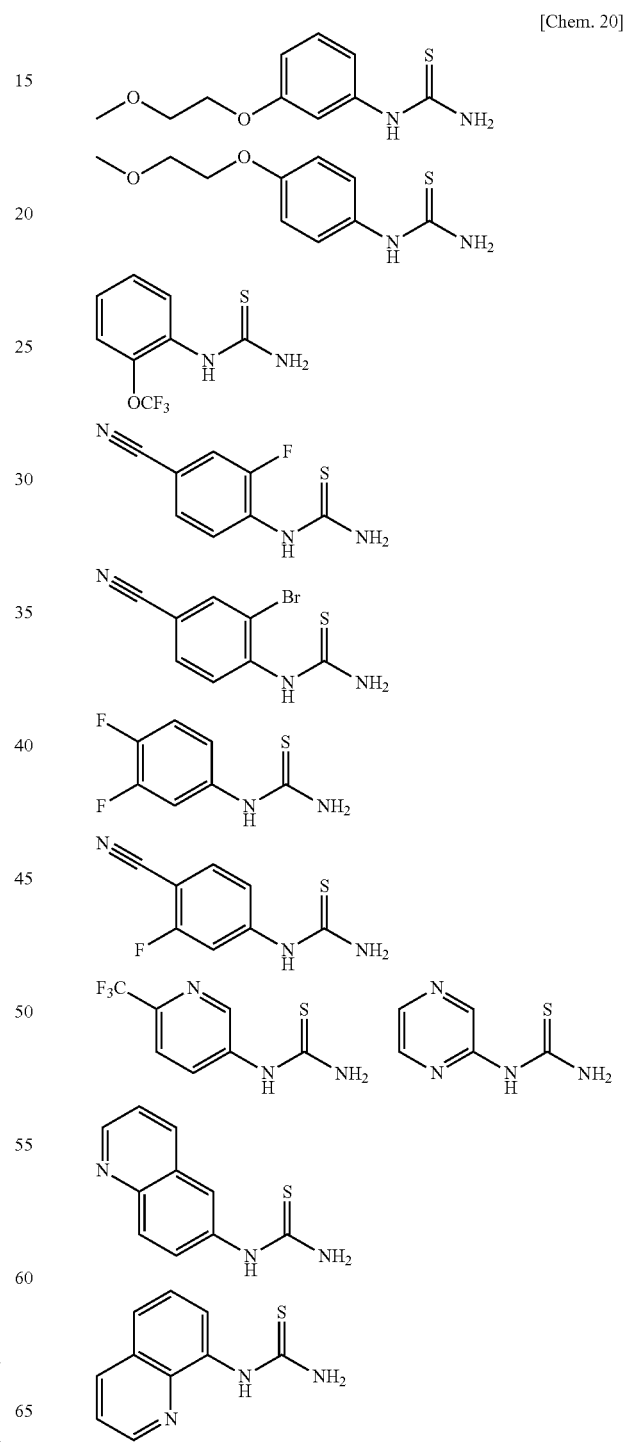

-continued

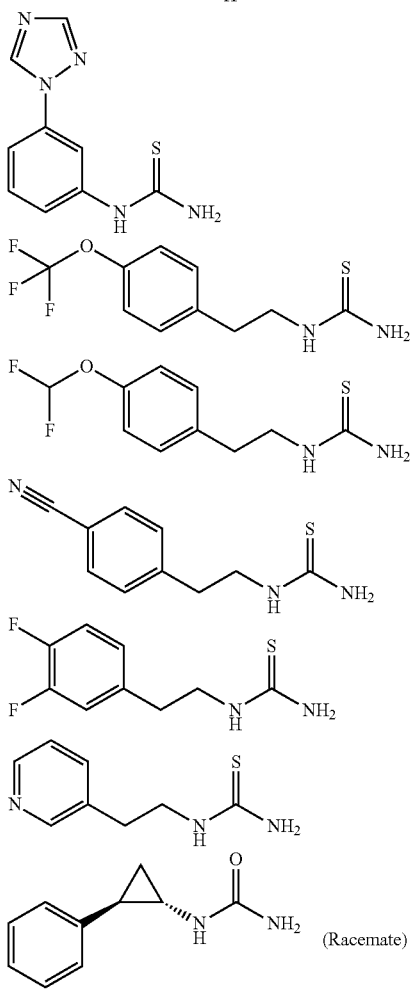

Reference Example 8

(3-pyridylmethyl)sulfonamide

[Chem. 21]

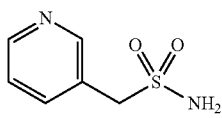

To a THF (2 mL) solution containing (3-pyridylmethyl)sulfonylchloride trifluoromethanesulfonate (100 mg, 0.293 mmol) was added ammonium hydroxide (28%, 1.00 mL), and the mixture was stirred at room temperature overnight. The solvent was removed by distillation and the resultant solid was extracted with ethyl acetate twice. Organic fractions were combined and the solvent was removed, and the mixture was purified using SCX column to obtain (3-pyridylmethyl)sulfonamide (46 mg, 91%) as a white solid.

$^1$H-NMR (DMSO-$d_6$) δ: 8.53-8.53 (2H, m), 7.77 (1H, d, J=7.8 Hz), 7.40 (1H, dd, J=7.8, 4.9 Hz), 6.92 (2H, s), 4.31 (2H, s).

The following intermediates, D-2 to D-15, were synthesized from corresponding alkylsulfonylchloride compounds in accordance with the method of Reference Example 8.

[Chem. 22]

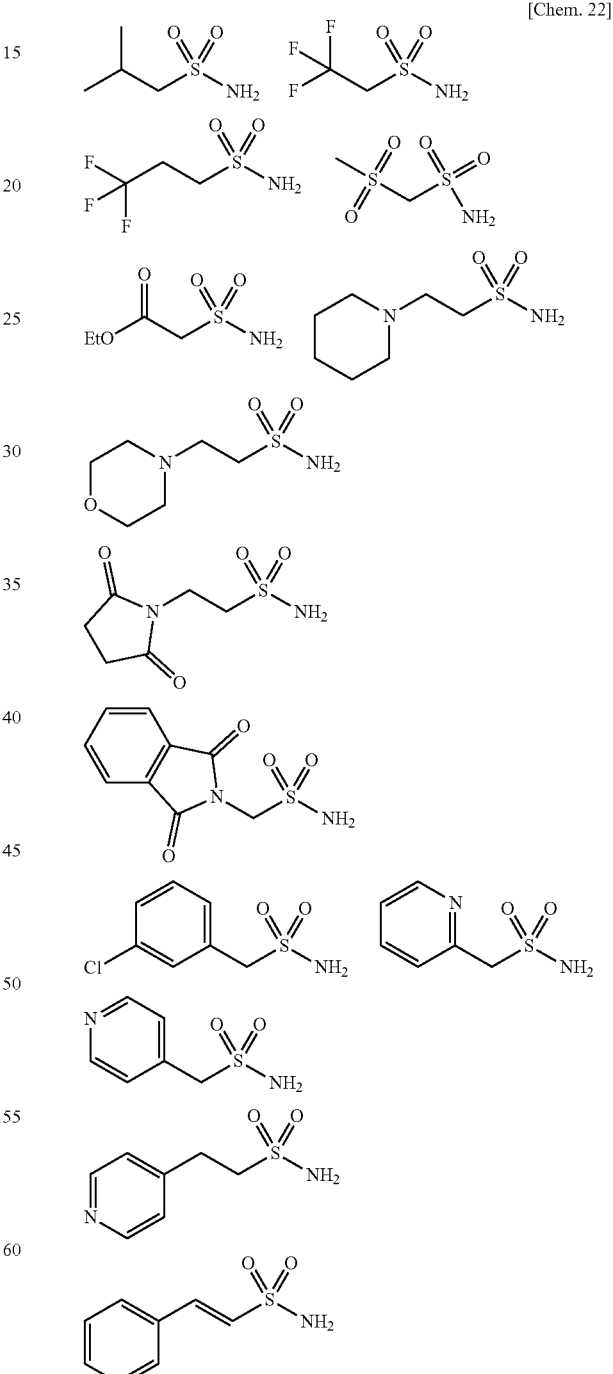

Reference Example 9

3-methoxypropane-1-sulfonamide

[Chem. 23]

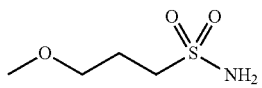

(1) To an acetone (50 mL) solution containing 1-bromo-3-methoxypropane (3.06 g, 20.0 mmol) was added thioacetic acid S-potassium (2.74 g, 24.0 mmol), and the mixture was stirred overnight while heating under refluxing. The reaction solution was subjected to celite filtration and the celite was further washed with acetone (100 mL) and the solvent was removed by distillation from the combined filtrate under reduced pressure to obtain ethanethioic acid S-(3-methoxypropyl) as an oily brown substance. The substance was used for the next reaction without further purification.

$^1$H-NMR (CDCl$_3$) δ: 3.42 (2H, t, J=6.3 Hz), 3.33 (3H, s), 2.95 (2H, t, J=7.3 Hz), 2.33 (3H, s), 1.89-1.80 (2H, m).

(2) To a mixed solution of 2 M hydrochloric acid (5.5 mL) and acetonitrile (30 mL) was added NCS (10.7 g, 80.0 mmol) in several batches. An acetonitrile (6.3 mL) solution containing ethanethioic acid S-(3-methoxypropyl) was added dropwise to the above mixture at 20-25° C., and the resultant mixture was stirred at room temperature for 1 hour. Separation procedure was conducted by adding dichloromethane (70 mL) and a saturated salt solution (70 mL), and the organic fraction was washed in a saturated salt solution twice and dried over magnesium sulfate. The solvent was removed by distillation and extraction was performed with hexane (100 mL) twice, and the solvent was removed again by distillation to obtain 3-methoxy-1-propane sulfonylchloride as a colorless oily substance. The crude product was used for the next reaction without further purification.

$^1$H-NMR (CDCl$_3$) δ: 3.83-3.77 (2H, m), 3.54 (2H, t, J=5.9 Hz), 3.36 (3H, s), 2.33-2.25 (2H, m).

(3) To a dichloromethane (67 mL) solution containing 2,4-dimethoxybenzylamine (3.68 g, 22.0 mmol) and triethylamine (2.23 g, 22.0 mmol) was added dropwise a dichloromethane (7 mL) solution containing 3-methoxy-1-propanesulfonyl chloride at room temperature while stirring. After the mixture was stirred overnight, a saturated ammonium aqueous solution (100 mL) was added and extraction was performed with dichloromethane twice. Organic fractions were combined and dried over magnesium sulfate. After the solvent was removed by distillation, N-[(2,4-dimethoxyphenyl)methyl]-3-methoxy-1-propane sulfonamide (4.98 g, three phases of 82%) was obtained by purifying by column chromatography.

$^1$H-NMR (CDCl$_3$) δ: 7.16 (1H, d, J=7.8 Hz), 6.48-6.42 (2H, m), 4.85 (1H, t, J=6.3 Hz), 4.22 (2H, d, J=6.3 Hz), 3.84 (3H, s), 3.81 (3H, s), 3.35 (2H, t, J=6.1 Hz), 3.27 (3H, s), 2.97-2.91 (2H, m), 1.96-1.87 (2H, m).

(4) N-[(2,4-dimethoxyphenyl)methyl]-3-methoxy-1-propane sulfonamide (4.98 g, 16.4 mmol) was dissolved in dichloromethane (20 mL) while stirring and TFA (20 mL) was added to this solution. After the reaction solution was stirred at room temperature for 5 hours, methanol (200 mL) was added to precipitate a solid. The solid was removed by celite filtration and the solvent and TFA were removed by distillation to obtain 3-methoxy-1-propane sulfonamide (2.34 g, 93%) as an oily substance.

$^1$H-NMR (CDCl$_3$) δ: 4.92 (2H, brs), 3.52 (2H, t, J=5.9 Hz), 3.35 (3H, s), 3.27-3.21 (2H, m), 2.17-2.08 (2H, m).

The following intermediates were synthesized from the corresponding halogenated alkyl in accordance with the method described in Reference Example 9.

[Chem. 24]

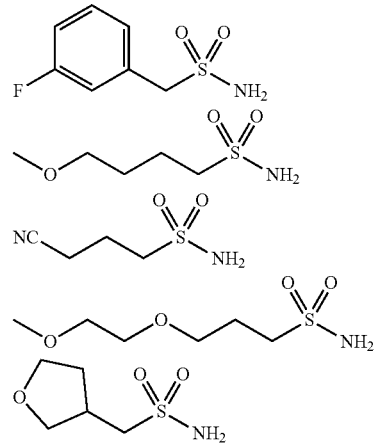

Reference Example 10

Ethyl 3-bromo-2-oxobutyrate

[Chem. 25]

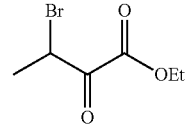

To a chloroform (250 mL) solution containing ethyl 2-hydroxybutyrate (25.0 g, 189 mmol) was added N-bromosuccinimide (67.3 g, 378 mmol) at room temperature, and the reaction solution was stirred at 60° C. for 4 hours. The reaction solution was cooled to room temperature and washed with hexane after filtration with celite. The filtrate was concentrated under reduced pressure to obtain ethyl 3-bromo-2-oxobutyrate (38.2 g, 97%) as a yellow oily substance.

$^1$H-NMR (CDCl$_3$) δ: 5.17 (1H, q, J=6.7 Hz), 4.39 (2H, qd, J=7.2, 1.8 Hz), 1.82 (3H, d, J=6.8 Hz), 1.40 (3H, t, J=7.3 Hz).

Reference Example 11

Ethyl 3-bromo-2-oxovalerate

[Chem. 26]

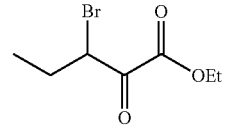

Ethyl 3-bromo-2-oxovalerate was synthesized using a method similar to Reference example 10 by using ethyl 2-hydroxvalerate as the raw material.

$^1$H-NMR (CDCl$_3$) δ: 4.98 (1H, dd, J=8.3, 5.9 Hz), 4.38 (2H, qd, J=7.2, 1.3 Hz), 2.14-2.01 (2H, m), 1.40 (3H, t, J=7.1 Hz), 1.08 (3H, t, J=7.3 Hz).

Reference Example 12

Methyl 3-bromo-2-oxobutyrate

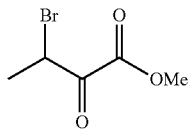

[Chem. 27]

To a carbon tetrachloride (172 mL) solution containing methyl 2-oxobutyrate (10.0 g, 86.1 mmol) was added one drop of concentrated sulfuric acid, and then was gradually added NBS (15.3 g, 86.1 mmol) while stirring. The mixture was heated up to 75° C. and stirred for 6 hours, ethyl acetate was added thereto and the resultant mixture was washed with water twice and with 1 M hydrochloric acid twice. After drying of the organic fraction over magnesium sulfate and removal of the solvent by distillation, the product was purified by column chromatography to obtain methyl 3-bromo-2-oxobutanate (15.0 g, 83%) as a yellow oily substance. $^1$H-NMR (CDCl$_3$) δ: 5.18 (1H, q, J=6.8 Hz), 3.94 (3H, s), 1.82 (3H, d, J=6.8 Hz).

Reference Example 13

Ethyl 2-amino-5-ethyloxazole-4-carboxylate

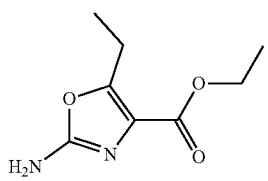

[Chem. 28]

To an ethanol (224 mL) solution containing 3-bromo-2-oxovaleric acid ethyl ester (10.0 g, 44.8 mmol) synthesized by the method mentioned in Reference Example 11, was added urea (5.12 g, 67.2 mmol), and the reaction solution was stirred for 15 hours while heating at 80° C. After cooling to room temperature, the solvent was removed by distillation under reduced pressure, a sodium bicarbonate aqueous solution was added, and the mixture was extracted with ethyl acetate three times. Organic fractions were combined and washed with a saturated salt solution and dried over magnesium sulfate. The solvent was removed by distillation under reduced pressure and the resultant residue was washed with a mixed solvent of ethyl acetate/hexane (1/4) to obtain ethyl 2-amino-5-ethyloxazole-4-carboxylate (5.70 g, 69%) as a solid.

$^1$H-NMR (DMSO-d$_6$) δ: 6.66 (2H, s), 4.17 (2H, q, J=7.0 Hz), 2.82 (2H, q, J=7.5 Hz), 1.23 (3H, t, J=7.1 Hz), 1.12 (3H, t, J=7.3 Hz).

Reference Example 14

Ethyl 2-amino-5-cyclopropyloxazole-4-carboxylate

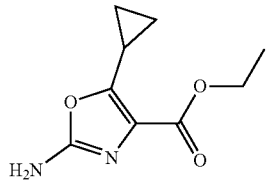

[Chem. 29]

The synthesis was performed using ethyl 3-cyclopropyl-2-oxoethyl propionate as the raw material and a method similar to Reference examples 12 and 13.

$^1$H-NMR (DMSO-d$_6$) δ: 6.62 (2H, s), 4.18 (2H, q, J=7.0 Hz), 2.53-2.51 (1H, m), 1.24 (3H, t, J=7.1 Hz), 1.02-0.99 (2H, m), 0.82-0.81 (2H, m).

Reference Example 15

Methyl 2-chloro-5-methylthiazol-4-carboxylate

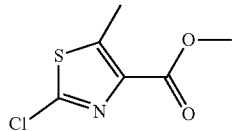

[Chem. 30]

An acetonitrile (130 mL) solution containing methyl 2-amino-5-methylthiazole-4-carboxylate (10.0 g, 58.1 mmol) was divided into two containers for 2 batches and each was stirred. To each container was added copper (II) chloride (5.86 g, 43.6 mmol) and added slowly dropwise tert-butyl nitrite (5.22 mL, 43.6 mmol). The mixture was stirred at room temperature for 16 hours, acetonitrile was removed under reduced pressure by distillation, water was added, and pH was adjusted to 3-4 by adding 1 M hydrochloric acid. The solution was extracted with ethyl acetate twice and organic fractions were combined. The combined organic fractions were washed with a saturated salt solution and dried over magnesium sulfate. After removing the solvent, methyl 2-chloro-5-methylthiazole-4-carboxylate (10.4 g, 93%) was obtained by purifying by column chromatography.

$^1$H-NMR (DMSO-d$_6$) δ: 3.81 (3H, s), 2.68 (3H, s)

Example 1

2-(N-benzyl-4-cyano-anilino)-5-methyl-N-methyl-sulfonyl-thiazole-4-carboxamide (Synthesis of Compound Number 1)

(1) To an ethanol (220 mL) solution containing (4-cyanophenyl)thiourea (30.0 g, 169 mmol) was added ethyl 3-bromo-2-oxobutyrate (42.5 g, 203 mmol) synthesized in accordance with the method described in Reference example 10, and the reaction solution was stirred at 80° C. for 3 hours. After the reaction solution was cooled to room temperature and the solvent was removed under reduced pressure by distillation, a sodium bicarbonate aqueous solution was added. The resultant solution was extracted with ethyl acetate twice. The organic fraction was washed with a saturated salt solution and dried over sodium sulfate. The solvent was removed under reduced pressure by distillation to obtain ethyl 2-(4-cyano-anilino)-5-methylthiazole-4-carboxylate (44 g, 90%) as a white solid.

$^1$H-NMR (DMSO) δ: 10.74 (1H, s), 7.76 (4H, s), 4.27 (2H, q, J=7.0 Hz), 2.60 (3H, s), 1.31 (3H, t, J=7.0 Hz).

(2) A DMF (50 mL) solution containing ethyl 2-(4-cyanoanilino)-5-methylthiazole-4-carboxylate (6.00 g, 20.9 mmol) was cooled to 0° C. After adding sodium hydride (1.25 g, 31.3 mmol) to this solution and stirring at 0° C. for 20 minutes, a benzylbromide (5.12 mL, 31.3 mmol) reaction solution was added, and then the resultant mixture was stirred for 1 hour. Water was added to the reaction solution and the mixture was extracted with ethyl acetate twice. The organic fraction was washed with a saturated salt solution and dried over sodium sulfate. The solvent was removed under reduced pressure by distillation, and the resultant residue was purified by column chromatography to obtain ethyl 2-(benzyl(4-cyanophenyl)amino)-5-methylthiazole-4-carboxylate (5.99 g, 76%) as a white solid.

$^1$H-NMR (CDCl$_3$) δ 7.55 (2H, d, J=8.8 Hz), 7.43 (2H, d, J=8.8 Hz), 7.32-7.24 (5H, m), 5.20 (2H, s), 4.35 (2H, q, J=7.1 Hz), 2.61 (3H, s), 1.38 (3H, t, J=7.1 Hz).

(3) To a mixed THF (40 mL)-methanol (40 mL) solution containing ethyl 2-(benzyl(4-cyanophenyl)amino)-5-methylthiazole-4-carboxylate (4.84 g, 12.8 mmol) was added 2.5 M sodium hydroxide aqueous solution (20 mL, 50 mmol), and the mixture was stirred at room temperature for 5 hours. After diluting the reaction solution by adding water, 6 M hydrochloric acid (8.3 mL, 50 mmol) was added to neutralize the solution. The mixture was extracted with ethyl acetate three times and the organic fractions were combined. The combined organic fractions were washed with a saturated salt solution and dried over sodium sulfate. The solvent was removed under reduced pressure by distillation and the resultant solid was washed with ethyl acetate to obtain 2-(N-benzyl-4-cyanoanilino)-5-methylthiazole-4-carboxylic acid (3.72 g, 83%) as a white solid.

$^1$H-NMR (CDCl$_3$) δ: 7.65 (2H, d, J=8.8 Hz), 7.46 (2H, d, J=8.8 Hz), 7.36-7.30 (3H, m), 7.24-7.23 (2H, m), 5.16 (2H, s), 2.65 (3H, s).

(4) 2-(N-benzyl-4-cyanoanilino)-5-methylthiazole-4-carboxylic acid (2.16 g, 22.7 mmol), methane sulfonamide (2.16 g, 22.7 mmol) and DMAP (1.39 g, 11.4 mmol) were dissolved in dichloromethane (50 mL) and 1-(3-dimethylaminopropyl)-3-ethylcarbodiimide hydrochloride (4.35 g, 22.7 mmol) was added. The resultant mixture was stirred at room temperature for 8 hours. Water was added to the reaction solution and the mixture was extracted with dichloromethane. The organic fraction was washed with a saturated salt solution and dried over sodium sulfate. The solvent was removed under reduced pressure by distillation and the resultant residue was purified by column chromatography to obtain 2-(N-benzyl-4-cyanoanilino)-5-methyl-N-methylsulfonyl-thiazole-4-carboxamide (3.00 g, 62%).

$^1$H-NMR (DMSO-d$_6$) δ: 11.17 (1H, s), 7.81 (2H, d, J=8.8 Hz), 7.65 (2H, d, J=8.8 Hz), 7.32-7.20 (5H, m), 5.45 (2H, s), 3.32 (3H, s), 2.57 (3H, s).

UPLC retention time=2.65 min.

Obs.Mass=427.02 (M+H)$^+$

Example 2

2-[4-cyano-N-[[2-(trifluoromethyl)thiazol-4-yl]methyl]anilino]-5-methyl-N-methylsulfonyl-thiazole-4-carboxamide (Synthesis of Compound Number 2)

(1) To a THF (15 mL) solution containing [2-(trifluoromethyl)thiazol-4-yl]methanol (525 mg, 2.87 mmol) was added triethylamine (0.799 mL, 5.73 mmol), and the mixture was cooled to 0° C. and stirred. Methanesulfonylchloride (361 mg, 3.15 mmol) was added dropwise to this solution and the temperature was elevated to room temperature while stirring for 2 hours. Water was added to the solution and the mixture was extracted with ethyl acetate to obtain a crude methyl [2-(trifluoromethyl)thiazol-4-yl]methanesulfonate by removing the solvent. The crude product was used for the next reaction without further purification.

(2) Ethyl 2-(4-cyanoanilino)-5-methylthiazole-4-carboxylate (783 mg, 2.87 mmol) was dissolved in 1,2-dimethoxyethane (2.9 mL) and sodium hydride (150 mg, 3.44 mmol) was added to the solution. The resultant mixture was stirred at room temperature for 30 minutes, methyl [2-(trifluoromethyl)thiazol-4-yl]methanesulfonate (749 mg, 2.87 mmol) was added and the mixture was stirred at room temperature for 5 hours. To the reaction solution was added 5 M sodium hydroxide aqueous solution (1.72 mL, 8.60 mmol), and the mixture was heated to 40° C. and further reacted for 3 hours. The reaction solution was neutralized with 2 M hydrochloric acid and the mixture was extracted with ethyl acetate twice. The organic fraction was washed with a saturated salt solution and dried over sodium sulfate. The solvent was removed under reduced pressure by distillation to obtain 2-[4-cyano-N-[[2-(trifluoromethyl)-4-yl]methyl]anilino]-5-methylthiazole-4-carboxylic acid (1.20 g, 99%).

$^1$H-NMR (DMSO-d$_6$) δ: 12.73 (1H, s), 8.00 (1H, s), 7.85 (2H, d, J=8.8 Hz), 7.71 (2H, d, J=8.8 Hz), 5.39 (2H, s), 2.54 (3H, s).

(3) For 2-[4-cyano-N-[[2-(trifluoromethyl)-4-yl]methyl]anilino]-5-methylthiazole-4-carboxylic acid (1.20 g, 2.83 mmol), the similar procedure to that in Example 1(4) was carried out to obtain a crude product (1.56 g). This was recrystallized from ethanol to obtain 2-[4-cyano-N-[[2-(trifluoromethyl)thiazol-4-yl]methyl]anilino]-5-methyl-N-methylsulfonyl-thiazole-4-carboxamide (474 mg).

$^1$H-NMR (DMSO-d$_6$) δ: 8.03 (1H, s), 7.88 (2H, d, J=8.8 Hz), 7.74 (2H, d, J=8.8 Hz), 5.63 (2H, s), 3.33 (3H, s), 2.57 (3H, s).

UPLC retention time=2.33 min.

Obs.Mass=501.88 (M+H)$^+$

The following compounds of Examples 3 to 202 were synthesized using corresponding starting materials, commercial reagents and/or intermediates in the Reference examples in accordance with a method of Example 1 or 2 with protection using an appropriate protecting group and de-protection if needed.

Example 3

2-[4-cyano-N-[(3-methoxyphenyl)methyl]anilino]-5-methyl-N-methylsulfonyl-thiazole-4-carboxamide (Synthesis of Compound Number 3)

$^1$H-NMR (DMSO-d$_6$) δ: 11.13 (0.9H, s), 7.73 (2.0H, d, J=8.8 Hz), 7.57 (2.0H, d, J=8.8 Hz), 7.12 (1.0H, t, J=7.8 Hz), 6.77 (1.1H, s), 6.74 (1.1H, d, J=7.8 Hz), 6.71 (1.0H, d, J=7.8 Hz), 5.33 (1.9H, s), 3.60 (3.0H, s), 3.24 (3.1H, s), 2.49 (3.0H, s).
UPLC retention time=2.29 min.
Obs.Mass=457.14 (M+H)$^+$

Example 4

2-[4-cyano-N-[[3-(difluoromethoxy)phenyl]methyl]anilino]-5-methyl-N-methylsulfonyl-thiazole-4-carboxamide (Synthesis of Compound Number 4)

$^1$H-NMR (DMSO-d$_6$) δ: 11.24 (1H, s), 7.83 (2H, t, J=4.4 Hz), 7.66 (2H, d, J=8.8 Hz), 7.35 (1H, t, J=7.8 Hz), 7.18 (1H, t, J=73.9 Hz), 7.15 (1H, d, J=7.8 Hz), 7.11 (1H, s), 7.03 (1H, d, J=8.3 Hz), 5.49 (2H, s), 3.33 (3H, s), 2.58 (3H, s).
UPLC retention time=2.33 min.
Obs.Mass=493.11 (M+H)$^+$

Example 5

2-[4-cyano-N-[[2-(difluoromethoxy)phenyl]methyl]anilino]-5-methyl-N-methylsulfonyl-thiazole-4-carboxamide (Synthesis of Compound Number 5)

$^1$H-NMR (CDCl$_3$) δ: 9.32 (1H, s), 7.67 (2H, d, J=8.8 Hz), 7.46 (2H, d, J=8.8 Hz), 7.33 (1H, t, J=7.6 Hz), 7.26-7.25 (1H, m), 7.19-7.15 (2H, m), 6.58 (1H, t, J=73.4 Hz), 5.21 (2H, s), 3.36 (3H, s), 2.65 (3H, s).
UPLC retention time=2.35 min.
Obs.Mass=493.15 (M+H)$^+$

Example 6

2-[4-cyano-N-[[3-(hydroxymethyl)phenyl]methyl]anilino]-5-methyl-N-methylsulfonyl-thiazole-4-carboxamide (Synthesis of Compound Number 6)

$^1$H-NMR (DMSO-d$_6$) δ: 11.18 (1H, s), 7.81 (2H, d, J=8.8 Hz), 7.66 (2H, d, J=8.8 Hz), 7.24 (2H, m), 7.14 (2H, m), 5.44 (2H, s), 5.14 (1H, s), 4.43 (2H, s), 3.33 (3H, s), 2.57 (3H, s).
UPLC retention time=1.95 min.
Obs.Mass=457.10 (M+H)$^+$

Example 7

2-[4-cyano-N-[[4-(trifluoromethoxy)phenyl]methyl]anilino]-5-methyl-N-methylsulfonyl-thiazole-4-carboxamide (Synthesis of Compound Number 7)

$^1$H-NMR (CDCl$_3$) δ: 9.19 (1H, s), 7.66 (2H, d, J=8.4 Hz), 7.41 (2H, d, J=8.4 Hz), 7.26 (2H, d, J=8.4 Hz), 7.19 (2H, d, J=8.4 Hz), 5.15 (2H, s), 3.35 (3H, s), 2.65 (3H, s).
UPLC retention time=2.54 min.
Obs.Mass=511.27 (M+H)$^+$

Example 8

2-[4-cyano-N-[(2-cyanophenyl)methyl]anilino]-5-methyl-N-methylsulfonyl-thiazole-4-carboxamide (Synthesis of Compound Number 8)

$^1$H-NMR (CDCl$_3$) δ: 9.22 (1H, s), 7.70-7.68 (3H, m), 7.57 (1H, t, J=7.2 Hz), 7.46-7.39 (4H, m), 5.36 (2H, s), 3.36 (3H, s), 2.63 (3H, s).
UPLC retention time=2.17 min.
Obs.Mass=452.02 (M+H)$^+$

Example 9

2-[4-cyano-N-[(3-cyanophenyl)methyl]anilino]-5-methyl-N-methylsulfonyl-thiazole-4-carboxamide (Synthesis of Compound Number 9)

$^1$H-NMR (CDCl$_3$) δ: 9.13 (1H, s), 7.68 (2H, d, J=8.4 Hz), 7.61-7.58 (1H, m), 7.50-7.48 (3H, m), 7.40 (2H, d, J=8.4 Hz), 5.19 (2H, s), 3.36 (3H, s), 2.66 (3H, s).
UPLC retention time=2.16 min.
Obs.Mass=451.98 (M+H)$^+$

Example 10

2-[4-cyano-N-[(4-cyanophenyl)methyl]anilino]-5-methyl-N-methylsulfonyl-thiazole-4-carboxamide (Synthesis of Compound Number 10)

$^1$H-NMR (CDCl$_3$) δ: 9.11 (1H, s), 7.67 (2H, d, J=8.4 Hz), 7.64 (2H, d, J=8.4 Hz), 7.40 (2H, d, J=8.4 Hz), 7.36 (2H, d, J=8.0 Hz), 5.21 (2H, s), 3.35 (3H, s), 2.66 (3H, s).
UPLC retention time=2.16 min.
Obs.Mass=452.02 (M+H)$^+$

Example 11

2-[4-cyano-N-[(4-methylsulfanylphenyl)methyl]anilino]-5-methyl-N-methylsulfonyl-thiazole-4-carboxamide (Synthesis of Compound Number 11)

$^1$H-NMR (CDCl$_3$) δ: 9.22 (1H, s), 7.65 (2H, d, J=8.4 Hz), 7.41 (2H, d, J=8.4 Hz), 7.20 (2H, d, J=8.0 Hz), 7.13 (2H, d, J=8.0 Hz), 5.09 (2H, s), 3.35 (3H, s), 2.64 (3H, s), 2.46 (3H, s).
UPLC retention time=2.42 min.
Obs.Mass=473.03 (M+H)$^+$

Example 12

2-[4-cyano-N-[(4-methylsulfonylphenyl)methyl]anilino]-5-methyl-N-methylsulfonyl-thiazole-4-carboxamide (Synthesis of Compound Number 12)

$^1$H-NMR (CDCl$_3$) δ: 9.08 (1H, s), 7.93 (2H, d, J=8.4 Hz), 7.69 (2H, d, J=8.4 Hz), 7.46-7.42 (4H, m), 5.25 (2H, s), 3.35 (3H, s), 3.06 (3H, s), 2.66 (3H, s).
UPLC retention time=1.97 min.
Obs.Mass=505.00 (M+H)$^+$

Example 13

2-[4-cyano-N-[(2-fluorophenyl)methyl]anilino]-5-methyl-N-methylsulfonyl-thiazole-4-carboxamide (Synthesis of Compound Number 13)

$^1$H-NMR (CDCl$_3$) δ: 9.29 (1H, s), 7.67 (2H, d, J=8.4 Hz), 7.44 (2H, d, J=8.4 Hz), 7.30-7.27 (1H, m), 7.24-7.20 (1H, m), 7.12-7.05 (2H, m), 5.17 (2H, s), 3.36 (3H, s), 2.64 (3H, s).
UPLC retention time=2.32 min.
Obs.Mass=444.98 (M+H)$^+$

Example 14

2-[4-cyano-N-[(3-fluorophenyl)methyl]anilino]-5-methyl-N-methylsulfonyl-thiazole-4-carboxamide (Synthesis of Compound Number 14)

$^1$H-NMR (CDCl$_3$) δ: 9.18 (1H, s), 7.66 (2H, d, J=8.4 Hz), 7.41 (2H, d, J=8.4 Hz), 7.31 (1H, dd, J=7.6, 6.0 Hz), 7.03-6.96 (2H, m), 6.92 (1H, d, J=9.2 Hz), 5.14 (2H, s), 3.35 (3H, s), 2.66 (3H, s).
UPLC retention time=2.34 min.
Obs.Mass=445.06 (M+H)$^+$

Example 15

2-[4-cyano-N-[(4-fluorophenyl)methyl]anilino]-5-methyl-N-methylsulfonyl-thiazole-4-carboxamide (Synthesis of Compound Number 15)

$^1$H-NMR (CDCl$_3$) δ: 9.21 (1H, s), 7.65 (2H, d, J=8.4 Hz), 7.39 (2H, d, J=8.4 Hz), 7.19 (2H, dd, J=8.4, 5.2 Hz), 7.02 (2H, t, J=8.4 Hz), 5.11 (2H, s), 3.36 (3H, s), 2.65 (3H, s).
UPLC retention time=2.36 min.
Obs.Mass=444.98 (M+H)$^+$

Example 16

2-[4-cyano-N-(m-tolylmethyl)anilino]-5-methyl-N-methylsulfonyl-thiazole-4-carboxamide (Synthesis of Compound Number 16)

$^1$H-NMR (CDCl$_3$) δ: 9.22 (1H, s), 7.64 (2H, d, J=8.4 Hz), 7.43 (2H, d, J=8.4 Hz), 7.21 (1H, t, J=7.6 Hz), 7.09 (1H, d, J=7.2 Hz), 7.02-6.99 (1H, m), 5.10 (2H, s), 3.35 (3H, s), 2.65 (3H, s), 2.32 (3H, s).
UPLC retention time=2.42 min.
Obs.Mass=441.01 (M+H)$^+$

Example 17

2-[4-cyano-N-(p-tolylmethyl)anilino]-5-methyl-N-methylsulfonyl-thiazole-4-carboxamide (Synthesis of Compound Number 17)

$^1$H-NMR (CDCl$_3$) δ: 9.22 (1H, s), 7.63 (2H, d, J=8.4 Hz), 7.42 (2H, d, J=8.4 Hz), 7.13 (2H, d, J=8.0 Hz), 7.10 (2H, d, J=8.0 Hz), 5.10 (2H, s), 3.35 (3H, s), 2.64 (3H, s), 2.32 (3H, s).
UPLC retention time=2.43 min.
Obs.Mass=441.01 (M+H)$^+$

Example 18

2-[N-[(3-chlorophenyl)methyl]-4-cyano-anilino]-5-methyl-N-methylsulfonyl-thiazole-4-carboxamide (Synthesis of Compound Number 18)

$^1$H-NMR (CDCl$_3$) δ: 9.18 (1H, s), 7.66 (2H, d, J=8.4 Hz), 7.41 (2H, d, J=8.4 Hz), 7.28-7.27 (2H, m), 7.20 (1H, s), 7.12-7.11 (1H, m), 5.13 (2H, s), 3.35 (3H, s), 2.66 (3H, s).
UPLC retention time=2.45 min.
Obs.Mass=460.98 (M+H)$^+$

Example 19

2-[4-cyano-N-(cyclopentylmethyl)anilino]-5-methyl-N-methylsulfonyl-thiazole-4-carboxamide (Synthesis of Compound Number 19)

$^1$H-NMR (CDCl$_3$) δ: 9.27 (1H, s), 7.70 (2H, d, J=8.4 Hz), 7.43 (2H, d, J=8.4 Hz), 3.88 (2H, d, J=7.6 Hz), 7.02-6.99 (1H, m), 3.37 (3H, s), 2.63 (3H, s), 2.20 (1H, quint, J=7.6 Hz), 1.62-1.55 (6H, m), 1.26-1.19 (2H, m).
UPLC retention time=2.53 min.
Obs.Mass=419.09 (M+H)$^+$

Example 20

2-[4-cyano-N-(2-phenoxyethyl)anilino]-5-methyl-N-methylsulfonyl-thiazole-4-carboxamide (Synthesis of Compound Number 20)

$^1$H-NMR (CDCl$_3$) δ: 9.26 (1H, s), 7.71 (2H, d, J=8.8 Hz), 7.57 (2H, d, J=8.8 Hz), 7.27 (2H, d, J=8.4 Hz), 6.96 (1H, t, J=7.2 Hz), 6.78 (2H, d, J=8.0 Hz), 4.32 (2H, t, J=4.8 Hz), 4.27 (2H, t, J=4.8 Hz), 3.38 (3H, s), 2.63 (3H, s).
UPLC retention time=2.39 min.
Obs.Mass=457.02 (M+H)$^+$

Example 21

2-(N-benzyl-4-methoxy-anilino)-5-methyl-N-methylsulfonyl-thiazole-4-carboxamide (Synthesis of Compound Number 21)

$^1$H-NMR (CDCl$_3$) δ: 7.33-7.31 (5H, m), 7.12 (2H, d, J=8.8 Hz), 6.89 (2H, d, J=8.8 Hz), 5.00 (2H, s), 3.81 (3H, s), 3.36 (3H, s), 2.57 (3H, s).
UPLC retention time=2.49 min.
Obs.Mass=432.09 (M+H)$^+$

Example 22

2-[N-benzyl-4-(2-methoxyethoxy)anilino]-5-methyl-N-methylsulfonyl-thiazole-4-carboxamide (Synthesis of Compound Number 22)

$^1$H-NMR (CDCl$_3$) δ: 9.42 (1H, brs), 7.31-7.24 (5H, m), 7.10 (2H, dd, J=6.9, 2.1 Hz), 6.92 (2H, dd, J=6.9, 2.1 Hz), 5.00 (2H, s), 4.12-4.09 (2H, m), 3.77-3.74 (2H, m), 3.46 (3H, s), 3.37 (3H, s), 2.57 (3H, s).
UPLC retention time=2.40 min.
Obs.Mass=476.11 (M+H)$^+$

Example 23

2-[N-[(4-chlorophenyl)methyl]-4-cyano-anilino]-5-methyl-N-methylsulfonyl-thiazole-4-carboxamide (Synthesis of Compound Number 23)

$^1$H-NMR (CDCl$_3$) δ: 9.20 (1H, s), 7.65 (2H, d, J=8.4 Hz), 7.40 (2H, d, J=8.8 Hz), 7.30 (2H, d, J=8.4 Hz), 7.16 (2H, d, J=8.4 Hz), 5.11 (2H, s), 3.35 (3H, s), 2.66 (3H, s).
UPLC retention time=2.46 min.
Obs.Mass=460.90 (M+H)$^+$

Example 24

2-[4-cyano-N-[[3-(trifluoromethyl)phenyl]methyl]anilino]-5-methyl-N-methylsulfonyl-thiazole-4-carboxamide (Synthesis of Compound Number 24)

$^1$H-NMR (CDCl$_3$) δ: 9.18 (1H, s), 7.67 (2H, d, J=8.8 Hz), 7.56 (1H, d, J=7.6 Hz), 7.49-7.40 (5H, m), 5.21 (2H, s), 3.35 (3H, s), 2.66 (3H, s).
UPLC retention time=2.44 min.
Obs.Mass=495.00 (M+H)$^+$

Example 25

2-[4-cyano-N-(2-naphthylmethyl)anilino]-5-methyl-N-methylsulfonyl-thiazole-4-carboxamide (Synthesis of Compound Number 25)

$^1$H-NMR (CDCl$_3$) δ: 9.26 (1H, s), 7.84-7.76 (3H, m), 7.65-7.63 (3H, m), 7.49-7.46 (4H, m), 7.35 (1H, d, J=8.4 Hz), 5.30 (2H, s), 3.33 (3H, s), 2.64 (3H, s).
UPLC retention time=2.50 min.
Obs.Mass=477.03 (M+H)$^+$

Example 26

2-[N-(benzofuran-5-ylmethyl)-4-cyano-anilino]-5-methyl-N-methylsulfonyl-thiazole-4-carboxamide (Synthesis of Compound Number 26)

$^1$H-NMR (DMSO-d$_6$) δ: 7.95 (1H, d, J=2.0 Hz), 7.71 (2H, d, J=8.8 Hz), 7.56-7.53 (4H, m), 7.25 (1H, d, J=8.8 Hz), 6.91 (1H, dd, J=1.7, 0.7 Hz), 5.32 (2H, s), 2.80 (3H, s), 2.54 (3H, s).
UPLC retention time=2.35 min.
Obs.Mass=467.07 (M+H)$^+$

Example 27

2-[N-benzyl-2-(trifluoromethoxy)anilino]-5-methyl-N-methylsulfonyl-thiazole-4-carboxamide (Synthesis of Compound Number 27)

$^1$H-NMR (CDCl$_3$) δ: 9.36 (1H, brs), 7.39 (2H, d, J=4.0 Hz), 7.32-7.20 (7H, m), 4.98 (2H, s), 3.37 (3H, s), 2.59 (3H, s).
UPLC retention time=2.63 min.
Obs.Mass=486.03 (M+H)$^+$

Example 28

2-(N-benzyl-4-fluoro-anilino)-5-methyl-N-methylsulfonyl-thiazole-4-carboxamide (Synthesis of Compound Number 28)

$^1$H-NMR (CDCl$_3$) δ: 9.35 (1H, brs), 7.32-7.17 (7H, m), 7.07 (2H, t, J=8.4 Hz), 5.02 (2H, s), 3.36 (3H, s), 2.59 (3H, s).
UPLC retention time=2.53 min.
Obs.Mass=420.09 (M+H)$^+$

Example 29

2-(N-benzyl-3-fluoro-anilino)-5-methyl-N-methylsulfonyl-thiazole-4-carboxamide (Synthesis of Compound Number 29)

$^1$H-NMR (CDCl$_3$) δ: 9.30 (1H, brs), 7.34-7.24 (6H, m), 7.02-6.99 (3H, m), 5.08 (2H, s), 3.35 (3H, s), 2.61 (3H, s).
UPLC retention time=2.51 min.
Obs.Mass=420.05 (M+H)$^+$

Example 30

2-(N-benzyl-2-fluoro-anilino)-5-methyl-N-methylsulfonyl-thiazole-4-carboxamide (Synthesis of Compound Number 30)

$^1$H-NMR (CDCl$_3$) δ: 9.35 (1H, brs), 7.34-7.26 (6H, m), 7.21-7.11 (3H, m), 5.00 (2H, s), 3.36 (3H, s), 2.59 (3H, s).
UPLC retention time=2.48 min.
Obs.Mass=420.05 (M+H)$^+$

Example 31

2-(N-benzyl-4-chloro-anilino)-5-methyl-N-methylsulfonyl-thiazole-4-carboxamide (Synthesis of Compound Number 31)

$^1$H-NMR (CDCl$_3$) δ: 9.33 (1H, brs), 7.37-7.17 (9H, m), 5.04 (2H, s), 3.36 (3H, s), 2.59 (3H, s).
UPLC retention time=2.68 min.
Obs.Mass=436.05 (M+H)$^+$

Example 32

2-(N-benzyl-3-chloro-anilino)-5-methyl-N-methylsulfonyl-thiazole-4-carboxamide (Synthesis of Compound Number 32)

$^1$H-NMR (CDCl$_3$) δ: 9.29 (1H, brs), 7.35-7.25 (8H, m), 7.19-7.16 (1H, m), 5.07 (2H, s), 3.35 (3H, s), 2.61 (3H, s).
UPLC retention time=2.64 min.
Obs.Mass=436.05 (M+H)$^+$

Example 33

2-(N-benzyl-2-chloro-anilino)-5-methyl-N-methylsulfonyl-thiazole-4-carboxamide (Synthesis of Compound Number 33)

$^1$H-NMR (CDCl$_3$) δ: 9.41 (1H, brs), 7.53 (1H, dd, J=8.0, 1.6 Hz), 7.35-7.22 (7H, m), 7.09 (1H, dd, J=8.0, 1.6 Hz), 4.99 (2H, brs), 3.37 (3H, s), 2.58 (3H, s).
UPLC retention time=2.58 min.
Obs.Mass=436.01 (M+H)$^+$

Example 34

2-[N-benzyl-4-(trifluoromethoxy)anilino]-5-methyl-N-methylsulfonyl-thiazole-4-carboxamide (Synthesis of Compound Number 34)

$^1$H-NMR (CDCl$_3$) δ: 9.30 (1H, brs), 7.33-7.21 (9H, m), 5.06 (2H, s), 3.36 (3H, s), 2.60 (3H, s).
UPLC retention time=2.72 min.
Obs.Mass=486.03 (M+H)$^+$

Example 35

2-[N-benzyl-3-(trifluoromethoxy)anilino]-5-methyl-N-methylsulfonyl-thiazole-4-carboxamide (Synthesis of Compound Number 35)

$^1$H-NMR (CDCl$_3$) δ: 9.28 (1H, brs), 7.41 (1H, t, J=8.4 Hz), 7.33-7.12 (8H, m), 5.08 (2H, s), 3.35 (3H, s), 2.62 (3H, s).
UPLC retention time=2.69 min.
Obs.Mass=486.07 (M+H)$^+$

Example 36

2-(N-benzyl-2,4-difluoro-anilino)-5-methyl-N-methylsulfonyl-thiazole-4-carboxamide (Synthesis of Compound Number 36)

$^1$H-NMR (CDCl$_3$) δ: 9.35 (1H, brs), 7.29-7.26 (5H, m), 7.13 (1H, dt, J=8.8, 5.6 Hz), 6.97-6.83 (2H, m), 4.97 (2H, s), 3.37 (3H, s), 2.60 (3H, s).
UPLC retention time=2.52 min.
Obs.Mass=438.05 (M+H)$^+$

Example 37

2-(N-benzyl-3,4-dichloro-anilino)-5-methyl-N-methylsulfonyl-thiazole-4-carboxamide (Synthesis of Compound Number 37)

$^1$H-NMR (CDCl$_3$) δ: 9.27 (1H, brs), 7.46-7.29 (7H, m), 7.12 (1H, dd, J=8.7, 2.4 Hz), 6.97-6.83 (2H, m), 5.05 (2H, s), 3.36 (3H, s), 2.62 (3H, s).
UPLC retention time=2.80 min.
Obs.Mass=469.99 (M+H)$^+$

Example 38

2-(N-benzyl-4-benzyloxy-anilino)-5-methyl-N-methylsulfonyl-thiazole-4-carboxamide (Synthesis of Compound Number 38)

$^1$H-NMR (CDCl$_3$) δ: 9.39 (1H, brs), 7.42-7.26 (10H, m), 7.13 (2H, d, J=9.2 Hz), 6.96 (2H, d, J=9.2 Hz), 5.05 (2H, s), 5.00 (2H, s), 3.36 (3H, s), 2.57 (3H, s).
UPLC retention time=2.80 min.
Obs.Mass=508.12 (M+H)$^+$

Example 39

2-[4-cyano-N-[(4,4-difluorocyclohexyl)methyl]anilino]-5-methyl-N-methylsulfonyl-thiazole-4-carboxamide (Synthesis of Compound Number 39)

$^1$H-NMR (CDCl$_3$) δ: 9.23 (1H, s), 7.74 (2H, d, J=8.3 Hz), 7.45 (2H, d, J=8.8 Hz), 3.87 (2H, d, J=6.8 Hz), 3.39 (3H, s), 2.65 (3H, s), 2.11-2.05 (2H, m), 1.78-1.66 (5H, m), 1.37-1.34 (2H, m).
UPLC retention time=2.38 min.
Obs.Mass=469.11 (M+H)$^+$

Example 40

2-[4-cyano-N-[(2-methylthiazol-4-yl)methyl]anilino]-5-methyl-N-methylsulfonyl-thiazole-4-carboxamide (Synthesis of Compound Number 40)

$^1$H-NMR (DMSO-d$_6$) δ: 11.16 (1H, s), 7.84 (2H, d, J=9.3 Hz), 7.75 (2H, d, J=9.3 Hz), 7.33 (1H, s), 5.39 (2H, s), 3.32 (3H, s), 2.60 (3H, s), 2.57 (3H, s).
UPLC retention time=2.03 min.
Obs.Mass=448.06 (M+H)$^+$

Example 41

2-[4-cyano-N-[[4-(difluoromethoxy)phenyl]methyl]anilino]-5-methyl-N-methylsulfonyl-thiazole-4-carboxamide (Synthesis of Compound Number 41)

$^1$H-NMR (DMSO-d$_6$) δ: 11.24 (1H, s), 7.82 (2H, d, J=8.8 Hz), 7.65 (2H, d, J=8.3 Hz), 7.36-6.99 (5H, m), 5.46 (2H, s), 3.34 (3H, s), 2.57 (3H, s).
UPLC retention time=2.37 min.
Obs.Mass=492.95 (M+H)$^+$

Example 42

2-[4-cyano-N-(2-pyridylmethyl)anilino]-5-methyl-N-methylsulfonyl-thiazole-4-carboxamide (Synthesis of Compound Number 42)

$^1$H-NMR (CDCl$_3$) δ: 9.30 (1H, brs), 8.65 (1H, d, J=4.8 Hz), 7.88 (1H, t, J=7.6 Hz), 7.70 (2H, d, J=8.4 Hz), 7.57 (2H, d, J=8.4 Hz), 7.43-7.40 (2H, m), 5.35 (2H, s), 3.33 (3H, s), 2.63 (3H, s).
UPLC retention time=1.56 min.
Obs.Mass=428.01 (M+H)$^+$

Example 43

2-[4-cyano-N-(3-pyridylmethyl) anilino]-5-methyl-N-methylsulfonyl-thiazole-4-carboxamide (Synthesis of Compound Number 43)

$^1$H-NMR (CDCl$_3$) δ: 9.20 (1H, brs), 8.89 (1H, s), 8.67 (1H, d, J=5.2 Hz), 8.04 (1H, d, J=8.0 Hz), 7.73-7.67 (3H, m), 7.44 (2H, d, J=8.4 Hz), 5.31 (2H, s), 3.37 (3H, s), 2.65 (3H, s).
UPLC retention time=1.44 min.
Obs.Mass=428.05 (M+H)$^+$

Example 44

2-[4-cyano-N-(4-pyridylmethyl)anilino]-5-methyl-N-methylsulfonyl-thiazole-4-carboxamide (Synthesis of Compound Number 44)

$^1$H-NMR (CDCl$_3$) δ: 9.02 (1H, s), 8.75 (2H, d, J=6.0 Hz), 7.72 (2H, d, J=8.4 Hz), 7.57 (2H, d, J=5.6 Hz), 7.44 (2H, d, J=8.4 Hz), 5.33 (2H, s), 3.34 (3H, s), 2.67 (3H, s).
UPLC retention time=1.42 min.
Obs.Mass=428.01 (M+H)$^+$

Example 45

2-[4-cyano-N-(o-tolylmethyl)anilino]-5-methyl-N-methylsulfonyl-thiazole-4-carboxamide (Synthesis of Compound Number 45)

$^1$H-NMR (CDCl$_3$) δ: 9.22 (1H, s), 7.67 (2H, d, J=8.4 Hz), 7.43 (2H, d, J=8.4 Hz), 7.23-7.22 (2H, m), 7.18-7.14 (1H, m), 7.11 (2H, d, J=7.6 Hz), 5.13 (2H, s), 3.38 (3H, s), 2.68 (3H, s), 2.35 (3H, s).
UPLC retention time=2.40 min.
Obs.Mass=441.05 (M+H)$^+$

Example 46

2-[4-cyano-N-[[4-(trifluoromethyl)phenyl]methyl]anilino]-5-methyl-N-methylsulfonyl-thiazole-4-carboxamide (Synthesis of Compound Number 46)

$^1$H-NMR (CDCl$_3$) δ: 9.12 (1H, s), 7.67 (2H, d, J=8.8 Hz), 7.61 (2H, d, J=8.0 Hz), 7.41 (2H, d, J=8.8 Hz), 7.36 (2H, d, J=8.0 Hz), 5.21 (2H, s), 3.34 (3H, s), 2.66 (3H, s).
UPLC retention time=2.47 min.
Obs.Mass=495.00 (M+H)$^+$

Example 47

2-(N-benzyl-2-methoxy-anilino)-5-methyl-N-methylsulfonyl-thiazole-4-carboxamide (Synthesis of Compound Number 47)

$^1$H-NMR (CDCl$_3$) δ: 9.46 (1H, brs), 7.34-7.24 (6H, m), 7.08 (1H, dd, J=7.5, 1.5 Hz), 7.01 (1H, d, J=8.1 Hz), 6.93-6.91 (1H, m), 4.95 (2H, s), 3.82 (3H, s), 3.37 (3H, s), 2.56 (3H, s).
UPLC retention time=2.50 min.
Obs.Mass=432.13 (M+H)$^+$

Example 48

2-(N-benzyl-3,4-difluoro-anilino)-5-methyl-N-methylsulfonyl-thiazole-4-carboxamide (Synthesis of Compound Number 48)

$^1$H-NMR (DMSO-d$_6$) δ: 9.33 (1H, brs), 7.36-6.989 (8H, m), 5.04 (2H, s), 3.37 (3H, s), 2.61 (3H, s).
UPLC retention time=2.55 min.
Obs.Mass=438.09 (M+H)$^+$

Example 49

2-[benzyl(3-pyridyl)amino]-5-methyl-N-methylsulfonyl-thiazole-4-carboxamide (Synthesis of Compound Number 49)

$^1$H-NMR (CDCl$_3$) δ: 9.31 (1H, brs), 8.58 (1H, d, J=2.4 Hz), 8.53 (1H, dd, J=4.5, 1.2 Hz), 7.58 (1H, dt, J=8.4, 2.1 Hz), 7.34-7.56 (6H, m), 5.08 (2H, s), 3.36 (3H, s), 2.61 (3H, s).
UPLC retention time=1.59 min.
Obs.Mass=403.12 (M+H)$^+$

Example 50

2-[N-(1,3-benzothiazol-6-ylmethyl)-4-cyano-anilino]-5-methyl-N-methylsulfonyl-thiazole-4-carboxamide (Synthesis of Compound Number 50)

$^1$H-NMR (DMSO-d$_6$) δ: 11.22 (1H, s), 9.33 (1H, s), 8.10 (1H, s), 8.01 (1H, d, J=8.3 Hz), 7.81 (2H, d, J=8.8 Hz), 7.69 (2H, d, J=8.3 Hz), 7.48 (1H, d, J=8.3 Hz), 5.62 (2H, s), 3.33 (3H, s), 2.58 (3H, s).
UPLC retention time=2.08 min.
Obs.Mass=484.11 (M+H)$^+$

Example 51

2-[N-(benzothiophen-2-ylmethyl)-4-cyano-anilino]-5-methyl-N-methylsulfonyl-thiazole-4-carboxamide (Synthesis of Compound Number 51)

$^1$H-NMR (CDCl$_3$) δ: 9.39 (1H, s), 7.78 (1H, d, J=6.3 Hz), 7.71-7.68 (3H, m), 7.49 (2H, d, J=8.8 Hz), 7.37-7.30 (2H, m), 7.14 (1H, s), 5.36 (2H, s), 3.38 (3H, s), 2.67 (3H, s).
UPLC retention time=2.47 min.
Obs.Mass=483.07 (M+H)$^+$

Example 52

2-[4-cyano-N-(2-phenylethyl)anilino]-5-methyl-N-methylsulfonyl-thiazole-4-carboxamide (Synthesis of Compound Number 52)

$^1$H-NMR (CDCl$_3$) δ: 9.26 (1H, s), 7.63 (2H, d, J=8.4 Hz), 7.31-7.21 (5H, m), 7.13 (2H, d, J=7.2 Hz), 4.16 (2H, t, J=7.2 Hz), 3.38 (3H, s), 3.00 (2H, t, J=7.2 Hz), 2.64 (3H, s).
UPLC retention time=2.43 min.
Obs.Mass=441.05 (M+H)$^+$

Example 53

2-[benzyl(8-quinolyl)amino]-5-methyl-N-methylsulfonyl-thiazole-4-carboxamide (Synthesis of Compound Number 53)

$^1$H-NMR (CDCl$_3$) δ: 9.49 (1H, brs), 8.99 (1H, dd, J=4.2, 1.6 Hz), 8.23 (1H, dd, J=8.4, 1.8 Hz), 7.85 (1H, dd, J=7.8, 1.8 Hz), 7.54-7.47 (3H, m), 7.31-7.22 (5H, m), 5.29 (2H, s), 3.36 (3H, s), 2.51 (3H, s).
UPLC retention time=2.17 min.
Obs.Mass=453.14 (M+H)$^+$

Example 54

2-[benzyl(6-quinolyl)amino]-5-methyl-N-methylsulfonyl-thiazole-4-carboxamide (Synthesis of Compound Number 54)

$^1$H-NMR (CDCl$_3$) δ: 9.34 (1H, s), 8.93 (1H, dd, J=4.2, 1.8 Hz), 8.14 (1H, d, J=8.0 Hz), 8.07 (1H, dd, J=8.4, 1.2 Hz), 7.72 (1H, d, J=2.4 Hz), 7.63 (1H, dd, J=9.0, 2.4 Hz), 7.43 (1H, dd, J=8.4, 4.2 Hz), 7.36-7.24 (5H, m), 5.19 (2H, s), 3.36 (3H, s), 2.60 (3H, s).
UPLC retention time=1.68 min.
Obs.Mass=453.14 (M+H)$^+$

Example 55

2-[benzyl(pyrazin-2-yl)amino]-5-methyl-N-methyl-sulfonyl-thiazole-4-carboxamide (Synthesis of Compound Number 55)

$^1$H-NMR (CDCl$_3$) δ: 9.28 (1H, s), 9.03 (1H, s), 8.42 (1H, d, J=1.6 Hz), 8.34 (1H, dd, J=2.8, 1.6 Hz), 8.25 (1H, d, J=2.4 Hz), 7.37-7.22 (4H, m), 5.63 (2H, s), 3.36 (3H, s), 2.76 (3H, s).
UPLC retention time=2.13 min.
Obs.Mass=404.12 (M+H)$^+$

Example 56

2-[4-cyano-N-[[2-(trifluoromethylsulfanyl)phenyl]methyl]anilino]-5-methyl-N-methylsulfonyl-thiazole-4-carboxamide (Synthesis of Compound Number 56)

$^1$H-NMR (CDCl$_3$) δ: 9.14 (1H, s), 7.74 (1H, d, J=7.6 Hz), 7.64 (2H, d, J=8.8 Hz), 7.49 (1H, t, J=7.2 Hz), 7.42-7.34 (4H, m), 5.45 (2H, s), 3.34 (3H, s), 2.66 (3H, s).
UPLC retention time=2.58 min.
Obs.Mass=527.01 (M+H)$^+$

Example 57

2-[4-cyano-N-[[3-(trifluoromethylsulfanyl)phenyl]methyl]anilino]-5-methyl-N-methylsulfonyl-thiazole-4-carboxamide (Synthesis of Compound Number 57)

$^1$H-NMR (CDCl$_3$) δ: 9.17 (1H, s), 7.66 (2H, d, J=8.8 Hz), 7.58 (1H, d, J=7.2 Hz), 7.49 (1H, s), 7.44-7.36 (4H, m), 5.18 (2H, s), 3.35 (3H, s), 2.65 (3H, s).
UPLC retention time=2.57 min.
Obs.Mass=527.01 (M+H)$^+$

Example 58

2-[4-cyano-N-(1-phenylethyl)anilino]-5-methyl-N-methylsulfonyl-thiazole-4-carboxamide (Synthesis of Compound Number 58)

$^1$H-NMR (CDCl$_3$) δ: 9.31 (1H, s), 7.62 (2H, d, J=8.4 Hz), 7.34-7.23 (5H, m), 7.09 (2H, d, J=8.4 Hz), 5.95 (1H, q, J=7.2 Hz), 3.37 (3H, s), 2.58 (3H, s), 1.60 (3H, d, J=7.2 Hz).
UPLC retention time=2.42 min.
Obs.Mass=441.05 (M+H)$^+$

Example 59

2-[N-[(3-benzyloxyphenyl)methyl]-4-cyano-anilino]-5-methyl-N-methylsulfonyl-thiazole-4-carboxamide (Synthesis of Compound Number 59)

$^1$H-NMR (CDCl$_3$) δ: 9.20 (1H, s), 7.61 (2H, d, J=8.8 Hz), 7.38-7.31 (8H, m), 6.90 (1H, d, J=8.8 Hz), 6.81-6.79 (2H, m), 5.10 (2H, s), 5.03 (2H, s), 3.34 (3H, s), 2.65 (3H, s).
UPLC retention time=2.58 min.
Obs.Mass=533.09 (M+H)$^+$

Example 60

2-(4-cyano-N-methyl-anilino)-5-methyl-N-methyl-sulfonyl-thiazole-4-carboxamide (Synthesis of Compound Number 60)

$^1$H-NMR (CDCl$_3$) δ: 9.33 (1H, s), 7.69 (2H, d, J=8.8 Hz), 7.46 (2H, d, J=8.8 Hz), 3.52 (3H, s), 3.37 (3H, s), 2.66 (3H, s).
UPLC retention time=1.94 min.
Obs.Mass=351.01 (M+H)$^+$

Examples 61

2-[N-benzyl-4-(1,2,4-triazol-1-yl)anilino]-5-methyl-N-methylsulfonyl-thiazole-4-carboxamide (Synthesis of Compound Number 61)

$^1$H-NMR (CDCl$_3$) δ: 9.32 (1H, s), 8.55 (1H, s), 8.11 (1H, s), 7.71 (2H, d, J=8.7 Hz), 7.42 (2H, d, J=8.7 Hz), 7.33-7.28 (5H, m), 5.11 (2H, s), 3.36 (3H, s), 2.62 (3H, s).
UPLC retention time=2.07 min.
Obs.Mass=469.15 (M+H)$^+$

Example 62

2-[4-cyano-N-[2-(4-hydroxyphenyl)ethyl]anilino]-5-methyl-N-methylsulfonyl-thiazole-4-carboxamide (Synthesis of Compound Number 62)

$^1$H-NMR (DMSO-d$_6$) δ: 10.91 (1H, s), 9.13 (1H, s), 7.78 (2H, d, J=8.8 Hz), 7.51 (2H, d, J=8.8 Hz), 6.95 (2H, d, J=8.3 Hz), 6.58 (2H, d, J=7.8 Hz), 4.15 (2H, t, J=7.3 Hz), 3.28 (3H, s), 2.74 (2H, t, J=7.6 Hz), 2.49 (3H, s).
UPLC retention time=2.08 min.
Obs.Mass=457.14 (M+H)$^+$

Example 63

2-(4-cyano-N-(3,3-dimethyl-2-oxo-butyl)anilino)-5-methyl-N-methylsulfonyl-thiazole-4-carboxamide (Synthesis of Compound Number 63)

$^1$H-NMR (CDCl$_3$) δ: 7.69 (2H, d, J=8.7 Hz), 7.48 (2H, d, J=8.7 Hz), 4.85 (2H, s), 3.33 (3H, s), 2.61 (3H, s), 1.27 (9H, s).
UPLC retention time=2.23 min.
Obs.Mass=435.05 (M+H)$^+$

Example 64

2-(N-butyl-4-cyano-anilino)-5-methyl-N-methylsulfonyl-thiazole-4-carboxamide (Synthesis of Compound Number 64)

$^1$H-NMR (CDCl$_3$) δ: 9.28 (1H, s), 7.69 (2H, d, J=8.4 Hz), 7.43 (2H, d, J=8.4 Hz), 3.91 (2H, t, J=7.6 Hz), 3.37 (3H, s), 2.64 (3H, s), 1.68-1.61 (2H, m), 1.41-1.32 (2H, m), 0.93 (3H, t, J=7.2 Hz).
UPLC retention time=2.38 min.
Obs.Mass=393.07 (M+H)$^+$

Example 65

2-[4-cyano-N-(2-ethylbutyl)anilino]-5-methyl-N-methylsulfonyl-thiazole-4-carboxamide (Synthesis of Compound Number 65)

$^1$H-NMR (CDCl$_3$) δ: 9.28 (1H, s), 7.70 (2H, d, J=8.4 Hz), 7.43 (2H, d, J=8.4 Hz), 3.84 (2H, d, J=7.2 Hz), 3.37 (3H, s), 2.63 (3H, s), 1.66-1.61 (1H, m), 1.34 (4H, quint, J=7.2 Hz), 0.86 (6H, t, J=7.2 Hz).
UPLC retention time=2.58 min.
Obs.Mass=421.09 (M+H)$^+$

Example 66

2-(4-cyano-N-isopentyl-anilino)-5-methyl-N-methylsulfonyl-thiazole-4-carboxamide (Synthesis of Compound Number 66)

$^1$H-NMR (DMSO-d$_6$) δ: 10.79 (1H, s), 7.89 (2H, d, J=8.8 Hz), 7.68 (2H, d, J=8.8 Hz), 4.08 (2H, t, J=7.6 Hz), 3.35 (3H, s), 2.57 (3H, s), 1.65-1.59 (1H, m), 1.47 (2H, q, J=7.2 Hz), 0.88 (6H, d, J=6.8 Hz).
UPLC retention time=2.50 min.
Obs.Mass=407.08 (M+H)$^+$

Example 67

2-[4-cyano-N-(cyclopropylmethyl)anilino]-5-methyl-N-methylsulfonyl-thiazole-4-carboxamide (Synthesis of Compound Number 67)

$^1$H-NMR (CDCl$_3$) δ: 9.31 (1H, s), 7.71 (2H, d, J=8.4 Hz), 7.47 (2H, d, J=8.4 Hz), 3.79 (2H, d, J=6.8 Hz), 3.37 (3H, s), 2.63 (3H, s), 1.13-1.10 (1H, m), 0.52 (2H, dd, J=13.2, 5.6 Hz), 0.16 (2H, q, J=5.2 Hz).
UPLC retention time=2.25 min.
Obs.Mass=391.07 (M+H)$^+$

Example 68

2-[4-cyano-N-(1-naphthylmethyl)anilino]-5-methyl-N-methylsulfonyl-thiazole-4-carboxamide (Synthesis of Compound Number 68)

$^1$H-NMR (CDCl$_3$) δ: 9.25 (1H, s), 7.95 (1H, d, J=8.0 Hz), 7.90 (1H, d, J=8.0 Hz), 7.80 (1H, d, J=8.4 Hz), 7.60-7.53 (4H, m), 7.38-7.34 (3H, m), 7.26-7.25 (1H, m), 5.60 (2H, s), 3.34 (3H, s), 2.65 (3H, s).
UPLC retention time=2.49 min.
Obs.Mass=477.03 (M+H)$^+$

Example 69

2-(N-benzyl-4-cyano-anilino)-N-(difluoromethylsulfonyl)-5-methyl-thiazole-4-carboxamide (Synthesis of Compound Number 69)

$^1$H-NMR (DMSO-d$_6$) δ: 7.73 (2H, d, J=8.3 Hz), 7.56 (2H, d, J=8.3 Hz), 7.23-7.15 (5H, m), 7.04 (1H, t, J=53.2 Hz), 5.36 (2H, s), 2.49 (3H, s).
UPLC retention time=2.48 min.
Obs.Mass=463.10 (M+H)$^+$

Example 70

2-[N-[(4-chloro-2-fluoro-phenyl)methyl]-4-cyano-anilino]-5-methyl-N-methylsulfonyl-thiazole-4-carboxamide (Synthesis of Compound Number 70)

$^1$H-NMR (DMSO-d$_6$) δ: 11.19 (1H, s), 7.86 (2H, d, J=7.8 Hz), 7.66 (2H, d, J=7.8 Hz), 7.41 (2H, q, J=8.3 Hz), 7.23 (1H, d, J=8.3 Hz), 5.48 (2H, s), 3.34 (3H, s), 2.56 (3H, s).
UPLC retention time=2.47 min.
Obs.Mass=479.03 (M+H)$^+$

Examples 71

2-[N-benzyl-3-(1,2,4-triazol-1-yl)anilino]-5-methyl-N-methylsulfonyl-thiazole-4-carboxamide (Synthesis of Compound Number 71)

$^1$H-NMR (CDCl$_3$) δ: 9.33 (1H, s), 8.49 (1H, s), 8.11 (1H, s), 7.74 (1H, t, J=2.0 Hz), 7.58-7.50 (2H, m), 7.36-7.27 (6H, m), 5.14 (2H, s), 3.36 (3H, s), 2.62 (3H, s).
UPLC retention time=2.10 min.
Obs.Mass=469.15 (M+H)$^+$

Example 72

2-(4-cyano-N-[2-oxo-2-(1-piperidyl)ethyl]anilino)-5-methyl-N-methylsulfonyl-thiazole-4-carboxamide (Synthesis of Compound Number 72)

$^1$H-NMR (CDCl$_3$) δ: 9.22 (1H, s), 7.68 (2H, d, J=8.6 Hz), 7.55 (2H, d, J=8.6 Hz), 4.69 (2H, s), 3.59-3.56 (2H, m), 3.45-3.43 (2H, m), 3.35 (3H, s), 2.62 (3H, s), 1.70-1.58 (6H, m).
UPLC retention time=1.98 min.
Obs.Mass=462.06 (M+H)$^+$

Example 73

2-(4-cyano-N-isobutyl-anilino)-5-methyl-N-methylsulfonyl-thiazole-4-carboxamide (Synthesis of Compound Number 73)

$^1$H-NMR (DMSO-d$_6$) δ: 10.90 (1H, s), 7.89 (2H, d, J=8.8 Hz), 7.70 (2H, d, J=8.8 Hz), 3.96 (2H, d, J=7.6 Hz), 3.35 (3H, s), 2.55 (3H, s), 1.88 (1H, quint, J=6.8 Hz), 0.89 (6H, d, J=6.8 Hz).
UPLC retention time=2.36 min.
Obs.Mass=393.07 (M+H)$^+$

Example 74

2-[4-cyano-N-(2,2-dimethylpropyl)anilino]-5-methyl-N-methylsulfonyl-thiazole-4-carboxamide (Synthesis of Compound Number 74)

$^1$H-NMR (DMSO-d$_6$) δ: 10.80 (1H, s), 7.91 (2H, d, J=8.8 Hz), 7.77 (2H, d, J=8.8 Hz), 4.06 (2H, s), 3.35 (3H, s), 2.52 (3H, s), 0.86 (9H, s).
UPLC retention time=2.44 min.
Obs.Mass=407.08 (M+H)$^+$

Example 75

2-(4-cyano-N-hexyl-anilino)-5-methyl-N-methylsulfonyl-thiazole-4-carboxamide (Synthesis of Compound Number 75)

$^1$H-NMR (CDCl$_3$) δ: 9.28 (1H, s), 7.70 (2H, d, J=8.4 Hz), 7.42 (2H, d, J=8.4 Hz), 3.90 (2H, t, J=7.6 Hz), 3.37 (3H, s), 2.64 (3H, s), 1.67-1.62 (2H, m), 1.35-1.27 (6H, m), 0.87 (3H, t, J=6.4 Hz).
UPLC retention time=2.64 min.
Obs.Mass=421.09 (M+H)$^+$

Example 76

2-[N-(1-adamantylmethyl)-4-cyano-anilino]-5-methyl-N-methylsulfonyl-thiazole-4-carboxamide (Synthesis of Compound Number 76)

$^1$H-NMR (CDCl$_3$) δ: 9.25 (1H, s), 7.70 (2H, d, J=8.4 Hz), 7.48 (2H, d, J=8.4 Hz), 3.71 (2H, s), 3.37 (3H, s), 2.61 (3H, s), 1.93 (3H, s), 1.68-1.55 (6H, m), 1.47 (6H, s).
UPLC retention time=2.87 min.
Obs.Mass=485.11 (M+H)$^+$

Example 77

2-[4-cyano-N-(2-thienylmethyl)anilino]-5-methyl-N-methylsulfonyl-thiazole-4-carboxamide (Synthesis of Compound Number 77)

$^1$H-NMR (CDCl$_3$) δ: 9.35 (1H, s), 7.68 (2H, d, J=8.4 Hz), 7.48 (2H, d, J=8.4 Hz), 7.25-7.23 (1H, m), 6.93-6.89 (2H, m), 5.25 (2H, s), 3.38 (3H, s), 2.65 (3H, s).
UPLC retention time=2.25 min.
Obs.Mass=432.97 (M+H)$^+$

Example 78

2-[4-cyano-N-(2-cyclopentylethyl)anilino]-5-methyl-N-methylsulfonyl-thiazole-4-carboxamide (Synthesis of Compound Number 78)

$^1$H-NMR (CDCl$_3$) δ: 9.30 (1H, s), 7.69 (2H, d, J=8.4 Hz), 7.43 (2H, d, J=8.4 Hz), 3.91 (2H, t, J=7.6 Hz), 3.37 (3H, s), 2.65 (3H, s), 1.78-1.57 (9H, m), 1.11 (2H, brs).
UPLC retention time=2.67 min.
Obs.Mass=433.05 (M+H)$^+$

Example 79

2-[4-cyano-N-[[2-(difluoromethylsulfanyl)phenyl]methyl]anilino]-5-methyl-N-methylsulfonyl-thiazole-4-carboxamide (Synthesis of Compound Number 79)

$^1$H-NMR (CDCl$_3$) δ: 9.19 (1H, s), 7.67 (1H, d, J=8.0 Hz), 7.64 (2H, d, J=8.7 Hz), 7.44-7.29 (5H, m), 6.82 (1H, t, J=56.2 Hz), 5.42 (2H, s), 3.33 (3H, s), 2.65 (3H, s).
UPLC retention time=2.43 min.
Obs.Mass=508.96 (M+H)$^+$

Example 80

2-[4-cyano-N-[2-(2-fluorophenyl)ethyl]anilino]-5-methyl-N-methylsulfonyl-thiazole-4-carboxamide (Synthesis of Compound Number 80)

$^1$H-NMR (CDCl$_3$) δ: 9.31 (1H, s), 7.66 (2H, d, J=8.4 Hz), 7.34 (2H, d, J=8.4 Hz), 7.22-7.19 (1H, m), 7.13-6.99 (3H, m), 4.19 (2H, t, J=7.2 Hz), 3.39 (3H, s), 3.06 (2H, t, J=7.2 Hz), 2.64 (3H, s).
UPLC retention time=2.43 min.
Obs.Mass=459.02 (M+H)$^+$

Example 81

2-[4-cyano-N-[2-(4-fluorophenyl)ethyl]anilino]-5-methyl-N-methylsulfonyl-thiazole-4-carboxamide (Synthesis of Compound Number 81)

$^1$H-NMR (CDCl$_3$) δ: 9.24 (1H, s), 7.65 (2H, d, J=8.4 Hz), 7.27 (2H, d, J=8.4 Hz), 7.11-7.07 (2H, m), 6.98 (2H, t, J=8.4 Hz), 4.14 (2H, t, J=7.2 Hz), 3.38 (3H, s), 2.97 (2H, t, J=7.2 Hz), 2.64 (3H, s).
UPLC retention time=2.45 min.
Obs.Mass=459.06 (M+H)$^+$

Example 82

2-[4-cyano-N-[(3-phenoxyphenyl)methyl]anilino]-5-methyl-N-methylsulfonyl-thiazole-4-carboxamide (Synthesis of Compound Number 82)

$^1$H-NMR (CDCl$_3$) δ: 9.20 (1H, s), 7.63 (2H, d, J=8.4 Hz), 7.39 (2H, d, J=8.4 Hz), 7.34-7.27 (3H, m), 7.12 (1H, t, J=7.2 Hz), 6.99-6.89 (4H, m), 6.81 (1H, m), 5.12 (2H, s), 3.35 (3H, s), 2.65 (3H, s).
UPLC retention time=2.58 min.
Obs.Mass=519.04 (M+H)$^+$

Example 83

2-[4-cyano-N-[2-(3-fluorophenyl)ethyl]anilino]-5-methyl-N-methylsulfonyl-thiazole-4-carboxamide (Synthesis of Compound Number 83)

$^1$H-NMR (CDCl$_3$) δ: 9.25 (1H, s), 7.65 (2H, d, J=8.4 Hz), 7.29-7.25 (3H, m), 6.94-6.90 (2H, m), 6.82 (1H, d, J=9.6 Hz), 4.17 (2H, t, J=7.2 Hz), 3.39 (3H, s), 3.01 (2H, t, J=7.2 Hz), 2.64 (3H, s).
UPLC retention time=2.42 min.
Obs.Mass=459.02 (M+H)$^+$

Example 84

2-[4-cyano-N-(1-phenylpropyl)anilino]-5-methyl-N-methylsulfonyl-thiazole-4-carboxamide (Synthesis of Compound Number 84)

$^1$H-NMR (CDCl$_3$) δ: 9.33 (1H, s), 7.61 (2H, d, J=8.4 Hz), 7.31-7.29 (3H, m), 7.18-7.16 (2H, m), 7.04 (2H, d, J=8.4 Hz), 5.70 (1H, t, J=7.8 Hz), 3.39 (3H, s), 2.58 (3H, s), 2.01 (2H, q, J=7.6 Hz), 1.04 (3H, t, J=7.2 Hz).
UPLC retention time=2.53 min.
Obs.Mass=455.06 (M+H)$^+$

Example 85

2-[4-cyano-N-(3-thienylmethyl)anilino]-5-methyl-N-methylsulfonyl-thiazole-4-carboxamide (Synthesis of Compound Number 85)

$^1$H-NMR (CDCl$_3$) δ: 9.26 (1H, s), 7.65 (2H, d, J=8.4 Hz), 7.40 (2H, d, J=8.4 Hz), 7.33-7.31 (1H, m), 7.08 (1H, s), 6.96 (1H, d, J=4.8 Hz), 5.12 (2H, s), 3.36 (3H, s), 2.65 (3H, s).
UPLC retention time=2.26 min.
Obs.Mass=432.93 (M+H)$^+$

Example 86

2-[4-cyano-N-(3-furylmethyl)anilino]-5-methyl-N-methylsulfonyl-thiazole-4-carboxamide (Synthesis of Compound Number 86)

$^1$H-NMR (CDCl$_3$) δ: 9.28 (1H, s), 7.67 (2H, d, J=8.4 Hz), 7.41 (2H, d, J=8.4 Hz), 7.37 (1H, s), 7.30 (1H, s), 6.28 (1H, s), 4.96 (2H, s), 3.37 (3H, s), 2.65 (3H, s).
UPLC retention time=2.15 min.
Obs.Mass=417.00 (M+H)$^+$

Example 87

2-[4-cyano-N-(2-furylmethyl)anilino]-5-methyl-N-methylsulfonyl-thiazole-4-carboxamide (Synthesis of Compound Number 87)

$^1$H-NMR (CDCl$_3$) δ: 9.32 (1H, s), 7.69 (2H, d, J=8.8 Hz), 7.48 (2H, d, J=8.8 Hz), 7.37 (1H, d, J=1.2 Hz), 6.33-6.31 (1H, m), 6.24 (1H, d, J=3.2 Hz), 5.04 (2H, s), 3.37 (3H, s), 2.64 (3H, s).
UPLC retention time=2.17 min.
Obs.Mass=417.04 (M+H)$^+$

Example 88

2-[4-cyano-N-[2-(2-naphthyl)ethyl]anilino]-5-methyl-N-methylsulfonyl-thiazole-4-carboxamide (Synthesis of Compound Number 88)

$^1$H-NMR (CDCl$_3$) δ: 9.30 (1H, s), 7.81-7.74 (3H, m), 7.60 (2H, d, J=8.4 Hz), 7.55 (1H, s), 7.47-7.44 (2H, m), 7.30-7.26 (3H, m), 4.26 (2H, t, J=7.2 Hz), 3.37 (3H, s), 3.17 (2H, t, J=7.2 Hz), 2.62 (3H, s).
UPLC retention time=2.60 min.
Obs.Mass=491.07 (M+H)$^+$

Example 89

2-[4-cyano-N-(2-methylbutyl)anilino]-5-methyl-N-methylsulfonyl-thiazole-4-carboxamide (Synthesis of Compound Number 89)

$^1$H-NMR (CDCl$_3$) δ: 9.26 (1H, s), 7.70 (2H, d, J=8.8 Hz), 7.43 (2H, d, J=8.4 Hz), 3.87 (1H, dd, J=14.4, 6.8 Hz), 3.71 (1H, dd, J=14.4, 8.0 Hz), 3.37 (3H, s), 2.63 (3H, s), 1.78-1.75 (1H, m), 1.45-1.40 (1H, m), 1.22-1.15 (1H, m), 0.91-0.87 (6H, m).
UPLC retention time=2.48 min.
Obs.Mass=407.08 (M+H)$^+$

Example 90

2-[4-cyano-N-(3,3-dimethylbutyl)anilino]-5-methyl-N-methylsulfonyl-thiazole-4-carboxamide (Synthesis of Compound Number 90)

$^1$H-NMR (CDCl$_3$) δ: 9.29 (1H, s), 7.69 (2H, d, J=8.8 Hz), 7.43 (2H, d, J=8.8 Hz), 3.94-3.90 (2H, m), 3.36 (3H, s), 2.65 (3H, s), 1.62-1.58 (2H, m), 0.97 (9H, s).
UPLC retention time=2.60 min.
Obs.Mass=421.09 (M+H)$^+$

Example 91

2-[N-benzyl-4-(difluoromethoxy)anilino]-5-methyl-N-methylsulfonyl-thiazole-4-carboxamide (Synthesis of Compound Number 91)

$^1$H-NMR (CDCl$_3$) δ: 9.33 (1H, s), 7.32-7.23 (7H, m), 7.13 (2H, d, J=8.7 Hz), 6.52 (1H, t, J=73.5 Hz), 5.04 (2H, s), 3.36 (3H, s), 2.59 (3H, s).
UPLC retention time=2.50 min.
Obs.Mass=468.11 (M+H)$^+$

Examples 92

2-[N-(2,1,3-benzoxadiazol-4-ylmethyl)-4-cyano-anilino]-5-methyl-N-methylsulfonyl-thiazole-4-carboxamide (Synthesis of Compound Number 92)

$^1$H-NMR (DMSO-d$_6$) δ: 11.19 (1H, s), 7.94 (1H, d, J=8.8 Hz), 7.84 (2H, d, J=8.3 Hz), 7.75 (2H, d, J=8.3 Hz), 7.53 (1H, t, J=7.8 Hz), 7.47 (1H, d, J=6.3 Hz), 5.87 (2H, s), 3.33 (3H, s), 2.59 (3H, s).
UPLC retention time=2.23 min.
Obs.Mass=469.11 (M+H)$^+$

Example 93

2-[4-cyano-N-[[2-(difluoromethyl)phenyl]methyl]anilino]-5-methyl-N-methylsulfonyl-thiazole-4-carboxamide (Synthesis of Compound Number 93)

$^1$H-NMR (DMSO-d$_6$) δ: 11.27 (1H, s), 7.84 (2H, d, J=8.8 Hz), 7.64-7.61 (3H, m), 7.42-7.31 (4H, m), 5.64 (2H, s), 3.36 (3H, s), 2.58 (3H, s).
UPLC retention time=2.33 min.
Obs.Mass=477.07 (M+H)$^+$

Example 94

2-[4-cyano-N-[[4-(difluoromethyl)phenyl]methyl]anilino]-5-methyl-N-methylsulfonyl-thiazole-4-carboxamide (Synthesis of Compound Number 94)

$^1$H-NMR (CDCl$_3$) δ: 9.17 (1H, s), 7.67 (2H, d, J=8.8 Hz), 7.50 (2H, d, J=7.3 Hz), 7.43 (2H, d, J=8.8 Hz), 7.33 (2H, d, J=7.8 Hz), 6.64 (1H, t, J=56.3 Hz), 5.20 (2H, s), 3.36 (3H, s), 2.66 (3H, s).
UPLC retention time=2.31 min.
Obs.Mass=477.11 (M+H)$^+$

Example 95

2-[N-[(3-acetylphenyl)methyl]-4-cyano-anilino]-5-methyl-N-methylsulfonyl-thiazole-4-carboxamide (Synthesis of Compound Number 95)

$^1$H-NMR (CDCl$_3$) δ: 9.17 (1H, s), 7.87-7.85 (2H, m), 7.66 (2H, d, J=8.4 Hz), 7.47-7.41 (4H, m), 5.21 (2H, s), 3.35 (3H, s), 2.65 (3H, s), 2.58 (3H, s).
UPLC retention time=2.14 min.
Obs.Mass=469.03 (M+H)$^+$

Example 96

2-[4-cyano-N-[(3,5-difluorophenyl)methyl]anilino]-5-methyl-N-methylsulfonyl-thiazole-4-carboxamide (Synthesis of Compound Number 96)

$^1$H-NMR (CDCl$_3$) δ: 9.16 (1H, s), 7.67 (2H, d, J=8.8 Hz), 7.41 (2H, d, J=8.8 Hz), 6.77-6.72 (3H, m), 5.14 (2H, s), 3.36 (3H, s), 2.67 (3H, s).
UPLC retention time=2.35 min.
Obs.Mass=462.98 (M+H)$^+$

Example 97

2-[4-cyano-N-[(3,4-difluorophenyl)methyl]anilino]-5-methyl-N-methylsulfonyl-thiazole-4-carboxamide (Synthesis of Compound Number 97)

$^1$H-NMR (DMSO-d$_6$) δ: 11.25 (1H, s), 7.83 (2H, d, J=9.3 Hz), 7.66 (2H, d, J=8.8 Hz), 7.39-7.35 (2H, m), 7.14 (1H, brs), 5.45 (2H, s), 3.33 (3H, s), 2.57 (3H, s).
UPLC retention time=2.37 min.
Obs.Mass=462.90 (M+H)$^+$

Example 98

2-[4-cyano-N-[(3-fluoro-5-methyl-phenyl)methyl]anilino]-5-methyl-N-methylsulfonyl-thiazole-4-carboxamide (Synthesis of Compound Number 98)

$^1$H-NMR (CDCl$_3$) δ: 9.20 (1H, s), 7.66 (2H, d, J=8.8 Hz), 7.42 (2H, d, J=8.8 Hz), 6.81-6.78 (2H, m), 6.70 (1H, d, J=9.2 Hz), 5.10 (2H, s), 3.35 (3H, s), 2.66 (3H, s), 2.32 (3H, s).
UPLC retention time=2.42 min.
Obs.Mass=459.02 (M+H)$^+$

Example 99

2-[N-[(3-chloro-5-fluoro-phenyl)methyl]-4-cyano-anilino]-5-methyl-N-methylsulfonyl-thiazole-4-carboxamide (Synthesis of Compound Number 99)

$^1$H-NMR (CDCl$_3$) δ: 9.17 (1H, s), 7.68 (2H, d, J=8.4 Hz), 7.41 (2H, d, J=8.4 Hz), 7.04-7.02 (2H, m), 6.84 (1H, d, J=8.8 Hz), 5.13 (2H, s), 3.36 (3H, s), 2.67 (3H, s).
UPLC retention time=2.48 min.
Obs.Mass=478.99 (M+H)$^+$

Example 100

2-[4-cyano-N-[(3,4-dichlorophenyl)methyl]anilino]-5-methyl-N-methylsulfonyl-thiazole-4-carboxamide (Synthesis of Compound Number 100)

$^1$H-NMR (CDCl$_3$) δ: 9.17 (1H, s), 7.67 (2H, d, J=8.4 Hz), 7.42-7.39 (3H, m), 7.31 (1H, d, J=1.2 Hz), 7.08 (1H, d, J=8.4 Hz), 5.11 (2H, s), 3.36 (3H, s), 2.66 (3H, s).
UPLC retention time=2.54 min.
Obs.Mass=494.96 (M+H)$^+$

Example 101

2-[4-cyano-N-[[2-(trifluoromethoxy)phenyl]methyl]anilino]-5-methyl-N-methylsulfonyl-thiazole-4-carboxamide (Synthesis of Compound Number 101)

$^1$H-NMR (CDCl$_3$) δ: 9.22 (1H, s), 7.66 (2H, d, J=8.4 Hz), 7.42 (2H, d, J=8.4 Hz), 7.37-7.33 (1H, m), 7.30-7.26 (3H, m), 5.21 (2H, s), 3.35 (3H, s), 2.64 (3H, s).
UPLC retention time=2.50 min.
Obs.Mass=511.00 (M+H)$^+$

Example 102

2-[4-cyano-N-[(2,3-difluorophenyl)methyl]anilino]-5-methyl-N-methylsulfonyl-thiazole-4-carboxamide (Synthesis of Compound Number 102)

$^1$H-NMR (CDCl$_3$) δ: 9.24 (1H, s), 7.68 (2H, d, J=8.4 Hz), 7.43 (2H, d, J=8.4 Hz), 7.14-6.99 (3H, m), 5.20 (2H, s), 3.36 (3H, s), 2.64 (3H, s).
UPLC retention time=2.37 min.
Obs.Mass=463.02 (M+H)$^+$

Example 103

2-[4-cyano-N-[(2,5-difluorophenyl)methyl]anilino]-5-methyl-N-methylsulfonyl-thiazole-4-carboxamide (Synthesis of Compound Number 103)

$^1$H-NMR (CDCl$_3$) δ: 9.25 (1H, s), 7.69 (2H, d, J=8.8 Hz), 7.44 (2H, d, J=8.8 Hz), 7.06 (1H, dt, J=9.2, 4.4 Hz), 6.99-6.93 (1H, m), 6.92-6.87 (1H, m), 5.17 (2H, s), 3.36 (3H, s), 2.65 (3H, s).
UPLC retention time=2.35 min.
Obs.Mass=463.06 (M+H)$^+$

Example 104

2-[4-cyano-N-[(2,4-difluorophenyl)methyl]anilino]-5-methyl-N-methylsulfonyl-thiazole-4-carboxamide (Synthesis of Compound Number 104)

$^1$H-NMR (CDCl$_3$) δ: 9.28 (1H, s), 7.68 (2H, d, J=8.8 Hz), 7.42 (2H, d, J=8.8 Hz), 7.22-7.18 (1H, m), 6.86-6.81 (2H, m), 5.13 (2H, s), 3.37 (3H, s), 2.64 (3H, s).
UPLC retention time=2.35 min.
Obs.Mass=463.02 (M+H)$^+$

Example 105

2-[4-cyano-N-[(5-fluoro-2-methoxy-phenyl)methyl]anilino]-5-methyl-N-methylsulfonyl-thiazole-4-carboxamide (Synthesis of Compound Number 105)

$^1$H-NMR (CDCl$_3$) δ: 9.24 (1H, s), 7.65 (2H, d, J=8.8 Hz), 7.44 (2H, d, J=8.8 Hz), 6.94 (1H, dt, J=8.4, 2.8 Hz), 6.85-6.80 (2H, m), 5.11 (2H, s), 3.82 (3H, s), 3.35 (3H, s), 2.66 (3H, s).
UPLC retention time=2.36 min.
Obs.Mass=475.03 (M+H)$^+$

Example 106

2-[N-[(2-chloro-4-fluoro-phenyl)methyl]-4-cyano-anilino]-5-methyl-N-methylsulfonyl-thiazole-4-carboxamide (Synthesis of Compound Number 106)

$^1$H-NMR (CDCl$_3$) δ: 9.24 (1H, s), 7.68 (2H, d, J=8.3 Hz), 7.43 (2H, d, J=8.3 Hz), 7.23 (1H, dd, J=8.8, 5.9 Hz), 7.17 (1H, dd, J=8.0, 2.7 Hz), 6.97 (1H, td, J=8.2, 2.6 Hz), 5.21 (2H, s), 3.37 (3H, s), 2.66 (3H, s).
UPLC retention time=2.49 min.
Obs.Mass=478.99 (M+H)$^+$

Example 107

2-[N-[(3-chloro-2-fluoro-phenyl)methyl]-4-cyano-anilino]-5-methyl-N-methylsulfonyl-thiazole-4-carboxamide (Synthesis of Compound Number 107)

$^1$H-NMR (CDCl$_3$) δ: 9.23 (1H, s), 7.68 (2H, d, J=8.8 Hz), 7.43 (2H, d, J=8.8 Hz), 7.35 (1H, t, J=7.2 Hz), 7.14 (1H, t, J=6.4 Hz), 7.06 (1H, t, J=8.0 Hz), 5.19 (2H, s), 3.36 (3H, s), 2.64 (3H, s).
UPLC retention time=2.47 min.
Obs.Mass=478.99 (M+H)$^+$

Example 108

2-[N-[(2-chloro-5-fluoro-phenyl)methyl]-4-cyano-anilino]-5-methyl-N-methylsulfonyl-thiazole-4-carboxamide (Synthesis of Compound Number 108)

$^1$H-NMR (CDCl$_3$) δ: 9.19 (1H, s), 7.67 (2H, d, J=8.8 Hz), 7.44 (2H, d, J=8.8 Hz), 7.38 (1H, dd, J=8.8, 5.2 Hz), 6.99-6.91 (2H, m), 5.22 (2H, s), 3.35 (3H, s), 2.67 (3H, s).
UPLC retention time=2.42 min.
Obs.Mass=478.99 (M+H)$^+$

Examples 109

2-[4-cyano-N-[(2,3,5-trifluorophenyl)methyl]anilino]-5-methyl-N-methylsulfonyl-thiazole-4-carboxamide (Synthesis of Compound Number 109)

$^1$H-NMR (CDCl$_3$) δ: 9.20 (1H, s), 7.70 (2H, d, J=8.4 Hz), 7.43 (2H, d, J=8.4 Hz), 6.91-6.85 (1H, m), 6.74-6.72 (1H, m), 5.22 (2H, s), 3.36 (3H, s), 2.66 (3H, s).
UPLC retention time=2.40 min.
Obs.Mass=481.03 (M+H)$^+$

Examples 110

2-[4-cyano-N-[(2,4,5-trifluorophenyl)methyl]anilino]-5-methyl-N-methylsulfonyl-thiazole-4-carboxamide (Synthesis of Compound Number 110)

$^1$H-NMR (CDCl$_3$) δ: 9.24 (1H, s), 7.70 (2H, d, J=8.4 Hz), 7.42 (2H, d, J=8.4 Hz), 7.04 (1H, q, J=8.4 Hz), 6.97 (1H, dt, J=9.6, 6.4 Hz), 7.04 (1H, t, J=9.2 Hz), 5.13 (2H, s), 3.37 (3H, s), 2.65 (3H, s).
UPLC retention time=2.40 min.
Obs.Mass=480.99 (M+H)$^+$

Example 111

2-[4-cyano-N-[(2,4-difluoro-3-methoxy-phenyl)methyl]anilino]-5-methyl-N-methylsulfonyl-thiazole-4-carboxamide (Synthesis of Compound Number 111)

$^1$H-NMR (CDCl$_3$) δ: 9.27 (1H, s), 7.68 (2H, d, J=8.8 Hz), 7.42 (2H, d, J=8.8 Hz), 6.88-6.84 (2H, m), 5.13 (2H, s), 3.98 (3H, s), 3.36 (3H, s), 2.64 (3H, s).
UPLC retention time=2.36 min.
Obs.Mass=493.03 (M+H)$^+$

Example 112

2-[4-cyano-N-[(2,3-difluoro-4-methoxy-phenyl)methyl]anilino]-5-methyl-N-methylsulfonyl-thiazole-4-carboxamide (Synthesis of Compound Number 112)

$^1$H-NMR (CDCl$_3$) δ: 9.26 (1H, s), 7.68 (2H, d, J=8.4 Hz), 7.41 (2H, d, J=8.8 Hz), 6.94 (1H, t, J=8.0 Hz), 6.70 (1H, t, J=8.0 Hz), 5.11 (2H, s), 3.87 (3H, s), 3.37 (3H, s), 2.63 (3H, s).
UPLC retention time=2.34 min.
Obs.Mass=493.03 (M+H)$^+$

Example 113

2-[4-cyano-N-[[4-(trifluoromethylsulfanyl)phenyl]methyl]anilino]-5-methyl-N-methylsulfonyl-thiazole-4-carboxamide (Synthesis of Compound Number 113)

$^1$H-NMR (CDCl$_3$) δ: 9.15 (1H, s), 7.67 (2H, d, J=8.8 Hz), 7.63 (2H, d, J=8.0 Hz), 7.42 (2H, d, J=8.8 Hz), 7.29 (2H, d, J=8.0 Hz), 5.19 (2H, s), 3.34 (3H, s), 2.66 (3H, s).
UPLC retention time=2.60 min.
Obs.Mass=527.01 (M+H)$^+$

Examples 114

2-[N-(2,1,3-benzothiadiazole-5-ylmethyl)-4-cyano-anilino]-5-methyl-N-methylsulfonyl-thiazole-4-carboxamide (Synthesis of Compound Number 114)

$^1$H-NMR (CDCl$_3$) δ: 9.16 (1H, s), 8.02 (1H, d, J=9.2 Hz), 7.80 (1H, s), 7.66 (2H, d, J=8.4 Hz), 7.53 (1H, dd, J=9.2, 1.2 Hz), 7.47 (2H, d, J=8.8 Hz), 5.35 (2H, s), 3.34 (3H, s), 2.66 (3H, s).
UPLC retention time=2.25 min.
Obs.Mass=485.03 (M+H)$^+$

Example 115

2-[4-cyano-N-[(3-fluoro-4-methyl-phenyl)methyl]anilino]-5-methyl-N-methylsulfonyl-thiazole-4-carboxamide (Synthesis of Compound Number 115)

$^1$H-NMR (CDCl$_3$) δ: 9.20 (1H, s), 7.65 (2H, d, J=8.8 Hz), 7.41 (2H, d, J=8.8 Hz), 7.14 (1H, t, J=7.6 Hz), 6.90 (1H, d, J=7.6 Hz), 6.86 (1H, d, J=10.4 Hz), 5.10 (2H, s), 3.35 (3H, s), 2.65 (3H, s), 2.24 (3H, s).
UPLC retention time=2.44 min.
Obs.Mass=459.02 (M+H)$^+$

Example 116

2-[N-[(4-chloro-3-fluoro-phenyl)methyl]-4-cyano-anilino]-5-methyl-N-methylsulfonyl-thiazole-4-carboxamide (Synthesis of Compound Number 116)

$^1$H-NMR (CDCl$_3$) δ: 9.16 (1H, s), 7.67 (2H, d, J=8.4 Hz), 7.41-7.35 (3H, m), 7.01 (1H, d, J=10.0 Hz), 6.98 (1H, d, J=8.0 Hz), 5.12 (2H, s), 3.36 (3H, s), 2.66 (3H, s).
UPLC retention time=2.45 min.
Obs.Mass=478.99 (M+H)$^+$

Example 117

2-[N-[(3-chloro-4-fluoro-phenyl)methyl]-4-cyano-anilino]-5-methyl-N-methylsulfonyl-thiazole-4-carboxamide (Synthesis of Compound Number 117)

$^1$H-NMR (CDCl$_3$) δ: 9.18 (1H, s), 7.68 (2H, d, J=8.8 Hz), 7.40 (2H, d, J=8.8 Hz), 7.27-7.25 (1H, m), 7.11 (2H, d, J=6.8 Hz), 5.10 (2H, s), 3.36 (3H, s), 2.66 (3H, s).
UPLC retention time=2.43 min.
Obs.Mass=478.99 (M+H)$^+$

Example 118

2-[N-[(4-chloro-2-methoxy-phenyl)methyl]-4-cyano-anilino]-5-methyl-N-methylsulfonyl-thiazole-4-carboxamide (Synthesis of Compound Number 118)

$^1$H-NMR (CDCl$_3$) δ: 9.23 (1H, s), 7.64 (2H, d, J=8.8 Hz), 7.42 (2H, d, J=8.8 Hz), 7.03 (1H, d, J=8.4 Hz), 6.89-6.88 (2H, m), 5.07 (2H, s), 3.80 (3H, s), 3.35 (3H, s), 2.65 (3H, s).
UPLC retention time=2.50 min.
Obs.Mass=490.99 (M+H)$^+$

Example 119

2-[N-[(4-acetamidophenyl)methyl]-4-cyano-anilino]-5-methyl-N-methylsulfonyl-thiazole-4-carboxamide (Synthesis of Compound Number 119)

$^1$H-NMR (CDCl$_3$) δ: 9.20 (1H, s), 7.64 (2H, d, J=8.4 Hz), 7.46 (2H, d, J=8.4 Hz), 7.41 (2H, d, J=8.4 Hz), 7.19-7.17 (3H, m), 5.09 (2H, s), 3.35 (3H, s), 2.64 (3H, s), 2.17 (3H, s).
UPLC retention time=1.91 min.
Obs.Mass=484.03 (M+H)$^+$

Example 120

2-[4-cyano-N-(tetrahydropyran-3-ylmethyl)anilino]-5-methyl-N-methylsulfonyl-thiazole-4-carboxamide (Synthesis of Compound Number 120)

$^1$H-NMR (CDCl$_3$) δ: 9.63 (1H, s), 7.70 (2H, d, J=8.4 Hz), 7.44 (2H, d, J=8.4 Hz), 4.16 (1H, dd, J=14.4, 9.6 Hz), 3.81-3.65 (4H, m), 3.48-3.43 (1H, m), 3.34 (3H, s), 2.64 (3H, s), 1.97-1.94 (1H, m), 1.81-1.78 (1H, m), 1.70-1.66 (1H, m), 1.49-1.42 (2H, m).
UPLC retention time=2.13 min.
Obs.Mass=435.05 (M+H)$^+$

Example 121

2-[4-cyano-N-[[4-(trifluoromethoxy)phenyl]methyl]anilino]-5-methyl-N-(3-pyridylmethylsulfonyl)thiazole-4-carboxamide (Synthesis of Compound Number 121)

$^1$H-NMR (CDCl$_3$) δ: 8.98 (1H, brs), 8.71 (1H, dd, J=5.4, 1.5 Hz), 8.66 (1H, d, J=2.0 Hz), 8.08-8.03 (1H, m), 7.69-7.63 (2H, m), 7.56 (1H, dd, J=7.8, 5.4 Hz), 7.42-7.37 (2H, m), 7.20 (2H, d, J=8.8 Hz), 7.15 (2H, d, J=8.8 Hz), 5.09 (2H, s), 4.82 (2H, s), 2.69 (3H, s).
UPLC retention time=2.19 min.
Obs.Mass=588.15 (M+H)$^+$

Example 122

2-[4-cyano-N-[(4-fluorophenyl)methyl]anilino]-5-methyl-N-(3-pyridylmethylsulfonyl)thiazole-4-carboxamide (Synthesis of Compound Number 122)

$^1$H-NMR (CDCl$_3$) δ: 8.94 (1H, s), 8.64 (1H, dd, J=4.9, 2.0 Hz), 8.57 (1H, d, J=2.0 Hz), 7.83-7.78 (1H, m), 7.67-7.62 (2H, m), 7.40-7.33 (3H, m), 7.15-7.10 (2H, m), 7.01-6.94 (2H, m), 5.03 (2H, s), 4.76 (2H, s), 2.69 (3H, s).
UPLC retention time=1.98 min.
Obs.Mass=522.17 (M+H)$^+$

Example 123

2-[4-cyano-N-(2,3-dihydro-1,4-benzodioxin-6-ylmethyl)anilino]-5-methyl-N-methylsulfonyl-thiazole-4-carboxamide (Synthesis of Compound Number 123)

$^1$H-NMR (CDCl$_3$) δ: 9.24 (1H, s), 7.65 (2H, dt, J=8.8, 2.2 Hz), 7.43 (2H, dt, J=9.1, 2.2 Hz), 6.82 (1H, d, J=8.3 Hz), 6.72 (1H, d, J=2.0 Hz), 6.69 (1H, dd, J=8.3, 2.4 Hz), 5.04 (2H, s), 4.25 (4H, s), 3.37 (3H, s), 2.66 (3H, s).
UPLC retention time=2.23 min.
Obs.Mass=485.11 (M+H)$^+$

Example 124

2-[4-cyano-N-[(2,6-difluorophenyl)methyl]anilino]-5-methyl-N-methylsulfonyl-thiazole-4-carboxamide (Synthesis of Compound Number 124)

$^1$H-NMR (CDCl$_3$) δ: 9.51 (1H, s), 7.71 (2H, d, J=8.4 Hz), 7.47 (2H, d, J=8.4 Hz), 7.30-7.23 (1H, m), 6.90 (2H, t, J=8.0 Hz), 5.12 (2H, s), 3.37 (3H, s), 2.59 (3H, s).
UPLC retention time=2.33 min.
Obs.Mass=463.02 (M+H)$^+$

Examples 125

2-[4-cyano-N-[(3,4,5-trifluorophenyl)methyl]anilino]-5-methyl-N-methylsulfonyl-thiazole-4-carboxamide (Synthesis of Compound Number 125)

$^1$H-NMR (CDCl$_3$) δ: 7.68 (2H, d, J=8.4 Hz), 7.39 (2H, d, J=8.4 Hz), 6.86 (2H, t, J=6.8 Hz), 5.11 (2H, s), 3.36 (3H, s), 2.66 (3H, s).
UPLC retention time=2.43 min.
Obs.Mass=481.03 (M+H)$^+$

Example 126

2-[N-[(5-chloro-2-fluoro-phenyl)methyl]-4-cyano-anilino]-5-methyl-N-methylsulfonyl-thiazole-4-carboxamide (Synthesis of Compound Number 126)

$^1$H-NMR (CDCl$_3$) δ: 9.24 (1H, s), 7.70 (2H, d, J=8.4 Hz), 7.44 (2H, d, J=8.4 Hz), 7.25-7.22 (1H, m), 7.17 (1H, dd, J=6.4, 2.4 Hz), 7.04 (1H, t, J=9.2 Hz), 5.15 (2H, s), 3.36 (3H, s), 2.65 (3H, s).
UPLC retention time=2.42 min.
Obs.Mass=478.95 (M+H)$^+$

Example 127

2-[4-cyano-N-[(3,5-difluoro-4-methoxy-phenyl)methyl]anilino]-5-methyl-N-methylsulfonyl-thiazole-4-carboxamide (Synthesis of Compound Number 127)

$^1$H-NMR (CDCl$_3$) δ: 9.17 (1H, s), 7.67 (2H, d, J=8.4 Hz), 7.40 (2H, d, J=8.8 Hz), 6.81-6.74 (2H, m), 5.07 (2H, s), 3.98 (3H, s), 3.36 (3H, s), 2.66 (3H, s).
UPLC retention time=2.35 min.
Obs.Mass=492.99 (M+H)$^+$

Example 128

2-[N-(1,3-benzodioxol-5-ylmethyl)-4-cyano-anilino]-5-methyl-N-methylsulfonyl-thiazole-4-carboxamide (Synthesis of Compound Number 128)

$^1$H-NMR (CDCl$_3$) δ: 9.25 (1H, s), 7.66 (2H, d, J=8.3 Hz), 7.42 (2H, d, J=8.3 Hz), 6.78-6.66 (3H, m), 5.96 (2H, s), 5.06 (2H, s), 3.37 (3H, s), 2.66 (3H, s).
UPLC retention time=2.24 min.
Obs.Mass=471.07 (M+H)$^+$

Example 129

2-[N-[(4-bromophenyl)methyl]-4-cyano-anilino]-5-methyl-N-methylsulfonyl-thiazole-4-carboxamide (Synthesis of Compound Number 129)

$^1$H-NMR (DMSO-d$_6$) δ: 11.23 (1H, s), 7.82 (2H, dd, J=6.8, 2.0 Hz), 7.64 (2H, t, J=4.6 Hz), 7.49 (2H, t, J=4.1 Hz), 7.25 (2H, d, J=8.3 Hz), 5.44 (2H, s), 3.33 (3H, s), 2.57 (3H, s).
UPLC retention time=2.47 min.
Obs.Mass=507.04 [Br] (M+H)$^+$

Example 130

2-[4-cyano-N-[2-(2-pyridyl)ethyl]anilino]-5-methyl-N-methylsulfonyl-thiazole-4-carboxamide (Synthesis of Compound Number 130)

$^1$H-NMR (CD$_3$OD) δ: 8.60 (1H, d, J=5.2 Hz), 8.22 (1H, t, J=8.0 Hz), 7.76 (1H, d, J=8.0 Hz), 7.65 (1H, t, J=6.8 Hz), 7.61 (2H, d, J=8.4 Hz), 6.99 (2H, d, J=8.4 Hz), 4.45 (2H, t, J=6.4 Hz), 3.47 (2H, t, J=6.4 Hz), 3.30 (3H, s), 2.30 (3H, s).
UPLC retention time=1.30 min.
Obs.Mass=442.02 (M+H)$^+$

Example 131

2-[4-cyano-N-[2-(2-thienyl)ethyl]anilino]-5-methyl-N-methylsulfonyl-thiazole-4-carboxamide (Synthesis of Compound Number 131)

$^1$H-NMR (DMSO-d$_6$) δ: 10.95 (1H, s), 7.87 (2H, d, J=8.4 Hz), 7.56 (2H, d, J=8.4 Hz), 7.32 (1H, d, J=4.8 Hz), 6.94-6.92 (2H, m), 4.33 (2H, t, J=7.2 Hz), 3.36 (3H, s), 3.18 (2H, t, J=6.8 Hz), 2.56 (3H, s).
UPLC retention time=2.37 min.
Obs.Mass=446.94 (M+H)$^+$

Example 132

2-[4-cyano-N-[2-(3-thienyl)ethyl]anilino]-5-methyl-N-methylsulfonyl-thiazole-4-carboxamide (Synthesis of Compound Number 132)

$^1$H-NMR (CD$_3$OD) δ: 7.72 (2H, d, J=8.4 Hz), 7.45 (2H, d, J=8.8 Hz), 7.31-7.28 (1H, m), 7.06 (1H, s), 6.97 (1H, d, J=4.8 Hz), 4.29 (2H, t, J=7.0 Hz), 3.34 (3H, s), 3.06 (2H, t, J=7.0 Hz), 2.60 (3H, s).
UPLC retention time=2.37 min.
Obs.Mass=446.98 (M+H)$^+$

Example 133

2-[N-[2-(4-chlorophenyl)ethyl]-4-cyano-anilino]-5-methyl-N-methylsulfonyl-thiazole-4-carboxamide (Synthesis of Compound Number 133)

$^1$H-NMR (DMSO-d$_6$) δ: 11.02 (1H, s), 7.86 (2H, d, J=8.8 Hz), 7.58 (2H, d, J=8.8 Hz), 7.31 (2H, d, J=8.4 Hz), 7.28 (2H, d, J=8.8 Hz), 4.33 (2H, t, J=7.2 Hz), 3.37 (3H, s), 2.95 (2H, t, J=7.2 Hz), 2.56 (3H, s).
UPLC retention time=2.54 min.
Obs.Mass=474.99 (M+H)$^+$

Example 134

2-[4-cyano-N-[2-(3-pyridyl)ethyl]anilino]-5-methyl-N-methylsulfonyl-thiazole-4-carboxamide (Synthesis of Compound Number 134)

$^1$H-NMR (CD$_3$OD) δ: 8.52 (1H, s), 8.48 (1H, d, J=5.2 Hz), 8.09 (1H, d, J=7.2 Hz), 7.77 (2H, d, J=8.8 Hz), 7.62-7.58 (1H, m), 7.54 (2H, d, J=8.8 Hz), 4.43 (2H, t, J=6.8 Hz), 3.35 (3H, s), 3.18 (2H, t, J=6.8 Hz), 2.59 (3H, s).
UPLC retention time=1.47 min.
Obs.Mass=442.02 (M+H)$^+$

Example 135

2-[4-cyano-N-[2-(2-methylthiazol-4-yl)ethyl]anilino]-5-methyl-N-methylsulfonyl-thiazole-4-carboxamide (Synthesis of Compound Number 135)

$^1$H-NMR (DMSO-d$_6$) δ: 10.99 (1H, s), 7.85 (2H, d, J=8.4 Hz), 7.55 (2H, d, J=8.8 Hz), 7.14 (1H, s), 4.39 (2H, t, J=7.2 Hz), 3.36 (3H, s), 3.04 (2H, t, J=7.2 Hz), 2.56 (3H, s), 2.54 (3H, s).
UPLC retention time=1.93 min.
Obs.Mass=461.98 (M+H)$^+$

Example 136

2-[4-cyano-N-[2-(4-methylthiazol-5-yl)ethyl]anilino]-5-methyl-N-methylsulfonyl-thiazole-4-carboxamide (Synthesis of Compound Number 136)

$^1$H-NMR (DMSO-d$_6$) δ: 11.00 (1H, s), 8.79 (1H, s), 7.87 (2H, d, J=8.8 Hz), 7.57 (2H, d, J=8.8 Hz), 4.29 (2H, t, J=7.2 Hz), 3.36 (3H, s), 3.18 (2H, t, J=6.8 Hz), 2.56 (3H, s), 2.25 (3H, s).
UPLC retention time=1.80 min.
Obs.Mass=461.98 (M+H)$^+$

Example 137

2-[4-cyano-N-[2-(2-oxopyrrolidin-1-yl)ethyl]anilino]-5-methyl-N-methylsulfonyl-thiazole-4-carboxamide (Synthesis of Compound Number 137)

$^1$H-NMR (CD$_3$OD) δ: 7.61 (2H, d, J=8.4 Hz), 7.19 (2H, d, J=8.4 Hz), 4.36 (2H, t, J=5.6 Hz), 3.65 (2H, t, J=4.8 Hz), 3.47 (2H, t, J=7.2 Hz), 3.09 (3H, s), 2.33 (2H, t, J=8.0 Hz), 2.28 (3H, s), 2.05-2.00 (2H, m).
UPLC retention time=1.41 min.
Obs.Mass=448.02 (M+H)$^+$

Example 138

2-[4-cyano-N-[(4-oxochroman-6-yl)methyl]anilino]-5-methyl-N-methylsulfonyl-thiazole-4-carboxamide (Synthesis of Compound Number 138)

$^1$H-NMR (DMSO-d$_6$) δ: 11.25 (1H, s), 7.83 (2H, d, J=9.3 Hz), 7.66-7.64 (3H, m), 7.50 (1H, dd, J=8.5, 2.2 Hz), 6.98 (1H, d, J=8.8 Hz), 5.44 (2H, s), 4.48 (2H, t, J=6.6 Hz), 3.33 (3H, s), 2.74 (2H, t, J=6.3 Hz), 2.57 (3H, s).
UPLC retention time=2.12 min.
Obs.Mass=497.00 (M+H)$^+$

Example 139

2-[N-[2-(3-chlorophenyl)ethyl]-4-cyano-anilino]-5-methyl-N-methylsulfonyl-thiazole-4-carboxamide (Synthesis of Compound Number 139)

$^1$H-NMR (DMSO-d$_6$) δ: 11.11 (1H, s), 7.86 (2H, d, J=7.6 Hz), 7.58 (2H, d, J=7.6 Hz), 7.35 (1H, s), 7.28-7.21 (3H, m), 4.36-4.34 (2H, m), 3.36 (3H, s), 2.99-2.96 (2H, m), 2.56 (3H, s).
UPLC retention time=2.52 min.
Obs.Mass=474.99 (M+H)$^+$

Example 140

2-[N-[2-(2-chlorophenyl)ethyl]-4-cyano-anilino]-5-methyl-N-methylsulfonyl-thiazole-4-carboxamide (Synthesis of Compound Number 140)

$^1$H-NMR (DMSO-d$_6$) δ: 10.79 (1H, s), 7.86 (2H, d, J=8.8 Hz), 7.60 (2H, d, J=8.8 Hz), 7.39-7.37 (2H, m), 7.27-7.22 (2H, m), 4.32 (2H, t, J=7.2 Hz), 3.37 (3H, s), 3.11 (2H, t, J=7.2 Hz), 2.56 (3H, s).
UPLC retention time=2.53 min.
Obs.Mass=474.99 (M+H)$^+$

Example 141

2-[4-cyano-N-[[4-(4-fluorophenyl)phenyl]methyl]anilino]-5-methyl-N-methylsulfonyl-thiazole-4-carboxamide (Synthesis of Compound Number 141)

$^1$H-NMR (CDCl$_3$) δ: 9.25 (1H, s), 7.67 (2H, d, J=8.8 Hz), 7.53-7.52 (4H, m), 7.47 (2H, d, J=8.8 Hz), 7.29 (2H, d, J=8.3 Hz), 7.12 (2H, t, J=8.5 Hz), 5.19 (2H, s), 3.36 (3H, s), 2.66 (3H, s).
UPLC retention time=2.62 min.
Obs.Mass=521.04 (M+H)$^+$

Example 142

2-(N-benzyl-2-bromo-4-cyano-anilino)-5-methyl-N-methylsulfonyl-thiazole-4-carboxamide (Synthesis of Compound Number 142)

$^1$H-NMR (DMSO-d$_6$) δ: 10.94 (1H, brs), 8.15 (1H, d, J=1.5 Hz), 7.70-7.67 (1H, m), 7.29 (1H, d, J=8.3 Hz), 7.11-6.99 (5H, m), 5.05 (2H, s), 3.12 (3H, s), 2.29 (3H, s).
UPLC retention time=2.45 min.
Obs.Mass=506.92 [Br] (M+H)$^+$

Example 143

2-[2-(4-chlorophenyl)ethyl-[(3-fluorophenyl)methyl]amino]-5-methyl-N-methylsulfonyl-thiazole-4-carboxamide (Synthesis of Compound Number 143)

$^1$H-NMR (CDCl$_3$) δ: 9.34 (1H, s), 7.34-7.26 (3H, m), 7.10-7.06 (2H, m), 7.03-6.94 (2H, m), 6.90-6.84 (1H, m), 4.47 (2H, s), 3.59 (2H, t, J=7.3 Hz), 3.37 (3H, s), 2.89 (2H, t, J=7.3 Hz), 2.66 (3H, s).
UPLC retention time=2.78 min.
Obs.Mass=481.99 (M+H)$^+$

Example 144

2-[2-(4-chlorophenyl)ethyl-[(3-chlorophenyl)methyl]amino]-5-methyl-N-methylsulfonyl-thiazole-4-carboxamide (Synthesis of Compound Number 144)

$^1$H-NMR (CDCl$_3$) δ: 9.34 (1H, s), 7.32-7.25 (4H, m), 7.16-7.03 (4H, m), 4.44 (2H, s), 3.59 (2H, t, J=7.3 Hz), 3.37 (3H, s), 2.89 (2H, t, J=7.3 Hz), 2.66 (3H, s).
UPLC retention time=2.89 min.
Obs.Mass=497.92 (M+H)$^+$

Example 145

2-[2-(4-chlorophenyl)ethyl-[[3-(trifluoromethoxy)phenyl]methyl]amino]-5-methyl-N-methylsulfonyl-thiazole-4-carboxamide (Synthesis of Compound Number 145)

$^1$H-NMR (CDCl$_3$) δ: 9.33 (1H, s), 7.37 (1H, t, J=7.8 Hz), 7.30-7.25 (2H, m), 7.19-7.01 (5H, m), 4.49 (2H, s), 3.59 (2H, t, J=7.3 Hz), 3.37 (3H, s), 2.89 (2H, t, J=7.3 Hz), 2.67 (3H, s).
UPLC retention time=2.93 min.
Obs.Mass=547.93 (M+H)$^+$

Example 146

2-[2-(4-chlorophenyl)ethyl-[2-[trans-2-hydroxycyclohexyl]ethyl]amino]-5-methyl-N-methylsulfonyl-thiazole-4-carboxamide (Synthesis of Compound Number 146)

$^1$H-NMR (CDCl$_3$) δ: 7.31-7.26 (2H, m), 7.15-7.10 (2H, m), 3.54-3.32 (8H, m), 2.89 (2H, t, J=7.6 Hz), 2.64 (3H, s), 2.00-1.56 (6H, m), 1.27-0.98 (5H, m).
UPLC retention time=2.69 min.
Obs.Mass=500.04 (M+H)$^+$

Example 147

2-[benzyl-[2-(3-pyridyl)ethyl]amino]-5-methyl-N-methylsulfonyl-thiazole-4-carboxamide (Synthesis of Compound Number 147)

$^1$H-NMR (DMSO-d$_6$) δ: 9.17 (1H, s), 9.04 (1H, d, J=5.9 Hz), 8.55 (1H, d, J=7.8 Hz), 8.10 (1H, t, J=7.1 Hz), 7.73 (1H, t, J=5.6 Hz), 7.46-7.40 (5H, m), 5.77 (2H, s), 3.69 (2H, q, J=6.2 Hz), 3.33 (3H, s), 3.10 (2H, t, J=6.3 Hz), 2.49 (3H, s).
UPLC retention time=1.32 min.
Obs.Mass=431.09 (M+H)$^+$

Example 148

2-[benzyl-[2-(3,4-difluorophenyl)ethyl]amino]-5-methyl-N-methylsulfonyl-thiazole-4-carboxamide (Synthesis of Compound Number 148)

$^1$H-NMR (DMSO-d$_6$) δ: 10.86 (1H, s), 7.36-7.24 (7H, m), 7.08 (1H, s), 4.66 (2H, s), 3.65 (2H, t, J=7.1 Hz), 3.33 (3H, s), 2.89 (2H, t, J=7.6 Hz), 2.53 (3H, s).
UPLC retention time=2.65 min.
Obs.Mass=466.14 (M+H)$^+$

Example 149

2-[(4-fluorophenyl)methyl-(trans-2-phenylcyclopropyl)amino]-5-methyl-N-methylsulfonyl-thiazole-4-carboxamide (Synthesis of Compound Number 149)

$^1$H-NMR (CDCl$_3$) δ: 9.35 (1H, s), 7.34-7.20 (5H, m), 7.08-6.97 (4H, m), 4.87 (1H, d, J=15.1 Hz), 4.64 (1H, d, J=15.1 Hz), 3.35 (3H, s), 2.76-2.71 (1H, m), 2.64 (3H, s), 2.31-2.25 (1H, m), 1.51-1.44 (1H, m), 1.36-1.29 (1H, m).
UPLC retention time=2.68 min.
Obs.Mass=460.18 (M+H)$^+$

Example 150

2-[(4-chlorophenyl)methyl-(trans-2-phenylcyclopropyl)amino]-5-methyl-N-methylsulfonyl-thiazole-4-carboxamide (Synthesis of Compound Number 150)

$^1$H-NMR (CDCl$_3$) δ: 9.32 (1H, s), 7.34-7.16 (7H, m), 7.08-7.02 (2H, m), 4.87 (1H, d, J=15.1 Hz), 4.64 (1H, d, J=15.1 Hz), 3.35 (3H, s), 2.77-2.72 (1H, m), 2.64 (3H, s), 2.32-2.24 (1H, m), 1.50-1.43 (1H, m), 1.36-1.29 (1H, m).
UPLC retention time=2.80 min.
Obs.Mass=476.11 (M+H)$^+$

Example 151

2-[2-(4-chlorophenyl)ethyl-[(3,5-dimethylisoxazol-4-yl)methyl]amino]-5-methyl-N-methylsulfonyl-thiazole-4-carboxamide (Synthesis of Compound Number 151)

$^1$H-NMR (CDCl$_3$) δ: 9.36 (1H, s), 7.32-7.27 (2H, m), 7.07-7.02 (2H, m), 4.27 (2H, s), 3.44-3.37 (5H, m), 2.83 (2H, t, J=7.3 Hz), 2.69 (3H, s), 2.31 (3H, s), 2.14 (3H, s).
UPLC retention time=2.46 min.
Obs.Mass=483.11 (M+H)$^+$

Example 152

2-[N-[(5-chloro-2-pyridyl)methyl]-4-cyano-anilino]-5-methyl-N-methylsulfonyl-thiazole-4-carboxamide (Synthesis of Compound Number 152)

$^1$H-NMR (DMSO-d$_6$) δ: 11.08 (1H, s), 8.47 (1H, d, J=2.4 Hz), 7.81 (1H, dd, J=8.3, 2.4 Hz), 7.75 (2H, d, J=9.3 Hz), 7.62 (2H, d, J=8.8 Hz), 7.40 (1H, d, J=8.3 Hz), 5.45 (2H, s), 3.25 (3H, s), 2.49 (3H, s).
UPLC retention time=2.19 min.
Obs.Mass=462.10 (M+H)$^+$

Example 153

2-[N-[(5-bromo-2-pyridyl)methyl]-4-cyano-anilino]-5-methyl-N-methylsulfonyl-thiazole-4-carboxamide (Synthesis of Compound Number 153)

$^1$H-NMR (DMSO-d$_6$) δ: 11.13 (1H, s), 8.62 (1H, d, J=2.4 Hz), 8.00 (1H, dd, J=8.3, 2.4 Hz), 7.83 (2H, d, J=8.8 Hz), 7.69 (2H, d, J=8.8 Hz), 7.41 (1H, d, J=8.3 Hz), 5.50 (2H, s), 3.32 (3H, s), 2.57 (3H, s).
UPLC retention time=2.22 min.
Obs.Mass=506.08 (M+H)$^+$

Example 154

2-[4-cyano-N-[[6-(trifluoromethyl)-3-pyridyl]methyl]anilino]-5-methyl-N-methylsulfonyl-thiazole-4-carboxamide (Synthesis of Compound Number 154)

$^1$H-NMR (DMSO-d$_6$) δ: 11.27 (1H, s), 8.75 (1H, s), 7.99 (1H, d, J=7.8 Hz), 7.86-7.84 (3H, m), 7.70 (2H, d, J=8.8 Hz), 5.64 (2H, s), 3.34 (3H, s), 2.58 (3H, s).
UPLC retention time=2.21 min.
Obs.Mass=496.11 (M+H)$^+$

Example 155

2-[4-cyano-N-[[4-(difluoromethyl)-3-fluoro-phenyl]
methyl]anilino]-5-methyl-N-methylsulfonyl-thiazole-4-carboxamide (Synthesis of Compound Number 155)

$^1$H-NMR (CDCl$_3$) δ: 9.14 (1H, s), 7.69 (2H, d, J=8.8 Hz), 7.59 (1H, t, J=7.6 Hz), 7.42 (2H, d, J=8.8 Hz), 7.14 (1H, d, J=7.8 Hz), 7.02 (1H, d, J=10.7 Hz), 6.86 (1H, t, J=55.1 Hz), 5.20 (2H, s), 3.36 (3H, s), 2.67 (3H, d, J=1.0 Hz).
UPLC retention time=2.32 min.
Obs.Mass=495.11 (M+H)$^+$

Example 156

2-[4-cyano-N-[[4-(difluoromethyl)-2-fluoro-phenyl]
methyl]anilino]-5-methyl-N-methylsulfonyl-thiazole-4-carboxamide (Synthesis of Compound Number 156)

$^1$H-NMR (CDCl$_3$) δ: 9.23 (1H, s), 7.70 (2H, d, J=8.8 Hz), 7.45 (2H, d, J=8.8 Hz), 7.34 (1H, t, J=7.6 Hz), 7.28 (1H, s), 6.62 (1H, t, J=56.3 Hz), 5.22 (2H, s), 3.36 (3H, s), 2.65 (3H, s).
UPLC retention time=2.32 min.
Obs.Mass=495.07 (M+H)$^+$

Example 157

2-[4-cyano-N-[[4-(trifluoromethoxy)phenyl]methyl]
anilino]-N-(3-methoxypropylsulfonyl)-5-methyl-thiazole-4-carboxamide (Synthesis of Compound Number 157)

$^1$H-NMR (CDCl$_3$) δ: 9.10 (1H, s), 7.70-7.65 (2H, m), 7.45-7.40 (2H, m), 7.29-7.25 (2H, m), 7.19 (2H, d, J=8.3 Hz), 5.16 (2H, s), 3.64-3.57 (2H, m), 3.49 (2H, t, J=6.1 Hz), 3.32 (3H, s), 2.65 (3H, s), 2.16-2.07 (2H, m).
UPLC retention time=2.58 min.
Obs.Mass=569.21 (M+H)$^+$

Example 158

2-[2-(4-chlorophenyl)ethyl-[(5-chloro-2-pyridyl)
methyl]amino]-5-methyl-N-methylsulfonyl-thiazole-4-carboxamide (Synthesis of Compound Number 158)

$^1$H-NMR (CDCl$_3$) δ: 9.30 (1H, s), 8.52 (1H, d, J=2.4 Hz), 7.62 (1H, dd, J=8.3, 2.4 Hz), 7.28 (2H, d, J=8.3 Hz), 7.13 (1H, d, J=8.3 Hz), 7.10 (2H, d, J=8.3 Hz), 4.57 (2H, s), 3.68 (2H, t, J=7.3 Hz), 3.36 (3H, s), 2.93 (2H, t, J=7.3 Hz), 2.64 (3H, s).
UPLC retention time=2.66 min.
Obs.Mass=499.04 (M+H)$^+$

Example 159

2-[2-[4-(difluoromethoxy)phenyl]ethyl-[(4-fluoro-phenyl)methyl]amino]-5-methyl-N-methylsulfonyl-thiazole-4-carboxamide (Synthesis of Compound Number 159)

$^1$H-NMR (CDCl$_3$) δ: 9.36 (1H, s), 7.19-7.00 (8H, m), 6.49 (1H, t, J=73.9 Hz), 4.46 (2H, s), 3.57 (2H, t, J=7.3 Hz), 3.37 (3H, s), 2.88 (2H, t, J=7.3 Hz), 2.65 (3H, s).
UPLC retention time=2.64 min.
Obs.Mass=514.12 (M+H)$^+$

Example 160

2-[benzyl-[2-[4-(difluoromethoxy)phenyl]ethyl]
amino]-5-methyl-N-methylsulfonyl-thiazole-4-carboxamide (Synthesis of Compound Number 160)

$^1$H-NMR (CDCl$_3$) δ: 9.38 (1H, s), 7.38-7.28 (3H, m), 7.19 (2H, d, J=7.8 Hz), 7.13 (2H, d, J=8.3 Hz), 7.06 (2H, d, J=8.3 Hz), 6.49 (1H, t, J=73.9 Hz), 4.49 (2H, s), 3.59 (2H, t, J=7.3 Hz), 3.37 (3H, s), 2.89 (2H, t, J=7.6 Hz), 2.65 (3H, s).
UPLC retention time=2.65 min.
Obs.Mass=496.12 (M+H)$^+$

Examples 161

2-[2-(4-chlorophenyl)ethyl-[(3-cyclopropyl-1,2,4-oxadiazol-5-yl)methyl]amino]-5-methyl-N-methylsulfonyl-thiazole-4-carboxamide (Synthesis of Compound Number 161)

$^1$H-NMR (CDCl$_3$) δ: 9.24 (1H, s), 7.30 (2H, d, J=8.8 Hz), 7.13 (2H, d, J=8.3 Hz), 4.65 (2H, s), 3.66 (2H, t, J=7.3 Hz), 3.36 (3H, s), 2.94 (2H, t, J=7.1 Hz), 2.66 (3H, s), 2.13-2.04 (1H, m), 1.11-0.99 (4H, m).
UPLC retention time=2.56 min.
Obs.Mass=496.12 (M+H)$^+$

Examples 162

2-[(3-cyclopropyl-1,2,4-oxadiazol-5-yl)methyl-[2-[4-(difluoromethoxy)phenyl]ethyl]amino]-5-methyl-N-methylsulfonyl-thiazole-4-carboxamide (Synthesis of Compound Number 162)

$^1$H-NMR (CDCl$_3$) δ: 9.26 (1H, s), 7.19 (2H, d, J=8.3 Hz), 7.08 (2H, d, J=8.3 Hz), 6.50 (1H, t, J=73.9 Hz), 4.67 (2H, s), 3.66 (2H, t, J=7.3 Hz), 3.36 (3H, s), 2.96 (2H, t, J=7.3 Hz), 2.66 (3H, s), 2.13-2.04 (1H, m), 1.11-0.99 (4H, m).
UPLC retention time=2.43 min.
Obs.Mass=528.17 (M+H)$^+$

Example 163

2-[N-[(5-chloro-2-pyridyl)methyl]-4-cyano-anilino]-
N-(3-methoxypropylsulfonyl)-5-methyl-thiazole-4-carboxamide (Synthesis of Compound Number 163)

$^1$H-NMR (CDCl$_3$) δ: 9.07 (1H, s), 8.53 (1H, d, J=2.0 Hz), 7.71-7.65 (3H, m), 7.62-7.57 (2H, m), 7.27 (1H, d, J=8.3 Hz), 5.19 (2H, s), 3.62-3.56 (2H, m), 3.49 (2H, t, J=5.9 Hz), 3.32 (3H, s), 2.63 (3H, s), 2.14-2.06 (2H, m).
UPLC retention time=2.34 min.
Obs.Mass=520.12 (M+H)$^+$

Example 164

2-[4-cyano-N-[[6-(trifluoromethyl)-3-pyridyl]
methyl]anilino]-N-(3-methoxypropylsulfonyl)-5-methyl-thiazole-4-carboxamide (Synthesis of Compound Number 164)

$^1$H-NMR (CDCl$_3$) δ: 9.04 (1H, s), 8.64 (1H, d, J=1.5 Hz), 7.80 (1H, dd, J=8.3, 1.5 Hz), 7.73-7.67 (3H, m), 7.45-7.40

(2H, m), 5.28 (2H, s), 3.64-3.58 (2H, m), 3.49 (2H, t, J=5.9 Hz), 3.32 (3H, s), 2.65 (3H, s), 2.15-2.07 (2H, m).
UPLC retention time=2.34 min.
Obs.Mass=554.18 (M+H)$^+$

Example 165

2-[4-cyano-N-[[4-(difluoromethoxy)phenyl]methyl]anilino]-N-(3-methoxypropylsulfonyl)-5-methyl-thiazole-4-carboxamide (Synthesis of Compound Number 165)

$^1$H-NMR (CDCl$_3$) δ: 9.09 (1H, s), 7.69-7.64 (2H, m), 7.45-7.40 (2H, m), 7.24 (2H, d, J=8.8 Hz), 7.10 (2H, d, J=8.3 Hz), 6.51 (1H, t, J=73.7 Hz), 5.13 (2H, s), 3.63-3.58 (2H, m), 3.49 (2H, t, J=6.1 Hz), 3.32 (3H, s), 2.65 (3H, s), 2.16-2.08 (2H, m).
UPLC retention time=2.44 min.
Obs.Mass=551.17 (M+H)$^+$

Example 166

2-[N-[(4-chlorophenyl)methyl]-4-cyano-anilino]-N-(3-methoxypropylsulfonyl)-5-methyl-thiazole-4-carboxamide (Synthesis of Compound Number 166)

$^1$H-NMR (CDCl$_3$) δ: 9.09 (1H, s), 7.69-7.64 (2H, m), 7.44-7.39 (2H, m), 7.34-7.29 (2H, m), 7.17 (2H, d, J=8.8 Hz), 5.12 (2H, s), 3.63-3.58 (2H, m), 3.49 (2H, t, J=5.9 Hz), 3.32 (3H, s), 2.65 (3H, s), 2.16-2.07 (2H, m).
UPLC retention time=2.54 min.
Obs.Mass=519.12 (M+H)$^+$

Example 167

2-[4-cyano-N-[[3-fluoro-4-(trifluoromethyl)phenyl]methyl]anilino]-5-methyl-N-methylsulfonyl-thiazole-4-carboxamide (Synthesis of Compound Number 167)

$^1$H-NMR (CDCl$_3$) δ: 9.13 (1H, s), 7.70 (2H, d, J=8.8 Hz), 7.61 (1H, t, J=7.8 Hz), 7.43 (2H, d, J=8.8 Hz), 7.15 (1H, d, J=7.8 Hz), 7.09 (1H, d, J=10.7 Hz), 5.22 (2H, s), 3.36 (3H, s), 2.68 (3H, s).
UPLC retention time=2.48 min.
Obs.Mass=513.12 (M+H)$^+$

Example 168

2-[N-[(5-chloro-3-fluoro-2-pyridyl)methyl]-4-cyano-anilino]-5-methyl-N-methylsulfonyl-thiazole-4-carboxamide (Synthesis of Compound Number 168)

$^1$H-NMR (CDCl$_3$) δ: 9.36 (1H, s), 8.38 (1H, d, J=1.5 Hz), 7.75-7.67 (4H, m), 7.52 (1H, dd, J=9.3, 2.0 Hz), 5.21 (2H, s), 3.36 (3H, s), 2.61 (3H, s).
UPLC retention time=2.32 min.
Obs.Mass=480.07 (M+H)$^+$

Example 169

2-[N-[(5-chloro-3-fluoro-2-pyridyl)methyl]-4-cyano-anilino]-N-(3-methoxypropylsulfonyl)-5-methyl-thiazole-4-carboxamide (Synthesis of Compound Number 169)

$^1$H-NMR (CDCl$_3$) δ: 9.25 (1H, s), 8.38 (1H, d, J=1.5 Hz), 7.75-7.67 (4H, m), 7.52 (1H, dd, J=9.3, 2.0 Hz), 5.20 (2H, d, J=1.5 Hz), 3.63-3.57 (2H, m), 3.50 (2H, t, J=6.1 Hz), 3.33 (3H, s), 2.60 (3H, s), 2.17-2.08 (2H, m).
UPLC retention time=2.44 min.
Obs.Mass=538.13 (M+H)$^+$

Example 170

2-[4-cyano-N-[[3-fluoro-5-(trifluoromethyl)-2-pyridyl]methyl]anilino]-5-methyl-N-methylsulfonyl-thiazole-4-carboxamide (Synthesis of Compound Number 170)

$^1$H-NMR (CDCl$_3$) δ: 9.27 (1H, s), 8.68 (1H, s), 7.75-7.64 (5H, m), 5.31 (2H, s), 3.35 (3H, s), 2.62 (3H, s).
UPLC retention time=2.38 min.
Obs.Mass=514.08 (M+H)$^+$

Example 171

2-[4-cyano-N-[[3-fluoro-5-(trifluoromethyl)-2-pyridyl]methyl]anilino]-N-(3-methoxypropylsulfonyl)-5-methyl-thiazole-4-carboxamide (Synthesis of Compound Number 171)

$^1$H-NMR (CDCl$_3$) δ: 9.18 (1H, s), 8.68 (1H, s), 7.76-7.65 (5H, m), 5.30 (2H, s), 3.62-3.56 (2H, m), 3.49 (2H, t, J=5.9 Hz), 3.32 (3H, s), 2.61 (3H, s), 2.15-2.06 (2H, m).
UPLC retention time=2.48 min.
Obs.Mass=572.22 (M+H)$^+$

Example 172

2-[4-cyano-N-[[4-(difluoromethoxy)-3-fluoro-phenyl]methyl]anilino]-5-methyl-N-methylsulfonyl-thiazole-4-carboxamide (Synthesis of Compound Number 172)

$^1$H-NMR (DMSO-d$_6$) δ: 11.25 (1H, s), 7.84 (2H, d, J=8.3 Hz), 7.68 (2H, d, J=8.8 Hz), 7.29 (1H, t, J=8.3 Hz), 7.19 (2H, m), 7.15 (1H, d, J=8.3 Hz), 5.48 (2H, s), 3.33 (3H, s), 2.57 (3H, s).
UPLC retention time=2.35 min.
Obs.Mass=511.12 (M+H)$^+$

Example 173

2-[4-cyano-N-[[4-fluoro-3-(trifluoromethyl)phenyl]methyl]anilino]-5-methyl-N-methylsulfonyl-thiazole-4-carboxamide (Synthesis of Compound Number 173)

$^1$H-NMR (CDCl$_3$) δ: 7.68 (2H, d, J=8.8 Hz), 7.47-7.38 (4H, m), 7.18 (1H, t, J=9.2 Hz), 5.17 (2H, s), 3.35 (3H, s), 2.65 (3H, s).
UPLC retention time=2.47 min.
Obs.Mass=512.96 (M+H)$^+$

Example 174

2-[4-cyano-N-[(6-fluoro-8-quinolyl)methyl]anilino]-5-methyl-N-methylsulfonyl-thiazole-4-carboxamide (Synthesis of Compound Number 174)

$^1$H-NMR (CDCl$_3$) δ: 8.88 (1H, d, J=4.0 Hz), 8.14 (1H, d, J=8.4 Hz), 7.63 (2H, d, J=8.8 Hz), 7.53-7.47 (3H, m), 7.38 (1H, dd, J=8.4, 2.4 Hz), 7.31 (1H, d, J=8.8 Hz), 5.89 (2H, s), 3.31 (3H, s), 2.67 (3H, s).

UPLC retention time=2.27 min.
Obs.Mass=495.96 (M+H)+

Example 175

2-[4-cyano-N-[(5-fluoro-8-quinolyl)methyl]anilino]-5-methyl-N-methylsulfonyl-thiazole-4-carboxamide (Synthesis of Compound Number 175)

$^1$H-NMR (CDCl$_3$) δ: 9.05 (1H, d, J=4.4 Hz), 8.58 (1H, d, J=7.2 Hz), 7.65-7.61 (3H, m), 7.57-7.51 (3H, m), 7.21 (1H, d, J=8.8 Hz), 5.81 (2H, s), 3.32 (3H, s), 2.66 (3H, s).
UPLC retention time=2.36 min.
Obs.Mass=496.00 (M+H)+

Example 176

2-[4-cyano-N-[[2-(difluoromethoxy)-4-fluoro-phenyl]methyl]anilino]-5-methyl-N-methylsulfonyl-thiazole-4-carboxamide (Synthesis of Compound Number 176)

$^1$H-NMR (CDCl$_3$) δ: 7.66 (2H, d, J=8.8 Hz), 7.42 (2H, d, J=8.8 Hz), 7.24-7.20 (1H, m), 6.92-6.88 (2H, m), 6.54 (1H, t, J=72.8 Hz), 5.14 (2H, s), 3.35 (3H, s), 2.64 (3H, s).
UPLC retention time=2.40 min.
Obs.Mass=510.96 (M+H)+

Example 177

2-[N-[(2-bromo-4-fluoro-phenyl)methyl]-4-cyano-anilino]-5-methyl-N-methylsulfonyl-thiazole-4-carboxamide (Synthesis of Compound Number 177)

$^1$H-NMR (CDCl$_3$) δ: 9.22 (1H, s), 7.66 (2H, d, J=8.8 Hz), 7.41 (2H, d, J=8.8 Hz), 7.34 (1H, dd, J=8.0, 2.4 Hz), 7.20 (1H, dd, J=8.4, 5.6 Hz), 6.99 (1H, dt, J=8.0, 2.4 Hz), 5.17 (2H, s), 3.35 (3H, s), 2.65 (3H, s).
UPLC retention time=2.49 min.
Obs.Mass=524.89 [Br] (M+H)+

Example 178

2-[4-cyano-N-[[2-fluoro-4-(trifluoromethoxy)phenyl]methyl]anilino]-5-methyl-N-methylsulfonyl-thiazole-4-carboxamide (Synthesis of Compound Number 178)

$^1$H-NMR (CDCl$_3$) δ: 7.69 (2H, d, J=8.4 Hz), 7.43 (2H, d, J=8.4 Hz), 7.28-7.26 (1H, m), 7.00-6.98 (2H, m), 5.16 (2H, s), 3.35 (3H, s), 2.64 (3H, s).
UPLC retention time=2.55 min.
Obs.Mass=529.26 (M+H)+

Example 179

2-[N-[(3-chloro-5-fluoro-2-pyridyl)methyl]-4-cyano-anilino]-5-methyl-N-methylsulfonyl-thiazole-4-carboxamide (Synthesis of Compound Number 179)

$^1$H-NMR (CDCl$_3$) δ: 9.30 (1H, s), 8.34 (1H, d, J=2.4 Hz), 7.68 (2H, d, J=8.8 Hz), 7.62 (2H, d, J=8.8 Hz), 7.52 (1H, dd, J=7.6, 2.4 Hz), 5.29 (2H, s), 3.33 (3H, s), 2.63 (3H, s).
UPLC retention time=2.30 min.
Obs.Mass=480.20 (M+H)+

Example 180

2-[4-cyano-N-[(3,5-dichloro-2-pyridyl)methyl]anilino]-5-methyl-N-methylsulfonyl-thiazole-4-carboxamide (Synthesis of Compound Number 180)

$^1$H-NMR (CDCl$_3$) δ: 9.28 (1H, s), 8.40 (1H, d, J=1.6 Hz), 7.75 (1H, d, J=1.6 Hz), 7.68 (2H, d, J=8.8 Hz), 7.61 (2H, d, J=8.8 Hz), 5.28 (2H, s), 3.33 (3H, s), 2.61 (3H, s).
UPLC retention time=2.43 min.
Obs.Mass=496.17 (M+H)+

Example 181

2-[N-[(4-bromo-3-fluoro-phenyl)methyl]-4-cyano-anilino]-5-methyl-N-methylsulfonyl-thiazole-4-carboxamide (Synthesis of Compound Number 181)

$^1$H-NMR (CDCl$_3$) δ: 9.16 (1H, s), 7.67 (2H, d, J=8.4 Hz), 7.52 (1H, t, J=7.6 Hz), 7.40 (2H, d, J=8.4 Hz), 6.99 (1H, d, J=9.2 Hz), 6.92 (1H, d, J=8.4 Hz), 5.12 (2H, s), 3.36 (3H, s), 2.66 (3H, s).
UPLC retention time=2.47 min.
Obs.Mass=522.89 (M+H)+

Example 182

2-[N-[(4-bromo-2-cyano-phenyl)methyl]-4-cyano-anilino]-5-methyl-N-methylsulfonyl-thiazole-4-carboxamide (Synthesis of Compound Number 182)

$^1$H-NMR (CDCl$_3$) δ: 7.80 (1H, d, J=1.6 Hz), 7.71-7.68 (3H, m), 7.44 (2H, d, J=8.4 Hz), 7.29 (1H, d, J=8.4 Hz), 5.31 (2H, s), 3.36 (3H, s), 2.64 (3H, s).
UPLC retention time=2.37 min.
Obs.Mass=530.18 (M+H)+

Example 183

2-[N-[(4-bromo-2-chloro-phenyl)methyl]-4-cyano-anilino]-5-methyl-N-methylsulfonyl-thiazole-4-carboxamide (Synthesis of Compound Number 183)

$^1$H-NMR (CDCl$_3$) δ: 9.20 (1H, s), 7.66 (2H, d, J=8.8 Hz), 7.58 (1H, d, J=2.0 Hz), 7.41 (2H, d, J=8.8 Hz), 7.35 (1H, dd, J=8.4, 1.6 Hz), 7.10 (1H, d, J=8.4 Hz), 5.17 (2H, s), 3.35 (3H, s), 2.65 (3H, s).
UPLC retention time=2.63 min.
Obs.Mass=541.14 [Br] (M+H)+

Example 184

2-[N-[(4-chloro-2-cyano-phenyl)methyl]-4-cyano-anilino]-5-methyl-N-methylsulfonyl-thiazole-4-carboxamide (Synthesis of Compound Number 184)

$^1$H-NMR (CDCl$_3$) δ: 7.70 (2H, d, J=8.8 Hz), 7.65 (1H, d, J=2.0 Hz), 7.54 (1H, dd, J=8.4, 2.0 Hz), 7.44 (2H, d, J=8.8 Hz), 7.36 (1H, d, J=8.4 Hz), 5.33 (2H, s), 3.36 (3H, s), 2.64 (3H, s).
UPLC retention time=2.34 min.
Obs.Mass=486.24 (M+H)+

Example 185

2-[N-[(4-bromo-2-fluoro-phenyl)methyl]-4-cyano-anilino]-5-methyl-N-methylsulfonyl-thiazole-4-carboxamide (Synthesis of Compound Number 185)

¹H-NMR (CDCl₃) δ: 9.24 (1H, s), 7.68 (2H, d, J=8.4 Hz), 7.42 (2H, d, J=8.4 Hz), 7.28-7.25 (2H, m), 7.10 (1H, t, J=8.0 Hz), 5.12 (2H, s), 3.36 (3H, s), 2.64 (3H, s).
UPLC retention time=2.51 min.
Obs.Mass=524.85 [Br] (M+H)⁺

Example 186

2-[4-cyano-N-[[4-(trifluoromethyl)-2-pyridyl]methyl]anilino]-5-methyl-N-methylsulfonyl-thiazole-4-carboxamide (Synthesis of Compound Number 186)

¹H-NMR (CDCl₃) δ: 9.19 (1H, s), 8.77 (1H, d, J=5.2 Hz), 7.69 (2H, d, J=8.4 Hz), 7.57 (2H, d, J=8.8 Hz), 7.51 (1H, s), 7.48 (1H, d, J=5.2 Hz), 5.33 (2H, s), 3.33 (3H, s), 2.64 (3H, s).
UPLC retention time=2.25 min.
Obs.Mass=496.25 (M+H)⁺

Example 187

2-[4-cyano-N-[[3-cyano-4-(trifluoromethyl)phenyl]methyl]anilino]-5-methyl-N-methylsulfonyl-thiazole-4-carboxamide (Synthesis of Compound Number 187)

¹H-NMR (CDCl₃) δ: 9.12 (1H, s), 7.80 (1H, d, J=8.3 Hz), 7.72 (3H, m), 7.64 (1H, d, J=8.3 Hz), 7.43 (2H, d, J=8.8 Hz), 5.30 (2H, s), 3.36 (3H, s), 2.68 (3H, s).
UPLC retention time=2.34 min.
Obs.Mass=520.12 (M+H)⁺

Example 188

2-[N-[(5-bromo-2-pyridyl)methyl]-4-cyano-anilino]-N-(3-methoxypropylsulfonyl)-5-methyl-thiazole-4-carboxamide (Synthesis of Compound Number 188)

¹H-NMR (CDCl₃) δ: 9.06 (1H, s), 8.63 (1H, d, J=2.0 Hz), 7.82 (1H, dd, J=8.3, 2.4 Hz), 7.69 (2H, d, J=8.8 Hz), 7.59 (2H, d, J=8.3 Hz), 7.21 (1H, d, J=8.3 Hz), 5.17 (2H, s), 3.62-3.56 (2H, m), 3.49 (2H, t, J=5.9 Hz), 3.32 (3H, s), 2.63 (3H, s), 2.15-2.06 (2H, m).
UPLC retention time=2.37 min.
Obs.Mass=566.10 [Br] (M+H)⁺

Example 189

2-[N-[[3-chloro-4-(difluoromethoxy)phenyl]methyl]-4-cyano-anilino]-N-(3-methoxypropylsulfonyl)-5-methyl-thiazole-4-carboxamide (Synthesis of Compound Number 189)

¹H-NMR (CDCl₃) δ: 9.06 (1H, s), 7.72-7.66 (2H, m), 7.45-7.40 (2H, m), 7.33 (1H, d, J=2.0 Hz), 7.22 (1H, d, J=8.3 Hz), 7.15 (1H, dd, J=8.5, 2.2 Hz), 6.54 (1H, t, J=73.2 Hz), 5.12 (2H, s), 3.64-3.58 (2H, m), 3.49 (2H, t, J=6.1 Hz), 3.32 (3H, s), 2.66 (3H, s), 2.17-2.07 (2H, m).
UPLC retention time=2.51 min.
Obs.Mass=585.15 (M+H)⁺

Example 190

2-[4-cyano-N-[(3,4-dichlorophenyl)methyl]anilino]-N-(3-methoxypropylsulfonyl)-5-methyl-thiazole-4-carboxamide (Synthesis of Compound Number 190)

¹H-NMR (CDCl₃) δ: 9.07 (1H, s), 7.71-7.66 (2H, m), 7.45-7.39 (3H, m), 7.33 (1H, d, J=2.0 Hz), 7.09 (1H, dd, J=8.3, 2.0 Hz), 5.11 (2H, s), 3.64-3.58 (2H, m), 3.49 (2H, t, J=5.9 Hz), 3.32 (3H, s), 2.66 (3H, s), 2.16-2.08 (2H, m).
UPLC retention time=2.63 min.
Obs.Mass=553.10 (M+H)⁺

Example 191

2-[N-[(4-bromophenyl)methyl]-4-cyano-anilino]-N-(3-methoxypropylsulfonyl)-5-methyl-thiazole-4-carboxamide (Synthesis of Compound Number 191)

¹H-NMR (CDCl₃) δ: 9.09 (1H, s), 7.69-7.64 (2H, m), 7.47 (2H, d, J=8.3 Hz), 7.41 (2H, d, J=8.8 Hz), 7.12 (2H, d, J=8.8 Hz), 5.10 (2H, s), 3.64-3.58 (2H, m), 3.49 (2H, t, J=5.9 Hz), 3.32 (3H, s), 2.65 (3H, s), 2.16-2.07 (2H, m).
UPLC retention time=2.57 min.
Obs.Mass=563.10 (M+H)⁺

Example 192

2-[N-[(2-chloro-4-fluoro-phenyl)methyl]-4-cyano-anilino]-N-(3-methoxypropylsulfonyl)-5-methyl-thiazole-4-carboxamide (Synthesis of Compound Number 192)

¹H-NMR (CDCl₃) δ: 9.13 (1H, s), 7.70-7.65 (2H, m), 7.45-7.40 (2H, m), 7.23 (1H, dd, J=8.3, 5.9 Hz), 7.17 (1H, dd, J=8.3, 2.4 Hz), 6.96 (1H, td, J=8.3, 2.4 Hz), 5.20 (2H, s), 3.64-3.58 (2H, m), 3.50 (2H, t, J=6.1 Hz), 3.32 (3H, s), 2.65 (3H, s), 2.17-2.08 (2H, m).
UPLC retention time=2.55 min.
Obs.Mass=537.13 (M+H)⁺

Example 193

2-[N-[[4-chloro-2-(difluoromethoxy)phenyl]methyl]-4-cyano-anilino]-5-methyl-N-methylsulfonyl-thiazole-4-carboxamide (Synthesis of Compound Number 193)

¹H-NMR (CDCl₃) δ: 9.29 (1H, s), 7.69 (2H, d, J=8.8 Hz), 7.43 (2H, d, J=8.8 Hz), 7.18 (3H, brs), 6.57 (1H, t, J=72.7 Hz), 5.16 (2H, s), 3.36 (3H, s), 2.65 (3H, s).
UPLC retention time=2.49 min.
Obs.Mass=527.09 (M+H)⁺

Example 194

2-[N-[[4-chloro-2-(difluoromethoxy)phenyl]methyl]-4-cyano-anilino]-N-(3-methoxypropylsulfonyl)-5-methyl-thiazole-4-carboxamide (Synthesis of Compound Number 194)

¹H-NMR (DMSO-d₆) δ: 11.13 (1H, s), 7.85 (2H, d, J=8.8 Hz), 7.64 (2H, d, J=8.8 Hz), 7.46-7.09 (4H, m), 5.41 (2H, s), 3.51 (2H, t, J=7.8 Hz), 3.40 (2H, t, J=6.1 Hz), 3.19 (3H, s), 2.54 (3H, s), 1.94-1.87 (2H, m).

UPLC retention time=2.58 min.

Obs.Mass=585.19 (M+H)+

Example 195

2-[N-(1,3-benzothiazol-6-ylmethyl)-4-cyano-anilino]-N-(3-methoxypropylsulfonyl)-5-methyl-thiazole-4-carboxamide (Synthesis of Compound Number 195)

$^1$H-NMR (CDCl$_3$) δ: 9.12 (1H, s), 9.00 (1H, s), 8.11 (1H, d, J=8.3 Hz), 7.83 (1H, d, J=1.0 Hz), 7.66 (2H, d, J=8.8 Hz), 7.45 (2H, d, J=8.8 Hz), 7.41 (1H, dd, J=8.5, 1.7 Hz), 5.31 (2H, s), 3.63-3.57 (2H, m), 3.47 (2H, t, J=5.9 Hz), 3.30 (3H, s), 2.65 (3H, s), 2.15-2.05 (2H, m).

UPLC retention time=2.20 min.

Obs.Mass=542.13 (M+H)+

Examples 196

2-[4-cyano-N-[(3-cyclopropyl-1,2,4-oxadiazol-5-yl)methyl]anilino]-5-methyl-N-methylsulfonyl-thiazole-4-carboxamide (Synthesis of Compound Number 196)

$^1$H-NMR (CDCl$_3$) δ: 9.19 (1H, s), 7.78-7.73 (2H, m), 7.62-7.56 (2H, m), 5.23 (2H, s), 3.37 (3H, s), 2.65 (3H, s), 2.14-2.05 (1H, m), 1.11-0.99 (4H, m).

UPLC retention time=2.12 min.

Obs.Mass=459.10 (M+H)+

Examples 197

2-[4-cyano-N-[(3-cyclopropyl-1,2,4-oxadiazol-5-yl)methyl]anilino]-N-(3-methoxypropylsulfonyl)-5-methyl-thiazole-4-carboxamide (Synthesis of Compound Number 197)

$^1$H-NMR (CDCl$_3$) δ: 9.11 (1H, s), 7.76 (2H, d, J=8.3 Hz), 7.59 (2H, d, J=8.8 Hz), 5.23 (2H, s), 3.65-3.58 (2H, m), 3.51 (2H, t, J=6.1 Hz), 3.32 (3H, s), 2.64 (3H, s), 2.19-2.05 (3H, m), 1.11-0.99 (4H, m).

UPLC retention time=2.24 min.

Obs.Mass=517.16 (M+H)+

Example 198

2-[4-cyano-N-[[4-(trifluoromethoxy)phenyl]methyl]anilino]-5-methyl-N-(methylsulfonylmethylsulfonyl)thiazole-4-carboxamide (Synthesis of Compound Number 198)

$^1$H-NMR (CDCl$_3$) δ: 7.72-7.65 (2H, m), 7.45-7.41 (2H, m), 7.29 (2H, d, J=8.3 Hz), 7.19 (2H, d, J=7.8 Hz), 5.15 (2H, s), 4.90 (2H, s), 3.26 (3H, s), 2.65 (3H, s).

UPLC retention time=2.49 min.

Obs.Mass=589.15 (M+H)+

Example 199

N-(3-cyanopropylsulfonyl)-2-[4-cyano-N-[[4-(trifluoromethoxy)phenyl]methyl]anilino]-5-methyl-thiazole-4-carboxamide (Synthesis of Compound Number 199)

$^1$H-NMR (CDCl$_3$) δ: 9.17 (1H, s), 7.71-7.66 (2H, m), 7.45-7.40 (2H, m), 7.30-7.25 (2H, m), 7.20 (2H, d, J=8.8 Hz), 5.16 (2H, s), 3.65 (2H, t, J=7.3 Hz), 2.68-2.60 (5H, m), 2.31-2.23 (2H, m).

UPLC retention time=2.52 min.

Obs.Mass=564.14 (M+H)+

Example 200

2-[4-cyano-N-[[4-(trifluoromethoxy)phenyl]methyl]anilino]-N-(3-hydroxypropylsulfonyl)-5-methyl-thiazole-4-carboxamide (Synthesis of Compound Number 200)

$^1$H-NMR (CDCl$_3$) δ: 9.13 (1H, s), 7.68 (2H, d, J=8.8 Hz), 7.43 (2H, d, J=8.3 Hz), 7.30-7.25 (2H, m), 7.20 (2H, d, J=8.3 Hz), 5.16 (2H, s), 3.83-3.78 (2H, m), 3.69-3.63 (2H, m), 2.65 (3H, s), 2.17-2.07 (2H, m).

UPLC retention time=2.36 min.

Obs.Mass=555.14 (M+H)+

Example 201

2-[4-cyano-N-[[4-(trifluoromethoxy)phenyl]methyl]anilino]-N-(4-hydroxybutylsulfonyl)-5-methyl-thiazole-4-carboxamide (Synthesis of Compound Number 201)

$^1$H-NMR (CDCl$_3$) δ: 9.10 (1H, s), 7.68 (2H, d, J=8.8 Hz), 7.43 (2H, d, J=8.8 Hz), 7.30-7.25 (2H, m), 7.20 (2H, d, J=8.8 Hz), 5.16 (2H, s), 3.74-3.67 (2H, m), 3.60-3.53 (2H, m), 2.65 (3H, s), 2.03-1.94 (2H, m), 1.77-1.69 (2H, m), 1.38 (1H, t, J=4.9 Hz).

UPLC retention time=2.38 min.

Obs.Mass=569.14 (M+H)+

Example 202

2-[4-cyano-N-[[4-(trifluoromethoxy)phenyl]methyl]anilino]-5-methyl-N-(tetrahydrofuran-3-ylmethylsulfonyl)thiazole-4-carboxamide (Synthesis of Compound Number 202)

$^1$H-NMR (CDCl$_3$) δ: 9.13 (1H, s), 7.71-7.66 (2H, m), 7.45-7.40 (2H, m), 7.30-7.25 (2H, m), 7.20 (2H, d, J=8.8 Hz), 5.16 (2H, s), 4.04-3.98 (1H, m), 3.93-3.86 (1H, m), 3.82-3.75 (1H, m), 3.68-3.54 (3H, m), 2.87-2.78 (1H, m), 2.65 (3H, s), 2.30-2.20 (1H, m), 1.84-1.72 (1H, m).

UPLC retention time=2.54 min.

Obs.Mass=581.18 (M+H)+

Examples 203

2-[N-[(3-aminophenyl)methyl]-4-cyano-anilino]-5-methyl-N-methylsulfonyl-thiazole-4-carboxamide (Synthesis of Compound Number 203)

The similar procedure to that in Example 1 was conducted and 2-[4-cyano-N-[(3-nitrophenyl)methyl]anilino]-5-methyl-N-methylsulfonyl-4-thiazole carboxamide (150 mg, 0.32 mmol) synthesized using 3-nitrobenzylbromide instead of benzylbromide was dissolved in ethyl acetate (3 mL), and the mixture was stirred at 30° C. for 16 hours under hydrogen atmosphere by adding palladium carbon (0.12 mmol). The reaction solution was subjected to celite filtration and the solvent was removed by distillation under reduced pressure. A crude product was purified by preparative isolation HPLC to obtain 2-[N-[(3-aminophenyl)methyl]-4-cyanoanilino]-5-methyl-N-methylsulfonyl-thiazole-4-carboxamide (9.6 mg, 7%).

$^1$H-NMR (CDCl$_3$) δ: 7.66 (2H, d, J=8.4 Hz), 7.46 (2H, d, J=8.4 Hz), 7.14 (1H, t, J=7.6 Hz), 6.71-6.66 (3H, m), 3.88 (2H, d, J=7.6 Hz), 7.02-6.99 (1H, m), 5.03 (2H, s), 3.35 (3H, s), 2.64 (3H, s).
UPLC retention time=1.59 min.
Obs.Mass=442.06 (M+H)$^+$ Example 204

2-(N-benzyl-3-methoxy-anilino)-5-methyl-N-methylsulfonyl-thiazole-4-carboxamide (Synthesis of Compound Number 204)

The similar procedure to that in Example 1 was conducted to obtain 2-(N-benzyl-3-methoxy-anilino)-5-methyl-N-methylsulfonyl-thiazole-4-carboxamide (1.4 g, four phases of 59%) by using (3-methoxyphenyl)thiourea (1.0 g, 5.5 mmol) instead of (4-cyanophenyl)thiourea.

$^1$H-NMR (CDCl$_3$) δ: 9.35 (1H, brs), 7.32-7.26 (6H, m), 6.87-6.84 (2H, m), 6.82-6.79 (1H, m), 5.06 (2H, s), 3.76 (3H, s), 2.58 (3H, s).
UPLC retention time=2.50 min.
Obs.Mass=432.09 (M+H)$^+$ Example 205

2-(N-benzyl-3-hydroxy-anilino)-5-methyl-N-methylsulfonyl-thiazole-4-carboxamide (Synthesis of Compound Number 205)

2-(N-benzyl-3-methoxy-anilino)-5-methyl-N-methylsulfonyl-thiazole-4-carboxamide (700 mg, 1.62 mmol) was dissolved in dichloromethane and the mixture was cooled to −78° C. and stirred for 10 minutes after adding boron tribromide (1.54 mL, 16.2 mmol). The solvent was removed by distillation to obtain 2-(N-benzyl-3-hydroxy-anilino)-5-methyl-N-methylsulfonyl-thiazole-4-carboxamide (650 mg, 90%) by purifying by column chromatography.

$^1$H-NMR (CD$_3$OD) δ: 7.30-7.18 (6H, m), 6.77 (1H, dd, J=8.0, 1.2 Hz), 6.73-6.71 (2H, m), 5.15 (2H, s), 3.31 (3H, s), 2.56 (3H, s).
UPLC retention time=2.15 min.
Obs.Mass=432.09 (M+H)$^+$ The following compounds of Examples 206 and 207 were synthesized using corresponding starting materials in accordance with the method of Example 205.

Example 206

2-(N-benzyl-4-hydroxy-anilino)-5-methyl-N-methylsulfonyl-thiazole-4-carboxamide (Synthesis of Compound Number 206)

$^1$H-NMR (CDCl$_3$) δ: 9.39 (1H, brs), 7.29-7.26 (5H, m), 7.07 (2H, d, J=8.8 Hz), 6.82 (2H, d, J=8.8 Hz), 4.99 (2H, s), 3.36 (3H, s), 2.57 (3H, s).
UPLC retention time=2.09 min.
Obs.Mass=418.08 (M+H)$^+$ Example 207

2-(N-benzyl-2-hydroxy-anilino)-5-methyl-N-methylsulfonyl-thiazole-4-carboxamide (Synthesis of Compound Number 207)

$^1$H-NMR (CDCl$_3$) δ: 9.38 (1H, brs), 7.32-7.25 (6H, m), 7.09 (1H, dd, J=7.8, 1.5 Hz), 7.00-6.94 (2H, m), 5.25 (1H, brs), 4.97 (2H, s), 3.39 (3H, s), 2.58 (3H, s).
UPLC retention time=2.26 min.
Obs.Mass=418.12 (M+H)$^+$ Example 208

2-[N-benzyl-3-(2-benzyloxyethoxy)anilino]-5-methyl-N-methylsulfonyl-thiazole-4-carboxamide (Synthesis of Compound Number 208)

2-(N-benzyl-3-hydroxy-anilino)-5-methyl-N-methylsulfonyl-thiazole-4-carboxamide (300 mg, 0.72 mmol) synthesized in Example 205 was dissolved in DMF (3 mL), ((2-bromoethoxy)methyl)benzene (155 mg, 0.72 mmol) and potassium carbonate (149 mg, 1.08 mmol) were added, and the mixture was heated and stirred at 90° C. for 5 hours. An ammonium chloride aqueous solution was added to the solution, and the resultant mixture was extracted with ethyl acetate twice. The organic fraction was washed with a saturated salt solution and dried over sodium sulfate. The solvent was removed by distillation under reduced pressure and the resultant residue was purified by column chromatography to obtain 2-[N-benzyl-3-(2-benzyloxyethoxy)anilino]-5-methyl-N-methylsulfonyl-thiazole-4-carboxamide (150 mg, 38%).

$^1$H-NMR (CDCl$_3$) δ: 9.32 (1H, brs), 7.35-7.27 (11H, m), 6.87-6.84 (3H, m), 5.05 (2H, s), 4.62 (2H, s), 4.09 (2H, t, J=3.6 Hz), 3.80 (2H, t, J=3.6 Hz), 3.35 (3H, s), 2.58 (3H, s).
UPLC retention time=2.76 min.
Obs.Mass=552.22 (M+H)$^+$ The compound of Example 209 was synthesized using corresponding starting materials in accordance with the method of Example 208.

Example 209

2-[N-benzyl-4-(2-benzyloxyethoxy)anilino]-5-methyl-N-methylsulfonyl-thiazole-4-carboxamide (Synthesis of Compound Number 209)

$^1$H-NMR (CDCl$_3$) δ: 9.41 (1H, s), 7.36-7.26 (10H, m), 7.10 (2H, d, J=8.8 Hz), 6.91 (2H, d, J=8.8 Hz), 5.00 (2H, s), 4.63 (2H, s), 4.14 (2H, t, J=4.6 Hz), 3.83 (2H, t, J=4.9 Hz), 3.37 (3H, s), 2.57 (3H, s).
UPLC retention time=2.76 min.
Obs.Mass=552.22 (M+H)$^+$ Example 210

2-[N-benzyl-3-(2-hydroxyethoxy)anilino]-5-methyl-N-methylsulfonyl-thiazole-4-carboxamide (Synthesis of Compound Number 210)

2-[N-benzyl-3-(2-benzyloxyethoxy)anilino]-5-methyl-N-methylsulfonyl-thiazole-4-carboxamide (40 mg, 0.072 mmol) synthesized by the method described in Example 208 was dissolved in methanol and palladium hydroxide on carbon (8.0 mg) was added. The mixture was stirred at room temperature for 15 hours under 1 atm of hydrogen gas atmosphere. THF was added to this solution and the mixture was further stirred under hydrogen gas atmosphere for 5 hours. The catalyst was removed by celite filtration and the solvent was removed by distillation. The resultant residue was purified by column chromatography to obtain 2-[N-benzyl-3-(2-hydroxyethoxy) anilino]-5-methyl-N-methylsulfonyl-thiazole-4-carboxamide (20 mg, 60%).

$^1$H-NMR (CDCl$_3$) δ: 9.34 (1H, s), 7.32-7.26 (6H, m), 6.85-6.84 (3H, m), 5.06 (2H, s), 4.04-4.02 (2H, m), 3.95-3.94 (2H, m), 3.35 (3H, s), 2.59 (3H, s), 1.93 (1H, brs).

UPLC retention time=2.09 min.

Obs.Mass=462.14 (M+H)$^+$

The compound of Example 211 was synthesized using corresponding starting materials in accordance with the method of Example 210.

Example 211

2-[N-benzyl-4-(2-hydroxyethoxy)anilino]-5-methyl-N-methylsulfonyl-thiazole-4-carboxamide (Synthesis of Compound Number 211)

$^1$H-NMR (CDCl$_3$) δ: 9.40 (1H, s), 7.30-7.25 (4H, m), 7.12 (2H, d, J=9.2 Hz), 6.91 (2H, d, J=8.8 Hz), 5.00 (2H, s), 4.09-4.07 (2H, m), 3.98-3.96 (2H, m), 3.36 (3H, s), 2.57 (3H, s), 1.94 (1H, t, J=6.0 Hz).

UPLC retention time=2.04 min.

Obs.Mass=462.14 (M+H)$^+$

Example 212

2-[4-[benzyl-[5-methyl-4-(methylsulfonylcarbamoyl)thiazol-2-yl]amino]phenoxy]acetic acid (Synthesis of Compound Number 212)

To a DMF (5 mL) solution containing 2-(N-benzyl-4-hydroxy-anilino)-5-methyl-N-methylsulfonyl-thiazole-4-carboxamide (624 mg, 1.50 mmol) synthesized by the method described in Example 206 was added tert-butyl bromoacetate (0.219 mL, 1.50 mmol) and potassium carbonate (311 mg, 2.25 mmol), and the mixture was stirred for 4 hours while heating at 85° C. To the reaction solution was added an ammonium chloride aqueous solution, and the mixture was extracted with ethyl acetate twice. The organic fraction was washed with a saturated salt solution and dried over sodium sulfate. After removing the solvent under reduced pressure by distillation, the resultant residue was purified by column chromatography to obtain tert-butyl 2-[4-[benzyl-[5-methyl-4-(methylsulfonyl carbamoyl)thiazol-2-yl]amino]phenoxy]acetate (220 mg, 28%). Among all, 62 mg (0.117 mmol) of the product was dissolved in dichloromethane (1 mL), TFA (0.090 m L, 1.17 mmol) was added to this solution, and the mixture was stirred at 50° C. for two days. The solvent was removed by distillation and the resultant residue was purified by preparative HPLC to obtain 2-[4-[benzyl-[5-methyl-4-(methylsulfonylcarbamoyl)thiazol-2-yl]amino]phenoxy]acetic acid (12 mg, 27%).

$^1$H-NMR (CDCl$_3$) δ: 9.40 (1H, brs), 7.32-7.24 (5H, m), 7.16 (2H, d, J=8.7 Hz), 6.92 (2H, d, J=8.7 Hz), 5.00 (2H, s), 4.67 (2H, s), 3.36 (3H, s), 2.57 (3H, s).

UPLC retention time=2.03 min.

Obs.Mass=476.11 (M+H)$^+$

Example 213

2-[N-benzyl-4-[2-(methylamino)-2-oxo-ethoxy]anilino]-5-methyl-N-methylsulfonyl-thiazole-4-carboxamide (Synthesis of Compound Number 213)

To a THF (1 mL) solution containing 2-[4-[benzyl-[5-methyl-4-(methylsulfonylcarbamoyl) thiazol-2-yl]amino] phenoxy]acetic acid (62 mg, 0.13 mmol) synthesized by the method described in Example 212 were added methylamine hydrochloride (44 mg, 0.65 mmol), WSC (25 mg, 0.13 mmol), diisopropylethylamine (0.17 mL, 1.0 mmol), and the mixture was stirred at room temperature for 2 days. The solvent was removed by distillation and the resultant residue was purified by preparative HPLC to obtain 2-[N-benzyl-4-[2-(methylamino)-2-oxo-ethoxy]anilino]-5-methyl-N-methylsulfonyl-thiazole-4-carboxamide (20 mg, 32%).

$^1$H-NMR (CDCl$_3$) δ: 9.38 (1H, s), 7.34-7.23 (5H, m), 7.17 (2H, d, J=9.0 Hz), 6.91 (2H, d, J=9.0 Hz), 6.54 (1H, s), 5.01 (2H, s), 4.48 (2H, s), 3.36 (3H, s), 2.92 (3H, d, J=4.8 Hz), 2.58 (3H, s).

UPLC retention time=1.99 min.

Obs.Mass=489.15 (M+H)$^+$

The compound of Example 214 was synthesized using corresponding reagents in accordance with the method of Example 213.

Example 214

2-[N-benzyl-4-[2-(dimethylamino)-2-oxo-ethoxy] anilino]-5-methyl-N-methylsulfonyl-thiazole-4-carboxamide (Synthesis of Compound Number 214)

$^1$H-NMR (CDCl$_3$) δ: 9.40 (1H, s), 7.33-7.24 (5H, m), 7.13 (2H, d, J=6.6 Hz), 6.94 (2H, d, J=6.6 Hz), 4.99 (2H, s), 4.67 (2H, s), 3.35 (3H, s), 3.08 (3H, s), 2.99 (3H, s), 2.57 (3H, s).

UPLC retention time=2.06 min.

Obs.Mass=503.16 (M+H)$^+$

Example 215

2-[4-cyano-N-[[3-(dimethylamino)phenyl]methyl] anilino]-5-methyl-N-methylsulfonyl-thiazole-4-carboxamide (Synthesis of Compound Number 215)

(1) Ethyl 2-[N-[(3-bromophenyl)methyl]-4-cyanoanilino]-5-methyl-4-thiazole carboxylate (200 mg, 0.44 mmol) synthesized by the similar method to that in Examples 1(1) and (2) using 3-bromobenzylbromide instead of benzylbromide was dissolved in 1,4-dioxane (3 mL). The mixture was degassed under argon gas atmosphere for 30 minutes after adding cesium carbonate (502 mg, 1.54 mmol). To this solution were added Pd$_2$(dba)$_3$ (101 mg, 0.11 mmol), X-phos (52.4 mg, 0.11 mmol) and 50% aqueous solution of dimethylamine (1.04 mL), and the mixture was degassed for 5 minutes and stirred at 100° C. for 12 hours. After cooling to room temperature and filtration with celite, the solvent was removed by distillation under reduced pressure. Water was added to the solution and the mixture was extracted with ethyl acetate 3 times, and the combined organic fractions were dried over sodium sulfate. After the solvent was removed by distillation under reduced pressure, the mixture was purified by column chromatography to obtain ethyl 2-[4-cyano-N-[[3-(dimethylamino)phenyl]methyl]anilino]-5-methyl-4-thiazolecarboxylate (150 mg, 81%).

¹H-NMR (CDCl₃) δ: 7.55 (2H, d, J=8.8 Hz), 7.47 (2H, d, J=8.8 Hz), 7.16 (1H, t, J=7.6 Hz), 6.62-6.60 (2H, m), 6.56 (1H, d, J=7.6 Hz), 5.14 (2H, s), 4.35 (2H, q, J=7.2 Hz), 2.89 (6H, s), 2.61 (3H, s), 1.38 (3H, t, J=7.2 Hz).

(2) For ethyl 2-[4-cyano-N-[[3-(dimethylamino)phenyl]methyl]anilino]-5-methyl-4-thiazolecarboxylate (150 mg, 0.356 mmol), the similar procedure to that in Examples 1 (3) and (4) was conducted to obtain 2-[4-cyano-N-[[3-(dimethylamino)phenyl]methyl]anilino]-5-methyl-N-methylsulfonyl-thiazole-4-carboxamide (34.6 mg, 21%).

¹H-NMR (CDCl₃) δ: 9.22 (1H, s), 7.67 (2H, d, J=8.4 Hz), 7.58 (1H, s), 7.51-7.46 (3H, m), 7.30 (1H, d.J=7.2 Hz), 7.25-7.23 (1H, m), 5.18 (2H, s), 3.35 (3H, s), 3.15 (6H, s), 2.17 (3H, s).

UPLC retention time=1.72 min.

Obs.Mass=470.07 (M+H)⁺

The following compounds of Examples 216 and 217 were synthesized using corresponding reagents in accordance with the method of Example 215.

Example 216

2-[4-cyano-N-[(3-pyrrolidin-1-ylphenyl)methyl]anilino]-5-methyl-N-methylsulfonyl-thiazole-4-carboxamide (Synthesis of Compound Number 216)

¹H-NMR (CDCl₃) δ: 9.25 (1H, s), 7.63 (2H, d, J=8.4 Hz), 7.47 (2H, d, J=8.4 Hz), 7.16 (1H, t, J=8.0 Hz), 6.49-6.46 (2H, m), 6.38 (1H, s), 5.08 (2H, s), 3.34 (3H, s), 3.24-3.21 (4H, m), 2.65 (3H, s), 2.00-1.97 (4H, m).

UPLC retention time=2.31 min.

Obs.Mass=496.04 (M+H)⁺

Example 217

2-[4-cyano-N-[[3-(1-piperidyl)phenyl]methyl]anilino]-5-methyl-N-methylsulfonyl-thiazole-4-carboxamide (Synthesis of Compound Number 217)

¹H-NMR (CDCl₃) δ: 9.34 (1H, s), 7.89 (1H, s), 7.66 (2H, d, J=8.4 Hz), 7.48-7.44 (3H, m), 7.36 (1H, d, J=8.0 Hz), 7.29 (1H, d, J=7.2 Hz), 5.16 (2H, s), 3.44-3.43 (4H, m), 3.36 (3H, s), 2.64 (3H, s), 2.16 (3H, s), 2.09-2.06 (4H, m), 1.73-1.71 (2H, m).

UPLC retention time=1.71 min.

Obs.Mass=510.08 (M+H)⁺

Example 218

2-[4-cyano-N-[(3-imidazol-1-ylphenyl)methyl]anilino]-5-methyl-N-methylsulfonyl-thiazole-4-carboxamide (Synthesis of Compound Number 218)

(1) 2-[N-[(3-bromophenyl)methyl]-4-cyanoanilino]-5-methyl-4-thiazolecarboxylate (250 mg, 0.55 mmol) was dissolved in DMSO (3 mL), and copper (I) iodide (32.3 mg, 0.17 mmol), imidazole (150 mg, 2.20 mmol), potassium carbonate (250 mg, 1.65 mmol), and L-proline (32.2 m g, 0.28 mmol) were added. After the solution was heated to 120° C., it was stirred for 50 hours. Then, an ammonium chloride aqueous solution was added to this solution, and the mixture was extracted with ethyl acetate twice. The organic fraction was washed with a saturated salt solution and dried over sodium sulfate. The solvent was removed by distillation under reduced pressure and the resultant residue was purified by column chromatography to obtain 2-[4-cyano-N-[[3-(1-imidazolyl)phenyl]methyl]anilino]-5-methyl-4-thiazolecarboxylate (150 mg, 61%).

¹H-NMR (CDCl₃) δ: 7.82 (1H, s), 7.60 (2H, d, J=8.8 Hz), 7.42-7.39 (4H, m), 7.29 (1H, d.J=8.0 Hz), 7.24-7.18 (3H.m), 5.27 (2H, s), 4.36 (2H, q, J=7.2 Hz), 2.61 (3H, s), 1.37 (3H, t, J=7.2 Hz).

(2) For ethyl 2-[4-cyano-N-[[3-(1-imidazolyl)phenyl]methyl]anilino]-5-methyl-4-thiazolecarboxylate (150 mg, 0.34 mmol), the similar procedure to that in Examples 1 (3) and (4) was conducted to obtain 2-[4-cyano-N-[(3-imidazol-1-ylphenyl)methyl]anilino]-5-methyl-N-methylsulfonyl-thiazole-4-carboxamide (29.1 mg, 17%).

¹H-NMR (CDCl₃) δ: 9.10 (1H, s), 8.86 (1H, s), 7.71 (2H, d, J=8.8 Hz), 7.58 (1H, t, J=8.0 Hz), 7.51-7.40 (7H, m), 5.25 (2H, s), 3.34 (3H, s), 2.65 (3H, s).

UPLC retention time=1.62 min.

Obs.Mass=493.03 (M+H)⁺

The compound of Example 219 was synthesized using corresponding reagents in accordance with the method of Example 218.

Example 219

2-[4-cyano-N-[(3-pyrazol-1-ylphenyl)methyl]anilino]-5-methyl-N-methylsulfonyl-thiazole-4-carboxamide (Synthesis of Compound Number 219)

¹H-NMR (CDCl₃) δ: 9.22 (1H, s), 7.89 (1H, d, J=2.0 Hz), 7.72 (1H, s), 7.68-7.65 (3H, m), 7.56 (1H, d, J=9.6 Hz), 7.46-7.39 (3H, m), 7.14 (1H, d, J=7.6 Hz), 6.47 (1H, s), 5.21 (2H, s), 3.35 (3H, s), 2.65 (3H, s).

UPLC retention time=2.23 min.

Obs.Mass=493.03 (M+H)⁺

Example 220

2-[benzyl-[2-(4-chlorophenyl)ethyl]amino]-5-methyl-N-methylsulfonyl-oxazole-4-carboxamide (Synthesis of Compound Number 220)

(1) 4-Chlorophenethyl isocyanate (2.00 g, 11.0 mmol) was dissolved in methanol (20 mL), ammonium hydroxide (28%, 2.00 mL) was added to the solution, and the mixture was stirred at room temperature overnight. After removing the solvent by distillation, ethyl acetate and water were added and the mixture was stirred. The organic fraction was washed with a saturated salt solution and dried over magnesium sulfate. The solvent was removed by distillation to obtain 1-(4-chlorophenethyl)urea (2.0 g, 91%). This was dissolved in ethanol (51 mL), methyl 3-bromo-2-oxobutyrate (2.0 g, 10 mmo l) synthesized by the method described in Reference Example 12 was added, and the resultant mixture was stirred for 15 hours while heating at 80° C. To the mixture was added a sodium bicarbonate aqueous solution and the mixture was extracted with ethyl acetate 4 times. The organic fractions were combined, dried over magnesium sulfate, and washed with a mixed solution of ethyl acetate: hexane (1:4, 40 mL) after removing the solvent by distillation to obtain methyl 2-((4-chlorophenethyl) amino)-5-methyloxazole-4-carboxylate (1.3 g, 43%).

¹H-NMR (CDCl₃) δ: 7.28 (2H, d, J=8.3 Hz), 7.13 (2H, d, J=8.3 Hz), 4.46 (1H, t, J=5.6 Hz), 3.87 (3H, s), 3.61 (2H, q, J=6.5 Hz), 2.88 (2H, t, J=6.6 Hz), 2.48 (3H, s).

(2) For methyl 2-((4-chlorophenethyl) amino)-5-methyloxazole-4-carboxylate (60.0 mg, 0.204 mmol), the similar procedure to that in Examples 1(2) to (4) was carried out to obtain 2-[benzyl-[2-(4-chlorophenyl)ethyl]amino]-5-methyl-N-methylsulfonyl-oxazole-4-carboxamide (37.1 mg, 41%).

$^1$H-NMR (CDCl$_3$) δ: 7.32-7.21 (7H, m), 7.05 (2H, d, J=8.3 Hz), 4.49 (2H, s), 3.52 (2H, t, J=7.1 Hz), 3.38 (3H, s), 2.82 (2H, t, J=7.1 Hz), 2.51 (3H, s).

UPLC retention time=2.66 min.

Obs.Mass=448.02 (M+H)$^+$

Example 221

2-[N-(benzofuran-5-ylmethyl)-4-cyano-anilino]-5-bromo-N-methylsulfonyl-thiazole-4-carboxamide (Synthesis of Compound Number 221)

(1) To a mixture of 4-bromobenzonitrile (814 mg, 4.47 mmol), ethyl 2-aminothiazole-4-carboxylate (700 mg, 4.07 mmol), X-phos (194 mg, 0.406 mmol), Pd$_2$(dba)$_3$ (112 mg, 0.122 mmol) and potassium carbonate (1.35 g, 9.76 mmol) was added tert-butanol (14 mL), and the mixture was stirred at 90° C. for 14 hours. The reaction solution was subjected to celite filtration, and the filtrate was removed by distillation under reduced pressure. The resultant residue was purified by culumn chromatography to obtain ethyl 2-(4-cyanoanilino)thiazole-4-carboxylate (891 mg, 80%).

$^1$H-NMR (CDCl$_3$) δ: 8.06 (1H, s), 7.65 (1H, s), 7.64 (2H, d, J=8.8 Hz), 7.46 (2H, d, J=8.3 Hz), 4.39 (2H, q, J=7.2 Hz), 1.39 (3H, t, J=7.1 Hz).

(2) 2-(4-Cyanoanilino)thiazole-4-carboxylate (891 mg, 3.26 mmol) was dissolved in acetonitrile (10 mL) and the solution was cooled to 0° C. while stirring. N-bromosuccinimide (580 mg, 3.26 mmol) was added and the mixture was stirred for 2.5 hours while gradually returning to room temperature. The solvent was removed by distillation and the resultant residue was purified by column chromatography to obtain ethyl 5-bromo-2-(4-cyanoanilino)thiazole-4-carboxylate (402 mg, 35%).

$^1$H-NMR (CDCl$_3$) δ: 7.66 (2H, d, J=9.3 Hz), 7.38 (2H, d, J=9.3 Hz), 4.43 (2H, q, J=7.0 Hz), 1.43 (3H, t, J=7.1 Hz).

(3) To a DMF (5.0 mL) solution containing ethyl 5-bromo-2-(4-cyanoanilino) thiazole-4-carboxylate (200 mg, 0.568 mmol) were added methanesulfonic acid benzofuran-5-yl methyl (265 mg, 1.17 mmol) synthesized by the similar procedure to that described in Example 2 (1) and cesium carbonate (371 mg, 1.14 mmol), and the mixed solution was heated and stirred at 80° C. for 16 hours. To the reaction solution was added water, and the mixture was extracted with ethyl acetate twice. The organic fraction was washed with a saturated salt solution and dried over sodium sulfate. The solvent was removed by distillation under reduced pressure and the resultant residue was purified by column chromatography to obtain ethyl 2-((benzofuran-5-yl methyl) (4-cyanophenyl)amino)-5-bromothiazole-4-carboxylate (70 mg, 26%). This solution was dissolved in a mixed solvent of THF (3 mL) and methanol (2 mL), and lithium hydroxide (27.3 mg, 1.14 mmol) and water (1 mL) were added. The resultant mixture was stirred at room temperature for four hours. After diluting the reaction solution with water, the solution was neutralized and by adding 6 M hydrochloric acid (8.3 mL, 50 mmol). The solution was extracted with ethyl acetate twice, the organic fractions were combined and washed with a saturated salt solution and dried over sodium sulfate. After the solvent was removed by distillation under reduced pressure, the resultant residue was dissolved in dichloromethane (4 mL). To this solution, DMAP (22 mg, 0.182 mol), methane sulfonamide (18.0 mg, 0.182 mmol) and 1-(3-dimethylaminopropyl)-3-ethylcarbodiimide hydrochloride (35 mg, 0.182 mmol) were added. The mixed solution was stirred at room temperature for 8 hours. To the reaction solution was added water, and the mixture was extracted with dichloromethane. The organic fraction was washed with a saturated salt solution and dried over magnesium sulfate. After the solvent was removed by distillation under reduced pressure, the resultant residue was purified by preparative HPLC to obtain 2-[N-(benzofuran-5-yl methyl)-4-cyanoanilino]-5-bromo-N-methylsulfonyl-thiazole-4-carboxamide (3.7 mg, 5%).

$^1$H-NMR (CD$_3$OD) δ: 7.75 (2H, d, J=8.4 Hz), 7.72 (1H, d, J=2.0 Hz), 7.60 (2H, d, J=8.4 Hz), 7.55 (1H, s), 7.43 (1H, d, J=8.8 Hz), 7.26 (1H, d, J=8.0 Hz), 5.41 (2H, s), 3.32 (3H, s).

UPLC retention time=2.38 min.

Obs.Mass=532.89 [Br] (M+H)$^+$

The following compounds of Examples 222 to 282 were synthesized using corresponding starting materials, commercial reagents and/or intermediates in the Reference examples in accordance with the methods of Example 221 (1) and (2), or (1) to (3) using protection with an appropriate protecting group and de-protection if needed.

Example 222

2-(N-benzyl-4-cyano-3-fluoro-anilino)-5-methyl-N-methylsulfonyl-thiazole-4-carboxamide (Synthesis of Compound Number 222)

$^1$H-NMR (DMSO-d$_6$) δ: 11.18 (1H, s), 7.67 (1H, d, J=8.8 Hz), 7.43 (1H, d, J=2.0 Hz), 7.32-7.25 (5H, m), 7.11-7.09 (1H, m), 5.47 (2H, s), 3.86 (3H, s), 3.33 (3H, s).

UPLC retention time=2.35 min.

Obs.Mass=445.14 (M+H)$^+$

Example 223

2-[benzyl-[6-(trifluoromethyl)-3-pyridyl]amino]-5-methyl-N-methylsulfonyl-thiazole-4-carboxamide (Synthesis of Compound Number 223)

$^1$H-NMR (DMSO-d$_6$) δ: 11.16 (1H, s), 8.95 (1H, d, J=2.4 Hz), 8.05 (1H, dd, J=8.5, 2.7 Hz), 7.80 (1H, d, J=8.8 Hz), 7.19 (5H, m), 5.35 (2H, s), 3.48 (1H, s), 3.25 (3H, s), 2.49 (3H, s).

UPLC retention time=2.42 min.

Obs.Mass=471.11 (M+H)$^+$

Example 224

2-[N-benzyl-3-(trifluoromethyl)anilino]-5-methyl-N-methylsulfonyl-thiazole-4-carboxamide (Synthesis of Compound Number 224)

$^1$H-NMR (CDCl$_3$) δ: 9.27 (1H, brs), 7.56-7.44 (4H, m), 7.36-7.24 (5H, m), 5.10 (2H, s), 3.36 (3H, s), 2.61 (3H, s).

UPLC retention time=2.64 min.

Obs.Mass=470.07 (M+H)$^+$

Example 225

2-(N-benzyl-3-cyano-anilino)-5-methyl-N-methylsulfonyl-thiazole-4-carboxamide (Synthesis of Compound Number 225)

$^1$H-NMR (CDCl$_3$) δ: 9.24 (1H, brs), 7.56-7.50 (4H, m), 7.34-7.22 (5H, m), 5.09 (2H, s), 3.36 (3H, s), 2.63 (3H, s).

UPLC retention time=2.32 min.
Obs.Mass=427.05 (M+H)+

Example 226

2-[N-benzyl-4-(hydroxymethyl)anilino]-5-methyl-N-methylsulfonyl-thiazole-4-carboxamide (Synthesis of Compound Number 226)

$^1$H-NMR (CDCl$_3$) δ: 9.34 (1H, brs), 7.40 (2H, d, J=8.4 Hz), 7.31-7.24 (7H, m), 5.06 (2H, s), 4.71 (2H, d, J=6.0 Hz), 3.35 (3H, s), 2.58 (3H, s), 1.53 (1H, brs).
UPLC retention time=2.03 min.
Obs.Mass=432.09 (M+H)+

Example 227

2-[benzyl(1-naphthyl)amino]-5-methyl-N-methylsulfonyl-thiazole-4-carboxamide (Synthesis of Compound Number 227)

$^1$H-NMR (DMSO-d$_6$) δ: 11.09 (1H, brs), 8.03-7.97 (2H, m), 7.75 (1H, d, J=9.0 Hz), 7.58-7.50 (3H, m), 7.38-7.21 (6H, m), 5.70 (1H, brs), 5.05 (1H, brs), 3.37 (3H, s), 2.43 (3H, s).
UPLC retention time=2.69 min.
Obs.Mass=452.10 (M+H)+

Example 228

2-[N-benzyl-2-(trifluoromethyl)anilino]-5-methyl-N-methylsulfonyl-thiazole-4-carboxamide (Synthesis of Compound Number 228)

$^1$H-NMR (DMSO) δ: 11.07 (1H, brs), 7.92 (1H, dd, J=7.2, 2.1 Hz), 7.72-7.63 (2H, m), 7.32-7.28 (5H, m), 7.09 (1H, dd, J=7.2, 1.5 Hz), 5.90 (1H, brs), 4.46 (1H, brs), 3.35 (3H, s), 2.91 (3H, s).
UPLC retention time=2.59 min.
Obs.Mass=470.11 (M+H)+

Example 229

2-[N-benzyl-3-(hydroxymethyl)anilino]-5-methyl-N-methylsulfonyl-thiazole-4-carboxamide (Synthesis of Compound Number 229)

$^1$H-NMR (CDCl$_3$) δ: 9.30 (1H, brs), 7.40-7.26 (7H, m), 7.18 (1H, d, J=7.8 Hz), 5.07 (2H, s), 4.70 (2H, s), 3.35 (3H, s), 2.58 (3H, s), 1.71 (1H, brs).
UPLC retention time=2.07 min.
Obs.Mass=432.13 (M+H)+

Example 230

2-(N-benzyl-4-cyano-anilino)-N-methylsulfonyl-5-(trifluoromethyl)thiazole-4-carboxamide (Synthesis of Compound Number 230)

$^1$H-NMR (DMSO-d$_6$) δ: 12.06 (1H, s), 7.92 (2H, d, J=8.3 Hz), 7.77 (2H, d, J=8.3 Hz), 7.31-7.24 (5H, m), 5.48 (2H, s), 3.31 (3H, s).

UPLC retention time=2.40 min.
Obs.Mass=481.03 (M+H)+

Example 231

2-[N-benzyl-3-(2-benzyloxyethyl)anilino]-5-methyl-N-methylsulfonyl-thiazole-4-carboxamide (Synthesis of Compound Number 231)

$^1$H-NMR (CDCl$_3$) δ: 9.35 (1H, s), 7.33-7.24 (11H, m), 7.18-7.10 (3H, m), 5.04 (2H, s), 4.50 (2H, s), 3.66 (2H, t, J=6.6 Hz), 3.34 (3H, s), 2.90 (2H, t, J=6.6 Hz), 2.55 (3H, s).
UPLC retention time=2.84 min.
Obs.Mass=536.21 (M+H)+

Example 232

2-[benzyl(2-naphthyl)amino]-5-methyl-N-methylsulfonyl-thiazole-4-carboxamide (Synthesis of Compound Number 232)

$^1$H-NMR (CDCl$_3$) δ: 9.39 (1H, s), 7.90-7.74 (4H, m), 7.53 (1H, d, J=3.3 Hz), 7.51 (1H, d, J=3.3 Hz), 7.39-7.26 (6H, m), 5.18 (2H, s), 3.37 (3H, s), 2.58 (3H, s).
UPLC retention time=2.72 min.
Obs.Mass=452.14 (M+H)+

Example 233

2-(N-benzyl-2-cyano-anilino)-5-methyl-N-methylsulfonyl-thiazole-4-carboxamide (Synthesis of Compound Number 233)

$^1$H-NMR (CDCl$_3$) δ: 9.28 (1H, s), 7.75 (1H, dd, J=7.8, 1.5 Hz), 7.60 (1H, dd, J=7.8, 1.5 Hz), 7.46 (1H, dd, J=7.8, 1.2 Hz), 7.31-7.26 (6H, m), 5.11 (2H, s), 3.37 (3H, s), 2.61 (3H, s).
UPLC retention time=2.26 min.
Obs.Mass=427.13 (M+H)+

Example 234

2-[N-benzyl-4-(2-hydroxyethyl)anilino]-5-methyl-N-methylsulfonyl-thiazole-4-carboxamide (Synthesis of Compound Number 234)

$^1$H-NMR (CDCl$_3$) δ: 9.35 (1H, s), 7.32-7.19 (9H, m), 5.05 (2H, s), 3.88 (2H, t, J=6.6 Hz), 3.35 (3H, s), 2.88 (2H, t, J=6.6 Hz), 2.58 (3H, s), 1.26 (1H, brs).
UPLC retention time=2.08 min.
Obs.Mass=446.14 (M+H)+

Example 235

2-[N-benzyl-4-(2-benzyloxyethyl)anilino]-5-methyl-N-methylsulfonyl-thiazole-4-carboxamide (Synthesis of Compound Number 235)

$^1$H-NMR (CDCl$_3$) δ: 9.35 (1H, s), 7.33-7.23 (12H, m), 7.18-7.15 (2H, m), 5.04 (2H, s), 4.52 (2H, s), 3.70 (2H, t, J=6.9 Hz), 3.35 (3H, s), 2.93 (2H, t, J=6.9 Hz), 2.57 (3H, s).

UPLC retention time=2.84 min.
Obs.Mass=536.21 (M+H)⁺

Example 236

2-[benzyl(4-quinolyl)amino]-5-methyl-N-methylsulfonyl-thiazole-4-carboxamide (Synthesis of Compound Number 236)

$^1$H-NMR (CDCl$_3$) δ: 9.38 (1H, s), 8.93 (1H, d, J=4.4 Hz), 8.21 (1H, d, J=8.4 Hz), 7.85-7.78 (2H, m), 7.60-7.58 (1H, m), 7.29-7.26 (5H, m), 7.20 (1H, d, J=4.4 Hz), 5.19 (2H, s), 3.39 (3H, s), 2.55 (3H, s).
UPLC retention time=1.69 min.
Obs.Mass=453.14 (M+H)⁺

Example 237

2-[benzyl-[6-(trifluoromethyl)pyridazin-3-yl]amino]-5-methyl-N-methylsulfonyl-thiazole-4-carboxamide (Synthesis of Compound Number 237)

$^1$H-NMR (CDCl$_3$) δ: 9.23 (1H, s), 7.71 (1H, d, J=9.3 Hz), 7.39-7.22 (6H, m), 5.69 (2H, s), 3.39 (3H, s), 2.81 (3H, s).
UPLC retention time=2.39 min.
Obs.Mass=472.07 (M+H)⁺

Example 238

2-[benzyl(pyridazin-3-yl)amino]-5-methyl-N-methylsulfonyl-thiazole-4-carboxamide (Synthesis of Compound Number 238)

$^1$H-NMR (CDCl$_3$) δ: 9.26 (1H, s), 8.08 (1H, d, J=9.6 Hz), 7.38-7.33 (4H, m), 7.22-7.16 (3H, m), 5.61 (2H, s), 3.36 (3H, s), 2.77 (3H, s).
UPLC retention time=1.86 min.
Obs.Mass=404.08 (M+H)⁺

Example 239 methyl 6-[benzyl-[5-methyl-4-(methylsulfonylcarbamoyl)thiazol-2-yl]amino]pyridazine-3-carboxylate (Synthesis of Compound Number 239)

$^1$H-NMR (CDCl$_3$) δ: 9.24 (1H, s), 8.08 (1H, d, J=9.6 Hz), 7.35-7.32 (3H, m), 7.22-7.19 (3H, m), 5.67 (2H, s), 4.06 (3H, s), 3.36 (3H, s), 2.77 (3H, s).
UPLC retention time=1.99 min.
Obs.Mass=462.10 (M+H)⁺

Example 240

5-bromo-2-[N-[(2-chlorophenyl)methyl]-4-cyano-anilino]-N-methylsulfonyl-thiazole-4-carboxamide (Synthesis of Compound Number 240)

$^1$H-NMR (DMSO-d$_6$) δ: 11.58 (1H, s), 7.88 (2H, d, J=8.4 Hz), 7.72 (2H, d, J=8.4 Hz), 7.45-7.42 (2H, m), 7.30-7.27 (2H, m), 5.54 (2H, s), 3.32 (3H, s).
UPLC retention time=2.44 min.
Obs.Mass=526.85 [Br] (M+H)⁺

Example 241

2-[N-benzyl-4-(pentafluorosulfanyl)anilino]-5-methyl-N-methylsulfonyl-thiazole-4-carboxamide (Synthesis of Compound Number 241)

$^1$H-NMR (DMSO-d$_6$) δ: 11.11 (1H, brs), 7.81 (2H, d, J=9.3 Hz), 7.59 (2H, d, J=8.8 Hz), 7.25-7.13 (5H, m), 5.37 (2H, s), 2.49 (3H, s).
UPLC retention time=2.70 min.
Obs.Mass=528.09 (M+H)⁺

Example 242

5-bromo-2-[4-cyano-N-[(2-fluorophenyl)methyl]anilino]-N-methylsulfonyl-thiazole-4-carboxamide (Synthesis of Compound Number 242)

$^1$H-NMR (DMSO-d$_6$) δ: 11.56 (1H, s), 7.89 (2H, d, J=8.8 Hz), 7.72 (2H, d, J=8.8 Hz), 7.43 (1H, dd, J=8.0, 6.4 Hz), 7.30 (1H, dd, J=13.6, 6.0 Hz), 7.18-7.12 (2H, m), 5.53 (2H, s), 3.36 (3H, s).
UPLC retention time=2.35 min.
Obs.Mass=510.88 [Br] (M+H)⁺

Example 243

5-bromo-2-[4-cyano-N-[(3-fluorophenyl)methyl]anilino]-N-methylsulfonyl-thiazole-4-carboxamide (Synthesis of Compound Number 243)

$^1$H-NMR (DMSO-d$_6$) δ: 11.61 (1H, s), 7.88 (2H, d, J=8.8 Hz), 7.73 (2H, d, J=8.8 Hz), 7.34 (1H, dd, J=14.0, 8.0 Hz), 7.18-7.13 (2H, m), 7.09-7.04 (1H, m), 5.52 (2H, s), 3.38 (3H, s).
UPLC retention time=2.34 min.
Obs.Mass=510.88 [Br] (M+H)⁺

Example 244

5-bromo-2-[4-cyano-N-[(4-fluorophenyl)methyl]anilino]-N-methylsulfonyl-thiazole-4-carboxamide (Synthesis of Compound Number 244)

$^1$H-NMR (DMSO-d$_6$) δ: 11.63 (1H, s), 7.88 (2H, d, J=8.4 Hz), 7.70 (2H, d, J=8.4 Hz), 7.35 (2H, dd, J=8.4, 5.6 Hz), 7.13 (2H, t, J=8.8 Hz), 5.47 (2H, s), 3.36 (3H, s).
UPLC retention time=2.35 min.
Obs.Mass=510.88 [Br] (M+H)⁺

Example 245

5-bromo-2-[4-cyano-N-(m-tolylmethyl)anilino]-N-methylsulfonyl-thiazole-4-carboxamide (Synthesis of Compound Number 245)

$^1$H-NMR (DMSO-d$_6$) δ: 11.58 (1H, s), 7.87 (2H, d, J=8.8 Hz), 7.72 (2H, d, J=8.8 Hz), 7.18 (1H, t, J=7.6 Hz), 7.12 (1H, s), 7.07-7.04 (2H, m), 5.43 (2H, s), 3.35 (3H, s), 2.25 (3H, s).

UPLC retention time=2.45 min.
Obs.Mass=506.92 [Br] (M+H)+

Example 246

5-bromo-2-[4-cyano-N-(p-tolylmethyl)anilino]-N-methylsulfonyl-thiazole-4-carboxamide (Synthesis of Compound Number 246)

$^1$H-NMR (DMSO-$d_6$) δ: 11.59 (1H, s), 7.86 (2H, d, J=8.8 Hz), 7.70 (2H, d, J=8.8 Hz), 7.18 (2H, d, J=8.0 Hz), 7.10 (2H, d, J=8.0 Hz), 5.43 (2H, s), 3.35 (3H, s), 2.24 (3H, s).
UPLC retention time=2.46 min.
Obs.Mass=506.92 [Br] (M+H)+

Example 247

5-bromo-2-[N-[(3-chlorophenyl)methyl]-4-cyano-anilino]-N-methylsulfonyl-thiazole-4-carboxamide (Synthesis of Compound Number 247)

$^1$H-NMR (DMSO-$d_6$) δ: 11.64 (1H, s), 7.89 (2H, d, J=8.4 Hz), 7.74 (2H, d, J=8.4 Hz), 7.41 (1H, s), 7.36-7.25 (3H, m), 5.52 (2H, s), 3.35 (3H, s).
UPLC retention time=2.44 min.
Obs.Mass=526.89 [Br] (M+H)+

Example 248

5-bromo-2-[N-[(4-chlorophenyl)methyl]-4-cyano-anilino]-N-methylsulfonyl-thiazole-4-carboxamide (Synthesis of Compound Number 248)

$^1$H-NMR (DMSO-$d_6$) δ: 11.63 (1H, s), 7.88 (2H, d, J=8.4 Hz), 7.71 (2H, d, J=8.4 Hz), 7.37 (2H, d, J=8.4 Hz), 7.33 (2H, d, J=8.4 Hz), 5.50 (2H, s), 3.36 (3H, s).
UPLC retention time=2.47 min.
Obs.Mass=526.85 [Br] (M+H)+

Example 249

5-bromo-2-[4-cyano-N-[(2-methoxyphenyl)methyl]anilino]-N-methylsulfonyl-thiazole-4-carboxamide (Synthesis of Compound Number 249)

$^1$H-NMR (DMSO-$d_6$) δ: 11.51 (1H, s), 7.86 (2H, d, J=8.4 Hz), 7.69 (2H, d, J=8.4 Hz), 7.26-7.23 (2H, m), 6.98 (1H, d, J=8.4 Hz), 6.87 (1H, t, J=7.2 Hz), 5.34 (2H, s), 3.72 (3H, s), 3.34 (3H, s).
UPLC retention time=2.39 min.
Obs.Mass=522.93 [Br] (M+H)+

Example 250

5-bromo-2-[4-cyano-N-[(4-methoxyphenyl)methyl]anilino]-N-methylsulfonyl-thiazole-4-carboxamide (Synthesis of Compound Number 250)

$^1$H-NMR (DMSO-$d_6$) δ: 11.61 (1H, s), 7.87 (2H, d, J=8.4 Hz), 7.69 (2H, d, J=8.4 Hz), 7.22 (2H, d, J=8.4 Hz), 6.85 (2H, d, J=8.4 Hz), 5.39 (2H, s), 3.70 (3H, s), 3.38 (3H, s).

UPLC retention time=2.33 min.
Obs.Mass=522.97 [Br] (M+H)+

Example 251

5-bromo-2-[4-cyano-N-[[4-(trifluoromethyl)phenyl]methyl]anilino]-N-methylsulfonyl-thiazole-4-carboxamide (Synthesis of Compound Number 251)

$^1$H-NMR (DMSO-$d_6$) δ: 11.60 (1H, s), 7.87 (2H, d, J=8.4 Hz), 7.72 (2H, d, J=8.4 Hz), 7.66 (2H, d, J=8.0 Hz), 7.52 (2H, d, J=8.0 Hz), 5.60 (2H, s), 3.33 (3H, s).
UPLC retention time=2.49 min.
Obs.Mass=560.90 [Br] (M+H)+

Example 252

5-bromo-2-[4-cyano-N-[[3-(trifluoromethoxy)phenyl]methyl]anilino]-N-methylsulfonyl-thiazole-4-carboxamide (Synthesis of Compound Number 252)

$^1$H-NMR (CDCl$_3$) δ: 9.14 (1H, s), 7.73 (2H, d, J=8.8 Hz), 7.42 (2H, d, J=8.8 Hz), 7.39 (1H, d, J=7.8 Hz), 7.19-7.17 (2H, m), 7.06 (1H, s), 5.18 (2H, s), 3.38 (3H, s).
UPLC retention time=2.62 min.
Obs.Mass=574.92 (M+H)+

Example 253

5-bromo-2-[4-cyano-N-[[4-(trifluoromethoxy)phenyl]methyl]anilino]-N-methylsulfonyl-thiazole-4-carboxamide (Synthesis of Compound Number 253)

$^1$H-NMR (DMSO-$d_6$) δ: 11.62 (1H, s), 7.89 (2H, d, J=8.4 Hz), 7.73 (2H, d, J=8.4 Hz), 7.44 (2H, d, J=8.4 Hz), 7.31 (2H, d, J=8.4 Hz), 5.54 (2H, s), 3.36 (3H, s).
UPLC retention time=2.54 min.
Obs.Mass=576.94 [Br] (M+H)+

Example 254

5-bromo-2-[4-cyano-N-[[2-(difluoromethoxy)phenyl]methyl]anilino]-N-methylsulfonyl-thiazole-4-carboxamide (Synthesis of Compound Number 254)

$^1$H-NMR (DMSO-$d_6$) δ: 11.53 (1H, s), 7.88 (2H, d, J=8.4 Hz), 7.70 (2H, d, J=8.4 Hz), 7.43 (1H, d, J=7.6 Hz), 7.33 (1H, t, J=8.0 Hz), 7.20 (1H, t, J=74.0 Hz), 7.18-7.15 (2H, m), 5.46 (2H, s), 3.35 (3H, s).
UPLC retention time=2.38 min.
Obs.Mass=558.90 [Br] (M+H)+

Example 255

5-bromo-2-[4-cyano-N-[[3-(difluoromethoxy)phenyl]methyl]anilino]-N-methylsulfonyl-thiazole-4-carboxamide (Synthesis of Compound Number 255)

$^1$H-NMR (DMSO-$d_6$) δ: 11.62 (1H, s), 7.88 (2H, d, J=8.4 Hz), 7.74 (2H, d, J=8.4 Hz), 7.35 (1H, t, J=8.0 Hz), 7.18 (1H, t, J=73.4 Hz), 7.16-7.13 (2H, m), 7.04 (1H, d, J=8.0 Hz), 5.52 (2H, s), 3.35 (3H, s).

UPLC retention time=2.37 min.
Obs.Mass=558.94 [Br] (M+H)+

Example 256

5-bromo-2-[4-cyano-N-[[4-(difluoromethoxy)phenyl]methyl]anilino]-N-methylsulfonyl-thiazole-4-carboxamide (Synthesis of Compound Number 256)

$^1$H-NMR (CDCl$_3$) δ: 9.14 (1H, s), 7.72 (2H, d, J=8.8 Hz), 7.42 (2H, d, J=8.8 Hz), 7.23 (2H, d, J=8.3 Hz), 7.11 (2H, d, J=8.8 Hz), 6.52 (1H, t, J=73.7 Hz), 5.13 (2H, s), 3.38 (3H, s).
UPLC retention time=2.38 min.
Obs.Mass=558.94 [Br] (M+H)+

Example 257

5-chloro-2-[4-cyano-N-[(2-fluorophenyl)methyl]anilino]-N-methylsulfonyl-thiazole-4-carboxamide (Synthesis of Compound Number 257)

$^1$H-NMR (CDCl$_3$) δ: 9.20 (1H, s), 7.71 (2H, d, J=8.0 Hz), 7.44 (2H, d, J=8.0 Hz), 7.32-7.20 (2H, m), 7.13-7.05 (2H, m), 5.15 (2H, s), 3.38 (3H, s).
UPLC retention time=2.33 min.
Obs.Mass=464.94 (M+H)+

Example 258

5-chloro-2-[4-cyano-N-[(3-fluorophenyl)methyl]anilino]-N-methylsulfonyl-thiazole-4-carboxamide (Synthesis of Compound Number 258)

$^1$H-NMR (CDCl$_3$) δ: 9.10 (1H, s), 7.71 (2H, d, J=8.0 Hz), 7.42 (2H, d, J=8.0 Hz), 7.32 (1H, d, J=7.2 Hz), 7.02-6.98 (2H, m), 6.91 (1H, d, J=8.8 Hz), 5.13 (2H, s), 3.37 (3H, s).
UPLC retention time=2.32 min.
Obs.Mass=464.98 (M+H)+

Example 259

5-chloro-2-[4-cyano-N-(o-tolylmethyl)anilino]-N-methylsulfonyl-thiazole-4-carboxamide (Synthesis of Compound Number 259)

$^1$H-NMR (CDCl$_3$) δ: 9.08 (1H, s), 7.67 (2H, d, J=8.0 Hz), 7.40 (2H, d, J=8.0 Hz), 7.21-7.19 (2H, m), 7.16-7.12 (1H, m), 7.08 (1H, d, J=7.6 Hz), 5.09 (2H, s), 3.36 (3H, s).
UPLC retention time=2.40 min.
Obs.Mass=460.94 (M+H)+

Example 260

5-chloro-2-[4-cyano-N-[(3-methoxyphenyl)methyl]anilino]-N-methylsulfonyl-thiazole-4-carboxamide (Synthesis of Compound Number 260)

$^1$H-NMR (CDCl$_3$) δ: 9.08 (1H, s), 7.69 (2H, d, J=8.8 Hz), 7.43 (2H, d, J=8.8 Hz), 7.28-7.24 (1H, m), 6.83 (1H, dd, J=8.4, 2.4 Hz), 6.79 (1H, d, J=7.6 Hz), 6.74 (1H, s), 5.09 (2H, s), 3.77 (3H, s), 3.36 (3H, m).
UPLC retention time=2.31 min.
Obs.Mass=476.99 (M+H)+

Example 261

2-(N-benzyl-4-methylsulfonyl-anilino)-5-methyl-N-methylsulfonyl-thiazole-4-carboxamide (Synthesis of Compound Number 261)

$^1$H-NMR (DMSO-d$_6$) δ: 11.08 (1H, brs), 7.81-7.78 (2H, m), 7.65-7.62 (2H, m), 7.23-7.20 (4H, m), 7.17-7.12 (1H, m), 5.39 (2H, s), 3.25 (3H, s), 3.12 (3H, s), 2.49 (3H, s).
UPLC retention time=2.06 min.
Obs.Mass=479.99 (M+H)+

Example 262

5-chloro-2-[4-cyano-N-[(4-fluorophenyl)methyl]anilino]-N-methylsulfonyl-thiazole-4-carboxamide (Synthesis of Compound Number 262)

$^1$H-NMR (CDCl$_3$) δ: 9.10 (1H, s), 7.70 (2H, d, J=8.0 Hz), 7.39 (2H, d, J=8.0 Hz), 7.19 (2H, t, J=6.4 Hz), 7.03 (2H, t, J=8.0 Hz), 5.09 (2H, s), 3.38 (3H, s).
UPLC retention time=2.33 min.
Obs.Mass=464.94 (M+H)+

Example 263

5-chloro-2-[N-[(2-chlorophenyl)methyl]-4-cyano-anilino]-N-methylsulfonyl-thiazole-4-carboxamide (Synthesis of Compound Number 263)

$^1$H-NMR (CDCl$_3$) δ: 9.12 (1H, s), 7.69 (2H, d, J=8.8 Hz), 7.44 (2H, d, J=8.8 Hz), 7.40 (1H, d, J=6.4 Hz), 7.29-7.23 (3H, m), 5.22 (2H, s), 3.37 (3H, s).
UPLC retention time=2.42 min.
Obs.Mass=480.87 (M+H)+

Example 264

5-bromo-2-[4-cyano-N-(o-tolylmethyl)anilino]-N-methylsulfonyl-thiazole-4-carboxamide (Synthesis of Compound Number 264)

$^1$H-NMR (DMSO-d$_6$) δ: 11.58 (1H, s), 7.85 (2H, d, J=8.4 Hz), 7.72 (2H, d, J=8.4 Hz), 7.20-7.08 (4H, m), 5.45 (2H, s), 3.35 (3H, s), 2.31 (3H, s).
UPLC retention time=2.42 min.
Obs.Mass=504.88 (M+H)+

Example 265

5-bromo-2-[4-cyano-N-[(3-methoxyphenyl)methyl]anilino]-N-methylsulfonyl-thiazole-4-carboxamide (Synthesis of Compound Number 265)

$^1$H-NMR (DMSO-d$_6$) δ: 11.62 (1H, s), 7.87 (2H, d, J=8.8 Hz), 7.73 (2H, d, J=8.8 Hz), 7.21 (1H, t, J=8.0 Hz), 6.88-6.79 (3H, m), 5.45 (2H, s), 3.70 (3H, s), 3.35 (3H, s).
UPLC retention time=2.33 min.
Obs.Mass=520.92 (M+H)+

Example 266

5-chloro-2-[4-cyano-N-(m-tolylmethyl)anilino]-N-methylsulfonyl-thiazole-4-carboxamide (Synthesis of Compound Number 266)

$^1$H-NMR (CDCl$_3$) δ: 9.09 (1H, s), 7.69 (2H, d, J=8.4 Hz), 7.43 (2H, d, J=8.4 Hz), 7.22-7.20 (1H, m), 7.11 (1H, d, J=8.0 Hz), 7.01-6.98 (2H, m), 5.08 (2H, s), 3.37 (3H, s), 2.33 (3H, m).

UPLC retention time=2.42 min.
Obs.Mass=460.94 (M+H)⁺

Example 267

5-chloro-2-[4-cyano-N-(p-tolylmethyl)anilino]-N-methylsulfonyl-thiazole-4-carboxamide (Synthesis of Compound Number 267)

¹H-NMR (CDCl₃) δ: 9.10 (1H, s), 7.68 (2H, d, J=8.4 Hz), 7.41 (2H, d, J=8.4 Hz), 7.14 (2H, d, J=8.0 Hz), 7.08 (2H, d, J=8.0 Hz), 5.07 (2H, s), 3.37 (3H, s), 2.33 (3H, s).
UPLC retention time=2.44 min.
Obs.Mass=460.98 (M+H)⁺

Example 268

5-chloro-2-[N-[(3-chlorophenyl)methyl]-4-cyano-anilino]-N-methylsulfonyl-thiazole-4-carboxamide (Synthesis of Compound Number 268)

¹H-NMR (CDCl₃) δ: 9.06 (1H, s), 7.71 (2H, d, J=8.4 Hz), 7.42 (2H, d, J=8.4 Hz), 7.29 (2H, d, J=4.4 Hz), 7.19 (1H, s), 7.11 (1H, t, J=4.0 Hz), 5.11 (2H, s), 3.37 (3H, s).
UPLC retention time=2.42 min.
Obs.Mass=480.91 (M+H)⁺

Example 269

5-chloro-2-[N-[(4-chlorophenyl)methyl]-4-cyano-anilino]-N-methylsulfonyl-thiazole-4-carboxamide (Synthesis of Compound Number 269)

¹H-NMR (CDCl₃) δ: 9.08 (1H, s), 7.70 (2H, d, J=8.4 Hz), 7.40 (2H, d, J=8.4 Hz), 7.31 (2H, d, J=8.4 Hz), 7.15 (2H, d, J=8.4 Hz), 5.10 (2H, s), 3.37 (3H, s).
UPLC retention time=2.45 min.
Obs.Mass=480.91 (M+H)⁺

Example 270

5-chloro-2-[4-cyano-N-[(2-methoxyphenyl)methyl]anilino]-N-methylsulfonyl-thiazole-4-carboxamide (Synthesis of Compound Number 270)

¹H-NMR (CDCl₃) δ: 9.17 (1H, s), 7.67 (2H, d, J=8.4 Hz), 7.44 (2H, d, J=8.4 Hz), 7.28 (1H, t, J=8.0 Hz), 7.12 (1H, d, J=7.2 Hz), 6.93-6.88 (2H, m), 5.09 (2H, s), 3.77 (3H, s), 3.36 (3H, s).
UPLC retention time=2.37 min.
Obs.Mass=476.95 (M+H)⁺

Example 271

5-chloro-2-[4-cyano-N-[(4-methoxyphenyl)methyl]anilino]-N-methylsulfonyl-thiazole-4-carboxamide (Synthesis of Compound Number 271)

¹H-NMR (CDCl₃) δ: 9.14 (1H, s), 7.69 (2H, d, J=8.4 Hz), 7.39 (2H, d, J=8.4 Hz), 7.12 (2H, d, J=8.4 Hz), 6.85 (2H, d, J=8.4 Hz), 5.04 (2H, s), 3.79 (3H, s), 3.38 (3H, s).

UPLC retention time=2.30 min.
Obs.Mass=476.99 (M+H)⁺

Example 272

5-chloro-2-[4-cyano-N-[[4-(trifluoromethyl)phenyl]methyl]anilino]-N-methylsulfonyl-thiazole-4-carboxamide (Synthesis of Compound Number 272)

¹H-NMR (CDCl₃) δ: 8.97 (1H, s), 7.72 (2H, d, J=8.4 Hz), 7.62 (2H, d, J=8.0 Hz), 7.42 (2H, d, J=8.4 Hz), 7.35 (2H, d, J=8.0 Hz), 5.20 (2H, s), 3.36 (3H, s).
UPLC retention time=2.47 min.
Obs.Mass=514.96 (M+H)⁺

Example 273

5-chloro-2-[4-cyano-N-[[3-(trifluoromethoxy)phenyl]methyl]anilino]-N-methylsulfonyl-thiazole-4-carboxamide (Synthesis of Compound Number 273)

¹H-NMR (CDCl₃) δ: 9.03 (1H, s), 7.71 (2H, d, J=8.4 Hz), 7.41-7.37 (3H, m), 7.17 (2H, d, J=7.6 Hz), 7.05 (1H, s), 5.15 (2H, s), 3.37 (3H, s).
UPLC retention time=2.50 min.
Obs.Mass=530.93 (M+H)⁺

Example 274

5-chloro-2-[4-cyano-N-[[4-(trifluoromethoxy)phenyl]methyl]anilino]-N-methylsulfonyl-thiazole-4-carboxamide (Synthesis of Compound Number 274)

¹H-NMR (CDCl₃) δ: 9.08 (1H, s), 7.71 (2H, d, J=8.4 Hz), 7.41 (2H, d, J=8.4 Hz), 7.25 (2H, d, J=8.4 Hz), 7.19 (2H, d, J=8.4 Hz), 5.13 (2H, s), 3.36 (3H, s).
UPLC retention time=2.52 min.
Obs.Mass=530.93 (M+H)⁺

Example 275

5-chloro-2-[4-cyano-N-[[2-(difluoromethoxy)phenyl]methyl]anilino]-N-methylsulfonyl-thiazole-4-carboxamide (Synthesis of Compound Number 275)

¹H-NMR (CDCl₃) δ: 9.22 (1H, s), 7.71 (2H, d, J=8.4 Hz), 7.45 (2H, d, J=8.4 Hz), 7.33 (1H, t, J=7.6 Hz), 7.25-7.24 (1H, m), 6.55 (1H, t, J=73.3 Hz), 7.21-7.13 (2H, m), 5.18 (2H, s), 3.36 (3H, s).
UPLC retention time=2.37 min.
Obs.Mass=512.96 (M+H)⁺

Example 276

5-chloro-2-[4-cyano-N-[[3-(difluoromethoxy)phenyl]methyl]anilino]-N-methylsulfonyl-thiazole-4-carboxamide (Synthesis of Compound Number 276)

¹H-NMR (CDCl₃) δ: 9.07 (1H, s), 7.71 (2H, d, J=8.4 Hz), 7.42 (2H, d, J=8.4 Hz), 7.35 (1H, t, J=8.0 Hz), 7.08-7.05 (2H, m), 6.99 (1H, s), 6.49 (1H, t, J=73.4 Hz), 5.13 (2H, s), 3.37 (3H, s).

UPLC retention time=2.35 min.
Obs.Mass=512.96 (M+H)+

Example 277

5-chloro-2-[4-cyano-N-[[4-(difluoromethoxy)phenyl]methyl]anilino]-N-methylsulfonyl-thiazole-4-carboxamide (Synthesis of Compound Number 277)

¹H-NMR (CDCl₃) δ: 9.07 (1H, s), 7.71 (2H, d, J=8.4 Hz), 7.41 (2H, d, J=8.0 Hz), 7.22 (2H, d, J=8.4 Hz), 7.10 (2H, d, J=8.4 Hz), 6.50 (1H, t, J=73.5 Hz), 5.11 (2H, s), 3.37 (3H, s).
UPLC retention time=2.36 min.
Obs.Mass=512.96 (M+H)+

Example 278

5-chloro-2-[4-cyano-N-[(2-methylthiazol-4-yl)methyl]anilino]-N-methylsulfonyl-thiazole-4-carboxamide (Synthesis of Compound Number 278)

¹H-NMR (CDCl₃) δ: 9.30 (1H, s), 7.72 (2H, d, J=8.4 Hz), 7.60 (2H, d, J=8.4 Hz), 6.95 (1H, s), 5.12 (2H, s), 3.37 (3H, s).
UPLC retention time=2.06 min.
Obs.Mass=467.91 (M+H)+

Example 279

2-[N-(benzofuran-5-ylmethyl)-4-cyano-anilino]-5-chloro-N-methylsulfonyl-thiazole-4-carboxamide (Synthesis of Compound Number 279)

¹H-NMR (CDCl₃) δ: 9.15 (1H, s), 7.68 (2H, d, J=8.4 Hz), 7.64 (1H, d, J=2.0 Hz), 7.48-7.41 (4H, m), 7.14 (1H, dd, J=8.4, 1.2 Hz), 6.74 (1H, d, J=1.6 Hz), 5.20 (2H, s), 3.37 (3H, s).
UPLC retention time=2.36 min.
Obs.Mass=486.95 (M+H)+

Example 280

2-[N-(benzothiophen-2-ylmethyl)-4-cyano-anilino]-5-chloro-N-methylsulfonyl-thiazole-4-carboxamide (Synthesis of Compound Number 280)

¹H-NMR (CDCl₃) δ: 9.26 (1H, s), 7.79-7.77 (1H, m), 7.73-7.69 (3H, m), 7.47 (2H, d, J=8.4 Hz), 7.37-7.31 (2H, m), 7.12 (1H, s), 5.33 (2H, s), 3.39 (3H, s).
UPLC retention time=2.49 min.
Obs.Mass=502.92 (M+H)+

Example 281

5-bromo-2-[4-cyano-N-[(2-methylthiazol-4-yl)methyl]anilino]-N-methylsulfonyl-thiazole-4-carboxamide (Synthesis of Compound Number 281)

¹H-NMR (CD₃OD) δ: 7.74 (2H, d, J=8.8 Hz), 7.68 (2H, d, J=8.8 Hz), 7.30 (1H, s), 5.29 (2H, s), 3.15 (3H, s), 2.65 (3H, s).
UPLC retention time=2.08 min.
Obs.Mass=513.88 [Br] (M+H)+

Example 282

5-bromo-2-[(4-fluorophenyl)methyl-[6-(trifluoromethyl)-3-pyridyl]amino]-N-methylsulfonyl-thiazole-4-carboxamide (Synthesis of Compound Number 282)

¹H-NMR (DMSO-d₆) δ: 11.63 (1H, s), 9.00 (1H, s), 8.19 (1H, d, J=8.8 Hz), 7.94 (1H, d, J=8.3 Hz), 7.37 (2H, dd, J=8.3, 5.9 Hz), 7.14 (2H, t, J=8.8 Hz), 5.43 (2H, s), 3.34 (3H, s).
UPLC retention time=2.46 min.
Obs.Mass=555.02 [Br] (M+H)+

Example 283

2-[N-[(5-chloro-2-pyridyl)methyl]-4-cyano-anilino]-5-cyclopropyl-N-(3-methoxypropylsulfonyl)thiazole-4-carboxamide (Synthesis of Compound Number 283)

(1) Ethyl5-bromo-2-(4-cyanoanilino)thiazole-4-carboxylate (88.0 mg, 0.250 mmol) synthesized by the method in Example 221 (2) was suspended in toluene (1 mL), and cyclopropylboronic acid monohydrate (38.9 mg, 0.375 mmol), [1,1'-bis(diphenylphosphino)ferrocene] palladium (II) dichloride dichloromethane adduct (20.4 mg, 0.025 mmol) and tripotassium phosphate (106 mg, 0.500 mmo l) were added, and the mixed solution was heated and stirred at 90° C. for 14 hours. After the reaction solution was filtered by celite filtration, the filtrate was removed by distillation under reduced pressure. The resultant residue was purified by column chromatography to obtain ethyl 2-(4-cyanoanilino)-5-cyclopropyl thiazole-4-carboxylate (41.0 mg, 52%).
¹H-NMR (CDCl₃) δ: 7.77 (1H, s), 7.60 (2H, dd, J=9.0, 2.2 Hz), 7.33 (2H, d, J=8.8 Hz), 4.40 (2H, q, J=7.2 Hz), 2.96-2.91 (1H, m), 1.39 (3H, t, J=7.1 Hz), 1.25-1.20 (2H, m), 0.76-0.74 (2H, m).
(2) For ethyl 2-(4-cyanoanilino)-5-cyclopropyl thiazole-4-carboxylate (41.0 mg, 0.130 mmol), the similar procedure to that in Examples 1 (2) to (4) was conducted to obtain 2-[N-[(5-chloro-2-pyridyl)methyl]-4-cyanoanilino]-5-cyclopropyl-N-(3-methoxy propyl sulfonyl) thiazole-4-carboxamide (25.8 mg, 36%) by using 2-bromomethyl-5-chloropyridine and 3-methoxypropane-1-sulfonamide (Reference Example 9) instead of benzylbromide and methane sulfonamide, respectively.
¹H-NMR (DMSO-d₆) δ: 11.04 (1H, s), 8.53 (1H, d, J=2.9 Hz), 7.87 (1H, dd, J=8.3, 2.4 Hz), 7.83 (2H, d, J=9.3 Hz), 7.68 (2H, d, J=8.8 Hz), 7.49 (1H, d, J=8.8 Hz), 5.50 (2H, s), 3.52-3.50 (2H, m), 3.39 (2H, t, J=6.1 Hz), 3.18 (3H, s), 2.94-2.88 (1H, m), 1.93-1.87 (2H, m), 1.14 (2H, td, J=7.4, 5.2 Hz), 0.61 (2H, td, J=5.7, 4.2 Hz).
UPLC retention time=2.46 min.
Obs.Mass=546.17 (M+H)+

Example 284

2-(N-benzyl-4-cyano-anilino)-5-(difluoromethyl)-N-methylsulfonyl-thiazole-4-carboxamide (Synthesis of Compound Number 284)

(1) For ethyl 2-(4-cyanoanilino)thiazole-4-carboxylate (181 mg, 0.662 mmol) synthesized by the method described in Example 221 (1), the similar procedure to that in Example 1(2) was conducted to obtain ethyl 2-(4-cyano-N-(phenylmethyl)anilino)-4-thiazole carboxylate (148 mg, 61%).

$^1$H-NMR (CDCl$_3$) δ: 7.61 (2H, d, J=8.8 Hz), 7.57 (1H, s), 7.49 (2H, d, J=8.8 Hz), 7.33-7.25 (5H, m), 5.28 (2H, s), 4.37 (2H, q, J=7.2 Hz), 1.38 (3H, t, J=7.1 Hz).

(2) Ethyl 2-(4-cyano-N-(phenylmethyl)anilino)-4-thiazole carboxylate (78 mg, 0.22 mmol), bis(difluoromethylsulfonyl) zinc (165 mg, 0.56 mmol) and trifluoroacetic acid (0.016 mL, 0.22 mmol) were dissolved in a mixed solvent of DMSO (0.75 mL)-water (0.3 mL) and tert-butyl hydroperoxide (0.150 mL, 1.08 mmol) was slowly added to this mixture while stirring. Addition of 0.1 mL of dichloromethane to the suspension-like reaction solution turned the reaction solution clear. After stirring for 1 hour, bis(difluoromethylsulfonyl) zinc (133 mg, 0.45 mmol) and tert-butyl hydroperoxide (0.075 mL, 0.54 mmol) were further added, and the resultant mixture was stirred at 50° C. for 15 hours. To the reaction solution was added water and the mixture was extracted with ethyl acetate. The organic fraction was washed with a saturated salt solution and dried over magnesium sulfate. The solvent was removed by distillation under reduced pressure to obtain ethyl 2-(4-cyano-N-(phenylmethyl)anilino)-5-(difluoromethyl)-4-thiazolecarboxylate as a crude product. The crude product was used for the next reaction without further purification.

(3) For the crude product of ethyl 2-(4-cyano-N-(phenylmethyl)anilino)-5-(difluoromethyl)-4-thiazolecarboxylate (0.22 mmol), the similar procedure to that in Examples 1 (3) and (4) was performed to obtain 2-(N-benzyl-4-cyanoanilino)-5-(difluoromethyl)-N-methylsulfonyl-thiazole-4-carboxamide (7.6 mg, 7%).

$^1$H-NMR (DMSO-d$_6$) δ: 11.88 (1H, s), 7.90 (2H, d, J=8.3 Hz), 7.75 (2H, d, J=8.3 Hz), 7.62 (1H, t, J=54.6 Hz), 7.30-7.23 (5H, m), 5.52 (2H, s), 3.32 (3H, s).

UPLC retention time=2.38 min.

Obs.Mass=463.06 (M+H)$^+$

Example 285

2-[N-[(4-bromophenyl)methyl]-4-cyano-anilino]-5-methyl-N-methylsulfonyl-oxazole-4-carboxamide (Synthesis of Compound Number 285)

(1) To a mixture of 4-bromobenzonitrile (4.40 g, 24.2 mmol), methyl 2-amino-5-methyloxazole-4-carboxylate (3.85 g, 24.7 mmol), X-phos (1.15 g, 2.42 mmol), Pd$_2$(dba)$_3$ (664 mg, 0.725 mmol) and potassium carbonate (8.02 g, 58.0 mmol) was added tert-butanol (121 mL), and the resultant mixture was heated and stirred at 90° C. for 14 hours. The reaction solution was filtered with celite and the filtrate was removed by distillation under reduced pressure to yield a residue, which was purified by column chromatography to obtain methy 2-(4-cyanoanilino)-5-methyloxazole-4-caroboxylate (3.70 g, 60%).

$^1$H-NMR (DMSO-d$_6$) δ: 10.82 (1H, s), 7.75 (2H, d, J=8.8 Hz), 7.69 (2H, d, J=9.3 Hz), 3.76 (3H, s), 2.49 (3H, s).

(2) For methyl 2-(4-cyanoanilino)-5-methyloxazole-4-carboxylate (3.70 g, 14.4 mmol), the similar procedure to that in Examples 1 (2)-(4) was conducted to obtain 2-[N-[(4-bromophenyl) methyl]-4-cyanoanilino]-5-methyl-N-methylsulfonyl-oxazole-4-carboxamide (3.00 g, 43%) by using 4-bromobenzylbromide instead of benzylbromide.

$^1$H-NMR (DMSO-d$_6$) δ: 11.39 (1H, s), 7.76 (2H, d, J=8.8 Hz), 7.66 (2H, d, J=8.8 Hz), 7.51 (2H, d, J=8.3 Hz), 7.26 (2H, d, J=8.3 Hz), 5.29 (2H, s), 3.32 (3H, s), 2.49 (3H, s).

UPLC retention time=2.32 min.

Obs.Mass=489.03 (M+H)$^+$

The compound of Example 286 was synthesized using corresponding reagents in accordance with the method of Example 285.

Example 286

2-[N-[(4-chlorophenyl)methyl]-4-cyano-anilino]-5-methyl-N-methylsulfonyl-oxazole-4-carboxamide (Synthesis of Compound Number 286)

$^1$H-NMR (DMSO-d$_6$) δ: 11.39 (1H, s), 7.76 (2H, d, J=8.8 Hz), 7.66 (2H, d, J=9.3 Hz), 7.37 (2H, d, J=8.8 Hz), 7.32 (2H, d, J=8.3 Hz), 5.31 (2H, s), 3.32 (3H, s), 2.49 (3H, s).

UPLC retention time=2.31 min.

Obs.Mass=445.06 (M+H)$^+$

Example 287

2-(N-[(1R)-1-benzyl-2-hydroxy-ethyl]-4-cyano-2-fluoro-anilino)-5-methyl-N-methylsulfonyl-thiazole-4-carboxamide (Synthesis of Compound Number 287)

(1) (R)-2-amino-3-phenyl-1-propanol (1.00 g, 6.61 mmol) was dissolved in THF (66 mL) and benzoyl isothiocyanate (0.955 mL, 6.61 mmol) was added, and the mixture was stirred at room temperature for 12 hours. The solvent was removed by distillation under reduced pressure, and ethanol (66 mL) and 1 M sodium hydroxide (6.61 mL, 6.61 mmol) were added thereto. The mixture was stirred at 60° C. for 12 hours. The solvent was removed by distillation, an ammonium chloride aqueous solution was added, and the mixture was extracted with ethyl acetate twice. The organic fraction was washed with a saturated salt solution and dried over magnesium sulfate. The solvent was removed by distillation under reduced pressure and the resultant was dissolved in methanol (33 mL), and methyl 3-bromo-2-oxobutyrater (7.32 mmol) synthesized by the method described in Reference Example 12 was added, and the mixture was stirred for 1 hour while heating under refluxing. The solvent was removed by distillation under reduced pressure and a sodium bicarbonate aqueous solution was added, and the mixture was extracted with ethyl acetate twice. The organic fraction was washed with a saturated salt solution and dried over magnesium sulfate. The solvent was removed by distillation under reduced pressure and the resultant residue was purified by column chromatography to obtain methyl 2-[[(2R)-1-hydroxy-3-phenylpropan-2-yl]amino]-5-methyl-4-thiazole carboxylate (1.75 g, 86%) as a white solid.

$^1$H-NMR (CDCl$_3$) δ: 7.38-7.30 (5H, m), 6.23 (1H, s), 4.49 (1H, s), 3.95-3.77 (7H, m), 2.51 (3H, s).

(2) Methyl2-[[(2R)-1-hydroxy-3-phenylpropan-2-yl]amino]-5-methyl-4-thiazole carboxylate (200 mg, 0.65 mmol) was dissolved in dimethyl acetamide (13 mL) and sodium hydride (60% in oil, 109 mg, 1.63 mmol) was added, and the mixture was stirred at 0° C. To this solution was added 3,4-difluorobenzonitrile (272 mg, 1.96 mmol), and the mixture was stirred at 0° C. for 15 minutes. To the solution was added an ammonium chloride aqueous solution and the mixture was extracted with ethyl acetate twice. The organic fraction was washed with a saturated salt solution and dried over sodium sulfate. The solvent was removed by distillation under reduced pressure and the resultant residue was purified by column chromatography to obtain methy 2-(4-cyano-2-fluoro-N-[(2R)-1-hydroxy-3-phenylpropan-2-yl]anilino)-5-methyl-4-thiazole carboxylate (119 mg, 43%) as a white solid.

¹H-NMR (CDCl₃) δ: 7.42-7.38 (2H, m), 7.32-7.20 (5H, m), 7.06 (1H, t, J=8.5 Hz), 5.26-5.23 (1H, brm), 4.14-4.08 (3H, m), 3.88 (3H, s), 3.12-3.10 (2H, brm), 2.61 (3H, s).

(3) For methyl 2-(4-cyano-2-fluoro-N-[(2R)-1-hydroxy-3-phenylpropan-2-yl]anilino)-5-methyl-4-thiazole carboxylate (119 mg, 0.28 mmol), the similar procedure to that in Examples 1 (3) and (4) was carried out to obtain 2-(N-[(1R)-1-benzyl-2-hydroxy-ethyl]-4-cyano-2-fluoro-anilino)-5-methyl-N-methylsulfonyl-thiazole-4-carboxamide (41.6 mg, 30%).

¹H-NMR (DMSO-d₆) δ: 10.64 (1H, s), 7.97 (1H, d, J=7.3 Hz), 7.86 (1H, dd, J=11.2, 2.0 Hz), 7.66 (1H, d, J=9.3 Hz), 7.39 (1H, t, J=8.8 Hz), 7.28 (4H, d, J=4.4 Hz), 7.19 (1H, td, J=8.5, 4.1 Hz), 4.49-4.48 (1H, m), 4.27 (1H, dd, J=10.2, 4.9 Hz), 4.16 (1H, dd, J=10.0, 4.6 Hz), 3.73 (3H, s), 3.33 (3H, s), 3.03 (1H, dd, J=14.1, 5.9 Hz), 2.92 (1H, dd, J=13.9, 8.0 Hz).

UPLC retention time=2.40 min.
Obs.Mass=489.15 (M+H)⁺

Example 288

2-(dibenzylamino)-5-methyl-N-methylsulfonyl-thiazole-4-carboxamide (Synthesis of Compound Number 288)

(1) Methyl 2-amino-5-methylthiazole-4-carboxylate (2.00 g, 11.6 mmol) was dissolved in methanol (15 mL), and acetic acid (1.5 mL), benzaldehyde (1.22 mL, 11.6 mmol) and 2-picoline borane (2.48 g, 23.2 mmol) were added, and the mixture was stirred at room temperature for 15 hours. The solvent was removed by distillation under reduced pressure and a sodium bicarbonate aqueous solution was added to the resultant residue, and the mixture was extracted with ethyl acetate twice. The organic fraction was washed with saturated salt solution and dried over magnesium sulfate. The residue resulting from removing the solvent by distillation under reduced pressure was purified by column chromatography to obtain methyl 2-(benzylamino)-5-methylthiazole-4-carboxylate (1.90 g, 62%).

¹H-NMR (CDCl₃) δ: 7.35-7.30 (5H, m), 5.89 (1H, brs), 4.44 (2H, d, J=5.4 Hz), 3.85 (3H, s), 2.59 (3H, s).

(2) For methyl 2-(benzylamino)-5-methylthiazole-4-carboxylate, the similar procedure to that in Examples 1 (2)-(4) was carried out to obtain 2-(dibenzylamino)-5-methyl-N-methylsulfonyl-thiazole-4-carboxamide (90 mg).

¹H-NMR (CDCl₃) δ: 9.39 (1H, brs), 7.35-7.32 (6H, m), 7.23-7.20 (4H, m), 4.59 (4H, s), 3.35 (3H, s), 2.64 (3H, s).

UPLC retention time=2.59 min.
Obs.Mass=493.11 (M+H)⁺

The following compounds of Examples 289 to 305 were synthesized using corresponding starting materials, commercial reagents and/or intermediates in the Reference examples in accordance with the method of Example 288.

Example 289

2-[benzyl-[(4-cyanophenyl)methyl]amino]-5-methyl-N-methylsulfonyl-thiazole-4-carboxamide (Synthesis of Compound Number 289)

¹H-NMR (CDCl₃) δ: 9.29 (1H, brs), 7.63 (2H, d, J=8.1 Hz), 7.36-7.16 (7H, m), 4.67 (2H, s), 4.58 (2H, s), 3.35 (3H, s), 2.66 (3H, s).

UPLC retention time=2.40 min.
Obs.Mass=441.05 (M+H)⁺

Example 290

2-[benzyl-[(3-cyanophenyl)methyl]amino]-5-methyl-N-methylsulfonyl-thiazole-4-carboxamide (Synthesis of Compound Number 290)

¹H-NMR (CDCl₃) δ: 9.30 (1H, brs), 7.61-7.58 (1H, m), 7.49-7.44 (3H, m), 7.38-7.34 (3H, m), 7.21-7.18 (2H, m), 4.65 (2H, s), 4.57 (2H, s), 3.35 (3H, s), 2.66 (3H, s).

UPLC retention time=2.40 min.
Obs.Mass=441.09 (M+H)⁺

Example 291

2-[benzyl-[(2-cyanophenyl)methyl]amino]-5-methyl-N-methylsulfonyl-thiazole-4-carboxamide (Synthesis of Compound Number 291)

¹H-NMR (CDCl₃) δ: 9.31 (1H, brs), 7.68 (1H, dd, J=7.6, 1.2 Hz), 7.58 (1H, dt, J=8.0, 1.2 Hz), 7.42-7.31 (5H, m), 7.22 (2H, d, J=6.4 Hz), 4.84 (2H, s), 4.67 (2H, s), 3.34 (3H, s), 2.64 (3H, s).

UPLC retention time=2.39 min.
Obs.Mass=441.09 (M+H)⁺

Example 292

2-[benzyl(methyl)amino]-5-methyl-N-methylsulfonyl-thiazole-4-carboxamide (Synthesis of Compound Number 292)

¹H-NMR (CDCl₃) δ: 9.46 (1H, brs), 7.36-7.31 (3H, m), 7.25-7.23 (2H, m), 4.84 (2H, s), 4.61 (2H, s), 3.36 (3H, s), 3.02 (3H, s), 2.66 (3H, s).

UPLC retention time=2.22 min.
Obs.Mass=340.05 (M+H)⁺

Example 293

2-[benzyl(3-pyridylmethyl)amino]-5-methyl-N-methylsulfonyl-thiazole-4-carboxamide (Synthesis of Compound Number 293)

¹H-NMR (CDCl₃) δ: 9.35 (1H, brs), 8.57 (1H, dd, J=4.8, 1.6 Hz), 8.47 (1H, d, J=2.0 Hz), 7.56 (1H, td, J=4.0, 1.6 Hz), 7.39-7.27 (4H, m), 7.22-7.20 (2H, m), 4.64 (2H, s), 4.56 (2H, s), 3.36 (3H, s), 2.66 (3H, s).

UPLC retention time=1.57 min.
Obs.Mass=417.08 (M+H)⁺

Example 294

2-[benzyl(2-phenylethyl)amino]-5-methyl-N-methylsulfonyl-thiazole-4-carboxamide (Synthesis of Compound Number 294)

¹H-NMR (CDCl₃) δ: 9.36 (1H, brs), 7.36-7.13 (10H, m), 4.48 (2H, s), 3.60 (2H, t, J=7.5 Hz), 3.36 (3H, s), 2.90 (2H, t, J=7.5 Hz), 2.65 (3H, s).

UPLC retention time=2.69 min.
Obs.Mass=430.09 (M+H)+

Example 295

2-[benzyl(2-pyridylmethyl)amino]-5-methyl-N-methylsulfonyl-thiazole-4-carboxamide (Synthesis of Compound Number 295)

$^1$H-NMR (CDCl$_3$) δ: 8.59-8.57 (1H, m), 7.66 (1H, dt, J=7.6, 1.6 Hz), 7.41-7.19 (7H, m), 4.71 (4H, s), 3.34 (3H, s), 2.63 (3H, s).
UPLC retention time=1.63 min.
Obs.Mass=417.08 (M+H)+

Example 296

2-[benzyl(4-pyridylmethyl)amino]-5-methyl-N-methylsulfonyl-thiazole-4-carboxamide (Synthesis of Compound Number 296)

$^1$H-NMR (CDCl$_3$) δ: 9.30 (1H, brs), 8.58 (2H, d, J=6.0 Hz), 7.38-7.31 (3H, m), 7.21 (2H, dd, J=7.6, 1.6 Hz), 7.12 (2H, d, J=6.0 Hz), 4.62 (2H, s), 4.60 (2H, s), 3.36 (3H, s), 2.67 (3H, s).
UPLC retention time=1.56 min.
Obs.Mass=417.12 (M+H)+

Example 297

2-[benzyl(3-phenylpropyl)amino]-5-methyl-N-methylsulfonyl-thiazole-4-carboxamide (Synthesis of Compound Number 297)

$^1$H-NMR (CDCl$_3$) δ: 9.35 (1H, s), 7.35-7.26 (5H, m), 7.22-7.12 (5H, m), 4.58 (2H, s), 3.39 (2H, t, J=7.5 Hz), 3.35 (3H, s), 2.65-2.60 (5H, m), 1.96 (2H, quint).
UPLC retention time=2.77 min.
Obs.Mass=444.14 (M+H)+

Example 298

2-[benzyl(2-cyclohexylethyl)amino]-5-methyl-N-methylsulfonyl-thiazole-4-carboxamide (Synthesis of Compound Number 298)

$^1$H-NMR (CDCl$_3$) δ: 9.40 (1H, brs), 7.35-7.22 (5H, m), 4.60 (2H, s), 3.39-3.33 (5H, m), 2.64 (3H, s), 1.71-1.49 (7H, m), 1.26-1.16 (4H, m), 0.99-0.85 (2H, m).
UPLC retention time=3.08 min.
Obs.Mass=436.17 (M+H)+

Example 299

2-[benzyl-[2-(4-chlorophenyl)ethyl]amino]-5-methyl-N-methylsulfonyl-thiazole-4-carboxamide (Synthesis of Compound Number 299)

$^1$H-NMR (CDCl$_3$) δ: 9.37 (1H, s), 7.35-7.26 (5H, m), 7.20-7.17 (2H, m), 7.06 (2H, d, J=8.1 Hz), 4.47 (2H, s), 3.59 (2H, t, J=7.5 Hz), 3.37 (3H, s), 2.87 (2H, t, J=7.5 Hz), 2.65 (3H, s).

UPLC retention time=2.79 min.
Obs.Mass=464.10 (M+H)+

Example 300

2-[benzyl(2-tetrahydropyran-4-ylethyl)amino]-5-methyl-N-methylsulfonyl-thiazole-4-carboxamide (Synthesis of Compound Number 300)

$^1$H-NMR (CDCl$_3$) δ: 9.38 (1H, s), 7.38-7.22 (5H, m), 4.60 (2H, s), 3.94 (2H, dd, J=11.4, 3.6 Hz), 3.42-3.30 (7H, m), 2.65 (3H, s), 1.60-1.31 (7H, m).
UPLC retention time=2.40 min.
Obs.Mass=438.17 (M+H)+

Example 301

2-[benzyl-[2-(4-cyanophenyl)ethyl]amino]-5-methyl-N-methylsulfonyl-thiazole-4-carboxamide (Synthesis of Compound Number 301)

$^1$H-NMR (CDCl$_3$) δ: 9.33 (1H, s), 7.59 (2H, d, J=8.1 Hz), 7.35-7.31 (3H, m), 7.25-7.17 (4H, m), 4.47 (2H, s), 3.64 (2H, t, J=7.5 Hz), 3.38 (3H, s), 2.96 (2H, t, J=7.5 Hz), 2.65 (3H, s).
UPLC retention time=2.48 min.
Obs.Mass=455.14 (M+H)+

Example 302

2-[benzyl-[2-(2-cyanophenyl)ethyl]amino]-5-methyl-N-methylsulfonyl-thiazole-4-carboxamide (Synthesis of Compound Number 302)

$^1$H-NMR (CDCl$_3$) δ: 9.42 (1H, s), 7.63-7.52 (2H, m), 7.36-7.23 (7H, m), 4.55 (2H, s), 3.75 (2H, t, J=7.5 Hz), 3.36 (3H, s), 3.14 (2H, t, J=7.5 Hz), 2.63 (3H, s).
UPLC retention time=2.49 min.
Obs.Mass=455.14 (M+H)+

Example 303

2-[benzyl-[2-(2-chlorophenyl)ethyl]amino]-5-methyl-N-methylsulfonyl-thiazole-4-carboxamide (Synthesis of Compound Number 303)

$^1$H-NMR (CDCl$_3$) δ: 9.44 (1H, s), 7.37-7.30 (4H, m), 7.23-7.12 (5H, m), 4.51 (2H, s), 3.65 (2H, t, J=7.5 Hz), 3.36 (3H, s), 3.05 (2H, t, J=7.5 Hz), 2.64 (3H, s).
UPLC retention time=2.79 min.
Obs.Mass=464.10 (M+H)+

Example 304

2-[benzyl-[(1-phenylcyclopropyl)methyl]amino]-5-methyl-N-methylsulfonyl-thiazole-4-carboxamide (Synthesis of Compound Number 304)

$^1$H-NMR (CDCl$_3$) δ: 9.26 (1H, s), 7.35-7.18 (8H, m), 7.09 (2H, d, J=6.8 Hz), 4.49 (2H, s), 3.62 (2H, s), 3.34 (3H, s), 2.56 (3H, s), 0.96-0.91 (2H, m), 0.85-0.80 (2H, m).

UPLC retention time=2.76 min.
Obs.Mass=456.18 (M+H)⁺

Example 305

2-[(4-chlorophenyl)methyl-[(6-cyanobenzothiophen-3-yl)methyl]amino]-5-methyl-N-methylsulfonyl-thiazole-4-carboxamide (Synthesis of Compound Number 305)

$^1$H-NMR (CDCl$_3$) δ: 8.21 (1H, s), 7.74 (1H, d, J=8.3 Hz), 7.62 (1H, dd, J=8.3, 1.5 Hz), 7.48 (1H, s), 7.29 (2H, d, J=8.8 Hz), 7.08 (2H, d, J=8.3 Hz), 4.87 (2H, s), 4.51 (2H, s), 3.37 (3H, s), 2.68 (3H, s).
UPLC retention time=2.62 min.
Obs.Mass=531.08 (M+H)⁺

Example 306

2-[(4-chlorophenyl)methyl-[2-(4-cyanophenyl)ethyl]amino]-5-methyl-N-methylsulfonyl-thiazole-4-carboxamide (Synthesis of Compound Number 306)

(1) To a methanol (24 mL) solution containing methy 3-bromo-2-oxobutyrate (2.53 g, 13.0 mmol) synthesized by the method described in Reference Example 12, was added 1-(4-chlorobenzyl)thiourea (2.37 g, 11.8 mmol), and the mixture was stirred overnight while heating under reflux. After the mixture was cooled to room temperature, the solvent was removed by distillation under reduced pressure, a sodium bicarbonate aqueous solution was added, and the resultant mixture was extracted with ethyl acetate twice. The combined organic fraction was washed with a saturated salt solution and dried over magnesium sulfate. The solvent was removed by distillation under reduced pressure and the resultant residue was washed with TBME (30 mL) to obtain methyl 2-[(4-chlorobenzyl)amino]-5-methylthiazole-4-carboxylate (2.88 g, 82%) as a solid.
$^1$H-NMR (CDCl$_3$) δ: 7.35-7.25 (4H, m), 6.09 (1H, brs), 4.42 (2H, s), 3.84 (3H, s), 2.58 (3H, s).
(2) To a dichloromethane (34 mL) solution containing 4-(2-hydroxyethyl)benzonitrile (1.00 g, 6.80 mmol) was added pyridine (0.58 mL, 7.14 mmol), and the mixture was cooled to −40° C. Trifluoromethanesulfonic acid anhydride (1.20 mL, 7.14 mmol) was slowly added dropwise and the mixture was stirred for 2 hours. To this mixture was added 50 mL of water, and the resultant mixture was extracted with dichloromethane twice. A part of methanesulfonate dichloromethane solution obtained by partial concentration of the organic fraction at 0° C. was used directly for the next reaction.
To a THF (2 mL) solution containing methyl 2-[(4-chlorobenzyl)amino]-5-methyl-thiazole-4-carboxylate (594 mg, 2.00 mmol) was slowly added dropwise a THF solution (8 mL) of sodium hydride (88.0 mg, 2.2 mmol). After letting it stand for 30 minutes, to the reaction solution was added methanesulfonate synthesized above, and the mixture was stirred for 1 hour. An ammonium chloride aqueous solution was added to the reactive solution and the mixture was extracted with ethyl acetate twice. The organic fraction was washed with a saturated salt solution and dried over magnesium sulfate. The crude product was dissolved in dioxane (10 mL), a 2 M sodium hydroxide aqueous solution (5 mL) was added, and the mixture was stirred overnight. The reaction solution was diluted with water and washed with hexane. The aqueous solution was adjusted to pH 2-3 with 2 M hydrochloric acid and the mixture was extracted with dichloromethane three times. The organic fraction was washed with a saturated salt solution and dried with magnesium sulfate. The solvent was removed by distillation to obtain 2-((4-chlorobenzyl) (4-cyanophenylethyl) amino))-5-methylthiazole-4-carboxylic acid (479 mg, 76%).
$^1$H-NMR (CDCl$_3$) δ: 7.59 (2H, d, J=8.3 Hz), 7.34-7.23 (4H, m), 7.13 (2H, d, J=8.3 Hz), 4.45 (2H, s), 3.63 (2H, t, J=7.3 Hz), 2.98 (2H, t, J=7.3 Hz), 2.65 (3H, s).
(3) For 2-((4-chlorobenzyl) (4-cyanophenylethyl)amino))-5-methylthiazole-4-carboxylic acid (41.2 mg, 0.10 mmol), the similar procedure to that in Example 1(4) was conducted to obtain 2-[(4-chlorophenyl)methyl-[2-(4-cyanophenyl)ethyl]amino]-5-methyl-N-methylsulfonyl-thiazole-4-carboxamide (30.0 mg, 61%).
$^1$H-NMR (CDCl$_3$) δ: 9.32 (1H, s), 7.61 (2H, d, J=8.3 Hz), 7.35-7.23 (6H, m), 7.12 (2H, d, J=8.3 Hz), 4.44 (2H, s), 3.62 (2H, t, J=7.3 Hz), 3.38 (3H, s), 2.97 (2H, t, J=7.3 Hz), 2.66 (3H, s).
UPLC retention time=2.57 min.
Obs.Mass=489.07 (M+H)⁺
The following compounds of Examples 307 to 333 were synthesized using corresponding starting materials, commercial reagents and/or intermediates in the Reference examples in accordance with the method of Example 306 by using protection with an appropriate protecting group and de-protection if needed.

Example 307

2-[benzyl-[2-(3,4-dimethoxyphenyl)ethyl]amino]-5-methyl-N-methylsulfonyl-thiazole-4-carboxamide (Synthesis of Compound Number 307)

$^1$H-NMR (CDCl$_3$) δ: 9.42 (1H, s), 7.37-7.27 (3H, m), 7.21-7.17 (2H, m), 6.81 (1H, d, J=7.8 Hz), 6.69 (1H, dd, J=8.3, 2.0 Hz), 6.62 (1H, d, J=2.0 Hz), 4.46 (2H, s), 3.87 (3H, s), 3.85 (3H, s), 3.60 (2H, t, J=7.3 Hz), 3.37 (3H, s), 2.86 (2H, t, J=7.3 Hz), 2.65 (3H, s).
UPLC retention time=2.48 min.
Obs.Mass=490.19 (M+H)⁺

Example 308

2-[benzyl-[2-(3-methoxyphenyl)ethyl]amino]-5-methyl-N-methylsulfonyl-thiazole-4-carboxamide (Synthesis of Compound Number 308)

$^1$H-NMR (CDCl$_3$) δ: 9.41 (1H, s), 7.36-7.18 (6H, m), 6.80-6.72 (2H, m), 6.67 (1H, d, J=2.0 Hz), 4.49 (2H, s), 3.79 (3H, s), 3.60 (2H, t, J=7.3 Hz), 3.37 (3H, s), 2.88 (2H, t, J=7.6 Hz), 2.65 (3H, s).
UPLC retention time=2.63 min.
Obs.Mass=460.14 (M+H)⁺

Example 309

2-[benzyl(2-pyrrol-1-ylethyl)amino]-5-methyl-N-methylsulfonyl-thiazole-4-carboxamide (Synthesis of Compound Number 309)

$^1$H-NMR (CDCl$_3$) δ: 9.36 (1H, s), 7.36-7.28 (3H, m), 7.13-7.08 (2H, m), 6.59 (2H, t, J=2.0 Hz), 6.19 (2H, t, J=2.0 Hz), 4.11 (2H, t, J=5.6 Hz), 4.04 (2H, s), 3.70 (2H, t, J=5.6 Hz), 3.38 (3H, s), 2.65 (3H, s).

UPLC retention time=2.46 min.
Obs.Mass=419.13 (M+H)+

Example 310

2-[benzyl-[2-(2-thienyl)ethyl]amino]-5-methyl-N-methylsulfonyl-thiazole-4-carboxamide (Synthesis of Compound Number 310)

$^1$H-NMR (CDCl$_3$) δ: 9.42 (1H, s), 7.38-7.28 (3H, m), 7.23-7.16 (3H, m), 6.94 (1H, dd, J=5.4, 3.4 Hz), 6.80 (1H, d, J=3.4 Hz), 4.50 (2H, s), 3.67 (2H, t, J=7.3 Hz), 3.37 (3H, s), 3.13 (2H, t, J=7.3 Hz), 2.65 (3H, s).
UPLC retention time=2.61 min.
Obs.Mass=436.09 (M+H)+

Example 311

2-[benzyl-[2-(4-methylthiazol-5-yl)ethyl]amino]-5-methyl-N-methylsulfonyl-thiazole-4-carboxamide (Synthesis of Compound Number 311)

$^1$H-NMR (CDCl$_3$) δ: 9.33 (1H, s), 9.10 (1H, s), 7.40-7.31 (3H, m), 7.22-7.15 (2H, m), 4.50 (2H, s), 3.67 (2H, t, J=7.1 Hz), 3.39 (3H, s), 3.10 (2H, t, J=6.8 Hz), 2.67 (3H, s), 2.38 (3H, s).
UPLC retention time=1.99 min.
Obs.Mass=451.10 (M+H)+

Example 312

2-[benzyl-[2-(2-naphthyl)ethyl]amino]-5-methyl-N-methylsulfonyl-thiazole-4-carboxamide (Synthesis of Compound Number 312)

$^1$H-NMR (CDCl$_3$) δ: 9.45 (1H, s), 7.84-7.76 (3H, m), 7.59 (1H, s), 7.51-7.42 (2H, m), 7.37-7.26 (4H, m), 7.21-7.17 (2H, m), 4.48 (2H, s), 3.70 (2H, t, J=7.3 Hz), 3.37 (3H, s), 3.07 (2H, t, J=7.3 Hz), 2.65 (3H, s).
UPLC retention time=2.88 min.
Obs.Mass=480.15 (M+H)+

Example 313

2-[benzyl-[2-(3-thienyl)ethyl]amino]-5-methyl-N-methylsulfonyl-thiazole-4-carboxamide (Synthesis of Compound Number 313)

$^1$H-NMR (CDCl$_3$) δ: 9.41 (1H, s), 7.38-7.27 (4H, m), 7.22-7.17 (2H, m), 6.98-6.95 (1H, m), 6.92 (1H, d, J=4.9 Hz), 4.49 (2H, s), 3.61 (2H, t, J=7.3 Hz), 3.37 (3H, s), 2.95 (2H, t, J=7.1 Hz), 2.65 (3H, s).
UPLC retention time=2.61 min.
Obs.Mass=436.09 (M+H)+

Example 314

2-[benzyl-[2-(1-naphthyl)ethyl]amino]-5-methyl-N-methylsulfonyl-thiazole-4-carboxamide (Synthesis of Compound Number 314)

$^1$H-NMR (CDCl$_3$) δ: 9.43 (1H, s), 7.91-7.84 (2H, m), 7.75 (1H, d, J=8.3 Hz), 7.59-7.46 (2H, m), 7.42-7.27 (5H, m), 7.19-7.15 (2H, m), 4.44 (2H, s), 3.75 (2H, t, J=7.6 Hz), 3.40-3.34 (5H, m), 2.67 (3H, s).
UPLC retention time=2.86 min.
Obs.Mass=480.15 (M+H)+

Example 315

2-[benzyl-[2-(2,4-dichlorophenyl)ethyl]amino]-5-methyl-N-methylsulfonyl-thiazole-4-carboxamide (Synthesis of Compound Number 315)

$^1$H-NMR (CDCl$_3$) δ: 9.43 (1H, s), 7.39-7.28 (4H, m), 7.24-7.16 (3H, m), 7.06 (1H, d, J=7.8 Hz), 4.50 (2H, s), 3.63 (2H, t, J=7.6 Hz), 3.38 (3H, s), 3.01 (2H, t, J=7.3 Hz), 2.65 (3H, s).
UPLC retention time=2.94 min.
Obs.Mass=498.04 (M+H)+

Example 316

2-[benzyl-[2-(2,6-dichlorophenyl)ethyl]amino]-5-methyl-N-methylsulfonyl-thiazole-4-carboxamide (Synthesis of Compound Number 316)

$^1$H-NMR (CDCl$_3$) δ: 9.52 (1H, s), 7.38-7.24 (7H, m), 7.10 (1H, t, J=8.0 Hz), 4.60 (2H, s), 3.66 (2H, t, J=7.8 Hz), 3.39-3.28 (5H, m), 2.64 (3H, s).
UPLC retention time=2.92 min.
Obs.Mass=498.04 (M+H)+

Example 317

2-[benzyl-[2-(4-methylsulfonylphenyl)ethyl]amino]-5-methyl-N-methylsulfonyl-thiazole-4-carboxamide (Synthesis of Compound Number 317)

$^1$H-NMR (CDCl$_3$) δ: 9.34 (1H, s), 7.90-7.85 (2H, m), 7.39-7.29 (5H, m), 7.22-7.17 (2H, m), 4.49 (2H, s), 3.68 (2H, t, J=7.3 Hz), 3.38 (3H, s), 3.05-2.96 (5H, m), 2.65 (3H, s).
UPLC retention time=2.26 min.
Obs.Mass=508.00 (M+H)+

Example 318

2-[benzyl-[2-[1-(p-tolylsulfonyl)indol-3-yl]ethyl]amino]-5-methyl-N-methylsulfonyl-thiazole-4-carboxamide (Synthesis of Compound Number 318)

$^1$H-NMR (CDCl$_3$) δ: 9.39 (1H, s), 7.99 (1H, d, J=7.8 Hz), 7.72 (2H, d, J=8.3 Hz), 7.39-7.18 (9H, m), 7.10 (2H, dd, J=7.1, 2.2 Hz), 4.38 (2H, s), 3.70 (2H, t, J=7.1 Hz), 3.37 (3H, s), 2.98 (2H, t, J=7.3 Hz), 2.65 (3H, s), 2.32 (3H, s).
UPLC retention time=2.87 min.
Obs.Mass=623.08 (M+H)+

Example 319 tert-butyl 4-[2-[benzyl-[5-methyl-4-(methylsulfonylcarbamoyl)thiazol-2-yl]amino]ethyl]piperidine-1-carboxylate (Synthesis of Compound Number 319)

$^1$H-NMR (CDCl$_3$) δ: 9.39 (1H, s), 7.39-7.21 (5H, m), 4.60 (2H, s), 4.13-4.00 (2H, brm), 3.42-3.32 (5H, m), 2.71-2.60 (5H, m), 1.63-1.24 (14H, m), 1.11 (2H, ddd, J=24.5, 12.3, 4.0 Hz).
UPLC retention time=2.81 min.
Obs.Mass=537.09 (M+H)+

Example 320

2-[benzyl-[2-(1H-indol-3-yl)ethyl]amino]-5-methyl-N-methylsulfonyl-thiazole-4-carboxamide (Synthesis of Compound Number 320)

$^1$H-NMR (CDCl$_3$) δ: 9.44 (1H, s), 8.01 (1H, s), 7.49 (1H, d, J=8.3 Hz), 7.39-7.26 (4H, m), 7.24-7.11 (4H, m), 6.99 (1H, d, J=2.4 Hz), 4.53 (2H, s), 3.69 (2H, t, J=7.6 Hz), 3.36 (3H, s), 3.08 (2H, t, J=7.6 Hz), 2.65 (3H, s).
UPLC retention time=2.55 min.
Obs.Mass=469.03 (M+H)$^+$

Example 321

2-[(4-chlorophenyl)methyl-[2-(4-cyanophenyl)ethyl]amino]-5-methyl-N-(3-pyridylmethylsulfonyl)thiazole-4-carboxamide (Synthesis of Compound Number 321)

$^1$H-NMR (CDCl$_3$) δ: 9.07 (1H, s), 8.63-8.59 (2H, m), 7.84-7.79 (1H, m), 7.58 (2H, d, J=8.3 Hz), 7.36-7.26 (3H, m), 7.18 (2H, d, J=8.3 Hz), 7.07 (2H, d, J=8.8 Hz), 4.77 (2H, s), 4.38 (2H, s), 3.55 (2H, t, J=7.6 Hz), 2.90 (2H, t, J=7.3 Hz), 2.70 (3H, s).
UPLC retention time=2.22 min.
Obs.Mass=566.09 (M+H)$^+$

Example 322

2-[(4-chlorophenyl)methyl-[2-(4-cyanophenyl)ethyl]amino]-N-[(3-fluorophenyl)methylsulfonyl]-5-methyl-thiazole-4-carboxamide (Synthesis of Compound Number 322)

$^1$H-NMR (CDCl$_3$) δ: 9.08 (1H, s), 7.58 (2H, d, J=8.3 Hz), 7.37-7.04 (10H, m), 4.74 (2H, s), 4.38 (2H, s), 3.56 (2H, t, J=7.6 Hz), 2.90 (2H, t, J=7.3 Hz), 2.70 (3H, s).
UPLC retention time=2.82 min.
Obs.Mass=583.10 (M+H)$^+$

Example 323

2-[2-(4-cyanophenyl)ethyl-[[4-(trifluoromethoxy)phenyl]methyl]amino]-5-methyl-N-methylsulfonyl-thiazole-4-carboxamide (Synthesis of Compound Number 323)

$^1$H-NMR (CDCl$_3$) δ: 9.31 (1H, s), 7.61 (2H, d, J=7.8 Hz), 7.28-7.18 (6H, m), 4.48 (2H, s), 3.63 (2H, t, J=7.3 Hz), 3.38 (3H, s), 2.98 (2H, t, J=7.3 Hz), 2.67 (3H, s).
UPLC retention time=2.63 min.
Obs.Mass=539.13 (M+H)$^+$

Example 324

2-[2-(4-cyanophenyl)ethyl-[[4-(trifluoromethoxy)phenyl]methyl]amino]-5-methyl-N-(3-pyridylmethylsulfonyl)thiazole-4-carboxamide (Synthesis of Compound Number 324)

$^1$H-NMR (CDCl$_3$) δ: 9.07 (1H, s), 8.63-8.59 (2H, m), 7.85-7.79 (1H, m), 7.58 (2H, d, J=8.3 Hz), 7.33 (1H, dd, J=7.6, 4.6 Hz), 7.21-7.14 (6H, m), 4.77 (2H, s), 4.41 (2H, s), 3.56 (2H, t, J=7.3 Hz), 2.91 (2H, t, J=7.6 Hz), 2.70 (3H, s).
UPLC retention time=2.30 min.
Obs.Mass=616.14 (M+H)$^+$

Example 325

2-[(4-chlorophenyl)methyl-(2-cyclohexylethyl)amino]-5-methyl-N-(3-pyridylmethylsulfonyl)thiazole-4-carboxamide (Synthesis of Compound Number 325)

$^1$H-NMR (CDCl$_3$) δ: 9.12 (1H, s), 8.64-8.61 (1H, m), 8.59 (1H, d, J=2.0 Hz), 7.81-7.77 (1H, m), 7.35-7.27 (3H, m), 7.11 (2H, d, J=8.8 Hz), 4.75 (2H, s), 4.50 (2H, s), 3.28 (2H, t, J=8.0 Hz), 2.68 (3H, s), 1.72-1.40 (8H, m), 1.33-1.10 (3H, m), 0.97-0.82 (2H, m).
UPLC retention time=2.74 min.
Obs.Mass=547.17 (M+H)$^+$

Example 326

2-[benzyl-[2-(4-cyanopyrazol-1-yl)ethyl]amino]-5-methyl-N-methylsulfonyl-thiazole-4-carboxamide (Synthesis of Compound Number 326)

$^1$H-NMR (CDCl$_3$) δ: 9.54 (1H, s), 7.88 (1H, s), 7.68 (1H, s), 7.39-7.31 (3H, m), 7.18-7.13 (2H, m), 4.38 (2H, t, J=5.9 Hz), 4.28 (2H, s), 3.95 (2H, t, J=5.6 Hz), 3.39 (3H, s), 2.65 (3H, s).
UPLC retention time=2.12 min.
Obs.Mass=445.10 (M+H)$^+$

Example 327 tert-butyl 4-[2-[benzyl-[5-methyl-4-(methylsulfonylcarbamoyl) thiazol-2-yl]amino]ethyl]benzoate (Synthesis of Compound Number 327)

$^1$H-NMR (CDCl$_3$) δ: 9.39 (1H, s), 7.92 (2H, d, J=8.3 Hz), 7.37-7.27 (3H, m), 7.21-7.15 (4H, m), 4.44 (2H, s), 3.62 (2H, t, J=7.3 Hz), 3.37 (3H, s), 2.95 (2H, t, J=7.3 Hz), 2.65 (3H, s), 1.59 (9H, s).
UPLC retention time=2.91 min.
Obs.Mass=530.20 (M+H)$^+$

Example 328

4-[2-[benzyl-[5-methyl-4-(methylsulfonylcarbamoyl)thiazol-2-yl]amino]ethyl]benzoic acid (Synthesis of Compound Number 328)

$^1$H-NMR (CDCl$_3$) δ: 9.40 (1H, s), 8.04 (2H, d, J=8.3 Hz), 7.38-7.17 (7H, m), 4.47 (2H, s), 3.66 (2H, t, J=7.3 Hz), 3.38 (3H, s), 2.98 (2H, t, J=7.3 Hz), 2.66 (3H, s).
UPLC retention time=2.22 min.
Obs.Mass=474.11 (M+H)$^+$

Example 329

2-[benzyl-[2-(4-chlorophenyl)-2,2-difluoro-ethyl]amino]-5-methyl-N-methylsulfonyl-thiazole-4-carboxamide (Synthesis of Compound Number 329)

$^1$H-NMR (CDCl$_3$) δ: 9.05 (1H, s), 7.46-7.30 (7H, m), 7.22-7.17 (2H, m), 4.68 (2H, s), 4.01 (2H, t, J=12.9 Hz), 3.36 (3H, s), 2.60 (3H, s).

UPLC retention time=2.71 min.
Obs.Mass=500.08 (M+H)$^+$

Example 330

2-[benzyl-[2-[3-(trifluoromethyl)phenyl]ethyl]
amino]-5-methyl-N-methylsulfonyl-thiazole-4-carboxamide (Synthesis of Compound Number 330)

$^1$H-NMR (CDCl$_3$) δ: 9.38 (1H, s), 7.52-7.28 (7H, m), 7.21-7.16 (2H, m), 4.48 (2H, s), 3.64 (2H, t, J=7.3 Hz), 3.37 (3H, s), 2.96 (2H, t, J=7.6 Hz), 2.65 (3H, s).
UPLC retention time=2.76 min.
Obs.Mass=498.12 (M+H)$^+$

Example 331

2-[benzyl-[2-(3-methylsulfonylphenyl)ethyl]amino]-5-methyl-N-methylsulfonyl-thiazole-4-carboxamide (Synthesis of Compound Number 331)

$^1$H-NMR (CDCl$_3$) δ: 9.37 (1H, s), 7.81 (1H, d, J=7.8 Hz), 7.72 (1H, s), 7.56-7.50 (1H, m), 7.45 (1H, d, J=7.3 Hz), 7.38-7.29 (3H, m), 7.20 (2H, d, J=6.8 Hz), 4.51 (2H, s), 3.69 (2H, t, J=7.1 Hz), 3.38 (3H, s), 3.05-2.97 (5H, m), 2.64 (3H, s).
UPLC retention time=2.23 min.
Obs.Mass=508.16 (M+H)$^+$

Example 332

2-[benzyl-[2-[3-(trifluoromethoxy)phenyl]ethyl]
amino]-5-methyl-N-methylsulfonyl-thiazole-4-carboxamide (Synthesis of Compound Number 332)

$^1$H-NMR (CDCl$_3$) δ: 9.37 (1H, s), 7.37-7.28 (4H, m), 7.18 (2H, d, J=7.3 Hz), 7.09 (2H, d, J=7.3 Hz), 6.97 (1H, s), 4.46 (2H, s), 3.62 (2H, t, J=7.1 Hz), 3.37 (3H, s), 2.92 (2H, t, J=7.1 Hz), 2.65 (3H, s).
UPLC retention time=2.81 min.
Obs.Mass=514.16 (M+H)$^+$

Example 333

2-[benzyl-[2-[4-(trifluoromethyl)phenyl]ethyl]
amino]-5-methyl-N-methylsulfonyl-thiazole-4-carboxamide (Synthesis of Compound Number 333)

$^1$H-NMR (CDCl$_3$) δ: 9.39 (1H, s), 7.56 (2H, d, J=7.8 Hz), 7.38-7.17 (7H, m), 4.48 (2H, s), 3.63 (2H, t, J=7.3 Hz), 3.37 (3H, s), 2.96 (2H, t, J=7.6 Hz), 2.65 (3H, s).
UPLC retention time=2.78 min.
Obs.Mass=498.16 (M+H)$^+$

Example 334

2-[benzyl-[2-(2-pyridyl)ethyl]amino]-5-methyl-N-methylsulfonyl-thiazole-4-carboxamide (Synthesis of Compound Number 334)

(1) To an acetic acid (0.20 mL, 2.7 mmol) solution containing ethyl 2-(benzylamino)-5-methylthiazole-4-carboxylate (74 mg, 0.27 mmol) synthesized by the similar procedure to that in Example 306 (1), was added 2-vinyl pyridine (0.14 mL, 1.4 mmol), and the mixture was stirred at 150° C. for 30 minutes under microwave radiation. The solvent and others were removed by distillation under reduced pressure to obtain ethyl 5-methyl-2-[(phenylmethyl)-[2-(2-pyridinyl)
ethyl]amino]-4-thiazolecarboxylate (90 mg, 88%) by purifying by column chromatography.

$^1$H-NMR (CDCl$_3$) δ: 8.54 (2H, dd, J=14.6, 4.9 Hz), 7.64-7.56 (2H, m), 7.31-7.11 (5H, m), 4.57 (2H, s), 4.46 (2H, t, J=6.6 Hz), 4.35 (2H, q, J=7.2 Hz), 3.80 (2H, t, J=7.3 Hz), 2.58 (3H, s), 1.39 (3H, t, J=6.8 Hz).

(2) For ethyl 5-methyl-2-[(phenylmethyl)-[2-(2-pyridinyl)
ethyl]amino]-4-thiazolecarboxylate (85 mg, 0.22 mmol), the similar procedure to that in Examples 1(3) and (4) was carried out to obtain 2-[benzyl-[2-(2-pyridyl)ethyl]amino]-5-methyl-N-methylsulfonyl-thiazole-4-carboxamide (12 mg, 13%).

$^1$H-NMR (DMSO-d$_6$) δ: 8.65 (1H, d, J=5.4 Hz), 8.15 (1H, t, J=7.6 Hz), 7.71 (1H, d, J=7.8 Hz), 7.62 (1H, t, J=6.3 Hz), 7.36-7.24 (5H, m), 4.64 (2H, s), 3.92 (2H, t, J=6.6 Hz), 3.34 (3H, s), 3.24 (2H, t, J=6.6 Hz), 2.50 (3H, s).
UPLC retention time=1.58 min.
Obs.Mass=431.17 (M+H)$^+$

Example 335

2-[1,3-benzothiazol-6-yl(benzyl)amino]-5-methyl-N-methylsulfonyl-thiazole-4-carboxamide (Synthesis of Compound Number 335)

(1) To a toluene (5 mL) suspension containing methyl 2-chloro-5-methylthiazole-4-carboxylate (300 mg, 1.57 mmol) synthesized by the method described in Reference Example 15, were added 6-aminobenzothiazole (282 mg, 1.88 mmol), Pd$_2$(dba)$_3$ (28.7 mg, 0.0313 mmol), xantphos (54.3 mg, 0.0939 mmol) and 2 M sodium carbonate aqueous solution (1.10 mL, 2.19 mmol), and the mixture was stirred for 18 hours while heating at 110° C. The reaction solution was filtered with celite to obtain methyl 2-(1,3-benzothiazol-6-ylamino)-5-methyl-4-thiazole carboxylate (115 mg, 25%) by purification by silica gel column chromatography after concentration.

$^1$H-NMR (CDCl$_3$) δ: 8.91 (1H, s), 8.08 (1H, d, J=8.8 Hz), 8.00 (1H, d, J=2.4 Hz), 7.55 (1H, s), 7.32 (1H, dd, J=8.8, 2.4 Hz), 3.90 (3H, s), 2.68 (3H, s).

(2) For methyl 2-(1,3-benzothiazol-6-ylamino)-5-methyl-4-thiazolecarboxylate (115 mg, 0.38 mmol), the similar procedure to that in Example 1 (2)-(4) was conducted to obtain 2-[1,3-benzothiazol-6-yl(benzyl)amino]-5-methyl-N-methylsulfonyl-thiazole-4-carboxamide (10 mg, 6%).

$^1$H-NMR (CDCl$_3$) δ: 9.30 (1H, s), 9.03 (1H, s), 8.14 (1H, d, J=8.7 Hz), 7.85 (1H, d, J=2.1 Hz), 7.42 (1H, dd, J=9.0, 2.4 Hz), 7.33-7.26 (5H, m), 5.14 (2H, s), 3.37 (3H, s), 2.59 (3H, s).
UPLC retention time=2.26 min.
Obs.Mass=459.06 (M+H)$^+$ The compounds of Examples 336 to 338 were synthesized using corresponding starting materials in accordance with the method of Example 335 by using protection with an appropriate protecting group and de-protection if needed.

Example 336

2-[benzyl(1H-indol-5-yl)amino]-5-methyl-N-methylsulfonyl-thiazole-4-carboxamide (Synthesis of Compound Number 336)

$^1$H-NMR (CDCl$_3$) δ: 9.42 (1H, s), 8.26 (1H, s), 7.50 (1H, d, J=1.8 Hz), 7.40 (1H, d, J=8.7 Hz), 7.32-7.27 (6H, m), 7.00 (1H, dd, J=8.7, 2.1 Hz), 6.54 (1H, t, J=2.4 Hz), 5.08 (2H, s), 3.36 (3H, s), 2.54 (3H, s).

UPLC retention time=2.30 min.
Obs.Mass=441.13 (M+H)⁺

Example 337

2-[benzyl-(1-methylindol-4-yl)amino]-5-methyl-N-methylsulfonyl-thiazole-4-carboxamide (Synthesis of Compound Number 337)

¹H-NMR (CDCl₃) δ: 8.26 (1H, s), 7.34-7.28 (5H, m), 7.23-7.16 (2H, m), 7.08 (1H, d, J=3.0 Hz), 6.96 (1H, d, J=6.9 Hz), 6.30 (1H, d, J=2.4 Hz), 5.14 (2H, s), 3.83 (3H, s), 3.37 (3H, s), 2.52 (3H, s).
UPLC retention time=2.52 min.
Obs.Mass=455.14 (M+H)⁺

Example 338

2-[benzyl-(1-methylindole-5-yl]amino]-5-methyl-N-methylsulfonyl-thiazole-4-carboxamide (Synthesis of Compound Number 338)

¹H-NMR (CDCl₃) δ: 9.45 (1H, s), 7.47 (1H, d, J=2.0 Hz), 7.47-7.27 (6H, m), 7.10 (1H, d, J=2.8 Hz), 7.02 (1H, dd, J=8.4, 2.0 Hz), 6.47 (1H, dd, J=2.4, 0.8 Hz), 5.08 (2H, s), 3.80 (3H, s), 3.37 (3H, s), 2.53 (3H, s).
UPLC retention time=2.52 min.
Obs.Mass=455.14 (M+H)⁺

Example 339

2-[benzyl-[2-(2-fluorophenyl)ethyl]amino]-5-methyl-N-methylsulfonyl-thiazole-4-carboxamide (Synthesis of Compound Number 339)

(1) To an NMP (1 mL) solution containing methyl 2-chloro-5-methylthiazole-4-carboxylate (100 mg, 0.486 mmol) synthesized by the method described in Reference Example 15, were added 2-fluorophenethylamine (0.0952 mL, 0.729 mmol) and diisopropylethylamine (0.168 mL, 0.972 mmol), and the mixture was stirred at 160° C. for 10 minute under microwave radiation. To the reaction solution was added an ammonium chloride aqueous solution and the mixture was extracted with ethyl acetate twice. The organic fraction was washed with a saturated salt solution and dried over magnesium sulfate. The solvent and the like were removed by distillation under reduced pressure and purified by column chromatography to obtain methyl 2-[2-(2-fluorophenyl)ethylamino]-5-methyl-4-thiazolecarboxylate (63.2 mg, 42%).

¹H-NMR (CDCl₃) δ: 7.23-7.02 (4H, m), 5.16 (1H, s), 4.35 (2H, q, J=7.2 Hz), 3.51-3.48 (4H, m), 2.98 (3H, q, J=6.5 Hz), 2.61 (3H, s), 1.37 (3H, t, J=7.1 Hz).

(2) For methyl 2-[2-(2-fluorophenyl)ethylamino]-5-methyl-4-thiazolecarboxylate (56.0 mg, 0.190 mmol), the similar procedure to that of Examples 1 (2) to (4) was conducted to obtain 2-[benzyl-[2-(2-fluorophenyl)ethyl]amino]-5-methyl-N-methylsulfonyl-thiazole-4-carboxamide (10.6 mg, 13%).

¹H-NMR (CDCl₃) δ: 9.44 (1H, s), 7.35-7.31 (3H, m), 7.24-7.19 (3H, m), 7.15-7.00 (3H, m), 4.52 (2H, s), 3.63 (2H, t, J=7.3 Hz), 3.37 (3H, s), 2.96 (2H, t, J=7.3 Hz), 2.64 (2H, s).
UPLC retention time=2.67 min.
Obs.Mass=448.14 (M+H)⁺

The compound of Example 340 was synthesized using corresponding reagents in accordance with the method of Example 339.

Example 340

2-[benzyl-[2-(4-fluorophenyl)ethyl]amino]-5-methyl-N-methylsulfonyl-thiazole-4-carboxamide (Synthesis of Compound Number 340)

¹H-NMR (DMSO-d₆) δ: 10.85 (1H, s), 7.35-7.33 (2H, m), 7.27-7.26 (5H, m), 7.10 (2H, t, J=8.8 Hz), 4.67 (2H, s), 3.59 (2H, t, J=7.3 Hz), 3.33 (3H, s), 2.87 (2H, t, J=7.3 Hz), 2.54 (3H, s).
UPLC retention time=2.66 min.
Obs.Mass=448.14 (M+H)⁺

The compounds in the following tables were synthesized using procedures similar to those in Examples 1 to 340 in accordance with any synthesis method of scheme A to G by protection using an appropriate protecting group and deprotection if needed.

They were assigned as Examples 341 to 746.

TABLE 69

| Example | Compound Number | Compound name | Synthesis Scheme | Exact MS | Obs. MS (M + H)⁺ | LC Retention time (min) |
|---|---|---|---|---|---|---|
| 341 | 341 | 2-[N-benzyl-4-(trifluoromethyl)anilino]-5-methyl-N-methylsulfonyl-thiazole-4-carboxamide | A | 469.07 | 470.11 | 2.66 |
| 342 | 342 | 2-[4-cyano-N-[(4-methoxyphenyl)methyl]anilino]-5-methyl-N-methylsulfonyl-thiazole-4-carboxamide | A | 456.09 | 457.14 | 2.29 |
| 343 | 343 | 2-[4-cyano-N-[[3-(trifluoromethoxy)phenyl]methyl]anilino]-5-methyl-N-methylsulfonyl-thiazole-4-carboxamide | A | 510.06 | 511.12 | 2.49 |
| 344 | 344 | 2-[4-cyano-N-(cyclohexylmethyl)anilino]-5-methyl-N-methylsulfonyl-thiazole-4-carboxamide | A | 432.13 | 433.15 | 2.62 |
| 345 | 345 | 2-[4-cyano-N-(tetrahydropyran-2-ylmethyl)anilino]-5-methyl-N-methylsulfonyl-thiazole-4-carboxamide | A | 434.11 | 435.13 | 2.24 |
| 346 | 346 | 2-[4-cyano-N-(tetrahydropyran-4-ylmethyl)anilino]-5-methyl-N-methylsulfonyl-thiazole-4-carboxamide | A | 434.11 | 435.13 | 2.03 |

TABLE 69-continued

| Example | Compound Number | Compound name | Synthesis Scheme | Exact MS | Obs. MS (M + H)+ | LC Retention time (min) |
|---|---|---|---|---|---|---|
| 347 | 347 | 2-[4-cyano-N-[[cis-3-(hydroxymethyl)cyclohexyl]methyl]anilino]-5-methyl-N-methylsulfonyl-thiazole-4-carboxamide | A | 462.14 | 463.18 | 2.10 |
| 348 | 348 | 2-[N-[[cis-3-(hydroxymethyl)cyclohexyl]methyl]-4-(trifluoromethyl)anilino]-5-methyl-N-methylsulfonyl-thiazole-4-carboxamide | A | 505.13 | 506.20 | 2.48 |
| 349 | 349 | 2-[4-cyano-N-[[cis-3-methoxycyclohexyl]methyl]anilino]-5-methyl-N-methylsulfonyl-thiazole-4-carboxamide | A | 462.14 | 463.18 | 2.29 |
| 350 | 350 | 2-[4-cyano-N-[(4-oxocyclohexyl)methyl]anilino]-5-methyl-N-methylsulfonyl-thiazole-4-carboxamide | A | 446.11 | 447.14 | 2.00 |
| 351 | 351 | 2-[4-cyano-N-[(1-methyl-4-piperidyl)methyl]anilino]-5-methyl-N-methylsulfonyl-thiazole-4-carboxamide | A | 447.14 | 448.18 | 1.51 |
| 352 | 352 | 2-[4-cyano-N-[[4-(dimethylamino)cyclohexyl]methyl]anilino]-5-methyl-N-methylsulfonyl-thiazole-4-carboxamide | A | 475.17 | 476.23 | 1.64 |
| 353 | 353 | 2-[4-cyano-N-[(cis-4-hydroxycyclohexyl)methyl]anilino]-5-methyl-N-methylsulfonyl-thiazole-4-carboxamide | A | 448.12 | 449.18 | 1.89 |
| 354 | 354 | 2-[4-cyano-N-[(trans-4-hydroxycyclohexyl)methyl]anilino]-5-methyl-N-methylsulfonyl-thiazole-4-carboxamide | A | 448.12 | 449.12 | 1.98 |
| 355 | 355 | 2-[4-cyano-N-[[2-(hydroxymethyl)phenyl]methyl]anilino]-5-methyl-N-methylsulfonyl-thiazole-4-carboxamide | A | 456.09 | 457.14 | 2.01 |
| 356 | 356 | 2-[4-cyano-N-[[4-(hydroxymethyl)phenyl]methyl]anilino]-5-methyl-N-methylsulfonyl-thiazole-4-carboxamide | A | 456.09 | 457.14 | 1.92 |
| 357 | 357 | 2-[4-cyano-N-(2-methoxyethyl)anilino]-5-methyl-N-methylsulfonyl-thiazole-4-carboxamide | A | 394.08 | 395.11 | 1.98 |

TABLE 70

| 358 | 358 | 2-[4-cyano-N-(4-hydroxybutyl)anilino]-5-methyl-N-methylsulfonyl-thiazole-4-carboxamide | A | 408.09 | 409.12 | 1.80 |
|---|---|---|---|---|---|---|
| 359 | 359 | 2-[N-(3-benzyloxypropyl)-4-cyano-anilino]-5-methyl-N-methylsulfonyl-thiazole-4-carboxamide | A | 484.12 | 485.15 | 2.47 |
| 360 | 360 | 2-[4-cyano-N-(3-cyanopropyl)anilino]-5-methyl-N-methylsulfonyl-thiazole-4-carboxamide | A | 403.08 | 404.12 | 1.94 |
| 361 | 361 | 2-[N-(2,1,3-benzoxadiazol-5-ylmethyl)-4-cyano-anilino]-5-methyl-N-methylsulfonyl-thiazole-4-carboxamide | A | 468.07 | 469.11 | 2.23 |
| 362 | 362 | 2-(N-benzyl-4-cyano-anilino)-N-ethylsulfonyl-5-methyl-thiazole-4-carboxamide | A | 440.10 | 441.13 | 2.40 |
| 363 | 363 | 2-(N-benzyl-4-cyano-anilino)-N-cyclopropylsulfonyl-5-methyl-thiazole-4-carboxamide | A | 452.10 | 453.06 | 2.43 |
| 364 | 364 | 2-(N-benzyl-4-cyano-anilino)-5-methyl-N-(trifluoromethylsulfonyl)thiazole-4-carboxamide | A | 480.05 | 480.99 | 2.42 |
| 365 | 365 | 2-[4-cyano-N-(cycloheptylmethyl)anilino]-5-methyl-N-methylsulfonyl-thiazole-4-carboxamide | A | 446.14 | 447.10 | 2.73 |
| 366 | 366 | 2-[4-cyano-N-(cyclohexen-1-ylmethyl)anilino]-5-methyl-N-methylsulfonyl-thiazole-4-carboxamide | A | 430.11 | 431.09 | 2.55 |

TABLE 70-continued

| 367 | 367 | 2-[N-(2-benzyloxyethyl)-4-cyano-anilino]-5-methyl-N-methylsulfonyl-thiazole-4-carboxamide | A | 470.11 | 471.11 | 2.38 |
| 368 | 368 | 2-[4-cyano-N-(3-phenoxypropyl)anilino]-5-methyl-N-methylsulfonyl-thiazole-4-carboxamide | A | 470.11 | 471.07 | 2.46 |
| 369 | 369 | 2-[4-cyano-N-(4-phenoxybutyl)anilino]-5-methyl-N-methylsulfonyl-thiazole-4-carboxamide | A | 484.12 | 485.11 | 2.54 |
| 370 | 370 | 2-[4-cyano-N-[2-(cyclohexoxy)ethyl]anilino]-5-methyl-N-methylsulfonyl-thiazole-4-carboxamide | A | 462.14 | 463.10 | 2.56 |
| 371 | 371 | 2-(N-benzyl-4-cyano-anilino)-N-isobutylsulfonyl-5-methyl-thiazole-4-carboxamide | A | 468.13 | 469.11 | 2.61 |
| 372 | 372 | 2-(N-benzyl-4-cyano-anilino)-5-methyl-N-(2,2,2-trifluoroethylsulfonyl)thiazole-4-carboxamide | A | 494.07 | 495.11 | 2.53 |
| 373 | 373 | 2-(N-benzyl-4-cyano-anilino)-N-[2-(1,3-dioxoisoindolin-2-yl)ethylsulfonyl]-5-methyl-thiazole-4-carboxamide | A | 585.11 | 586.19 | 2.44 |
| 374 | 374 | 2-(N-benzyl-4-cyano-anilino)-N-benzylsulfonyl-5-methyl-thiazole-4-carboxamide | A | 502.11 | 503.09 | 2.59 |
| 375 | 375 | N-(benzenesulfonyl)-2-(N-benzyl-4-cyano-anilino)-5-methyl-thiazole-4-carboxamide | A | 488.10 | 489.11 | 2.58 |

TABLE 71

| 376 | 376 | 2-[4-cyano-N-[2-(2-methoxyphenyl)ethyl]anilino]-5-methyl-N-methylsulfonyl-thiazole-4-carboxamide | A | 470.11 | 471.07 | 2.49 |
| 377 | 377 | 2-(4-cyano-N-(3-methoxy-2-phenyl-propyl)anilino)-5-methyl-N-methylsulfonyl-thiazole-4-carboxamide | A | 484.12 | 485.11 | 2.42 |
| 378 | 378 | 2-[N-(benzothiophen-7-ylmethyl)-4-cyano-anilino]-5-methyl-N-methylsulfonyl-thiazole-4-carboxamide | A | 482.05 | 483.03 | 2.42 |
| 379 | 379 | 2-[4-cyano-N-[2-(2-hydroxyphenyl)ethyl]anilino]-5-methyl-N-methylsulfonyl-thiazole-4-carboxamide | A | 456.09 | 457.06 | 2.23 |
| 380 | 380 | 2-[4-cyano-N-(thiazol-4-ylmethyl)anilino]-5-methyl-N-methylsulfonyl-thiazole-4-carboxamide | A | 433.03 | 434.01 | 1.94 |
| 381 | 381 | 2-(N-benzyl-4-cyano-anilino)-5-methyl-N-(3-pyridylsulfonyl)thiazole-4-carboxamide | A | 489.09 | 490.07 | 2.36 |
| 382 | 382 | 2-(N-benzyl-4-cyano-anilino)-5-methyl-N-(methylsulfonylmethylsulfonyl)thiazole-4-carboxamide | A | 504.06 | 505.04 | 2.30 |
| 383 | 383 | 2-(N-benzyl-4-cyano-anilino)-N-[2-(2,5-dioxopyrrolidin-1-yl)ethylsulfonyl]-5-methyl-thiazole-4-carboxamide | A | 537.11 | 538.17 | 2.24 |
| 384 | 384 | ethyl 2-[[2-(N-benzyl-4-cyano-anilino)-5-methyl-thiazole-4-carbonyl]sulfamoyl]acetate | A | 498.10 | 499.10 | 2.45 |
| 385 | 385 | 2-(N-benzyl-4-cyano-anilino)-5-methyl-N-[(E)-styryl]sulfonyl-thiazole-4-carboxamide | A | 514.11 | 515.16 | 2.69 |
| 386 | 386 | 2-(N-benzyl-4-cyano-anilino)-N-[(3-chlorophenyl)methylsulfonyl]-5-methyl-thiazole-4-carboxamide | A | 536.07 | 537.17 | 2.69 |
| 387 | 387 | 2-(N-benzyl-4-cyano-anilino)-5-methyl-N-(3,3,3-trifluoropropylsulfonyl)thiazole-4-carboxamide | A | 508.09 | 509.12 | 2.58 |

TABLE 71-continued

| | | | | | | |
|---|---|---|---|---|---|---|
| 388 | 388 | 2-(4-cyano-N-[dideuterio-(2,3,4,5,6-pentadeuteriophenyl)methyl]anilino)-5-methyl-N-methylsulfonyl-thiazole-4-carboxamide | A | 433.13 | 434.17 | 2.30 |
| 389 | 389 | 2-[N-(3H-benzimidazol-5-ylmethyl)-4-cyano-anilino]-5-methyl-N-methylsulfonyl-thiazole-4-carboxamide | A | 466.09 | 467.15 | 1.54 |
| 390 | 390 | 2-[4-cyano-N-(8-quinolylmethyl)anilino]-5-methyl-N-methylsulfonyl-thiazole-4-carboxamide | A | 477.09 | 478.15 | 2.00 |
| 391 | 391 | 2-(N-benzyl-4-cyano-anilino)-5-methyl-N-(2-phenylethylsulfonyl)thiazole-4-carboxamide | A | 516.13 | 517.20 | 2.66 |
| 392 | 392 | 2-[4-cyano-N-(thiazol-2-ylmethyl)anilino]-5-methyl-N-methylsulfonyl-thiazole-4-carboxamide | A | 433.03 | 434.05 | 1.96 |
| 393 | 393 | 2-[N-[(4-benzyloxyphenyl)methyl]-4-cyano-anilino]-5-methyl-N-methylsulfonyl-thiazole-4-carboxamide | A | 532.12 | 533.13 | 2.60 |

TABLE 72

| | | | | | | |
|---|---|---|---|---|---|---|
| 394 | 394 | 2-(N-benzyl-4-cyano-anilino)-5-methyl-N-(1-methylimidazol-4-yl)sulfonyl-thiazole-4-carboxamide | A | 492.10 | 493.11 | 2.16 |
| 395 | 395 | 2-(N-benzyl-4-cyano-anilino)-5-methyl-N-(4-pyridylmethylsulfonyl)thiazole-4-carboxamide | A | 503.11 | 504.16 | 1.92 |
| 396 | 396 | 2-(N-benzyl-4-cyano-anilino)-5-methyl-N-(2-pyridylmethylsulfonyl)thiazole-4-carboxamide | A | 503.11 | 504.16 | 2.25 |
| 397 | 397 | 2-(N-benzyl-4-cyano-anilino)-5-methyl-N-(3-pyridylmethylsulfonyl)thiazole-4-carboxamide | A | 503.11 | 504.16 | 1.97 |
| 398 | 398 | 2-[N-benzyl-3-(2-methoxyethoxy)anilino]-5-methyl-N-methylsulfonyl-thiazole-4-carboxamide | A | 475.12 | 476.19 | 2.42 |
| 399 | 399 | 2-[4-cyano-N-[2-(3-methoxyphenyl)ethyl]anilino]-5-methyl-N-methylsulfonyl-thiazole-4-carboxamide | A | 470.11 | 471.15 | 2.39 |
| 400 | 400 | 2-[4-cyano-N-[2-(4-methoxyphenyl)ethyl]anilino]-5-methyl-N-methylsulfonyl-thiazole-4-carboxamide | A | 470.11 | 471.15 | 2.39 |
| 401 | 401 | 2-[4-cyano-N-[2-(3-hydroxyphenyl)ethyl]anilino]-5-methyl-N-methylsulfonyl-thiazole-4-carboxamide | A | 456.09 | 457.10 | 2.11 |
| 402 | 402 | 2-[4-cyano-N-(5-isoquinolylmethyl)anilino]-5-methyl-N-methylsulfonyl-thiazole-4-carboxamide | A | 477.09 | 478.11 | 1.59 |
| 403 | 403 | 2-[4-cyano-N-(6-quinolylmethyl)anilino]-5-methyl-N-methylsulfonyl-thiazole-4-carboxamide | A | 477.09 | 478.11 | 1.59 |
| 404 | 404 | 2-[4-cyano-N-(quinoxalin-6-ylmethyl)anilino]-5-methyl-N-methylsulfonyl-thiazole-4-carboxamide | A | 478.09 | 479.11 | 1.95 |
| 405 | 405 | 2-[4-cyano-N-[(2-hydroxycyclopentyl)methyl]anilino]-5-methyl-N-methylsulfonyl-thiazole-4-carboxamide | A | 434.11 | 435.13 | 1.99 |
| 406 | 406 | 2-[4-cyano-N-[2-(2-hydroxycyclopentyl)ethyl]anilino]-5-methyl-N-methylsulfonyl-thiazole-4-carboxamide | A | 448.12 | 449.14 | 2.09 |
| 407 | 407 | 2-[4-cyano-N-(2-cyclohexylethyl)anilino]-5-methyl-N-methylsulfonyl-thiazole-4-carboxamide | A | 446.14 | 447.10 | 2.78 |
| 408 | 408 | 2-[benzyl(2-pyridyl)amino]-5-methyl-N-methylsulfonyl-thiazole-4-carboxamide | A | 402.08 | 403.12 | 2.45 |
| 409 | 409 | 2-[4-cyano-N-[2-[cis-2-hydroxycyclohexyl]ethyl]anilino]-5-methyl-N-methylsulfonyl-thiazole-4-carboxamide | A | 462.14 | 463.14 | 2.27 |

TABLE 72-continued

| 410 | 410 | 2-[4-cyano-N-[2-[trans-2-hydroxycyclohexyl]ethyl]anilino]-5-methyl-N-methylsulfonyl-thiazole-4-carboxamide | A | 462.14 | 463.14 | 2.26 |
| 411 | 411 | 2-[4-cyano-N-[[trans-2-hydroxycyclohexyl]methyl]anilino]-5-methyl-N-methylsulfonyl-thiazole-4-carboxamide | A | 448.12 | 449.14 | 2.14 |

TABLE 73

| 412 | 412 | 2-(4-cyano-N-[2-(cyclopropylamino)-2-oxo-ethyl]anilino)-5-methyl-N-methylsulfonyl-thiazole-4-carboxamide | A | 433.09 | 434.09 | 1.71 |
| 413 | 413 | 2-[4-cyano-N-[(2,4-dichlorophenyl)methyl]anilino]-5-methyl-N-methylsulfonyl-thiazole-4-carboxamide | A | 494.00 | 495.04 | 2.58 |
| 414 | 414 | 2-[N-[[2,4-bis(trifluoromethyl)phenyl]methyl]-4-cyano-anilino]-5-methyl-N-methylsulfonyl-thiazole-4-carboxamide | A | 562.06 | 563.10 | 2.62 |
| 415 | 415 | 2-[N-[[2,5-bis(trifluoromethyl)phenyl]methyl]-4-cyano-anilino]-5-methyl-N-methylsulfonyl-thiazole-4-carboxamide | A | 562.06 | 563.10 | 2.56 |
| 416 | 416 | 2-[4-cyano-N-[[3-fluoro-5-(trifluoromethyl)phenyl]methyl]anilino]-5-methyl-N-methylsulfonyl-thiazole-4-carboxamide | A | 512.06 | 513.08 | 2.48 |
| 417 | 417 | 2-[N-[[2-chloro-5-(trifluoromethyl)phenyl]methyl]-4-cyano-anilino]-5-methyl-N-methylsulfonyl-thiazole-4-carboxamide | A | 528.03 | 529.09 | 2.52 |
| 418 | 418 | 2-[4-cyano-N-[[2,3,6-trifluoro-5-methoxy-4-(trifluoromethyl)phenyl]methyl]anilino]-5-methyl-N-methylsulfonyl-thiazole-4-carboxamide | A | 578.05 | 579.10 | 2.55 |
| 419 | 419 | 2-[4-cyano-N-[[4-(trifluoromethylsulfinyl)phenyl]methyl]anilino]-5-methyl-N-methylsulfonyl-thiazole-4-carboxamide | A | 542.04 | 543.09 | 2.24 |
| 420 | 420 | 2-[4-cyano-N-[[3-fluoro-4-(trifluoromethoxy)phenyl]methyl]anilino]-5-methyl-N-methylsulfonyl-thiazole-4-carboxamide | A | 528.05 | 529.13 | 2.52 |
| 421 | 421 | 2-[N-[[3-chloro-4-(trifluoromethoxy)phenyl]methyl]-4-cyano-anilino]-5-methyl-N-methylsulfonyl-thiazole-4-carboxamide | A | 544.03 | 545.05 | 2.59 |
| 422 | 422 | 2-[benzyl(4-pyridyl)amino]-5-methyl-N-methylsulfonyl-thiazole-4-carboxamide | A | 402.08 | 403.08 | 1.41 |
| 423 | 423 | 2-(4-cyano-N-[2-(cyclohexylamino)-2-oxo-ethyl]anilino)-5-methyl-N-methylsulfonyl-thiazole-4-carboxamide | A | 475.13 | 476.11 | 2.09 |
| 424 | 424 | 2-(4-cyano-N-[2-[cyclohexyl(methyl)amino]-2-oxo-ethyl]anilino)-5-methyl-N-methylsulfonyl-thiazole-4-carboxamide | A | 489.15 | 490.15 | 2.23 |
| 425 | 425 | 2-(N-(2-anilino-2-oxo-ethyl)-4-cyano-anilino)-5-methyl-N-methylsulfonyl-thiazole-4-carboxamide | A | 469.09 | 470.07 | 2.08 |
| 426 | 426 | 2-(4-cyano-N-[2-(N-methylanilino)-2-oxo-ethyl]anilino)-5-methyl-N-methylsulfonyl-thiazole-4-carboxamide | A | 483.10 | 484.11 | 2.16 |
| 427 | 427 | 2-[4-cyano-N-[(3-hydroxycyclohexyl)methyl]anilino]-5-methyl-N-methylsulfonyl-thiazole-4-carboxamide | A | 448.12 | 449.14 | 1.96 |

TABLE 74

| 428 | 428 | 2-(N-benzylanilino)-5-methyl-N-methylsulfonyl-thiazole-4-carboxamide | A | 401.09 | 402.12 | 2.51 |

TABLE 74-continued

| | | | | | | |
|---|---|---|---|---|---|---|
| 429 | 429 | 2-(N-benzyl-4-cyano-anilino)-5-methyl-N-(2-morpholinoethylsulfonyl)thiazole-4-carboxamide | A | 525.15 | 526.17 | 1.86 |
| 430 | 430 | 2-(N-benzyl-4-cyano-anilino)-5-methyl-N-[2-(1-piperidyl)ethylsulfonyl]thiazole-4-carboxamide | A | 523.17 | 524.17 | 1.95 |
| 431 | 431 | 2-[4-cyano-N-[(3-methylsulfanylphenyl)methyl]anilino]-5-methyl-N-methylsulfonyl-thiazole-4-carboxamide | A | 472.07 | 473.07 | 2.40 |
| 432 | 432 | 2-(4-cyano-N-(2-cyclohexyl-2-oxo-ethyl)anilino)-5-methyl-N-methylsulfonyl-thiazole-4-carboxamide | A | 460.12 | 461.06 | 2.25 |
| 433 | 433 | 2-[4-cyano-N-(3-phenylpropyl)anilino]-5-methyl-N-methylsulfonyl-thiazole-4-carboxamide | A | 454.11 | 455.06 | 2.11 |
| 434 | 434 | 2-(4-cyano-N-phenacyl-anilino)-5-methyl-N-methylsulfonyl-thiazole-4-carboxamide | A | 454.08 | 455.02 | 2.04 |
| 435 | 435 | 2-[4-cyano-N-[(2-methylthiazol-5-yl)methyl]anilino]-5-methyl-N-methylsulfonyl-thiazole-4-carboxamide | A | 447.05 | 448.06 | 1.83 |
| 436 | 436 | 2-[4-cyano-N-[2-[cis-3-hydroxycyclopentyl]ethyl]anilino]-5-methyl-N-methylsulfonyl-thiazole-4-carboxamide | A | 448.12 | 449.14 | 2.00 |
| 437 | 437 | 2-[N-(2,1,3-benzothiadiazol-4-ylmethyl)-4-cyano-anilino]-5-methyl-N-methylsulfonyl-thiazole-4-carboxamide | A | 484.04 | 485.07 | 2.31 |
| 438 | 438 | 2-(4-cyano-N-isohexyl-anilino)-5-methyl-N-methylsulfonyl-thiazole-4-carboxamide | A | 420.13 | 421.17 | 2.60 |
| 439 | 439 | 2-[4-cyano-N-(3-methylbut-2-enyl)anilino]-5-methyl-N-methylsulfonyl-thiazole-4-carboxamide | A | 404.10 | 405.12 | 2.39 |
| 440 | 440 | 2-[4-cyano-N-(cyclobutylmethyl)anilino]-5-methyl-N-methylsulfonyl-thiazole-4-carboxamide | A | 404.10 | 405.12 | 2.41 |
| 441 | 441 | 2-[4-cyano-N-[2-(1-naphthyl)ethyl]anilino]-5-methyl-N-methylsulfonyl-thiazole-4-carboxamide | A | 490.11 | 491.07 | 2.59 |
| 442 | 442 | 2-[4-cyano-N-[2-(3-hydroxycyclohexyl)ethyl]anilino]-5-methyl-N-methylsulfonyl-thiazole-4-carboxamide | A | 462.14 | 463.14 | 2.08 |
| 443 | 443 | 2-[4-cyano-N-(2-tetrahydropyran-2-ylethyl)anilino]-5-methyl-N-methylsulfonyl-thiazole-4-carboxamide | A | 448.12 | 449.14 | 2.35 |
| 444 | 444 | 2-(4-cyano-N-(3-methoxy-3-methyl-butyl)anilino)-5-methyl-N-methylsulfonyl-thiazole-4-carboxamide | A | 436.12 | 437.13 | 2.27 |
| 445 | 445 | 2-[4-cyano-N-[(5-methylisoxazol-3-yl)methyl]anilino]-5-methyl-N-methylsulfonyl-thiazole-4-carboxamide | A | 431.07 | 432.09 | 2.03 |

TABLE 75

| | | | | | | |
|---|---|---|---|---|---|---|
| 446 | 446 | 2-(4-cyano-N-[(2S)-2-methylbutyl]anilino)-5-methyl-N-methylsulfonyl-thiazole-4-carboxamide | A | 406.11 | 407.16 | 2.47 |
| 447 | 447 | 2-[4-cyano-N-(norbornan-2-ylmethyl)anilino]-5-methyl-N-methylsulfonyl-thiazole-4-carboxamide | A | 444.13 | 445.18 | 2.64 |
| 448 | 448 | 2-(N-but-3-enyl-4-cyano-anilino)-5-methyl-N-methylsulfonyl-thiazole-4-carboxamide | A | 390.08 | 391.11 | 2.26 |
| 449 | 449 | 2-[4-cyano-N-(2-isopropoxyethyl)anilino]-5-methyl-N-methylsulfonyl-thiazole-4-carboxamide | A | 422.11 | 423.13 | 2.24 |
| 450 | 450 | 2-[4-cyano-N-[[3-(difluoromethyl)phenyl]methyl]anilino]-5-methyl-N-methylsulfonyl-thiazole-4-carboxamide | A | 476.08 | 477.07 | 2.31 |
| 451 | 451 | 2-[N-benzyl-4-cyano-3-(trifluoromethyl)anilino]-5-methyl-N-methylsulfonyl-thiazole-4-carboxamide | A | 494.07 | 495.12 | 2.46 |

TABLE 75-continued

| | | | | | | |
|---|---|---|---|---|---|---|
| 452 | 452 | 2-[4-cyano-N-[(2-methylsulfanylphenyl)methyl]anilino]-5-methyl-N-methylsulfonyl-thiazole-4-carboxamide | A | 472.07 | 473.11 | 2.43 |
| 453 | 453 | 2-[4-cyano-N-[2-[trans-3-fluorocyclopentyl]ethyl]anilino]-5-methyl-N-methylsulfonyl-thiazole-4-carboxamide | A | 450.12 | 451.14 | 2.40 |
| 454 | 454 | 2-[4-cyano-N-(indan-2-ylmethyl)anilino]-5-methyl-N-methylsulfonyl-thiazole-4-carboxamide | A | 466.11 | 467.15 | 2.55 |
| 455 | 455 | 2-[4-cyano-N-[(2-methoxyphenyl)methyl]anilino]-5-methyl-N-methylsulfonyl-thiazole-4-carboxamide | A | 456.09 | 457.10 | 2.36 |
| 456 | 456 | 2-[4-cyano-N-[(2-isopropylthiazol-4-yl)methyl]anilino]-5-methyl-N-methylsulfonyl-thiazole-4-carboxamide | A | 475.08 | 476.11 | 2.33 |
| 457 | 457 | 2-[4-cyano-N-[2-[trans-4-hydroxytetrahydrofuran-2-yl]ethyl]anilino]-5-methyl-N-methylsulfonyl-thiazole-4-carboxamide | A | 450.10 | 451.14 | 1.76 |
| 458 | 458 | 2-[4-cyano-N-(2-imidazol-1-ylethyl)anilino]-5-methyl-N-methylsulfonyl-thiazole-4-carboxamide | A | 430.09 | 431.05 | 1.27 |
| 459 | 459 | 2-[4-cyano-N-[2-[trans-3-hydroxycyclopentyl]ethyl]anilino]-5-methyl-N-methylsulfonyl-thiazole-4-carboxamide | A | 448.12 | 449.14 | 1.99 |
| 460 | 460 | 2-[N-(1H-benzimidazol-2-ylmethyl)-4-cyano-anilino]-5-methyl-N-methylsulfonyl-thiazole-4-carboxamide | A | 466.09 | 467.11 | 1.51 |
| 461 | 461 | 2-[4-cyano-N-[(2-hydroxyphenyl)methyl]anilino]-5-methyl-N-methylsulfonyl-thiazole-4-carboxamide | A | 442.08 | 443.14 | 2.09 |
| 462 | 462 | 2-[benzyl-(2-hydroxy-2-phenyl-ethyl)amino]-5-methyl-N-methylsulfonyl-thiazole-4-carboxamide | A | 445.11 | 446.14 | 2.34 |
| 463 | 463 | 2-[benzyl(phenacyl)amino]-5-methyl-N-methylsulfonyl-thiazole-4-carboxamide | A | 443.10 | 444.10 | 2.41 |

TABLE 76

| | | | | | | |
|---|---|---|---|---|---|---|
| 464 | 464 | 2-[4-cyano-N-[(4-methylbenzothiophen-3-yl)methyl]anilino]-5-methyl-N-methylsulfonyl-thiazole-4-carboxamide | A | 496.07 | 497.12 | 2.55 |
| 465 | 465 | 2-[4-cyano-N-[[2-(phenoxymethyl)thiazol-4-yl]methyl]anilino]-5-methyl-N-methylsulfonyl-thiazole-4-carboxamide | A | 539.08 | 540.13 | 2.44 |
| 466 | 466 | 2-[4-cyano-N-[(2-cyclopropylthiazol-5-yl)methyl]anilino]-5-methyl-N-methylsulfonyl-thiazole-4-carboxamide | A | 473.06 | 474.07 | 2.04 |
| 467 | 467 | 2-(4-cyano-N-[(1S)-2-hydroxy-1-phenyl-ethyl]anilino)-5-methyl-N-methylsulfonyl-thiazole-4-carboxamide | A | 456.09 | 457.06 | 2.11 |
| 468 | 468 | 2-(4-cyano-N-(2-hydroxy-2-phenyl-ethyl)anilino)-5-methyl-N-methylsulfonyl-thiazole-4-carboxamide | A | 456.09 | 457.10 | 2.12 |
| 469 | 469 | 2-[(4-fluorophenyl)methyl-[6-(trifluoromethyl)-3-pyridyl]amino]-5-methyl-N-methylsulfonyl-thiazole-4-carboxamide | A | 488.06 | 489.07 | 2.42 |
| 470 | 470 | 2-[(4-chlorophenyl)methyl-[6-(trifluoromethyl)-3-pyridyl]amino]-5-methyl-N-methylsulfonyl-thiazole-4-carboxamide | A | 504.03 | 505.04 | 2.55 |
| 471 | 471 | 5-methyl-N-methylsulfonyl-2-[[4-(trifluoromethoxy)phenyl]methyl-[6-(trifluoromethyl)-3-pyridyl]amino]thiazole-4-carboxamide | A | 554.05 | 555.10 | 2.61 |
| 472 | 472 | 2-[[4-(difluoromethoxy)phenyl]methyl-[6-(trifluoromethyl)-3-pyridyl]amino]-5-methyl-N-methylsulfonyl-thiazole-4-carboxamide | A | 536.06 | 537.13 | 2.44 |

TABLE 76-continued

| | | | | | | |
|---|---|---|---|---|---|---|
| 473 | 473 | 2-[4-cyano-N-[[cis-3-hydroxycycloheptyl]methyl]anilino]-5-methyl-N-methylsulfonyl-thiazole-4-carboxamide | A | 462.14 | 463.14 | 2.08 |
| 474 | 474 | 2-[4-cyano-N-[[trans-3-hydroxycycloheptyl]methyl]anilino]-5-methyl-N-methylsulfonyl-thiazole-4-carboxamide | A | 462.14 | 463.10 | 2.17 |
| 475 | 475 | 2-[4-cyano-N-[2-[3-(dimethylamino)phenyl]ethyl]anilino]-5-methyl-N-methylsulfonyl-thiazole-4-carboxamide | A | 483.14 | 484.03 | 1.71 |
| 476 | 476 | 2-[4-cyano-N-(2-trimethylsilylethyl)anilino]-5-methyl-N-methylsulfonyl-thiazole-4-carboxamide | A | 436.11 | 437.13 | 2.66 |
| 477 | 477 | 2-[4-cyano-N-[[dimethyl(phenyl)silyl]methyl]anilino]-5-methyl-N-methylsulfonyl-thiazole-4-carboxamide | A | 484.11 | 485.11 | 2.61 |
| 478 | 478 | 2-[4-cyano-N-(2,3-dihydrobenzofuran-5-ylmethyl)anilino]-5-methyl-N-methylsulfonyl-thiazole-4-carboxamide | A | 468.09 | 469.11 | 2.27 |
| 479 | 479 | 2-[N-(benzofuran-2-ylmethyl)-4-cyano-anilino]-5-methyl-N-methylsulfonyl-thiazole-4-carboxamide | A | 466.08 | 467.11 | 2.40 |
| 480 | 480 | 2-[4-cyano-N-[2-[4-(dimethylamino)phenyl]ethyl]anilino]-5-methyl-N-methylsulfonyl-thiazole-4-carboxamide | A | 483.14 | 484.07 | 1.67 |

TABLE 77

| | | | | | | |
|---|---|---|---|---|---|---|
| 481 | 481 | 2-[4-cyano-N-[2-(1-methylpyrrolidin-2-yl)ethyl]anilino]-5-methyl-N-methylsulfonyl-thiazole-4-carboxamide | A | 447.14 | 448.06 | 1.50 |
| 482 | 482 | 2-[4-cyano-N-(2-norbornan-2-ylethyl)anilino]-5-methyl-N-methylsulfonyl-thiazole-4-carboxamide | A | 458.14 | 459.06 | 2.80 |
| 483 | 483 | 2-(4-cyano-N-[(1R)-2-hydroxy-1-phenyl-ethyl]anilino)-5-methyl-N-methylsulfonyl-thiazole-4-carboxamide | A | 456.09 | 457.02 | 2.11 |
| 484 | 484 | 2-[4-cyano-N-[(3-hydroxyindan-5-yl)methyl]anilino]-5-methyl-N-methylsulfonyl-thiazole-4-carboxamide | A | 482.11 | 483.03 | 2.08 |
| 485 | 485 | 2-[4-cyano-N-(3-cyclopentylpropyl)anilino]-5-methyl-N-methylsulfonyl-thiazole-4-carboxamide | A | 446.14 | 447.10 | 2.79 |
| 486 | 486 | 2-[4-cyano-N-[(4-hydroxychroman-6-yl)methyl]anilino]-5-methyl-N-methylsulfonyl-thiazole-4-carboxamide | A | 498.10 | 499.04 | 2.02 |
| 487 | 487 | 2-(N-benzyl-4-cyano-2-fluoro-anilino)-5-methyl-N-methylsulfonyl-thiazole-4-carboxamide | A | 444.07 | 444.98 | 2.34 |
| 488 | 488 | 2-[(4-chlorophenyl)methyl-[2-(3-pyridyl)ethyl]amino]-5-methyl-N-methylsulfonyl-thiazole-4-carboxamide | A | 464.07 | 465.02 | 1.49 |
| 489 | 489 | 2-[4-cyano-N-(spiro[2.5]octan-6-ylmethyl)anilino]-5-methyl-N-methylsulfonyl-thiazole-4-carboxamide | A | 458.14 | 459.10 | 2.71 |
| 490 | 490 | 2-[N-[(3-benzyloxy-2-pyridyl)methyl]-4-cyano-anilino]-5-methyl-N-methylsulfonyl-thiazole-4-carboxamide | A | 533.12 | 534.13 | 2.05 |
| 491 | 491 | 2-[4-cyano-N-[(6-methox-2-pyridyl)methyl]anilino]-5-methyl-N-methylsulfonyl-thiazole-4-carboxamide | A | 457.09 | 458.10 | 2.23 |
| 492 | 492 | 2-[4-cyano-N-[(3-hydroxyl-pyridyl)methyl]anilino]-5-methyl-N-methylsulfonyl-thiazole-4-carboxamide | A | 443.07 | 444.10 | 1.45 |
| 493 | 493 | 2-[4-cyano-N-[(6-oxo-1H-pyridin-2-yl)methyl]anilino]-5-methyl-N-methylsulfonyl-thiazole-4-carboxamide | A | 443.07 | 444.10 | 1.60 |
| 494 | 494 | 2-[4-cyano-N-[[2-(4-fluorophenyl)thiazol-5-yl]methyl]anilino]-5-methyl-N-methylsulfonyl-thiazole-4-carboxamide | A | 527.06 | 528.08 | 2.38 |

TABLE 77-continued

| | | | | | | |
|---|---|---|---|---|---|---|
| 495 | 495 | 2-[4-cyano-N-[[2-(2-fluorophenyl)thiazol-5-yl]methyl]anilino]-5-methyl-N-methylsulfonyl-thiazole-4-carboxamide | A | 527.06 | 528.12 | 2.36 |
| 496 | 496 | 2-[N-[(6-bromo-3-pyridyl)methyl]-4-cyano-anilino]-5-methyl-N-methylsulfonyl-thiazole-4-carboxamide | A | 504.99 | 506.04 | 2.13 |
| 497 | 497 | 2-[N-(1,3-benzothiazol-2-ylmethyl)-4-cyano-anilino]-5-methyl-N-methylsulfonyl-thiazole-4-carboxamide | A | 483.05 | 484.11 | 2.25 |
| 498 | 498 | 2-[4-cyano-N-[[2-fluoro-4-(trifluoromethyl)phenyl]methyl]anilino]-5-methyl-N-methylsulfonyl-thiazole-4-carboxamide | A | 512.06 | 513.12 | 2.47 |

TABLE 78

| | | | | | | |
|---|---|---|---|---|---|---|
| 499 | 499 | 2-[4-cyano-N-[(4-fluorophenyl)methyl]anilino]-N-(3-methoxypropylsulfonyl)-5-methyl-thiazole-4-carboxamide | A | 502.11 | 503.16 | 2.40 |
| 500 | 500 | 2-[4-cyano-N-[[4-(trifluoromethoxy)phenyl]methyl]anilino]-5-methyl-N-(4-pyridylmethylsulfonyl)thiazole-4-carboxamide | A | 587.09 | 588.14 | 2.13 |
| 501 | 501 | 2-[4-cyano-N-[(4-fluorophenyl)methyl]anilino]-5-methyl-N-(4-pyridylmethylsulfonyl)thiazole-4-carboxamide | A | 521.10 | 522.20 | 1.92 |
| 502 | 502 | 2-[2-(4-chlorophenyl)ethyl-[(6-methoxy-2-pyridyl)methyl]amino]-5-methyl-N-methylsulfonyl-thiazole-4-carboxamide | A | 494.08 | 495.11 | 2.70 |
| 503 | 503 | 2-[2-(4-chlorophenyl)ethyl-[(4-cyanophenyl)methyl]amino]-5-methyl-N-methylsulfonyl-thiazole-4-carboxamide | A | 488.07 | 489.15 | 2.58 |
| 504 | 504 | 2-[2-(4-chlorophenyl)ethyl-[(2-methylthiazol-4-yl)methyl]amino]-5-methyl-N-methylsulfonyl-thiazole-4-carboxamide | A | 484.05 | 485.11 | 2.47 |
| 505 | 505 | 2-[(6-methoxy-2-pyridyl)methyl-[2-[4-(trifluoromethoxy)phenyl]ethyl]amino]-5-methyl-N-methylsulfonyl-thiazole-4-carboxamide | A | 544.11 | 545.17 | 2.75 |
| 506 | 506 | 2-[(4-cyanophenyl)methyl-[2-[4-(trifluoromethoxy)phenyl]ethyl]amino]-5-methyl-N-methylsulfonyl-thiazole-4-carboxamide | A | 538.10 | 539.17 | 2.64 |
| 507 | 507 | 5-methyl-N-methylsulfonyl-2-[(2-methylthiazol-4-yl)methyl-[2-[4-(trifluoromethoxy)phenyl]ethyl]amino]thiazole-4-carboxamide | A | 534.07 | 535.17 | 2.55 |
| 508 | 508 | 2-[2-(4-chlorophenyl)ethyl-[(5-methylisoxazol-3-yl)methyl]amino]-5-methyl-N-methylsulfonyl-thiazole-4-carboxamide | A | 468.07 | 469.11 | 2.50 |
| 509 | 509 | 5-methyl-2-[(5-methylisoxazol-3-yl)methyl-[2-[4-(trifluoromethoxy)phenyl]ethyl]amino]-N-methylsulfonyl-thiazole-4-carboxamide | A | 518.09 | 519.08 | 2.57 |
| 510 | 510 | 2-[N-(chroman-3-ylmethyl)-4-cyano-anilino]-5-methyl-N-methylsulfonyl-thiazole-4-carboxamide | A | 482.11 | 483.07 | 2.44 |
| 511 | 511 | 2-[4-cyano-N-[[5-(difluoromethoxy)-2-pyridyl]methyl]anilino]-5-methyl-N-methylsulfonyl-thiazole-4-carboxamide | A | 493.07 | 494.08 | 2.15 |
| 512 | 512 | 2-[(5-chloro-2-pyridyl)methyl-[2-[4-(trifluoromethoxy)phenyl]ethyl]amino]-5-methyl-N-methylsulfonyl-thiazole-4-carboxamide | A | 548.06 | 549.09 | 2.72 |
| 513 | 513 | 2-[2-[4-(difluoromethoxy)phenyl]ethyl-[(2-methylthiazol-4-yl)methyl]amino]-5-methyl-N-methylsulfonyl-thiazole-4-carboxamide | A | 516.08 | 517.12 | 2.37 |

TABLE 78-continued

| | | | | | | |
|---|---|---|---|---|---|---|
| 514 | 514 | 2-[4-cyano-N-[[5-(trifluoromethyl)-2-pyridyl]methyl]anilino]-5-methyl-N-methylsulfonyl-thiazole-4-carboxamide | A | 495.06 | 496.08 | 2.29 |

TABLE 79

| | | | | | | |
|---|---|---|---|---|---|---|
| 515 | 515 | 2-[4-cyano-N-[(5-methoxy-2-pyridyl)methyl]anilino]-5-methyl-N-methylsulfonyl-thiazole-4-carboxamide | A | 457.09 | 458.10 | 1.78 |
| 516 | 516 | 2-[4-cyano-N-[(6-methoxypyridazin-3-yl)methyl]anilino]-5-methyl-N-methylsulfonyl-thiazole-4-carboxamide | A | 458.08 | 459.10 | 1.89 |
| 517 | 517 | 2-[4-cyano-N-[(5-fluoro-2-pyridyl)methyl]anilino]-5-methyl-N-methylsulfonyl-thiazole-4-carboxamide | A | 445.07 | 446.10 | 2.07 |
| 518 | 518 | 2-[4-cyano-N-[[3-(difluoromethoxy)-5-fluoro-phenyl]methyl]anilino]-5-methyl-N-methylsulfonyl-thiazole-4-carboxamide | A | 510.06 | 511.12 | 2.37 |
| 519 | 519 | 2-[4-cyano-N-[[3-(difluoromethoxy)-5-fluoro-phenyl]methyl]anilino]-N-(3-methoxypropylsulfonyl)-5-methyl-thiazole-4-carboxamide | A | 568.11 | 569.18 | 2.47 |
| 520 | 520 | 2-[4-cyano-N-[[5-(difluoromethoxy)-2-fluoro-phenyl]methyl]anilino]-5-methyl-N-methylsulfonyl-thiazole-4-carboxamide | A | 510.06 | 511.12 | 2.35 |
| 521 | 521 | 2-[4-cyano-N-[[5-(difluoromethoxy)-2-fluoro-phenyl]methyl]anilino]-N-(3-methoxypropylsulfonyl)-5-methyl-thiazole-4-carboxamide | A | 568.11 | 569.22 | 2.45 |
| 522 | 522 | 2-[4-cyano-N-[[4-(difluoromethoxy)-2-fluoro-phenyl]methyl]anilino]-5-methyl-N-methylsulfonyl-thiazole-4-carboxamide | A | 510.06 | 511.08 | 2.38 |
| 523 | 523 | 2-[4-cyano-N-[[4-(difluoromethoxy)-2-fluoro-phenyl]methyl]anilino]-N-(3-methoxypropylsulfonyl)-5-methyl-thiazole-4-carboxamide | A | 568.11 | 569.18 | 2.48 |
| 524 | 524 | 2-[4-cyano-N-[[6-(difluoromethoxy)-3-pyridyl]methyl]anilino]-5-methyl-N-methylsulfonyl-thiazole-4-carboxamide | A | 493.07 | 494.12 | 2.28 |
| 525 | 525 | 2-[4-cyano-N-[[6-(difluoromethoxy)-3-pyridyl]methyl]anilino]-N-(3-methoxypropylsulfonyl)-5-methyl-thiazole-4-carboxamide | A | 551.11 | 552.18 | 2.38 |
| 526 | 526 | 2-[4-cyano-N-[[4-(difluoromethoxy)-3-fluoro-phenyl]methyl]anilino]-N-(3-methoxypropylsulfonyl)-5-methyl-thiazole-4-carboxamide | A | 568.11 | 569.18 | 2.44 |
| 527 | 527 | 2-[4-cyano-N-[(3,5-difluoro-2-pyridyl)methyl]anilino]-5-methyl-N-methylsulfonyl-thiazole-4-carboxamide | A | 463.06 | 464.23 | 2.19 |
| 528 | 528 | 2-[N-[(4-bromo-3-chloro-phenyl)methyl]-4-cyano-anilino]-5-methyl-N-methylsulfonyl-thiazole-4-carboxamide | A | 537.95 | 541.14 [Br] | 2.49 |
| 529 | 529 | 2-[4-cyano-N-(3-isoquinolylmethyl)anilino]-5-methyl-N-methylsulfonyl-thiazole-4-carboxamide | A | 477.09 | 478.28 | 1.83 |
| 530 | 530 | 2-[N-[[5-chloro-6-(trifluoromethyl)-3-pyridyl]methyl]-4-cyano-anilino]-5-methyl-N-methylsulfonyl-thiazole-4-carboxamide | A | 529.03 | 530.05 | 2.39 |

TABLE 80

| | | | | | | |
|---|---|---|---|---|---|---|
| 531 | 531 | 2-[N-[[5-chloro-6-(trifluoromethyl)-3-pyridyl]methyl]-4-cyano-anilino]-N-(3-methoxypropylsulfonyl)-5-methyl-thiazole-4-carboxamide | A | 587.07 | 588.15 | 2.50 |
| 532 | 532 | 2-[4-cyano-N-[[5-methoxy-6-(trifluoromethyl)-3-pyridyl]methyl]anilino]-N-(3- | A | 583.12 | 584.23 | 2.37 |

TABLE 80-continued

| | | | | | | |
|---|---|---|---|---|---|---|
| 533 | 533 | 2-[4-cyano-N-[[5-fluoro-6-(trifluoromethyl)-3-pyridyl]methyl]anilino]-N-(3-methoxypropylsulfonyl)-5-methyl-thiazole-4-carboxamide | A | 571.10 | 572.14 | 2.43 |
| 534 | 534 | 2-[4-cyano-N-[[3-cyano-4-(trifluoromethyl)phenyl]methyl]anilino]-N-(3-methoxypropylsulfonyl)-5-methyl-thiazole-4-carboxamide | A | 577.11 | 578.18 | 2.44 |
| 535 | 535 | 2-[N-[(5-bromo-3-fluoro-2-pyridyl)methyl]-4-cyano-anilino]-N-(3-methoxypropylsulfonyl)-5-methyl-thiazole-4-carboxamide | A | 581.02 | 584.11 [Br] | 2.47 |
| 536 | 536 | 2-[N-[[3-chloro-4-(difluoromethoxy)phenyl]methyl]-4-cyano-anilino]-5-methyl-N-methylsulfonyl-thiazole-4-carboxamide | A | 526.03 | 527.09 | 2.42 |
| 537 | 537 | 2-[4-cyano-N-[[5-(trifluoromethyl)pyrazin-2-yl]methyl]anilino]-5-methyl-N-methylsulfonyl-thiazole-4-carboxamide | A | 496.06 | 497.08 | 2.25 |
| 538 | 538 | 2-[4-cyano-N-[[2-(trifluoromethyl)-4-pyridyl]methyl]anilino]-5-methyl-N-methylsulfonyl-thiazole-4-carboxamide | A | 495.06 | 496.08 | 2.18 |
| 539 | 539 | 2-[4-cyano-N-[[4-(trifluoromethoxy)phenyl]methyl]anilino]-N-(4-methoxybutylsulfonyl)-5-methyl-thiazole-4-carboxamide | A | 582.12 | 583.18 | 2.64 |
| 540 | 540 | 2-[4-cyano-N-[[4-(trifluoromethoxy)phenyl]methyl]anilino]-N-[3-(2-methoxyethoxy)propylsulfonyl]-5-methyl-thiazole-4-carboxamide | A | 612.13 | 613.23 | 2.57 |
| 541 | 541 | 2-[4-cyano-N-[[4-(trifluoromethoxy)phenyl]methyl]anilino]-5-methyl-N-(3-morpholinopropylsulfonyl)thiazole-4-carboxamide | A | 623.15 | 624.24 | 2.09 |
| 542 | 542 | 2-[2-(4-chlorophenyl)ethyl-[[3-(trifluoromethoxy)phenyl]methyl]amino]-5-methyl-N-methylsulfonyl-oxazole-4-carboxamide | A | 531.08 | 531.97 | 2.81 |
| 543 | 543 | 2-[2-(4-chlorophenyl)ethyl-[[2-(difluoromethoxy)phenyl]methyl]amino]-5-methyl-N-methylsulfonyl-oxazole-4-carboxamide | A | 513.09 | 513.96 | 2.65 |
| 544 | 544 | 2-[2-(4-chlorophenyl)ethyl-[[4-(trifluoromethoxy)phenyl]methyl]amino]-5-methyl-N-methylsulfonyl-oxazole-4-carboxamide | A | 531.08 | 531.97 | 2.83 |

TABLE 81

| | | | | | | |
|---|---|---|---|---|---|---|
| 545 | 545 | 2-[1,3-benzothiazol-6-ylmethyl-[2-(4-chlorophenyl)ethyl]amino]-5-methyl-N-methylsulfonyl-oxazole-4-carboxamide | A | 504.07 | 504.96 | 2.42 |
| 546 | 546 | 2-[2-(4-chlorophenyl)ethyl-[(2-methylthiazol-4-yl)methyl]amino]-5-methyl-N-methylsulfonyl-oxazole-4-carboxamide | A | 468.07 | 468.95 | 2.31 |
| 547 | 547 | 2-[2-(4-chlorophenyl)ethyl-[2-[trans-2-hydroxycyclohexyl]ethyl]amino]-5-methyl-N-methylsulfonyl-oxazole-4-carboxamide | A | 483.16 | 484.07 | 2.50 |
| 548 | 548 | 2-[(4-chlorophenyl)methyl-[2-(4-cyanophenyl)ethyl]amino]-5-methyl-N-methylsulfonyl-oxazole-4-carboxamide | A | 472.10 | 473.11 | 2.46 |
| 549 | 549 | 2-[2-(4-chlorophenyl)ethyl-[(5-chloro-2-pyridyl)methyl]amino]-5-methyl-N-methylsulfonyl-oxazole-4-carboxamide | A | 482.06 | 483.07 | 2.50 |
| 550 | 550 | 2-[2-(4-chlorophenyl)ethyl-[(4-fluorophenyl)methyl]amino]-5-methyl-N-methylsulfonyl-oxazole-4-carboxamide | A | 465.09 | 466.10 | 2.64 |
| 551 | 551 | 2-[2-(4-chlorophenyl)ethyl-[[6-(trifluoromethyl)-3- | A | 516.08 | 517.12 | 2.51 |

TABLE 81-continued

| | | | | | | |
|---|---|---|---|---|---|---|
| | | pyridyl]methyl]amino]-5-methyl-N-methylsulfonyl-oxazole-4-carboxamide | | | | |
| 552 | 552 | 2-[2-(4-cyanophenyl)ethyl-[(4-fluorophenyl)methyl]amino]-5-methyl-N-methylsulfonyl-oxazole-4-carboxamide | A | 456.13 | 457.14 | 2.33 |
| 553 | 553 | 2-[2-(4-cyanophenyl)ethyl-[[4-(difluoromethoxy)phenyl]methyl]amino]-5-methyl-N-methylsulfonyl-oxazole-4-carboxamide | A | 504.13 | 505.18 | 2.35 |
| 554 | 554 | 2-[(2-chloro-4-fluoro-phenyl)methyl-[2-(4-cyanophenyl)ethyl]amino]-5-methyl-N-methylsulfonyl-oxazole-4-carboxamide | A | 490.09 | 491.11 | 2.47 |
| 555 | 555 | 2-[2-(4-cyanophenyl)ethyl-[[6-(trifluoromethyl)-3-pyridyl]methyl]amino]-5-methyl-N-methylsulfonyl-oxazole-4-carboxamide | A | 507.12 | 508.16 | 2.21 |
| 556 | 556 | 2-[2-(4-cyanophenyl)ethyl-[(4-fluorophenyl)methyl]amino]-N-(3-methoxypropylsulfonyl)-5-methyl-oxazole-4-carboxamide | A | 514.17 | 515.20 | 2.44 |
| 557 | 557 | 2-[2-(4-cyanophenyl)ethyl-[[4-(difluoromethoxy)phenyl]methyl]amino]-N-(3-methoxypropylsulfonyl)-5-methyl-oxazole-4-carboxamide | A | 562.17 | 563.22 | 2.45 |
| 558 | 558 | 2-[(2-chloro-4-fluoro-phenyl)methyl-[2-(4-cyanophenyl)ethyl]amino]-N-(3-methoxypropylsulfonyl)-5-methyl-oxazole-4-carboxamide | A | 548.13 | 549.21 | 2.57 |

TABLE 82

| | | | | | | |
|---|---|---|---|---|---|---|
| 559 | 559 | 2-[2-(4-cyanophenyl)ethyl-[[6-(trifluoromethyl)-3-pyridyl]methyl]amino]-N-(3-methoxypropylsulfonyl)-5-methyl-oxazole-4-carboxamide | A | 565.16 | 566.22 | 2.32 |
| 560 | 560 | 2-[(3-cyclopropyl-1,2,4-oxadiazol-5-yl)methyl-[2-[4-(trifluoromethoxy)phenyl]ethyl]amino]-5-methyl-N-methylsulfonyl-oxazole-4-carboxamide | A | 529.12 | 530.21 | 2.49 |
| 561 | 561 | 2-[(5-chloro-2-pyridyl)methyl-[2-[4-(trifluoromethoxy)phenyl]ethyl]amino]-5-methyl-N-methylsulfonyl-oxazole-4-carboxamide | A | 532.08 | 533.13 | 2.58 |
| 562 | 562 | 5-methyl-N-methylsulfonyl-2-[2-[4-(trifluoromethoxy)phenyl]ethyl-[[6-(trifluoromethyl)-3-pyridyl]methyl]amino]oxazole-4-carboxamide | A | 566.11 | 567.18 | 2.58 |
| 563 | 563 | 2-[(3-cyclopropyl-1,2,4-oxadiazol-5-yl)methyl-[2-[4-(trifluoromethoxy)phenyl]ethyl]amino]-N-(3-methoxypropylsulfonyl)-5-methyl-oxazole-4-carboxamide | A | 587.17 | 588.27 | 2.58 |
| 564 | 564 | 2-[(5-chloro-2-pyridyl)methyl-[2-[4-(trifluoromethoxy)phenyl]ethyl]amino]-N-(3-methoxypropylsulfonyl)-5-methyl-oxazole-4-carboxamide | A | 590.12 | 591.23 | 2.67 |
| 565 | 565 | N-(3-methoxypropylsulfonyl)-5-methyl-2-[2-[4-(trifluoromethoxy)phenyl]ethyl-[[6-(trifluoromethyl)-3-pyridyl]methyl]amino]oxazole-4-carboxamide | A | 624.15 | 625.24 | 2.67 |
| 566 | 566 | 2-[4-cyano-N-[[4-(2-methoxyethoxy)phenyl]methyl]anilino]-5-methyl-N-methylsulfonyl-thiazole-4-carboxamide | A | 500.12 | 501.16 | 2.23 |
| 567 | 567 | 2-[4-cyano-N-[[4-(3-pyridylmethoxy)phenyl]methyl]anilino]-5-methyl-N-methylsulfonyl-thiazole-4-carboxamide | A | 533.12 | 534.21 | 1.76 |
| 568 | 568 | 2-[4-cyano-N-[[4-(2-pyridylmethoxy)phenyl]methyl]anilino]- | A | 533.12 | 534.17 | 1.82 |

TABLE 82-continued

| | | | | | | |
|---|---|---|---|---|---|---|
| | | 5-methyl-N-methylsulfonyl-thiazole-4-carboxamide | | | | |
| 569 | 569 | 2-[4-cyano-N-[[4-(2-hydroxyethoxy)phenyl]methyl]anilino]-5-methyl-N-methylsulfonyl-thiazole-4-carboxamide | A | 486.10 | 487.15 | 1.95 |
| 570 | 570 | 2-[4-cyano-N-[[4-[2-(dimethylamino)-2-oxo-ethoxy]phenyl]methyl]anilino]-5-methyl-N-methylsulfonyl-thiazole-4-carboxamide | A | 527.13 | 528.21 | 1.97 |
| 571 | 571 | 2-[4-cyano-N-[[4-(4-pyridylmethoxy)phenyl]methyl]anilino]-5-methyl-N-methylsulfonyl-thiazole-4-carboxamide | A | 533.12 | 534.21 | 1.74 |
| 572 | 572 | 2-[4-cyano-N-[[4-(2-morpholinoethoxy)phenyl]methyl]anilino]-5-methyl-N-methylsulfonyl-thiazole-4-carboxamide | A | 555.16 | 556.26 | 1.70 |
| 573 | 573 | 2-[4-cyano-N-[[4-(2-morpholino-2-oxo-ethoxy)phenyl]methyl]anilino]-5-methyl-N-methylsulfonyl-thiazole-4-carboxamide | A | 569.14 | 570.22 | 1.96 |

TABLE 83

| | | | | | | |
|---|---|---|---|---|---|---|
| 574 | 574 | 2-[4-cyano-N-[[4-[2-(methylamino)-2-oxo-ethoxy]phenyl]methyl]anilino]-5-methyl-N-methylsulfonyl-thiazole-4-carboxamide | A | 513.11 | 514.12 | 1.92 |
| 575 | 575 | 2-[4-cyano-N-[[4-[2-(2-oxopyrrolidin-1-yl)ethoxy]phenyl]methyl]anilino]-5-methyl-N-methylsulfonyl-thiazole-4-carboxamide | A | 553.15 | 554.22 | 2.03 |
| 576 | 576 | 2-[4-cyano-N-[[4-(tetrahydropyran-4-ylmethoxy)phenyl]methyl]anilino]-5-methyl-N-methylsulfonyl-thiazole-4-carboxamide | A | 540.15 | 541.21 | 2.37 |
| 577 | 577 | 2-[4-cyano-N-[[4-(2,2-difluoroethoxy)phenyl]methyl]anilino]-5-methyl-N-methylsulfonyl-thiazole-4-carboxamide | A | 506.09 | 507.12 | 2.33 |
| 578 | 578 | 2-[4-cyano-N-[[4-[3-(2-oxopyrrolidin-1-yl)propoxy]phenyl]methyl]anilino]-5-methyl-N-methylsulfonyl-thiazole-4-carboxamide | A | 567.16 | 568.26 | 2.09 |
| 579 | 579 | 2-[4-cyano-N-[[4-(3-hydroxypropoxy)phenyl]methyl]anilino]-5-methyl-N-methylsulfonyl-thiazole-4-carboxamide | A | 500.12 | 501.16 | 2.03 |
| 580 | 580 | 2-[4-cyano-N-[[4-(2,2,2-trifluoroethoxy)phenyl]methyl]anilino]-5-methyl-N-methylsulfonyl-thiazole-4-carboxamide | A | 524.08 | 525.13 | 2.44 |
| 581 | 581 | 2-[4-cyano-N-[[4-(cyclopentoxy)phenyl]methyl]anilino]-5-methyl-N-methylsulfonyl-thiazole-4-carboxamide | A | 510.14 | 511.16 | 2.69 |
| 582 | 582 | 2-[4-cyano-N-[[4-(3-methoxypropoxy)phenyl]methyl]anilino]-5-methyl-N-methylsulfonyl-thiazole-4-carboxamide | A | 514.13 | 515.16 | 2.36 |
| 583 | 583 | 2-[4-cyano-N-[[4-[(1R)-2-methoxy-1-methyl-ethoxy]phenyl]methyl]anilino]-5-methyl-N-methylsulfonyl-thiazole-4-carboxamide | A | 514.13 | 515.16 | 2.35 |
| 584 | 584 | 2-[4-cyano-N-[[4-[(1S)-2-methoxy-1-methyl-ethoxy]phenyl]methyl]anilino]-5-methyl-N-methylsulfonyl-thiazole-4-carboxamide | A | 514.13 | 515.20 | 2.35 |
| 585 | 585 | 2-[4-cyano-N-[(3-isopropoxyphenyl)methyl]anilino]-5-methyl-N-methylsulfonyl-thiazole-4-carboxamide | A | 484.12 | 485.15 | 2.48 |
| 586 | 586 | 2-[4-cyano-N-[(3-isobutoxyphenyl)methyl]anilino]-5-methyl-N-methylsulfonyl-thiazole-4-carboxamide | A | 498.14 | 499.16 | 2.65 |

TABLE 83-continued

| | | | | | | |
|---|---|---|---|---|---|---|
| 587 | 587 | 2-[4-cyano-N-[[3-(2-hydroxyethoxy)phenyl]methyl]anilino]-5-methyl-N-methylsulfonyl-thiazole-4-carboxamide | A | 486.10 | 487.11 | 1.97 |
| 588 | 588 | 2-[4-cyano-N-[(4-cyclopropylphenyl)methyl]anilino]-5-methyl-N-methylsulfonyl-thiazole-4-carboxamide | A | 466.11 | 467.03 | 2.53 |
| 589 | 589 | 2-[4-cyano-N-[[4-(2-oxopyrrolidin-1-yl)phenyl]methyl]anilino]-5-methyl-N-methylsulfonyl-thiazole-4-carboxamide | A | 509.12 | 510.16 | 2.04 |

TABLE 84

| | | | | | | |
|---|---|---|---|---|---|---|
| 590 | 590 | 2-[4-cyano-N-[[4-(2-fluorophenyl)phenyl]methyl]anilino]-5-methyl-N-methylsulfonyl-thiazole-4-carboxamide | A | 520.10 | 521.04 | 2.60 |
| 591 | 591 | 2-[4-cyano-N-[[6-(2-fluorophenyl)-3-pyridyl]methyl]anilino]-5-methyl-N-methylsulfonyl-thiazole-4-carboxamide | A | 521.10 | 522.16 | 2.07 |
| 592 | 592 | 2-[4-cyano-N-[[6-(4-fluorophenyl)-3-pyridyl]methyl]anilino]-5-methyl-N-methylsulfonyl-thiazole-4-carboxamide | A | 521.10 | 522.16 | 2.06 |
| 593 | 593 | 2-[4-cyano-N-[(6-cyclopropyl-3-pyridyl)methyl]anilino]-5-methyl-N-methylsulfonyl-thiazole-4-carboxamide | A | 467.11 | 468.15 | 1.55 |
| 594 | 594 | 2-[4-cyano-N-[[5-(2-fluorophenyl)-2-pyridyl]methyl]anilino]-5-methyl-N-methylsulfonyl-thiazole-4-carboxamide | A | 521.10 | 522.16 | 2.23 |
| 595 | 595 | 2-[4-cyano-N-[[5-(4-fluorophenyl)-2-pyridyl]methyl]anilino]-5-methyl-N-methylsulfonyl-thiazole-4-carboxamide | A | 521.10 | 522.16 | 2.18 |
| 596 | 596 | 2-[4-cyano-N-[[6-(5-fluoro-2-pyridyl)-3-pyridyl]methyl]anilino]-5-methyl-N-methylsulfonyl-thiazole-4-carboxamide | A | 522.09 | 523.09 | 2.02 |
| 597 | 597 | 2-(N-benzyl-4-cyano-anilino)-N-methylsulfonyl-thiazole-4-carboxamide | C | 412.07 | 413.12 | 2.12 |
| 598 | 598 | 2-(N-benzyl-4-cyano-anilino)-5-methyl-N-methylsulfonyl-oxazole-4-carboxamide | C | 410.11 | 411.06 | 2.16 |
| 599 | 599 | 2-(N-benzyl-4-cyano-anilino)-5-ethyl-N-methylsulfonyl-thiazole-4-carboxamide | C | 440.10 | 441.13 | 2.43 |
| 600 | 600 | 2-(N-benzyl-4-cyano-anilino)-5-isopropyl-N-methylsulfonyl-thiazole-4-carboxamide | C | 454.11 | 455.14 | 2.53 |
| 601 | 601 | 2-(N-benzyl-4-cyano-anilino)-N-methylsulfonyl-5-phenyl-thiazole-4-carboxamide | C | 488.10 | 489.15 | 2.52 |
| 602 | 602 | 2-[benzyl-(5-cyano-2-pyridyl)amino]-5-methyl-N-methylsulfonyl-thiazole-4-carboxamide | C | 427.08 | 428.09 | 2.29 |
| 603 | 603 | 2-(N-benzyl-4-cyano-anilino)-5-bromo-N-methylsulfonyl-thiazole-4-carboxamide | C | 489.98 | 492.99 [Br] | 2.33 |
| 604 | 604 | 2-[benzyl-(6-cyano-3-pyridyl)amino]-5-methyl-N-methylsulfonyl-thiazole-4-carboxamide | C | 427.08 | 428.13 | 2.12 |
| 605 | 605 | 2-[N-benzyl-3-(2-hydroxyethyl)anilino]-5-methyl-N-methylsulfonyl-thiazole-4-carboxamide | C | 445.11 | 446.18 | 2.12 |
| 606 | 606 | 2-[N-benzyl-2-(hydroxymethyl)anilino]-5-methyl-N-methylsulfonyl-thiazole-4-carboxamide | C | 431.10 | 432.13 | 2.15 |
| 607 | 607 | 2-[4-cyano-N-[[4-(trifluoromethoxy)phenyl]methyl]anilino]-5-methyl-N-methylsulfonyl-oxazole-4-carboxamide | C | 494.09 | 495.00 | 2.41 |

TABLE 85

| | | | | | | |
|---|---|---|---|---|---|---|
| 608 | 608 | 2-[4-cyano-N-[(3,4-dichlorophenyl)methyl]anilino]-5-methyl-N-methylsulfonyl-oxazole-4-carboxamide | C | 478.03 | 478.99 | 2.43 |

TABLE 85-continued

| | | | | | | |
|---|---|---|---|---|---|---|
| 609 | 609 | 2-[N-(benzothiophen-2-ylmethyl)-4-cyano-anilino]-5-bromo-N-methylsulfonyl-thiazole-4-carboxamide | C | 545.95 | 548.89 [Br] | 2.51 |
| 610 | 610 | 2-[4-cyano-N-[(4-fluorophenyl)methyl]anilino]-5-methyl-N-methylsulfonyl-oxazole-4-carboxamide | C | 428.10 | 429.05 | 2.18 |
| 611 | 611 | 2-[N-[(3-chlorophenyl)methyl]-4-cyano-anilino]-5-methyl-N-methylsulfonyl-oxazole-4-carboxamide | C | 444.07 | 444.98 | 2.29 |
| 612 | 612 | 2-[4-cyano-N-[(3-fluorophenyl)methyl]anilino]-5-methyl-N-methylsulfonyl-oxazole-4-carboxamide | C | 428.10 | 429.05 | 2.18 |
| 613 | 613 | 2-[4-cyano-N-[[3-(trifluoromethoxy)phenyl]methyl]anilino]-5-methyl-N-methylsulfonyl-oxazole-4-carboxamide | C | 494.09 | 495.00 | 2.38 |
| 614 | 614 | 2-[4-cyano-N-[[2-(difluoromethoxy)phenyl]methyl]anilino]-5-methyl-N-methylsulfonyl-oxazole-4-carboxamide | C | 476.10 | 476.99 | 2.24 |
| 615 | 615 | 2-[4-cyano-N-[(4-cyanophenyl)methyl]anilino]-5-methyl-N-methylsulfonyl-oxazole-4-carboxamide | C | 435.10 | 436.01 | 2.01 |
| 616 | 616 | 2-[N-(1,3-benzothiazol-6-ylmethyl)-4-cyano-anilino]-5-methyl-N-methylsulfonyl-oxazole-4-carboxamide | C | 467.07 | 467.99 | 1.93 |
| 617 | 617 | 2-[4-cyano-N-[(3-cyanophenyl)methyl]anilino]-5-methyl-N-methylsulfonyl-oxazole-4-carboxamide | C | 435.10 | 436.01 | 2.02 |
| 618 | 618 | 2-[N-(benzothiophen-2-ylmethyl)-4-cyano-anilino]-5-methyl-N-methylsulfonyl-oxazole-4-carboxamide | C | 466.08 | 466.99 | 2.36 |
| 619 | 619 | 2-[4-cyano-N-[(2-methylthiazol-4-yl)methyl]anilino]-5-methyl-N-methylsulfonyl-oxazole-4-carboxamide | C | 431.07 | 431.97 | 1.87 |
| 620 | 620 | 2-[benzyl-[6-(trifluoromethyl)-3-pyridyl]amino]-5-methyl-N-methylsulfonyl-oxazole-4-carboxamide | C | 454.09 | 454.98 | 2.30 |
| 621 | 621 | 2-[4-cyano-N-[(4,4-difluorocyclohexyl)methyl]anilino]-5-methyl-N-methylsulfonyl-oxazole-4-carboxamide | C | 452.13 | 453.06 | 2.25 |
| 622 | 622 | 2-[4-cyano-N-(2-cyclopentylethyl)anilino]-5-methyl-N-methylsulfonyl-oxazole-4-carboxamide | C | 416.15 | 417.08 | 2.55 |
| 623 | 623 | 2-[N-[(4-chlorophenyl)methyl]-4-cyano-anilino]-5-ethyl-N-methylsulfonyl-oxazole-4-carboxamide | C | 458.08 | 458.98 | 2.44 |
| 624 | 624 | 2-[4-cyano-N-[2-[trans-2-hydroxycyclohexyl]ethyl]anilino]-5-methyl-N-methylsulfonyl-oxazole-4-carboxamide | C | 446.16 | 447.14 | 2.05 |
| 625 | 625 | 2-[4-cyano-N-(2-phenylethyl)anilino]-5-methyl-N-methylsulfonyl-oxazole-4-carboxamide | C | 424.12 | 425.13 | 2.26 |

TABLE 86

| | | | | | | |
|---|---|---|---|---|---|---|
| 626 | 626 | 2-[N-(benzothiophen-2-ylmethyl)-4-cyano-anilino]-5-ethyl-N-methylsulfonyl-oxazole-4-carboxamide | C | 480.09 | 481.07 | 2.44 |
| 627 | 627 | 2-[N-[(4-chlorophenyl)methyl]-4-cyano-anilino]-N-ethylsulfonyl-5-methyl-oxazole-4-carboxamide | C | 458.08 | 459.10 | 2.42 |
| 628 | 628 | 2-[N-[(4-chlorophenyl)methyl]-4-cyano-anilino]-N-cyclopropylsulfonyl-5-methyl-oxazole-4-carboxamide | C | 470.08 | 471.11 | 2.42 |
| 629 | 629 | 2-[4-cyano-N-[2-[trans-2-hydroxycyclohexyl]ethyl]anilino]-5-ethyl-N-methylsulfonyl-oxazole-4-carboxamide | C | 460.18 | 461.18 | 2.21 |
| 630 | 630 | 2-[N-(1,3-benzothiazol-2-ylmethyl)-4-cyano-anilino]-5-methyl-N-methylsulfonyl-oxazole-4-carboxamide | C | 467.07 | 468.11 | 2.11 |
| 631 | 631 | 2-[N-[(3-chlorophenyl)methyl]-4-cyano-anilino]-5-ethyl-N-methylsulfonyl-oxazole-4-carboxamide | C | 458.08 | 459.06 | 2.40 |

TABLE 86-continued

| | | | | | | |
|---|---|---|---|---|---|---|
| 632 | 632 | 2-[4-cyano-N-[[4-(trifluoromethoxy)phenyl]methyl]anilino]-5-ethyl-N-methylsulfonyl-oxazole-4-carboxamide | C | 508.10 | 509.12 | 2.50 |
| 633 | 633 | 2-[4-cyano-N-[(3,4-dichlorophenyl)methyl]anilino]-5-ethyl-N-methylsulfonyl-oxazole-4-carboxamide | C | 492.04 | 493.07 | 2.53 |
| 634 | 634 | 2-[4-cyano-N-[[4-(difluoromethoxy)phenyl]methyl]anilino]-5-ethyl-N-methylsulfonyl-oxazole-4-carboxamide | C | 490.11 | 491.11 | 2.33 |
| 635 | 635 | 2-[4-cyano-N-[[5-(difluoromethoxy)-2-pyridyl]methyl]anilino]-5-ethyl-N-methylsulfonyl-oxazole-4-carboxamide | C | 491.11 | 492.11 | 2.14 |
| 636 | 636 | 2-[N-[(5-bromo-2-pyridyl)methyl]-4-cyano-anilino]-5-ethyl-N-methylsulfonyl-oxazole-4-carboxamide | C | 503.03 | 504.04 | 2.24 |
| 637 | 637 | 2-[4-cyano-N-[[2-(difluoromethoxy)phenyl]methyl]anilino]-5-ethyl-N-methylsulfonyl-oxazole-4-carboxamide | C | 490.11 | 491.11 | 2.34 |
| 638 | 638 | 2-[4-cyano-N-[[5-(trifluoromethyl)-2-pyridyl]methyl]anilino]-5-ethyl-N-methylsulfonyl-oxazole-4-carboxamide | C | 493.10 | 494.12 | 2.27 |
| 639 | 639 | 2-[4-cyano-N-[[6-(trifluoromethyl)-3-pyridyl]methyl]anilino]-5-ethyl-N-methylsulfonyl-oxazole-4-carboxamide | C | 493.10 | 494.12 | 2.22 |
| 640 | 640 | 5-bromo-2-[4-cyano-N-[(5-fluoro-2-pyridyl)methyl]anilino]-N-methylsulfonyl-thiazole-4-carboxamide | C | 508.96 | 512.00 [Br] | 2.12 |
| 641 | 641 | 5-bromo-2-[N-[(5-chloro-2-pyridyl)methyl]-4-cyano-anilino]-N-methylsulfonyl-thiazole-4-carboxamide | C | 524.93 | 528.01 [Br] | 2.26 |
| 642 | 642 | 5-bromo-2-[N-[(5-bromo-2-pyridyl)methyl]-4-cyano-anilino]-N-methylsulfonyl-thiazole-4-carboxamide | C | 568.88 | 571.94 [Br] | 2.29 |

TABLE 87

| | | | | | | |
|---|---|---|---|---|---|---|
| 643 | 643 | 5-bromo-2-[4-cyano-N-[[5-(trifluoromethyl)-2-pyridyl]methyl]anilino]-N-methylsulfonyl-thiazole-4-carboxamide | C | 558.96 | 562.02 [Br] | 2.33 |
| 644 | 644 | 5-bromo-2-[(5-chloro-2-pyridyl)methyl-[6-(trifluoromethyl)-3-pyridyl]amino]-N-methylsulfonyl-thiazole-4-carboxamide | C | 568.92 | 571.98 [Br] | 2.41 |
| 645 | 645 | 5-bromo-2-[4-cyano-N-[[6-(trifluoromethyl)-3-pyridyl]methyl]anilino]-N-methylsulfonyl-thiazole-4-carboxamide | C | 558.96 | 560.02 [Br] | 2.26 |
| 646 | 646 | 2-[N-[(4-chlorophenyl)methyl]-4-cyano-anilino]-5-cyclopropyl-N-methylsulfonyl-oxazole-4-carboxamide | C | 470.08 | 471.11 | 2.43 |
| 647 | 647 | 2-[4-cyano-N-[(3,4-dichlorophenyl)methyl]anilino]-5-cyclopropyl-N-methylsulfonyl-oxazole-4-carboxamide | C | 504.04 | 505.04 | 2.53 |
| 648 | 648 | 2-[4-cyano-N-[[4-(difluoromethoxy)phenyl]methyl]anilino]-5-cyclopropyl-N-methylsulfonyl-oxazole-4-carboxamide | C | 502.11 | 503.12 | 2.33 |
| 649 | 649 | 2-[4-cyano-N-[[5-(trifluoromethyl)-2-pyridyl]methyl]anilino]-5-cyclopropyl-N-methylsulfonyl-oxazole-4-carboxamide | C | 505.10 | 506.12 | 2.28 |
| 650 | 650 | 2-[N-[(4-bromo-3-chloro-phenyl)methyl]-4-cyano-anilino]-5-ethyl-N-methylsulfonyl-oxazole-4-carboxamide | C | 535.99 | 539.05 [Br] | 2.55 |
| 651 | 651 | 2-[N-[(4-chloro-3-fluoro-phenyl)methyl]-4-cyano-anilino]-5-ethyl-N-methylsulfonyl-oxazole-4-carboxamide | C | 476.07 | 477.11 | 2.44 |
| 652 | 652 | 2-[N-[(4-bromo-3-fluoro-phenyl)methyl]-4-cyano-anilino]-5- | C | 520.02 | 521.04 | 2.46 |

TABLE 87-continued

| | | | | | | |
|---|---|---|---|---|---|---|
| | | ethyl-N-methylsulfonyl-oxazole-4-carboxamide | | | | |
| 653 | 653 | 2-[N-[(4-bromophenyl)methyl]-4-cyano-anilino]-5-ethyl-N-methylsulfonyl-oxazole-4-carboxamide | C | 502.03 | 505.04 [Br] | 2.46 |
| 654 | 654 | 2-[4-cyano-N-[[4-(difluoromethoxy)-3-fluoro-phenyl]methyl]anilino]-5-ethyl-N-methylsulfonyl-oxazole-4-carboxamide | C | 508.10 | 509.12 | 2.33 |
| 655 | 655 | 2-[4-cyano-N-[[3-fluoro-4-(trifluoromethyl)phenyl]methyl]anilino]-5-ethyl-N-methylsulfonyl-oxazole-4-carboxamide | C | 510.10 | 511.12 | 2.47 |
| 656 | 656 | 2-[4-cyano-N-[[3-(difluoromethoxy)-5-fluoro-phenyl]methyl]anilino]-5-ethyl-N-methylsulfonyl-oxazole-4-carboxamide | C | 508.10 | 509.12 | 2.36 |
| 657 | 657 | 2-(N-benzyl-4-cyano-anilino)-5-chloro-N-methylsulfonyl-thiazole-4-carboxamide | C | 446.03 | 447.02 | 2.31 |
| 658 | 658 | 2-[N-[(5-chloro-2-pyridyl)methyl]-4-cyano-anilino]-5-cyclopropyl-N-methylsulfonyl-thiazole-4-carboxamide | C | 487.05 | 488.07 | 2.35 |

TABLE 88

| | | | | | | |
|---|---|---|---|---|---|---|
| 659 | 659 | 2-[4-cyano-N-[[6-(trifluoromethyl)-3-pyridyl]methyl]anilino]-5-cyclopropyl-N-methylsulfonyl-thiazole-4-carboxamide | C | 521.08 | 522.13 | 2.35 |
| 660 | 660 | 2-(N-benzyl-4-cyano-anilino)-5-cyclopropyl-N-methylsulfonyl-thiazole-4-carboxamide | C | 452.10 | 453.10 | 2.43 |
| 661 | 661 | 2-[N-[(4-chlorophenyl)methyl]-4-cyano-anilino]-5-cyclopropyl-N-methylsulfonyl-thiazole-4-carboxamide | C | 486.06 | 487.07 | 2.55 |
| 662 | 662 | 2-[4-cyano-N-[[4-(difluoromethoxy)phenyl]methyl]anilino]-5-cyclopropyl-N-methylsulfonyl-thiazole-4-carboxamide | C | 518.09 | 519.12 | 2.45 |
| 663 | 663 | 2-[4-cyano-N-[[6-(trifluoromethyl)-3-pyridyl]methyl]anilino]-5-cyclopropyl-N-(3-methoxypropylsulfonyl)thiazole-4-carboxamide | C | 579.12 | 580.22 | 2.46 |
| 664 | 664 | 2-(N-benzyl-4-cyano-anilino)-5-cyclopropyl-N-(3-methoxypropylsulfonyl)thiazole-4-carboxamide | C | 510.14 | 511.16 | 2.53 |
| 665 | 665 | 2-[N-[(4-chlorophenyl)methyl]-4-cyano-anilino]-5-cyclopropyl-N-(3-methoxypropylsulfonyl)thiazole-4-carboxamide | C | 544.10 | 545.17 | 2.65 |
| 666 | 666 | 2-[4-cyano-N-[[4-(difluoromethoxy)phenyl]methyl]anilino]-5-cyclopropyl-N-(3-methoxypropylsulfonyl)thiazole-4-carboxamide | C | 576.13 | 577.22 | 2.54 |
| 667 | 667 | 2-(4-cyano-2-fluoro-N-[(1R)-2-hydroxy-1-phenyl-ethyl]anilino)-5-methyl-N-methylsulfonyl-thiazole-4-carboxamide | D | 474.08 | 475.15 | 2.30 |
| 668 | 668 | 2-[benzyl(cyclohexylmethyl)amino]-5-methyl-N-methylsulfonyl-thiazole-4-carboxamide | E | 421.15 | 422.17 | 2.95 |
| 669 | 669 | 2-[benzyl(cyclopentyl)amino]-5-methyl-N-methylsulfonyl-thiazole-4-carboxamide | E | 393.12 | 394.15 | 2.66 |
| 670 | 670 | 2-[benzyl(cyclohexyl)amino]-5-methyl-N-methylsulfonyl-thiazole-4-carboxamide | E | 407.13 | 408.12 | 2.79 |
| 671 | 671 | 2-[benzyl-[2-(3-chlorophenyl)ethyl]amino]-5-methyl-N-methylsulfonyl-thiazole-4-carboxamide | E | 463.08 | 464.10 | 2.78 |
| 672 | 672 | 2-[benzyl-[2-(3-cyanophenyl)ethyl]amino]-5-methyl-N-methylsulfonyl-thiazole-4-carboxamide | E | 454.11 | 455.14 | 2.48 |
| 673 | 673 | 2-[benzyl(2-phenylpropyl)amino]-5-methyl-N-methylsulfonyl-thiazole-4-carboxamide | E | 443.13 | 444.38 | 2.75 |

TABLE 88-continued

| 674 | 674 | 2-[benzyl-(1-methyl-2-phenyl-ethyl)amino]-5-methyl-N-methylsulfonyl-thiazole-4-carboxamide | E | 443.13 | 444.18 | 2.73 |
| 675 | 675 | 2-[benzyl-[(6-cyanobenzothiophen-3-yl)methyl]amino]-5-methyl-N-methylsulfonyl-thiazole-4-carboxamide | E | 496.07 | 497.12 | 2.52 |

TABLE 89

| 676 | 676 | 2-[benzyl-[[6-(trifluoromethyl)benzothiophen-3-yl]methyl]amino]-5-methyl-N-methylsulfonyl-thiazole-4-carboxamide | E | 539.06 | 540.17 | 2.85 |
| 677 | 677 | 2-[(4-chlorophenyl)methyl-[[6-(trifluoromethyl)benzothiophen-3-yl]methyl]amino]-5-methyl-N-methylsulfonyl-thiazole-4-carboxamide | E | 573.02 | 574.09 | 2.94 |
| 678 | 678 | 2-[benzyl-[2-(4-methoxyphenyl)ethyl]amino]-5-methyl-N-methylsulfonyl-thiazole-4-carboxamide | F | 459.13 | 460.14 | 2.63 |
| 679 | 679 | 2-[benzyl-[2-(triazol-2-yl)ethyl]amino]-5-methyl-N-methylsulfonyl-thiazole-4-carboxamide | F | 420.10 | 421.09 | 1.94 |
| 680 | 680 | 2-[benzyl-[2-(1,2,4-triazol-1-yl)ethyl]amino]-5-methyl-N-methylsulfonyl-thiazole-4-carboxamide | F | 420.10 | 421.01 | 1.81 |
| 681 | 681 | 2-[benzyl-[2-(3-methylpyrazol-1-yl)ethyl]amino]-5-methyl-N-methylsulfonyl-thiazole-4-carboxamide | F | 433.12 | 434.05 | 2.13 |
| 682 | 682 | 2-[benzyl-[2-(5-methylpyrazol-1-yl)ethyl]amino]-5-methyl-N-methylsulfonyl-thiazole-4-carboxamide | F | 433.12 | 434.05 | 2.15 |
| 683 | 683 | 2-[benzyl(2-cyclopentylethyl)amino]-5-methyl-N-methylsulfonyl-thiazole-4-carboxamide | F | 421.15 | 422.09 | 2.97 |
| 684 | 684 | 2-[benzyl-[2-[4-(trifluoromethoxy)phenyl]ethyl]amino]-5-methyl-N-methylsulfonyl-thiazole-4-carboxamide | F | 513.10 | 514.28 | 2.85 |
| 685 | 685 | 2-[benzyl-[2-(3-fluorophenyl)ethyl]amino]-5-methyl-N-methylsulfonyl-thiazole-4-carboxamide | F | 447.11 | 448.06 | 2.67 |
| 686 | 686 | 2-[benzyl(3,3-dimethylbutyl)amino]-5-methyl-N-methylsulfonyl-thiazole-4-carboxamide | F | 409.15 | 410.08 | 2.88 |
| 687 | 687 | 2-[benzyl(2-cyclopropylethyl)amino]-5-methyl-N-methylsulfonyl-thiazole-4-carboxamide | F | 393.12 | 394.03 | 2.66 |
| 688 | 688 | 2-[benzyl(2-pyrazol-1-ylethyl)amino]-5-methyl-N-methylsulfonyl-thiazole-4-carboxamide | F | 419.11 | 420.05 | 2.13 |
| 689 | 689 | 2-[benzyl-[2-(3,5-dimethylpyrazol-1-yl)ethyl]amino]-5-methyl-N-methylsulfonyl-thiazole-4-carboxamide | F | 447.14 | 448.06 | 1.99 |
| 690 | 690 | 2-[benzyl(2-quinoxalin-6-ylethyl)amino]-5-methyl-N-methylsulfonyl-thiazole-4-carboxamide | F | 481.12 | 482.07 | 2.27 |
| 691 | 691 | 2-[benzyl-[2-(3,5-dimethylisoxazol-4-yl)ethyl]amino]-5-methyl-N-methylsulfonyl-thiazole-4-carboxamide | F | 448.12 | 449.06 | 2.32 |
| 692 | 692 | 2-[2-(4-chlorophenyl)ethyl-[(4-chlorophenyl)methyl]amino]-5-methyl-N-methylsulfonyl-thiazole-4-carboxamide | F | 497.04 | 497.96 | 2.91 |
| 693 | 693 | 2-[2-(4-chlorophenyl)ethyl-[(4-chlorophenyl)methyl]amino]-N-ethylsulfonyl-5-methyl-thiazole-4-carboxamide | F | 511.06 | 511.96 | 2.99 |

TABLE 90

| 694 | 694 | 2-[2-(4-chlorophenyl)ethyl-[(4-chlorophenyl)methyl]amino]-N-cyclopropylsulfonyl-5-methyl-thiazole-4-carboxamide | F | 523.06 | 523.97 | 3.01 |

TABLE 90-continued

| | | | | | | |
|---|---|---|---|---|---|---|
| 695 | 695 | 2-[2-(4-chlorophenyl)ethyl-[(4-chlorophenyl)methyl]amino]-5-methyl-N-(3-pyridylmethylsulfonyl)thiazole-4-carboxamide | F | 574.07 | 575.02 | 2.52 |
| 696 | 696 | 2-[2-(4-chlorophenyl)ethyl-[(4-chlorophenyl)methyl]amino]-5-methyl-N-(trifluoromethylsulfonyl)thiazole-4-carboxamide | F | 551.01 | 551.98 | 2.66 |
| 697 | 697 | 2-[2-(4-chlorophenyl)ethyl-(cyclohexylmethyl)amino]-5-methyl-N-methylsulfonyl-thiazole-4-carboxamide | F | 469.13 | 470.07 | 3.14 |
| 698 | 698 | 2-[2-(4-chlorophenyl)ethyl-(cyclohexylmethyl)amino]-N-ethylsulfonyl-5-methyl-thiazole-4-carboxamide | F | 483.14 | 484.07 | 3.22 |
| 699 | 699 | 2-[2-(4-chlorophenyl)ethyl-(cyclohexylmethyl)amino]-5-methyl-N-(3-pyridylmethylsulfonyl)thiazole-4-carboxamide | F | 546.15 | 547.09 | 2.68 |
| 700 | 700 | 2-[2-(4-chlorophenyl)ethyl-(cyclohexylmethyl)amino]-5-methyl-N-(trifluoromethylsulfonyl)thiazole-4-carboxamide | F | 523.10 | 524.05 | 2.65 |
| 701 | 701 | 2-[2-(4-chlorophenyl)ethyl-[[4-(trifluoromethoxy)phenyl]methyl]amino]-N-ethylsulfonyl-5-methyl-thiazole-4-carboxamide | F | 561.08 | 562.02 | 3.01 |
| 702 | 702 | 2-[2-(4-chlorophenyl)ethyl-[[4-(trifluoromethoxy)phenyl]methyl]amino]-N-cyclopropylsulfonyl-5-methyl-thiazole-4-carboxamide | F | 573.08 | 574.02 | 3.03 |
| 703 | 703 | 2-[2-(4-chlorophenyl)ethyl-[[4-(trifluoromethoxy)phenyl]methyl]amino]-5-methyl-N-(3-pyridylmethylsulfonyl)thiazole-4-carboxamide | F | 624.09 | 625.04 | 2.58 |
| 704 | 704 | 2-[2-(4-chlorophenyl)ethyl-[[4-(trifluoromethoxy)phenyl]methyl]amino]-5-methyl-N-(trifluoromethylsulfonyl)thiazole-4-carboxamide | F | 601.03 | 601.99 | 2.74 |
| 705 | 705 | 2-[benzyl-[2-(4-piperidyl)ethyl]amino]-5-methyl-N-methylsulfonyl-thiazole-4-carboxamide | F | 436.16 | 437.09 | 1.67 |
| 706 | 706 | 2-[benzyl-[2-(2-methylthiazol-4-yl)ethyl]amino]-5-methyl-N-methylsulfonyl-thiazole-4-carboxamide | F | 450.09 | 451.02 | 2.10 |
| 707 | 707 | 2-[2-(benzofuran-3-yl)ethyl-benzyl-amino]-5-methyl-N-methylsulfonyl-thiazole-4-carboxamide | F | 469.11 | 470.03 | 2.72 |
| 708 | 708 | 2-[2-(1,3-benzodioxol-5-yl)ethyl-benzyl-amino]-5-methyl-N-methylsulfonyl-thiazole-4-carboxamide | F | 473.11 | 474.03 | 2.59 |
| 709 | 709 | 2-[benzyl-[2-(4-chloropyrazol-1-yl)ethyl]amino]-5-methyl-N-methylsulfonyl-thiazole-4-carboxamide | F | 453.07 | 453.98 | 2.36 |

TABLE 91

| | | | | | | |
|---|---|---|---|---|---|---|
| 710 | 710 | 2-[benzyl-[2-(3,4-dichlorophenyl)ethyl]amino]-5-methyl-N-methylsulfonyl-thiazole-4-carboxamide | F | 497.04 | 497.96 | 2.89 |
| 711 | 711 | 2-[benzyl(3,3,3-trifluoropropyl)amino]-5-methyl-N-methylsulfonyl-thiazole-4-carboxamide | F | 421.07 | 422.01 | 2.47 |
| 712 | 712 | 2-[benzyl(3,4-dihydroxybutyl)amino]-5-methyl-N-methylsulfonyl-thiazole-4-carboxamide | F | 413.11 | 414.00 | 1.72 |
| 713 | 713 | 2-[(4-chlorophenyl)methyl-[2-(4-cyanophenyl)ethyl]amino]-N-ethylsulfonyl-5-methyl-thiazole-4-carboxamide | F | 502.09 | 503.12 | 2.66 |
| 714 | 714 | 2-[(4-chlorophenyl)methyl-[2-(4-cyanophenyl)ethyl]amino]-N-cyclopropylsulfonyl-5-methyl-thiazole-4-carboxamide | F | 514.09 | 515.12 | 2.68 |

TABLE 91-continued

| | | | | | | |
|---|---|---|---|---|---|---|
| 715 | 715 | 2-[(4-chlorophenyl)methyl-[2-(4-cyanophenyl)ethyl]amino]-5-methyl-N-(trifluoromethylsulfonyl)thiazole-4-carboxamide | F | 542.05 | 543.09 | 2.37 |
| 716 | 716 | 2-[2-(4-cyanophenyl)ethyl-(cyclohexylmethyl)amino]-5-methyl-N-methylsulfonyl-thiazole-4-carboxamide | F | 460.16 | 461.18 | 2.81 |
| 717 | 717 | 2-[2-(4-cyanophenyl)ethyl-(cyclohexylmethyl)amino]-N-ethylsulfonyl-5-methyl-thiazole-4-carboxamide | F | 474.18 | 475.19 | 2.90 |
| 718 | 718 | 2-[2-(4-cyanophenyl)ethyl-(cyclohexylmethyl)amino]-N-cyclopropylsulfonyl-5-methyl-thiazole-4-carboxamide | F | 486.18 | 487.19 | 2.92 |
| 719 | 719 | 2-[2-(4-cyanophenyl)ethyl-(cyclohexylmethyl)amino]-5-methyl-N-(trifluoromethylsulfonyl)thiazole-4-carboxamide | F | 514.13 | 515.16 | 2.36 |
| 720 | 720 | 2-[2-(4-cyanophenyl)ethyl-(cyclohexylmethyl)amino]-N-[(3-fluorophenyl)methylsulfonyl]-5-methyl-thiazole-4-carboxamide | F | 554.18 | 555.21 | 3.04 |
| 721 | 721 | 2-[2-(4-cyanophenyl)ethyl-[[4-(trifluoromethoxy)phenyl]methyl]amino]-N-cyclopropylsulfonyl-5-methyl-thiazole-4-carboxamide | F | 564.11 | 565.17 | 2.73 |
| 722 | 722 | 2-[2-(4-cyanophenyl)ethyl-[[4-(trifluoromethoxy)phenyl]methyl]amino]-5-methyl-N-(trifluoromethylsulfonyl)thiazole-4-carboxamide | F | 592.07 | 593.10 | 2.47 |
| 723 | 723 | 2-[(4-chlorophenyl)methyl-(2-cyclohexylethyl)amino]-5-methyl-N-(trifluoromethylsulfonyl)thiazole-4-carboxamide | F | 523.10 | 524.16 | 2.80 |
| 724 | 724 | 2-[2-cyclohexylethyl-[[4-(trifluoromethoxy)phenyl]methyl]amino]-5-methyl-N-(trifluoromethylsulfonyl)thiazole-4-carboxamide | F | 573.12 | 574.13 | 2.86 |

TABLE 92

| | | | | | | |
|---|---|---|---|---|---|---|
| 725 | 725 | 2-[2-(4-cyanophenyl)ethyl-(cyclohexylmethyl)amino]-5-methyl-N-(3-pyridylmethylsulfonyl)thiazole-4-carboxamide | F | 537.19 | 538.25 | 2.37 |
| 726 | 726 | 2-[2-(4-cyanophenyl)ethyl-[[4-(trifluoromethoxy)phenyl]methyl]amino]-N-ethylsulfonyl-5-methyl-thiazole-4-carboxamide | F | 552.11 | 553.17 | 2.70 |
| 727 | 727 | 2-[2-(4-cyanophenyl)ethyl-[[4-(trifluoromethoxy)phenyl]methyl]amino]-N-[(3-fluorophenyl)methylsulfonyl]-5-methyl-thiazole-4-carboxamide | F | 632.12 | 633.14 | 2.86 |
| 728 | 728 | 2-[(4-chlorophenyl)methyl-(2-cyclohexylethyl)amino]-5-methyl-N-methylsulfonyl-thiazole-4-carboxamide | F | 469.13 | 470.15 | 3.17 |
| 729 | 729 | 2-[(4-chlorophenyl)methyl-(2-cyclohexylethyl)amino]-N-ethylsulfonyl-5-methyl-thiazole-4-carboxamide | F | 483.14 | 484.15 | 3.24 |
| 730 | 730 | 2-[(4-chlorophenyl)methyl-(2-cyclohexylethyl)amino]-N-cyclopropylsulfonyl-5-methyl-thiazole-4-carboxamide | F | 495.14 | 496.15 | 3.26 |
| 731 | 731 | 2-[(4-chlorophenyl)methyl-(2-cyclohexylethyl)amino]-N-[(3-fluorophenyl)methylsulfonyl]-5-methyl-thiazole-4-carboxamide | F | 563.15 | 564.17 | 3.33 |
| 732 | 732 | 2-[2-cyclohexylethyl-[[4-(trifluoromethoxy)phenyl]methyl]amino]-5-methyl-N-methylsulfonyl-thiazole-4-carboxamide | F | 519.15 | 520.16 | 3.18 |
| 733 | 733 | 2-[2-cyclohexylethyl-[[4-(trifluoromethoxy)phenyl]methyl]amino]- | F | 533.16 | 534.21 | 3.25 |

TABLE 92-continued

| | | | | | | |
|---|---|---|---|---|---|---|
| | | N-ethylsulfonyl-5-methyl-thiazole-4-carboxamide | | | | |
| 734 | 734 | 2-[2-cyclohexylethyl-[[4-(trifluoromethoxy)phenyl]methyl]amino]-N-cyclopropylsulfonyl-5-methyl-thiazole-4-carboxamide | F | 545.16 | 546.21 | 3.26 |
| 735 | 735 | 2-[2-cyclohexylethyl-[[4-(trifluoromethoxy)phenyl]methyl]amino]-N-[(3-fluorophenyl)methylsulfonyl]-5-methyl-thiazole-4-carboxamide | F | 613.17 | 614.22 | 3.33 |
| 736 | 736 | 2-[(4-chlorophenyl)methyl-[2-(4-cyanopyrazol-1-yl)ethyl]amino]-5-methyl-N-methylsulfonyl-thiazole-4-carboxamide | F | 478.06 | 479.07 | 2.28 |
| 737 | 737 | 2-[benzyl-[2-(4-carbamoylphenyl)ethyl]amino]-5-methyl-N-methylsulfonyl-thiazole-4-carboxamide | F | 472.12 | 473.19 | 2.02 |
| 738 | 738 | 2-[benzyl-[2-[4-(methylcarbamoyl)phenyl]ethyl]amino]-5-methyl-N-methylsulfonyl-thiazole-4-carboxamide | F | 486.14 | 487.15 | 2.10 |
| 739 | 739 | 2-[(4-chlorophenyl)methyl-[2-(4-cyanophenyl)ethyl]amino]-N-(3-methoxypropylsulfonyl)-5-methyl-thiazole-4-carboxamide | F | 546.12 | 547.17 | 2.67 |

TABLE 93

| | | | | | | |
|---|---|---|---|---|---|---|
| 740 | 740 | 2-[2-(4-cyanophenyl)ethyl-[[4-(trifluoromethoxy)phenyl]methyl]amino]-N-(3-methoxypropylsulfonyl)-5-methyl-thiazole-4-carboxamide | F | 596.14 | 597.22 | 2.72 |
| 741 | 741 | 2-[(4-chlorophenyl)methyl-[2-(4-cyanophenyl)ethyl]amino]-5-methyl-N-(4-pyridylmethylsulfonyl)thiazole-4-carboxamide | F | 565.10 | 566.17 | 2.16 |
| 742 | 742 | 2-[2-(4-cyanophenyl)ethyl-[[4-(trifluoromethoxy)phenyl]methyl]amino]-5-methyl-N-(4-pyridylmethylsulfonyl)thiazole-4-carboxamide | F | 615.12 | 616.18 | 2.25 |
| 743 | 743 | 2-[benzyl-[2-(4-pyridyl)ethyl]amino]-5-methyl-N-methylsulfonyl-thiazole-4-carboxamide | F | 430.11 | 431.09 | 1.61 |
| 744 | 744 | 2-[benzyl(quinoxalin-6-yl)amino]-5-methyl-N-methylsulfonyl-thiazole-4-carboxamide | G | 453.09 | 454.14 | 2.13 |
| 745 | 745 | 2-[benzyl(3-isoquinolyl)amino]-5-methyl-N-methylsulfonyl-thiazole-4-carboxamide | G | 452.10 | 453.10 | 2.72 |
| 746 | 746 | 2-[benzyl-(1-methylindol-6-yl)amino]-5-methyl-N-methylsulfonyl-thiazole-4-carboxamide | G | 454.11 | 455.10 | 2.57 |

Example 747

Evaluation of an Androgen Receptor Affinity

To examine the interaction of a compound with an androgen receptor, evaluation was carried out in accordance with the following procedure using PolarScreen™ Androgen Receptor Competitor Assay Kit, Red (Invitrogen). To 2 wells each of a 384 well black plate was added 5 μL of the compound solution. To each well was added 5 μL of 2×AR-LBD/Fluoromone AL Red Complex contained in the kit and the samples were reacted at 22° C. for 5 hours. After 5 hours of the reaction, fluorescence polarization was measured and the affinity was evaluated. The affinity of the compound was determined by comparing to the binding rate of 1 μM of dihydrotestosterone (DHT), and quantified the logarithm value ($pEC_{50}$) of reciprocal value of the effective concentration of the compound which is equal to 50% of the binding rate by applying a 4 parameter goodness-of-fit calculation. The results are shown in the Tables.

TABLE 94

| Compound number | AR affinity (pEC50) |
|---|---|
| 1 | 7.2 |
| 2 | 7.0 |
| 3 | 7.2 |
| 4 | 7.6 |
| 5 | 7.0 |
| 6 | 6.7 |
| 7 | 7.5 |
| 8 | <5.7 |
| 9 | 7.0 |

TABLE 94-continued

| Compound number | AR affinity (pEC50) |
|---|---|
| 10 | 6.9 |
| 11 | 7.6 |
| 12 | 6.5 |
| 13 | 7.3 |
| 14 | 7.1 |
| 15 | 7.2 |
| 16 | 7.6 |
| 17 | 7.6 |
| 18 | 7.6 |
| 19 | 6.8 |
| 20 | 7.2 |
| 21 | 5.8 |
| 22 | 6.3 |
| 23 | 7.2 |
| 24 | 7.7 |
| 25 | 7.6 |
| 26 | 7.2 |
| 27 | <5.7 |
| 28 | 6.0 |
| 29 | <5.7 |
| 30 | <5.7 |
| 31 | 7.0 |
| 32 | <5.7 |
| 33 | <5.7 |
| 34 | 7.2 |
| 35 | <5.7 |
| 36 | 5.9 |
| 37 | 7.3 |
| 38 | <5.7 |
| 39 | 6.6 |
| 40 | 6.0 |
| 41 | 7.5 |
| 42 | <5.7 |
| 43 | <5.7 |
| 44 | <5.7 |
| 45 | 6.8 |
| 46 | 7.5 |
| 47 | <5.7 |
| 48 | 6.4 |
| 49 | <5.7 |
| 50 | 7.1 |
| 51 | 7.3 |
| 52 | 6.4 |
| 53 | <5.7 |
| 54 | 6.4 |
| 55 | <5.7 |
| 56 | 7.2 |
| 57 | 7.5 |
| 58 | <5.7 |
| 59 | 7.5 |
| 60 | <5.7 |
| 61 | 6.3 |
| 62 | 5.8 |
| 63 | <5.7 |
| 64 | 6.6 |
| 65 | 6.9 |
| 66 | 7.1 |
| 67 | <5.7 |
| 68 | 7.3 |
| 69 | 7.6 |
| 70 | 7.5 |
| 71 | <5.7 |
| 72 | <5.7 |
| 73 | <5.7 |
| 74 | <5.7 |
| 75 | 7.5 |
| 76 | 7.3 |
| 77 | 7.3 |
| 78 | 7.6 |
| 79 | 7.8 |
| 80 | 6.5 |
| 81 | 6.8 |
| 82 | 7.1 |
| 83 | 6.9 |
| 84 | <5.7 |
| 85 | 6.7 |

TABLE 94-continued

| Compound number | AR affinity (pEC50) |
|---|---|
| 86 | 6.6 |
| 87 | 6.8 |
| 88 | 6.5 |
| 89 | 6.3 |
| 90 | 6.4 |
| 91 | 7.0 |
| 92 | 6.8 |
| 93 | 6.2 |
| 94 | 7.4 |
| 95 | 6.6 |
| 96 | 7.1 |
| 97 | 7.3 |
| 98 | 7.4 |
| 99 | 7.2 |
| 100 | 7.5 |
| 101 | 6.2 |
| 102 | 7.1 |
| 103 | 6.8 |
| 104 | 7.3 |
| 105 | 6.9 |
| 106 | 7.1 |
| 107 | 7.3 |
| 108 | 7.0 |
| 109 | 7.0 |

TABLE 95

| Compound number | AR affinity (pEC50) |
|---|---|
| 110 | 7.2 |
| 111 | 7.3 |
| 112 | 7.5 |
| 113 | 7.6 |
| 114 | 6.9 |
| 115 | 7.5 |
| 116 | 7.5 |
| 117 | 7.6 |
| 118 | 7.3 |
| 119 | 5.7 |
| 120 | <5.7 |
| 121 | 7.6 |
| 122 | 7.6 |
| 123 | 7.3 |
| 124 | 7.2 |
| 125 | 7.5 |
| 126 | 7.2 |
| 127 | 7.5 |
| 128 | 7.4 |
| 129 | 7.4 |
| 130 | <5.7 |
| 131 | 6.6 |
| 132 | 6.5 |
| 133 | 6.8 |
| 134 | <5.7 |
| 135 | <5.7 |
| 136 | <5.7 |
| 137 | <5.7 |
| 138 | 7.0 |
| 139 | 7.1 |
| 140 | 7.0 |
| 141 | 7.3 |
| 142 | 6.2 |
| 143 | 7.6 |
| 144 | 7.6 |
| 145 | 7.3 |
| 146 | 7.3 |
| 147 | <5.7 |
| 148 | 7.6 |
| 149 | 6.8 |
| 150 | 7.1 |
| 151 | <5.7 |
| 152 | 6.7 |
| 153 | 7.0 |
| 154 | 6.7 |
| 155 | 7.5 |

TABLE 95-continued

| | |
|---|---|
| 156 | 7.4 |
| 157 | 7.5 |
| 158 | 7.0 |
| 159 | 7.2 |
| 160 | 7.0 |
| 161 | 6.9 |
| 162 | 6.8 |
| 163 | 6.7 |
| 164 | 6.6 |
| 165 | 7.3 |
| 166 | 7.6 |
| 167 | 7.6 |
| 168 | 7.0 |
| 169 | 6.7 |
| 170 | 7.2 |
| 171 | 6.9 |
| 172 | 7.5 |
| 173 | 7.6 |
| 174 | 7.0 |
| 175 | 7.1 |
| 176 | 7.2 |
| 177 | 7.1 |
| 178 | 7.4 |
| 179 | 6.3 |
| 180 | 6.6 |
| 181 | 7.5 |
| 182 | 6.2 |
| 183 | 7.2 |
| 184 | 6.3 |
| 185 | 7.4 |
| 186 | 6.7 |
| 187 | 7.2 |
| 188 | 6.5 |
| 189 | 7.5 |
| 190 | 7.8 |
| 191 | 7.5 |
| 192 | 7.2 |
| 193 | 7.5 |
| 194 | 7.2 |
| 195 | 6.8 |
| 196 | 6.2 |
| 197 | 5.9 |
| 198 | 7.4 |
| 199 | 7.4 |
| 200 | 7.6 |
| 201 | 7.4 |
| 202 | 7.5 |
| 203 | 6.5 |
| 204 | <5.7 |
| 205 | <5.7 |
| 206 | <5.7 |
| 207 | <5.7 |
| 208 | <5.7 |
| 209 | <5.7 |
| 210 | <5.7 |
| 211 | <5.7 |
| 212 | <5.7 |
| 213 | <5.7 |
| 214 | <5.7 |
| 215 | 7.3 |
| 216 | 7.2 |
| 217 | 7.3 |
| 218 | 6.6 |
| 219 | 7.2 |
| 220 | 7.4 |
| 221 | 7.4 |
| 222 | 6.7 |
| 223 | 6.4 |

TABLE 96

| | |
|---|---|
| 224 | 5.9 |
| 225 | <5.7 |
| 226 | <5.7 |
| 227 | <5.7 |
| 228 | <5.7 |
| 229 | <5.7 |

TABLE 96-continued

| | |
|---|---|
| 230 | 6.9 |
| 231 | <5.7 |
| 232 | 6.7 |
| 233 | <5.7 |
| 234 | <5.7 |
| 235 | <5.7 |
| 236 | <5.7 |
| 237 | 6.2 |
| 238 | <5.7 |
| 239 | <5.7 |
| 240 | 7.1 |
| 241 | 6.5 |
| 242 | 7.2 |
| 243 | 7.3 |
| 244 | 7.2 |
| 245 | 7.1 |
| 246 | 7.4 |
| 247 | 7.5 |
| 248 | 7.5 |
| 249 | 7.0 |
| 250 | 7.2 |
| 251 | 7.4 |
| 252 | 7.5 |
| 253 | 7.5 |
| 254 | 7.4 |
| 255 | 7.3 |
| 256 | 7.3 |
| 257 | 7.0 |
| 258 | 7.2 |
| 259 | 7.1 |
| 260 | 7.4 |
| 261 | 5.9 |
| 262 | 7.3 |
| 263 | 7.2 |
| 264 | 6.8 |
| 265 | 7.3 |
| 266 | 7.5 |
| 267 | 7.6 |
| 268 | 7.3 |
| 269 | 7.6 |
| 270 | 7.1 |
| 271 | 7.1 |
| 272 | 7.5 |
| 273 | 7.5 |
| 274 | 7.4 |
| 275 | 7.2 |
| 276 | 7.3 |
| 277 | 7.2 |
| 278 | 6.1 |
| 279 | 7.5 |
| 280 | 7.3 |
| 281 | 6.4 |
| 282 | 7.4 |
| 283 | 6.7 |
| 284 | 6.9 |
| 285 | 7.3 |
| 286 | 6.3 |
| 287 | <5.7 |
| 288 | <5.7 |
| 289 | <5.7 |
| 290 | <5.7 |
| 291 | <5.7 |
| 292 | <5.7 |
| 293 | <5.7 |
| 294 | 7.0 |
| 295 | <5.7 |
| 296 | <5.7 |
| 297 | 6.3 |
| 298 | 7.0 |
| 299 | 7.5 |
| 300 | 6.4 |
| 301 | 7.3 |
| 302 | 5.9 |
| 303 | 6.9 |
| 304 | <5.7 |
| 305 | <5.7 |
| 306 | 7.5 |
| 307 | <5.7 |
| 308 | 7.1 |
| 309 | <5.7 |

TABLE 96-continued

| | |
|---|---|
| 310 | 6.7 |
| 311 | <5.7 |
| 312 | 6.2 |
| 313 | 6.8 |
| 314 | <5.7 |
| 315 | 7.1 |
| 316 | <5.7 |
| 317 | 6.3 |
| 318 | <5.7 |
| 319 | <5.7 |
| 320 | 6.2 |
| 321 | 7.7 |
| 322 | 7.2 |
| 323 | 7.6 |
| 324 | 7.7 |
| 325 | 7.5 |
| 326 | 6.2 |
| 327 | <5.7 |
| 328 | <5.7 |
| 329 | 6.9 |
| 330 | 6.6 |
| 331 | <5.7 |
| 332 | 6.4 |
| 333 | 7.6 |
| 334 | <5.7 |
| 335 | 6.2 |
| 336 | <5.7 |
| 337 | <5.7 |

TABLE 97

| | |
|---|---|
| 338 | <5.7 |
| 339 | 7.4 |
| 340 | 7.0 |
| 341 | 7.2 |
| 342 | 7.2 |
| 343 | 7.5 |
| 344 | 7.4 |
| 345 | <5.7 |
| 346 | <5.7 |
| 347 | 5.9 |
| 348 | 5.9 |
| 349 | 6.3 |
| 350 | <5.7 |
| 351 | <5.7 |
| 352 | <5.7 |
| 353 | <5.7 |
| 354 | <5.7 |
| 355 | 6.3 |
| 356 | 6.2 |
| 357 | <5.7 |
| 358 | <5.7 |
| 359 | 6.9 |
| 360 | <5.7 |
| 361 | 7.4 |
| 362 | 7.2 |
| 363 | 7.2 |
| 364 | 7.5 |
| 365 | 7.6 |
| 366 | 7.4 |
| 367 | 6.8 |
| 368 | 7.0 |
| 369 | 7.1 |
| 370 | 7.1 |
| 371 | 6.7 |
| 372 | 7.5 |
| 373 | <5.7 |
| 374 | 7.4 |
| 375 | <5.7 |
| 376 | 7.0 |
| 377 | <5.7 |
| 378 | 7.6 |
| 379 | 7.6 |
| 380 | 6.1 |
| 381 | 6.1 |
| 382 | 7.1 |
| 383 | <5.7 |

TABLE 97-continued

| | |
|---|---|
| 384 | 7.4 |
| 385 | 6.1 |
| 386 | 6.9 |
| 387 | 7.2 |
| 388 | 7.3 |
| 389 | 5.8 |
| 390 | 6.9 |
| 391 | 7.1 |
| 392 | <5.7 |
| 393 | 7.5 |
| 394 | <5.7 |
| 395 | 7.0 |
| 396 | 6.5 |
| 397 | 7.2 |
| 398 | <5.7 |
| 399 | 6.6 |
| 400 | 6.2 |
| 401 | 6.8 |
| 402 | 6.0 |
| 403 | 6.6 |
| 404 | 6.0 |
| 405 | <5.7 |
| 406 | 6.1 |
| 407 | 7.3 |
| 408 | <5.7 |
| 409 | 6.6 |
| 410 | 6.8 |
| 411 | 6.1 |
| 412 | <5.7 |
| 413 | 7.6 |
| 414 | 6.3 |
| 415 | <5.7 |
| 416 | 7.6 |
| 417 | 6.5 |
| 418 | 7.3 |
| 419 | 7.2 |
| 420 | 7.7 |
| 421 | 7.7 |
| 422 | 5.9 |
| 423 | <5.7 |
| 424 | <5.7 |
| 425 | 5.9 |
| 426 | <5.7 |
| 427 | <5.7 |
| 428 | <5.7 |
| 429 | <5.7 |
| 430 | <5.7 |
| 431 | 7.7 |
| 432 | <5.7 |
| 433 | <5.7 |
| 434 | <5.7 |
| 435 | 6.2 |
| 436 | 6.3 |
| 437 | 7.3 |
| 438 | 7.6 |
| 439 | 7.3 |
| 440 | 6.3 |
| 441 | 6.6 |
| 442 | 6.5 |
| 443 | 6.7 |
| 444 | 5.9 |
| 445 | 6.2 |
| 446 | 6.5 |
| 447 | 7.3 |
| 448 | 5.9 |
| 449 | 6.4 |
| 450 | 7.5 |
| 451 | 7.6 |

TABLE 98

| | |
|---|---|
| 452 | 7.3 |
| 453 | 6.6 |
| 454 | 7.3 |
| 455 | 7.0 |
| 456 | 7.3 |
| 457 | <5.7 |

TABLE 98-continued

| | |
|---|---|
| 458 | <5.7 |
| 459 | 5.9 |
| 460 | 5.9 |
| 461 | 7.0 |
| 462 | 5.9 |
| 463 | 6.5 |
| 464 | 7.2 |
| 465 | 7.6 |
| 466 | 7.0 |
| 467 | <5.7 |
| 468 | <5.7 |
| 469 | 6.8 |
| 470 | 6.9 |
| 471 | 7.0 |
| 472 | 6.9 |
| 473 | 6.2 |
| 474 | 6.1 |
| 475 | 6.1 |
| 476 | 6.7 |
| 477 | <5.7 |
| 478 | 7.2 |
| 479 | 7.2 |
| 480 | <5.7 |
| 481 | <5.7 |
| 482 | 7.3 |
| 483 | <5.7 |
| 484 | 6.8 |
| 485 | 7.7 |
| 486 | 6.6 |
| 487 | 7.1 |
| 488 | <5.7 |
| 489 | 7.1 |
| 490 | <5.7 |
| 491 | 7.0 |
| 492 | 6.1 |
| 493 | <5.7 |
| 494 | 7.5 |
| 495 | 7.4 |
| 496 | 6.9 |
| 497 | 6.9 |
| 498 | 7.5 |
| 499 | 7.4 |
| 500 | 7.7 |
| 501 | 7.4 |
| 502 | 7.4 |
| 503 | 7.5 |
| 504 | 7.2 |
| 505 | 7.4 |
| 506 | 7.6 |
| 507 | 7.4 |
| 508 | 6.5 |
| 509 | 6.7 |
| 510 | 6.9 |
| 511 | 6.8 |
| 512 | 7.0 |
| 513 | 6.7 |
| 514 | 6.9 |
| 515 | 6.1 |
| 516 | <5.7 |
| 517 | 6.5 |
| 518 | 7.6 |
| 519 | 7.6 |
| 520 | 7.6 |
| 521 | 7.5 |
| 522 | 7.6 |
| 523 | 7.5 |
| 524 | 7.4 |
| 525 | 7.3 |
| 526 | 7.4 |
| 527 | 6.3 |
| 528 | <5.7 |
| 529 | 6.4 |
| 530 | 7.3 |
| 531 | 7.0 |
| 532 | 6.7 |
| 533 | 6.8 |
| 534 | 7.0 |
| 535 | 6.9 |
| 536 | 7.7 |
| 537 | 6.5 |
| 538 | 6.4 |
| 539 | 7.8 |
| 540 | 6.5 |
| 541 | <5.7 |
| 542 | 7.1 |
| 543 | 7.3 |
| 544 | 7.4 |
| 545 | 7.4 |
| 546 | 6.7 |
| 547 | 6.5 |
| 548 | 7.6 |
| 549 | 7.2 |
| 550 | 7.2 |
| 551 | 7.4 |
| 552 | 7.1 |
| 553 | 7.5 |
| 554 | 7.4 |
| 555 | 6.5 |
| 556 | 7.0 |
| 557 | 7.4 |
| 558 | 7.2 |
| 559 | 6.5 |
| 560 | 7.3 |
| 561 | 7.4 |
| 562 | 7.4 |
| 563 | 7.1 |
| 564 | 6.8 |
| 565 | 7.2 |

TABLE 99

| | |
|---|---|
| 566 | 6.7 |
| 567 | 7.0 |
| 568 | 6.8 |
| 569 | 6.2 |
| 570 | 5.9 |
| 571 | 6.8 |
| 572 | 5.8 |
| 573 | 5.9 |
| 574 | <5.7 |
| 575 | 6.4 |
| 576 | 7.2 |
| 577 | 7.2 |
| 578 | 6.1 |
| 579 | 6.7 |
| 580 | 7.6 |
| 581 | 7.6 |
| 582 | 7.4 |
| 583 | 7.4 |
| 584 | 7.1 |
| 585 | 7.1 |
| 586 | 7.1 |
| 587 | 6.3 |
| 588 | 7.5 |
| 589 | 6.0 |
| 590 | 7.5 |
| 591 | 6.8 |
| 592 | 7.0 |
| 593 | 6.6 |
| 594 | 7.1 |
| 595 | 7.0 |
| 596 | 6.5 |
| 597 | 6.4 |
| 598 | 6.6 |
| 599 | 7.2 |
| 600 | 7.0 |
| 601 | <5.7 |
| 602 | 6.3 |
| 603 | 7.3 |
| 604 | <5.7 |
| 605 | <5.7 |
| 606 | <5.7 |
| 607 | 7.4 |
| 608 | 7.5 |
| 609 | 7.5 |
| 610 | 7.0 |
| 611 | 7.1 |

TABLE 99-continued

| | |
|---|---|
| 612 | 6.9 |
| 613 | 7.6 |
| 614 | 6.7 |
| 615 | 6.4 |
| 616 | 6.6 |
| 617 | 6.6 |
| 618 | 7.7 |
| 619 | <5.7 |
| 620 | 6.2 |
| 621 | <5.7 |
| 622 | 7.1 |
| 623 | 7.5 |
| 624 | 6.1 |
| 625 | 6.6 |
| 626 | 7.8 |
| 627 | 7.3 |
| 628 | 6.7 |
| 629 | 6.5 |
| 630 | 6.8 |
| 631 | 7.4 |
| 632 | 7.4 |
| 633 | 7.5 |
| 634 | 7.4 |
| 635 | 6.4 |
| 636 | 6.4 |
| 637 | 6.8 |
| 638 | 6.7 |
| 639 | 6.6 |
| 640 | 6.4 |
| 641 | 6.9 |
| 642 | 7.1 |
| 643 | 7.1 |
| 644 | 6.7 |
| 645 | 7.2 |
| 646 | 7.4 |
| 647 | 7.6 |
| 648 | 7.3 |
| 649 | 6.2 |
| 650 | 7.5 |
| 651 | 7.4 |
| 652 | 7.6 |
| 653 | 7.3 |
| 654 | 7.4 |
| 655 | 7.4 |
| 656 | 7.7 |
| 657 | 7.5 |
| 658 | 7.0 |
| 659 | 6.9 |
| 660 | 7.1 |
| 661 | 7.8 |
| 662 | 7.7 |
| 663 | 6.6 |
| 664 | 6.8 |
| 665 | 7.7 |
| 666 | 7.4 |
| 667 | <5.7 |
| 668 | <5.7 |
| 669 | 6.2 |
| 670 | <5.7 |
| 671 | 7.3 |
| 672 | 6.6 |
| 673 | 5.7 |
| 674 | <5.7 |
| 675 | <5.7 |
| 676 | <5.7 |
| 677 | <5.7 |
| 678 | 7.3 |
| 679 | <5.7 |

TABLE 100

| | |
|---|---|
| 680 | <5.7 |
| 681 | <5.7 |
| 682 | <5.7 |
| 683 | 7.0 |
| 684 | 7.4 |
| 685 | 7.3 |

TABLE 100-continued

| | |
|---|---|
| 686 | <5.7 |
| 687 | <5.7 |
| 688 | <5.7 |
| 689 | <5.7 |
| 690 | 6.0 |
| 691 | <5.7 |
| 692 | 7.7 |
| 693 | 7.5 |
| 694 | 7.2 |
| 695 | 7.6 |
| 696 | 6.7 |
| 697 | 6.6 |
| 698 | 6.1 |
| 699 | 7.2 |
| 700 | <5.7 |
| 701 | 7.2 |
| 702 | 6.7 |
| 703 | 7.5 |
| 704 | 6.5 |
| 705 | <5.7 |
| 706 | <5.7 |
| 707 | <5.7 |
| 708 | 7.1 |
| 709 | 6.7 |
| 710 | 7.3 |
| 711 | <5.7 |
| 712 | <5.7 |
| 713 | 7.5 |
| 714 | 7.1 |
| 715 | 6.9 |
| 716 | 6.2 |
| 717 | 6.0 |
| 718 | <5.7 |
| 719 | <5.7 |
| 720 | <5.7 |
| 721 | 6.8 |
| 722 | 6.6 |
| 723 | 6.3 |
| 724 | 6.3 |
| 725 | 7.0 |
| 726 | 7.5 |
| 727 | 6.7 |
| 728 | 7.4 |
| 729 | 6.9 |
| 730 | 5.7 |
| 731 | 6.3 |
| 732 | 7.0 |
| 733 | 6.7 |
| 734 | 6.0 |
| 735 | 6.0 |
| 736 | 6.7 |
| 737 | <5.7 |
| 738 | 6.3 |
| 739 | 7.5 |
| 740 | 7.6 |
| 741 | 7.6 |
| 742 | 7.6 |
| 743 | 6.2 |
| 744 | 6.5 |
| 745 | <5.7 |
| 746 | <5.7 |

Example 748

Reporter Assay of an Androgen Receptor Responsive Sequence

To examine the agonist activity of compounds for androgen, a reporter assay using an androgen receptor responsive sequence was conducted.

Using Lipofectamine 2000 (Invitrogen), a plasmid mixture (pGL4-ARE (200 ng/well), pcDNA3-hAR (20 ng/well), pRL-TK (Promega) (150 ng/well)) was transiently transfected into HEK293 cells. The contents of the plasmid (mixture) are as follows:

pGL4-ARE is a reporter plasmid containing firefly luciferase sequence under the control of androgen receptor responsive sequence; pcDNA3-hAR is a plasmid containing full-length sequence of human androgen receptor under the constant control of CMV promoter; pRL-TK is a plasmid containing *Renilla* Luciferase sequence under the control of herpes simplex virus thymidine kinase and used as an internal standard for evaluations of transfection efficiency and compound toxicity.

After the incubation of Lipofectamine 2000 and the plasmid mixture in Opti-MEM for 20 minutes, the mixture was mixed with a cell suspension prepared with Opti-MEM in the similar way, and the cell suspension was plated to a 96-well plate at 20000 cells/well. The transfection was conducted by incubating the plates under the condition of 5% $CO_2$ at 37° C. for 3 hours. Three hours after the transfection, the culture medium was removed and a compound solution prepared by DMEM supplemented with 5% FBS and treated with charcoal was added, and the mixture was incubated under the condition of 5% $CO_2$ at 37° C. for 24 hours. After the incubation with the compound, luciferase activities were measured with a luminometer using Dual-Glo™ Luciferase Assay System (Promega). The measurement of the luciferase activities was performed in accordance with the protocol recommended by Promega. The activity of the compound was determined by comparing to the activity of 100 nM of DHT, and quantified the logarithm value ($pEC_{50}$) of reciprocal value of the effective concentration of the compound which is equal to 50% of the activity value by applying a 4 parameter goodness-of-fit calculation. The results are shown in the Tables.

TABLE 101

| Compound number | AR transcriptive activity (pEC50) |
|---|---|
| 1 | 7.1 |
| 2 | 7.0 |
| 3 | 6.9 |
| 4 | 7.2 |
| 5 | 6.6 |
| 6 | 6.5 |
| 7 | 7.2 |
| 9 | 6.4 |
| 10 | 6.0 |
| 11 | 7.3 |
| 12 | <5.0 |
| 13 | 6.5 |
| 14 | 7.3 |
| 15 | 7.4 |
| 16 | 7.5 |
| 17 | 7.6 |
| 18 | 7.3 |
| 19 | <5.0 |
| 20 | 5.8 |
| 23 | 7.6 |
| 24 | 6.7 |
| 25 | 7.3 |
| 26 | 7.6 |
| 31 | 5.6 |
| 34 | 5.5 |
| 37 | 5.9 |
| 39 | 5.9 |
| 40 | 6.3 |
| 41 | 7.5 |
| 45 | 6.3 |
| 46 | 7.5 |
| 50 | 7.3 |
| 51 | 7.5 |
| 52 | 5.6 |
| 54 | 5.8 |
| 56 | 5.2 |
| 57 | 6.5 |
| 59 | <5.0 |
| 61 | 5.5 |
| 64 | 5.6 |
| 65 | <5.0 |
| 66 | 6.1 |
| 68 | 6.1 |
| 69 | 5.9 |
| 70 | 7.2 |
| 75 | 6.4 |
| 76 | <5.0 |
| 77 | 6.2 |
| 78 | 6.8 |
| 79 | 7.3 |
| 80 | <5.0 |
| 81 | 5.8 |
| 82 | <5.0 |
| 83 | 5.6 |
| 85 | 6.5 |
| 86 | 5.8 |
| 87 | 6.0 |
| 88 | <5.0 |
| 89 | <5.0 |
| 90 | <5.0 |
| 91 | 5.8 |
| 94 | 7.6 |
| 96 | 7.0 |
| 97 | 7.5 |
| 99 | 6.9 |
| 100 | 7.8 |
| 102 | 7.3 |
| 103 | 6.5 |
| 104 | 6.9 |
| 105 | 6.5 |
| 106 | 6.5 |
| 107 | 7.5 |
| 108 | 6.3 |
| 109 | 6.7 |
| 110 | 6.9 |
| 111 | 7.2 |
| 112 | 7.1 |
| 113 | 6.8 |
| 114 | 6.8 |
| 115 | 7.5 |
| 116 | 7.6 |
| 117 | 7.2 |
| 118 | 6.4 |
| 121 | 7.3 |
| 122 | 7.7 |
| 123 | 7.0 |
| 124 | 6.2 |
| 125 | 6.9 |
| 126 | 6.1 |
| 127 | 6.9 |
| 128 | 7.0 |
| 129 | 7.7 |
| 131 | 6.0 |
| 132 | 5.8 |
| 133 | 5.8 |
| 138 | 6.6 |
| 139 | 5.8 |
| 140 | 6.1 |
| 141 | 6.5 |
| 143 | 7.3 |
| 144 | 7.2 |
| 145 | 6.5 |
| 146 | 6.1 |
| 147 | <5.0 |
| 148 | 7.0 |
| 149 | 6.0 |
| 150 | 6.2 |
| 152 | 7.0 |

TABLE 102

| | |
|---|---|
| 153 | 7.3 |
| 154 | 6.7 |
| 155 | 7.8 |
| 156 | 7.2 |
| 157 | 6.7 |
| 158 | 6.2 |
| 159 | 6.4 |
| 160 | 6.3 |
| 161 | 6.3 |
| 162 | 6.0 |
| 163 | 6.6 |
| 164 | 6.2 |
| 165 | 6.8 |
| 166 | 7.1 |
| 167 | 7.5 |
| 168 | 6.7 |
| 169 | 6.3 |
| 170 | 6.7 |
| 171 | 6.2 |
| 172 | 7.5 |
| 173 | 7.1 |
| 174 | 6.5 |
| 175 | 6.9 |
| 176 | 6.3 |
| 177 | 6.3 |
| 178 | 6.3 |
| 179 | 6.0 |
| 180 | 6.3 |
| 181 | 7.6 |
| 182 | <5.0 |
| 183 | 6.3 |
| 184 | <5.0 |
| 185 | 7.2 |
| 186 | 6.2 |
| 187 | 7.1 |
| 188 | 6.7 |
| 189 | 6.8 |
| 190 | 7.2 |
| 191 | 7.3 |
| 192 | 5.9 |
| 193 | 6.3 |
| 194 | 5.6 |
| 195 | 6.9 |
| 196 | 5.8 |
| 197 | 5.4 |
| 198 | <5.0 |
| 199 | 6.0 |
| 200 | 6.5 |
| 201 | 7.4 |
| 202 | 6.9 |
| 203 | 6.2 |
| 215 | 6.7 |
| 216 | 5.9 |
| 217 | 5.5 |
| 218 | <5.0 |
| 219 | 5.8 |
| 220 | 6.5 |
| 221 | 7.3 |
| 222 | 6.6 |
| 223 | 6.2 |
| 230 | 5.9 |
| 232 | <5.0 |
| 240 | 6.7 |
| 241 | 6.0 |
| 242 | 7.0 |
| 243 | 7.2 |
| 244 | 7.4 |
| 247 | 7.5 |
| 248 | 7.6 |
| 251 | 7.6 |
| 252 | 7.1 |
| 253 | 7.1 |
| 254 | 6.8 |
| 255 | 7.1 |
| 256 | 7.3 |
| 257 | 7.1 |
| 258 | 7.0 |
| 262 | 7.4 |
| 263 | 6.5 |
| 265 | 6.8 |

TABLE 102-continued

| | |
|---|---|
| 268 | 7.2 |
| 269 | 7.7 |
| 270 | 6.6 |
| 271 | 7.3 |
| 272 | 7.6 |
| 273 | 7.2 |
| 274 | 7.1 |
| 275 | 6.5 |
| 276 | 6.9 |
| 277 | 7.3 |
| 279 | 7.3 |
| 280 | 7.6 |
| 281 | 6.2 |
| 282 | 6.5 |
| 283 | <5.0 |
| 284 | <5.0 |
| 285 | 6.7 |
| 286 | 6.5 |
| 294 | 6.0 |
| 298 | <5.0 |
| 299 | 6.9 |
| 301 | 6.8 |
| 303 | <5.0 |
| 305 | <5.0 |
| 306 | 7.0 |
| 308 | 5.3 |
| 310 | 5.6 |
| 313 | 6.0 |
| 315 | 6.8 |
| 321 | 7.0 |
| 322 | <5.0 |
| 323 | 6.6 |
| 324 | 7.0 |
| 325 | 6.4 |

TABLE 103

| | |
|---|---|
| 326 | 6.0 |
| 329 | 5.4 |
| 330 | <5.0 |
| 333 | 7.0 |
| 335 | 5.8 |
| 339 | 5.7 |
| 340 | 6.6 |
| 341 | 5.9 |
| 342 | 7.6 |
| 343 | 7.0 |
| 344 | 6.1 |
| 351 | <5.0 |
| 359 | <5.0 |
| 361 | 6.2 |
| 362 | 6.6 |
| 363 | 5.9 |
| 364 | <5.0 |
| 365 | 6.2 |
| 366 | 7.3 |
| 367 | <5.0 |
| 368 | <5.0 |
| 369 | <5.0 |
| 370 | 5.6 |
| 371 | <5.0 |
| 372 | 5.9 |
| 374 | 6.3 |
| 376 | 5.2 |
| 378 | 7.3 |
| 379 | 6.6 |
| 382 | <5.0 |
| 384 | 6.6 |
| 386 | <5.0 |
| 387 | 6.4 |
| 388 | 7.2 |
| 390 | 6.7 |
| 391 | <5.0 |
| 393 | 6.4 |
| 395 | 6.8 |
| 396 | 5.2 |
| 397 | 6.9 |

TABLE 103-continued

| | |
|---|---|
| 399 | <5.0 |
| 400 | <5.0 |
| 401 | 5.8 |
| 403 | 6.6 |
| 404 | 5.5 |
| 406 | 5.6 |
| 407 | 6.7 |
| 409 | 6.6 |
| 410 | 6.5 |
| 413 | 6.3 |
| 416 | 6.8 |
| 417 | <5.0 |
| 418 | 6.8 |
| 419 | 6.2 |
| 420 | 6.8 |
| 421 | 6.7 |
| 431 | 6.5 |
| 436 | 5.8 |
| 437 | 6.9 |
| 438 | 6.4 |
| 439 | 6.9 |
| 442 | 5.9 |
| 443 | 6.3 |
| 447 | 5.6 |
| 450 | 7.3 |
| 451 | 7.3 |
| 452 | 6.7 |
| 454 | 6.6 |
| 455 | 6.3 |
| 456 | 6.7 |
| 461 | 6.8 |
| 463 | 5.3 |
| 464 | 5.3 |
| 465 | 6.1 |
| 466 | 6.4 |
| 469 | 6.5 |
| 470 | 6.8 |
| 471 | 6.0 |
| 472 | 6.4 |
| 473 | 5.9 |
| 474 | 6.0 |
| 476 | <5.0 |
| 478 | 7.6 |
| 479 | 7.2 |
| 482 | 6.8 |
| 484 | 6.9 |
| 485 | 6.9 |
| 486 | 6.6 |
| 487 | 6.8 |
| 488 | <5.0 |
| 489 | 6.0 |
| 491 | 6.5 |
| 492 | 5.9 |
| 493 | <5.0 |
| 494 | 6.0 |
| 495 | <5.0 |
| 496 | 6.8 |
| 497 | 6.7 |
| 498 | 7.0 |
| 499 | 6.8 |
| 500 | 6.9 |
| 501 | 7.2 |
| 502 | 6.1 |
| 503 | 5.9 |
| 504 | 6.2 |
| 505 | 5.7 |
| 506 | <5.0 |
| 507 | 6.3 |
| 508 | 5.3 |
| 509 | <5.0 |
| 510 | 5.9 |
| 511 | 6.5 |
| 512 | 5.9 |
| 513 | 5.8 |

TABLE 104

| | |
|---|---|
| 514 | 6.8 |
| 515 | 6.3 |
| 516 | 5.2 |
| 517 | 6.2 |
| 518 | 7.4 |
| 519 | 6.8 |
| 520 | 6.5 |
| 521 | 5.9 |
| 522 | 6.6 |
| 523 | 6.4 |
| 524 | 6.3 |
| 525 | 6.2 |
| 526 | 7.0 |
| 527 | 6.0 |
| 528 | 5.1 |
| 529 | 6.5 |
| 530 | 6.3 |
| 531 | 6.0 |
| 532 | 5.8 |
| 533 | 6.1 |
| 534 | 6.8 |
| 535 | 6.5 |
| 536 | 7.4 |
| 537 | 6.2 |
| 538 | 5.4 |
| 539 | 6.8 |
| 540 | <5.0 |
| 542 | 6.3 |
| 543 | 5.9 |
| 544 | 6.5 |
| 545 | 6.8 |
| 546 | 5.8 |
| 547 | 5.6 |
| 548 | 6.9 |
| 549 | 5.9 |
| 550 | 6.6 |
| 551 | 6.3 |
| 552 | 6.3 |
| 553 | 6.5 |
| 554 | 6.1 |
| 555 | 5.3 |
| 556 | 5.9 |
| 557 | 6.2 |
| 558 | <5.0 |
| 559 | 5.1 |
| 560 | 6.0 |
| 561 | 5.5 |
| 562 | 6.1 |
| 563 | 5.8 |
| 564 | <5.0 |
| 565 | 5.7 |
| 566 | 5.8 |
| 567 | <5.0 |
| 568 | 6.1 |
| 571 | <5.0 |
| 576 | 5.9 |
| 577 | 6.3 |
| 579 | 5.1 |
| 580 | 6.2 |
| 581 | 6.3 |
| 582 | 6.1 |
| 583 | 5.7 |
| 584 | 5.5 |
| 585 | 6.3 |
| 586 | 5.1 |
| 588 | 6.7 |
| 589 | <5.0 |
| 590 | 6.8 |
| 591 | 6.1 |
| 592 | 6.1 |
| 593 | 6.7 |
| 594 | 5.8 |
| 595 | 5.9 |
| 596 | 5.4 |
| 597 | 6.0 |
| 598 | 5.7 |
| 599 | 7.1 |
| 600 | <5.0 |
| 603 | 7.5 |
| 607 | 5.3 |

TABLE 104-continued

| | |
|---|---|
| 608 | 6.5 |
| 609 | 7.4 |
| 610 | 5.6 |
| 611 | 5.7 |
| 612 | 5.4 |
| 613 | <5.0 |
| 614 | <5.0 |
| 616 | <5.0 |
| 617 | <5.0 |
| 618 | 6.9 |
| 620 | <5.0 |
| 621 | <5.0 |
| 622 | <5.0 |
| 623 | 6.8 |
| 624 | 5.1 |
| 625 | 5.4 |
| 626 | 7.1 |
| 627 | 6.0 |
| 628 | <5.0 |
| 629 | 5.6 |
| 630 | 5.6 |
| 631 | 6.1 |
| 632 | 6.0 |
| 633 | 6.9 |
| 634 | 6.4 |
| 635 | <5.0 |
| 636 | 5.8 |
| 637 | <5.0 |
| 638 | 5.5 |
| 639 | 5.1 |
| 640 | 6.5 |
| 641 | 7.1 |
| 642 | 7.3 |
| 643 | 7.2 |

TABLE 105

| | |
|---|---|
| 644 | 6.3 |
| 645 | 5.9 |
| 646 | <5.0 |
| 647 | <5.0 |
| 648 | <5.0 |
| 649 | <5.0 |
| 650 | 6.7 |
| 651 | 6.7 |
| 652 | 6.8 |
| 653 | 6.8 |
| 654 | 6.2 |
| 655 | 6.4 |
| 656 | 6.2 |
| 657 | 7.3 |
| 658 | 5.3 |
| 659 | <5.0 |
| 660 | <5.0 |
| 661 | 6.3 |
| 662 | 5.3 |
| 663 | <5.0 |
| 664 | <5.0 |
| 665 | <5.0 |
| 666 | <5.0 |
| 671 | 5.8 |
| 672 | 5.9 |
| 677 | <5.0 |
| 678 | 5.8 |
| 683 | <5.0 |
| 684 | 6.6 |
| 685 | 6.5 |
| 692 | 7.1 |
| 693 | 6.7 |
| 694 | 5.5 |
| 695 | 7.2 |
| 696 | 6.2 |
| 697 | <5.0 |
| 699 | <5.0 |
| 701 | 5.9 |
| 702 | <5.0 |
| 703 | 6.8 |

TABLE 105-continued

| | |
|---|---|
| 704 | <5.0 |
| 708 | 6.3 |
| 709 | 6.2 |
| 710 | 6.4 |
| 713 | 6.6 |
| 714 | 5.9 |
| 715 | 5.6 |
| 716 | <5.0 |
| 717 | <5.0 |
| 721 | <5.0 |
| 722 | <5.0 |
| 723 | <5.0 |
| 724 | <5.0 |
| 725 | <5.0 |
| 726 | 6.0 |
| 727 | <5.0 |
| 728 | 6.2 |
| 729 | 5.3 |
| 730 | <5.0 |
| 731 | <5.0 |
| 732 | <5.0 |
| 733 | <5.0 |
| 734 | <5.0 |
| 735 | <5.0 |
| 736 | 6.3 |
| 738 | 5.2 |
| 739 | 6.6 |
| 740 | 6.0 |
| 741 | 6.8 |
| 742 | 5.7 |
| 744 | 5.9 |

Example 749

Evaluation of Protein Anabolic Action in a Male Rat Model with Orchiectomy

Using an orchiectomy male rat model, the protein anabolic effect of compounds was screened. For male Sprague Dawley rats of 8-10 weeks of age, orchiectomy was surgically conducted under Nembutal anesthesia and kept them untreated for 14 days. After 14 days, animals were randomly assigned to test groups based on their body weights. Test compounds were subcutaneously or orally given them for 14 days. Approximately 24 hours after the last administration, animals were euthanized and the wet weight of levator ani muscle was measured.

Protein anabolic effect (% Eff.) was determined as follows:

% Eff.=((wet weight of the levator ani muscle of a test animal/body weight of a test animal)−average value of (wet weight of the levator ani muscle of a control animal/body weight of a control animal))/(average value of (wet weight of the levator ani muscle of a sham operation animal/body weight of a sham operation animal)−average value of (wet weight of levator ani muscle of a control animal/body weight of a control animal))×100. The results are shown in the Tables. In addition, the symbols (−, +, ++, +++) indicating the intensity of drug efficacy in a table represent the following % Eff.

% Eff.≥130%: +++

130%>% Eff.≥100%: ++

100%>% Eff.≥65%: +

% Eff.<65%: −

TABLE 106

| Compound number | Dose (mg · kg) | Intensity of drug efficacy |
|---|---|---|
| 1 | 10 | + |
| 2 | 1 | + |
| 4 | 1 | + |
| 5 | 1 | +++ |
| 7 | 1 | +++ |
| 14 | 10 | ++ |
| 15 | 1 | +++ |
| 23 | 1 | +++ |
| 26 | 1 | +++ |
| 39 | 3 | + |
| 40 | 10 | ++ |
| 41 | 1 | +++ |
| 50 | 1 | +++ |
| 51 | 3 | + |
| 70 | 1 | ++ |
| 94 | 10 | + |
| 97 | 1 | +++ |
| 106 | 1 | ++ |
| 129 | 1 | ++ |
| 141 | 3 | + |
| 152 | 1 | +++ |
| 153 | 1 | ++ |
| 154 | 3 | +++ |
| 157 | 3 | + |
| 165 | 3 | +++ |
| 167 | 1 | ++ |
| 172 | 1 | ++ |
| 187 | 1 | +++ |
| 252 | 10 | + |
| 285 | 3 | + |
| 286 | 10 | ++ |

From these results, it was clear that the compound of the present invention, a medically acceptable salt thereof or a solvate thereof had an excellent protein anabolic effect.

INDUSTRIAL APPLICABILITY

A compound of the present invention or a medically acceptable salt or a solvate thereof are used as a pharmaceutical compound.

The invention claimed is:

1. A compound represented by the following formula (I) or a medically acceptable salt thereof,

[Chem. 1]

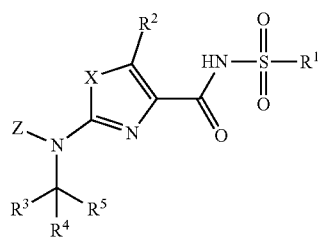

(I)

wherein,

X represents a sulfur atom or an oxygen atom,

Z represents a group selected among the following $Z^1$ to $Z^3$,

[Chem. 2]

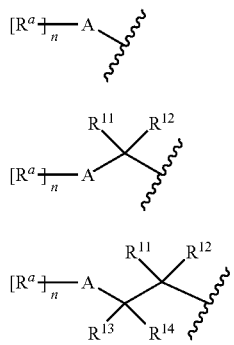

A represents a C6-C12 aryl or a 5-12 membered heteroaryl group, $R^{11}$ to $R^{14}$ represent each independently a hydrogen atom; a halogen; a hydroxyl group; a C1-C3 alkyl group optionally substituted with a halogen or a hydroxyl group; a C1-C3 alkoxy group optionally substituted with a halogen or a hydroxyl group; also, two selected from $R^{11}$ to $R^{14}$ may form a ring, n is an integer of 0 or more and 3 or less, $R^a$'s are the same or different, and represent a halogen; a hydroxyl group; a C1-C6 alkyl group optionally substituted with a halogen, a hydroxyl group, a phenoxy group or a benzyloxy group; a C3-C8 cycloalkyl group optionally substituted with a halogen; a C1-C6 alkoxy group optionally substituted with a halogen, a hydroxyl group, a carboxyl group, a carbamoyl group optionally substituted with a C1-C4 alkyl group, a C1-C4 alkoxy group or a benzyloxy group; a C3-C8 cycloalkoxy group optionally substituted with a halogen; a C1-C4 alkoxy C1-C4 alkyl group optionally substituted with a halogen, a hydroxyl group, a cyano group, a C1-C4 alkoxy group or a benzyloxy group; a phenoxy group; a benzyloxy group; a cyano group; a nitro group; a carboxyl group; a C1-C6 acyl group; a C1-C4 alkoxycarbonyl group; an amino group; a C1-C6 monoalkylamino group; a C1-C6 dialkylamino group; a carbamoyl group optionally substituted with a C1-C4 alkyl group; a C6-C12 aryl group optionally substituted with a halogen, a cyano group, a C1-C4 alkyl group optionally substituted with a halogen, or a hydroxyl group; a 3-12 membered heterocyclic group optionally substituted with a halogen; a sulfanyl group optionally substituted with a C1-C6 alkyl group optionally substituted with a halogen; a C1-C6 alkylsulfinyl group optionally substituted with a halogen; a C1-C6 alkylsulfonyl group optionally substituted with a halogen; or a pentafluorosulfanyl group, $R^1$ represents a C1-C9 alkyl group optionally substituted with a halogen, a hydroxyl group, a cyano group, a carboxyl group, a C1-C4 alkoxycarbonyl group, an amino group, a C1-C6 monoalkylamino group, a C1-C6 dialkylamino group or a C1-C6 alkylsulfonyl group; a C3-C8 cycloalkyl group optionally substituted with a halogen, a hydroxyl group or a cyano group; a C2-C6 alkenyl group optionally substituted with a halogen or a phenyl group; a C2-C6 alkynyl group optionally substituted with a halogen or a phenyl group; a C1-C6 alkoxy C1-C6 alkyl group optionally substituted with a halogen, a hydroxyl group, a cyano group or a C1-C4 alkoxy group; a C6-C12 aryl group optionally substituted with 1 to 3 moieties of R$^c$; a C6-C12 aryl C1-C6 alkyl group optionally substituted with 1 to 3 moieties of R$^d$; a 3-12 membered heterocyclic group optionally substituted with 1 to 3 moieties of R$^e$; or a 3-12 membered heterocyclic C1-C6 alkyl group optionally substituted with 1 to 3 moieties of R$^f$, R$^2$ represents a hydrogen atom; a halogen; a C1-C6 alkyl group optionally substituted with a halogen, a hydroxyl group or a cyano group; a C3-C8 cycloalkyl group optionally substituted with a halogen, a hydroxyl group or a cyano group; or a phenyl group optionally substituted with a halogen, a hydroxyl group or a cyano group, R$^3$ represents a hydrogen atom; a halogen; a C1-C12 alkyl group optionally substituted with a halogen, a hydroxyl group, a cyano group, a carboxyl group, a C3-C8 cycloalkyl group optionally substituted with a halogen or a hydroxyl group, a C3-C8 cycloalkoxy group optionally substituted with a halogen or a hydroxyl group, a C1-C4 alkoxy group optionally substituted with a phenyl group, a C1-C4 alkoxycarbonyl group, an amino group, a C1-C6 monoalkylamino group, a C1-C6 dialkylamino group, a C1-C6 alkylsulfonyl group, a phenoxy group or a silyl group substituted with a C1-C4 alkyl group or a phenyl group; a C3-C8 cycloalkyl group optionally substituted with a halogen, a hydroxyl group, a cyano group, a carboxyl group, a C1-C4 alkyl group optionally substituted with a halogen or a hydroxyl group, a C1-C4 alkoxy group optionally substituted with a halogen or a hydroxyl group, a C1-C4 alkoxycarbonyl group, an amino group, a C1-C6 monoalkylamino group, a C1-C6 dialkylamino group or a C1-C6 alkylsulfonyl group; a C1-C6 alkoxy C1-C6 alkyl group optionally substituted with a halogen, a hydroxyl group, a cyano group or a C1-C4 alkoxy group; a C2-C9 alkenyl group optionally substituted with a halogen, a hydroxyl group or a cyano group; a C2-C9 alkynyl group optionally substituted with a halogen or a cyano group; a C3-C8 cycloalkenyl group optionally substituted with halogen, a hydroxyl group or a cyano group; a C6-C12 aryl group optionally substituted with 1 to 5 moieties of R$^g$; a C6-C12 aryl C1-C6 alkyl group optionally substituted with 1 to 5 moieties of R$^h$; a 3-12 membered heterocyclic group optionally substituted with 1 to 5 moieties of R$^i$; a 3-12 membered heterocyclic C1-C6 alkyl group optionally substituted with 1 to 5 moieties of R$^j$; a C1-C9 acyl group optionally substituted with a halogen, a hydroxyl group or a cyano group; a C3-C8 cycloalkylcarbonyl group; a benzoyl group; a C5-C12 spiroalkyl group; an adamantyl group; a silyl group substituted with 1 to 3 moieties of C1-C4 alkyl group or a phenyl group; or R$^{30}$,

[Chem. 3]

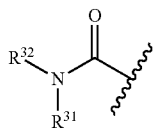

wherein,

R$^{30}$ is a substituent represented by the above-mentioned formula,

R$^{31}$ and R$^{32}$ represent each independently a hydrogen atom; a C1-C6 alkyl group optionally substituted with a halogen; a C3-C8 cycloalkyl group optionally substituted with a halogen; or a phenyl group optionally substituted with a halogen; and R$^{31}$ and R$^{32}$ may form a ring by connecting directly with each other or via an oxygen atom, a nitrogen atom or a sulfur atom, R$^4$ and R$^5$ represent each independently a hydrogen atom; a halogen; a C1-C6 alkyl group optionally substituted with a halogen, a hydroxyl group or a cyano group; a phenyl group or a C3-C8 cycloalkyl group optionally substituted with a halogen, a hydroxyl group or a cyano group; and R$^3$ and R$^4$ may form a ring, R$^c$, R$^d$, R$^e$ and R$^f$ represent a halogen; a hydroxyl group; a C1-C6 alkyl group optionally substituted with a halogen; a C3-C8 cycloalkyl group optionally substituted with a halogen; a C1-C6 alkoxy group optionally substituted with a halogen; a C3-C8 cycloalkoxy group optionally substituted with a halogen; a C1-C4 alkoxy C1-C4 alkyl group optionally substituted with a halogen, a hydroxyl group, a phenyl group or a C1-C4 alkoxy group; a cyano group; a nitro group; an oxo group; a carboxyl group; a C1-C6 acyl group; a C1-C4 alkoxycarbonyl group; an amino group; a C1-C6 monoalkylamino group; a C1-C6 dialkylamino group; a sulfanyl group; a C1-C6 alkylsulfanyl group optionally substituted with a halogen; a C1-C6 alkylsulfinyl group optionally substituted with a halogen; or a C1-C6 alkylsulfonyl group optionally substituted with a halogen, R$^g$, R$^h$, R$^i$ and R$^j$ represent a halogen; a hydroxyl group; an amino group; a C1-C6 monoalkylamino group; a C1-C6 dialkylamino group; an acetamido group; a C1-C6 alkyl group optionally substituted with a halogen, a hydroxyl group, a phenoxy group or a benzyloxy group; a C3-C8 cycloalkyl group; a C2-C6 alkenyl group optionally substituted with a halogen, a hydroxyl group or a cyano group; a C2-C6 alkynyl group optionally substituted with a halogen or a cyano group; a C1-C6 alkoxy group optionally substituted with a halogen, a hydroxyl group, a C1-C4 alkoxy group, an amino group, a C1-C6 monoalkylamino group, a C1-C6 dialkylamino group, a C6-C10 aryl group or a 3-10 membered heterocyclic group optionally substituted with an oxo group; a C1-C6 alkoxy C1-C6 alkyl group optionally substituted with a halogen, a phenyl group, a phenoxy group or a benzyloxy group; a C3-C8 cycloalkoxy group; a cyano group; a nitro group; an oxo group; a carboxyl group; a sulfanyl group; a C1-C6 alkylsulfanyl group optionally substituted with a halogen; a C1-C6 alkylsulfinyl group optionally substituted with a halogen; a phenylsulfonyl group optionally substituted with a C1-C4 alkyl group; a C1-C6 alkylsulfonyl group optionally substituted with a halogen; a C1-C6 acyl group; a C1-C4 alkoxycarbonyl group; a phenyl group optionally substituted with a halogen, a cyano group, a trifluoromethyl group or a hydroxyl group; a 3-12 membered heterocyclic group optionally substituted with a halogen or an oxo group; a phenoxy group; a C6-C12 aryl C1-C6 alkoxy group; a 3-12 membered heterocyclic C1-C6 alkoxy group or a group represented by the formula $R^{30}$—$CH_2$—O—.

2. The compound or a medically acceptable salt thereof according to claim 1, wherein $R^1$ is a C1-C9 alkyl group optionally substituted with a halogen, a hydroxyl group, a cyano group, a carboxyl group, a C1-C4 alkoxycarbonyl group, an amino group, a C1-C6 monoalkylamino group, a C1-C6 dialkylamino group or a C1-C6 alkylsulfonyl group; or a C1-C6 alkoxy C1-C6 alkyl group optionally substituted with a halogen, a hydroxyl group, a cyano group or a C1-C4 alkoxy group.

3. The compound or a medically acceptable salt thereof according to claim 1, wherein $R^2$ is a halogen; a C1-C6 alkyl group optionally substituted with a halogen, a hydroxyl group or a cyano group; a C3-C8 cycloalkyl group optionally substituted with a halogen, a hydroxyl group or a cyano group; or a phenyl group optionally substituted with a halogen, a hydroxyl group or a cyano group.

4. The compound or a medically acceptable salt thereof according to claim 1, wherein $R^2$ is a hydrogen atom; a halogen; a C1-C6 alkyl group optionally substituted with a halogen, a hydroxyl group or a cyano group; or a C3-C8 cycloalkyl group optionally substituted with a halogen.

5. The compound or a medically acceptable salt thereof according to claim 1, wherein $R^4$ and $R^5$ each are a hydrogen atom.

6. The compound or a medically acceptable salt thereof according to claim 1, wherein X is a sulfur atom.

7. The compound or a medically acceptable salt thereof according to claim 1, wherein X is an oxygen atom.

8. The compound or a medically acceptable salt thereof according to claim 1, wherein Z is Z1.

9. The compound or a medically acceptable salt thereof according to claim 1, wherein Z is Z2.

10. The compound or a medically acceptable salt thereof according to claim 1, wherein Z is Z3.

11. A compound selected from the following compounds (1) to (31) or a medically acceptable salt thereof:
   (1) 2-(N-benzyl-4-cyano-anilino)-5-methyl-N-methylsulfonyl-thiazole-4-carboxamide
   (2) 2-[4-cyano-N-[[3-(difluoromethoxy)phenyl]methyl]anilino]-5-methyl-N-methylsulfonyl-thiazole-4-carboxamide
   (3) 2-[4-cyano-N-[[2-(difluoromethoxy)phenyl]methyl]anilino]-5-methyl-N-methylsulfonyl-thiazole-4-carboxamide
   (4) 2-[4-cyano-N-[[4-(trifluoromethoxy)phenyl]methyl]anilino]-5-methyl-N-methylsulfonyl-thiazole-4-carboxamide
   (5) 2-[4-cyano-N-[(3-fluorophenyl)methyl]anilino]-5-methyl-N-methylsulfonyl-thiazole-4-carboxamide
   (6) 2-[4-cyano-N-[(4-fluorophenyl)methyl]anilino]-5-methyl-N-methylsulfonyl-thiazole-4-carboxamide
   (7) 2-[N-[(4-chlorophenyl)methyl]-4-cyano-anilino]-5-methyl-N-methylsulfonyl-thiazole-4-carboxamide
   (8) 2-[N-(benzofuran-5-ylmethyl)-4-cyano-anilino]-5-methyl-N-methylsulfonyl-thiazole-4-carboxamide
   (9) 2-[4-cyano-N-[(4,4-difluorocyclohexyl)methyl]anilino]-5-methyl-N-methylsulfonyl-thiazole-4-carboxamide
   (10) 2-[4-cyano-N-[(2-methylthiazol-4-yl)methyl]anilino]-5-methyl-N-methylsulfonyl-thiazole-4-carboxamide
   (11) 2-[4-cyano-N-[[4-(difluoromethoxy)phenyl]methyl]anilino]-5-methyl-N-methylsulfonyl-thiazole-4-carboxamide
   (12) 2-[N-(1,3-benzothiazol-6-ylmethyl)-4-cyano-anilino]-5-methyl-N-methylsulfonyl-thiazole-4-carboxamide
   (13) 2-[N-(benzothiophen-2-ylmethyl)-4-cyano-anilino]-5-methyl-N-methylsulfonyl-thiazole-4-carboxamide
   (14) 2-[N-[(4-chloro-2-fluorophenyl)methyl]-4-cyano-anilino]-5-methyl-N-methylsulfonyl-thiazole-4-carboxamide
   (15) 2-[4-cyano-N-[[4-(difluoromethyl)phenyl]methyl]anilino]-5-methyl-N-methyl sulfonyl-thiazole-4-carboxamide
   (16) 2-[4-cyano-N-[(3,4-difluorophenyl)methyl]anilino]-5-methyl-N-methylsulfonyl-thiazole-4-carboxamide
   (17) 2-[N-[(2-chloro-4-fluorophenyl)methyl]-4-cyano-anilino]-5-methyl-N-methyl sulfonyl-thiazole-4-carboxamide
   (18) 2-[N-[(4-bromophenyl)methyl]-4-cyano-anilino]-5-methyl-N-methylsulfonyl-thiazole-4-carboxamide
   (19) 2-[N-[(4-chlorophenyl)methyl]-4-cyano-anilino]-5-methyl-N-methylsulfonyl-oxazole-4-carboxamide
   (20) 5-bromo-2-[4-cyano-N-[[3-(trifluoromethoxy)phenyl]methyl]anilino]-N-methylsulfonyl-thiazole-4-carboxamide
   (21) 2-[4-cyano-N-[[4-(4-fluorophenyl)phenyl]methyl]anilino]-5-methyl-N-methylsulfonyl-thiazole-4-carboxamide
   (22) 2-[N-[(5-chloro-2-pyridyl)methyl]-4-cyano-anilino]-5-methyl-N-methylsulfonyl-thiazole-4-carboxamide
   (23) 2-[N-[(5-bromo-2-pyridyl)methyl]-4-cyano-anilino]-5-methyl-N-methylsulfonyl-thiazole-4-carboxamide
   (24) 2-[N-[(4-bromophenyl)methyl]-4-cyano-anilino]-5-methyl-N-methylsulfonyl-oxazole-4-carboxamide
   (25) 2-[4-cyano-N-[[6-(trifluoromethyl)-3-pyridyl]methyl]anilino]-5-methyl-N-methyl sulfonyl-thiazole-4-carboxamide
   (26) 2-[4-cyano-N-[[4-(trifluoromethoxy)phenyl]methyl]anilino]-N-(3-methoxypropylsulfonyl)-5-methyl-thiazole-4-carboxamide
   (27) 2-[4-cyano-N-[[4-(difluoromethoxy)phenyl]methyl]anilino]-N-(3-methoxypropylsulfonyl)-5-methyl-thiazole-4-carboxamide
   (28) 2-[4-cyano-N-[[3-fluoro-4-(trifluoromethyl)phenyl]methyl]anilino]-5-methyl-N-methylsulfonyl-thiazole-4-carboxamide
   (29) 2-[4-cyano-N-[[4-(difluoromethoxy)-3-fluorophenyl]methyl]anilino]-5-methyl-N-methylsulfonyl-thiazole-4-carboxamide
   (30) 2-[4-cyano-N-[[2-(trifluoromethyl)thiazol-4-yl]methyl]anilino]-5-methyl-N-methylsulfonyl-thiazole-4-carboxamide
   (31) 2-[4-cyano-N-[[3-cyano-4-(trifluoromethyl)phenyl]methyl]anilino]-5-methyl-N-methylsulfonyl-thiazole-4-carboxamide.

12. A pharmaceutical composition comprising the compound according to claim 1 or a medically acceptable salt thereof, and a pharmaceutically acceptable carrier.

13. A method for treating one or more diseases selected from the group consisting of sarcopenia, disuse muscle atrophy, cachexia and muscular dystrophy, comprising administering the compound according to claim 1 or the medically acceptable salt thereof to a subject in need thereof.

14. A compound represented by any one of the following chemical formula:

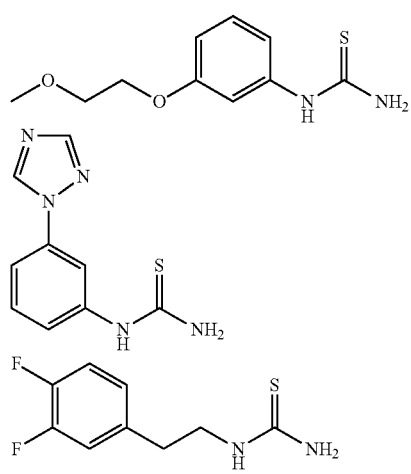
[Chem. 4]
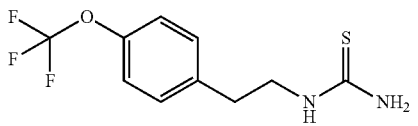
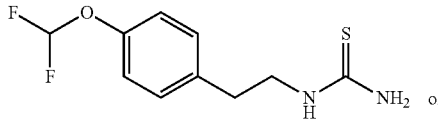
or
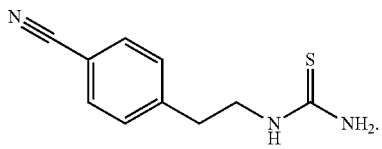.
* * * * *